US012502376B2

(12) United States Patent
Clark et al.

(10) Patent No.: US 12,502,376 B2
(45) Date of Patent: Dec. 23, 2025

(54) PYRANO[4,3-B]INDOLE DERIVATIVES AS ALPHA-1-ANTITRYPSIN MODULATORS FOR TREATING ALPHA-1-ANTITRYPSIN DEFICIENCY (AATD)

(71) Applicant: Vertex Pharmaceuticals Incorporated, Boston, MA (US)

(72) Inventors: Michael Philip Clark, Concord, MA (US); Simon Giroux, Cambridge, MA (US); Philip Noel Collier, Hingham, MA (US); Qing Tang, Boxborough, MA (US); Nathan D. Waal, Somerville, MA (US); Sarathy Kesavan, Quincy, MA (US); Peter Jones, Sharon, MA (US); Michael Aaron Brodney, Newton, MA (US); Wenxin Gu, Concord, MA (US); Diane Marie Boucher, Beverly, MA (US); Lev T.D. Fanning, San Marcos, CA (US); Amy B. Hall, Wellesley Hills, MA (US); Dennis James Hurley, San Marcos, CA (US); Mac Arthur Johnson, Jr., Derry, NH (US); John Patrick Maxwell, Hingham, MA (US); Rebecca Jane Swett, Somerville, MA (US); Timothy Lewis Tapley, Cardiff, CA (US); Stephen A. Thomson, Durham, NC (US); Veronique Damagnez, Framingham, MA (US); Kevin Michael Cottrell, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 474 days.

(21) Appl. No.: 17/916,448

(22) PCT Filed: Apr. 2, 2021

(86) PCT No.: PCT/US2021/025601

§ 371 (c)(1),
(2) Date: Sep. 30, 2022

(87) PCT Pub. No.: WO2021/203014

PCT Pub. Date: Oct. 7, 2021

(65) Prior Publication Data

US 2023/0157999 A1 May 25, 2023

Related U.S. Application Data

(60) Provisional application No. 63/004,702, filed on Apr. 3, 2020.

(51) Int. Cl.

| | |
|---|---|
| *A61K 31/407* | (2006.01) |
| *A61K 31/4155* | (2006.01) |
| *A61K 31/427* | (2006.01) |
| *A61K 31/438* | (2006.01) |
| *A61K 38/57* | (2006.01) |
| *C07D 491/052* | (2006.01) |
| *C07D 491/20* | (2006.01) |
| *C07D 495/20* | (2006.01) |

(52) U.S. Cl.

CPC ........ *A61K 31/407* (2013.01); *A61K 31/4155* (2013.01); *A61K 31/427* (2013.01); *A61K 31/438* (2013.01); *A61K 38/57* (2013.01); *C07D 491/052* (2013.01); *C07D 491/20* (2013.01); *C07D 495/20* (2013.01)

(58) Field of Classification Search

CPC .............. A61K 31/407; A61K 31/4155; A61K 31/427; A61K 31/438; C07D 491/052

See application file for complete search history.

(56) References Cited

U.S. PATENT DOCUMENTS

| | | | |
|---|---|---|---|
| 2,538,341 | A | 1/1951 | Ullyot |
| 2,612,503 | A | 9/1952 | Ullyot |
| 4,198,415 | A | 4/1980 | Kornfeld et al. |
| 4,647,667 | A | 3/1987 | Schaus et al. |
| 4,778,894 | A | 10/1988 | Schaus et al. |
| 5,216,001 | A | 6/1993 | Perregaard et al. |
| 5,358,949 | A | 10/1994 | Tabusa et al. |
| 6,201,129 | B1 | 3/2001 | Miller et al. |
| 11,623,924 | B2 | 4/2023 | Bandarage et al. |
| 11,884,672 | B2 | 1/2024 | Bandarage et al. |
| 2001/0051620 | A1 | 12/2001 | Berger et al. |

(Continued)

FOREIGN PATENT DOCUMENTS

| | | | |
|---|---|---|---|
| CN | 1704404 | A | 7/2001 |
| CN | 1505613 | A | 6/2004 |

(Continued)

OTHER PUBLICATIONS

American Thoracic Society & European Respiratory Society (2003) "American Thoracic Society/European Respiratory Society Statement: Standards for the Diagnosis and Management of Individuals with Alpha-1 Antitrypsin Deficiency," *Am J Respir Crit Care Med.*, 168:818-900.

Balle, T. et al. (2003) "Synthesis and Structure-Affinity Relationship Investigations of 5-Aminomethyl and 5-Carbamoyl Analogues of the Antipsychotic Sertindole. A New Class of Selective $\alpha_1$ Adrenoceptor Antagonists," *Bioorg. Med. Chem.*, 11:1065-1078.

Bergin, D.A. et al. (2014) "The circulating proteinase inhibitor alpha-1 antitrypsin regulates neutrophil degranulation and autoimmunity," *Sci Transl Med.*, 6(217):217ra1 (70 pages).

(Continued)

*Primary Examiner* — Marcos L Sznaidman

(74) *Attorney, Agent, or Firm* — Finnegan, Henderson, Farabow, Garrett & Dunner, LLP

(57) ABSTRACT

Pyrano[4,3-b]indole derivatives as alpha-1-antitrypsin modulators for treating alpha-1-antitrypsin deficiency (AATD).

33 Claims, No Drawings

(56) References Cited

U.S. PATENT DOCUMENTS

| | | | |
|---|---|---|---|
| 2003/0097000 | A1 | 5/2003 | Bovy et al. |
| 2003/0165712 | A1 | 9/2003 | Lin et al. |
| 2003/0212085 | A1 | 11/2003 | McCall et al. |
| 2004/0077865 | A1 | 4/2004 | Zhao et al. |
| 2005/0009754 | A1 | 1/2005 | Pan et al. |
| 2005/0043381 | A1 | 2/2005 | Johnson et al. |
| 2005/0153957 | A1 | 7/2005 | Cuenoud et al. |
| 2007/0027177 | A1 | 2/2007 | Trotter et al. |
| 2007/0232682 | A1 | 10/2007 | Beard et al. |
| 2007/0248947 | A1 | 10/2007 | Cezar |
| 2008/0021056 | A1 | 1/2008 | Konradi et al. |
| 2010/0016285 | A1 | 1/2010 | Uchida et al. |
| 2010/0076018 | A1 | 3/2010 | Liu et al. |
| 2011/0118221 | A1 | 5/2011 | Nussbaum et al. |
| 2013/0167932 | A1 | 7/2013 | Maeda et al. |
| 2013/0319530 | A1 | 12/2013 | Maeda et al. |
| 2014/0135359 | A1 | 5/2014 | Martineau |
| 2014/0341899 | A1 | 11/2014 | Dinarello et al. |
| 2016/0083363 | A1 | 3/2016 | Hamm et al. |
| 2016/0145271 | A1 | 5/2016 | Vakalopoulos et al. |
| 2018/0251460 | A1 | 9/2018 | Aktoudianakis et al. |
| 2020/0361939 | A1 | 11/2020 | Bandarage et al. |
| 2021/0260036 | A1 | 8/2021 | Bozic et al. |
| 2023/0159502 | A1 | 5/2023 | Giroux et al. |
| 2023/0159504 | A1 | 5/2023 | Giroux et al. |
| 2023/0159521 | A1 | 5/2023 | Giroux et al. |
| 2023/0159580 | A1 | 5/2023 | Giroux et al. |
| 2023/0265080 | A1 | 8/2023 | Bandarage et al. |
| 2023/0279010 | A1 | 9/2023 | Bligh et al. |
| 2023/0339915 | A1 | 10/2023 | Giroux et al. |
| 2024/0002386 | A1 | 1/2024 | Shi et al. |
| 2024/0012010 | A1 | 1/2024 | Penney et al. |
| 2024/0158404 | A1 | 5/2024 | Grey, Jr. et al. |
| 2024/0336614 | A1 | 10/2024 | Bandarage et al. |

FOREIGN PATENT DOCUMENTS

| | | | |
|---|---|---|---|
| CN | 102850324 | A | 1/2013 |
| CN | 103239451 | | 8/2013 |
| CN | 107698505 | A | 2/2018 |
| CN | 109414596 | A | 3/2019 |
| CN | 110776459 | A | 2/2020 |
| CN | 113164761 | A | 7/2021 |
| CN | 115361946 | A | 11/2022 |
| EP | 0 465 398 | A2 | 1/1992 |
| EP | 1 396 488 | A1 | 3/2004 |
| EP | 3571187 | B1 | 11/2019 |
| EP | 3 699 179 | A1 | 8/2020 |
| ES | 323287 | A1 | 3/1967 |
| JP | 4856667 | A | 8/1973 |
| JP | 2000-072751 | A | 3/2000 |
| JP | 2000-281654 | A | 10/2000 |
| JP | 5107589 | B2 | 12/2012 |
| RU | 2337915 | C1 | 11/2008 |
| RU | 2617405 | C2 | 4/2017 |
| WO | WO 1996/037467 | A1 | 11/1996 |
| WO | WO 2000/075114 | A1 | 12/2000 |
| WO | WO 2001/044197 | A2 | 6/2001 |
| WO | WO 2002/008224 | A1 | 1/2002 |
| WO | WO 2002/094790 | A1 | 11/2002 |
| WO | WO 2003/099824 | * | 4/2003 |
| WO | WO 2003/099824 | A1 | 12/2003 |
| WO | WO 2004/065367 | A1 | 8/2004 |
| WO | WO 2004/108120 | A1 | 12/2004 |
| WO | WO 2006/019831 | A1 | 2/2006 |
| WO | WO 2006/093823 | A1 | 9/2006 |
| WO | WO 2007/115315 | A2 | 10/2007 |
| WO | WO 2009/060209 | A1 | 5/2009 |
| WO | WO 2009/127686 | A1 | 10/2009 |
| WO | WO 2009/158587 | A1 | 12/2009 |
| WO | WO 2011/056222 | A1 | 5/2011 |
| WO | WO 2011/110852 | A1 | 9/2011 |
| WO | WO 2012/016695 | A2 | 2/2012 |
| WO | WO 2012/038820 | A2 | 3/2012 |
| WO | WO 2016/154051 | A1 | 9/2016 |
| WO | WO 2017/035418 | A1 | 3/2017 |
| WO | WO 2017/117304 | A1 | 7/2017 |
| WO | WO 2017/197240 | A1 | 11/2017 |
| WO | WO 2017/207118 | A1 | 12/2017 |
| WO | WO 2018/218192 | A1 | 11/2018 |
| WO | WO 2019/076336 | A1 | 4/2019 |
| WO | WO 2019/089667 | A1 | 5/2019 |
| WO | WO 2019/116302 | A1 | 6/2019 |
| WO | WO 2019/149522 | A1 | 8/2019 |
| WO | WO 2019/243841 | A1 | 12/2019 |
| WO | WO 2020/002611 | A1 | 1/2020 |
| WO | WO 2020/033288 | A1 | 2/2020 |
| WO | WO 2020/048694 | A1 | 3/2020 |
| WO | WO 2020/081257 | A1 | 4/2020 |
| WO | WO 2020/247160 | A1 | 12/2020 |
| WO | WO 2021/067584 | A1 | 4/2021 |
| WO | WO 2021/155087 | A1 | 8/2021 |
| WO | WO 2021/203007 | A1 | 10/2021 |
| WO | WO 2021/203010 | A1 | 10/2021 |
| WO | WO 2021/203014 | A1 | 10/2021 |
| WO | WO 2021/203023 | A1 | 10/2021 |
| WO | WO 2021/203025 | A1 | 10/2021 |
| WO | WO 2021/203028 | A1 | 10/2021 |
| WO | WO 2022/026372 | A2 | 2/2022 |
| WO | WO 2022/104353 | A1 | 5/2022 |
| WO | WO 2022/109553 | A2 | 5/2022 |
| WO | WO 2024/054624 | A1 | 3/2024 |

OTHER PUBLICATIONS

Chemical Abstracts Service, CAS Registry No. 1516110-75-0. CA Index Name: Pyrrolo[2,3-f]benzimidazole-7-methanamine, 6-ethyl-3,5-dihydro-2-methyl-6-Ethyl-3,5-dihydro-2-methylpyrrolo[2,3-f]benzimidazole-7-methanamine Date: Jan. 10, 2014.

Chemical Abstracts Service, CAS Registry No. 2103889-64-9. CA Index Name: Pyrrolo[2,3-f]benzimidazole-7-carbonitrile, 3,5-dihydro-2,5,6-trimethyl Date: Jul. 27, 2017.

Donawade, D.S. et al. (Apr. 2007.) "Synthesis and antimicrobial activity of novel linearly fused 5-substituted-7-acetyl-2,6-dimethyloxazolo[4,5-f] indoles," *Indian Journal of Chemistry*, 46B:690-693.

Forbes, I.T. et al. (1996) "Synthesis, Biological Activity, and Molecular Modeling Studies of Selective 5-$HT_{2C/2B}$ Receptor Antagonists," *J. Med. Chem.*, 39:4966-4977.

Fregonese, F. & J. Stolk (2008) "Hereditary alpha-1-antitrypsin deficiency and its clinical consequences," *Orphanet J. Rare Dis.*, 3:16 (9 pages).

Geraghty, P. et al. (Dec. 2014.), "α1-Antitrypsin Activates Protein Phosphatase 2A to Counter Lung Inflammatory Responses," *Am J Respir Crit Care Med*, 190(11):1229-1242.

Grant & Hackh's Chemical Dictionary (5th ed. 1987), at p. 148.

Grinev, A.N. et al. (1975), "Synthesis of Aldehydes and Nitriles in the 5-Hydroxyindole Series," *Chem. Heterocycl. Compd.*, 11:1087-1090.

Gadaginamath, G.S. et al. (2000) "Chemoselective Reaction of 3,6-Diacetylindole Towards Hydroxylamine: Synthesis and Antimicrobial Activity of Novel Isoxazolo[4,5-f]indole Derivatives," *Rev. Roum. Chim.*, 45(10):929-933.

Ghorai, J. et al. (2016) "Cobalt(III)-Catalyzed Intramolecular Cross-Dehydrogenative C—H/X-H Coupling: Efficient Synthesis of Indoles and Benzofurans," *Chem. Eur. J.*, 22:16042-16046.

Ghorai, J. et al. (2018) "Divergent Functionalization of N-Alkyl-2-alkenylanilines: Efficient Synthesis of Substituted Indoles and Quinolines," *Chem. Asian J.*, 13(17):2499-2504.

Gosai, S. et al. (Nov. 2010.) "Automated High-Content Live Animal Drug Screening Using C. elegans Expressing the Aggregation Prone Serpin αl-antitrypsin Z," *PLoS One*, 5(11):e15460 (16 pages).

He, L. et al. (2014) "Transition-metal-free synthesis of multisubstituted N-arylindoles via reaction of arynes and α-amino ketones," *Tetrahedron*, 70:2400-2405.

International Search Report and Written Opinion for International Application No. PCT/US2021/025601, mailed Jun. 15, 2021 (13 pages).

(56) References Cited

OTHER PUBLICATIONS

Jafarpour, F. et al. (2019) "A Fast Track to Indoles and Annulated Indoles through ortho- vs ipso-Amination of Aryl Halides," *Org. Lett.*, 21:10143-10148.
Jiang, H. et al. (2016) "Multiple Roles of the Pyrimidyl Group in the Rhodium-Catalyzed Regioselective Synthesis and Functionalization of Indole-3-carboxylic Acid Esters," *Advanced Synthesis & Catalysis*, 358:188-194.
Kamat, A.G. et al. (Mar. 1994.), "Synthesis and Antimicrobial Activity of Furoindole Derivatives," *Indian J. Chem. Sect. B*, 33B(3):255-259.
Maity, S. et al. (2012 Sept.) "A Visible-Light-Mediated Oxidative C—N Bond Formation/Aromatization Cascade: A New Photocatalytic Preparation of N-Arylindoles," *Angew Chem Int Ed Engl.*, 51(38):9562-9566. NIH Public Access Author Manuscript; available in PMC Sep. 17, 2013 (11 pages).
Mali, R.S. et al. (1994) "Useful Syntheses of Pyrano- and Pyridoindoles," *Organic Preparations and Procedures International: The New Journal for Organic Synthesis*, 26(5):573-577.
Meti, P. et al. (2017) "Regioselective synthesis of dipyrrolopyrazine (DPP) derivatives via metal free and metal catalyzed amination and investigation of their optical and thermal properties," *RSC Adv.*, 7:18120-18131.
Notice of Allowance and Fee(s) Due for U.S. Appl. No. 16/593,118, mailed Nov. 9, 2022.
Ogushi, F. et al. (1987) "Z-type $\alpha$1-antitrypsin is less competent than M1-type $\alpha$1-antitrypsin as an inhibitor of neutrophil elastase," *J Clin Invest.*, 80(5):1366-1374.
Piitulainen, E. & H.A. Tanash (2015), "The Clinical Profile of Subjects Included in the Swedish National Register on Individuals with Severe Alpha 1-Antitrypsin deficiency," *COPD*, 12(S1):36-41.
Saccarello, M.L. et al. (1979 Sept.) "A New Synthesis of 1-Alkyl-3-aminoindoles," *Synthesis*, 1979(9):727-729.
Song, X. et al. (2018) "Regioselective Synthesis of 2-Alkenylindoles and 2-Alkenylindole-3-carboxylates through the Cascade Reactions of N-Nitrosoanilines with Propargyl Alcohols," *J. Org. Chem.*, 83:8509-8521.
Tanash, H.A. et al. (2016) "Cause-specific mortality in individuals with severe alpha 1-antitrypsin deficiency in comparison with the general population in Sweden," *International Journal of COPD*, 2016(11):1663-1669.
Tidwell, R.R. et al. (1978) "Diarylamidine Derivatives with One or Both of the Aryl Moieties Consisting of an Indole or Indole-like Ring. Inhibitors of Arginine-Specific Esteroproteases," *J Med Chem*, vol. 21, No. 7:613-623.
Wen, W. et al. (2014) "Substituted indoles as selective protease activated receptor 4 (PAR-4) antagonists: Discovery and SAR of ML354," *Bioorg. Med. Chem. Lett.*, http://dx.doi.org/10.1016/j.bmcl.2014.08.021.
*Vertex Provides Update on its Clinical Programs Targeting Alpha-1 Antitrypsin Deficiency*, Vertex (Oct. 14, 2020), https://news.vrtx.com/press-release/vertex-provides-update-its-clinical-programs-targeting-alpha-1-antitrypsin-deficiency (4 pages).
*Vertex Announces Primary Endpoint Achieved in Phase 2 Study of VX-864 in Alpha-1 Antitrypsin Deficiency*, Vertex (Jun. 10, 2021), https://news.vrtx.com/press-release/vertex-announces-primary-endpoint-achieved-phase-2-study-vx-864-alpha-1-antitrypsin (5 pages).
U.S. Appl. No. 17/060,945, filed Oct. 1, 2020, by Bozic et al.
U.S. Appl. No. 17/916,388, filed Sep. 30, 2022, by Giroux et al.
U.S. Appl. No. 17/916,405, filed Sep. 30, 2022, by Giroux et al.
U.S. Appl. No. 17/916,448, filed Sep. 30, 2022, by Clark et al.
U.S. Appl. No. 17/916,453, filed Sep. 30, 2022, by Giroux et al.
U.S. Appl. No. 17/916,481, filed Sep. 30, 2022, by Giroux et al.
U.S. Appl. No. 17/916,484, filed Sep. 30, 2022, by Giroux et al.
Akhapkina, V.I. et al. (2012) "Fundamental bases of modulatory concept and classification of modulatory drugs", Russian Medical Journal, 19: 933-951.
Aldonyte, R. et al. (2004) "Analysis of systemic biomarkers in COPD patients", Journal of Chronic Obstructive Pulmonarydisease, 1(2):155-164.
Belikov, V.G. (2007) "Pharmaceutical Chemistry", textbook, Moscow, MEDpress-inform, pp. 27-29.
Chemical Abstracts Service, CAS Registry No. 2255-53-0. CA Index Name: Carbostyril, 3-ethyl-8-hydroxy-4-methoxy-(8CI) Date: Nov. 16, 1984.
Chemical Abstracts Service, CAS Registry No. 56513-01-0. CA Index Name: 8-Hydroxy-3-methyl-1(2H)-isoquinolinone, Date: Nov. 16, 1984.
Chemical Abstracts Service, CAS Registry No. 73109-03-2. CA Index Name: 7-Hydroxy-3-methyl-2-phenyl-1(2H)-isoquinolinone, Date: Nov. 16, 1984.
Chemical Abstracts Service, CAS Registry No. 73828-43-0. CA Index Name: 1(2H)-Isoquinolinone, 3-ethyl-7-hydroxy—Date: Nov. 16, 1984.
Chemical Abstracts Service, CAS Registry No. 73828-46-3. CA Index Name: 1(2H)-Isoquinolinone, 3-ethyl-7-hydroxy-2-methyl—Date: Nov. 16, 1984.
Chemical Abstracts Service, CAS Registry No. 73828-51-0. CA Index Name: 7-Hydroxy-2-(2-hydroxyethyl)-3-methyl-I(2H)-isoquinolinone. Date: Nov. 16, 1984.
Chemical Abstracts Service, CAS Registry No. 73828-52-1. CA Index Name: 1(2H)-Isoquinolinone, 3-ethyl-7-hydroxy-2-(2-hydroxyethyl)—Date: Nov. 16, 1984.
Chemical Abstracts Service, CAS Registry No. 73828-55-4. CA Index Name: 1(2H)-Isoquinolinone, 3-ethyl-2,7-dihydroxy—Date: Nov. 16, 1984.
Chemical Abstracts Service, CAS Registry No. 91348-44-6. CA Index Name: 3-(2-Bromoethyl)- 8-hydroxy-2(1H)-quinolinone. Date: Nov. 16, 1984.
Chemical Abstracts Service, CAS Registry No. 872787-19-4. CA Index Name: 1(2H)-Isoquinolinone, 7-amino-3-ethyl—Date: Jan. 27, 2006.
Chemical Abstracts Service, CAS Registry No. 102559-86-4. CA Index Name: 8-Quinolinol, 4-chloro-2-[2-(diethylamino)ethyl]-3-ethyl—Date: Jun. 7, 1986.
Chemical Abstracts Service, CAS Registry No. 1045710-22-2. Index Name: 8-Quinolinol, 3-(1-methylethyl)-2-(2-methylpropyl)—Date: Sep. 2, 2008.
Chemical Abstracts Service, CAS Registry No. 105909-75-9. Index Name: 8-Quinolinol, 3-ethyl-2-methyl—Date: Dec. 25, 1986.
Chemical Abstracts Service, CAS Registry No. 1078095-05-2. CA Index Name: 8-Quinolinol, 3-ethyl-2-phenyl—Date: Dec. 1, 2008.
Chemical Abstracts Service, CAS Registry No. 1780592-67-7. CA Index Name: 2-(7-hydroxy-2-methoxyquinolin-3-yl)acetic acid. Date: Jun. 15, 2015.
Chemical Abstracts Service, CAS Registry No. 1785114-56-8. CA Index Name: 7-Hydroxy-3-methyl-I-isoquinolinecarboxylic acid. Date: Jun. 21, 2015.
Chemical Abstracts Service, CAS Registry No. 1854272-23-3. CA Index Name: 4-Chloro-3-ethyl-2-methyl-8-(phenylmethoxy)quinoline Date: Jan. 28, 2016.
Chemical Abstracts Service, CAS Registry No. 1869801-41-1. CA Index Name: 3-Ethyl-N-methyl-7-(phenylmethoxy)-2-quinolinamine Date: Feb. 18, 2016.
Chemical Abstracts Service, CAS Registry No. 1873904-99-4. CA Index Name: 4-Chloro-3-ethyl-2-methyl-7-(phenylmethoxy)quinoline Date: Feb. 25, 2016.
Chemical Abstracts Service, CAS Registry No. 1875846-68-6. CA Index Name: N,3-Diethyl-7-(phenylmethoxy)-2-quinolinamine Date: Feb. 29, 2016.
Chemical Abstracts Service, CAS Registry No. 1877816-72-2. CA Index Name: N-Methyl-3-(1-methylethyl)-7-(phenylmethoxy)-2-quinolinamine Date: Mar. 2, 2016.
Chemical Abstracts Service, CAS Registry No. 1878025-01-4. CA Index Name: 4-Chloro-2-methyl-3-(1-methylethyl)-7-(phenylmethoxy)quinoline Date: Mar. 2, 2016.
Chemical Abstracts Service, CAS Registry No. 1880486-29-2. CA Index Name: 4-Chloro-2-methyl-3-(1-methylethyl)-8-(phenylmethoxy)quinoline- Date: Mar. 6, 2016.
Chemical Abstracts Service, CAS Registry No. 1893503-08-6. CA Index Name: 1,2-Dihydro-8-hydroxy-l-methyl-2-oxo-3-quinolineacetic acid.—Date: Apr. 20, 2016.

(56) References Cited

OTHER PUBLICATIONS

Chemical Abstracts Service, CAS Registry No. 1936181-19-9. CA Index Name: 8-Hydroxy-3-(hydroxymethyl)-1(2H)-isoquinolinone,—Date: Jun. 21, 2016.
Chemical Abstracts Service, CAS Registry No. RN 2106364-27-4. Index Name: Pyrrolo[2,3-f]benzimidazole-7-carboxylic acid, 3,5-dihydro-2,5,6-trimethyl-, ethyl ester Date: Aug. 1, 2017.
Chemical Abstracts Service, CAS Registry No. RN 2137577-83-2. Index Name: 7-Hydroxy-3-(methylamino)-1(2H)-isoquinolinone, Date: Nov. 1, 2017.
Chou, T.-C. (2010) "Drug Combination Studies and Their Synergy Quantification Using the Chou-Talalay Method", Cancer Res; 70(2):440-446.
Dafforn, T. R. et al. (1999) ""A kinetic mechanism for the polymerization of alpha1-antitrypsin"", The Journal of Biological Chemistry, 274 (4): 9548-9555.
Eggenschwiler, R. et al. (2013) "Sustained Knockdown of a Disease-Causing Gene in Patient-Specific Induced Pluripotent Stem Cells Using Lentiviral Vector-Based Gene Therapy", Stem Cells Translational Medicine, 2 (9): 641-654.
Ferrarotti, I. et al. (2020) "Quantification of circulating alpha-1-antitrypsin polymers in dried blood spots", Molecular Pathology and Funct. Genomics, 56, p. 326.
Fujisawa, T. (1959) "Studies on the Utilisation of Safrole as Medicinal Raw Materials XII. Synthesis of Indole Derivatives" Journal of the Pharmaceutical Society of Japan, 79(6): 778-783.
Harkevich, D.A. (2010) Pharmacology/Textbook, 10th edition, pp. 72-82.
International Search Report and Written Opinion from International Application No. PCT/US2021/043154, mailed Feb. 4, 2022 (21 pages).
International Search Report and Written Opinion from International Application No. PCT/US2021/072352, mailed Apr. 25, 2022 (25 pages).
International Search Report and Written Opinion from International Application No. PCT/US2021/072451, mailed May 24, 2022 (19 pages).
International Search Report and Written Opinion from International Application No. PCT/US2023/032282, mailed Dec. 7, 2023 (13 pages).
Jiang, B. et al. (2011) "A multi-component domino reaction for the direct access to polyfunctionalized indolesvia intermolecular allylic esterification and indolation," Chem. Commun., 2012,48,808-810.
Kapetanovic IM. (2008). Computer-aided drug discovery and development (CADDD): in silico-chemico-biological approach. Chem Biol Interact. 30;171(2):165-76.
Kathuria, A. et al. (2011). Substrate specificity of acetoxy derivatives of coumarins and quinolones towards Calreticulin mediated transacetylation: Investigations on antiplatelet function. Bioorganic & Medicinal Chemistry, vol. 20: 1624-1638.
Khusnutdinov, R. et al. (2015), "Quinoline Synthesis by the Reaction of Anilines with 1,2-diols Catalyzed by Iron Compounds," J. Heterocyclic Chem., vol. 53: 1022-1029.
Kummerer, K. (2010) "Pharmaceuticals in the environment", Annual Review of Environment and Resources, 35:57-75.
Kuznetsova, G.A. (2005) "Methodological instructions", Irkutsk State University, Department of General Physics, pp. 2-3.
Laffranchi, M. et al. (2018) "Heteropolymerization of [alpha]-1-antitrypsin mutants in cell models mimicking heterozygosity", Human Molecular Genetics, 27 (10): 1785-1793.
Liu, M. et al. (2016) "Synthesis and Antifungal Activities of Novel Strobilurin Derivatives Containing Quinolin-2(1H)-one Moiety," Chem. Res. Chin. Univ., 32(4): 600-606.
Lyubchanskaya, V. M. et al., Nenitzescu synthesis of derivatives of 5-hydroxybenzofuran and 5- and 6-hydroxyindoles, Khimiko-Farmatsevtichesik Zhurnal, 1992, 26(9-10), 108-112.
Mashkovsky (2001) M.D. Drugs, 14th edition, Moscow, 1:11.
Modi, A. R. et al., "Synthesis of 3-Methyl, 3-Formyl & Other 3-Substituted N-Arylisoquinolones", Indian Journal of Chemistry, 1979, vol. 18B, pp. 304-306.
Modi, A. R. et al., "Synthesis of 7-hydroxy-3-alkylisoquinolones and 7-hydroxy-3-alkylisocoumarins from 4-hydroxyhomophthalic acid", Indian Journal of Chemistry, 1979, vol. 17B, No. 4, pp. 360-363.
Priya, N. et al. (2010) "Characterization of 4-methyl-2-oxo-1,2-dihydroquinolin-6-yl acetate as an effective antiplatelet agent," Bioorganic & Medicinal Chemistry, vol. 18: 4085-4094.
Stoller, J.K. "Alpha-1 antitrypsin deficiency: An underrecognized, treatable cause of COPD." *Cleve Clin J Med* 83, No. 7 (2016): 507-14.
U.S. Appl. No. 18/630,559, filed Apr. 9, 2024, by Bozic et al.
Xu, M. et al, Facile Assembly of 11H-Indolo[3,2-c]quinoline by a Two-Step Protocol Involving a Regioselective 6-endo-Cyclization Promoted by the Hendrickson Reagent, Synthesis 2011, No. 4, pp. 0626-0634.
Zorgdrager, J. et al. (1989) "Synthesis of indoles using (N-arylaminomethyl)diphenylphosphine oxides," *Recueil des Travaux Chimiques des Pays-Bas*, 108 (12): 441-444.

* cited by examiner

PYRANO[4,3-B]INDOLE DERIVATIVES AS ALPHA-1-ANTITRYPSIN MODULATORS FOR TREATING ALPHA-1-ANTITRYPSIN DEFICIENCY (AATD)

This application claims the benefit of priority of U.S. Provisional Application No. 63/004,702, filed Apr. 3, 2020, the contents of which are incorporated by reference herein in their entirety.

The disclosure provides compounds that are capable of modulating alpha-1 antitrypsin (AAT) activity and methods of treating alpha-1 antitrypsin deficiency (AATD) by administering one or more such compounds.

AATD is a genetic disorder characterized by low circulating levels of AAT. While treatments for AATD exist, there is currently no cure. AAT is produced primarily in liver cells and secreted into the blood, but it is also made by other cell types including lung epithelial cells and certain white blood cells. AAT inhibits several serine proteases secreted by inflammatory cells (most notably neutrophil elastase [NE], proteinase 3, and cathepsin G) and thus protects organs such as the lung from protease-induced damage, especially during periods of inflammation.

The mutation most commonly associated with AATD involves a substitution of lysine for glutamic acid (E342K) in the SERPINA1 gene that encodes the AAT protein. This mutation, known as the Z mutation or the Z allele, leads to misfolding of the translated protein, which is therefore not secreted into the bloodstream and can polymerize within the producing cell. Consequently, circulating AAT levels in individuals homozygous for the Z allele (PiZZ) are markedly reduced; only approximately 15% of mutant Z-AAT protein folds correctly and is secreted by the cell. An additional consequence of the Z mutation is that the secreted Z-AAT has reduced activity compared to wild-type protein, with 40% to 80% of normal antiprotease activity (American thoracic society/European respiratory society, Am J Respir Crit Care Med. 2003; 168(7):818-900; and Ogushi et al. J Clin Invest. 1987; 80(5):1366-74).

The accumulation of polymerized Z-AAT protein within hepatocytes results in a gain-of-function cytotoxicity that can result in cirrhosis or liver cancer later in life and neonatal liver disease in 12% of patients. This accumulation may spontaneously remit but can be fatal in a small number of children. The deficiency of circulating AAT results in unregulated protease activity that degrades lung tissue over time, resulting in emphysema, a form of chronic obstructive pulmonary disease (COPD). This effect is severe in PiZZ individuals and typically manifests in middle age, resulting in a decline in quality of life and shortened lifespan (mean 68 years of age) (Tanash et al. Int J Chron Obstruct Pulm Dis. 2016; 11:1663-9). The effect is more pronounced in PiZZ individuals who smoke, resulting in an even further shortened lifespan (58 years). (Piitulainen and Tanash, COPD 2015; 12(1):36-41). PiZZ individuals account for the majority of those with clinically relevant AATD lung disease. Accordingly, there is a need for additional and effective treatments for AATD.

A milder form of AATD is associated with the SZ genotype in which the Z-allele is combined with an S-allele. The S allele is associated with somewhat reduced levels of circulating AAT but causes no cytotoxicity in liver cells. The result is clinically significant lung disease but not liver disease. (Fregonese and Stolk, Orphanet J Rare Dis. 2008; 33:16). As with the ZZ genotype, the deficiency of circulating AAT in subjects with the SZ genotype results in unregulated protease activity that degrades lung tissue over time and can result in emphysema, particularly in smokers.

The current standard of care for AAT deficient individuals who have or show signs of developing significant lung or liver disease is augmentation therapy or protein replacement therapy. Augmentation therapy involves administration of a human AAT protein concentrate purified from pooled donor plasma to augment the missing AAT. Although infusions of the plasma protein have been shown to improve survival or slow the rate of emphysema progression, augmentation therapy is often not sufficient under challenging conditions such as during an active lung infection. Similarly, although protein replacement therapy shows promise in delaying progression of disease, augmentation does not restore the normal physiological regulation of AAT in patients and efficacy has been difficult to demonstrate. In addition, augmentation therapy requires weekly visits for treatment and augmentation therapy cannot address liver disease, which is driven by the toxic gain-of-function of the Z allele. Thus, there is a continuing need for new and more effective treatments for AATD.

One aspect of the disclosure provides compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) as well as tautomers of those compounds, deuterated derivatives of those compounds and tautomers, and pharmaceutically acceptable salts of those compounds, tautomers, or deuterated derivatives that can be employed in the treatment of AATD. For example, compounds of Formula (Ia) or (Ib), tautomers of those compounds, deuterated derivatives of those compounds or tautomers, or pharmaceutically acceptable salts of any of the foregoing, can be depicted as:

(Ia)

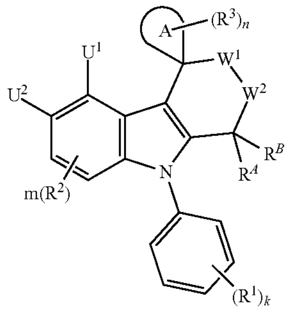

(Ib)

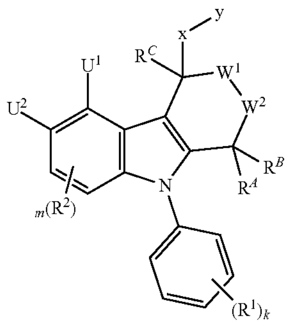

wherein:

$W^1$ is absent or a bond, —O—, or —$CR^DR^D$—;

$W^2$ is —O—, —$(CR^DR^D)_p$—, or —C═O;

provided that $W^1$ and $W^2$ are not both —O—;

$R^A$ and $R^B$ are each independently hydrogen, halogen, —OH, $C_1$-$C_3$ alkyl, $C_1$-$C_3$ haloalkyl, or $C_1$-$C_3$ alkoxy;

or alternatively $R^A$ and $R^B$ are each independently $C_1$-$C_3$ alkyl or $C_1$-$C_3$ alkoxy, and $R^A$ and $R^B$ together with their intervening C atom form a $C_3$-$C_6$ cycloalkyl or a 3 to 6-membered heterocyclyl containing at least one oxygen atom;

$R^C$ is independently hydrogen, —OH, $C_1$-$C_3$ alkyl, or $C_1$-$C_3$ haloalkyl $R^D$, for each occurrence, is independently hydrogen, halogen, —OH, $C_1$-$C_3$ alkyl, $C_1$-$C_3$ haloalkyl, or $C_1$-$C_3$ alkoxy;

or alternatively $R^D$, for each occurrence, is independently $C_1$-$C_3$ alkyl or $C_1$-$C_3$ alkoxy, and two $R^D$ groups together with their intervening C atom form a $C_3$-$C_6$ cycloalkyl or a 3 to 6-membered heterocyclyl containing at least one oxygen atom;

$U^1$ and $U^2$ are each independently hydrogen, halogen, —$NH_2$, —$CH_3$, or —OH;

provided that one of $U^1$ and $U^2$ is —OH or —$NH_2$ but $U^1$ and $U^2$ are not both —OH or —$NH_2$ and $U^1$ and $U^2$ are not both hydrogen;

Ring A is $C_3$-$C_{12}$ carbocyclyl or 3 to 12-membered heterocyclyl;

X is absent, —$(CR^ER^E)_q$—, or —$CH_2OCH_2$—; wherein:

$R^E$, for each occurrence, is independently hydrogen, halogen, —OH, $C_1$-$C_3$ alkyl, $C_1$-$C_3$ haloalkyl, or $C_1$-$C_3$ alkoxy;

Y is —COOH or

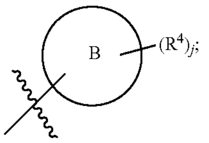

Ring B is $C_3$-$C_{12}$ cycloalkyl, a 3 to 12-membered heterocyclyl, a phenyl, or a 5 or 6-membered heteroaryl;

$R^1$ and $R^2$, for each occurrence, are each independently halogen, cyano, $C_1$-$C_3$ alkyl, $C_1$-$C_3$ haloalkyl, $C_1$-$C_3$ alkoxy, $C_1$-$C_3$ haloalkoxy, or O—($C_3$-$C_6$ cycloalkyl); and $R^3$, for each occurrence, is independently halogen, cyano, $C_1$-$C_3$ alkyl, $C_1$-$C_3$ haloalkyl, $C_1$-$C_3$ alkoxy, —OH, —$O(CR^fR^f)_r$COOH, =O, —COOH, —C(=O)$NR^fR^f$, —$(CR^fR^f)_r$COOH, phenyl, or 5 or 6-membered heteroaryl; wherein:

$R^f$, for each occurrence, is independently hydrogen, halogen, or —$CH_3$; and the phenyl, or the 5 or 6-membered heteroaryl of $R^3$ is optionally substituted with 1 to 3 groups selected from halogen, cyano, $C_1$-$C_2$ alkyl, $C_1$-$C_2$ haloalkyl, $C_1$-$C_2$ alkoxy, —OH, and —COOH;

$R^4$, for each occurrence, is independently halogen, cyano, $C_1$-$C_2$ alkyl, $C_1$-$C_2$ haloalkyl, $C_1$-$C_2$ alkoxy, —COOH, —$CH_2$COOH, or —$OCH_2$COOH;

k and n are each independently an integer selected from 0, 1, 2, and 3;

j and m are each independently an integer selected from 0, 1, and 2;

p and r are each independently an integer selected from 1 and 2; and q is an integer selected from 1, 2, and 3.

The compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) are modulators of AAT activity. In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay. In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay.

In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $IC_{50}$ of 5.0 μM or less when tested in a Z-AAT Elastase Activity Assay. In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $IC_{50}$ of less than 2.0 μM when tested in a Z-AAT Elastase Activity Assay.

In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay and have an $IC_{50}$ of 5.0 μM or less when tested in a Z-AAT Elastase Activity Assay. In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay and have an $IC_{50}$ of 5.0 μM or less when tested in a Z-AAT Elastase Activity Assay. In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay and have an $IC_{50}$ of less than 2.0 μM when tested in a Z-AAT Elastase Activity Assay. In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay and have an $IC_{50}$ of less than 2.0 μM when tested in a Z-AAT Elastase Activity Assay.

In some embodiments, the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), as well as tautomers of those compounds, deuterated derivatives of those tautomers and compounds, and pharmaceutically acceptable salts of those compounds, tautomers, or deuterated derivatives are provided for use in the treatment of AATD.

In one aspect of the disclosure, the compounds of Formula (Ia) or Formula (Ib) are selected from Compounds 1-189 and 192-210, tautomers of those compounds, deuterated derivatives of those compounds or tautomers, and pharmaceutically acceptable salts of any of the foregoing for use in the treatment of AATD. In some embodiments of the disclosure, the compounds are selected from Compounds 1-210, tautomers of Compounds 1-210, deuterated derivatives of those compounds or tautomers, and pharmaceutically acceptable salts of any of the foregoing for use in the treatment of AATD.

In some embodiments, the disclosure provides pharmaceutical compositions comprising at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing. In some embodiments, the pharmaceutical compositions may comprise a compound selected from Compounds 1-210, tautomers of those compounds, deuterated derivatives of those compounds and tautomers, and pharmaceutically acceptable salts of any of the foregoing. These compositions may further include at least one additional active pharmaceutical ingredient and/or at least one carrier.

Another aspect of the disclosure provides methods of treating AATD comprising administering to a subject in need thereof, at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing or a pharmaceutical composition comprising the at least one such compound, tautomer, deuterated derivative, or pharmaceutically acceptable salt. In some embodiments, the methods comprise administering a compound selected from Compounds 1-210, tautomers of those compounds, deuterated derivatives of those compounds and tautomers, and pharmaceutically acceptable salts of any of the foregoing.

In some embodiments, the methods of treatment include administration of at least one additional active agent to the subject in need thereof, either in the same pharmaceutical composition as the at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing, or as separate compositions. In some embodiments, the methods comprise administering a compound selected from Compounds 1-210, tautomers of those compounds, deuterated derivatives of those compounds and tautomers, and pharmaceutically acceptable salts of any of the foregoing with at least one additional active agent either in the same pharmaceutical composition or in a separate composition. In some embodiments, the subject in need of treatment carries the ZZ mutation. In some embodiments, the subject in need of treatment carries the SZ mutation.

In some embodiments, the methods of treatment include administration of at least one additional active agent to the subject in need thereof, either in the same pharmaceutical composition as the at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing, or as separate compositions, wherein the additional active agent is alpha-1 antitrypsin protein (AAT) from the blood plasma of healthy human donors. In some embodiments, the methods comprise administering a compound selected from Compounds 1-210, tautomers of those compounds, deuterated derivatives of those compounds and tautomers, and pharmaceutically acceptable salts of any of the foregoing with at least one additional active agent either in the same pharmaceutical composition or in a separate composition, wherein the additional active agent is alpha-1 antitrypsin protein (AAT) from the blood plasma of healthy human donors.

In some embodiments, the methods of treatment include administration of at least one additional active agent to the subject in need thereof, either in the same pharmaceutical composition as the at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing, or as separate compositions, wherein the additional active agent is recombinant AAT. In some embodiments, the methods comprise administering a compound selected from Compounds 1-210, tautomers of those compounds, deuterated derivatives of those compounds and tautomers, and pharmaceutically acceptable salts of any of the foregoing with at least one additional active agent either in the same pharmaceutical composition or in a separate composition, wherein the additional active agent is recombinant AAT.

Also provided are methods of modulating AAT, comprising administering to a subject in need thereof, at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), and tautomers of those compounds, deuterated derivatives of those compounds and tautomers, and pharmaceutically acceptable salts of any of the foregoing or a pharmaceutical composition comprising the at least one compound, tautomer, deuterated derivative, or pharmaceutically acceptable salt. In some embodiments, the methods of modulating AAT comprise administering at least one compound selected from Compounds 1-210, tautomers of those compounds, deuterated derivatives of those compounds and tautomers, and pharmaceutically acceptable salts of any of the foregoing or a pharmaceutical composition comprising the at least one such compound, tautomer, deuterated derivative or pharmaceutically acceptable salt.

Also provided is a compound of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), and tautomers of those compounds, deuterated derivatives of those compounds and tautomers, and pharmaceutically acceptable salts of any of the foregoing, for use in therapy. In some embodiments, there is provided a compound selected from Compounds 1-210 (e.g., Compounds 1-189 and 192-210), tautomers of those compounds, deuterated derivatives of those compounds and tautomers, and pharmaceutically acceptable salts of any of the foregoing, for use in therapy.

Also provided is a pharmaceutical composition comprising a compound of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), and tautomers of those compounds, deuterated derivatives of those compounds and tautomers, and pharmaceutically acceptable salts of any of the foregoing, for use in therapy. In some embodiments, there is provided a pharmaceutical composition comprising a compound selected from Compounds 1-210 (e.g., Compounds 1-189 and 192-210), tautomers of those compounds, deuterated derivatives of those compounds and tautomers, and pharmaceutically acceptable salts of any of the foregoing, for use in therapy.

I. Definitions

The term "AAT" as used herein means alpha-1 antitrypsin or a mutation thereof, including, but not limited to, the AAT gene mutations such as Z mutations. As used herein, "Z-AAT" means AAT mutants which have the Z mutation.

As used herein, "mutations" can refer to mutations in the SERPINA1 gene (the gene encoding AAT) or the effect of alterations in the gene sequence on the AAT protein. A "SERPINA1 gene mutation" refers to a mutation in the SERPINA1 gene, and an "AAT protein mutation" refers to a mutation that results in an alteration in the amino acid sequence of the AAT protein. A genetic defect or mutation, or a change in the nucleotides in a gene in general, results in a mutation in the AAT protein translated from that gene.

As used herein, a patient who is "homozygous" for a particular gene mutation has the same mutation on each allele.

As used herein, a patient who has the PiZZ genotype is a patient who is homozygous for the Z mutation in the AAT protein.

The term "AATD" as used herein means alpha-1 antitrypsin deficiency, which is a genetic disorder characterized by low circulating levels of AAT.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

Compounds of the disclosure may optionally be substituted with one or more substituents. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of a compound that exist together in equilibrium, and are readily interchanged by migration of an atom or group within the molecule.

"Stereoisomer" refers to both enantiomers and diastereomers.

As used herein, "deuterated derivative" refers to a compound having the same chemical structure as a reference compound, but with one or more hydrogen atoms replaced by a deuterium atom ("D"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at lease 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl" as used herein, means a straight-chain (i.e., linear or unbranched) or branched, substituted or unsubstituted hydrocarbon chain that is completely saturated or may contain one or more units of saturation, without being fully aromatic. Unless otherwise specified, alkyl groups contain 1-12 alkyl carbon atoms. In some embodiments, alkyl groups contain 1-10 aliphatic carbon atoms. In other embodiments, alkyl groups contain 1-8 aliphatic carbon atoms. In still other embodiments, alkyl groups contain 1-6 alkyl carbon atoms, in other embodiments alkyl groups contain 1-4 alkyl carbon atoms, and in yet other embodiments alkyl groups contain 1-3 alkyl carbon atoms and 1-2 alkyl carbon atoms.

The term "heteroalkyl" as used herein, refers to aliphatic groups wherein one or two carbon atoms are independently replaced by one or more of oxygen, sulfur, nitrogen, phosphorus, or silicon. Heteroalkyl groups may be substituted or unsubstituted, branched or unbranched.

The term "alkenyl" as used herein, means a straight-chain (i.e., linear or unbranched), branched, substituted or unsubstituted hydrocarbon chain that contains one or more carbon-to-carbon double bonds.

The terms "cycloalkyl," "cyclic alkyl," "carbocyclyl," and "carbocycle" refer to a fused, spirocyclic, or bridged monocyclic $C_{3-9}$ hydrocarbon or a fused, spirocyclic, or bridged bicyclic or tricyclic, $C_{8-14}$ hydrocarbon that is completely saturated or that contains one or more units of unsaturation, but which is not fully aromatic, wherein any individual ring in said bicyclic ring system has 3-9 members. Typically, a cycloalkyl is completely saturated, while a carbocyclyl may contain one or more units of unsaturation but is not aromatic. In some embodiments, the cycloalkyl or carbocycle group contains 3 to 12 carbon atoms. In some embodiments, the cycloalkyl or carbocycle group contains 3 to 8 carbon atoms. In some embodiments, the cycloalkyl or carbocycle group contains 3 to 6 carbon atoms.

The term "heterocycle," "heterocyclyl," or "heterocyclic" as used herein refers to fused, spirocyclic, or bridged non-aromatic, monocyclic, bicyclic, or tricyclic ring systems in which one or more ring members is a heteroatom. In some embodiments, "heterocycle," "heterocyclyl," or "heterocyclic" group has 3 to 14 ring members in which one or more ring members is a heteroatom independently selected from oxygen, sulfur, nitrogen, phosphorus, and silicon and each ring in the system contains 3 to 9 ring members. In some embodiments, the heterocyclyl contains 3 to 12 ring member atoms. In some embodiments, the heterocyclyl contains 3 to 8 ring member atoms. In some embodiments, the heterocyclyl contains 3 to 6 ring member atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "alkoxy" as used herein, refers to an alkyl group, as previously defined, wherein one carbon of the alkyl group is replaced by an oxygen ("alkoxy") atom, respectively, provided that the oxygen atom is linked between two carbon atoms. A "cyclic alkoxy" refers to a monocyclic, fused, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl.

The terms "haloalkyl" and "haloalkoxy" means an alkyl or alkoxy, as the case may be, which is substituted with one or more halogen atoms. The term "halogen" or means F, Cl, Br, or I. In some embodiments, the halogen is selected from F, Cl, and Br. Examples of haloalkyls include —$CHF_2$, —$CH_2F$, —$CF_3$, —$CF_2$—, or perhaloalkyl, such as, —$CF_2CF_3$.

As used herein, "=O" refers to an oxo group.

As used herein, a "cyano" or "nitrile" groups refers to —C≡N.

As used herein, a "hydroxy" group refers to —OH.

As used herein, "aromatic groups" or "aromatic rings" refer to chemical groups that contain conjugated, planar ring systems with delocalized pi electron orbitals comprised of [4n+2]p orbital electrons, wherein n is an integer ranging from 0 to 6. Nonlimiting examples of aromatic groups include aryl and heteroaryl groups.

The term "aryl" refers to monocyclic, bicyclic, and tricyclic ring systems having a total of 5 to 14 ring members, wherein at least one ring in the system is aromatic and wherein each ring in the system contains 3 to 7 ring members. In some embodiments, an aryl contains 6 or 10 carbon atoms. A nonlimiting example of an aryl group is a phenyl ring.

The term "heteroaryl" refers to monocyclic, bicyclic, and tricyclic ring systems having a total of 5 to 10 ring members, wherein at least one ring in the system is aromatic, at least one ring in the system contains one or more heteroatoms, and wherein each ring in the system contains 3 to 7 ring members. In some embodiments, a heteroaryl contains 6 or 10 ring atoms.

Examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999).

Examples of suitable solvents that may be used in this disclosure include, but not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Examples of suitable bases that may be used in this disclosure include, but not limited to, 1,8-diazabicyclo [5.4.0]undec-7-ene (DBU), potassium tert-butoxide (KOtBu), potassium carbonate ($K_2CO_3$), N-methylmorpholine (NN), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the disclosed compounds. A salt of a compound of is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66, 1-19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The terms "patient" and "subject" are used interchangeably and refer to an animal including a human.

The terms "effective dose," "effective amount," "therapeutically effective dose," and "therapeutically effective amount" are used interchangeably herein and refer to that amount of a compound that produces the desired effect for which it is administered (e.g., improvement in AATD or a symptom of AATD, lessening the severity of AATD or a symptom of AATD, and/or reducing the rate of onset or incidence of AATD or a symptom of AATD). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the term "treatment and its cognates (e.g., "treat," "treating") refer to improving AATD or its symptoms in a subject, delaying the onset of AATD or its symptoms in a subject, or lessening the severity of AATD or its symptoms in a subject. "Treatment" and its cognates as used herein, include, but are not limited to the following: improved liver and/or spleen function, lessened jaundice, improved lung function, lessened lung diseases and/or pulmonary exacerbations (e.g., emphysema), lessened skin disease (e.g., necrotizing panniculitis), increased growth in children, improved appetite, and reduced fatigue. Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. Typically, the term "about" refers to a variation of up to 10%, up to 5%, or up to 2% of a stated value.

Any one or more of the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds or tautomers, and pharmaceutically acceptable salts of any of the foregoing may be administered once daily, twice daily, or three times daily for the treatment of AATD. In some embodiments, the any one or more compounds are selected from Compounds 1-210, tautomers of those compounds, deuterated derivatives of those compounds or tautomers, and pharmaceutically acceptable salts of any of the foregoing. In some embodiments, at least one compound chosen from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds or tautomers, and pharmaceutically acceptable salts of any of the foregoing is administered once daily. In some embodiments, a compound selected from Compounds 1-210, tautomers of those compounds, deuterated derivatives of those compounds or tautomers, and pharmaceutically acceptable salts of any of the foregoing is administered once daily. In some embodiments, at least one compound selected from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds or tautomers, and pharmaceutically acceptable salts of any of the foregoing are administered twice daily. In some embodiments, a compound selected from Compounds 1-210, tautomers of those compounds, deuterated derivatives of those compounds or tautomers, and pharmaceutically acceptable salts of any of the foregoing is administered twice daily. In some embodiments, at least one compound chosen from compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds or tautomers, and pharmaceutically acceptable salts of any of the foregoing are administered three times daily. In some embodiments, a compound selected from Compounds 1-210, tautomers of those compounds, deuterated derivatives of those compounds or tautomers, and pharmaceutically acceptable salts of any of the foregoing is administered three times daily.

Any one or more of the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2), tautomers of those compounds, deuterated derivatives of those compounds or tautomers, and pharmaceutically acceptable salts of any of the foregoing may be administered in combination with AAT augmentation therapy or AAT replacement therapy for the treatment of AATD. In some embodiments, the any one or more compounds are selected from Compounds 1-210, tautomers of those compounds, deuterated derivatives of those compounds or tautomers, and pharmaceutically acceptable salts of any of the foregoing.

As used herein, "AAT augmentation therapy" refers to the use of alpha-1 antitrypsin protein (AAT) from the blood plasma of healthy human donors to augment (increase) the alpha-1 antitrypsin levels circulating in the blood. "AAT replacement therapy" refers to administration of recombinant AAT.

In some embodiments, 10 mg to 1,500 mg, 100 mg to 1,800 mg, 100 mg to 500 mg, 200 mg to 600 mg, 200 mg to 800 mg, 400 mg to 2,000 mg, 400 mg to 2,500 mg or 400 mg to 600 mg of a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds or tautomers, and pharmaceutically acceptable salts of any of the foregoing is administered once daily, twice daily, or three times daily. In some embodiments, 10 mg to 1,500 mg, 100 mg to 1,800 mg, 100 mg to 500 mg, 200 mg to 600 mg, 200 mg to 800 mg, 400 mg to 2000 mg, or 400 mg to 600 mg of a compound selected from Compounds 1-210 is administered once daily, twice daily, or three times daily.

One of ordinary skill in the art would recognize that, when an amount of a compound is disclosed, the relevant amount of a pharmaceutically acceptable salt form of the compound is an amount equivalent to the concentration of the free base of the compound. It is noted that the disclosed amounts of the compounds, tautomers, deuterated derivatives, and pharmaceutically acceptable salts are based upon the free base form of the reference compound. For example, "10 mg of at least one compound chosen from compounds of Formula (Ia) or Formula (Ib) and pharmaceutically acceptable salts thereof" includes 10 mg of a compound of Formula (Ia) or Formula (Ib) and a concentration of a pharmaceutically acceptable salt of compounds of Formula (Ia) or Formula (Ib) equivalent to 10 mg of compounds of Formula (Ia) or Formula (Ib).

As used herein, the term "ambient conditions" means room temperature, open air condition and uncontrolled humidity condition.

It should be understood that references herein to methods of treatment (e.g., methods of treating AATD) using one or more compounds (e.g., compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2))), as well as tautomers of those compounds, deuterated derivatives of those compounds and tautomers, and pharmaceutically acceptable salts of those compounds) should also be interpreted as references to:

- one or more compounds (e.g., compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2))), as well as tautomers of those compounds, deuterated derivatives of those compounds and tautomers, and pharmaceutically acceptable salts of those compounds) for use in methods of treating, e.g., AATD; and/or
- the use of one or more compounds (e.g., compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2))), as well as tautomers of those compounds, deuterated derivatives of those compounds and tautomers, and pharmaceutically acceptable salts of those compounds) in the manufacture of a medicament for treating, e.g., AATD.

EXAMPLE EMBODIMENTS

Without limitation, some embodiments of the disclosure include:

1. A compound represented by one of the following structural formulae:

(Ia)

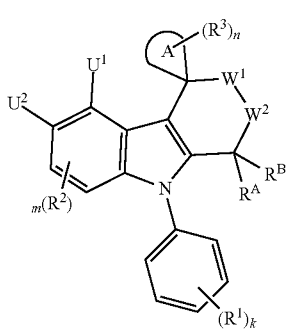

-continued (Ib)

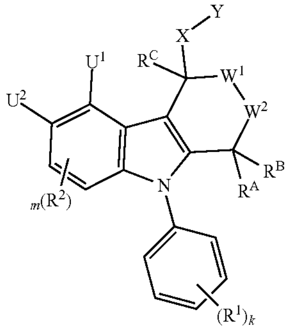

a tautomer thereof, a deuterated derivative of the compound or tautomer, or a pharmaceutically acceptable salt of any of the foregoing, wherein:

$W^1$ is absent or a bond, —O—, or —$CR^DR^D$—;

$W^2$ is —O—, —$(CR^DR^D)_p$—, or —C═O;

provided that $W^1$ and $W^2$ are not both —O—;

$R^A$ and $R^B$ are each independently hydrogen, halogen, —OH, $C_1$-$C_3$ alkyl, $C_1$-$C_3$ haloalkyl, or $C_1$-$C_3$ alkoxy;

or alternatively $R^A$ and $R^B$ are each independently $C_1$-$C_3$ alkyl or $C_1$-$C_3$ alkoxy, and $R^A$ and $R^B$ together with their intervening C atom form a $C_3$-$C_6$ cycloalkyl or a 3 to 6-membered heterocyclyl containing at least one oxygen atom;

$R^C$ is independently hydrogen, —OH, $C_1$-$C_3$ alkyl, or $C_1$-$C_3$ haloalkyl;

$R^D$, for each occurrence, is independently hydrogen, halogen, —OH, $C_1$-$C_3$ alkyl, $C_1$-$C_3$ haloalkyl, or $C_1$-$C_3$ alkoxy;

or alternatively $R^D$, for each occurrence, is independently $C_1$-$C_3$ alkyl or $C_1$-$C_3$ alkoxy, and two $R^D$ groups together with their intervening C atom form a $C_3$-$C_6$ cycloalkyl or a 3 to 6-membered heterocyclyl containing at least one oxygen atom;

$U^1$ and $U^2$ are each independently hydrogen, halogen, —$NH_2$, —$CH_3$, or —OH;

provided that one of $U^1$ and $U^2$ is —OH or —$NH_2$ but $U^1$ and $U^2$ are not both —OH or —$NH_2$ and $U^1$ and $U^2$ are not both hydrogen;

Ring A is $C_3$-$C_{12}$ carbocyclyl or 3 to 12-membered heterocyclyl;

X is absent, —$(CR^ER^E)_q$—, or —$CH_2OCH_2$—; wherein:

$R^E$, for each occurrence, is independently hydrogen, halogen, —OH, $C_1$-$C_3$ alkyl, $C_1$-$C_3$ haloalkyl, or $C_1$-$C_3$ alkoxy;

Y is —COOH or

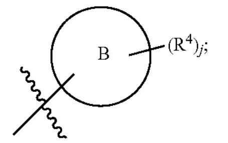

Ring B is $C_3$-$C_{12}$ cycloalkyl, a 3 to 12-membered heterocyclyl, a phenyl, or a 5 or 6-membered heteroaryl;

$R^1$ and $R^2$, for each occurrence, are each independently halogen, cyano, $C_1$-$C_3$ alkyl, $C_1$-$C_3$ haloalkyl, $C_1$-$C_3$ alkoxy, $C_1$-$C_3$ haloalkoxy, or O—($C_3$-$C_6$ cycloalkyl); and $R^3$, for each occurrence, is independently halogen, cyano, $C_1$-$C_3$ alkyl, $C_1$-$C_3$ haloalkyl, $C_1$-$C_3$ alkoxy, —OH, —$O(CR^fR^f)_r$COOH, ═O, —COOH, —C(═O)$NR^fR^f$, —$(CR^fR^f)_r$COOH, phenyl, or 5 or 6-membered heteroaryl; wherein:

$R^f$, for each occurrence, is independently hydrogen, halogen, or —$CH_3$; and the phenyl, or the 5 or 6-membered heteroaryl of $R^3$ is optionally substituted with 1 to 3 groups selected from halogen, cyano, $C_1$-$C_2$ alkyl, $C_1$-$C_2$ haloalkyl, $C_1$-$C_2$ alkoxy, —OH, and —COOH;

$R^4$, for each occurrence, is independently halogen, cyano, $C_1$-$C_2$ alkyl, $C_1$-$C_2$ haloalkyl, $C_1$-$C_2$ alkoxy, —COOH, —$CH_2$COOH, or —$OCH_2$COOH;

k and n are each independently an integer selected from 0, 1, 2, and 3;

j and m are each independently an integer selected from 0, 1, and 2;

p and r are each independently an integer selected from 1 and 2; and q is an integer selected from 1, 2, and 3.

2. The compound, tautomer, deuterated derivative, or pharmaceutically acceptable salt according to Embodiment 1, wherein:

$R^A$ and $R^B$ are each independently hydrogen, halogen, —OH, $C_1$-$C_2$ alkyl, $C_1$-$C_2$ haloalkyl, or $C_1$-$C_2$ alkoxy;

or alternatively $R^A$ and $R^B$ are each independently $C_1$-$C_3$ alkyl, and $R^A$ and $R^B$ together with their intervening C atom form a cyclopropyl or a cyclobutyl;

$R^D$, for each occurrence, is independently hydrogen, halogen, —OH, $C_1$-$C_2$ alkyl, $C_1$-$C_2$ haloalkyl, or $C_1$-$C_2$ alkoxy;

or alternatively $R^D$, for each occurrence, is independently $C_1$-$C_3$ alkyl, and two $R^D$ groups together with their intervening C atom form a cyclopropyl or a cyclobutyl; and wherein all other variables not specifically defined herein are as defined in the preceding Embodiment.

3. The compound, tautomer, deuterated derivative, or pharmaceutically acceptable salt according to Embodiment 1 or Embodiment 2, represented by one of the following structural formulae:

(IIa-1)

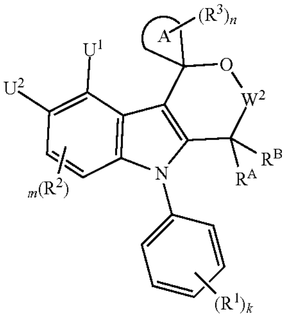

-continued (IIa-2)

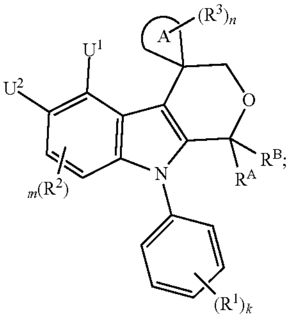

wherein $R^A$ and $R^B$ are each independently hydrogen or $C_1$-$C_2$ alkyl; and wherein all other variables not specifically defined herein are as defined in any one of the preceding Embodiments.

4. The compound, tautomer, deuterated derivative, or pharmaceutically acceptable salt according to any one of Embodiments 1 to 3, wherein:

$U^1$ is —$NH_2$ or —OH;

$U^2$ is hydrogen, halogen, or —$CH_3$;

and wherein all other variables not specifically defined herein are as defined in any one of the preceding Embodiments.

5. The compound, tautomer, deuterated derivative, or pharmaceutically acceptable salt according to any one of Embodiments 1 to 4, wherein the compound is represented by the following structural formula:

(IIIa)

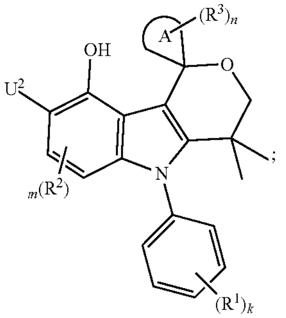

wherein $U^2$ is hydrogen, F, or Cl; and wherein all other variables not specifically defined herein are as defined in any one of the preceding Embodiments.

6. The compound, tautomer, deuterated derivative, or pharmaceutically acceptable salt according to any one of Embodiments 1 to 5, wherein Ring A is optionally substituted with $R^3$ and Ring A is 4 to 9-membered carbocyclyl or 5 or 6-membered heterocyclyl; and wherein all other variables not specifically defined herein are as defined in any one of the preceding Embodiments.

7. The compound, tautomer, deuterated derivative, or pharmaceutically acceptable salt according to any one of Embodiments 1 to 6, wherein Ring A is optionally substituted with $R^3$ and Ring A is cyclobutyl; cyclopentyl; cyclohexyl; spiro[3.3]heptanyl; tetrahydro-2H-pyranyl; piperidinyl; spiro[2.3]hexanyl; 1-iminohexahydro-1$\lambda^6$-thiopyranyl 1-oxide; tetrahydro-2H-thiopyranyl 1,1-dioxide; or 2,3-dihydro-1H-indenyl and wherein all other variables not specifically defined herein are as defined in any one of the preceding Embodiments.

8. The compound, tautomer, deuterated derivative, or pharmaceutically acceptable salt according to any one of Embodiments 1 to 7, wherein Ring A is optionally substituted with $R^3$ and Ring A is

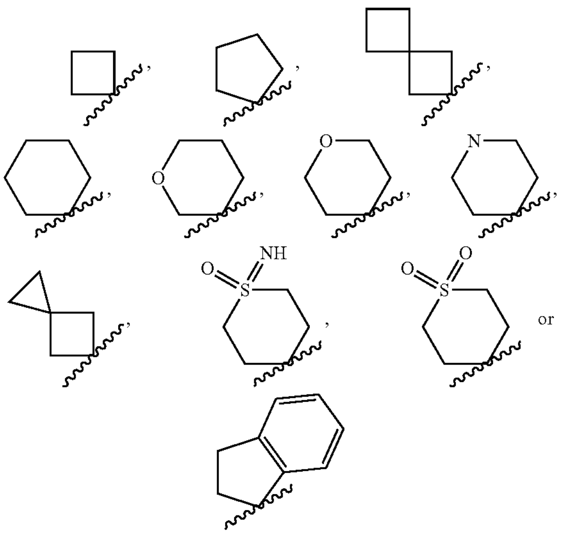

and wherein all other variables not specifically defined herein are as defined in any one of the preceding Embodiments.

9. The compound, tautomer, deuterated derivative, or pharmaceutically acceptable salt according to any one of Embodiments 1 to 7, wherein $R^3$, for each occurrence, is independently halogen, $C_1$-$C_2$ alkyl, $C_1$-$C_2$ haloalkyl, $C_1$-$C_2$ alkoxy, —OH, —O($CR^fR^f$)$_r$COOH, =O, —COOH, —C(=O)$NR^fR^f$, —($CR^fR^f$)$_r$COOH, phenyl, or a 5-membered heteroaryl; wherein:
   $R^f$, for each occurrence, is independently hydrogen or —$CH_3$; and
   the phenyl or the 5-membered heteroaryl of $R^3$ is optionally substituted with 1 to 3 groups selected from halogen, $C_1$-$C_2$ alkyl, $C_1$-$C_2$ alkoxy, —OH, and —COOH;

and wherein all other variables not specifically defined herein are as defined in any one of the preceding Embodiments.

10. The compound, tautomer, deuterated derivative, or pharmaceutically acceptable salt according to any one of Embodiments 1 to 9, wherein:
   $R^3$, for each occurrence, is independently F, —$CH_3$, —$CF_3$, —$CHF_2$, —$CH_2F$, —OH, —$OCH_3$, —COOH, —$CH_2COOH$, —$CF_2COOH$, —C(=O)$NH_2$, —C(=O)$NHCH_3$, —C(=O)$N(CH_3)_2$, =O, —$OCH_2COOH$, —$OCHCH_3COOH$, phenyl, pyrazolyl, or oxazolyl; wherein:
   the phenyl of $R^3$ is substituted with —COOH;
   the pyrazolyl of $R^3$ is substituted with —COOH and —$CH_3$; and
   the oxazolyl of $R^3$ is substituted with —COOH;

and wherein all other variables not specifically defined herein are as defined in any one of the preceding Embodiments.

11. The compound, tautomer, deuterated derivative, or pharmaceutically acceptable salt according to any one of Embodiments 1 to 10, represented by one of the following structural formulae:

(IVa-1)

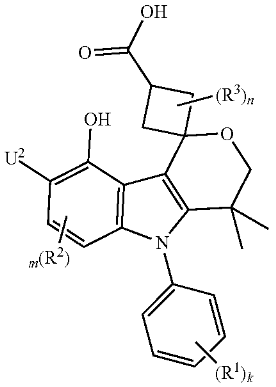

(IVa-2)

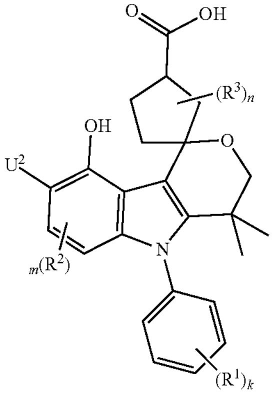

(IVa-3)

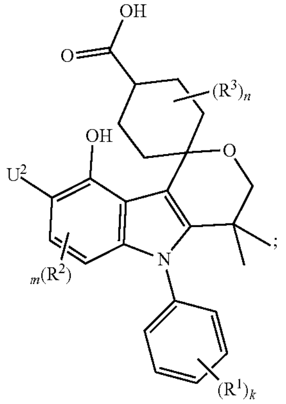

wherein n is an integer selected from 0, 1, and 2 and wherein all other variables not specifically defined herein are as defined in any one of the preceding Embodiments.

12. The compound, tautomer, deuterated derivative, or pharmaceutically acceptable salt according to any one of Embodiments 1 to 11, represented by one of the following structural formulae:

(Va-1)

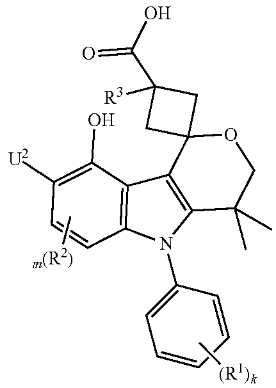

(Va-2)

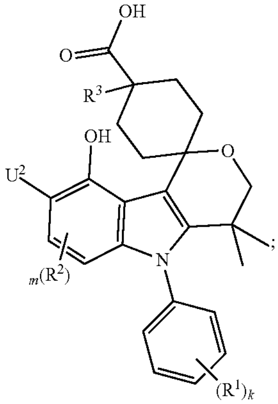

wherein $R^3$ is F, $—CH_3$, $—CF_3$, $—CHF_2$, $—CH_2F$, —OH, or $—OCH_3$; and wherein all other variables not specifically defined herein are as defined in any one of the preceding Embodiments.

13. The compound, tautomer, deuterated derivative, or pharmaceutically acceptable salt according to Embodiment 1, represented by one of the following structural formulae:

(IIb-1)

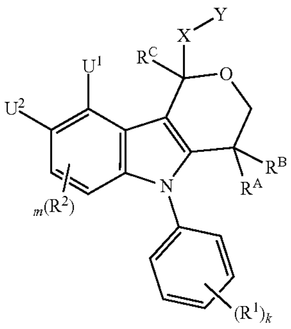

-continued (IIb-2)

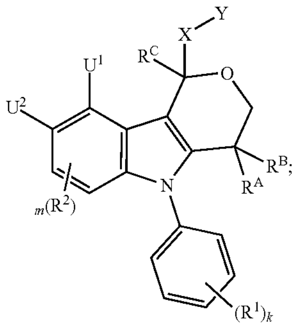

wherein:

$R^A$ and $R^B$ are each independently hydrogen, halogen, —OH, $C_1$-$C_2$ alkyl, $C_1$-$C_2$ haloalkyl, or $C_1$-$C_2$ alkoxy;

$R^C$ is independently hydrogen, $C_1$-$C_2$ alkyl, or $C_1$-$C_2$ haloalkyl;

X is absent, $—(CR^ER^E)_q—$, or $—CH_2OCH_2—$; wherein:

$R^E$, for each occurrence, is independently hydrogen, $C_1$-$C_2$ alkyl, or $C_1$-$C_2$ alkoxy; and wherein all other variables not specifically defined herein are as defined in Embodiment 1.

14. The compound, tautomer, deuterated derivative, or pharmaceutically acceptable salt according to any one of Embodiment 1 or Embodiment 13, wherein:

$R^A$ and $R^B$ are each independently hydrogen or $C_1$-$C_2$ alkyl;

$U^1$ is $—NH_2$ or —OH;

$U^2$ is hydrogen, halogen, or $—CH_3$;

X is absent, $—CH_2—$, $—(CH_2)_2—$, $—(CH_2)_3—$, or $—CH_2OCH_2—$;

and wherein all other variables not specifically defined herein are as defined in Embodiment 1 or Embodiment 13.

15. The compound, tautomer, deuterated derivative, or pharmaceutically acceptable salt according to any one of Embodiments 1, 13, and 14, represented by one of the following structural formulae:

(IIIb-1)

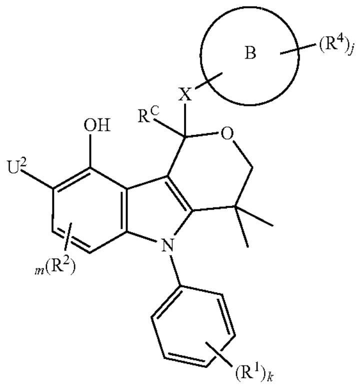

-continued (IIIb-2)

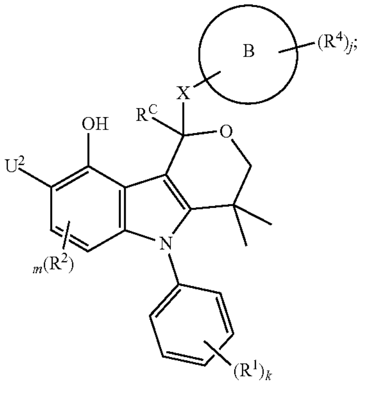

wherein:

$U^2$ is hydrogen, F, or Cl;

$R^C$ is hydrogen, —$CH_3$, or —$CF_3$; and

X is absent or —$CH_2$—;

and wherein all other variables not specifically defined herein are as defined in any one of Embodiments 1, 13, and 14.

16. The compound, tautomer, deuterated derivative, or pharmaceutically acceptable salt according to any one of Embodiments 1 and 13 to 15, represented by one of the following structural formulae:

(IVb-1)

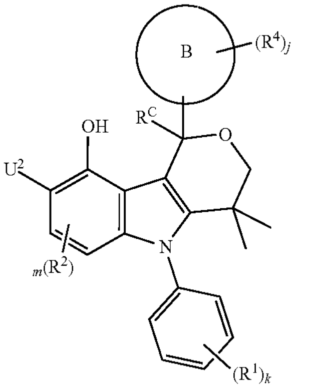

(IVb-2)

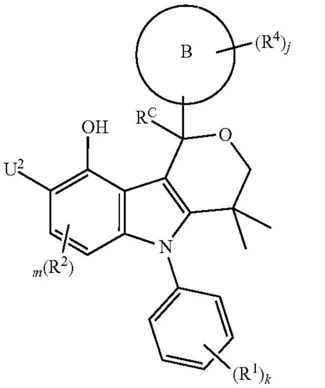

wherein all other variables not specifically defined herein are as defined in any one of Embodiments 1 and 13 to 15.

17. The compound, tautomer, deuterated derivative, or pharmaceutically acceptable salt according to any one of Embodiments 1 and 13 to 16, wherein Ring B is optionally substituted with $R^4$ and Ring B is $C_3$-$C_6$ cycloalkyl, phenyl, or 5-membered heteroaryl; and wherein all other variables not specifically defined herein are as defined in any one of Embodiments 1 and 13 to 16.

18. The compound, tautomer, deuterated derivative, or pharmaceutically acceptable salt according to any one of Embodiments 1 and 13 to 17, wherein Ring B is optionally substituted with $R^4$ and Ring B is

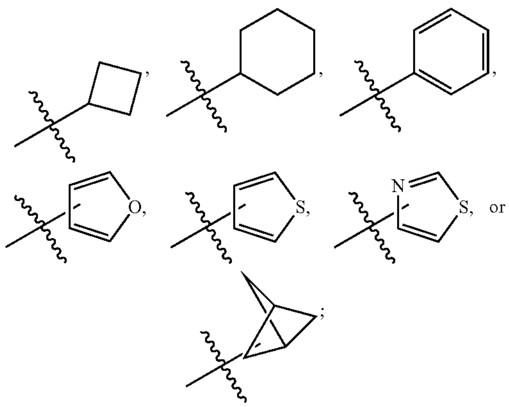

or and wherein all other variables not specifically defined herein are as defined in any one of Embodiments 1 and 14 to 17.

19. The compound, tautomer, deuterated derivative, or pharmaceutically acceptable salt according to any one of Embodiments 1 and 13 to 18, wherein Ring B is optionally substituted with $R^4$ and Ring B is

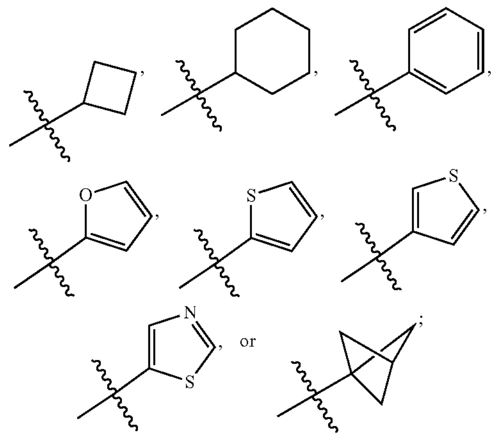

or and wherein all other variables not specifically defined herein are as defined in any one of Embodiments 1 and 14 to 18.

20. The compound, tautomer, deuterated derivative, or pharmaceutically acceptable salt according to any one of Embodiments 1 and 13 to 19, wherein $R^4$, for each occurrence, is independently F, Cl, —$CH_3$, —$OCH_3$, —COOH, or —$OCH_2COOH$; and wherein all other variables not specifically defined herein are as defined in any one of Embodiments 1 and 14 to 19.

21. The compound, tautomer, deuterated derivative, or pharmaceutically acceptable salt according to any one of Embodiments 1 and 13 to 20 represented by one of the following structural formulae:

(Vb-1)

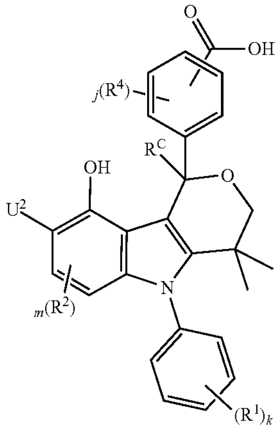

(Vb-2)

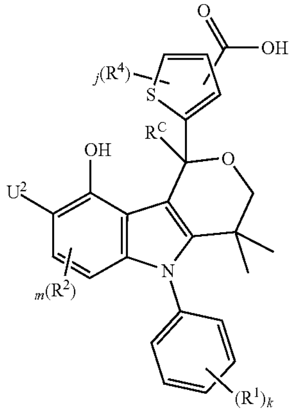

(Vb-3)

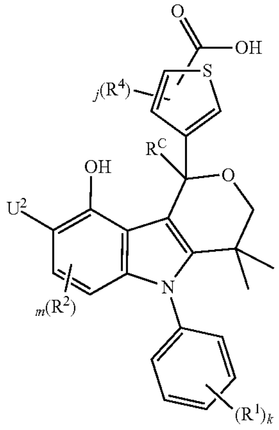

-continued (Vb-4)

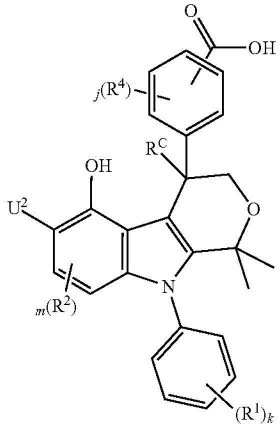

(Vb-5)

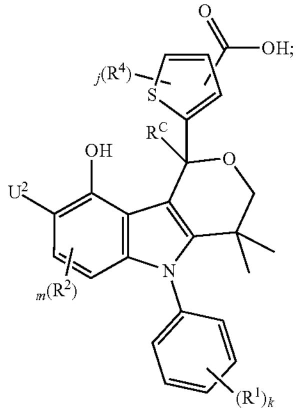

wherein j is an integer selected from 0, 1, and 2; and wherein all other variables not specifically defined herein are as defined in any one of Embodiments 1 and 13 to 20.

22. The compound, tautomer, deuterated derivative, or pharmaceutically acceptable salt according to any one of Embodiments 1 and 13 to 21, represented by one of the following structural formulae:

(VIb-1)

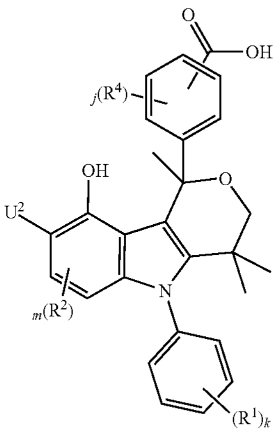

-continued (VIb-2)

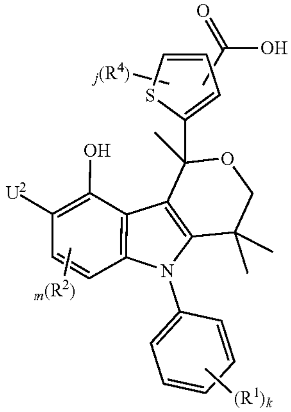

(VIb-3)

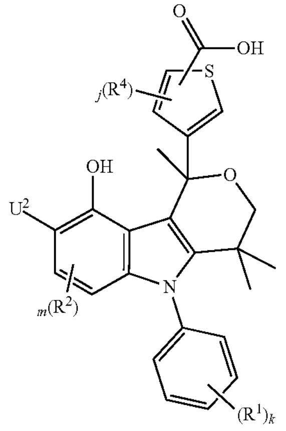

(VIb-4)

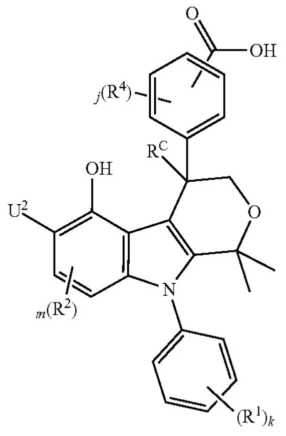

-continued (VIb-5)

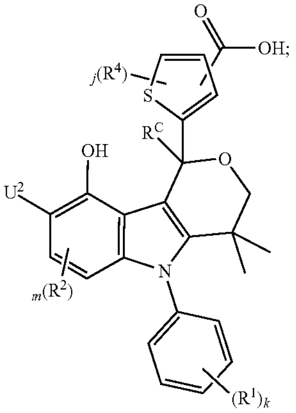

wherein j is an integer selected from 0, 1, and 2; and wherein all other variables not specifically defined herein are as defined in any one of Embodiments 1 and 13 to 21.

23. The compound, tautomer, deuterated derivative, or pharmaceutically acceptable salt according to any one of Embodiments 1, 13, and 14, wherein:

X is $-(CH_2)_2-$, $-(CH_2)_3-$, or $-CH_2OCH_2-$;

Y is $-COOH$;

and wherein all other variables not specifically defined herein are as defined in Embodiment 1, 13, or 14.

24. The compound, tautomer, deuterated derivative, or pharmaceutically acceptable salt according to any one of Embodiments 1 to 23, wherein $R^1$ and $R^2$, for each occurrence, are each independently halogen, $C_1$-$C_2$ alkyl, or $C_1$-$C_2$ alkoxy; and wherein all other variables not specifically defined herein are as defined in any one of the preceding Embodiments.

25. The compound, tautomer, deuterated derivative, or pharmaceutically acceptable salt according to any one of Embodiments 1 to 24, wherein $R^1$, for each occurrence, is independently F, Cl, $-CH_3$, or $-OCH_3$; and wherein all other variables not specifically defined herein are as defined in any one of the preceding Embodiments.

26. The compound, tautomer, deuterated derivative, or pharmaceutically acceptable salt according to any one of Embodiments 1 to 25, wherein $R^2$, for each occurrence, is F; and wherein m is an integer selected from 0 and 1; and wherein all other variables not specifically defined herein are as defined in any one of the preceding Embodiments.

27. The compound, tautomer, deuterated derivative, or pharmaceutically acceptable salt according to any one of Embodiments 1 to 26, wherein k is an integer selected from 1 and 2; and wherein all other variables not specifically defined herein are as defined in any one of the preceding Embodiments.

28. The compound, tautomer, deuterated derivative, or pharmaceutically acceptable salt according to any one of Embodiments 1 to 27, wherein m is 0; and wherein all other variables not specifically defined herein are as defined in any one of the preceding Embodiments.

29. A compound selected from Compound 1-210, a tautomer thereof, a deuterated derivative of the compound or tautomer, or a pharmaceutically acceptable salt of any of the foregoing.

30. A pharmaceutical composition comprising at least one compound according to any one of Embodiments 1 to 29, a tautomer thereof, a deuterated derivative of that compound or tautomer, or a pharmaceutically acceptable salt of any of the foregoing.

31. A method of treating alpha-1 antitrypsin (AAT) deficiency comprising administering to a patient in need thereof a therapeutically effective amount of at least one compound, tautomer, deuterated derivative, or pharmaceutically acceptable salt according to any one of Embodiments 1 to 29, or a therapeutically effective amount of a pharmaceutical composition according to Embodiment 30.

32. A method of modulating alpha-1 antitrypsin (AAT) activity comprising the step of contacting said AAT with a therapeutically effective amount of at least one compound, tautomer, deuterated derivative, or pharmaceutically acceptable salt according to any one of Embodiments 1 to 29, or a therapeutically effective amount of a pharmaceutical composition according to Embodiment 30.

33. The method of Embodiment 31 or Embodiment 32, wherein said therapeutically effective amount of the at least one compound, tautomer, deuterated derivative, or pharmaceutically acceptable salt is administered in combination with AAT augmentation therapy and/or AAT replacement therapy.

II. Compounds and Compositions

In some embodiments, a compound of the disclosure is a compound of Formula (Ia) or (Ib):

(Ia)

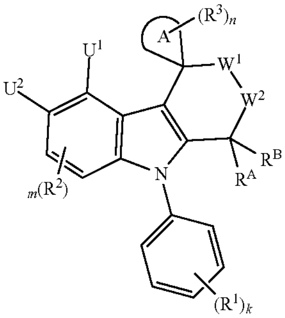

(Ib)

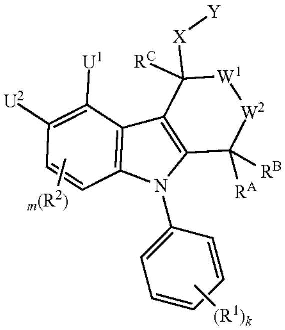

a tautomer thereof, a deuterated derivative of the compound or tautomer, or a pharmaceutically acceptable salt of any of the foregoing, wherein:

$W^1$ is absent or a bond, —O—, or —$CR^DR^D$—;

$W^2$ is —O—, —$(CR^DR^D)_p$—, or —C═O;

provided that $W^1$ and $W^2$ are not both —O—;

$R^A$ and $R^B$ are each independently hydrogen, halogen, —OH, $C_1$-$C_3$ alkyl, $C_1$-$C_3$ haloalkyl, or $C_1$-$C_3$ alkoxy;

or alternatively $R^A$ and $R^B$ are each independently $C_1$-$C_3$ alkyl or $C_1$-$C_3$ alkoxy, and $R^A$ and $R^B$ together with their intervening C atom form a $C_3$-$C_6$ cycloalkyl or a 3 to 6-membered heterocyclyl containing at least one oxygen atom;

$R^C$ is independently hydrogen, —OH, $C_1$-$C_3$ alkyl, or $C_1$-$C_3$ haloalkyl;

$R^D$, for each occurrence, is independently hydrogen, halogen, —OH, $C_1$-$C_3$ alkyl, $C_1$-$C_3$ haloalkyl, or $C_1$-$C_3$ alkoxy;

or alternatively $R^D$, for each occurrence, is independently $C_1$-$C_3$ alkyl or $C_1$-$C_3$ alkoxy, and two $R^D$ groups together with their intervening C atom form a $C_3$-$C_6$ cycloalkyl or a 3 to 6-membered heterocyclyl containing at least one oxygen atom;

$U^1$ and $U^2$ are each independently hydrogen, halogen, —$NH_2$, —$CH_3$, or —OH;

provided that one of $U^1$ and $U^2$ is —OH or —$NH_2$ but $U^1$ and $U^2$ are not both —OH or —$NH_2$ and $U^1$ and $U^2$ are not both hydrogen;

Ring A is $C_3$-$C_{12}$ carbocyclyl or 3 to 12-membered heterocyclyl;

X is absent, —$(CR^ER^E)_q$—, or —$CH_2OCH_2$—; wherein:

$R^E$, for each occurrence, is independently hydrogen, halogen, —OH, $C_1$-$C_3$ alkyl, $C_1$-$C_3$ haloalkyl, or $C_1$-$C_3$ alkoxy;

Y is —COOH or

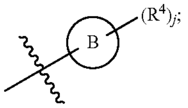

Ring B is $C_3$-$C_{12}$ cycloalkyl, a 3 to 12-membered heterocyclyl, a phenyl, or a 5 or 6-membered heteroaryl;

$R^1$ and $R^2$, for each occurrence, are each independently halogen, cyano, $C_1$-$C_3$ alkyl, $C_1$-$C_3$ haloalkyl, $C_1$-$C_3$ alkoxy, $C_1$-$C_3$ haloalkoxy, or O—($C_3$-$C_6$ cycloalkyl); and $R^3$, for each occurrence, is independently halogen, cyano, $C_1$-$C_3$ alkyl, $C_1$-$C_3$ haloalkyl, $C_1$-$C_3$ alkoxy, —OH, —$O(CR^fR^f)_rCOOH$, ═O, —COOH, —C(═O)$NR^fR^f$, —$(CR^fR^f)_rCOOH$, phenyl, or 5 or 6-membered heteroaryl; wherein:

$R^f$, for each occurrence, is independently hydrogen, halogen, or —$CH_3$; and the phenyl, or the 5 or 6-membered heteroaryl of $R^3$ is optionally substituted with 1 to 3 groups selected from halogen, cyano, $C_1$-$C_2$ alkyl, $C_1$-$C_2$ haloalkyl, $C_1$-$C_2$ alkoxy, —OH, and —COOH;

$R^4$, for each occurrence, is independently halogen, cyano, $C_1$-$C_2$ alkyl, $C_1$-$C_2$ haloalkyl, $C_1$-$C_2$ alkoxy, —COOH, —$CH_2COOH$, or —$OCH_2COOH$;

k and n are each independently an integer selected from 0, 1, 2, and 3;

j and m are each independently an integer selected from 0, 1, and 2;

p and r are each independently an integer selected from 1 and 2; and q is an integer selected from 1, 2, and 3.

In some embodiments, in the compound, tautomer, deuterated derivative, or pharmaceutically acceptable salt of the disclosure, wherein:

$R^A$ and $R^B$ are each independently hydrogen, halogen, —OH, $C_1$-$C_2$ alkyl, $C_1$-$C_2$ haloalkyl, or $C_1$-$C_2$ alkoxy;

or alternatively $R^A$ and $R^B$ are each independently $C_1$-$C_3$ alkyl, and $R^A$ and $R^B$ together with their intervening C atom form a cyclopropyl or a cyclobutyl;

$R^D$, for each occurrence, is independently hydrogen, halogen, —OH, $C_1$-$C_2$ alkyl, $C_1$-$C_2$ haloalkyl, or $C_1$-$C_2$ alkoxy;

or alternatively $R^D$, for each occurrence, is independently $C_1$-$C_3$ alkyl, and two $R^D$ groups together with their intervening C atom form a cyclopropyl or a cyclobutyl; and wherein all other variables not specifically defined herein are as defined in the preceding embodiment.

In some embodiments, the compound, tautomer, deuterated derivative, or pharmaceutically acceptable salt of the disclosure is represented by Formula (IIa-1) or Formula (IIa-2):

(IIa-1)

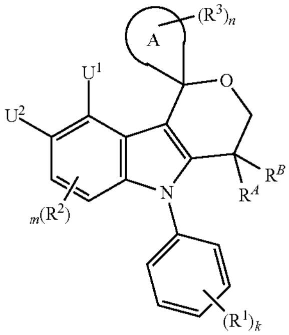

(IIa-2)

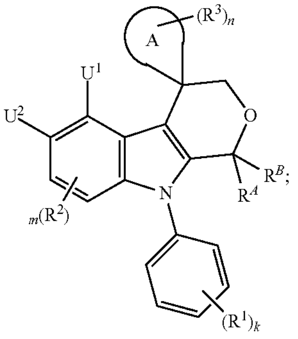

wherein $R^A$ and $R^B$ are each independently hydrogen or $C_1$-$C_2$ alkyl; and wherein all other variables not specifically defined herein are as defined in the preceding embodiment.

In some embodiments, in the compound, tautomer, deuterated derivative, or pharmaceutically acceptable salt of the disclosure, wherein:

$U^1$ is —$NH_2$ or —OH;

$U^2$ is hydrogen, halogen, or —$CH_3$;

and wherein all other variables not specifically defined herein are as defined in any one of the preceding embodiments.

In some embodiments, the compound, tautomer, deuterated derivative, or pharmaceutically acceptable salt of the disclosure is represented by Formula (IIIa):

(IIIa)

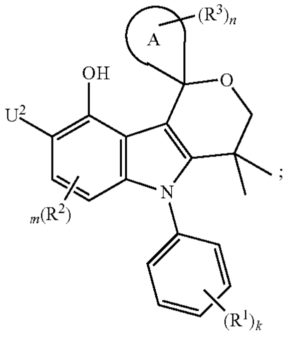

wherein $U^2$ is hydrogen, F, or Cl; and wherein all other variables not specifically defined herein are as defined in any one of the preceding embodiments.

In some embodiments, in the compound, tautomer, deuterated derivative, or pharmaceutically acceptable salt of the disclosure, Ring A is a 4 to 9-membered carbocyclyl or 5 or 6-membered heterocyclyl and is optionally substituted with $R^3$; and all other variables not specifically defined herein are as defined in any one of the preceding embodiments.

In some embodiments, in the compound, tautomer, deuterated derivative, or pharmaceutically acceptable salt of the disclosure, wherein Ring A is selected from cyclobutyl; cyclopentyl; cyclohexyl; spiro[3.3]heptanyl; tetrahydro-2H-pyranyl; piperidinyl; spiro[2.3]hexanyl; 1-iminohexahydro-1λ$^6$-thiopyranyl 1-oxide; tetrahydro-2H-thiopyranyl 1,1-dioxide; or 2,3-dihydro-1H-indenyl; and Ring A is optionally substituted with $R^3$; wherein all other variables not specifically defined herein are as defined in any one of the preceding embodiments.

In some embodiments, in the compound, tautomer, deuterated derivative, or pharmaceutically acceptable salt of the disclosure, Ring A is selected from

 , 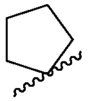 ,

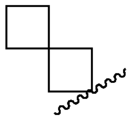 , 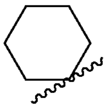 , 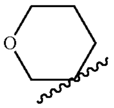 ,

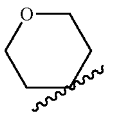 , 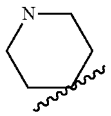 , 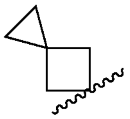 ,

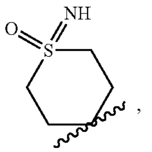 , 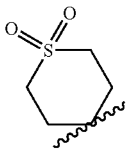 , and 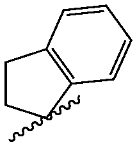 ;

and; and is optionally substituted with $R^3$; and all other variables not specifically defined herein are as defined in any one of the preceding embodiments.

In some embodiments, in the compound, tautomer, deuterated derivative, or pharmaceutically acceptable salt of the disclosure, $R^3$, for each occurrence, is independently halogen, $C_1$-$C_2$ alkyl, $C_1$-$C_2$ haloalkyl, $C_1$-$C_2$ alkoxy, —OH, $—O(CR^fR^f)_rCOOH$, =O, —COOH, $—C(=O)NR^fR^f$, $—(CR^fR^f)_rCOOH$, phenyl, or a 5-membered heteroaryl; wherein:

$R^f$, for each occurrence, is independently hydrogen or $—CH_3$; and the phenyl or the 5-membered heteroaryl of $R^3$ is optionally substituted with 1 to 3 groups selected from halogen, $C_1$-$C_2$ alkyl, $C_1$-$C_2$ alkoxy, —OH, and —COOH;

and wherein all other variables not specifically defined herein are as defined in any one of the preceding embodiments.

In some embodiments, in the compound, tautomer, deuterated derivative, or pharmaceutically acceptable salt of the disclosure, $R^3$, for each occurrence, is independently F, $—CH_3$, $—CF_3$, $—CHF_2$, $—CH_2F$, —OH, $—OCH_3$, —COOH, $—CH_2COOH$, $—CF_2COOH$, $—C(=O)NH_2$, $—C(=O)NHCH_3$, $—C(=O)N(CH_3)_2$, =O, $—OCH_2COOH$, $—OCHCH_3COOH$, phenyl, pyrazolyl, or oxazolyl; wherein:

the phenyl of $R^3$ is substituted with —COOH;

the pyrazolyl of $R^3$ is substituted with —COOH and $—CH_3$; and the oxazolyl of $R^3$ is substituted with —COOH;

and wherein all other variables not specifically defined herein are as defined in any one of the preceding embodiments.

In some embodiments, the compound, tautomer, deuterated derivative, or pharmaceutically acceptable salt of the disclosure is represented by Formula (IVa-1), Formula (IVa-2), or Formula (IVa-3):

(IVa-1)

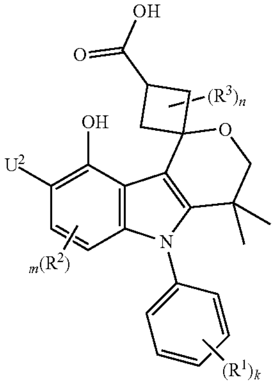

(IVa-2)

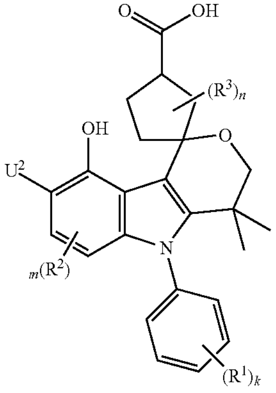

-continued (IVa-3)

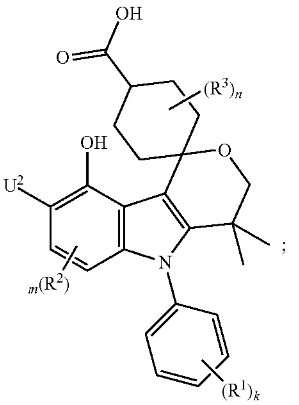

wherein n is an integer selected from 0, 1, and 2; and wherein all other variables not specifically defined herein are as defined in the any one of the preceding embodiments.

In some embodiments, the compound, tautomer, deuterated derivative, or pharmaceutically acceptable salt of the disclosure is represented by Formula (Va-1) or Formula (Va-2):

(Va-1)

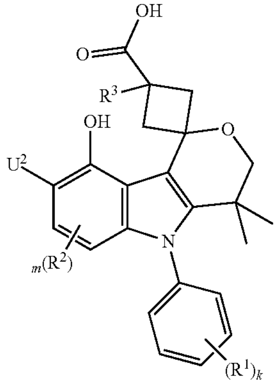

(Va-2)

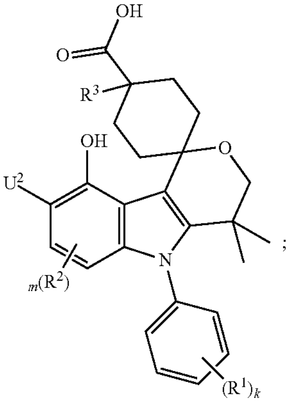

wherein $R^3$ is F, $—CH_3$, $—CF_3$, $—CHF_2$, $—CH_2F$, —OH, or $—OCH_3$; and wherein all other variables not specifically defined herein are as defined in the any one of the preceding embodiments.

In some embodiments, the compound, tautomer, deuterated derivative, or pharmaceutically acceptable salt of the disclosure is represented by Formula (IIb-1) or Formula (IIb-2):

(IIb-1)

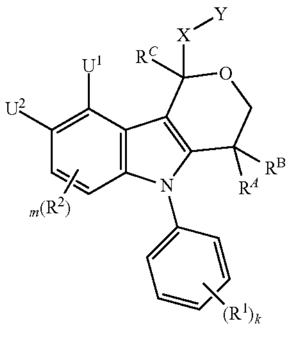

(IIb-2)

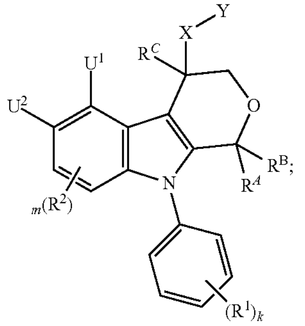

wherein:

$R^A$ and $R^B$ are each independently hydrogen, halogen, —OH, $C_1$-$C_2$ alkyl, $C_1$-$C_2$ haloalkyl, or $C_1$-$C_2$ alkoxy;

$R^C$ is independently hydrogen, $C_1$-$C_2$ alkyl, or $C_1$-$C_2$ haloalkyl;

X is absent, —$(CR^ER^E)_q$—, or —$CH_2OCH_2$—; wherein:

$R^E$, for each occurrence, is independently hydrogen, $C_1$-$C_2$ alkyl, or $C_1$-$C_2$ alkoxy; and wherein all other variables not specifically defined herein are as defined for Formulae (Ia) or (Ib).

In some embodiments, in the compound, tautomer, deuterated derivative, or pharmaceutically acceptable salt of the disclosure:

$R^A$ and $R^B$ are each independently hydrogen or $C_1$-$C_2$ alkyl;

$U^1$ is —$NH_2$ or —OH;

$U^2$ is hydrogen, halogen, or —$CH_3$;

X is absent, —$CH_2$—, —$(CH_2)_2$—, —$(CH_2)_3$—, or —$CH_2OCH_2$—;

and all other variables not specifically defined herein are as defined for any one of Formulae (Ia), (Ib), (Va-1), and (Va-2).

In some embodiments, the compound, tautomer, deuterated derivative, or pharmaceutically acceptable salt of the disclosure is represented by Formula (IIIb-1) or Formula (IIIb-2):

(IIIb-1)

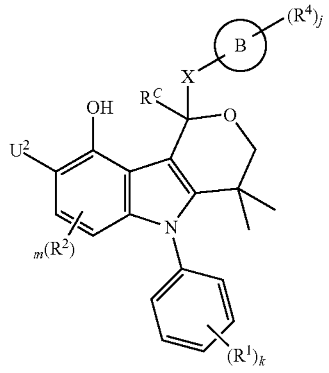

(IIIb-2)

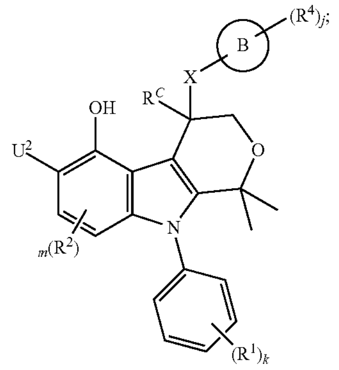

wherein:

$U^2$ is hydrogen, F, or Cl;

$R^C$ is hydrogen, —$CH_3$, or —$CF_3$; and

X is absent or —$CH_2$—;

and wherein all other variables not specifically defined herein are as defined for in any one of Formulae (Ia), (Ib), (Va-1), (Va-2), (IIb-1), and (IIb-2).

In some embodiments, the compound, tautomer, deuterated derivative, or pharmaceutically acceptable salt of the disclosure is represented by Formula (IVb-1) or Formula (IVb-2):

(IVb-1)

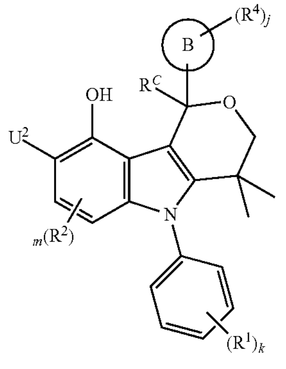

-continued (IVb-2)

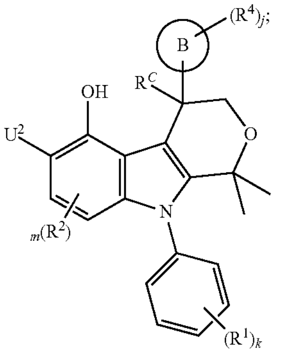

wherein all other variables not specifically defined herein are as defined for any one of Formulae (Ia), (Ib), (Va-1), (Va-2), (IIb-1), (IIb-2), (IIIb-1), and (IIIb-2).

In some embodiments, in the compound, tautomer, deuterated derivative, or pharmaceutically acceptable salt of the disclosure, wherein Ring B is optionally substituted with $R^4$ and Ring B is $C_3$-$C_6$ cycloalkyl, phenyl, or 5-membered heteroaryl; and wherein all other variables not specifically defined herein are as defined for any one of Formulae (Ia), (Ib), (Va-1), (Va-2), (IIb-1), (IIb-2), (IIIb-1), (IIIb-2), (IVb-1), and (IVb-2).

In some embodiments, in the compound, tautomer, deuterated derivative, or pharmaceutically acceptable salt of the disclosure, Ring B is selected from

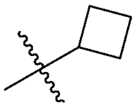, 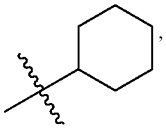, 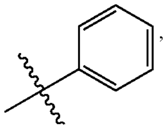, 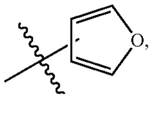, 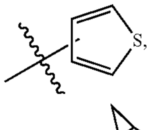, 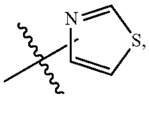, and 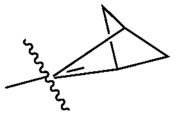;

and is optionally substituted with $R^4$; and all other variables not specifically defined herein are as defined for any one of Formulae (Ia), (Ib), (Va-1), (Va-2), (IIb-1), (IIb-2), (IIIb-1), (IIIb-2), (IVb-1), and (IVb-2).

In some embodiments, in the compound, tautomer, deuterated derivative, or pharmaceutically acceptable salt of the disclosure, Ring B is selected from

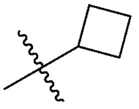, 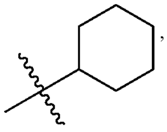, 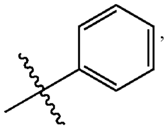, 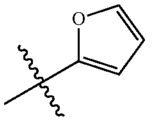, 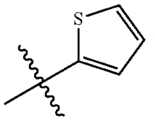, 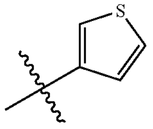,

-continued

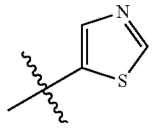, and 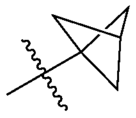;

and is optionally substituted with $R^4$; and all other variables not specifically defined herein are as defined for any one of Formulae (Ia), (Ib), (Va-1), (Va-2), (IIb-1), (IIb-2), (IIIb-1), (IIIb-2), (IVb-1), and (IVb-2).

In some embodiments, in the compound, tautomer, deuterated derivative, or pharmaceutically acceptable salt of the disclosure, $R^4$, for each occurrence, is independently F, Cl, $—CH_3$, $—OCH_3$, —COOH, or $—OCH_2COOH$; and all other variables are as defined for any one of the preceding embodiments.

In some embodiments, the compound, tautomer, deuterated derivative, or pharmaceutically acceptable salt of the disclosure is represented by Formula (Vb-1), Formula (Vb-2), Formula (Vb-3), Formula (Vb-4), or Formula (Vb-5):

(Vb-1)

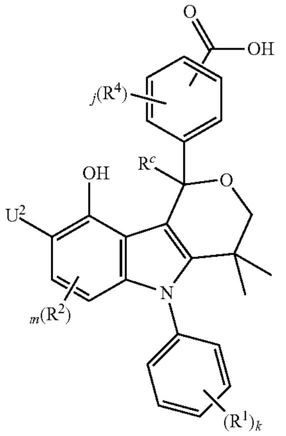

(Vb-2)

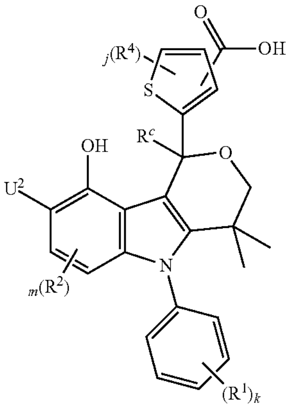

-continued (Vb-3)

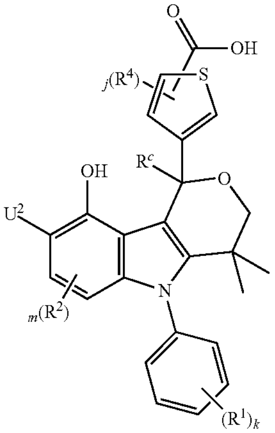

(Vb-4)

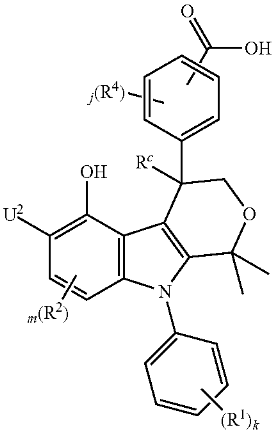

(Vb-5)

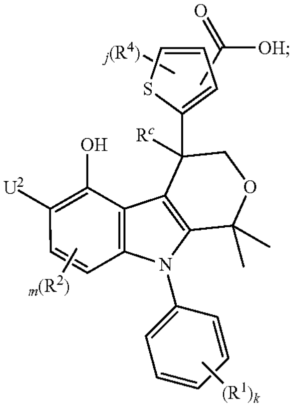

wherein j is an integer selected from 0, 1, and 2; and wherein all other variables not specifically defined herein are as defined for Formula (Ia), (Ib), or any of preceding embodiments.

In some embodiments, the compound, tautomer, deuterated derivative, or pharmaceutically acceptable salt of the disclosure is represented by Formula (VIb-1), Formula (VIb-2), Formula (VIb-3), Formula (VIb-4), or Formula (VIb-5):

(VIb-1)

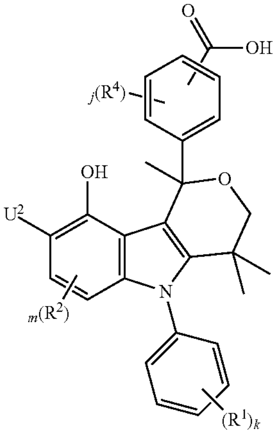

(VIb-2)

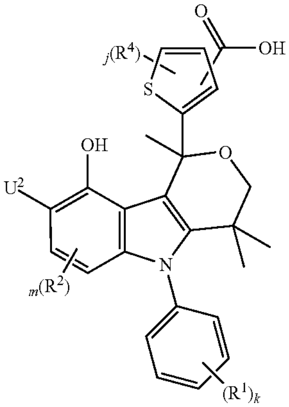

(VIb-3)

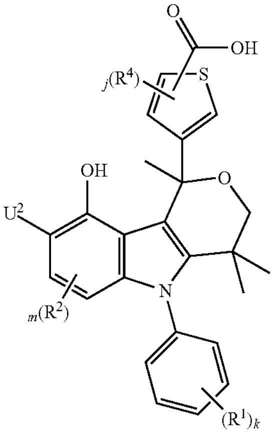

-continued (VIb-4)

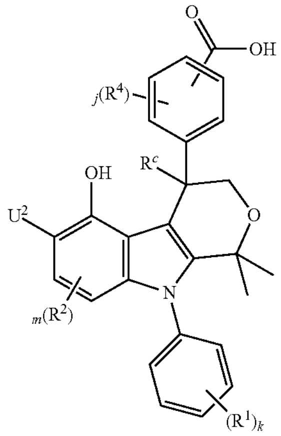

(VIb-5)

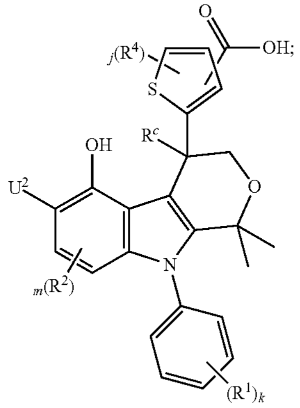

herein j is an integer selected from 0, 1, and 2; and wherein all other variables not specifically defined herein are as defined for Formula (I) or any of the preceding embodiments.

In some embodiments, in the compound, tautomer, deuterated derivative, or pharmaceutically acceptable salt of Formula (IIb-1) or (IIb-2):

$R^A$ and $R^B$ are each independently hydrogen or $C_1$-$C_2$ alkyl;

$U^1$ is —$NH_2$ or —OH;

$U^2$ is hydrogen, halogen, or —$CH_3$;

X is absent, —$CH_2$—, —$(CH_2)_2$—, —$(CH_2)_3$—, or —$CH_2OCH_2$—;

and wherein all other variables not specifically defined herein are as defined for any one of Formulae (Ia), (Ib), (IIb-1), and (IIb-2).

In some embodiments, in the compound, tautomer, deuterated derivative, or pharmaceutically acceptable salt of Formula (IIb-1) or (IIb-2):

X is —$(CH_2)_2$—, —$(CH_2)_3$—, or —$CH_2OCH_2$—;

Y is —COOH;

and wherein all other variables not specifically defined herein are as defined for any one of Formulae (Ia), (Ib), (IIb-1), and (IIb-2).

In some embodiments, in the compound, tautomer, deuterated derivative, or pharmaceutically acceptable salt of the disclosure, $R^1$ and $R^2$, for each occurrence, are each independently halogen, $C_1$-$C_2$ alkyl, or $C_1$-$C_2$ alkoxy; and all other variables not specifically defined herein are as defined in any one of the preceding embodiments.

In some embodiments, in the compound, tautomer, deuterated derivative, or pharmaceutically acceptable salt of the disclosure, $R^1$, for each occurrence, is independently F, $C_1$, —$CH_3$, or —$OCH_3$; and all other variables are as defined in any one of the preceding embodiments.

In some embodiments, in the compound, tautomer, deuterated derivative, or pharmaceutically acceptable salt of the disclosure, $R^2$, for each occurrence, is F; and m is an integer selected from 0 and 1; and all other variables are as defined in any one of the preceding embodiments.

In some embodiments, in the compound, tautomer, deuterated derivative, or pharmaceutically acceptable salt of the disclosure, wherein k is an integer selected from 1 and 2; and all other variables are as defined in any one of the preceding embodiments.

In some embodiments, in the compound, tautomer, deuterated derivative, or pharmaceutically acceptable salt of the disclosure, m is 0; and all other variables are as defined in any one of the preceding embodiments.

In some embodiments, the compound, tautomer, deuterated derivative or pharmaceutically acceptable salt of the disclosure is selected from Compounds 1-210 (Table A), tautomers of those compounds, deterated derivatives of those compounds and tautomers, and pharmaceutically acceptable salts of any of the foregoing.

TABLE A

| Compounds 1-210 | |
|---|---|
| 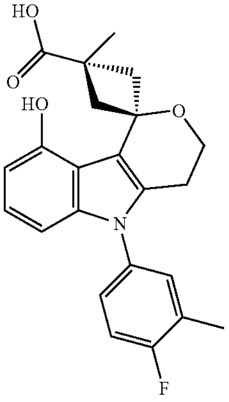 [SMILES: Cc1cc(-n2c3c(c4c(O)cccc42)[C@]2(C[C@@](C)(C(=O)O)C2)OCC3)ccc1F] | 1 |
| 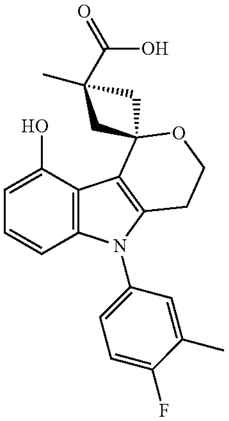 [SMILES: Cc1cc(-n2c3c(c4c(O)cccc42)[C@]2(C[C@](C)(C(=O)O)C2)OCC3)ccc1F] | 2 |

TABLE A-continued
Compounds 1-210
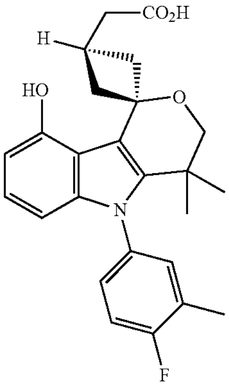 [SMILES: Cc1cc(-n2c3c(c4c(O)cccc42)[C@]2(C[C@H](CC(=O)O)C2)OCC3(C)C)ccc1F]
3
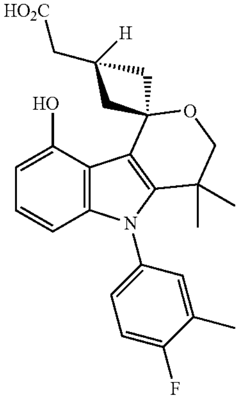 [SMILES: Cc1cc(-n2c3c(c4c(O)cccc42)[C@]2(C[C@@H](CC(=O)O)C2)OCC3(C)C)ccc1F]
4
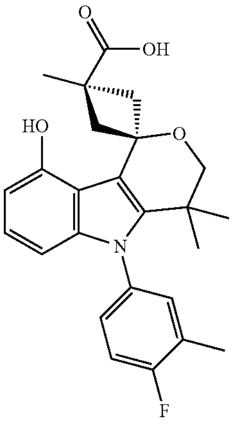 [SMILES: Cc1cc(-n2c3c(c4c(O)cccc42)[C@]2(C[C@](C)(C(=O)O)C2)OCC3(C)C)ccc1F]
5
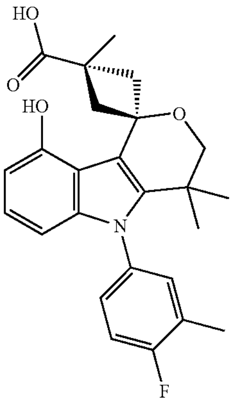 [SMILES: Cc1cc(-n2c3c(c4c(O)cccc42)[C@]2(C[C@@](C)(C(=O)O)C2)OCC3(C)C)ccc1F]
6
TABLE A-continued
Compounds 1-210
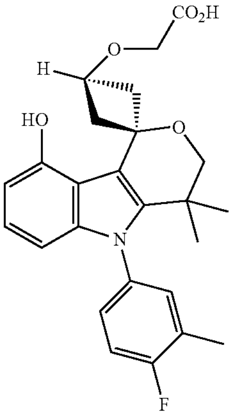 [SMILES: Cc1cc(-n2c3c(c4c(O)cccc42)[C@]2(C[C@H](OCC(=O)O)C2)OCC3(C)C)ccc1F]
7
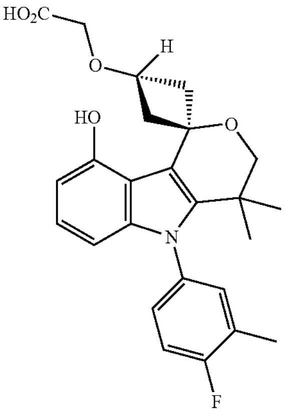 [SMILES: Cc1cc(-n2c3c(c4c(O)cccc42)[C@]2(C[C@@H](OCC(=O)O)C2)OCC3(C)C)ccc1F]
8
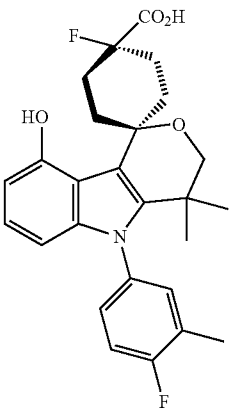
9

TABLE A-continued
Compounds 1-210
10
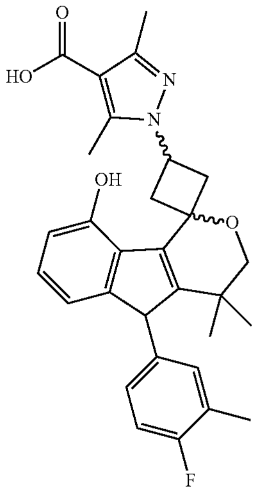 [SMILES: Cc1cc(C2C3=C(c4c(O)cccc42)C2(CC(n4nc(C)c(C(=O)O)c4C)C2)OCC3(C)C)ccc1F]
11
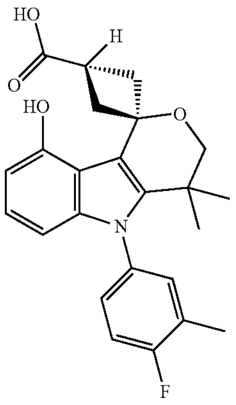 [SMILES: Cc1cc(-n2c3c(c4c(O)cccc42)[C@]2(C[C@@H](C(=O)O)C2)OCC3(C)C)ccc1F]
12
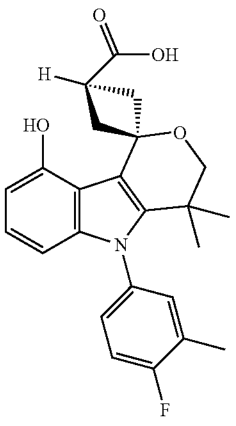 [SMILES: Cc1cc(-n2c3c(c4c(O)cccc42)[C@]2(C[C@H](C(=O)O)C2)OCC3(C)C)ccc1F]
TABLE A-continued
Compounds 1-210
13
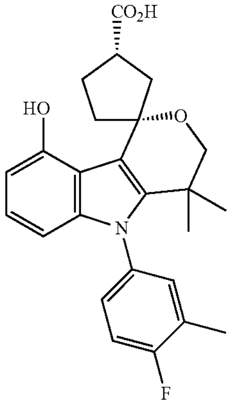 [SMILES: Cc1cc(-n2c3c(c4c(O)cccc42)[C@]2(CC[C@H](C(=O)O)C2)OCC3(C)C)ccc1F]
14
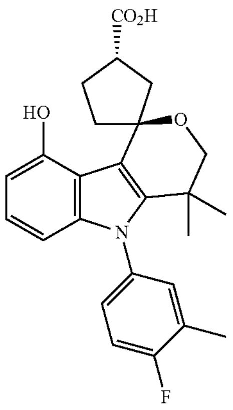 [SMILES: Cc1cc(-n2c3c(c4c(O)cccc42)[C@@]2(CC[C@H](C(=O)O)C2)OCC3(C)C)ccc1F]
15
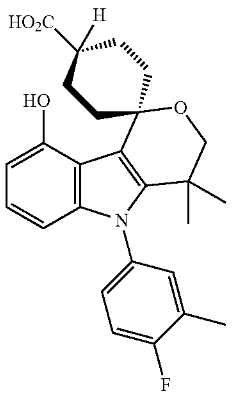
16
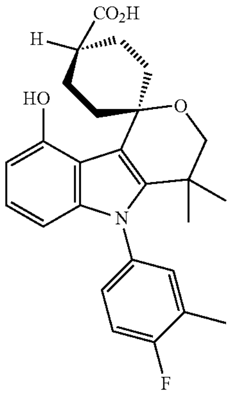

TABLE A-continued
| Compounds 1-210 | |
|---|---|
| 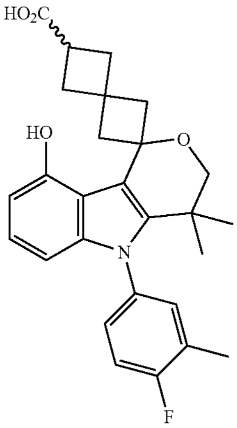 [SMILES: Cc1cc(-n2c3c(c4c(O)cccc42)C2(CC4(CC(C(=O)O)C4)C2)OCC3(C)C)ccc1F] | 17 |
| 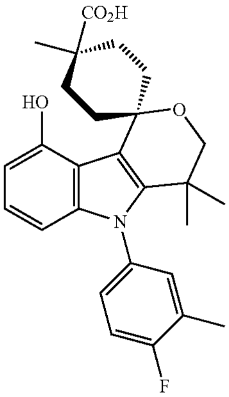 | 18 |
| 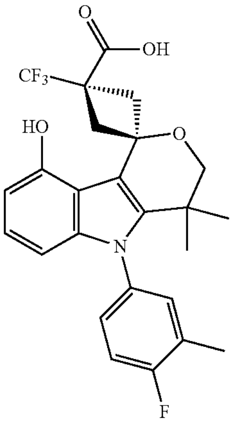 [SMILES: Cc1cc(-n2c3c(c4c(O)cccc42)[C@]2(C[C@@](C(=O)O)(C(F)(F)F)C2)OCC3(C)C)ccc1F] | 19 |
TABLE A-continued
| Compounds 1-210 | |
|---|---|
| 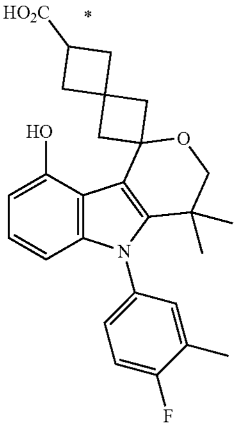 [SMILES: Cc1cc(-n2c3c(c4c(O)cccc42)C2(CC4(CC(C(=O)O)C4)C2)OCC3(C)C)ccc1F] | 20 |
| 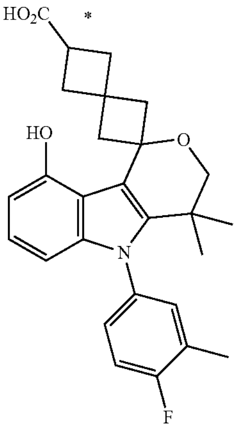 [SMILES: Cc1cc(-n2c3c(c4c(O)cccc42)C2(CC4(CC(C(=O)O)C4)C2)OCC3(C)C)ccc1F] | 21 |
| 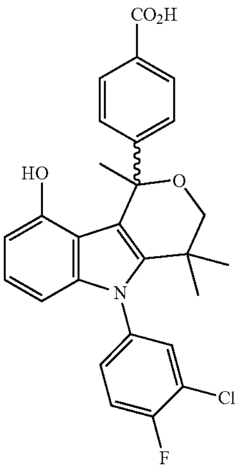 [SMILES: CC1(C)COC(C)(c2ccc(C(=O)O)cc2)c2c1n(-c1ccc(F)c(Cl)c1)c1cccc(O)c21] | 22 |

TABLE A-continued
| Compounds 1-210 | |
|---|---|
| 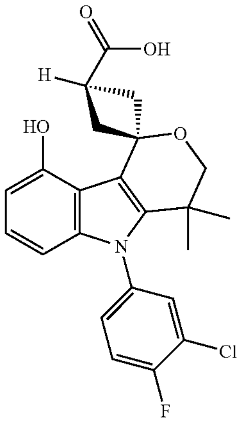 [SMILES: CC1(C)CO[C@]2(C[C@@H](C(=O)O)C2)c2c1n(-c1ccc(F)c(Cl)c1)c1cccc(O)c12] | 23 |
| 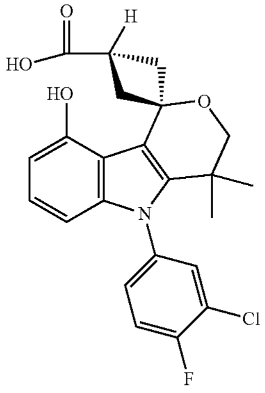 [SMILES: CC1(C)CO[C@]2(C[C@H](C(=O)O)C2)c2c1n(-c1ccc(F)c(Cl)c1)c1cccc(O)c12] | 24 |
| 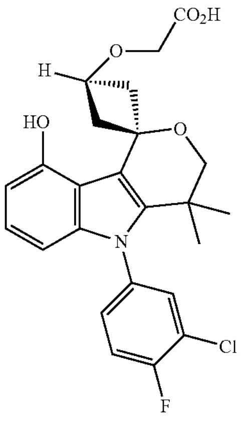 [SMILES: CC1(C)CO[C@]2(C[C@@H](OCC(=O)O)C2)c2c1n(-c1ccc(F)c(Cl)c1)c1cccc(O)c12] | 25 |
TABLE A-continued
| Compounds 1-210 | |
|---|---|
| 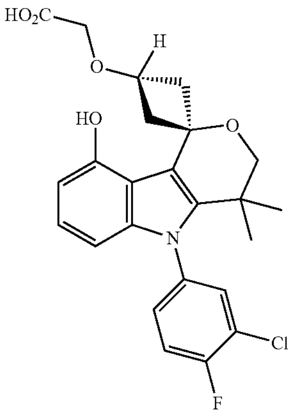 [SMILES: CC1(C)CO[C@]2(C[C@H](OCC(=O)O)C2)c2c1n(-c1ccc(F)c(Cl)c1)c1cccc(O)c12] | 26 |
| 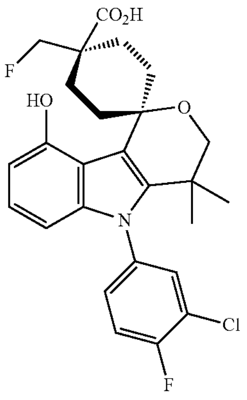 | 27 |
| 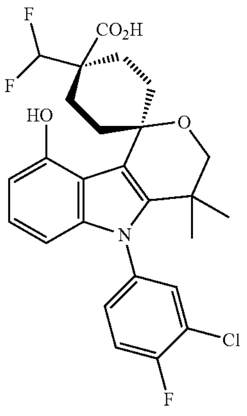 | 28 |

TABLE A-continued
| Compounds 1-210 |
| --- |
29
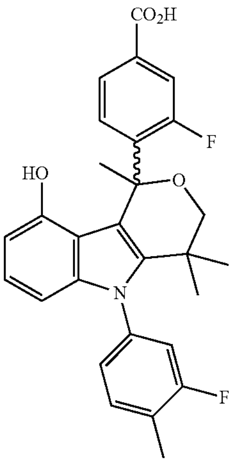 [SMILES: Cc1ccc(-n2c3c(c4c(O)cccc42)C(C)(c2ccc(C(=O)O)cc2F)OCC3(C)C)cc1F]
30
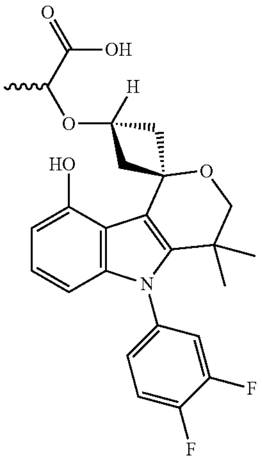 [SMILES: CC(O[C@H]1C[C@@]2(C1)OCC(C)(C)c1c2c2c(O)cccc2n1-c1ccc(F)c(F)c1)C(=O)O]
31
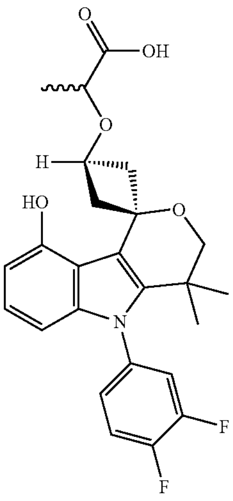 [SMILES: CC(O[C@H]1C[C@]2(C1)OCC(C)(C)c1c2c2c(O)cccc2n1-c1ccc(F)c(F)c1)C(=O)O]
32
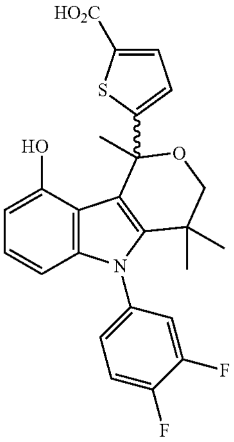 [SMILES: CC1(C)COC(C)(c2ccc(C(=O)O)s2)c2c1n(-c1ccc(F)c(F)c1)c1cccc(O)c21]
33
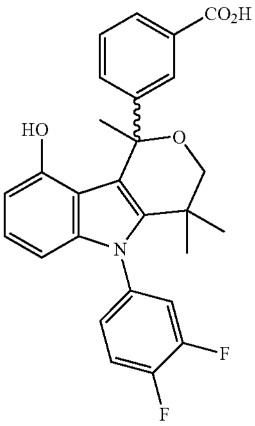 [SMILES: CC1(C)COC(C)(c2cccc(C(=O)O)c2)c2c1n(-c1ccc(F)c(F)c1)c1cccc(O)c21]
34
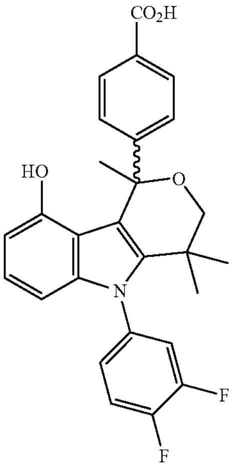 [SMILES: CC1(C)COC(C)(c2ccc(C(=O)O)cc2)c2c1n(-c1ccc(F)c(F)c1)c1cccc(O)c21]

TABLE A-continued
| Compounds 1-210 | |
|---|---|
| 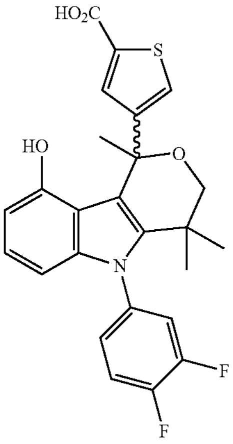 [SMILES: CC1(C)COC(C)(c2csc(C(=O)O)c2)c2c1n(-c1ccc(F)c(F)c1)c1cccc(O)c21] | 35 |
| 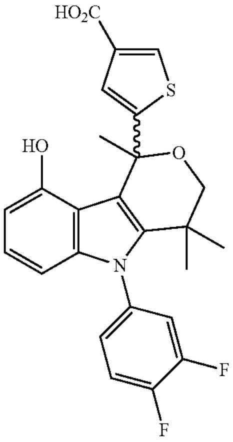 [SMILES: CC1(C)COC(C)(c2cc(C(=O)O)cs2)c2c1n(-c1ccc(F)c(F)c1)c1cccc(O)c21] | 36 |
| 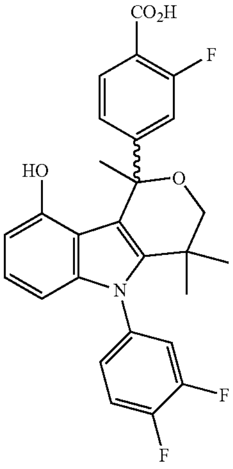 [SMILES: CC1(C)COC(C)(c2ccc(C(=O)O)c(F)c2)c2c1n(-c1ccc(F)c(F)c1)c1cccc(O)c21] | 37 |
| 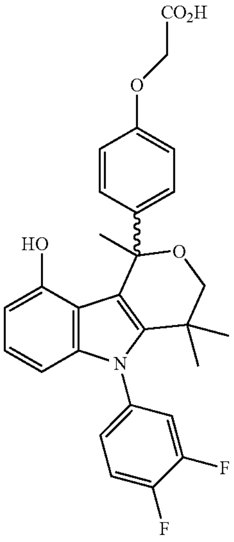 [SMILES: CC1(C)COC(C)(c2ccc(OCC(=O)O)cc2)c2c1n(-c1ccc(F)c(F)c1)c1cccc(O)c21] | 38 |
| 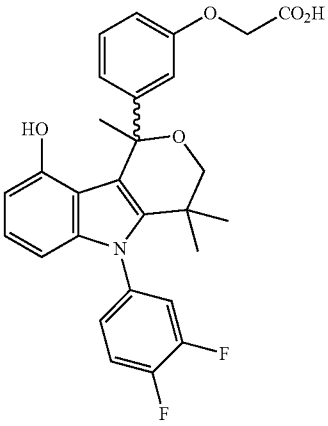 [SMILES: CC1(C)COC(C)(c2cccc(OCC(=O)O)c2)c2c1n(-c1ccc(F)c(F)c1)c1cccc(O)c21] | 39 |
| 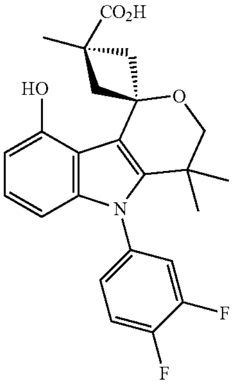 [SMILES: CC1(C)CO[C@]2(C[C@@](C)(C(=O)O)C2)c2c1n(-c1ccc(F)c(F)c1)c1cccc(O)c12] | 40 |

TABLE A-continued
Compounds 1-210
41
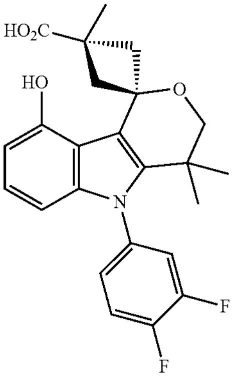 [SMILES: CC1(C)CO[C@]2(C[C@](C)(C(=O)O)C2)c2c1n(-c1ccc(F)c(F)c1)c1cccc(O)c12]
42
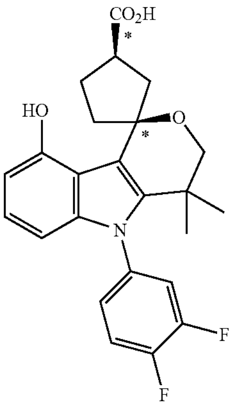 [SMILES: CC1(C)CO[C@]2(CC[C@@H](C(=O)O)C2)c2c1n(-c1ccc(F)c(F)c1)c1cccc(O)c21]
43
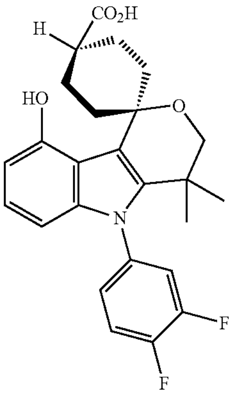
TABLE A-continued
Compounds 1-210
44
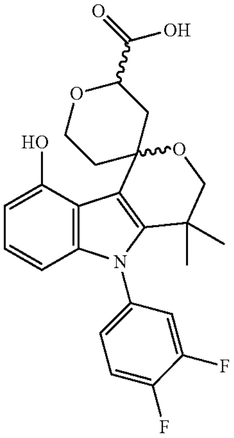 [SMILES: CC1(C)COC2(CCOC(C(=O)O)C2)c2c1n(-c1ccc(F)c(F)c1)c1cccc(O)c21]
45
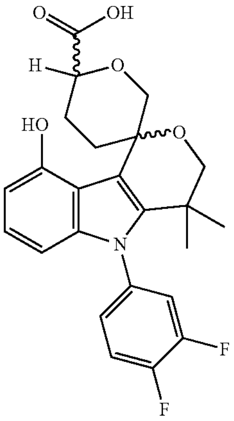 [SMILES: CC1(C)COC2(CCC(C(=O)O)OC2)c2c1n(-c1ccc(F)c(F)c1)c1cccc(O)c21]
46
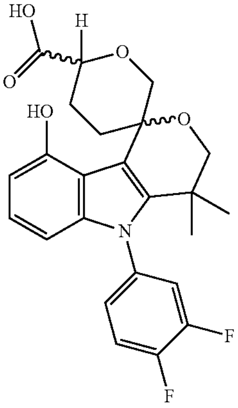 [SMILES: CC1(C)COC2(CCC(C(=O)O)OC2)c2c1n(-c1ccc(F)c(F)c1)c1cccc(O)c21]

TABLE A-continued
| Compounds 1-210 |
| --- |
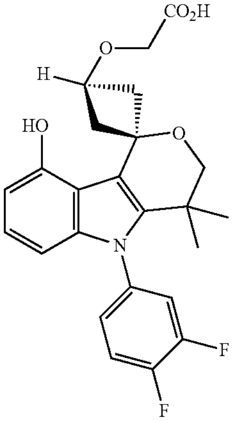 [SMILES: CC1(C)CO[C@]2(C[C@@H](OCC(=O)O)C2)c2c1n(-c1ccc(F)c(F)c1)c1cccc(O)c12]
47
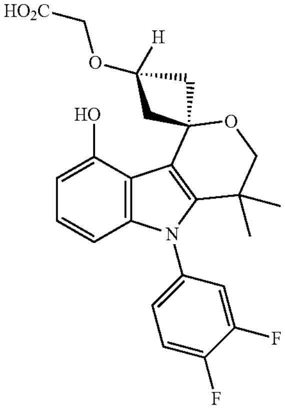 [SMILES: CC1(C)CO[C@]2(C[C@H](OCC(=O)O)C2)c2c1n(-c1ccc(F)c(F)c1)c1cccc(O)c12]
48
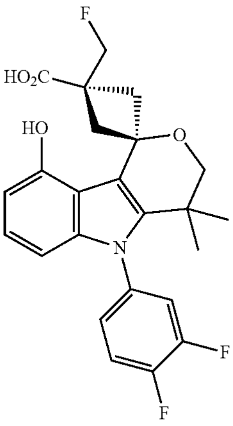 [SMILES: CC1(C)CO[C@]2(C[C@](CF)(C(=O)O)C2)c2c1n(-c1ccc(F)c(F)c1)c1cccc(O)c12]
49
TABLE A-continued
| Compounds 1-210 |
| --- |
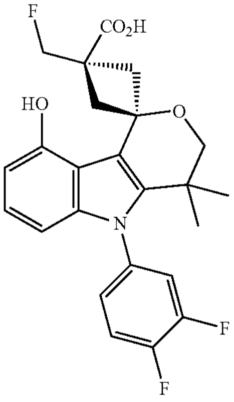 [SMILES: CC1(C)CO[C@]2(C[C@@](CF)(C(=O)O)C2)c2c1n(-c1ccc(F)c(F)c1)c1cccc(O)c12]
50
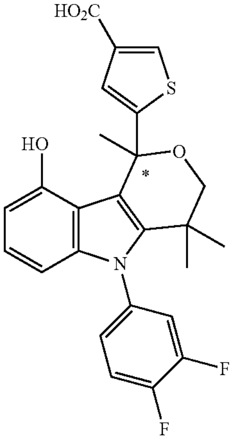 [SMILES: CC1(C)COC(C)(c2cc(C(=O)O)cs2)c2c1n(-c1ccc(F)c(F)c1)c1cccc(O)c21]
51
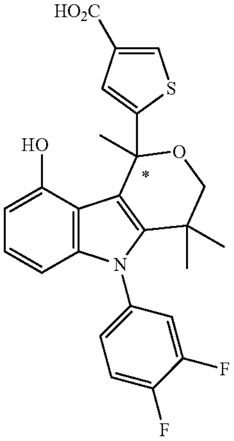 [SMILES: CC1(C)COC(C)(c2cc(C(=O)O)cs2)c2c1n(-c1ccc(F)c(F)c1)c1cccc(O)c21]
52

TABLE A-continued
| Compounds 1-210 |
| --- |
53
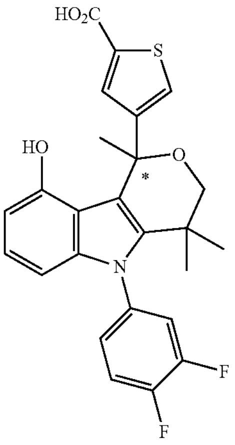 [SMILES: CC1(C)COC(C)(c2csc(C(=O)O)c2)c2c1n(-c1ccc(F)c(F)c1)c1cccc(O)c21]
54
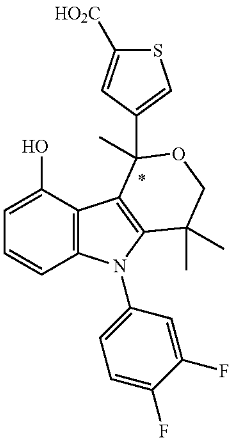 [SMILES: CC1(C)COC(C)(c2csc(C(=O)O)c2)c2c1n(-c1ccc(F)c(F)c1)c1cccc(O)c21]
55
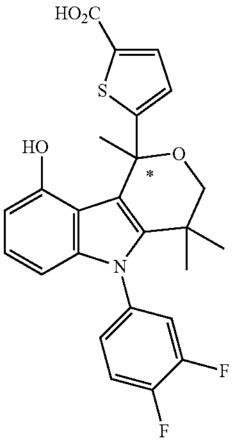 [SMILES: CC1(C)COC(C)(c2ccc(C(=O)O)s2)c2c1n(-c1ccc(F)c(F)c1)c1cccc(O)c21]
TABLE A-continued
| Compounds 1-210 |
| --- |
56
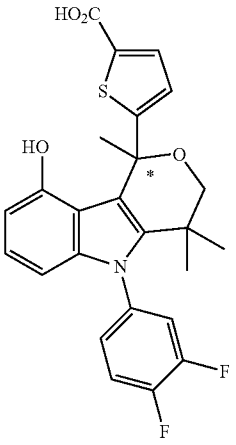 [SMILES: CC1(C)COC(C)(c2ccc(C(=O)O)s2)c2c1n(-c1ccc(F)c(F)c1)c1cccc(O)c21]
57
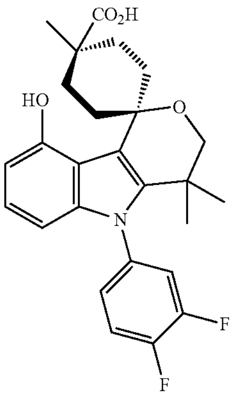
58
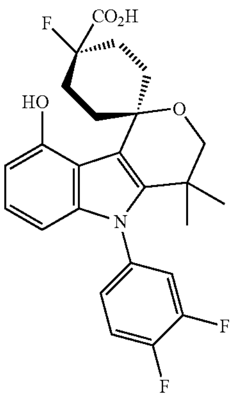

TABLE A-continued
Compounds 1-210
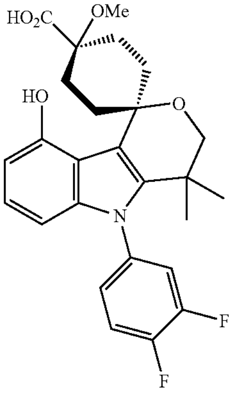
59
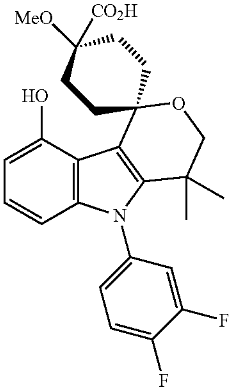
60
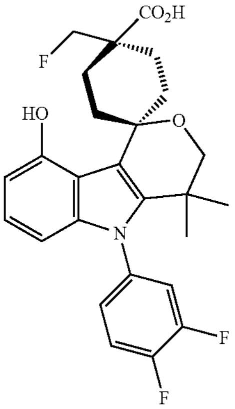
61
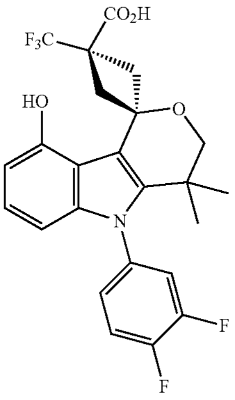 [SMILES: CC1(C)CO[C@]2(C[C@](C(=O)O)(C(F)(F)F)C2)c2c1n(-c1ccc(F)c(F)c1)c1cccc(O)c12]
62
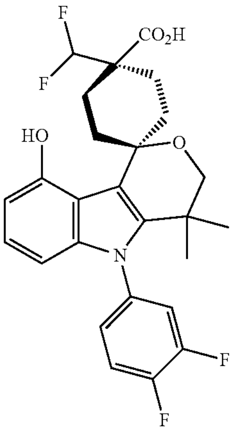
63
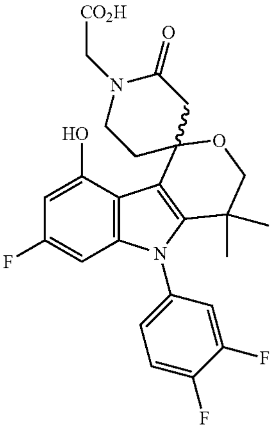 [SMILES: CC1(C)COC2(CCN(CC(=O)O)C(=O)C2)c2c1n(-c1ccc(F)c(F)c1)c1cc(F)cc(O)c21]
64
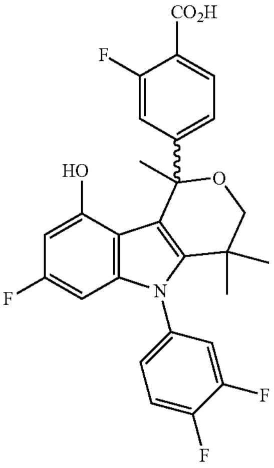 [SMILES: CC1(C)COC(C)(c2ccc(C(=O)O)c(F)c2)c2c1n(-c1ccc(F)c(F)c1)c1cc(F)cc(O)c21]
65

TABLE A-continued
Compounds 1-210
66
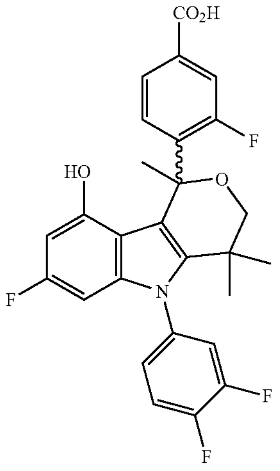 [SMILES: CC1(C)COC(C)(c2ccc(C(=O)O)cc2F)c2c1n(-c1ccc(F)c(F)c1)c1cc(F)cc(O)c21]
67
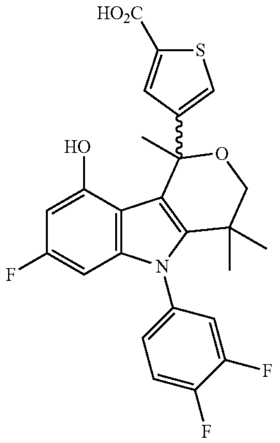 [SMILES: CC1(C)COC(C)(c2csc(C(=O)O)c2)c2c1n(-c1ccc(F)c(F)c1)c1cc(F)cc(O)c21]
68
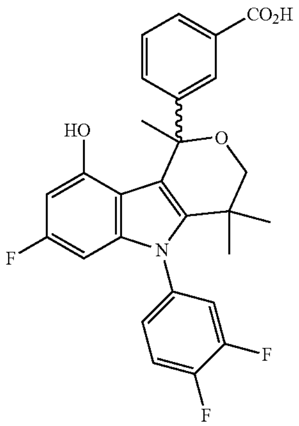 [SMILES: CC1(C)COC(C)(c2cccc(C(=O)O)c2)c2c1n(-c1ccc(F)c(F)c1)c1cc(F)cc(O)c21]
TABLE A-continued
Compounds 1-210
69
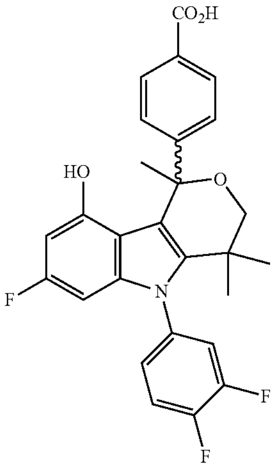 [SMILES: CC1(C)COC(C)(c2ccc(C(=O)O)cc2)c2c1n(-c1ccc(F)c(F)c1)c1cc(F)cc(O)c21]
70
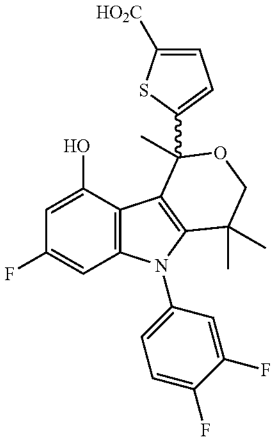 [SMILES: CC1(C)COC(C)(c2ccc(C(=O)O)s2)c2c1n(-c1ccc(F)c(F)c1)c1cc(F)cc(O)c21]
71
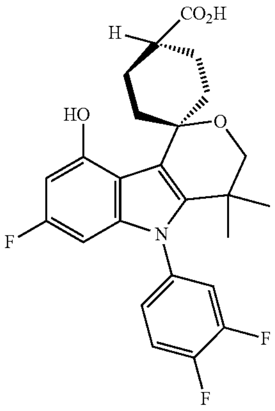

TABLE A-continued
Compounds 1-210
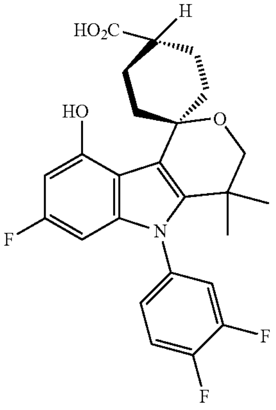
72
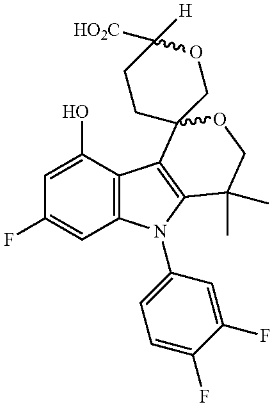 [SMILES: CC1(C)COC2(CCC(C(=O)O)OC2)c2c1n(-c1ccc(F)c(F)c1)c1cc(F)cc(O)c21]
73
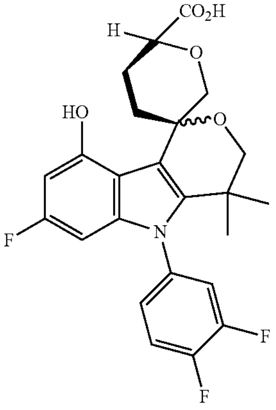
74
TABLE A-continued
Compounds 1-210
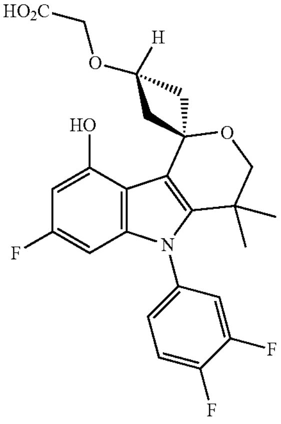 [SMILES: CC1(C)CO[C@]2(C[C@H](OCC(=O)O)C2)c2c1n(-c1ccc(F)c(F)c1)c1cc(F)cc(O)c12]
75
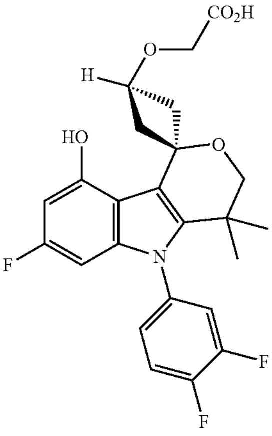 [SMILES: CC1(C)CO[C@]2(C[C@@H](OCC(=O)O)C2)c2c1n(-c1ccc(F)c(F)c1)c1cc(F)cc(O)c12]
76
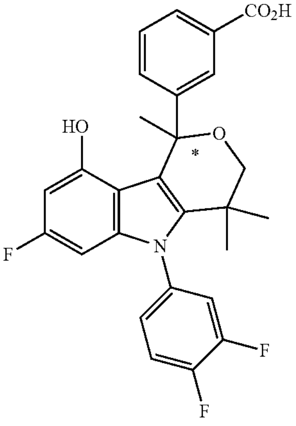 [SMILES: CC1(C)COC(C)(c2cccc(C(=O)O)c2)c2c1n(-c1ccc(F)c(F)c1)c1cc(F)cc(O)c21]
77

TABLE A-continued
Compounds 1-210
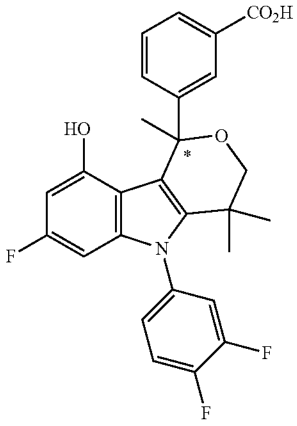 [SMILES: CC1(C)COC(C)(c2cccc(C(=O)O)c2)c2c1n(-c1ccc(F)c(F)c1)c1cc(F)cc(O)c21]
78
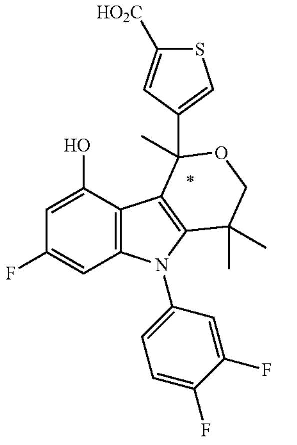 [SMILES: CC1(C)COC(C)(c2csc(C(=O)O)c2)c2c1n(-c1ccc(F)c(F)c1)c1cc(F)cc(O)c21]
79
80
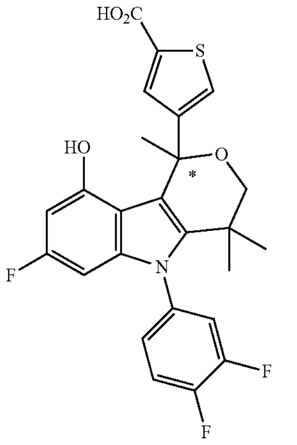 [SMILES: CC1(C)COC(C)(c2csc(C(=O)O)c2)c2c1n(-c1ccc(F)c(F)c1)c1cc(F)cc(O)c21]
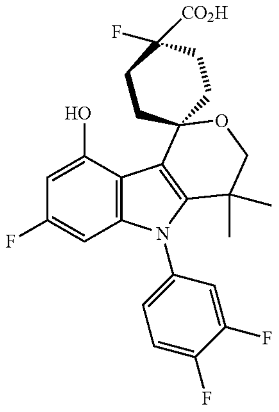
81
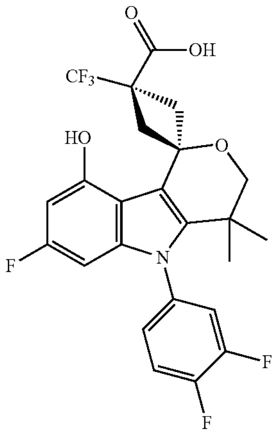 [SMILES: CC1(C)CO[C@]2(C[C@](C(=O)O)(C(F)(F)F)C2)c2c1n(-c1ccc(F)c(F)c1)c1cc(F)cc(O)c12]
82
83
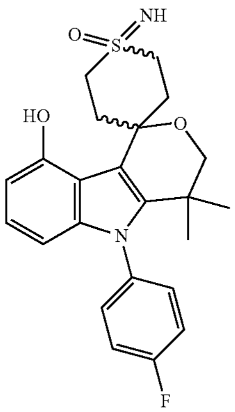 [SMILES: CC1(C)COC2(CCS(=N)(=O)CC2)c2c1n(-c1ccc(F)cc1)c1cccc(O)c21]

TABLE A-continued
Compounds 1-210
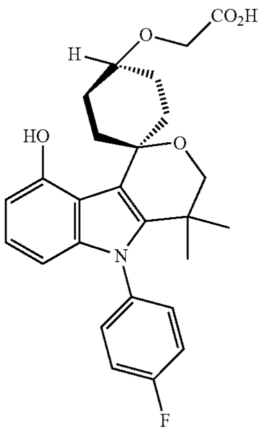
84
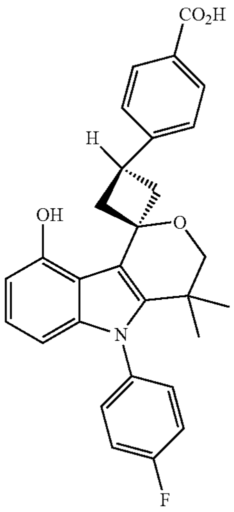 [SMILES: CC1(C)CO[C@]2(C[C@@H](c3ccc(C(=O)O)cc3)C2)c2c1n(-c1ccc(F)cc1)c1cccc(O)c12]
85
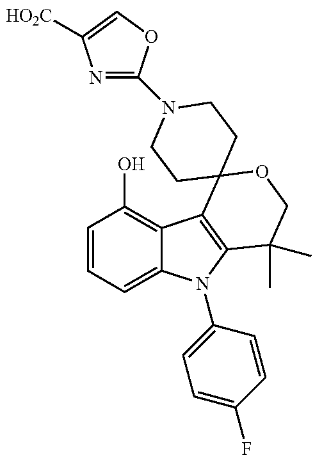 [SMILES: CC1(C)COC2(CCN(c3nc(C(=O)O)co3)CC2)c2c1n(-c1ccc(F)cc1)c1cccc(O)c21]
86
TABLE A-continued
Compounds 1-210
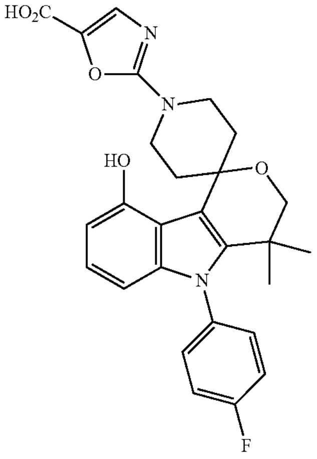 [SMILES: CC1(C)COC2(CCN(c3ncc(C(=O)O)o3)CC2)c2c1n(-c1ccc(F)cc1)c1cccc(O)c21]
87
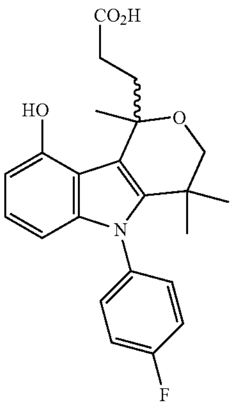 [SMILES: CC1(C)COC(C)(CCC(=O)O)c2c1n(-c1ccc(F)cc1)c1cccc(O)c21]
88
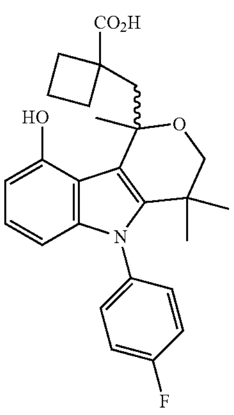 [SMILES: CC1(C)COC(C)(CC2(C(=O)O)CCC2)c2c1n(-c1ccc(F)cc1)c1cccc(O)c21]
89

TABLE A-continued
| Compounds 1-210 |
|---|
| 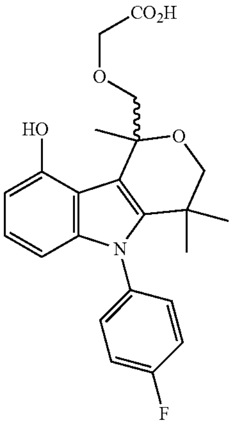 [SMILES: CC1(C)COC(C)(COCC(=O)O)c2c1n(-c1ccc(F)cc1)c1cccc(O)c21] 90 |
| 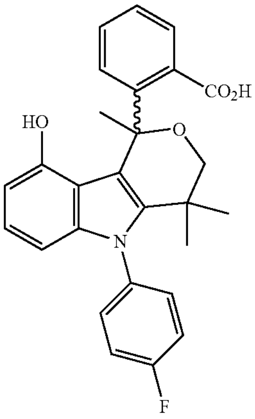 [SMILES: CC1(C)COC(C)(c2ccccc2C(=O)O)c2c1n(-c1ccc(F)cc1)c1cccc(O)c21] 91 |
| 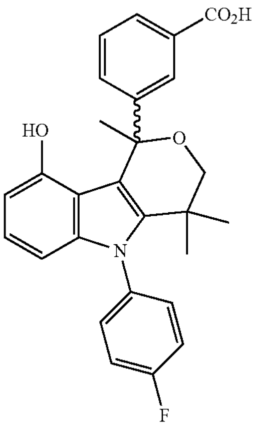 [SMILES: CC1(C)COC(C)(c2cccc(C(=O)O)c2)c2c1n(-c1ccc(F)cc1)c1cccc(O)c21] 92 |
TABLE A-continued
| Compounds 1-210 |
|---|
| 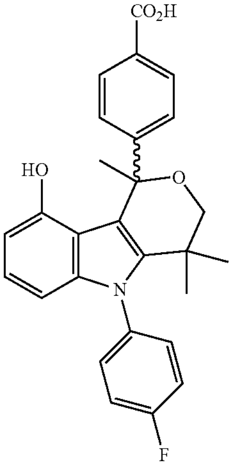 [SMILES: CC1(C)COC(C)(c2ccc(C(=O)O)cc2)c2c1n(-c1ccc(F)cc1)c1cccc(O)c21] 93 |
| 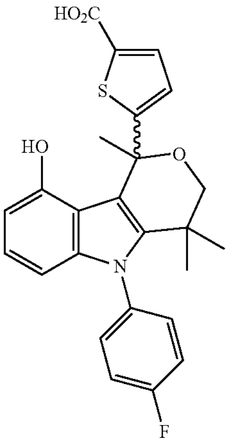 [SMILES: CC1(C)COC(C)(c2ccc(C(=O)O)s2)c2c1n(-c1ccc(F)cc1)c1cccc(O)c21] 94 |
| 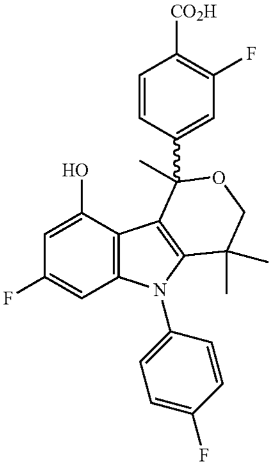 [SMILES: CC1(C)COC(C)(c2ccc(C(=O)O)c(F)c2)c2c1n(-c1ccc(F)cc1)c1cc(F)cc(O)c21] 95 |

TABLE A-continued
| Compounds 1-210 | |
|---|---|
| 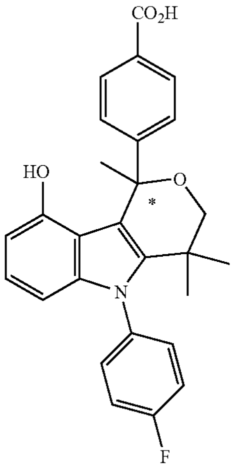 [SMILES: CC1(C)COC(C)(c2ccc(C(=O)O)cc2)c2c1n(-c1ccc(F)cc1)c1cccc(O)c21] | 96 |
| 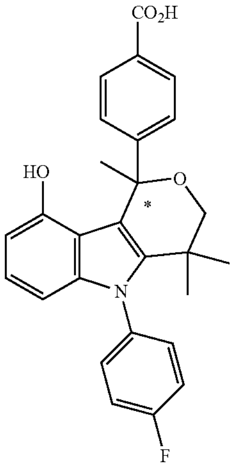 [SMILES: CC1(C)COC(C)(c2ccc(C(=O)O)cc2)c2c1n(-c1ccc(F)cc1)c1cccc(O)c21] | 97 |
| 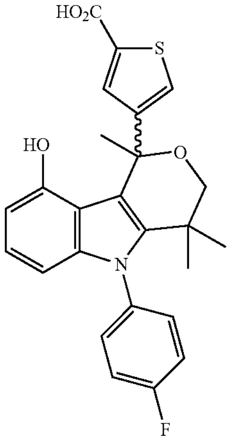 [SMILES: CC1(C)COC(C)(c2csc(C(=O)O)c2)c2c1n(-c1ccc(F)cc1)c1cccc(O)c21] | 98 |
| 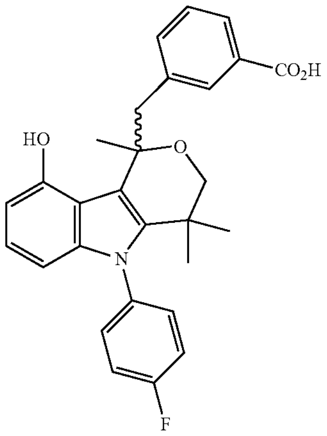 [SMILES: CC1(C)COC(C)(Cc2cccc(C(=O)O)c2)c2c1n(-c1ccc(F)cc1)c1cccc(O)c21] | 99 |
| 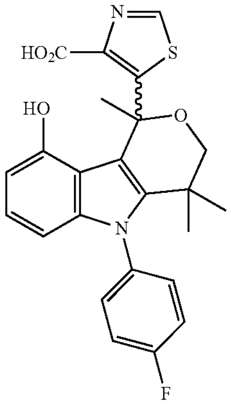 [SMILES: CC1(C)COC(C)(c2scnc2C(=O)O)c2c1n(-c1ccc(F)cc1)c1cccc(O)c21] | 100 |
| 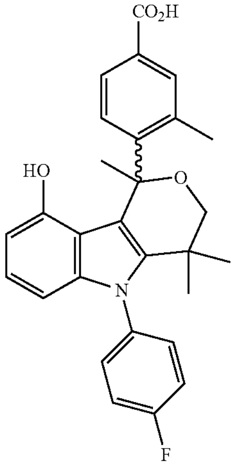 [SMILES: Cc1cc(C(=O)O)ccc1C1(C)OCC(C)(C)c2c1c1c(O)cccc1n2-c1ccc(F)cc1] | 101 |

TABLE A-continued
| Compounds 1-210 | |
|---|---|
| 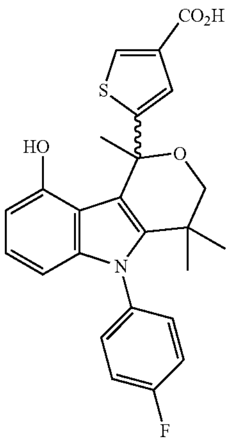 [SMILES: CC1(C)COC(C)(c2cc(C(=O)O)cs2)c2c1n(-c1ccc(F)cc1)c1cccc(O)c21] | 102 |
| 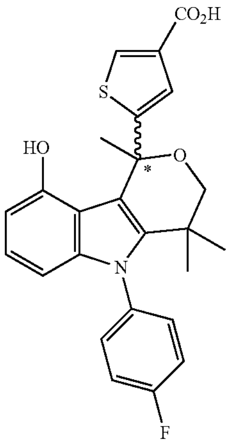 [SMILES: CC1(C)COC(C)(c2cc(C(=O)O)cs2)c2c1n(-c1ccc(F)cc1)c1cccc(O)c21] | 103 |
| 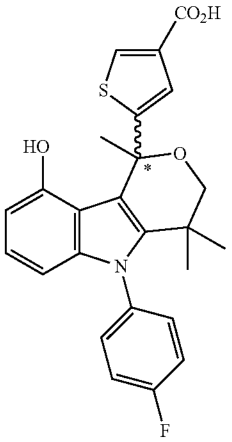 [SMILES: CC1(C)COC(C)(c2cc(C(=O)O)cs2)c2c1n(-c1ccc(F)cc1)c1cccc(O)c21] | 104 |
TABLE A-continued
| Compounds 1-210 | |
|---|---|
| 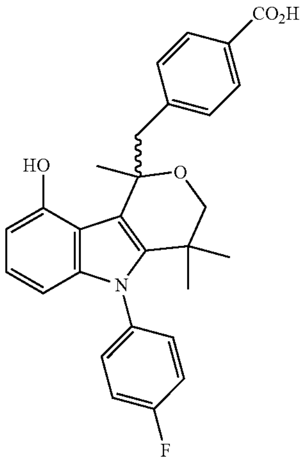 [SMILES: CC1(C)COC(C)(Cc2ccc(C(=O)O)cc2)c2c1n(-c1ccc(F)cc1)c1cccc(O)c21] | 105 |
| 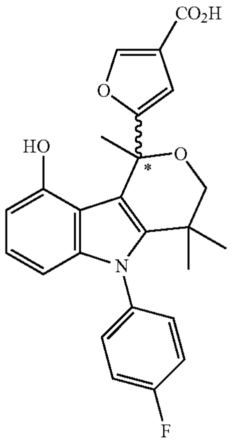 [SMILES: CC1(C)COC(C)(c2cc(C(=O)O)co2)c2c1n(-c1ccc(F)cc1)c1cccc(O)c21] | 106 |
| 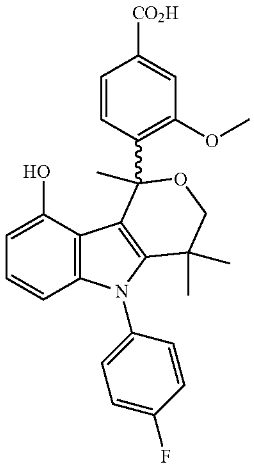 [SMILES: COc1cc(C(=O)O)ccc1C1(C)OCC(C)(C)c2c1c1c(O)cccc1n2-c1ccc(F)cc1] | 107 |

TABLE A-continued
| Compounds 1-210 | |
|---|---|
| 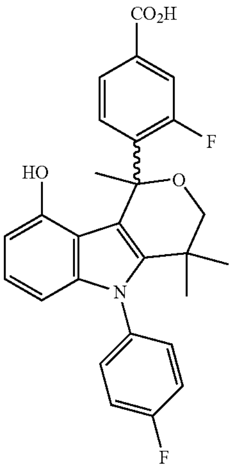 [SMILES: CC1(C)COC(C)(c2ccc(C(=O)O)cc2F)c2c1n(-c1ccc(F)cc1)c1cccc(O)c21] | 108 |
| 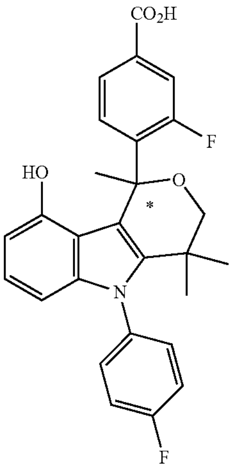 [SMILES: CC1(C)COC(C)(c2ccc(C(=O)O)cc2F)c2c1n(-c1ccc(F)cc1)c1cccc(O)c21] | 109 |
| 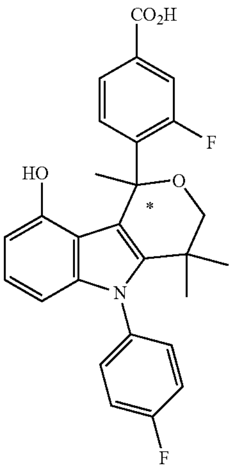 [SMILES: CC1(C)COC(C)(c2ccc(C(=O)O)cc2F)c2c1n(-c1ccc(F)cc1)c1cccc(O)c21] | 110 |
TABLE A-continued
| Compounds 1-210 | |
|---|---|
| 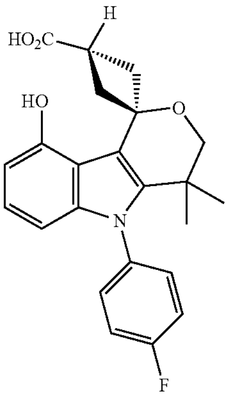 [SMILES: CC1(C)CO[C@]2(C[C@H](C(=O)O)C2)c2c1n(-c1ccc(F)cc1)c1cccc(O)c12] | 111 |
| 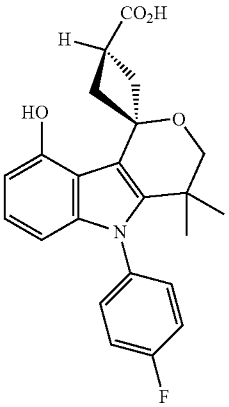 [SMILES: CC1(C)CO[C@]2(C[C@@H](C(=O)O)C2)c2c1n(-c1ccc(F)cc1)c1cccc(O)c12] | 112 |
| 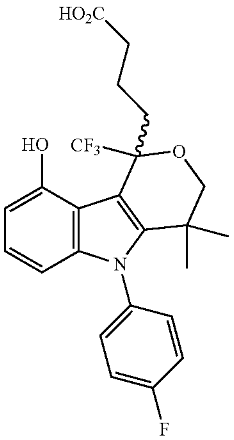 [SMILES: CC1(C)COC(CCCC(=O)O)(C(F)(F)F)c2c1n(-c1ccc(F)cc1)c1cccc(O)c21] | 113 |

TABLE A-continued
| Compounds 1-210 |
| --- |
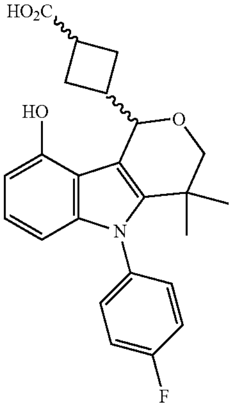 [SMILES: CC1(C)COC(C2CC(C(=O)O)C2)c2c1n(-c1ccc(F)cc1)c1cccc(O)c21]
114
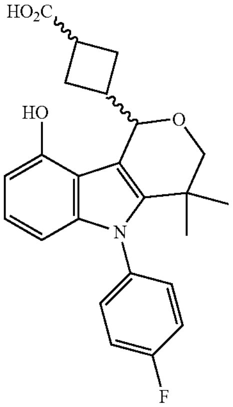 [SMILES: CC1(C)COC(C2CC(C(=O)O)C2)c2c1n(-c1ccc(F)cc1)c1cccc(O)c21]
115
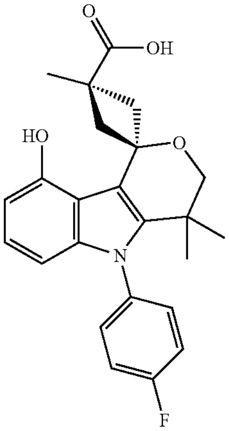 [SMILES: CC1(C)CO[C@]2(C[C@@](C)(C(=O)O)C2)c2c1n(-c1ccc(F)cc1)c1cccc(O)c12]
116
TABLE A-continued
| Compounds 1-210 |
| --- |
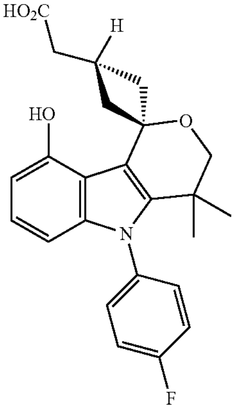 [SMILES: CC1(C)CO[C@]2(C[C@H](CC(=O)O)C2)c2c1n(-c1ccc(F)cc1)c1cccc(O)c12]
117
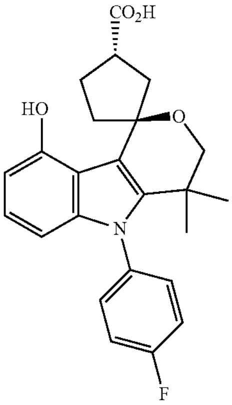 [SMILES: CC1(C)CO[C@]2(CC[C@H](C(=O)O)C2)c2c1n(-c1ccc(F)cc1)c1cccc(O)c21]
118
119
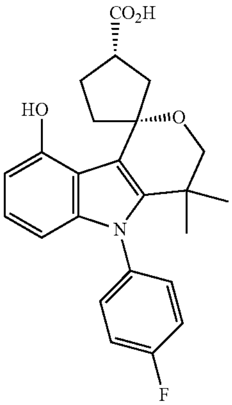 [SMILES: CC1(C)CO[C@@]2(CC[C@H](C(=O)O)C2)c2c1n(-c1ccc(F)cc1)c1cccc(O)c21]

TABLE A-continued
| Compounds 1-210 |
|---|
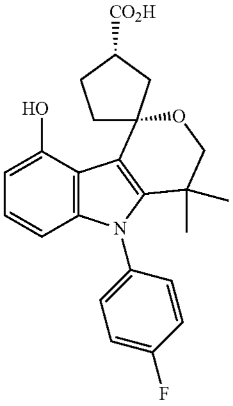 [SMILES: CC1(C)CO[C@@]2(CC[C@H](C(=O)O)C2)c2c1n(-c1ccc(F)cc1)c1cccc(O)c21]
120
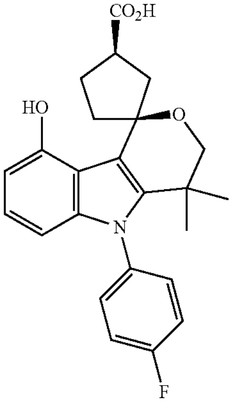 [SMILES: CC1(C)CO[C@]2(CC[C@@H](C(=O)O)C2)c2c1n(-c1ccc(F)cc1)c1cccc(O)c21]
121
122
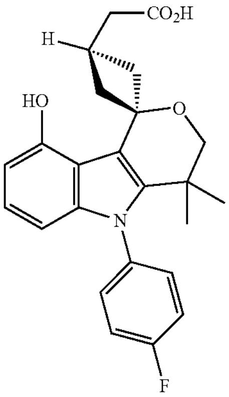 [SMILES: CC1(C)CO[C@]2(C[C@@H](CC(=O)O)C2)c2c1n(-c1ccc(F)cc1)c1cccc(O)c12]
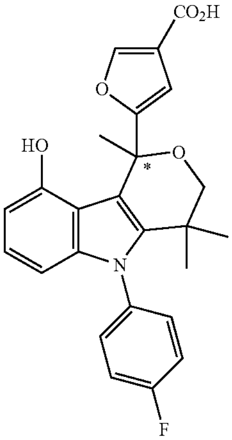 [SMILES: CC1(C)COC(C)(c2cc(C(=O)O)co2)c2c1n(-c1ccc(F)cc1)c1cccc(O)c21]
123
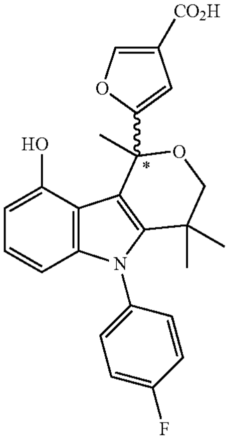 [SMILES: CC1(C)COC(C)(c2cc(C(=O)O)co2)c2c1n(-c1ccc(F)cc1)c1cccc(O)c21]
124
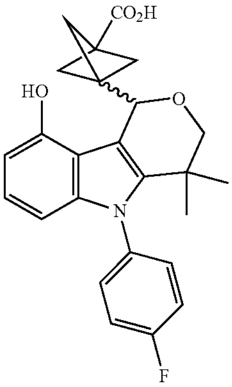 [SMILES: CC1(C)COC(C23CC(C(=O)O)(C2)C3)c2c1n(-c1ccc(F)cc1)c1cccc(O)c21]
125

TABLE A-continued
Compounds 1-210
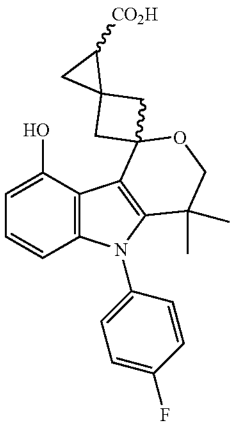 [SMILES: CC1(C)COC2(CC3(CC3C(=O)O)C2)c2c1n(-c1ccc(F)cc1)c1cccc(O)c21]
126
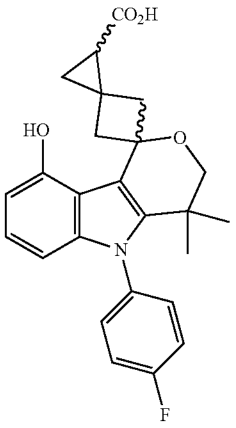 [SMILES: CC1(C)COC2(CC3(CC3C(=O)O)C2)c2c1n(-c1ccc(F)cc1)c1cccc(O)c21]
127
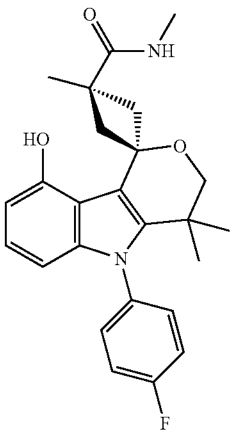 [SMILES: CNC(=O)[C@]1(C)C[C@@]2(C1)OCC(C)(C)c1c2c2c(O)cccc2n1-c1ccc(F)cc1]
128
TABLE A-continued
Compounds 1-210
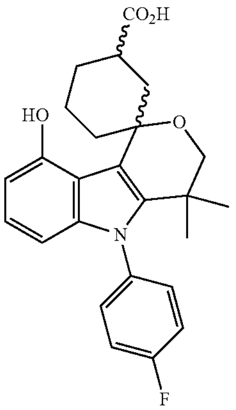 [SMILES: CC1(C)COC2(CCCC(C(=O)O)C2)c2c1n(-c1ccc(F)cc1)c1cccc(O)c21]
129
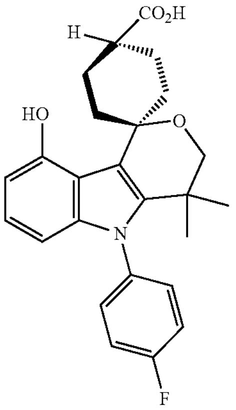
130
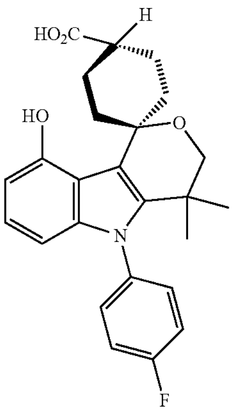
131

TABLE A-continued
Compounds 1-210
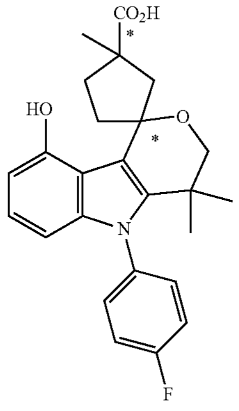 [SMILES: CC1(C(=O)O)CCC2(C1)OCC(C)(C)c1c2c2c(O)cccc2n1-c1ccc(F)cc1]
132
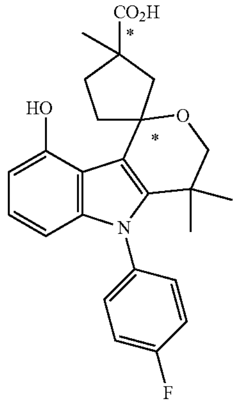 [SMILES: CC1(C(=O)O)CCC2(C1)OCC(C)(C)c1c2c2c(O)cccc2n1-c1ccc(F)cc1]
133
134
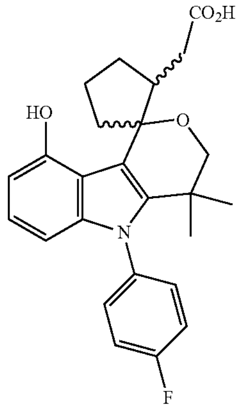 [SMILES: CC1(C)COC2(CCCC2CC(=O)O)c2c1n(-c1ccc(F)cc1)c1cccc(O)c21]
TABLE A-continued
Compounds 1-210
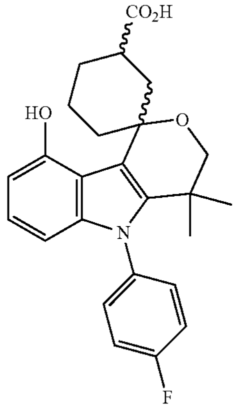 [SMILES: CC1(C)COC2(CCCC(C(=O)O)C2)c2c1n(-c1ccc(F)cc1)c1cccc(O)c21]
135
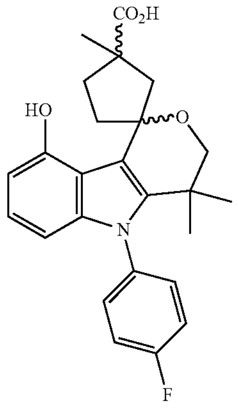 [SMILES: CC1(C(=O)O)CCC2(C1)OCC(C)(C)c1c2c2c(O)cccc2n1-c1ccc(F)cc1]
136
137
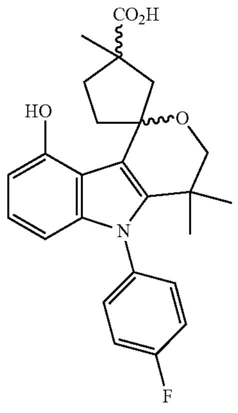 [SMILES: CC1(C(=O)O)CCC2(C1)OCC(C)(C)c1c2c2c(O)cccc2n1-c1ccc(F)cc1]

TABLE A-continued
Compounds 1-210
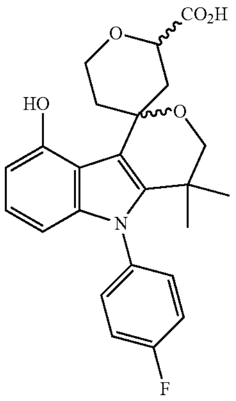 [SMILES: CC1(C)COC2(CCOC(C(=O)O)C2)c2c1n(-c1ccc(F)cc1)c1cccc(O)c21]
138
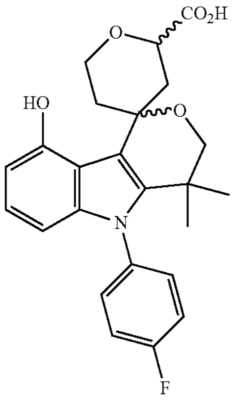 [SMILES: CC1(C)COC2(CCOC(C(=O)O)C2)c2c1n(-c1ccc(F)cc1)c1cccc(O)c21]
139
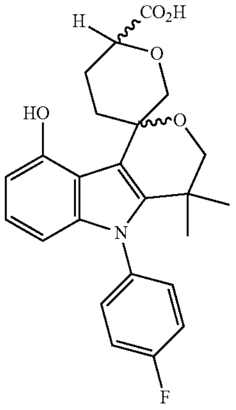 [SMILES: CC1(C)COC2(CCC(C(=O)O)OC2)c2c1n(-c1ccc(F)cc1)c1cccc(O)c21]
140
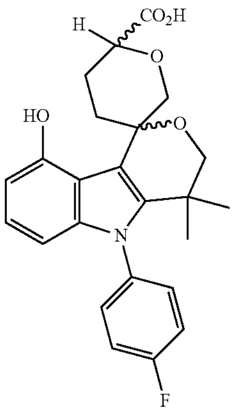 [SMILES: CC1(C)COC2(CCC(C(=O)O)OC2)c2c1n(-c1ccc(F)cc1)c1cccc(O)c21]
141
TABLE A-continued
Compounds 1-210
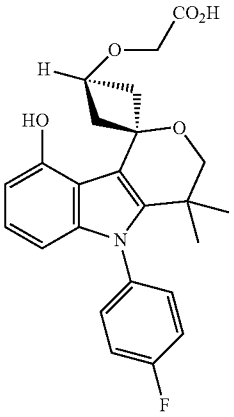 [SMILES: CC1(C)CO[C@]2(C[C@@H](OCC(=O)O)C2)c2c1n(-c1ccc(F)cc1)c1cccc(O)c12]
142
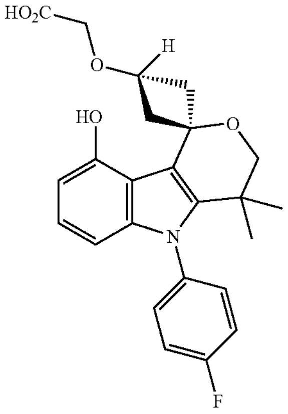 [SMILES: CC1(C)CO[C@]2(C[C@H](OCC(=O)O)C2)c2c1n(-c1ccc(F)cc1)c1cccc(O)c12]
143
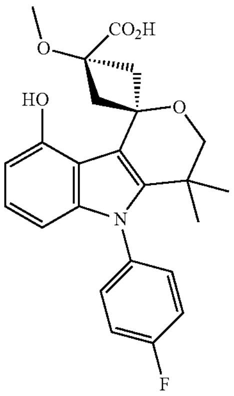 [SMILES: CO[C@]1(C(=O)O)C[C@]2(C1)OCC(C)(C)c1c2c2c(O)cccc2n1-c1ccc(F)cc1]
144

TABLE A-continued
| Compounds 1-210 |
|---|
| 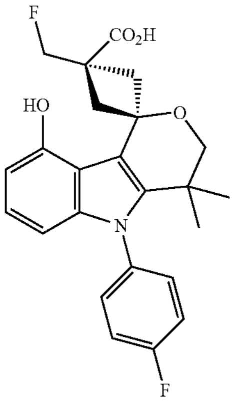 [SMILES: CC1(C)CO[C@]2(C[C@@](CF)(C(=O)O)C2)c2c1n(-c1ccc(F)cc1)c1cccc(O)c12] 145 |
| 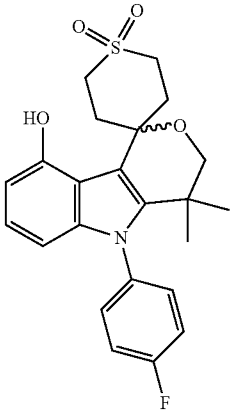 [SMILES: CC1(C)COC2(CCS(=O)(=O)CC2)c2c1n(-c1ccc(F)cc1)c1cccc(O)c21] 146 |
| 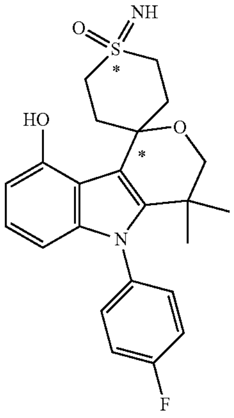 [SMILES: CC1(C)COC2(CCS(=N)(=O)CC2)c2c1n(-c1ccc(F)cc1)c1cccc(O)c21] 147 |
TABLE A-continued
| Compounds 1-210 |
|---|
| 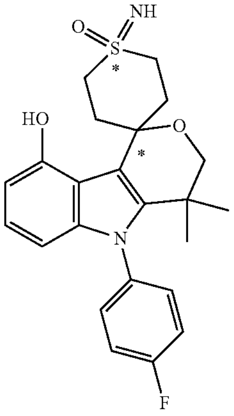 [SMILES: CC1(C)COC2(CCS(=N)(=O)CC2)c2c1n(-c1ccc(F)cc1)c1cccc(O)c21] 148 |
| 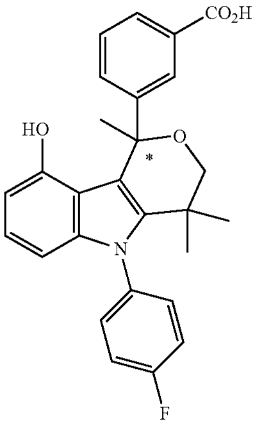 [SMILES: CC1(C)COC(C)(c2cccc(C(=O)O)c2)c2c1n(-c1ccc(F)cc1)c1cccc(O)c21] 149 |
| 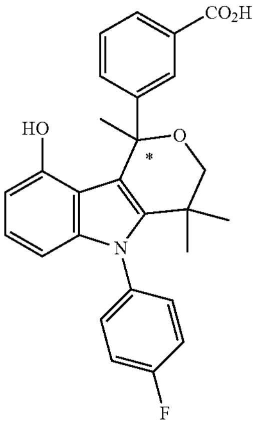 [SMILES: CC1(C)COC(C)(c2cccc(C(=O)O)c2)c2c1n(-c1ccc(F)cc1)c1cccc(O)c21] 150 |

TABLE A-continued
| Compounds 1-210 |
| --- |
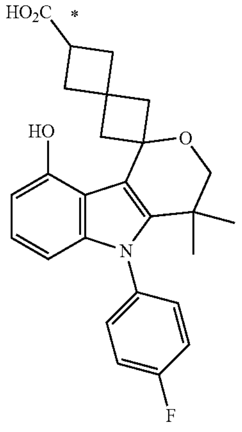 [SMILES: CC1(C)COC2(CC3(CC(C(=O)O)C3)C2)c2c1n(-c1ccc(F)cc1)c1cccc(O)c21]
151
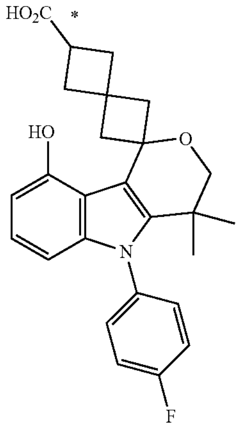 [SMILES: CC1(C)COC2(CC3(CC(C(=O)O)C3)C2)c2c1n(-c1ccc(F)cc1)c1cccc(O)c21]
152
153
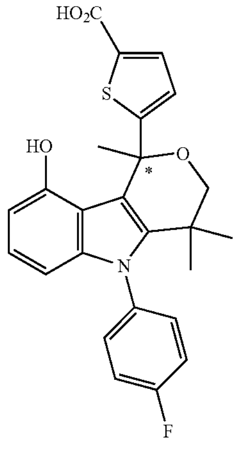 [SMILES: CC1(C)COC(C)(c2ccc(C(=O)O)s2)c2c1n(-c1ccc(F)cc1)c1cccc(O)c21]
TABLE A-continued
| Compounds 1-210 |
| --- |
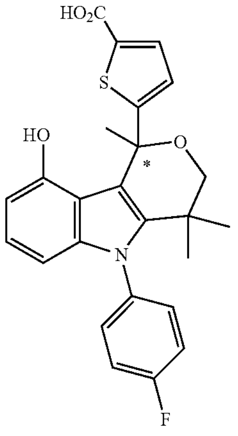 [SMILES: CC1(C)COC(C)(c2ccc(C(=O)O)s2)c2c1n(-c1ccc(F)cc1)c1cccc(O)c21]
154
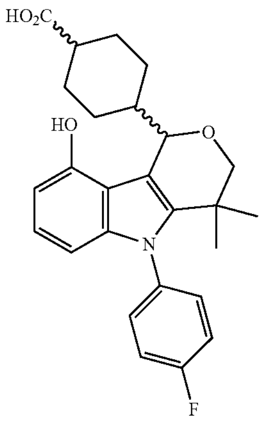 [SMILES: CC1(C)COC(C2CCC(C(=O)O)CC2)c2c1n(-c1ccc(F)cc1)c1cccc(O)c21]
155
156
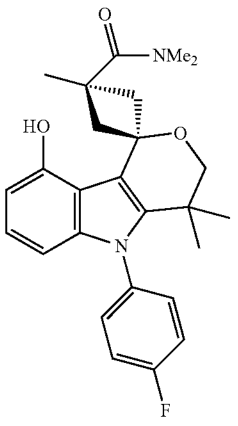 [SMILES: CN(C)C(=O)[C@]1(C)C[C@@]2(C1)OCC(C)(C)c1c2c2c(O)cccc2n1-c1ccc(F)cc1]

TABLE A-continued
| Compounds 1-210 | |
|---|---|
| 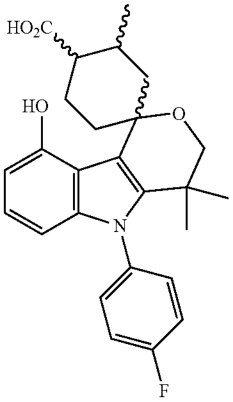 [SMILES: CC1CC2(CCC1C(=O)O)OCC(C)(C)c1c2c2c(O)cccc2n1-c1ccc(F)cc1] | 157 |
| 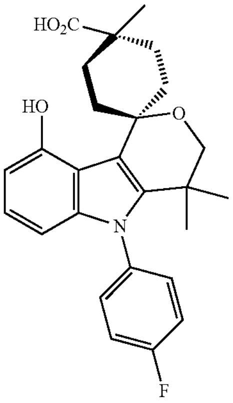 | 158 |
| 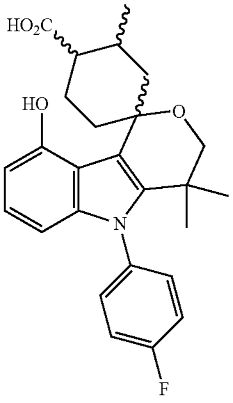 [SMILES: CC1CC2(CCC1C(=O)O)OCC(C)(C)c1c2c2c(O)cccc2n1-c1ccc(F)cc1] | 159 |
TABLE A-continued
| Compounds 1-210 | |
|---|---|
| 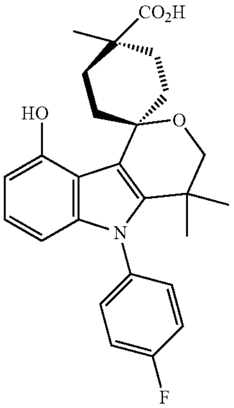 | 160 |
| 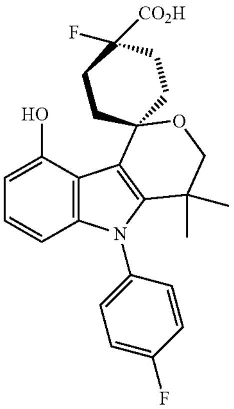 | 161 |
| 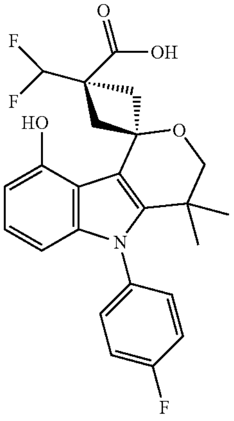 [SMILES: CC1(C)CO[C@]2(C[C@](C(=O)O)(C(F)F)C2)c2c1n(-c1ccc(F)cc1)c1cccc(O)c12] | 162 |

TABLE A-continued
| Compounds 1-210 | |
|---|---|
| 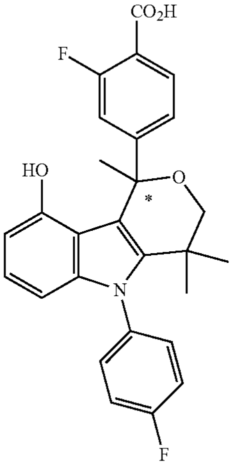 [SMILES: CC1(C)COC(C)(c2ccc(C(=O)O)c(F)c2)c2c1n(-c1ccc(F)cc1)c1cccc(O)c21] | 163 |
| 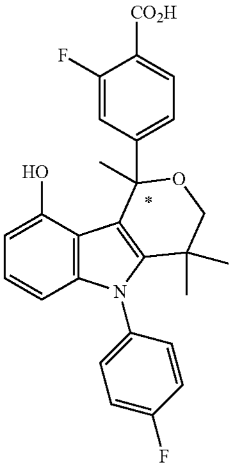 [SMILES: CC1(C)COC(C)(c2ccc(C(=O)O)c(F)c2)c2c1n(-c1ccc(F)cc1)c1cccc(O)c21] | 164 |
| 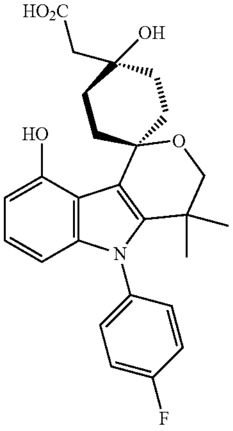 | 165 |
TABLE A-continued
| Compounds 1-210 | |
|---|---|
| 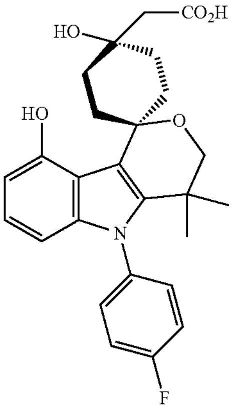 | 166 |
| 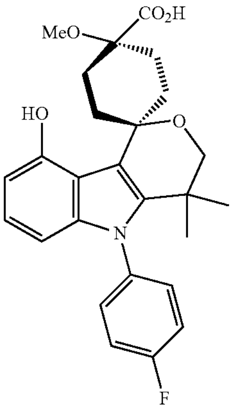 | 167 |
| 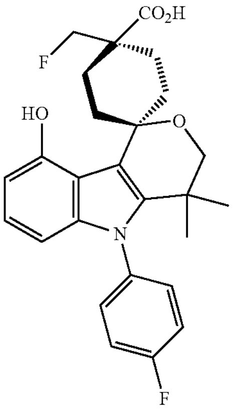 | 168 |

TABLE A-continued
Compounds 1-210
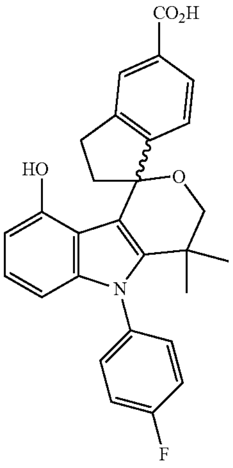 [SMILES: CC1(C)COC2(CCc3cc(C(=O)O)ccc32)c2c1n(-c1ccc(F)cc1)c1cccc(O)c21]
169
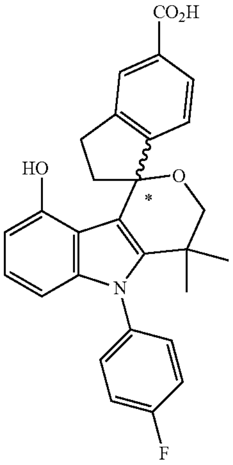 [SMILES: CC1(C)COC2(CCc3cc(C(=O)O)ccc32)c2c1n(-c1ccc(F)cc1)c1cccc(O)c21]
170
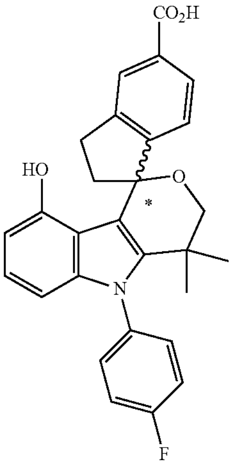 [SMILES: CC1(C)COC2(CCc3cc(C(=O)O)ccc32)c2c1n(-c1ccc(F)cc1)c1cccc(O)c21]
171
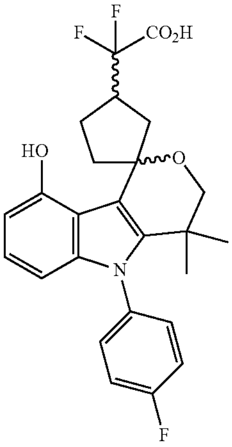 [SMILES: CC1(C)COC2(CCC(C(F)(F)C(=O)O)C2)c2c1n(-c1ccc(F)cc1)c1cccc(O)c21]
172
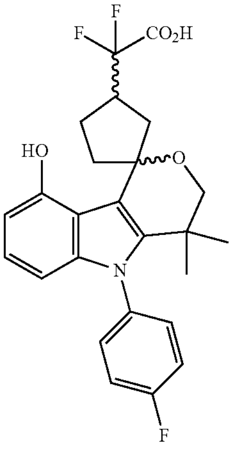 [SMILES: CC1(C)COC2(CCC(C(F)(F)C(=O)O)C2)c2c1n(-c1ccc(F)cc1)c1cccc(O)c21]
173
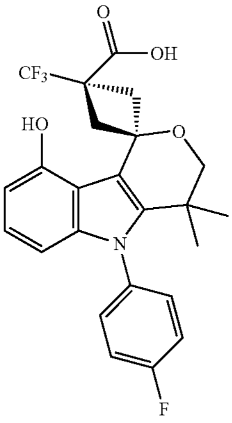 [SMILES: CC1(C)CO[C@]2(C[C@](C(=O)O)(C(F)(F)F)C2)c2c1n(-c1ccc(F)cc1)c1cccc(O)c12]
174

TABLE A-continued
| Compounds 1-210 | |
|---|---|
| 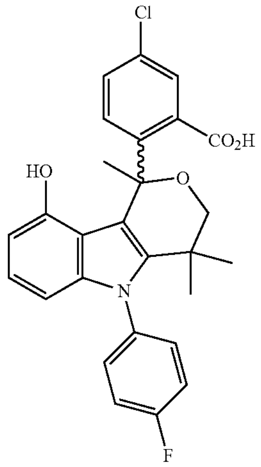 [SMILES: CC1(C)COC(C)(c2ccc(Cl)cc2C(=O)O)c2c1n(-c1ccc(F)cc1)c1cccc(O)c21] | 175 |
| 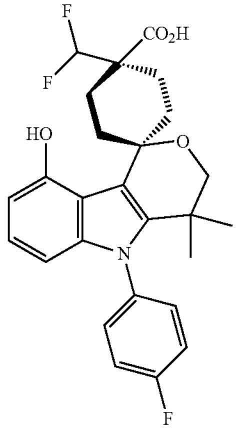 | 176 |
| 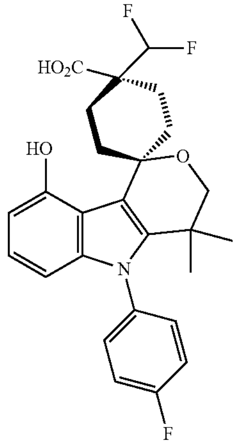 | 177 |
| 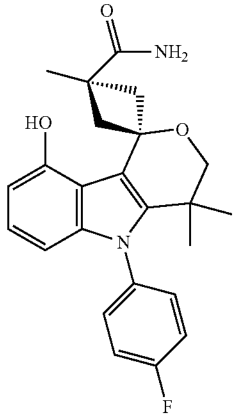 [SMILES: CC1(C)CO[C@]2(C[C@@](C)(C(N)=O)C2)c2c1n(-c1ccc(F)cc1)c1cccc(O)c12] | 178 |
| 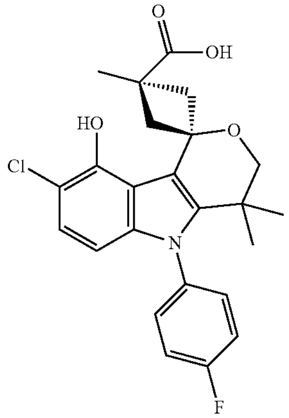 [SMILES: CC1(C)CO[C@]2(C[C@@](C)(C(=O)O)C2)c2c1n(-c1ccc(F)cc1)c1ccc(Cl)c(O)c12] | 179 |
| 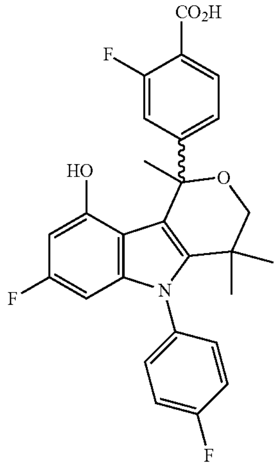 [SMILES: CC1(C)COC(C)(c2ccc(C(=O)O)c(F)c2)c2c1n(-c1ccc(F)cc1)c1cc(F)cc(O)c21] | 180 |

TABLE A-continued
Compounds 1-210
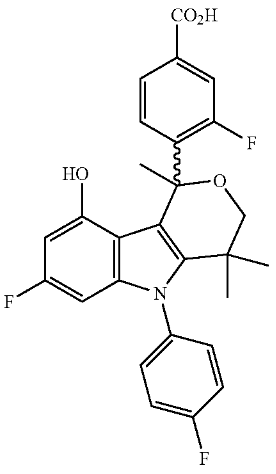
181
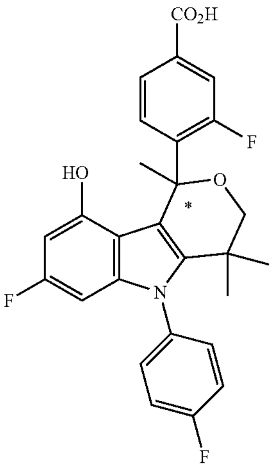
182
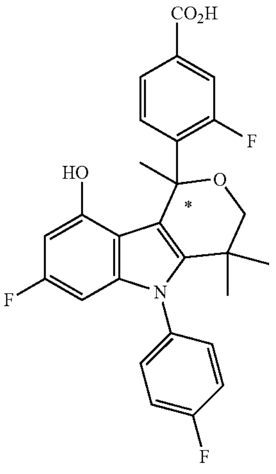 [SMILES: CC1(C)COC(C)(c2ccc(C(=O)O)cc2F)c2c1n(-c1ccc(F)cc1)c1cc(F)cc(O)c21]
183
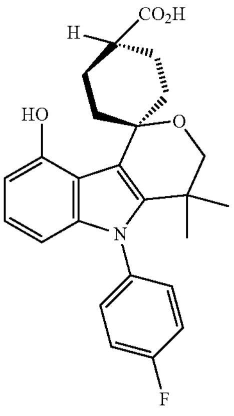
184
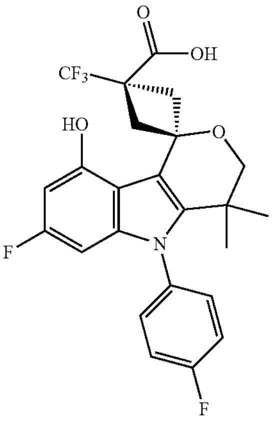 [SMILES: CC1(C)CO[C@]2(C[C@](C(=O)O)(C(F)(F)F)C2)c2c1n(-c1ccc(F)cc1)c1cc(F)cc(O)c12]
185
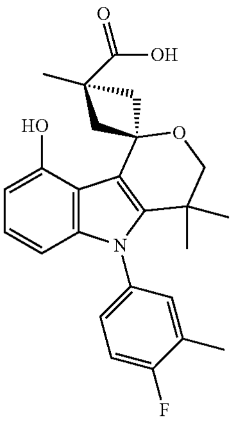 [SMILES: Cc1cc(-n2c3c(c4c(O)cccc42)[C@]2(C[C@](C)(C(=O)O)C2)OCC3(C)C)ccc1F]
186

TABLE A-continued
| Compounds 1-210 |
| --- |
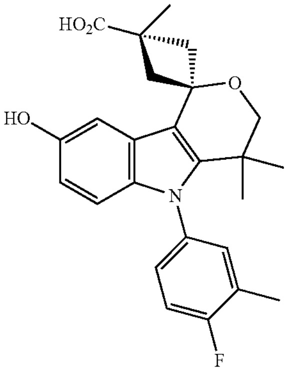 [SMILES: Cc1cc(-n2c3c(c4cc(O)ccc42)[C@]2(C[C@@](C)(C(=O)O)C2)OCC3(C)C)ccc1F]
187
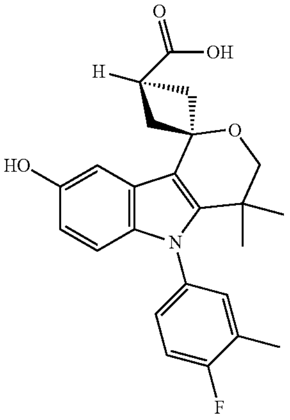 [SMILES: Cc1cc(-n2c3c(c4cc(O)ccc42)[C@]2(C[C@H](C(=O)O)C2)OCC3(C)C)ccc1F]
188
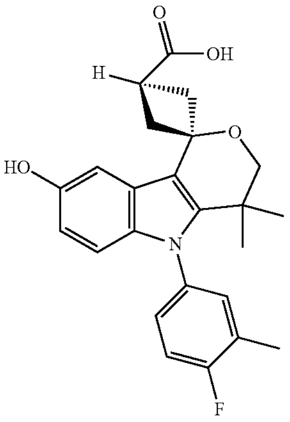 [SMILES: Cc1cc(-n2c3c(c4cc(O)ccc42)[C@]2(C[C@H](C(=O)O)C2)OCC3(C)C)ccc1F]
189
TABLE A-continued
| Compounds 1-210 |
| --- |
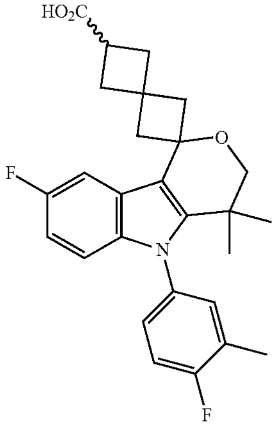 [SMILES: Cc1cc(-n2c3c(c4cc(F)ccc42)C2(CC4(CC(C(=O)O)C4)C2)OCC3(C)C)ccc1F]
190
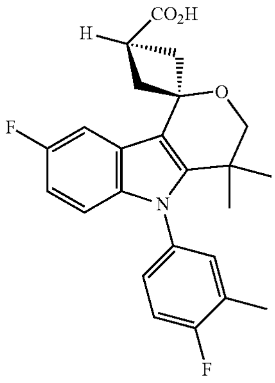 [SMILES: Cc1cc(-n2c3c(c4cc(F)ccc42)[C@]2(C[C@H](C(=O)O)C2)OCC3(C)C)ccc1F]
191
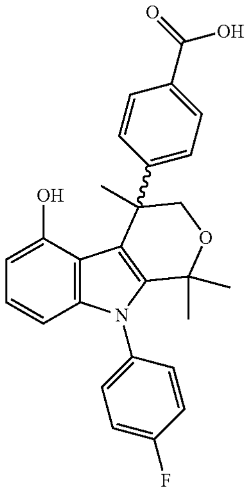 [SMILES: CC1(C)OCC(C)(c2ccc(C(=O)O)cc2)c2c1n(-c1ccc(F)cc1)c1cccc(O)c21]
192

TABLE A-continued
| Compounds 1-210 |
|---|
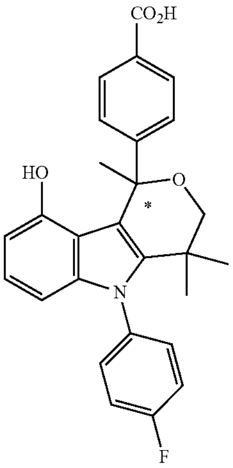 [SMILES: CC1(C)COC(C)(c2ccc(C(=O)O)cc2)c2c1n(-c1ccc(F)cc1)c1cccc(O)c21]
193
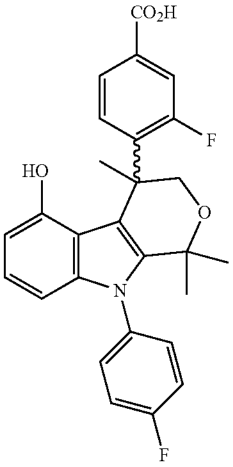 [SMILES: CC1(C)OCC(C)(c2ccc(C(=O)O)cc2F)c2c1n(-c1ccc(F)cc1)c1cccc(O)c21]
194
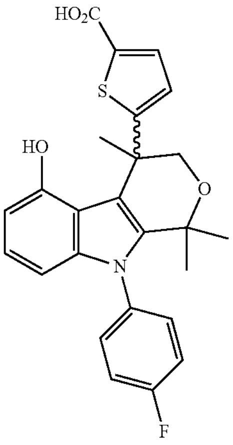 [SMILES: CC1(C)OCC(C)(c2ccc(C(=O)O)s2)c2c1n(-c1ccc(F)cc1)c1cccc(O)c21]
195
TABLE A-continued
| Compounds 1-210 |
|---|
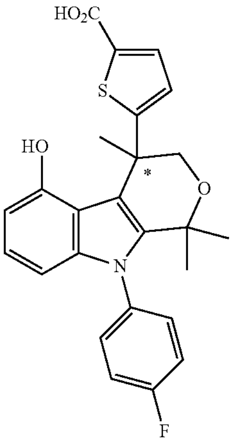 [SMILES: CC1(C)OCC(C)(c2ccc(C(=O)O)s2)c2c1n(-c1ccc(F)cc1)c1cccc(O)c21]
196
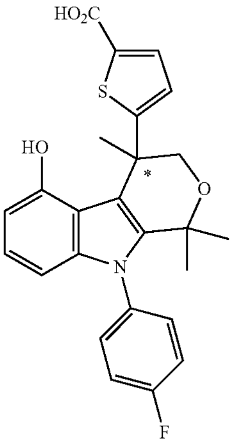 [SMILES: CC1(C)OCC(C)(c2ccc(C(=O)O)s2)c2c1n(-c1ccc(F)cc1)c1cccc(O)c21]
197
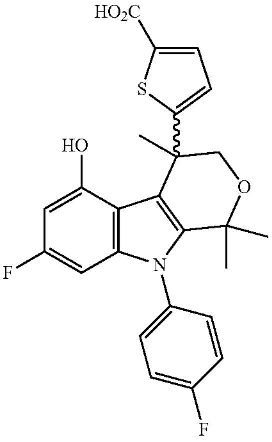 [SMILES: CC1(C)OCC(C)(c2ccc(C(=O)O)s2)c2c1n(-c1ccc(F)cc1)c1cc(F)cc(O)c21]
198

TABLE A-continued
Compounds 1-210
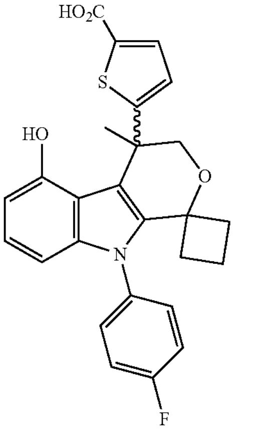 [SMILES: CC1(c2ccc(C(=O)O)s2)COC2(CCC2)c2c1c1c(O)cccc1n2-c1ccc(F)cc1]
199
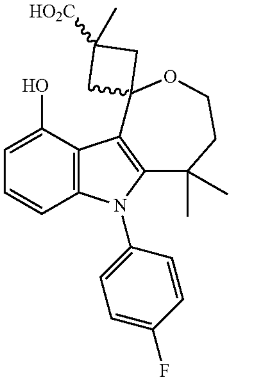 [SMILES: CC1(C(=O)O)CC2(C1)OCCC(C)(C)c1c2c2c(O)cccc2n1-c1ccc(F)cc1]
200
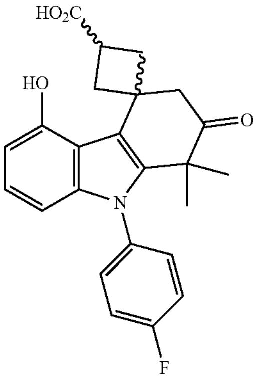 [SMILES: CC1(C)C(=O)CC2(CC(C(=O)O)C2)c2c1n(-c1ccc(F)cc1)c1cccc(O)c21]
201
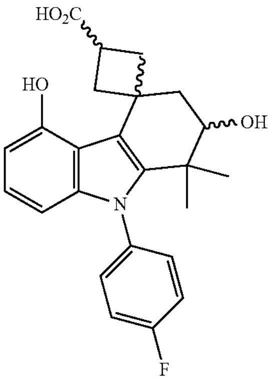 [SMILES: CC1(C)c2c(c3c(O)cccc3n2-c2ccc(F)cc2)C2(CC(C(=O)O)C2)CC1O]
202
TABLE A-continued
Compounds 1-210
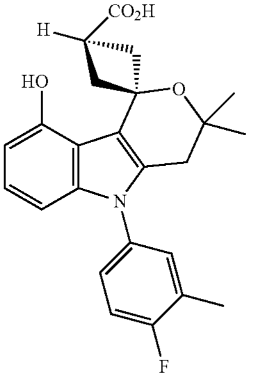 [SMILES: Cc1cc(-n2c3c(c4c(O)cccc42)[C@]2(C[C@H](C(=O)O)C2)OC(C)(C)C3)ccc1F]
203
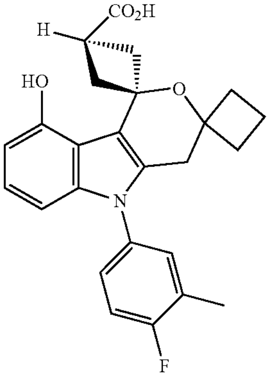 [SMILES: Cc1cc(-n2c3c(c4c(O)cccc42)[C@]2(C[C@H](C(=O)O)C2)OC2(CCC2)C3)ccc1F]
204
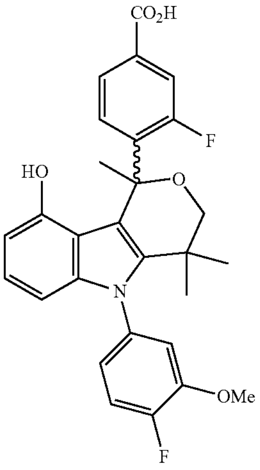 [SMILES: COc1cc(-n2c3c(c4c(O)cccc42)C(C)(c2ccc(C(=O)O)cc2F)OCC3(C)C)ccc1F]
205

TABLE A-continued

| Compounds 1-210 | |
|---|---|
| 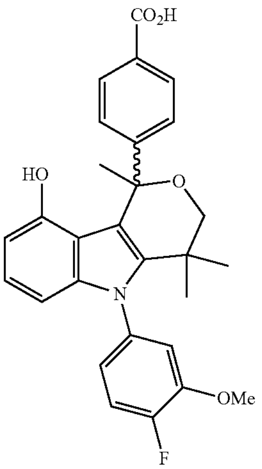 [SMILES: COc1cc(-n2c3c(c4c(O)cccc42)C(C)(c2ccc(C(=O)O)cc2)OCC3(C)C)ccc1F] | 206 |
| 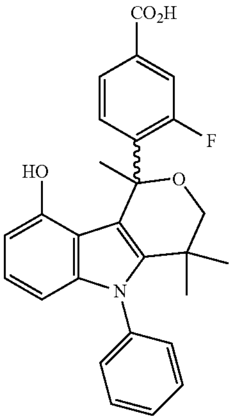 [SMILES: CC1(C)COC(C)(c2ccc(C(=O)O)cc2F)c2c1n(-c1ccccc1)c1cccc(O)c21] | 207 |
| 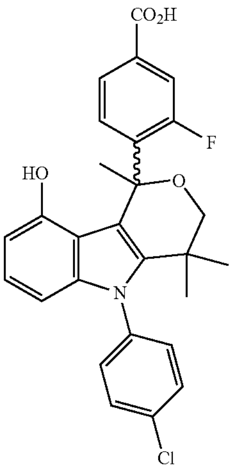 | 208 |
| 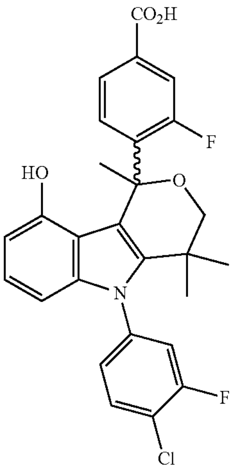 [SMILES: CC1(C)COC(C)(c2ccc(C(=O)O)cc2F)c2c1n(-c1ccc(Cl)c(F)c1)c1cccc(O)c21] | 209 |
| 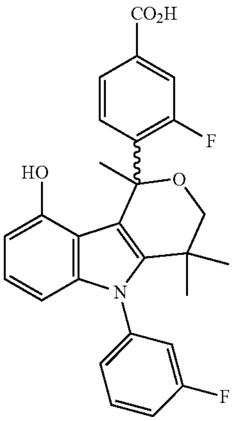 [SMILES: CC1(C)COC(C)(c2ccc(C(=O)O)cc2F)c2c1n(-c1cccc(F)c1)c1cccc(O)c21] | 210 |

Some embodiments of the disclosure include derivatives of Compounds 1-210 or compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) or tautomers thereof. In some embodiments, the derivatives are silicon derivatives in which at least one carbon atom in a compound selected from Compounds 1-210 or compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) has been replaced by silicon. In some embodiments, the derivatives are boron derivatives, in which at least one carbon atom in a compound selected from Compounds 1-210 or compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) or tautomers thereof has been replaced by boron. In other embodiments, the derivatives are phosphate derivatives, in which at least one carbon atom in a compound selected from Compounds 1-210 or compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) or tautomers thereof has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom in a compound selected from Compounds 1-210 or compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) and tautomers thereof has been replaced by silicon. In other embodiments, two carbon atoms have been replaced by silicon. The carbon replaced by silicon may be a non-aromatic carbon. In some embodiments a quaternary carbon atom of a tert-butyl moiety may be replaced by silicon. In some embodiments, the silicon derivatives of the disclosure may include one or more hydrogen atoms replaced by deuterium. For example, one or more hydrogens of a tert-butyl moiety in which the carbon has been replaced by silicon, may be replaced by deuterium. In other embodiments, a silicon derivative of a compound selected from Compounds 1-210 or compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) and tautomers thereof may have silicon incorporated into a heterocycle ring.

Another aspect of the disclosure provides pharmaceutical compositions comprising a compound selected from compounds according to any of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), Compounds 1-210, tautomers of those compounds, deuterated derivatives of those compounds and tautomers, and pharmaceutically acceptable salts of any of the foregoing. In some embodiments, the pharmaceutical composition comprising at least one compound chosen from Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)) and Compounds 1-210, tautomers of those compounds, deuterated derivatives of those compounds and tautomers, and pharmaceutically acceptable salts of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one other active agent. Alternatively, a pharmaceutical composition comprising at least one compound of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing can be administered as a separate composition concurrently with, prior to, or subsequent to, a composition comprising at least one additional active agent. In some embodiments, a pharmaceutical composition comprising at least one compound selected from Compounds 1-210, tautomers of those compounds, deuterated derivatives of those compounds and tautomers, and pharmaceutically acceptable salts of any of the foregoing can be administered as a separate composition concurrently with, prior to, or subsequent to, a composition comprising at least one additional active agent.

In some embodiments, a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing, is combined with at least one additional active agent for simultaneous, separate, or sequential use in the treatment of AATD. In some embodiments, when the use is simultaneous, the compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing, and the at least one additional active agent are in separate pharmaceutical compostions. In some embodiments, when the use is simultaneous, the compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing, and the at least one additional active agent are together in the same pharmaceutical composition. In some embodiments, the compound is a compound selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing, is provided for use in a method of treating AATD, wherein the method comprises co-administering the compound and an additional active agent. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, a combination of a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing, and an additional active agent, is provided for use in a method of treating AATD. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, an additional active agent is provided for use in a method of treating AATD, wherein the method comprises co-administrating the additional active agent and a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing, is provided for use in a method of treating AATD, wherein the compound is prepared for administration in combination with an additional active agent. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, a combination of a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing, and an additional active agent, is provided for use in a method of treating AATD. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, an additional active agent is provided for use in a method of treating AATD, wherein the additional active agent is prepared for administration in combination with a compound of Formula (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), or (VIb-1)-(VIb-2)), tautomers of those compounds, deuterated derivatives of those compounds and tautomers, and pharmaceutically acceptable salts of any of the foregoing. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-210 (e.g., Compounds 1-189 and 192-210), tautomers of those compounds, deuterated derivatives of those compounds and tautomers, and pharmaceutically acceptable salts of any of the foregoing.

In some embodiments, the additional active agent is selected the group consisting of alpha-1 antitrypsin protein (AAT) from the blood plasma of healthy human donors and recombinant AAT. In some embodiments, the additional active agent is alpha-1 antitrypsin protein (AAT) from the blood plasma of healthy human donors. In some embodiments, the additional active agent is alpha-1 antitrypsin protein (AAT) from the blood plasma of healthy human donors.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants).

In another aspect of the disclosure, the compounds and the pharmaceutical compositions, described herein, are used to treat AATD. In some embodiments, the subject in need of treatment with the compounds and compositions of the disclosure carries the ZZ mutation. In some embodiments, the subject in need of treatment with the compounds and compositions of the disclosure carries the SZ mutation.

In some embodiments, the methods of the disclosure comprise administering to a patient in need thereof a compound chosen from any of the compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing. In some embodiments, the compound of Formula (I) is selected from Compounds 1-210, tautomers of those compounds, deuterated derivatives of those compounds and tautomers, and pharmaceutically acceptable salts of any of the foregoing. In some embodiments, said patient in need thereof has a Z mutation in the alpha-1 antitrypsin gene. In some embodiments said patient in need thereof is homozygous for the Z-mutation in the alpha-1 antitrypsin gene.

Another aspect of the disclosure provides methods of modulating alpha-1 antitrypsin activity comprising the step of contacting said alpha-1-antitrypsin with at least one compound of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), tautomers of those compounds, deuterated derivatives of those compounds and tautomers, and pharmaceutically acceptable salts of any of the foregoing. In some embodiments, the methods of modulating alpha-1 antitrypsin activity comprising the step of contacting said alpha-1-antitrypsin with at least one compound selected from Compounds 1-210, tautomers of those compounds, deuterated derivatives of those compounds and tautomers, and pharmaceutically acceptable salts of any of the foregoing.

In some embodiments, the methods of modulating alpha-1 antitrypsin activity take place in vivo. In some embodiments, the methods of modulating alpha-1 antitrypsin activity take place ex vivo and said alpha-1-antitrypsin is from a biological sample obtained from a human subject. In some embodiments, the methods of modulating AAT take place in vitro and said alpha-1-antitrypsin is from a biological sample obtained from a human subject. In some embodiments, the biological sample is a blood sample. In some embodiments, the biological sample is a sample taken from a liver biopsy.

III. Preparation of Compounds

All the generic, subgeneric, and specific compound formulae disclosed herein are considered part of the disclosure.

A. Compounds of Formula I

The compounds of the disclosure may be made according to standard chemical practices or as described herein. Throughout the following synthetic schemes and in the descriptions for preparing compounds of Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-5) (e.g., Formulae (Ia), (Ib), (IIa-1)-(IIa-2), (IIb-1)-(IIb-2), (IIIa), (IIIb-1)-(IIIb-2), (IVa-1)-(IVa-3), (IVb-1)-(IVb-2), (Va-1)-(Va-2), (Vb-1)-(Vb-5), and (VIb-1)-(VIb-2)), Compounds 1-210, tautomers of those compounds, deuterated derivatives of those compounds and tautomers, and pharmaceutically acceptable salts of any of the foregoing, the following abbreviations are used:

Abbreviations

BrettPhos Pd G4=dicyclohexyl-[3,6-dimethoxy-2-[2,4,6-tri(propan-2-yl)phenyl]phenyl]phosphane;methanesulfonic acid;N-methyl-2-phenylaniline; palladium
DIPEA=N,N-Diisopropylethylamine or N-ethyl-N-isopropyl-propan-2-amine
DMA=dimethyl acetamide
DMAP=dimethylamino pyridine
DME=dimethoxyethane
DMF=dimethylformamide
DMSO=dimethyl sulfoxide
EtOH=ethanol
EtOAc=ethyl acetate
HATU=[dimethylamino(triazolo[4,5-b]pyridin-3-yloxy)methylene]-dimethyl-ammonium (Phosphorus Hexafluoride Ion)
MeOH=methanol
MP-TMT scavenger resin=a macroporous polystyrene-bound trimercaptotriazine, a resin bound equivalent of 2,4,6-trimercaptotriazine (TMT).
MTBE=Methyl tert-butyl ether
NMM=N-methyl morpholine
NMP=N-methyl pyrrolidine
$Pd(dppf)_2Cl_2$=[1,1'-Bis(diphenylphosphino)ferrocene]dichloropalladium(II)
$PdCl_2$=palladium(II) dichloride
$PdCl_2(PPh_3)_2$=Bis(triphenylphosphine)palladium(II) dichloride
SFC=super critical fluid chromatography
SPhos Pd G3=(2-Dicyclohexylphosphino-2',6'-dimethoxybiphenyl) [2-(2'-amino-1,1'-biphenyl)]palladium (II) methanesulfonate
TBAF=Tetrabutylammonium fluoride
tBuXPhos Pd G1=Chloro[2-(di-tert-butylphosphino)-2',4',6'-triisopropyl-1,1'-biphenyl][2-(2-aminoethyl)phenyl)]palladium(II) or t-BuXPhos palladium(II) phenethylamine chloride
tBuXPhos Pd G3=[(2-Di-tert-butylphosphino-2',4',6'-triisopropyl-1,1'-biphenyl)-2-(2'-amino-1,1'-biphenyl)] palladium(II) methanesulfonate
tBuXPhos Pd G4=ditert-butyl-[2-(2,4,6-triisopropylphenyl)phenyl]phosphane; dichloromethane; methanesulfonate; N-methyl-2-phenyl-aniline palladium (II)
TFA=trifluoroacetic acid
THE=tetrahydrofuran
XPhos Pd G1=(2-Dicyclohexylphosphino-2',4',6'-triisopropyl-1,1'-biphenyl)[2-(2-aminoethyl)phenyl)]palladium(II) chloride or (XPhos) palladium(II) phenethylamine chloride In some embodiments, processes for preparing compounds of Formula (Ia) or Formula (Ib), tautomers thereof, deuterated derivatives of those compounds and tautomers, or pharmaceutically acceptable salts of any of the foregoing, comprise reacting a compound of Formula (Ia) or (Ib), tautomer, deuterated derivative, or pharmaceutically acceptable salt with a deprotection reagent as depicted in Schemes 1 through 8 below (wherein all variables are as defined for Formula (Ia) or Formula (Ib) above).

Scheme 1

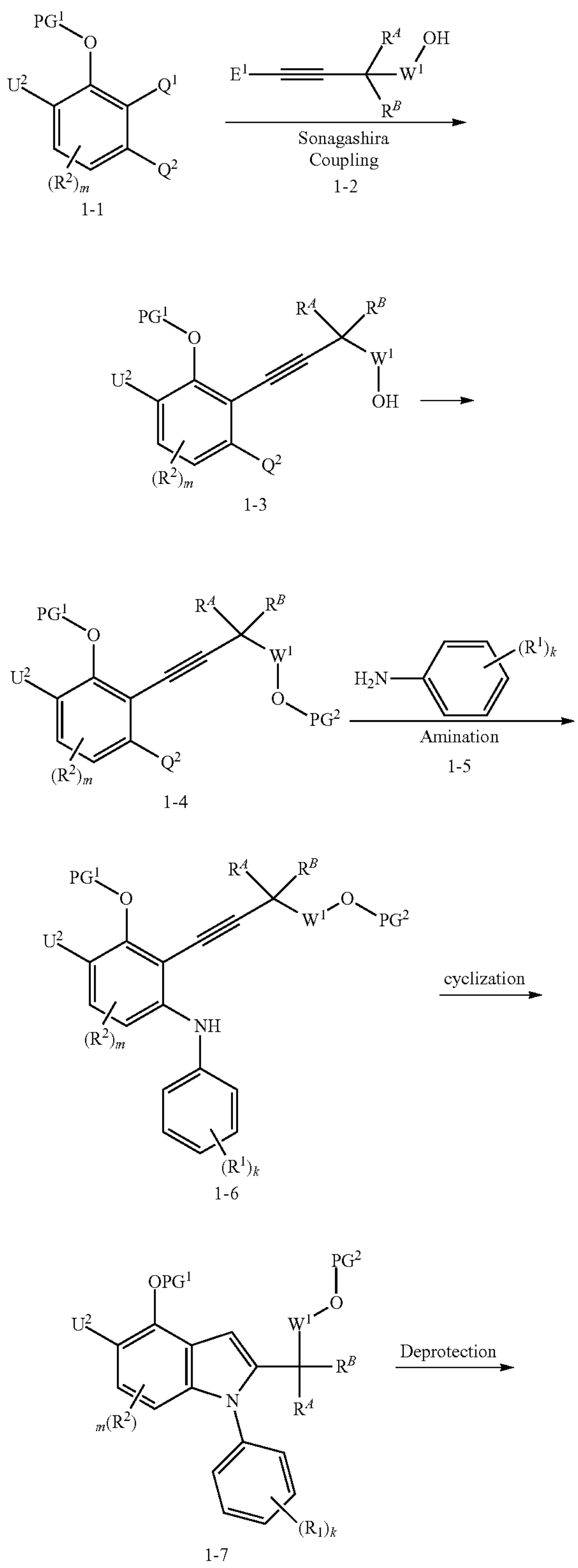

-continued

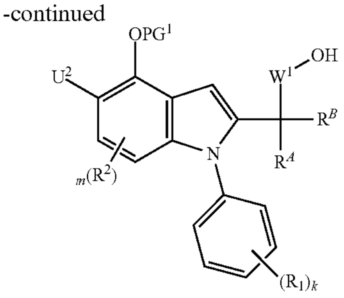

1-8

Scheme 1 refers to processes for the preparation of an intermediate of general formula 1-7, which may be used as an intermediate in the preparation of compound of formula Ia and 1b. $PG^1$ is any suitable alcohol protecting group. For example, $PG^1$ may be Benzyl, methyl, or MOM. $PG^2$ is any suitable alcohol protecting group, which may be removed orthogonally to $PG^1$. For example, $PG^2$ may be a silicon based protecting group such as TBS or TBDPS. $Q^1$ and $Q^2$ are halogens such as $C_1$, Br, or I. A compound of formula 1-3 may be prepared from 1-1 and 1-2 using any suitable conditions for a Sonagashira coupling reaction. For example, the reaction may be performed in the presence of a catalyst such as $Pd(PPh_3)_2Cl_2$ and CuI. A base such as diisopropyl ethyl amine may be used. The reaction may be performed in a solvent such as 1,4-dioxane with added heat (e.g. 50° C.). A compound of formula 1-4 may be prepared from compounds of 1-3 using any suitable reagent for the addition of alcohol protecting group. In some embodiments, TBS chloride in the presence of imidazole, in dichloromethane solvent may be used. A compound of formula 1-5 may be prepared by amination of compounds of formula 1-4 with any suitable conditions for Buchwald amination. For example, in some embodiments a tBuXPhos Pd G3 catalyst in the presence of NaOtBu may be used. The reaction may be performed in a solvent such as m-xylene. The reaction may be performed at ambient temperature. In some embodiments, a compound of formula 1-7 forms spontaneously in the course of the reaction conditions for amination. In some embodiments, compounds of formula 1-7 are formed from 1-6 using any suitable conditions for cyclization of an amine onto an alkyne. For example, in some embodiments, treatment with a palladium catalyst such as $PdCl_2$ or $PdCl_2(MeCN)_2$ may be used. The reaction may be performed in the presence of added heat. The reaction may be performed in methanol and ethyl acetate solvent. In some embodiments, a base such as KOtBu may be used. A compound of formula 1-8 may be prepared from a compound of formula 1-7 using any suitable conditions for the removal of a silicon protecting group. For example, a reagent such as TBAF may be used. The reaction may be performed in a solvent such as 2-methyl-TIF at 70° C.

Scheme 2

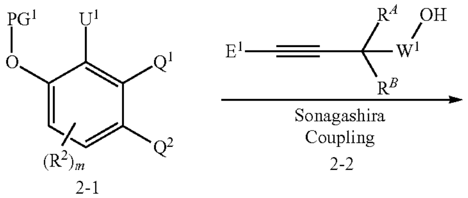

2-1

-continued

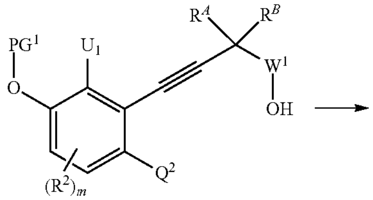

2-3

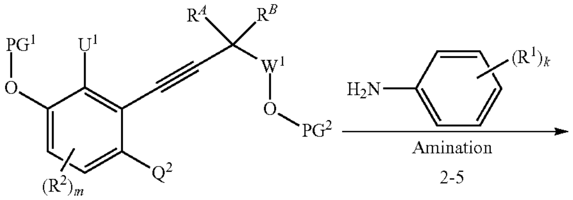

2-4

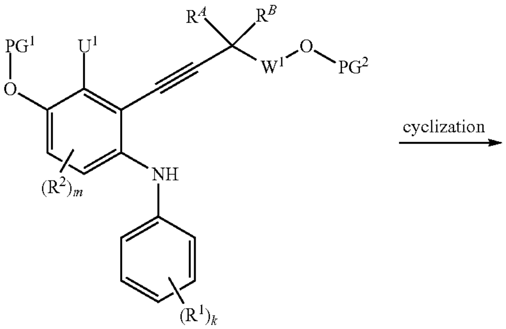

2-6

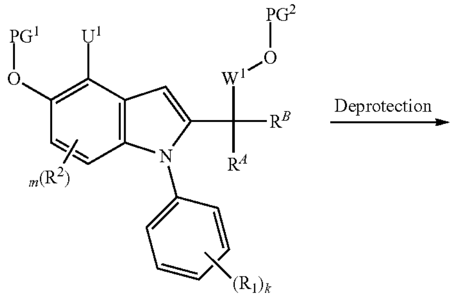

2-7

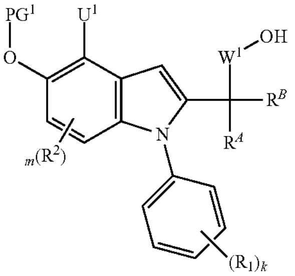

2-8

Scheme 2 shows processed for the preparation of compounds of formula 2-8 which may be used as intermediates in the preparation of compounds of formula Ia and Ib. Compounds of formula 2-8 may be prepared from compounds of formula 2-1 using the methods described for the preparation of compounds of formula 1-8.

Scheme 3

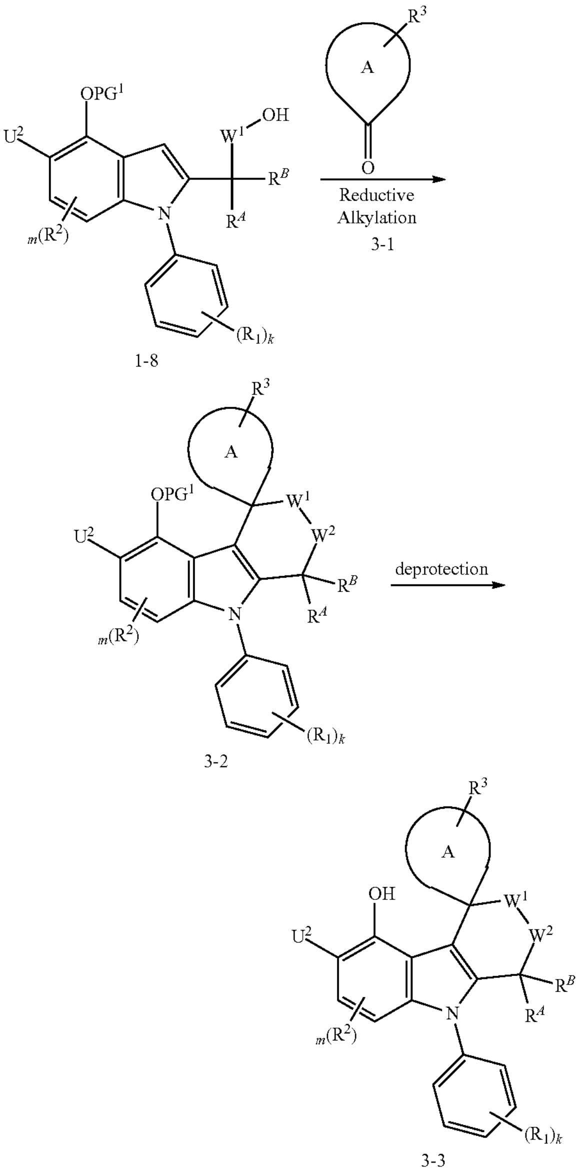

1-8

3-2

3-3

Scheme 3 shows processes for the preparation of compounds of formula 3-3 from compounds of formula 1-8. A compound of formula 3-2 may be prepared from 1-8 by a reductive alkylation, followed by an intramolecular cyclization onto a ketone for formula 3-1. In some embodiments, this reaction may be performed in the presence of a reagent such as triethylsilane and an acid such as methanesulfonic acid. In alternative embodiments, an acid such as trifluoroacetic acid may be used. The reaction may be performed in a solvent such as dichloroethane at room temperature. A compound of formula 3-3 may be prepared from 3-2 using any suitable method for removal on an alcohol protecting group that is appropriate for $PG^1$. In some embodiments, where $PG^1$ is a benzyl group, a transfer hydrogenation conditions may be used. For example, a compound of formula 3-2 may be treated with Pd on carbon and ammonium formate, in a solvent such as ethanol and ethylacetate to afford a compound of formula 3-3. In some embodiment, a $Pd(OH)_2$ catalyst may be used. In some example, a de-alkylating agent such as $BBr_3$ in a solvent such as dichloromethane may be used to remove a benzyl protecting group.

Scheme 4

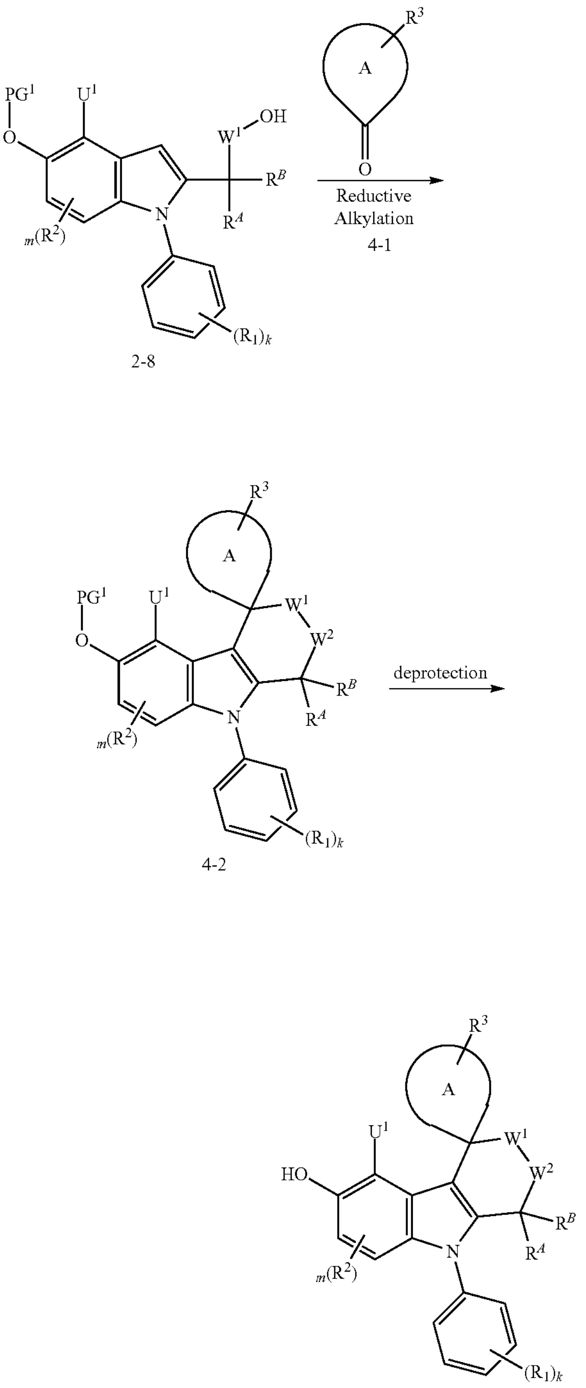

2-8

4-2

4-3

Scheme 4 shows methods for preparation of compounds of formula 4-3. Compounds of formula 4-3 may be prepared from compounds 2-8 using analogous processed used to prepared compounds of formula 3-3.

Scheme 5

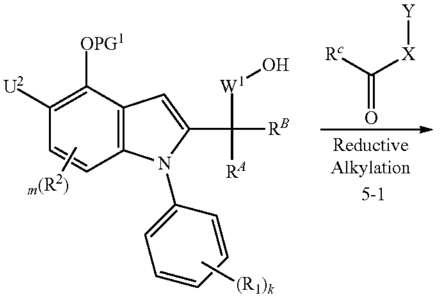

1-8

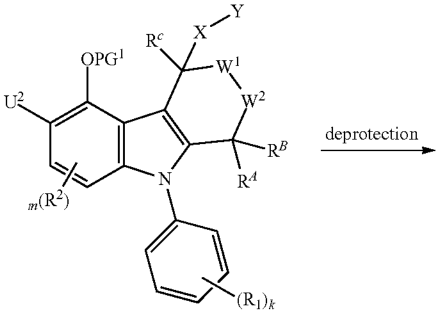

5-2

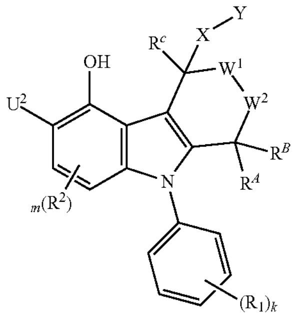

5-3

Scheme 5 shows processes for the preparation of compounds of formula 5-3. Reductive alkylation and cyclization reaction between a compound of formula 1-8 and a ketone of formula 5-1 affords a compound of formula 5-2. The reaction may be performed in the presence of triethylsilane and methanesulfonic acid. The reaction may be performed in a solvent such as dichloroethane or dichloromethane. The reaction may also be performed in the presence of added heat. For example, up to 50° C. Standard alcohol deprotection methods may be used to prepare a compound of formula 5-3 from a compound of formula 5-2.

Scheme 6

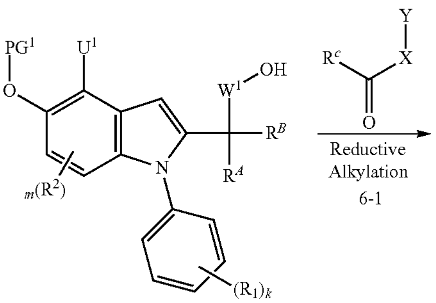

2-8

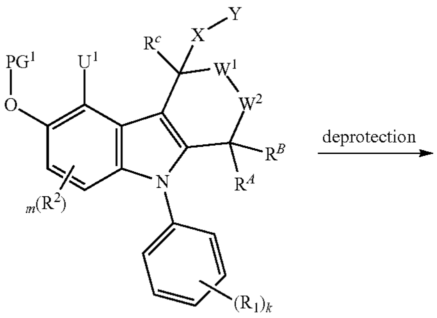

6-2

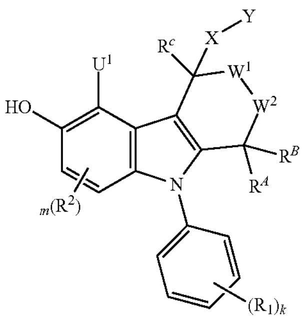

6-3

Scheme 6 shows a process for the preparation of a compound of formula 6-3 from a compound of formula 2-8. Compound of formula 6-3 may be prepared from compounds of formula 2-8 using methods analogous to those used to prepare compounds of formula 5-3.

Scheme 7

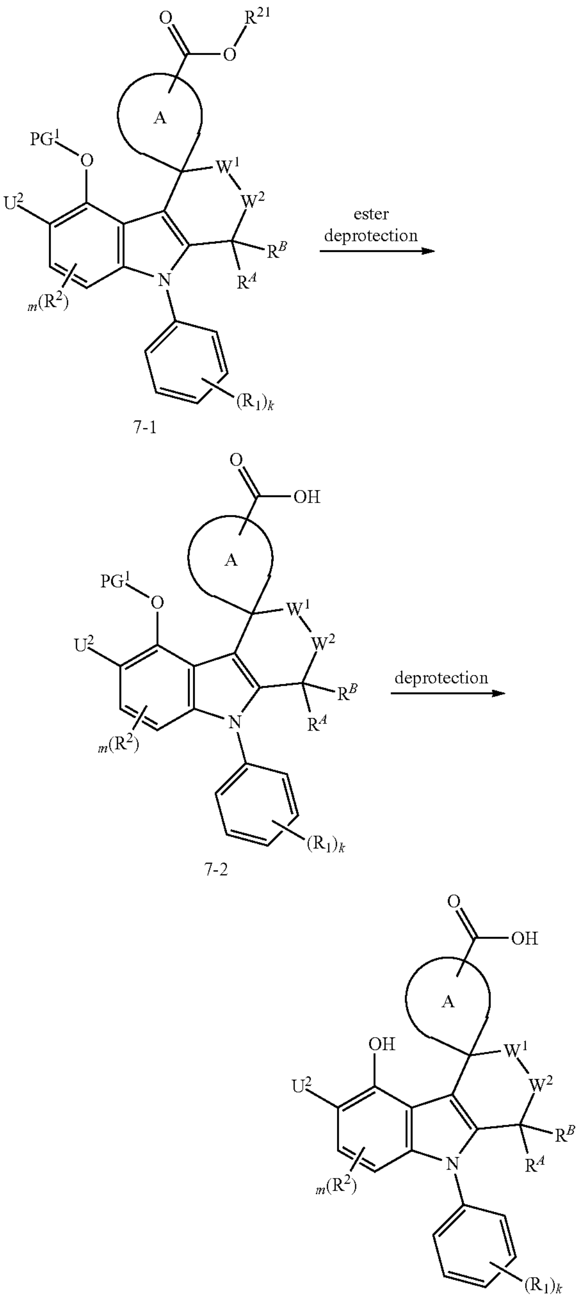

7-1

7-2

7-3

Scheme 7 shows methods for preparation of compounds of formula 7-3 from compounds of formula 7-1. $R^{21}$ is any suitable alkyl group which forms an ester protecting group. For example, $R^{21}$ may be Me, Et, iPr, or tBu. A compound of formula 7-2 may be prepared from 7-1 using any suitable method for ester group deprotection. For example, in some embodiments, hydrolysis with a base such as LiOH in a solvent such as THE and water may be used. In other examples, treatment with $BBr_3$ may be performed. In some embodiments, where $R^{21}$ is a tert-butyl group, a compound of formula 7-1 may be treated with trifluoroacetic acid to afford a compound of formula 7-2.

Scheme 8

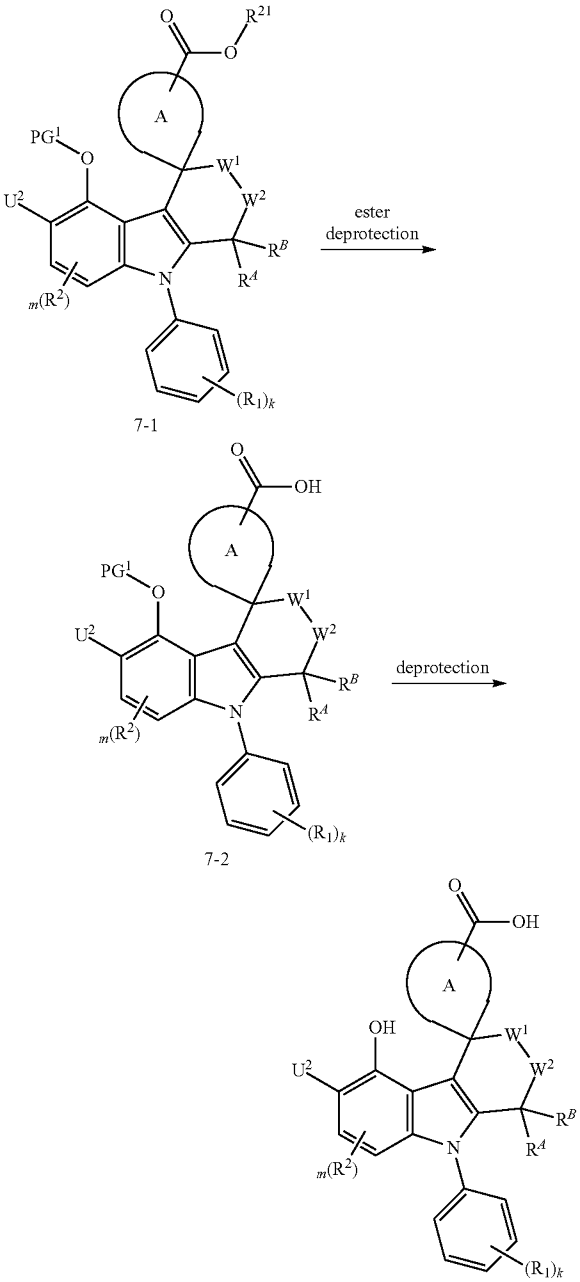

7-1

7-2

7-3

Scheme 8 shows a process for the preparation of compounds of formula 8-2 from compounds of formula 8-1. Analogous conditions to that used for the preparation of compounds of formula 7-3 may be used.

EXAMPLES

In order that the disclosure described herein may be more fully understood, the following examples are set forth. It should be understood that these examples are for illustrative purposes only and are not to be construed as limiting this disclosure in any manner.

Example 1. Synthesis of Compounds

All the specific and generic compounds, the methods for making those compounds, and the intermediates disclosed for making those compounds, are considered to be part of the disclosure.

A. Synthesis of Starting Materials

Preparations of S1-S22 describe synthetic routes to intermediates used in the synthesis of Compound 1-210.

Preparation of S1

2-(4-(Benzyloxy)-1-(4-fluoro-3-methylphenyl)-1H-indol-2-yl)-2-methylpropan-1-ol (S1)

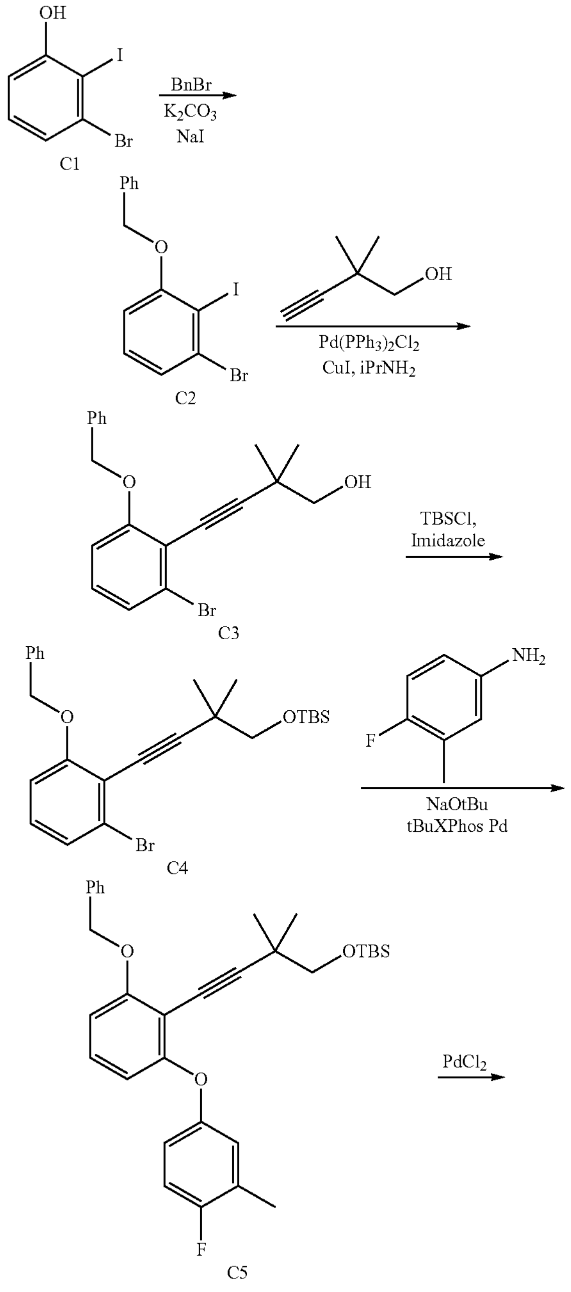

C1, C2, C3, C4, C5

-continued

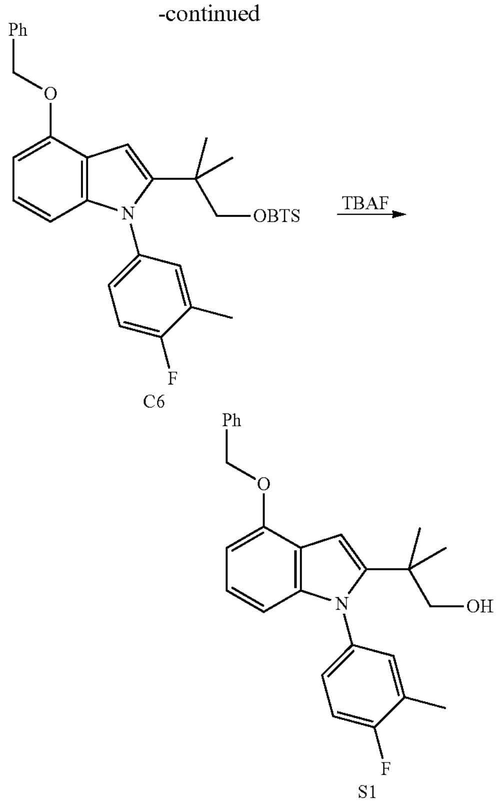

C6, S1

Step 1. Synthesis of 1-benzyloxy-3-bromo-2-iodo-benzene (C2)

A solution of 3-bromo-2-iodo-phenol $C_1$ (129 g, 431.6 mmol) in acetone (1.5 L) was stirred for 5 min. $K_2CO_3$ (75 g, 542.7 mmol), NaI (21 g, 140.1 mmol) and bromomethylbenzene (55 mL, 462.4 mmol) were added. The reaction mixture was stirred at 55° C. for 7 hours. The mixture was then cooled to room temperature, filtered, and washed with acetone (2×100 mL). The combined filtrates were concentrated in vacuo. The residue was dissolved in dichloromethane (1.5 L), washed with water (2×100 mL) and brine (100 mL). The organic phase was dried over $MgSO_4$, filtered and concentrated in vacuo. Purification by silica gel chromatography (0-50% ethyl acetate in heptane) afforded the product C2 as a white solid (162 g, 96%). $^1H$ NMR (300 MHz, Chloroform-d) δ 7.54-7.46 (m, 2H), 7.40 (ddd, J=7.9, 7.0, 1.1 Hz, 2H), 7.37-7.31 (m, 1H), 7.28 (dd, J=8.0, 1.3 Hz, 1H), 7.15 (t, J=8.1 Hz, 1H), 6.76 (dd, J=8.2, 1.3 Hz, 1H), 5.16 (s, 2H).

Step 2. Synthesis of 4-(2-benzyloxy-6-bromo-phenyl)-2,2-dimethyl-but-3-yn-1-ol (C3)

A 3 L 3-neck round bottom flask with overhead stirrer, temperature probe, reflux condenser and nitrogen inlet was charged with 1-benzyloxy-3-bromo-2-iodo-benzene C2 (160 g, 411.3 mmol) and 2,2-dimethylbut-3-yn-1-ol (51 g, 519.6 mmol) in 1,4-dioxane (1.1 L), and stirred for 5 minutes. N-isopropylpropan-2-amine (370 mL, 2.64 mol) was then added. The reaction mixture was purged with nitrogen for ~15 minutes, then iodocopper (3.7 g, 19.4 mmol) and $PdCl_2$ (12.5 g, 17.8 mmol) were added. The resulting reaction mixture was warmed to 50° C., and stirred for 3 h. The reaction mixture was cooled to room temperature, poured into water (300 mL). Sat. aqueous $NH_4Cl$ solution (~400 mL), followed by ethyl acetate (~2 L) were added, and the mixture stirred for 15 minutes. The organic layer was separated, washed with 1 N HCl solution (2×200 mL), brine (200 mL), then dried over $MgSO_4$, filtered and concentrated under reduced pressure. Purified by silica gel chromatography (Gradient: 0-50% ethyl acetate in heptane) afforded the product as a yellow solid. 4-(2-benzyloxy-6-bromo-phenyl)-2,2-dimethyl-but-3-yn-1-ol (130 g, 88%). $^1$H NMR (400 MHz, Chloroform-d) δ 7.48 (ddt, J=7.4, 1.5, 0.7 Hz, 2H), 7.44-7.37 (m, 2H), 7.36-7.29 (m, 1H), 7.19 (dd, J=8.1, 1.0 Hz, 1H), 7.08 (t, J=8.2 Hz, 1H), 6.86 (dd, J=8.3, 1.0 Hz, 1H), 5.13 (s, 2H), 3.48 (d, J=7.2 Hz, 2H), 2.12 (t, J=7.2 Hz, 1H), 1.33 (s, 6H). LCMS m/z 359.02 $[M+1]^+$.

Step 3. Synthesis of [4-(2-benzyloxy-6-bromo-phenyl)-2,2-dimethyl-but-3-ynoxy]-tert-butyl-dimethyl-silane (C4)

A 3 L 3-neck round-bottom flask with overhead stirrer, temperature probe, reflux condenser and nitrogen inlet was charged with 4-(2-benzyloxy-6-bromo-phenyl)-2,2-dimethyl-but-3-yn-1-ol C3 (130 g, 361.9 mmol) in DMF (850 mL). The mixture was stirred for 5 minutes at ambient temperature and then imidazole (64 g, 940.1 mmol) and TBSCl (64 g, 424.6 mmol) were added (observed Tmax=31° C.). The reaction mixture was poured into ice/water (~1 L), and extracted with MTBE (2×1 L). The organic phase was washed with 1 NHCl (2×200 mL), and brine (200 mL), then dried over $MgSO_4$, filtered and concentrated under reduced pressure. The residue was purified by silica gel chromatography (Column: 1.5 kg Isco. Gradient, 0-50% ethyl acetate in heptane) afforded the product C4 as a clear, light yellow color oil. [4-(2-benzyloxy-6-bromo-phenyl)-2,2-dimethyl-but-3-ynoxy]-tert-butyl-dimethyl-silane (164 g, 96%). $^1$H NMR (400 MHz, Chloroform-d) δ 7.55-7.44 (m, 2H), 7.42-7.35 (m, 2H), 7.35-7.28 (m, 1H), 7.19 (dd, J=8.1, 1.0 Hz, 1H), 7.04 (t, J=8.2 Hz, 1H), 6.83 (dd, J=8.4, 1.0 Hz, 1H), 5.12 (s, 2H), 3.59 (s, 2H), 1.31 (s, 6H), 0.90 (s, 9H), 0.05 (s, 6H).

Step 4. Synthesis of 3-benzyloxy-2-[4-[tert-butyl(dimethyl)silyl]oxy-3,3-dimethyl-but-1-ynyl]-N-(4-fluoro-3-methyl-phenyl)aniline (C5)

A solution of [4-(2-benzyloxy-6-bromo-phenyl)-2,2-dimethyl-but-3-ynoxy]-tert-butyl-dimethyl-silane C4 (2 g, 4.224 mmol), 4-fluoro-2-methyl-aniline (600 mg, 4.794 mmol) in dioxane (8 mL) were bubbled with nitrogen for 5 min. To the mixture was added sodium t-butoxide (5 mL of 2 M, 10.00 mmol) then tBuXphosPalladacycle (150 mg, 0.2184 mmol). The reaction was monitored by LC-MS. The reaction is done in 30 min. After stirred overnight at room temperature, water and dichloromethane were added and the layers separated with the aid of a phase separator. The aqueous layer was re-extracted with dichloromethane and the layers were separated through a phase separator again and the combined organics concentrated. Purification by column chromatography (40 g column; 0-20% EtOAc in heptane) gave the product C5 as a straw colored oil (2.1 g, 96%). $^1$H NMR (400 MHz, Chloroform-d) δ 7.49 (dtd, J=6.9, 1.5, 0.8 Hz, 2H), 7.43-7.26 (m, 2H), 7.05-6.87 (m, 3H), 6.65-6.58 (m, 1H), 6.39-6.31 (m, 2H), 5.10 (s, 2H), 3.54 (s, 2H), 2.23 (dd, J=2.0, 0.7 Hz, 2H), 1.53 (s, 3H), 1.29 (s, 6H), 0.96-0.85 (m, 9H), 0.00 (s, 6H).

Step 5. Synthesis of [2-[4-benzyloxy-]-(4-fluoro-3-methyl-phenyl)indol-2-yl]-2-methyl-propoxy]-tert-butyl-dimethyl-silane (C6)

To a mixture of 3-benzyloxy-2-[4-[tert-butyl(dimethyl)silyl]oxy-3,3-dimethyl-but-1-ynyl]-N-(4-fluoro-3-methyl-phenyl)aniline C5 (2.1 g, 96%) in $CH_3CN$ (20 mL) was added $PdCl_2$ (150 mg, 0.846 mmol) and stirred for 20 min. The reaction mixture was concentrated and then purified by 40 g silica gel cartridge eluting with 0-30% EtOAc/heptane to give the product (1.3 g, 59%). $^1$H NMR (400 MHz, Chloroform-d) δ 7.66-7.55 (m, 3H), 7.51-7.35 (m, 3H), 7.28-7.11 (m, 2H), 7.04-6.91 (m, 1H), 6.68 (d, J=0.8 Hz, 1H), 6.61 (dd, J=7.8, 0.7 Hz, 1H), 6.34 (dt, J=8.2, 0.7 Hz, 1H), 5.28 (s, 2H), 3.56 (s, 2H), 2.36 (d, J=2.0 Hz, 3H), 1.60 (s, 2H), 1.25 (d, J=11.6 Hz, 6H), 0.88 (s, 9H), 0.00 (s, 6H).

Step 6. Synthesis of 2-[4-benzyloxy-]-(4-fluoro-3-methyl-phenyl)indol-2-yl]-2-methyl-propan-1-ol (S1)

To a solution of $C_6$ (1.6 g, 3.09 mmol) in THE (5 mL) was added tetrabutylammonium fluoride (1M in THF, 4 mmol) at room temperature. 8:47 AM TLC shows around 50% conversion to product (confirmed by LCMS). After 90 min, a further 2 mL of TBAF was added at room temperature. After 2 hours, the reaction was concentrated and purified by column chromatography (80 g column; 0-100% EtOAc in heptane) to give the product S1 as an off-white solid. $^1$H NMR (400 MHz, Chloroform-d) δ 7.45-7.41 (m, 2H), 7.35-7.22 (m, 3H), 7.11-7.00 (m, 3H), 6.90-6.84 (m, 1H), 6.49 (dd, J=7.8, 0.6 Hz, 1H), 6.21 (dt, J=8.2, 0.7 Hz, 1H), 5.13 (s, 2H), 3.40 (d, J=6.1 Hz, 2H), 2.23 (d, J=2.0 Hz, 3H), 1.14 (s, 6H). LCMS m/z 404.23 $[M+1]^+$

Preparation of S2

2-(4-(Benzyloxy)-1-(3-chloro-4-fluorophenyl)-1H-indol-2-yl)-2-methylpropan-1-ol (S2)

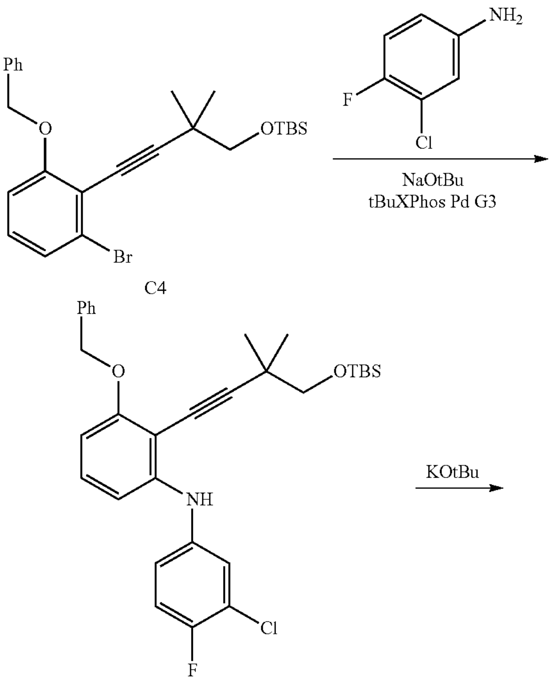

C4

C7

-continued

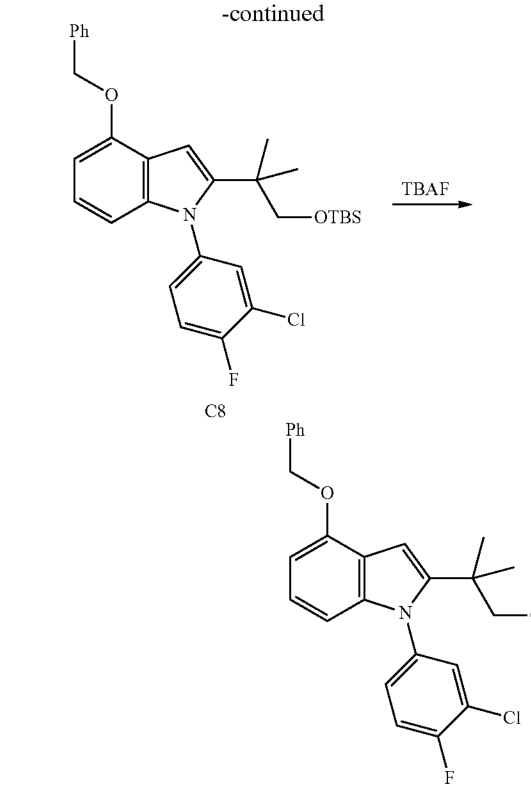

C8

S2

Step 1. Synthesis of 3-(benzyloxy)-2-(4-((tert-butyldimethylsilyl)oxy)-3,3-dimethylbut-1-yn-1-yl)-N-(3-chloro-4-fluorophenyl)aniline (C7)

To a solution of [4-(2-benzyloxy-6-bromo-phenyl)-2,2-dimethyl-but-3-ynoxy]-tert-butyl-dimethyl-silane C7 (1.94 g, 4.10 mmol) and 3-chloro-4-fluoro-aniline (650 mg, 4.47 mmol) in xylene (50 mL) under nitrogen was added NaOtBu (1.18 g, 12.3 mmol) followed by tBuXPhos Pd G3 (145 mg, 0.183 mmol). The reaction mixture was stirred at room temperature for 4 hours then diluted with water, sat aq. $NH_4Cl$ and extracted with EtOAc (twice). The combined organics were concentrated to dryness and purified via silica gel chromatography (eluting with 0-50% EtOAc in heptane). Pure fractions were combined and concentrated to give a light brown oil (2.21 g, 100%).

Step 2. Synthesis of 4-(benzyloxy)-2-(1-((tert-butyldimethylsilyl)oxy)-2-methylpropan-2-yl)-1-(3-chloro-4-fluorophenyl)-1H-indole (C8)

To a solution of 3-(benzyloxy)-2-(4-((tert-butyldimethylsilyl)oxy)-3,3-dimethylbut-1-yn-1-yl)-N-(3-chloro-4-fluorophenyl)aniline C7 in 2-MeTHF (5 mL) was added potassium 2-methylpropan-2-olate (1 M, 5 mL, 5 mmol) at room temperature. After 5 h, the reaction was quenched with sat aq. $NH_4Cl$ and extracted twice with EtOAc. The organic layers were dried ($Na_2SO_4$), filtered and concentrated to give the product (2.21 g, 100%) which was taken into the next reaction without further purification. LCMS m/z 538.36 $[M+1]^+$ Step 3. Synthesis of 2-(4-(Benzyloxy)-1-(3-chloro-4-fluorophenyl)-1H-indol-2-yl)-2-methylpropan-1-ol (S2)

To a solution of 4-(benzyloxy)-2-(1-((tert-butyldimethylsilyl)oxy)-2-methylpropan-2-yl)-1-(3-chloro-4-fluorophenyl)-1H-indole C8 (2.21 g, 4.10 mmol) in 2-MeTHF (5 mL) was added TBAF (1 M solution in THF, 8 mL, 8 mmol). After 4 d, a further 10 mL of TBAF solution was added and the mixture heated at 70° C. overnight. The reaction mixture was concentrated. Purification by column chromatography (120 g column; 0-75% EtOAc in heptane) gave product as a straw colored oil (625 mg, 36%). $^1H$ NMR (400 MHz, Chloroform-d) δ 7.57-7.30 (m, 8H), 7.02 (t, J=8.0 Hz, 1H), 6.74 (d, J=0.8 Hz, 1H), 6.63 (d, J=7.8 Hz, 1H), 6.33 (d, J=8.3 Hz, 1H), 5.26 (s, 2H), 3.53 (d, J=6.3 Hz, 2H), 1.28 (s, 3H), 1.27 (d, J=1.8 Hz, 3H). LCMS m/z 424.21 $[M+1]^+$ Preparation of S3

2-(4-(Benzyloxy)-1-(3-fluoro-4-methylphenyl)-1H-indol-2-yl)-2-methylpropan-1-ol (S3)

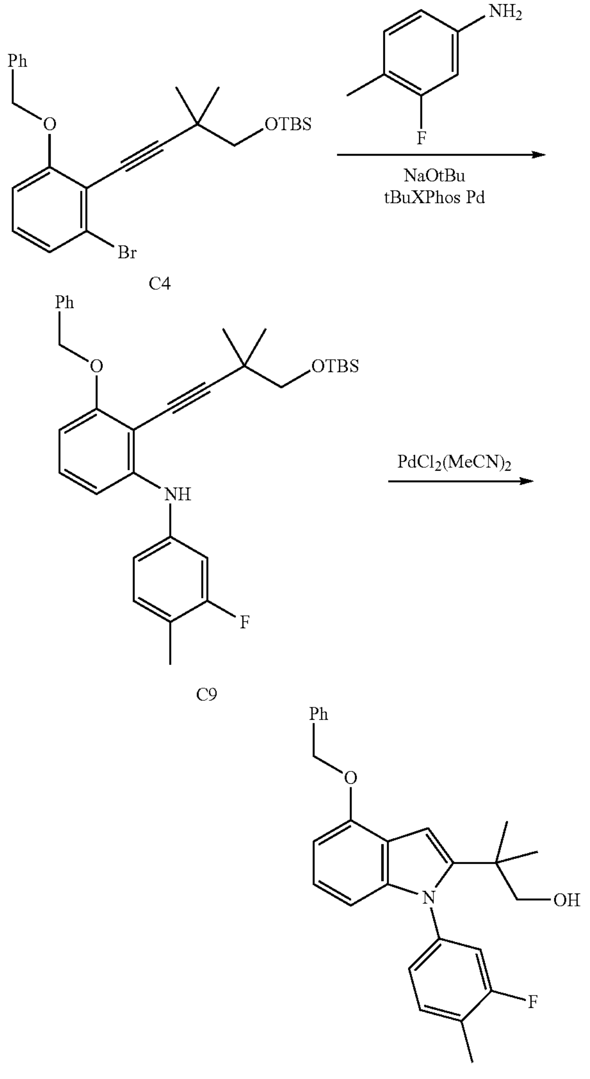

C4

C9

S3

Step 1. Synthesis of 3-(benzyloxy)-2-(4-((tert-butyldimethylsilyl)oxy)-3,3-dimethylbut-1-yn-1-yl)-N-(3-fluoro-4-methylphenyl)aniline (C9)

[4-(2-benzyloxy-6-bromo-phenyl)-2,2-dimethyl-but-3-ynoxy]-tert-butyl-dimethyl-silane C4 (4 g, 8.45 mmol), 3-fluoro-4-methyl-aniline (1.5 g, 12.0 mmol) and sodium 2-methylpropan-2-olate (2 g, 20.8 mmol) were charged into a flask then THE (25 mL). The mixture was stirred for 5 min then degassed with nitrogen for ~10 min. tBuXPhos Pd G1 (0.2 g, 0.3071 mmol) was added then the reaction mixture was degassed for a further few minutes. The resulting reaction mixture was warmed to 60° C. and stirred at this temperature for 3 hours. The solvent was evaporated. Purification by column chromatography (20 g column, eluting with 0-100% ethyl acetate in heptane) gave product (3.58 g, 75%). LCMS m/z 518.51 $[M+1]^+$

Step 2. Synthesis of 2-(4-(Benzyloxy)-1-(3-fluoro-4-methylphenyl)-1H-indol-2-yl)-2-methylpropan-1-ol (S3)

3-(benzyloxy)-2-(4-((tert-butyldimethylsilyl)oxy)-3,3-dimethylbut-1-yn-1-yl)-N-(3-fluoro-4-methylphenyl)aniline C9 (3.50 g, 6.19 mmol) was charged into nitrogen degassed methanol (15 mL)/ethyl acetate (15 mL), then $PdCl_2(CH_3CN)_2$ (320 mg, 1.23 mmol) was added. The reaction was heated at 60° C. for 4 hours then the solvent was evaporated. Purification by column chromatography (80 g column, eluting with 0-100% ethyl acetate in heptane) gave 2-[4-benzyloxy-1-(3-fluoro-4-methyl-phenyl)indol-2-yl]-2-methyl-propan-1-ol (2.3 g, 84%). $^1H$ NMR (400 MHz, Methanol-d4) δ 7.53-7.46 (m, 2H), 7.44-7.34 (m, 3H), 7.34-7.27 (m, 1H), 7.17-7.09 (m, 2H), 6.87 (t, J=8.0 Hz, 1H), 6.59 (d, J=0.8 Hz, 1H), 6.58-6.54 (m, 1H), 6.21 (dt, J=8.3, 0.7 Hz, 1H), 5.19 (s, 2H), 3.48 (s, 2H), 2.38 (d, J=1.9 Hz, 3H), 1.22 (d, J=7.2 Hz, 6H). LCMS m/z 404.36 $[M+1]^+$

Preparation of S4

2-(4-(Benzyloxy)-1-(3,4-difluorophenyl)-1H-indol-2-yl)-2-methylpropan-1-ol (S4)

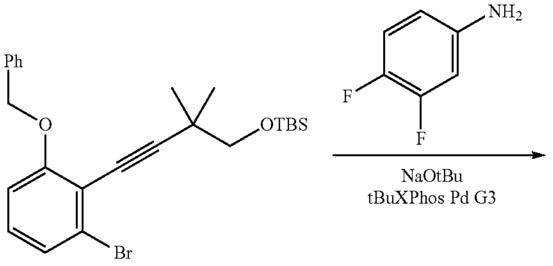

C4

-continued

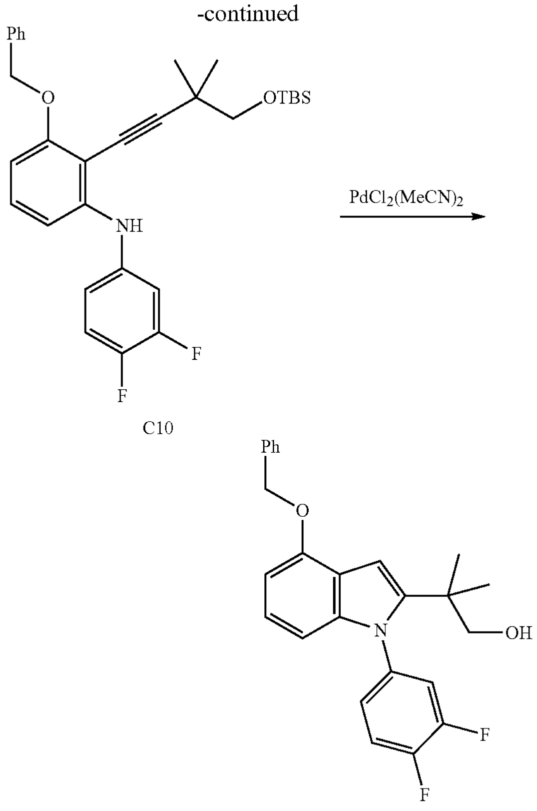

C10

S4

Step 1. Synthesis of 3-benzyloxy-2-[4-[tert-butyl(dimethyl)silyl]oxy-3,3-dimethyl-but-1-ynyl]-N-(3,4-difluorophenyl)aniline (C10)

To a solution of [4-(2-benzyloxy-6-bromo-phenyl)-2,2-dimethyl-but-3-ynoxy]-tert-butyl-dimethyl-silane C4 (11 g, 23.2 mmol) and 3,4-difluoroaniline (3.27 g, 25.33 mmol) in xylene (60 mL) under nitrogen was added NaOtBu (6 g, 62.4 mmol) followed by tBuXPhos Pd G3 (315 mg, 0.40 mmol). The reaction mixture was stirred at room temperature overnight. The reaction was diluted with water and sat aq. $NH_4Cl$ and extracted with EtOAc (×2). The combined organics were concentrated to dryness and purified by silica gel chromatography (Column: 220 g Silica. Gradient: 0-50% EtOAc in heptane) to afford the product as a yellow oil (11.6 g, 96%). $^1H$ NMR (400 MHz, Chloroform-d) δ 7.49 (ddt, J=7.4, 1.3, 0.7 Hz, 2H), 7.38-7.32 (m, 2H), 7.31-7.25 (m, 1H), 7.10-6.96 (m, 3H), 6.86-6.80 (m, 1H), 6.70 (dd, J=8.3, 0.8 Hz, 1H), 6.43-6.39 (m, 2H), 5.11 (s, 2H), 3.53 (s, 2H), 1.28 (s, 6H), 0.84 (s, 9H), 0.00 (s, 6H). LCMS m/z 522.52 $[M+1]^+$.

Step 2. Synthesis of 2-[4-benzyloxy-]-(3,4-difluoro-phenyl)indol-2-yl]-2-methyl-propan-1-ol (C24)

A solution of 3-benzyloxy-2-[4-[tert-butyl(dimethyl)silyl]oxy-3,3-dimethyl-but-1-ynyl]-N-(3,4-difluorophenyl)aniline C10 (11.6 g, 22.2 mmol) in MeOH (100 mL) and EtOAc (51 mL) was purged with nitrogen for 1 hour. $PdCl_2(CH_3CN)_2$ (336 mg, 1.30 mmol) was added and the mixture heated to 60° C. overnight. The reaction was concentrated under reduced pressure and then purified by silica gel chromatography (Gradient: 0-75% EtOAc in heptane) to afford the product as a white solid (8.2 g, 91%). $^1$H NMR (400 MHz, Chloroform-d) δ 7.55 (dt, J=6.3, 1.4 Hz, 2H), 7.48-7.41 (m, 2H), 7.41-7.31 (m, 2H), 7.31-7.24 (m, 3H), 7.22-7.15 (m, 1H), 7.02 (t, J=8.0 Hz, 1H), 6.74 (d, J=0.8 Hz, 1H), 6.63 (d, J=7.8 Hz, 1H), 6.33 (d, J=8.2 Hz, 1H), 5.26 (s, 2H), 3.53 (dd, J=6.0, 1.6 Hz, 2H), 1.28 (s, 3H), 1.27 (s, 3H). LCMS m/z 408.37 [M+1]$^+$.

Preparation of S5

2-(4-(Benzyloxy)-1-(3,4-difluorophenyl)-6-fluoro-1H-indol-2-yl)-2-methylpropan-1-ol (S5)

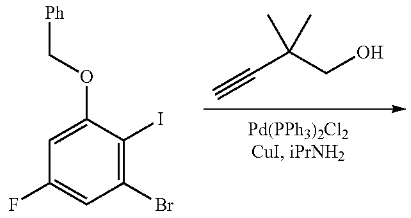

C11

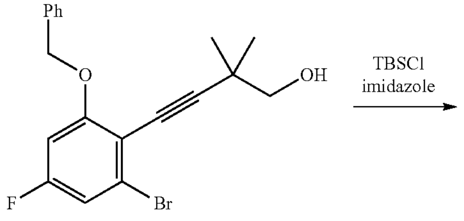

C12

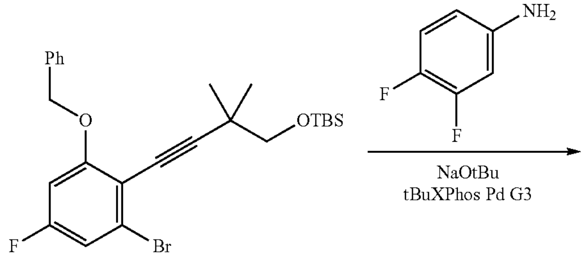

C13

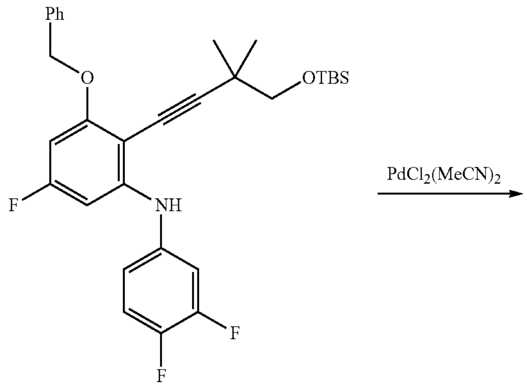

C14

-continued

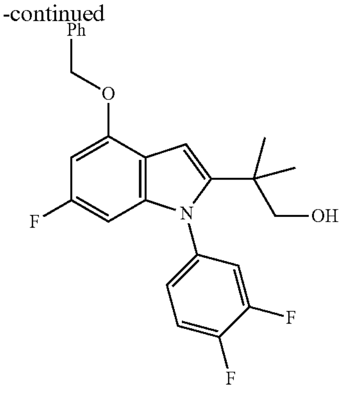

S5

Step 1. Synthesis of 4-(2-benzyloxy-6-bromo-4-fluoro-phenyl)-2,2-dimethyl-but-3-yn-1-ol (C12)

A solution of 1-benzyloxy-3-bromo-5-fluoro-2-iodo-benzene C11 (5 g, 12.3 mmol), 2,2-dimethylbut-3-yn-1-ol (1.8 g, 18.3 mmol) in 1,4-dioxane (40 mL) and $Et_3N$ (40 mL) was purged with nitrogen for 10 min, then added CuI (157 mg, 0.82 mmol) and $PdCl_2(PPh_3)_2$ (500 mg, 0.71 mmol) were added. The resulting reaction mixture was warmed to 50° C., and stirred overnight. The reaction mixture was cooled to room temperature, poured into water (50 mL), and partitioned between sat. aqueous $NH_4Cl$ solution (~50 mL) and ethyl acetate (~150 mL). Upon stirring for 10 minutes, the organic layer was separated, was washed with 1 N HCl solution (2×50 mL), water (30 mL), brine (30 mL), dried over $MgSO_4$, filtered and concentrated under reduced pressure. The residue was purified by silica gel chromatography (Gradient: 0-70% ethyl acetate in heptane) to afford the product as a clear yellow viscous oil. 4-(2-benzyloxy-6-bromo-4-fluoro-phenyl)-2,2-dimethyl-but-3-yn-1-ol $Cl_2$ (4.23 g, 90%). 1H NMR (400 MHz, Chloroform-d) δ 7.49 (dtd, J=6.9, 1.4, 0.7 Hz, 2H), 7.46-7.32 (m, 3H), 6.98 (dd, J=8.0, 2.4 Hz, 1H), 6.65 (dd, J=10.2, 2.4 Hz, 1H), 5.12 (s, 2H), 3.49 (d, J=7.1 Hz, 2H), 1.34 (s, 6H). LCMS m/z 377.01 [M+1]$^+$.

Step 2. Synthesis of ((4-(2-(benzyloxy)-6-bromo-4-fluorophenyl)-2,2-dimethylbut-3-yn-1-yl)oxy)(tert-butyl)dimethylsilane (C13)

To a mixture of 4-(2-benzyloxy-6-bromo-4-fluoro-phenyl)-2,2-dimethyl-but-3-yn-1-ol $Cl_2$ (2.05 g, 5.43 mmol) and TBSCl (1.41 g, 9.36 mmol) in dichloromethane (20 mL) was added imidazole (561 mg, 8.24 mmol) in one portion at room temperature. After 40 min, water and dichloromethane were added. The layers were separated with the aid of a phase separator. The aqueous layer was re-extracted with dichloromethane and the layers were separated through a phase separator again and the combined organics concentrated. Purification by column chromatography (80 g column; 0-40% EtOAc in heptane) gave the product C13. $^1$H NMR (400 MHz, Chloroform-d) δ 7.45-7.40 (m, 2H), 7.37-7.25 (m, 3H), 6.90 (dd, J=8.1, 2.4 Hz, 1H), 6.55 (dd, J=10.3, 2.4 Hz, 1H), 5.05 (s, 2H), 3.52 (s, 2H), 1.25 (s, 6H), 0.85 (s, 9H), 0.00 (s, 6H).

Step 3. Synthesis of 3-(benzyloxy)-2-(4-((tert-butyldimethylsilyl)oxy)-3,3-dimethylbut-1-yn-1-yl)-N-(3,4-difluorophenyl)-5-fluoroaniline (C14)

To a solution of [4-(2-benzyloxy-6-bromo-4-fluoro-phenyl)-2,2-dimethyl-but-3-ynoxy]-tert-butyl-dimethyl-silane C13 (2.35 g, 4.78 mmol) and 3,4-difluoroaniline (540 μL, 5.45 mmol) in xylene (20 mL) under nitrogen was added NaOtBu (1.2 g, 12.5 mmol). Nitrogen was bubbled through the mixture for 10 min. tBuXPhos Pd G3 (48 mg, 60.4 μmol) was added and the reaction mixture was stirred at room temperature overnight. The reaction was diluted with water and extracted 2×EtOAc. The combined organics were dried ($Na_2SO_4$), filtered and concentrated. Purification via silica gel chromatography (80 g) eluting with 0-50% EtOAc in heptane gave product C14 (2.56 g, 99%). $^1$H NMR (300 MHz, Chloroform-d) δ 7.50-7.44 (m, 2H), 7.40-7.26 (m, 3H), 7.10 (dt, J=10.0, 8.8 Hz, 1H), 7.00 (ddd, J=11.6, 6.9, 2.6 Hz, 1H), 6.86 (dt, J=8.3, 4.1 Hz, 1H), 6.52 (s, 1H), 6.34 (dd, J=11.0, 2.3 Hz, 1H), 6.14 (dd, J=10.5, 2.3 Hz, 1H), 5.08 (s, 2H), 3.53 (s, 2H), 1.28 (s, 6H), 0.84 (s, 9H), 0.00 (s, 6H). LCMS m/z 540.52 [M+1]$^+$.

Step 4. Synthesis of 2-(4-(Benzyloxy)-1-(3,4-difluorophenyl)-6-fluoro-]H-indol-2-yl)-2-methylpropan-1-ol (S5)

A flask was charged with 3-benzyloxy-2-[4-[tert-butyl(dimethyl)silyl]oxy-3,3-dimethyl-but-1-ynyl]-N-(3,4-difluorophenyl)-5-fluoro-aniline C14 (2.56 g, 4.74 mmol), methanol (30 mL) ethyl acetate (15 mL) and degassed with nitrogen for 30 min. $PdCl_2(CH_3CN)_2$ (100 mg, 0.386 mmol) was added and the mixture heated to 60° C. overnight. The reaction was concentrated under reduced pressure and then purified by column chromatography (80 g column; 0-30% EtOAc in heptane) to give product S5 as an orange solid (1.75 g, 87%). 1H NMR (400 MHz, Chloroform-d) δ 7.56-7.51 (m, 2H), 7.48-7.43 (m, 2H), 7.42-7.36 (m, 1H), 7.36-7.32 (m, 1H), 7.28-7.23 (m, 1H), 7.21-7.14 (m, 1H), 6.67 (d, J=0.8 Hz, 1H), 6.43 (dd, J=11.5, 2.0 Hz, 1H), 6.02 (ddd, J=9.4, 2.0, 0.8 Hz, 1H), 5.21 (s, 2H), 3.51 (d, J=5.6 Hz, 2H), 1.26 (s, 3H), 1.25 (s, 3H). LCMS m/z 426.37 [M+1]$^+$.

Preparation of S6

2-(4-(Benzyloxy)-1-(4-fluorophenyl)-1H-indol-2-yl)-2-methylpropan-1-ol (S6)

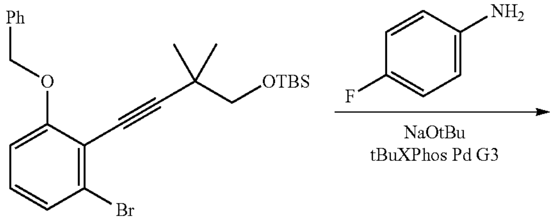

C4

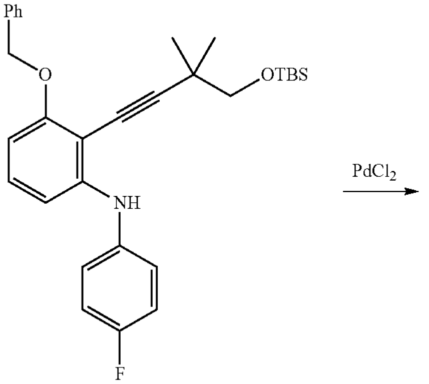

C15

-continued

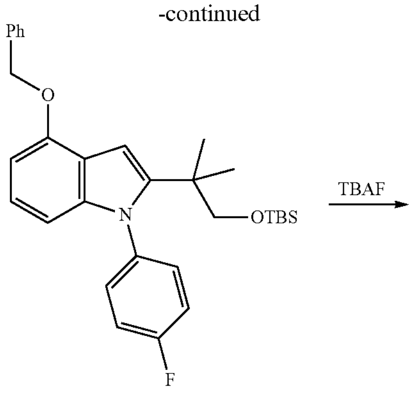

C16

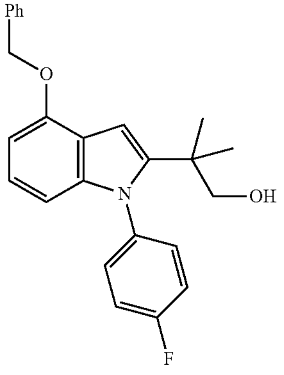

S6

Step 1. 3-(Benzyloxy)-2-(4-((tert-butyldimethylsilyl)oxy)-3,3-dimethylbut-1-yn-1-yl)-N-(4-fluorophenyl)aniline (C5)

A solution of [4-(2-benzyloxy-6-bromo-phenyl)-2,2-dimethyl-but-3-ynoxy]-tert-butyl-dimethyl-silane C4 (40.3 g, 85.1 mmol) and 4-fluoroaniline (12.1 mL, 128 mmol) in m-xylene (400 mL) was purged with nitrogen for 10 minutes. NaOtBu (24.5 g, 255 mmol) and tBuXPhos Pd G3 (2.03 g, 2.56 mmol) were then added in one portion and the reaction mixture was stirred at 35° C. for 4 h, then filtered over Celite®. The filtered solids were rinsed with xylene and the filtrate was concentrated. The filtered solids were washed with 1:1 EtOAc and water, and the organic layer of the filtrate was combined and concentrated with the xylene filtrate to give a dark brown oil. Purification by silica gel chromatography (Gradient: 0-20% EtOAc in heptane) afforded the product C15 as a light yellow oil. (40.3 g, 94%). $^1$H NMR (400 MHz, Chloroform-d) δ 7.53 (ddt, J=7.4, 1.3, 0.7 Hz, 2H), 7.41-7.35 (m, 2H), 7.34-7.28 (m, 1H), 7.18-7.13 (m, 2H), 7.06-6.99 (m, 3H), 6.63 (dd, J=8.3, 0.8 Hz, 1H), 6.42 (s, 1H), 6.39 (dd, J=8.3, 0.8 Hz, 1H), 5.14 (s, 2H), 3.57 (s, 2H), 1.32 (s, 6H), 0.87 (s, 9H), 0.03 (s, 6H). LCMS m/z 504.0 [M+H]$^+$.

Step 2. Synthesis of [2-[4-benzyloxy-]-(4-fluorophenyl)indol-2-yl]-2-methyl-propoxy]-tert-butyl-dimethyl-silane (C16)

To a solution of 3-benzyloxy-2-[4-[tert-butyl(dimethyl)silyl]oxy-3,3-dimethyl-but-1-ynyl]-N-(4-fluorophenyl)aniline C15 (40.3 g, 80.0 mmol) in MeCN (400 mL) was added $PdCl_2$ (567 mg, 3.2 mmol). The reaction mixture was stirred at 60° C. overnight, then filtered. The filtrate was concentrated to dryness, triturated with MeCN, and filtered again. The process was repeated 3-4 times and all solids were combined and dried under vacuum to afford the product $C_{16}$ as a tan solid (38.1 g, 95%). $^1$H NMR (400 MHz, Chloroform-d) δ 7.60-7.55 (m, 2H), 7.48-7.43 (m, 2H), 7.42-7.35 (m, 3H), 7.25-7.18 (m, 2H), 6.98 (t, J=8.0 Hz, 1H), 6.69 (d, J=0.8 Hz, 1H), 6.64-6.59 (m, 1H), 6.32 (dt, J=8.3, 0.7 Hz, 1H), 5.28 (s, 2H), 3.54 (s, 2H), 1.24 (s, 6H), 0.88 (s, 9H), 0.00 (s, 6H). LCMS m/z 504.0 $[M+H]^+$.

Step 3. Synthesis of 2-[4-benzyloxy-]-(4-fluorophenyl)indol-2-yl]-2-methyl-propan-1-ol (S6)

To a solution of [2-[4-benzyloxy-1-(4-fluorophenyl)indol-2-yl]-2-methyl-propoxy]-tert-butyl-dimethyl-silane C16 (4.8 g, 9.53 mmol) in THE (40 mL) was added TBAF (40 mL of 1 M, 40.0 mmol). The mixture was stirred for 4 hours at 55° C. then concentrated, and purified by silica gel chromatography (Gradient: 0-50% EtOAc in heptane) to afford the product 2-[4-benzyloxy-1-(4-fluorophenyl)indol-2-yl]-2-methyl-propan-1-ol S6 (3.15 g, 85%) as an off white solid. $^1$H NMR (400 MHz, Chloroform-d) δ 7.51-7.17 (m, 7H), 7.08 (q, J=8.3, 7.9 Hz, 2H), 6.88 (t, J=7.9 Hz, 1H), 6.62 (s, 1H), 6.50 (d, J=7.8 Hz, 1H), 6.21 (d, J=8.3 Hz, 1H), 5.13 (s, 2H), 3.35 (s, 2H), 1.12 (s, 6H). LCMS m/z 390.0 $[M+H]^+$.

Preparation of S7

2-(4-(Benzyloxy)-6-fluoro-]-(4-fluorophenyl)-1H-indol-2-yl)-2-methylpropan-1-ol (S7)

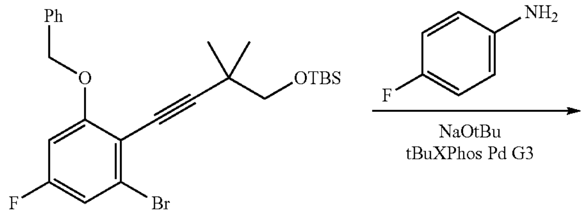

C13

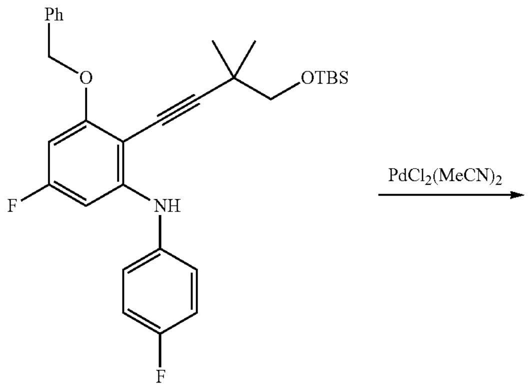

C17

-continued

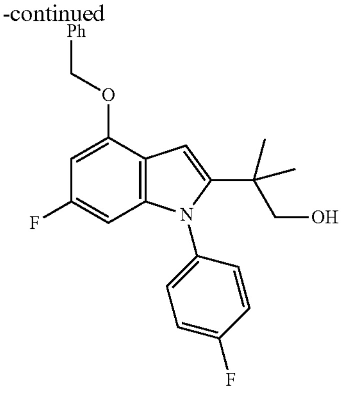

S7

Step 1. Synthesis of 3-(benzyloxy)-2-(4-((tert-butyldimethylsilyl)oxy)-3,3-dimethylbut-1-yn-1-yl)-5-fluoro-N-(4-fluorophenyl)aniline (C17)

To a solution of [4-(2-benzyloxy-6-bromo-4-fluoro-phenyl)-2,2-dimethyl-but-3-ynoxy]-tert-butyl-dimethyl-silane C13 (2.76 g, 5.62 mmol) and 4-fluoroaniline (600 μL, 6.33 mmol) in xylene (50 mL) under nitrogen was added NaOtBu (1.35 g, 14.1 mmol) and nitrogen bubbled through the mixture for 10 min. Then tBuXPhos Pd G3 (130 mg, 0.164 mmol) was added and the reaction mixture was stirred at room temperature overnight. The reaction was diluted with water and brine and extracted twice with EtOAc. The combined organics were dried ($Na_2SO_4$), filtered and concentrated and purified via silica gel chromatography (120 g) eluting with 0-20% EtOAc in heptane to give product C17 as a pale yellow oil which solidified on standing to give an off white solid (2.76 g, 94%). $^1$H NMR (400 MHz, Chloroform-d) δ 7.50-7.46 (m, 2H), 7.40-7.34 (m, 2H), 7.33-7.28 (m, 1H), 7.14 (dd, J=8.9, 4.8 Hz, 2H), 7.06-7.00 (m, 2H), 6.50 (s, 1H), 6.25 (dd, J=11.3, 2.3 Hz, 1H), 6.09 (dd, J=10.5, 2.3 Hz, 1H), 5.08 (s, 2H), 3.54 (s, 2H), 1.29 (s, 6H), 0.84 (s, 9H), 0.00 (s, 6H). LCMS m/z 522.43 $[M+H]^+$.

Step 2. Synthesis of 2-(4-(Benzyloxy)-6-fluoro-]-(4-fluorophenyl)-1H-indol-2-yl)-2-methylpropan-1-ol (S7)

A flask was charged with 3-benzyloxy-2-[4-[tert-butyl(dimethyl)silyl]oxy-3,3-dimethyl-but-1-ynyl]-5-fluoro-N-(4-fluorophenyl)aniline C17 (2.76 g, 5.29 mmol), methanol (32 mL), ethyl acetate (16 mL) and degassed with nitrogen for 35 min. $PdCl_2(CH_3CN)_2$ (220 mg, 0.8480 mmol) was added and the mixture heated at 60° C. A precipitate appeared so a further portion of EtOAc (20 mL) was added. The reaction was concentrated after two months under reduced pressure and then purified by column chromatography (80 g column; 50-100% EtOAc in heptane) to give product S7 a tan solid (2 g, 93%). LCMS m/z 408.14 $[M+H]^+$.

Preparation of S8

2-(5-(Benzyloxy)-1-(4-fluoro-3-methylphenyl)-1H-indol-2-yl)-2-methylpropan-1-ol (S8)

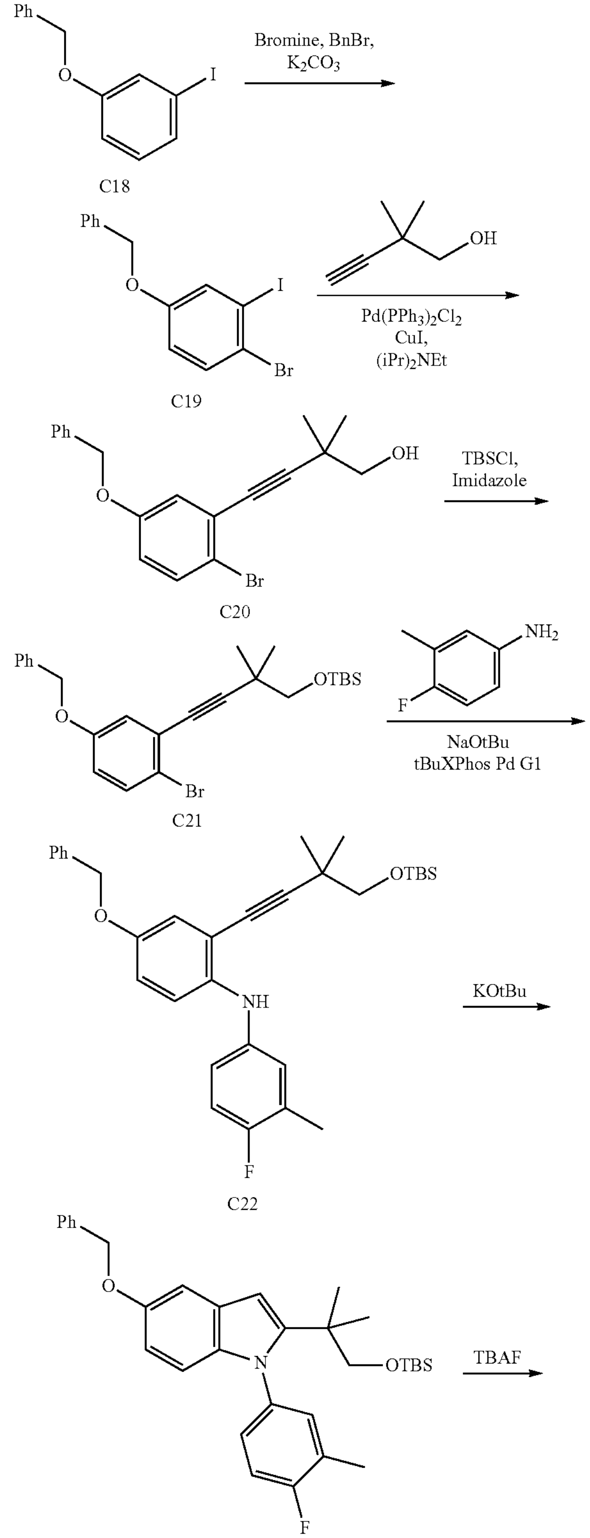

C18

C19

C20

C21

C22

C23

-continued

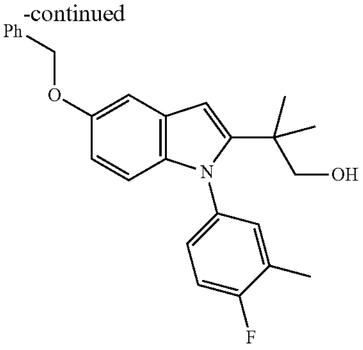

S8

Step 1. Synthesis of 4-(benzyloxy)-1-bromo-2-iodobenzene (C19)

1-Benzyloxy-3-iodo-benzene (30 g, 96.7 mmol) was dissolved in HOAc (300 mL) and cooled in an ice-bath to 5° C. Bromine (5 mL, 97.1 mmol) was added via addition funnel. The temperature rose to 15° C. during the addition. After stirring overnight, the reaction was poured into 1 L of water forming a milky suspension that was extracted with dichloromethane (3×100 mL). The extracts were washed with sat. aq. $NaHCO_3$ and the organic layer was dried ($Na_2SO_4$), filtered and concentrated. The crude oil was purified by flash chromatography (Combiflash ISCO, 330 g Gold column) eluting with 0-20% EtOAc/hex to afford the product C19 (18 g, 47%). $^1H$ NMR (400 MHz, Chloroform-d) δ 7.54-7.31 (m, 7H), 6.83-6.81 (s, 1H), 5.00 (s, 2H).

Step 2. Synthesis of 4-(5-(benzyloxy)-2-bromophenyl)-2,2-dimethylbut-3-yn-1-ol (C20)

4-Benzyloxy-1-bromo-2-iodo-benzene C19 (13.3 g, 34.2 mmol) and 2,2-dimethylbut-3-yn-1-ol (4 g, 40.8 mmol) were dissolved into dioxane (75 mL) and DIEA (15 mL, 86.1 mmol) and the solution was purged with nitrogen for 5-10 minutes. Bistriphenylphosphine Pd chloride (1.2 g, 1.71 mmol) was added followed by CuI (710 mg, 3.73 mmol). The reaction mixture was stirred at room temperature under nitrogen and foil overnight. The reaction was filtered off with the aid of EtOAc and then concentrated. Purification by column chromatography (330 g column; 0-100% EtOAc in heptane) gave product C20 (10 g, 81%) as a pale yellow oil. 4-(5-benzyloxy-2-bromo-phenyl)-2,2-dimethyl-but-3-yn-1-ol (10 g, 81%) $^1H$ NMR (400 MHz, Chloroform-d) δ 7.45 (d, J=8.9 Hz, 1H), 7.44-7.34 (m, 5H), 7.09 (d, J=3.0 Hz, 1H), 6.82 (dd, J=8.9, 3.0 Hz, 1H), 5.05 (s, 2H), 3.55 (d, J=7.2 Hz, 2H), 2.10 (d, J=7.1 Hz, 1H), 1.35 (s, 6H). LCMS m/z 359.17 $[M+H]^+$.

Step 3. Synthesis of ((4-(5-(benzyloxy)-2-bromophenyl)-2,2-dimethylbut-3-yn-1-yl)oxy)(tert-butyl)dimethylsilane (C21)

To a solution of 4-(5-benzyloxy-2-bromo-phenyl)-2,2-dimethyl-but-3-yn-1-ol C20 (4.08 g, 11.4 mmol) in DMF (15 mL) was added tert-butyl-chloro-diphenyl-silane (3 mL, 11.5 mmol) followed by imidazole (1.93 g, 28.4 mmol) and the mixture stirred overnight at room temperature. A further portion of tert-butyl-chloro-diphenyl-silane (3 mL, 11.5 mmol) was added and the mixture heated at 80° C. for 30 min. Water and heptane were added. The extracts were dried ($Na_2SO_4$), filtered and concentrated. Purification by column chromatography (120 g GOLD column; 0-10% EtOAc in heptane) gave product C21 (2 g, 31%). $^1$H NMR (400 MHz, Chloroform-d) δ 7.78-7.72 (m, 4H), 7.48-7.32 (m, 12H), 7.06 (d, J=3.0 Hz, 1H), 6.79 (dd, J=8.9, 3.0 Hz, 1H), 5.00 (s, 2H), 3.66 (s, 2H), 1.40 (s, 6H), 1.12 (s, 9H).

Step 4. Synthesis of 4-(benzyloxy)-2-(4-((tert-butyldimethylsilyl)oxy)-3,3-dimethylbut-1-yn-1-yl)-N-(4-fluoro-3-methylphenyl)aniline (C22)

((4-(5-(benzyloxy)-2-bromophenyl)-2,2-dimethylbut-3-yn-1-yl)oxy)(tert-butyl)dimethylsilane C21 (2.1 g, 3.51 mmol) and 4-fluoro-3-methyl-aniline (500 mg, 4.00 mmol) were dissolved in dioxane (6 mL) and t-BuOH (6 mL). Sodium t-butoxide (767 mg, 7.98 mmol) and tBuXphosPalladacycle (154 mg, 0.224 mmol) [tBuXPhosPd Gen I] were added and the reaction mixture was stirred under nitrogen overnight at room temperature. The reaction mixture was filtered through Celite® with the aid of EtOAc and then concentrated. Purification by column chromatography (80 g GOLD column, heptane) gave product C22 as a straw colored oil (1.22 g, 54%). $^1$H NMR (400 MHz, Chloroform-d) δ 7.73 (m, 3H), 7.47-7.31 (m, 11H), 7.06-6.99 (m, 2H), 6.94-6.76 (m, 3H), 5.97 (s, 1H), 5.04 (s, 1H), 5.00 (s, 2H), 3.62 (s, 2H), 2.22 (s, 3H), 1.36 (s, 6H), 1.09 (d, J=1.2 Hz, 9H).

Step 5. Synthesis of 5-(benzyloxy)-2-(1-((tert-butyldimethylsilyl)oxy)-2-methylpropan-2-yl)-1-(4-fluoro-3-methylphenyl)-1H-indole (C23)

To a solution of 4-(benzyloxy)-2-(4-((tert-butyldimethylsilyl)oxy)-3,3-dimethylbut-1-yn-1-yl)-N-(4-fluoro-3-methylphenyl)aniline C22 (2.19 g, 4.22 mmol) in 2-MeTHF (10 mL) was added potassium 2-methylpropan-2-olate (1 M in THF, 5.1 mL, 5.1 mmol) at room temperature. After 4 h, the reaction was diluted with water and saturated ammonium chloride and extracted twice with EtOAc. The combined organics were dried ($Na_2SO_4$), filtered and concentrated to give product C23 (2.19 g, 100%) which was taken into the next reaction without further characterization.

Step 6. Synthesis of 2-(5-(Benzyloxy)-1-(4-fluoro-3-methylphenyl)-1H-indol-2-yl)-2-methylpropan-1-ol (S8)

To a solution of 5-(benzyloxy)-2-(1-((tert-butyldimethylsilyl)oxy)-2-methylpropan-2-yl)-1-(4-fluoro-3-methylphenyl)-1H-indole C23 (2.19 g, 4.23 mmol) in THE (10 mL) was added TBAF (1M in THF, 5.5 mL, 5.5 mmol) at room temperature. After 1 hour, a further 2.5 mL of TBAF solution was added at room temperature and the mixture stirred overnight. The reaction was diluted with water and saturated ammonium chloride and extracted twice with EtOAc. The combined organics were dried ($Na_2SO_4$), filtered and concentrated and purified via silica gel chromatography (80 g silica column; 0-100% ethyl acetate in heptane) to give the product S8 as a yellowish-white solid (970 mg, 57%). $^1$H NMR (400 MHz, Chloroform-d) δ 7.51-7.31 (m, 6H), 7.23-7.12 (m, 4H), 6.84 (dd, J=8.8, 2.4 Hz, 1H), 6.60 (d, J=8.9 Hz, 1H), 6.49 (d, J=0.8 Hz, 1H), 5.13 (s, 2H), 3.52 (d, J=6.3 Hz, 2H), 2.35 (d, J=2.0 Hz, 3H), 1.39 (t, J=6.4 Hz, 1H), 1.33 (d, J=1.2 Hz, 1H), 1.26 (s, 6H). LCMS m/z 404.14 [M+H]$^+$.

Preparation of S9

2-(5-Fluoro-1-(4-fluoro-3-methylphenyl)-1H-indol-2-yl)-2-methylpropan-1-ol (S9)

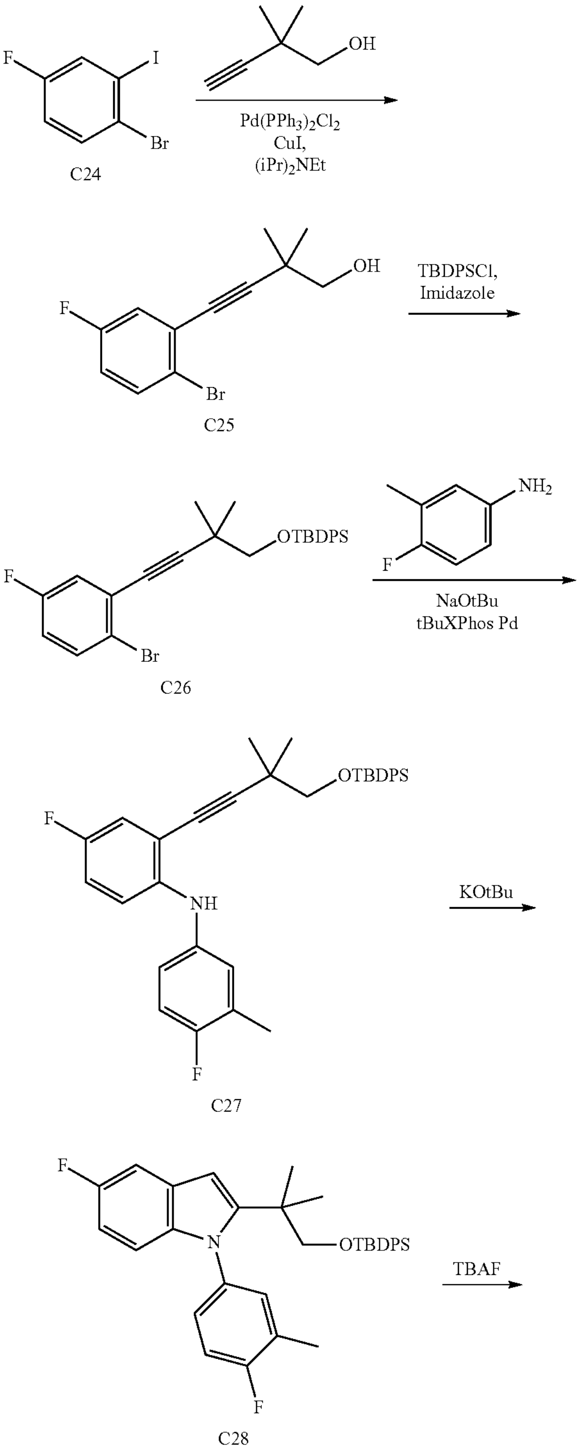

C24

C25

C26

C27

C28

-continued

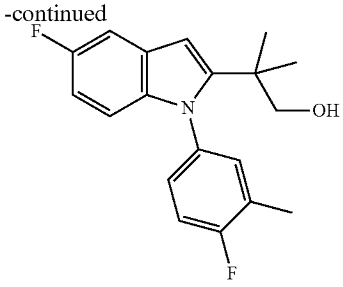

S9

Step 1. Synthesis of 4-(2-bromo-5-fluorophenyl)-2,2-dimethylbut-3-yn-1-ol (C25)

1-Bromo-4-fluoro-2-iodo-benzene C24 (1.7 mL, 13.0 mmol) and 2,2-dimethylbut-3-yn-1-ol (1.5 g, 15.3 mmol) were dissolved in dioxane (15 mL) and DIEA (5.6 mL, 32.2 mmol) and the solution was purged with nitrogen for 5-10 min. Bistriphenylphosphine Pd chloride (456 mg, 0.648 mmol) was added followed by CuI (270 mg, 1.42 mmol). The reaction mixture was stirred at room temperature under nitrogen and foil overnight. The reaction was filtered off with the aid of EtOAc and then concentrated. Purification by column chromatography (80 g column; 0-100% EtOAc in heptane) gave product C25 (2.73 g, 78%). $^1$H NMR (400 MHz, Chloroform-d) δ 7.54 (dd, J=8.9, 5.3 Hz, 1H), 7.18 (dd, J=8.9, 3.0 Hz, 1H), 6.91 (ddd, J=8.9, 7.9, 3.0 Hz, 1H), 3.55 (d, J=5.6 Hz, 2H), 2.03 (t, J=6.6 Hz, 1H), 1.35 (s, 6H). LCMS m/z 271.1 [M+H]$^+$.

Step 2. Synthesis of ((4-(2-bromo-5-fluorophenyl)-2,2-dimethylbut-3-yn-1-yl)oxy)(tert-butyl)diphenylsilane (C26)

To a solution of 4-(2-bromo-5-fluoro-phenyl)-2,2-dimethyl-but-3-yn-1-ol C25 (2.73 g, 10.1 mmol) in DMF (8 mL) was added tert-butyl-chloro-diphenyl-silane (2.66 mL, 10.2 mmol) followed by imidazole (1.5 g, 22.0 mmol) and the mixture stirred for 4 hours. Purification by column chromatography (C18 AQ 275 g column; aq. TFA/MeCN) gave pure compound C26 as a colorless oil (4.25 g, 83%). $^1$H NMR (400 MHz, Chloroform-d) δ 7.70-7.64 (m, 4H), 7.46 (dd, J=8.8, 5.3 Hz, 1H), 7.42-7.31 (m, 6H), 7.06 (dd, J=9.0, 3.0 Hz, 1H), 6.82 (ddd, J=8.9, 7.9, 3.1 Hz, 1H), 3.58 (s, 2H), 1.33 (s, 6H), 1.06 (s, 9H).

Step 3. Synthesis of 2-(4-((tert-butyldiphenylsilyl)oxy)-3,3-dimethylbut-1-yn-1-yl)-4-fluoro-N-(4-fluoro-3-methylphenyl)aniline (C27)

C26 (2.06 g, 4.04 mmol), 4-fluoro-3-methyl-aniline (610 mg, 4.874 mmol) and sodium t-butoxide (880 mg, 9.16 mmol) were suspended/dissolved in dioxane (8 mL) and t-BuOH (8 mL) and the reaction purged with nitrogen for several minutes. During the purge was added tBuXphosPalladacycle (139 mg, 0.202 mmol) and the reaction mixture was stirred at 45° C. for 4 h. The reaction mixture was diluted with water and dichloromethane. The layers were separated with the aid of a phase separator and the combined organics concentrated. Purification by column chromatography (80 g gold column, heptane) gave product C27 as a straw-colored oil (2.24 g, 100%). $^1$H NMR (400 MHz, Chloroform-d) δ 7.75-7.67 (m, 4H), 7.50-7.34 (m, 6H), 7.04 (dd, J=9.0, 2.9 Hz, 1H), 6.98-6.82 (m, 5H), 6.06 (s, 1H), 3.62 (s, 2H), 2.23 (d, J=2.0 Hz, 3H), 1.36 (s, 6H), 1.08 (s, 9H).

Step 4. Synthesis of 2-(1-((tert-butyldiphenylsilyl)oxy)-2-methylpropan-2-yl)-5-fluoro-1-(4-fluoro-3-methylphenyl)-1H-indole (C28)

To a solution of C27 (2.24 g, 4.05 mmol) in 2-MeTHF (5 mL) was added potassium 2-methylpropan-2-olate (4.1 mL of 1 M, 4.100 mmol) at room temperature. After 2 h, the reaction was added to brine and EtOAc. The layers were separated, and the organics dried ($Na_2SO_4$), filtered and concentrated. Purification by column chromatography (80 g gold column, heptane) gave product C28 as a straw-colored oil (1.394 g, 62%). $^1$H NMR (400 MHz, Chloroform-d) δ 7.72-7.68 (m, 1H), 7.48 (m, 3H), 7.45-7.38 (m, 4H), 7.27-7.21 (m, 3H), 6.92-6.84 (m, 3H), 6.79 (td, J=9.1, 2.5 Hz, 1H), 6.54-6.46 (m, 2H), 3.61 (s, 3H), 2.16 (d, J=2.0 Hz, 3H), 1.29 (s, 6H), 1.01 (s, 9H).

Step 5. Synthesis of 2-(5-fluoro-1-(4-fluoro-3-methylphenyl)-1H-indol-2-yl)-2-methylpropan-1-ol (S9)

To a solution of tert-butyl-[2-[5-fluoro-1-(4-fluoro-3-methyl-phenyl)indol-2-yl]-2-methyl-propoxy]-diphenyl-silane C28 (750 mg, 1.35 mmol) in 2-MeTHF (10 mL) was added TBAF (1M in THF, 3 mL, 3 mmol) at room temperature and the mixture was heated at 70° C. overnight. Water and dichloromethane were added, the layers were separated, and the organics dried ($Na_2SO_4$), filtered and concentrated. Purification by column chromatography (40 g column; 0-75% EtOAc in heptane) gave product S9 as a straw-colored oil (350 mg, 82%). LCMS m/z 316.13 [M+H]$^+$.

Preparation of S10

4-(Benzyloxy)-1-(4-fluorophenyl)-1H-indole (S10)

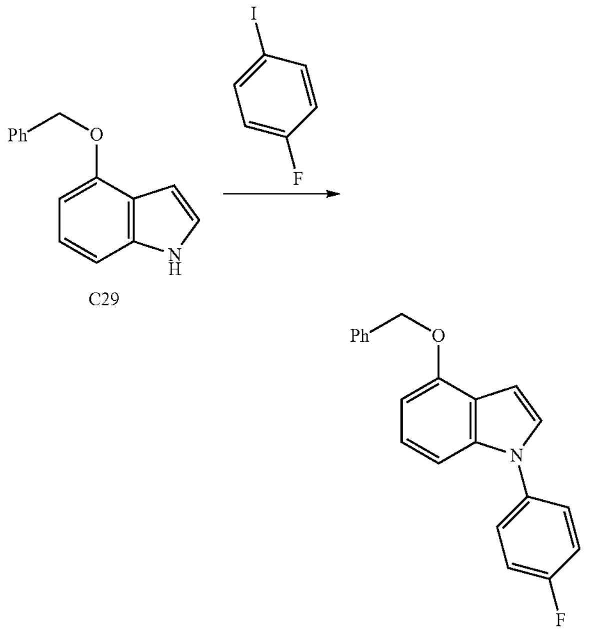

C29

S10

Step 1. Synthesis of 4-(Benzyloxy)-1-(4-fluorophenyl)-1H-indole (S10)

Nitrogen was bubbled through a mixture of 4-benzyloxy-1H-indole C29 (20 g, 89.6 mmol), 1-fluoro-4-iodo-benzene (15 mL, 130 mmol), CuI (1 g, 5.25 mmol) and cesium carbonate (50 g, 154 mmol) in DMF (125 mL) and then stirred at 120° C. for 48 h. The reaction mixture was diluted with water (1 L) and EtOAc (500 mL). The organic layer was separated and the aqueous layer was extracted with EtOAc (2×100 mL). The combined organic layers were washed with brine, dried ($Na_2SO_4$), filtered and concentrated to give a brown solid. The solid was triturated with ether and filtered to give the product S10 (19 g, 64%) as a grey colored solid. $^1$H NMR (400 MHz, DMSO-$d_6$) δ 7.66-7.58 (m, 2H), 7.55-7.50 (m, 4H), 7.45-7.37 (m, 5H), 7.36-7.27 (m, 1H), 7.09 (d, J=6.0 Hz, 2H), 6.73 (q, J=2.7, 2.2 Hz, 2H), 5.28 (s, 2H). LCMS m/z 318.16 $[M+H]^+$.

Preparation of S11

4-Benzyloxy-6-fluoro-1-(4-fluorophenyl)indole (S11)

Step 1. Synthesis of 4-bromo-6-fluoro-1-(4-fluorophenyl)indole (C31)

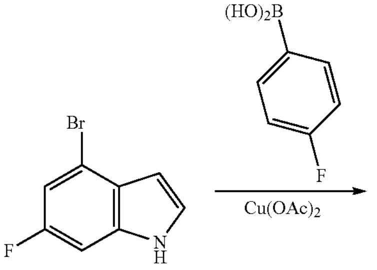

C30

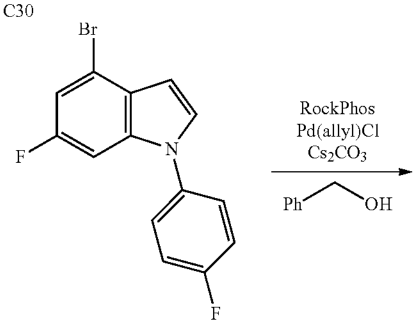

C31

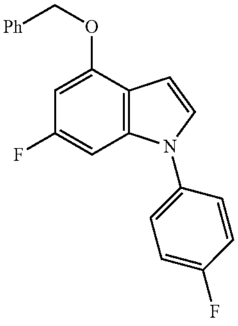

S11

To a mixture of 4-bromo-6-fluoro-1H-indole C30 (5 g, 23.4 mmol), (4-fluorophenyl)boronic acid (6.54 g, 46.74 mmol) and copper (II) acetate (8.5 g, 46.8 mmol) in dichloromethane (100 mL) was added triethylamine (6.5 mL, 46.6 mmol) and the mixture stirred vigorously in air. Additional dichloromethane (100 mL), 4-fluorophenyl boronic acid (5.7 g), $Cu(OAc)_2$, and $NEt_3$ (6 mL) were added and the mixture was stirred vigorously. The reaction mixture was filtered through Celite® with the aid of EtOAc and then concentrated. Purification by column chromatography (Gradient: 0-50% EtOAc in heptane) afforded the product C31 as a white solid (2.84 g, 39%). $^1$H NMR (400 MHz, DMSO-$d_6$) δ 7.78 (d, J=3.3 Hz, 1H), 7.69-7.62 (m, 2H), 7.47-7.40 (m, 2H), 7.38 (dd, J=9.1, 2.1 Hz, 1H), 7.31 (ddd, J=9.9, 2.1, 0.9 Hz, 1H), 6.66 (dd, J=3.4, 0.8 Hz, 1H). LCMS m/z 308.02 $[M+1]^+$.

Step 2. Synthesis of 4-benzyloxy-6-fluoro-1-(4-fluorophenyl)indole (S11)

A vial was charged with 4-bromo-6-fluoro-1-(4-fluorophenyl)indole C31 (2.14 g, 6.95 mmol), palladium allyl chloride (38 mg, 0.21 mmol), ditert-butyl-[6-methoxy-3-methyl-2-(2,4,6-triisopropylphenyl)phenyl]phosphane (293 mg, 0.63 mmol), $Cs_2CO_3$ (4.2 g, 12.9 mmol) then toluene (14 mL) and benzyl alcohol (1.4 mL, 13.5 mmol). The mixture was stirred under nitrogen at 90-100° C. The mixture filtered through Celite®, and the filtrate concentrated. EtOAc was added, the mixture sonicated and filtered to afford the product S11 as a white solid (1.8 g, 77%). $^1$H NMR (400 MHz, DMSO-$d_6$) δ 7.65-7.58 (m, 2H), 7.55-7.49 (m, 3H), 7.46-7.32 (m, 5H), 6.85 (ddd, J=10.0, 2.0, 0.8 Hz, 1H), 6.73-6.67 (m, 2H), 5.29 (s, 2H).

Preparation of S12

3-(4-(Benzyloxy)-1-(4-fluorophenyl)-1H-indol-2-yl)-3-methylbutan-1-ol (S12)

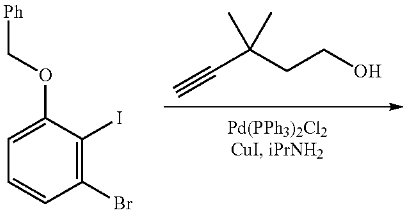

C2

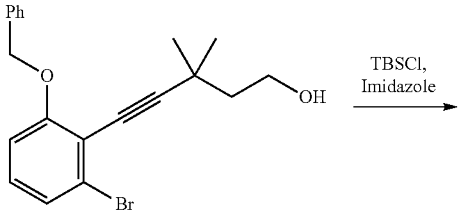

C32

-continued

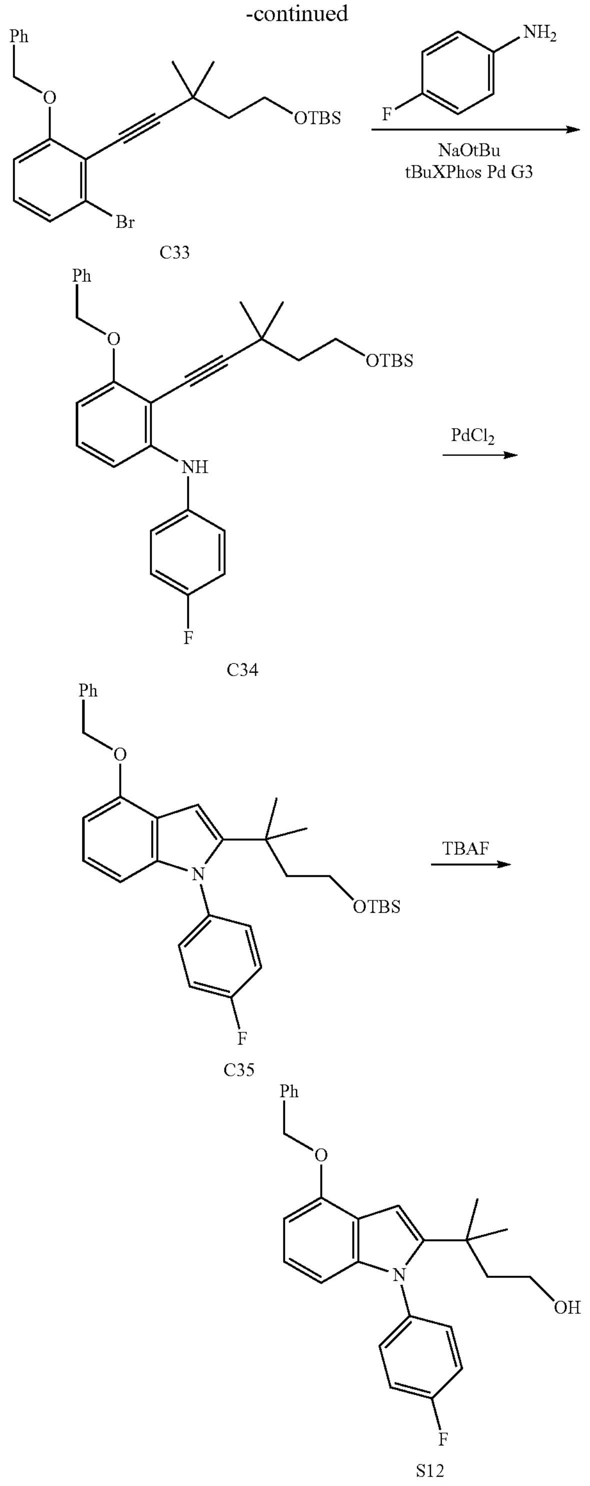

C33

C34

C35

S12

Step 1. Synthesis of 5-(2-benzyloxy-6-bromo-phenyl)-3,3-dimethyl-pent-4-yn-1-ol (C32)

A solution of 1-benzyloxy-3-bromo-2-iodo-benzene C2 (60 g, 154.2 mmol), 3,3-dimethylpent-4-yn-1-ol (23 g, 205.0 mmol) and N-isopropylpropan-2-amine (140 mL, 998.9 mmol) in 1,4-dioxane (400 mL) was purged with nitrogen for 10 minutes, then CuI (1.38 g, 7.25 mmol) and $Pd(PPh_3)_2Cl_2$ (4.65 g, 6.63 mmol) were added. The reaction mixture was stirred at 50° C. for 4 h, then cooled to room temperature and filtered to remove a light tan solid. The filtrate was concentrated to dryness then partitioned between water and EtOAc. The mixture was filtered over Celite® to aid separation of the layers. The organic layer was concentrated to dryness and purified via silica gel chromatography (Gradient: 0-50% EtOAc in heptane) afforded the product C32 as an orange oil (47 g, 82%). $^1H$ NMR (400 MHz, Chloroform-d) δ 7.52-7.48 (m, 2H), 7.44-7.39 (m, 2H), 7.38-7.32 (m, 1H), 7.20 (dd, J=8.1, 1.0 Hz, 1H), 7.07 (t, J=8.2 Hz, 1H), 6.85 (dd, J=8.4, 0.9 Hz, 1H), 5.15 (s, 2H), 3.89 (q, J=6.1 Hz, 2H), 2.23 (t, J=5.9 Hz, 1H), 1.82 (t, J=6.3 Hz, 2H), 1.39 (s, 6H). LCMS m/z 373.0 $[M+H]^+$.

Step 2. Synthesis of [5-(2-benzyloxy-6-bromo-phenyl)-3,3-dimethyl-pent-4-ynoxy]-tert-butyl-dimethyl-silane (C33)

To a solution of 5-(2-benzyloxy-6-bromo-phenyl)-3,3-dimethyl-pent-4-yn-1-ol C32 (47 g, 125.9 mmol) in dichloromethane (500 mL) was added TBS-$C_1$ (19.9 g, 132.0 mmol) and imidazole (9.0 g, 132.2 mmol). The reaction mixture was stirred at room temperature over the weekend. A tan precipitate was removed by filtration and the filtrate was washed with water (2×). The organic layer was dried over magnesium sulfate, filtered, and concentrated to afford the product C33 as light yellow oil (59.3 g, 97%). $^1H$ NMR (400 MHz, Chloroform-d) δ 7.50 (ddq, J=6.8, 1.5, 0.7 Hz, 2H), 7.41-7.36 (m, 2H), 7.35-7.30 (m, 1H), 7.19 (dd, J=8.1, 1.0 Hz, 1H), 7.05 (t, J=8.2 Hz, 1H), 6.84 (dd, J=8.3, 1.0 Hz, 1H), 5.13 (s, 2H), 3.98-3.90 (m, 2H), 1.85-1.77 (m, 2H), 1.36 (s, 6H), 0.89 (s, 9H), 0.05 (s, 6H). LCMS m/z 487.0 $[M+H]^+$.

Step 3. Synthesis of 3-benzyloxy-2-[5-[tert-butyl(dimethyl)silyl]oxy-3,3-dimethyl-pent-1-ynyl]-N-(4-fluorophenyl)aniline (C34)

A solution of $C_{33}$ (59.3 g, 121.7 mmol) and 4-fluoroaniline (17.3 mL, 182.6 mmol) in m-xylene (500 mL) was degassed with nitrogen for 10 minutes and then NaOtBu (35.1 g, 365.2 mmol) and tBuXPhos Pd G3 (2.9 g, 3.65 mmol) were added in one portion. The reaction mixture was stirred at 35° C. for 1 h, and then filtered over Celite®. The filter pad was washed with 1:1 EtOAc/water, and then the organic layer of the filtrate was combined with the xylene and concentrated to dryness. The resulting brown oil was purified via silica gel chromatography (Gradient: 0-25% EtOAc in heptane) to afford the desired product C34 as an amber oil (56.1 g, 89%). $^1H$ NMR (400 MHz, Chloroform-d) δ 7.52 (ddq, J=7.0, 1.5, 0.8 Hz, 2H), 7.42-7.37 (m, 2H), 7.34-7.29 (m, 1H), 7.19-7.14 (m, 2H), 7.07-7.00 (m, 3H), 6.68 (dd, J=8.3, 0.8 Hz, 1H), 6.40 (dd, J=8.3, 0.8 Hz, 1H), 6.38 (s, 1H), 5.15 (s, 2H), 3.94-3.86 (m, 2H), 1.85-1.77 (m, 2H), 1.38 (s, 6H), 0.86 (s, 9H), 0.00 (s, 6H). LCMS m/z 518.0 $[M+H]^+$.

Step 4. Synthesis of [3-[4-benzyloxy-]-(4-fluorophenyl)indol-2-yl]-3-methyl-butoxy]-tert-butyl-dimethyl-silane (C35)

To a solution of $C_{34}$ (56.1 g, 108.4 mmol) in MeCN (500 mL) was added $PdCl_2$ (965 mg, 5.44 mmol). The reaction mixture was stirred at 65° C. overnight, then cooled to room temperature and filtered. The filtrate was concentrated to dryness, triturated with MeCN, and filtered again. The solids were combined and rinsed with cold MeCN, then dried under vacuum to afford the product C35 as a white solid (48.7 g, 87%). $^1$H NMR (400 MHz, Chloroform-d) δ 7.54 (ddt, J=7.5, 1.4, 0.7 Hz, 2H), 7.45-7.39 (m, 2H), 7.35 (tdd, J=5.8, 3.9, 2.6 Hz, 3H), 7.21-7.14 (m, 2H), 6.94 (t, J=8.0 Hz, 1H), 6.61-6.56 (m, 2H), 6.27 (dt, J=8.2, 0.7 Hz, 1H), 5.24 (s, 2H), 3.57-3.49 (m, 2H), 1.76-1.66 (m, 2H), 1.27 (s, 6H), 0.83 (s, 9H), −0.04 (s, 6H). LCMS m/z 518.0 [M+H]$^+$.

Step 5. Synthesis of 3-(4-(Benzyloxy)-1-(4-fluorophenyl)-1H-indol-2-yl)-3-methylbutan-1-ol (S12)

To a solution of [3-[4-benzyloxy-1-(4-fluorophenyl)indol-2-yl]-3-methyl-butoxy]-tert-butyl-dimethyl-silane (1.0 g, 1.67 mmol) in THE (24 mL) was added a solution of TBAF (1 M in THF, 24 mL, 24 mmol). The mixture was stirred at 60° C. for 2 h and then concentrated. Purification via silica gel chromatography (Gradient: 0-50% EtOAc in heptane) gave S12 (540 mg, 71%). LCMS m/z 404.32 [M+H]$^+$.

Preparation of S13

5-(Benzyloxy)-1-(4-fluoro-3-methylphenyl)-1H-indole (S13)

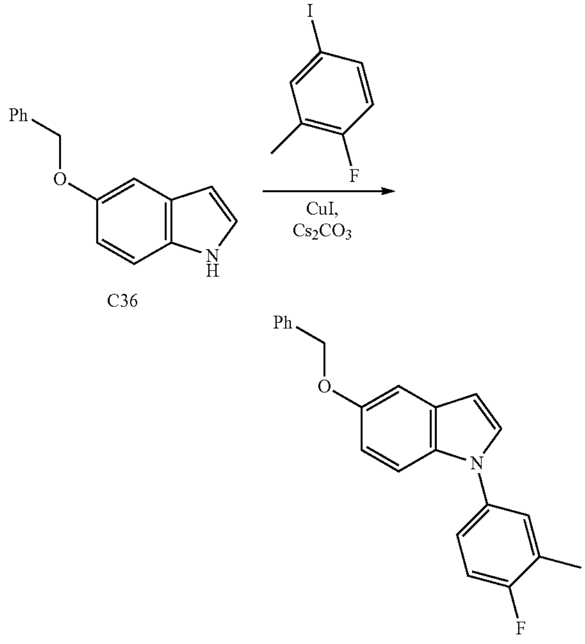

C36

S13

Step 1. Synthesis of 5-(benzyloxy)-1-(4-fluoro-3-methylphenyl)-1H-indole (S13)

Nitrogen was bubbled through a mixture of 5-benzyloxy-1H-indole C36 (2 g, 8.96 mmol), 1-fluoro-4-iodo-2-methylbenzene (2.1 g, 8.90 mmol), CuI (100 mg, 0.525 mmol) and cesium carbonate (5.2 g, 16.0 mmol) in DMF (10 mL) and the mixture then stirred overnight at 120° C. The reaction mixture was diluted with water and EtOAc. The organic layer was separated and the aqueous layer was extracted with EtOAc. The combined organic layers were washed with brine, dried ($Na_2SO_4$), filtered and concentrated. Purification via silica gel chromatography (Gradient: 0-15% EtOAc in heptane) gave S13 (2.4 g, 81%). $^1$H NMR (400 MHz, Chloroform-d) δ 7.58-7.46 (m, 3H), 7.15 (t, J=8.8 Hz, 1H), 6.98 (dd, J=9.0, 2.5 Hz, 1H), 6.59 (dd, J=3.3, 0.9 Hz, 1H), 5.16 (s, 2H), 2.38 (d, J=2.1 Hz, 3H).

Preparation of S14

2-(4-(Benzyloxy)-1-(4-fluoro-3-methoxyphenyl)-1H-indol-2-yl)-2-methylpropan-1-ol (S14)

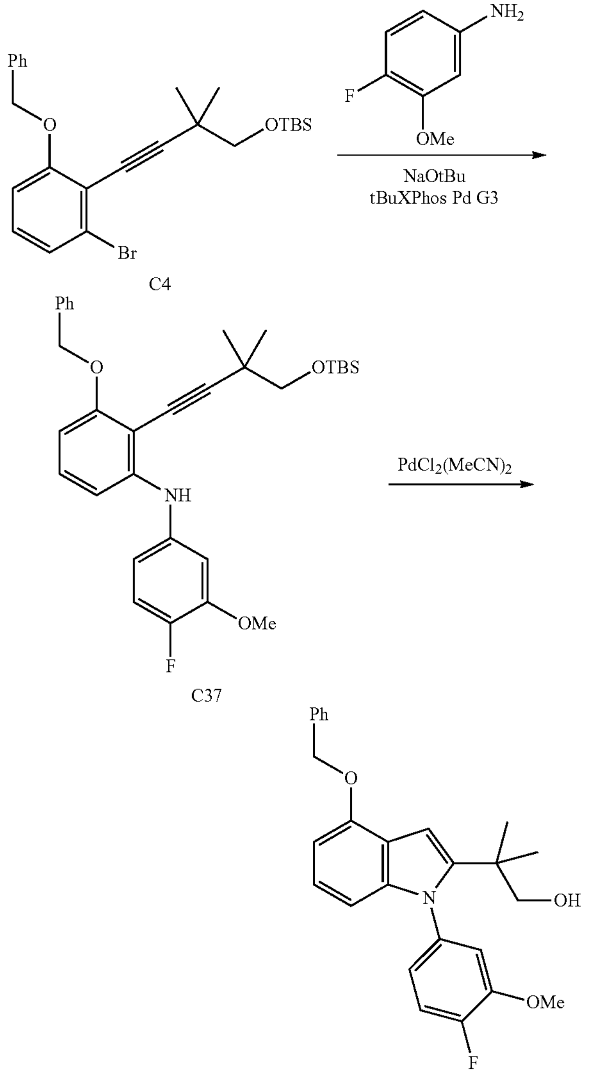

C4

C37

S14

Step 1. Synthesis of 3-(benzyloxy)-2-(4-((tert-butyldimethylsilyl)oxy)-3,3-dimethylbut-1-yn-1-yl)-N-(4-fluoro-3-methoxyphenyl)aniline (C37)

To a solution of C4 (3.39 g, 7.16 mmol) and 4-fluoro-3-methoxy-aniline (1.10 g, 7.794 mmol) in xylene (30 mL) under nitrogen was added NaOtBu (1.75 g, 18.2 mmol) followed by tBuXPhos Pd G3 (240 mg, 0.302 mmol). The reaction mixture was stirred at room temperature for 2.5 h. The reaction was diluted with water and sat aq. $NH_4Cl$ and extracted twice with EtOAc. The combined organics were concentrated to dryness and purified via silica gel chromatography (80 g column) eluting with 0-50% EtOAc in heptane. Pure fractions were combined and concentrated to give product C37 as a yellow oil (3.65 g, 96%). $^1$H NMR (400 MHz, Chloroform-d) δ 7.52-7.47 (m, 2H), 7.38-7.32 (m, 2H), 7.31-7.25 (m, 1H), 7.04-6.96 (m, 2H), 6.80 (dd, J=7.6, 2.5 Hz, 1H), 6.68 (ddd, J=8.7, 3.8, 2.6 Hz, 1H), 6.63 (dd, J=8.3, 0.8 Hz, 1H), 6.40-6.33 (m, 2H), 5.11 (s, 2H), 3.83 (s, 3H), 3.54 (s, 2H), 1.53 (s, 6H), 1.29 (s, 6H), 0.84 (s, 9H). LCMS m/z 534.33 [M+H]$^+$.

Step 2. Synthesis of 2-(4-(Benzyloxy)-1-(4-fluoro-3-methoxyphenyl)-1H-indol-2-yl)-2-methylpropan-1-ol (S14)

Nitrogen was bubbled through a mixture of 3-benzyloxy-2-[4-[tert-butyl(dimethyl)silyl]oxy-3,3-dimethyl-but-1-ynyl]-N-(4-fluoro-3-methoxy-phenyl)aniline C37 (3.65 g, 6.84 mmol) in methanol (50 mL) and ethyl acetate (25 mL) for 20 min, then $PdCl_2(CH_3CN)_2$ (75 mg, 0.289 mmol) was added and the mixture stirred overnight and then concentrated. Purification by column chromatography (80 g column; 0-75% EtOAc in heptane) gave product S14 (1 g, 35%). $^1$H NMR (400 MHz, Chloroform-d) δ 7.57-7.50 (m, 2H), 7.46-7.39 (m, 2H), 7.39-7.33 (m, 1H), 7.24-7.17 (m, 1H), 7.03-6.93 (m, 3H), 6.72 (d, J=0.8 Hz, 1H), 6.61 (dd, J=7.8, 0.6 Hz, 1H), 6.36 (dt, J=8.2, 0.7 Hz, 1H), 5.25 (s, 2H), 3.86 (s, 3H), 3.52 (dd, J=6.3, 3.0 Hz, 2H), 1.27 (s, 6H). LCMS m/z 420.39 [M+H]$^+$.

Preparation of S15

2-(4-(Benzyloxy)-1-(4-chloro-3-fluorophenyl)-1H-indol-2-yl)-2-methylpropan-1-ol (S15)

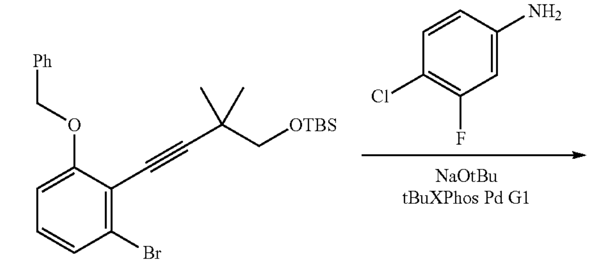

C4

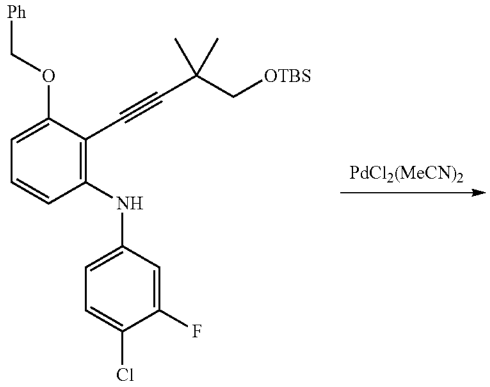

C38

-continued

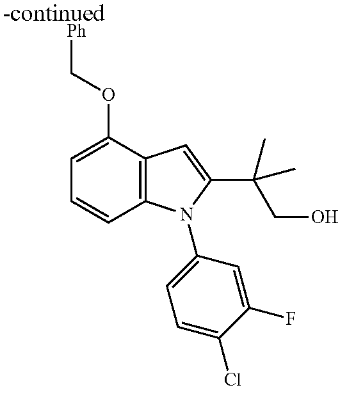

S15

Step 1. Synthesis of 3-(benzyloxy)-2-(4-((tert-butyldimethylsilyl)oxy)-3,3-dimethylbut-1-yn-1-yl)-N-(4-chloro-3-fluorophenyl)aniline (C38)

A reaction vessel was charged with [4-(2-benzyloxy-6-bromo-phenyl)-2,2-dimethyl-but-3-ynoxy]-tert-butyl-dimethyl-silane C4 (4 g, 8.45 mmol), 4-chloro-3-fluoro-aniline (2 g, 13.7 mmol) and sodium 2-methylpropan-2-olate (2 g, 20.8 mmol) in THE (25 mL). Nitrogen was bubbled through the mixture for 10 min. tBuXPhos Pd G1 (0.2 g, 0.307 mmol) was added and nitrogen was bubbled through the mixture for a further 5 min. The reaction mixture was heated at 60° C. for 3 hours. LCMS showed partial conversion so a further quantity of tBuXPhos Pd G1 (0.2 g, 0.307 mmol) was added and the heating continued overnight at 100° C. The solvent was evaporated. Purification by column chromatography (80 g column; 0-100% EtOAc in heptane) gave product C38 (840 mg, 43% purity, 8%). LCMS m/z 538.45 [M+H]$^+$.

Step 2. Synthesis of 2-(4-(benzyloxy)-1-(4-chloro-3-fluorophenyl)-1H-indol-2-yl)-2-methylpropan-1-ol (S15)

Nitrogen was bubbled through a mixture of 3-benzyloxy-2-[4-[tert-butyl(dimethyl)silyl]oxy-3,3-dimethyl-but-1-ynyl]-N-(4-chloro-3-fluoro-phenyl)aniline C38 (840 mg, 1.56 mmol) in methanol (15 mL) and ethyl acetate (15 mL) for 10 min, then $PdCl_2(CH_3CN)_2$ (50 mg, 0.193 mmol) was added and the mixture stirred overnight at 60° C. and then concentrated. Purification by column chromatography (80 g column; 0-100% EtOAc in heptane) gave product S15 (210 mg, 92% purity, 29%). LCMS m/z 424.3 [M+H]$^+$.

Preparation of S16

2-(4-(Benzyloxy)-1-(4-chlorophenyl)-1H-indol-2-yl)-2-methylpropan-1-ol (S16)

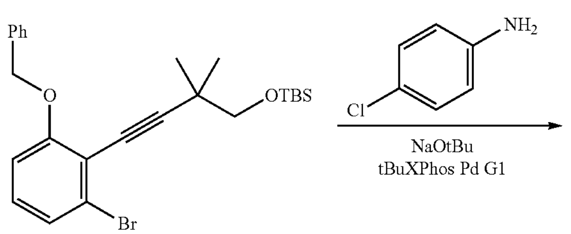

C4

-continued

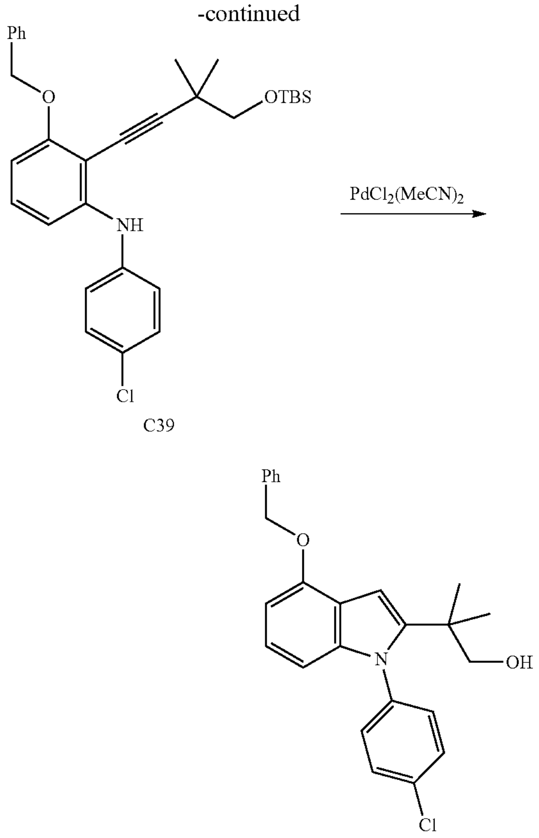

C39

S16

Step 1. Synthesis of 3-(benzyloxy)-2-(4-((tert-butyldimethylsilyl)oxy)-3,3-dimethylbut-1-yn-1-yl)-N-(4-chlorophenyl)aniline (C39)

A reaction vessel was charged with [4-(2-benzyloxy-6-bromo-phenyl)-2,2-dimethyl-but-3-ynoxy]-tert-butyl-dimethyl-silane C4 (4 g, 8.45 mmol), 4-chloroaniline (1.5 g, 11.8 mmol), and sodium 2-methylpropan-2-olate (2 g, 20.8 mmol) in THE (25 mL). Nitrogen was bubbled through the mixture for 10 min. tBuXPhos Pd G1 (0.2 g, 0.307 mmol) was added and nitrogen was bubbled through the mixture for a further 5 min. The reaction mixture was heated at 60° C. for 3 h. LCMS showed partial conversion so a further quantity of tBuXPhos Pd G1 (0.2 g, 0.307 mmol) was added and the heating continued overnight at 100° C. The solvent was evaporated. Purification by column chromatography (80 g column; 0-100% EtOAc in heptane) gave product C39 (3.47 g, 72% purity, 57%). LCMS m/z 520.49 $[M+H]^+$.

Step 2. Synthesis of 2-(4-(benzyloxy)-1-(4-chlorophenyl)-1H-indol-2-yl)-2-methylpropan-1-ol (S16)

Nitrogen was bubbled through a mixture of C39 (1.75 g, 3.36 mmol) in methanol (15 mL) and ethyl acetate (15 mL) for 10 min, then $PdCl_2(CH_3CN)_2$ (100 mg, 0.386 mmol) was added and the mixture stirred overnight at 60° C. and then concentrated. Purification by column chromatography (80 g column; 0-100% EtOAc in heptane) gave product S16 (370 mg, 92% purity, 25%). LCMS m/z 406.34 $[M+H]^+$.

Preparation of S17

2-(4-(Benzyloxy)-1-(4-fluoro-3-methylphenyl)-1H-indol-2-yl)ethan-1-ol (S17)

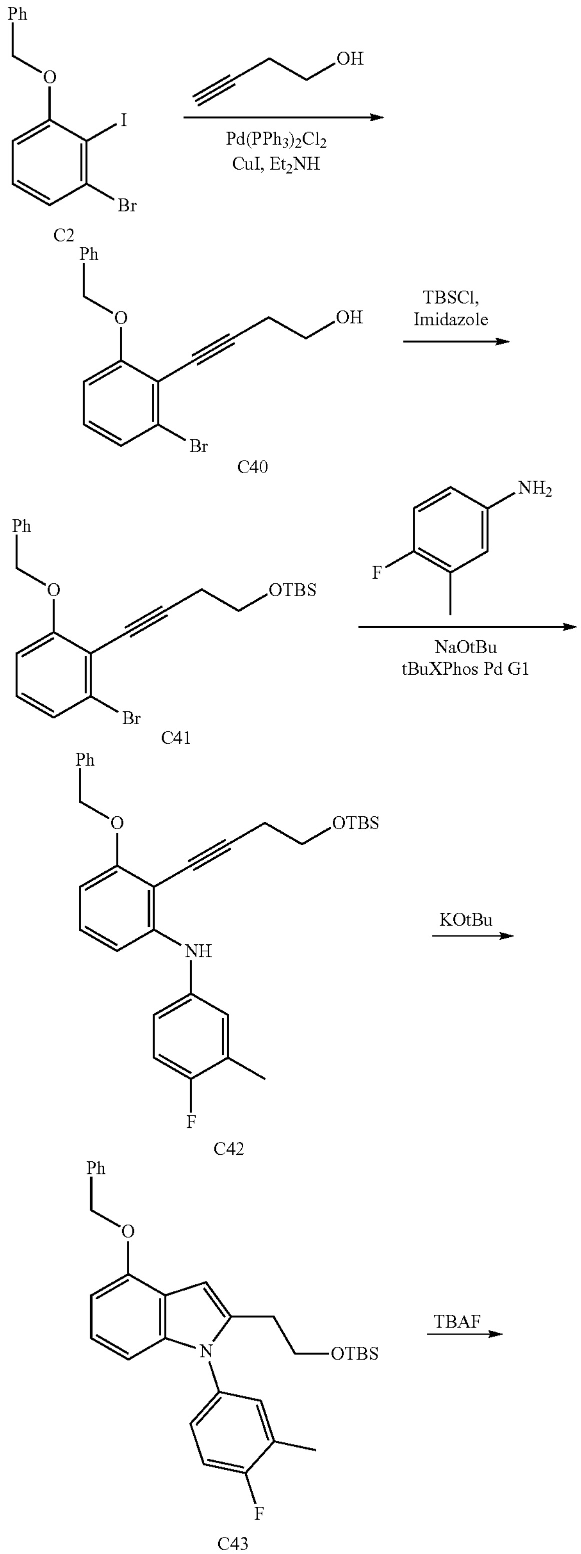

C2

C40

C41

C42

C43

-continued

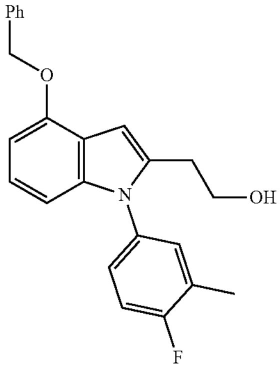

S17

Step 1: Synthesis of 4-(2-(benzyloxy)-6-bromophenyl)but-3-yn-1-ol (C40)

A 20 mL dram vial with a red pressure relief cap was successively charged with 1-benzyloxy-3-bromo-2-iodo-benzene C2 (10.2 g, 26.2 mmol), but-3-yn-1-ol (2.02 g, 28.8 mmol) and then DMF (35 mL). Nitrogen gas was bubbled through the mixture for 15-20 min. To this solution, was added $Pd(PPh_3)_2Cl_2$ (1.2 g, 1.71 mmol). CuI (500 mg, 2.63 mmol) was added, then diethylamine (4.1 mL, 39.6 mmol) and the mixture left stirring at room temperature for 15 min, and subsequently heated to 40° C. for 65 h. The reaction was purified by reverse phase column chromatography (C18 275 g column; 5-95% MeCN in aq. TFA). The combined fractions were partially concentrated under reduced pressure. The mixture was extracted with two ~100 mL portions of ethyl acetate. The organic layers were combined and dried over sodium sulfate, filtered and then concentrated under reduced pressure to afford 4-(2-benzyloxy-6-bromo-phenyl)but-3-yn-1-ol C40 (6.09 g, 70%) $^1$H NMR (400 MHz, Chloroform-d) δ 7.49-7.29 (m, 5H), 7.19 (dd, J=8.1, 1.0 Hz, 1H), 7.06 (t, J=8.2 Hz, 1H), 6.85 (dd, J=8.4, 1.0 Hz, 1H), 5.15 (s, 2H), 3.80 (t, J=5.9 Hz, 2H), 2.78 (t, J=6.0 Hz, 2H), 2.14 (s, 1H).

Step 2: Synthesis of ((4-(2-(benzyloxy)-6-bromophenyl)but-3-yn-1-yl)oxy)(tert-butyl)dimethylsilane (C41)

To a mixture of 4-(2-benzyloxy-6-bromo-phenyl)but-3-yn-1-ol C40 (6.09 g, 18.4 mmol) and TBSCl (4.5 mL, 24.18 mmol) in dichloromethane (70 mL) was added imidazole (1.9 g, 27.91 mmol) in one portion at room temperature. The reaction was left stirring overnight. Water was added to the reaction mixture and the mixture re-extracted with dichloromethane. The layers were separated with a phase separator. The aqueous layer was re-extracted with dichloromethane and the layers were separated through a phase separator again and the combined organics concentrated. Purification by column chromatography (120 g column; 0-100% EtOAc in heptane) gave 4-(2-benzyloxy-6-bromo-phenyl)but-3-ynoxy-tert-butyl-dimethyl-silane C41 (7.65 g, 93%). $^1$H NMR (400 MHz, Chloroform-d) δ 7.40-7.19 (m, 5H), 7.10 (dd, J=8.1, 1.0 Hz, 1H), 6.95 (t, J=8.2 Hz, 1H), 6.74 (dd, J=8.3, 1.0 Hz, 1H), 5.07 (s, z2H), 3.78 (t, J=7.5 Hz, 2H), 2.67 (t, J=7.5 Hz, 2H), 0.82 (s, 9H), 0.00 (s, 6H).

Step 3: Synthesis of 3-(benzyloxy)-2-(4-((tert-butyldimethylsilyl)oxy)but-1-yn-1-yl)-N-(4-fluoro-3-methylphenyl)aniline (C42)

Nitrogen was passed through a solution of 4-(2-benzyloxy-6-bromo-phenyl)but-3-ynoxy-tert-butyl-dimethyl-silane C41 (7.65 g, 17.17 mmol) and 4-fluoro-2-methyl-aniline (2.6 g, 20.78 mmol) in dioxane (7 mL) for 4 min. To this solution was added t-BuOH (8 mL), followed by sodium t-butoxide (2.5 g, 26.01 mmol) and then tBuXphosPalladacycle G1 (590 mg, 0.859 mmol). Bubbling was continued for another 3 min and then the vial was placed in a heating block set at 45° C. After 16 hours, water and ethyl acetate were added. The aqueous layer was re-extracted with ethyl acetate and the organic layers were separated and dried over sodium sulfate. The combined organic layers were concentrated under reduced pressure and dissolved again in dichloromethane. Purification by column chromatography (80 g column; 0-20% EtOAc in heptane) gave $C_{42}$ (5.85 g, 70%). $^1$H NMR (400 MHz, Chloroform-d) δ 7.50-7.21 (m, 5H), 7.14-6.86 (m, 4H), 6.61-6.51 (m, 1H), 6.34-6.25 (m, 1H), 5.10 (s, 1H), 3.79 (t, J=7.2 Hz, 1H), 2.71 (t, J=7.1 Hz, 1H), 2.20 (d, J=2.0 Hz, 2H), 0.80 (d, J=13.9 Hz, 6H), −0.09 (s, 1H).

Step 4: Synthesis of 4-(benzyloxy)-2-(2-((tert-butyldimethylsilyl)oxy)ethyl)-1-(4-fluoro-3-methylphenyl)-1H-indole (C43)

To a solution of 3-benzyloxy-2-[4-[tert-butyl(dimethyl)silyl]oxybut-1-ynyl]-N-(4-fluoro-3-methyl-phenyl)aniline C42 (5.85 g, 11.9 mmol) in 2-MeTHF (74 mL) was added potassium 2-methylpropan-2-olate (1 M, 12 mL, 12 mmol) at room temperature and the reaction mixture stirred overnight. EtOAc, brine and saturated ammonium chloride were added, the layers separated and the organic layers dried over sodium sulfate, filtered and concentrated under reduced pressure to give C43 (5.85 g, 100%).

Step 5: Synthesis of 2-(4-(benzyloxy)-1-(4-fluoro-3-methylphenyl)-1H-indol-2-yl)ethan-1-ol (S17)

To a solution of 2-[4-benzyloxy-1-(4-fluoro-3-methyl-phenyl)indol-2-yl]ethoxy-tert-butyl-dimethyl-silane C43 (5.85 g, 11.95 mmol) in THE (70 mL) was added TBAF (1M in THF, 12 mL, 12 mmol) and the reaction was allowed to stir overnight. Water was added and the product was extracted with two portions of ethyl acetate. The organic layers were dried over sodium sulfate, filtered and concentrated under reduced pressure. The crude product was purified via column chromatography (0-100% ethyl acetate in heptane) gave 2-[4-benzyloxy-1-(4-fluoro-3-methyl-phenyl)indol-2-yl]ethanol S17 (310 mg, 7%). $^1$H NMR (400 MHz, Chloroform-d) δ 7.57-7.53 (m, 2H), 7.47-7.34 (m, 3H), 7.21-7.14 (m, 3H), 7.04 (t, J=8.1 Hz, 1H), 6.71-6.67 (m, 2H), 6.64 (d, J=8.0 Hz, 1H), 5.27 (s, 2H), 3.82 (q, J=6.2 Hz, 2H), 2.91 (td, J=6.5, 0.8 Hz, 2H), 2.37 (d, J=1.9 Hz, 3H), 1.60 (s, 2H). LCMS m/z 376.42 $[M+H]^+$.

Preparation of S18

2-(4-(Benzyloxy)-1-(4-fluoro-3-methylphenyl)-1H-indol-2-yl)ethan-1-ol (S18)

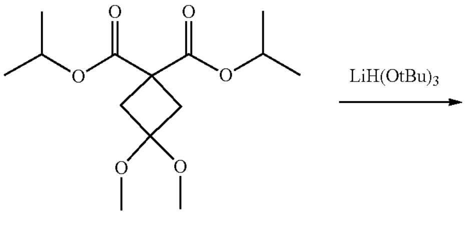

C44

-continued

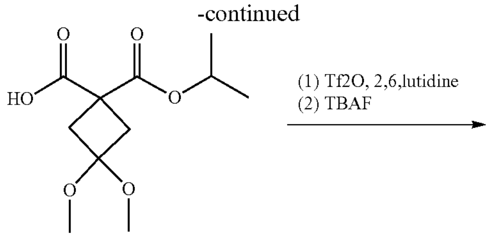

C45

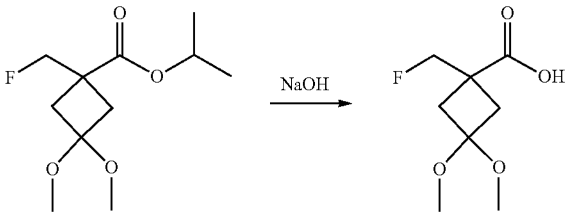

C46 S18

Step 1: Synthesis of Isopropyl 1-(hydroxymethyl)-3,3-dimethoxycyclobutane-1-carboxylate (C45)

A solution of diisopropyl 3,3-dimethoxycyclobutane-1,1-dicarboxylate C44 (3.5 g, 12.1 mmol) in THE (10 mL) at −78° C. was added lithium tri-tert-butoxyaluminum hydride solution (28 mL of 1 M, 28 mmol). The mixture was stirred overnight at room temperature then heated to 50° C. for 2 h. The reaction was quenched at room temperature with $NH_4Cl$ solution, extracted with dichloromethane, dried over $Na_2SO_4$, filtered and concentrated. Purification by column chromatography (80 g column; 0-40% EtOAc in heptane) gave 2-(4-(benzyloxy)-1-(4-fluoro-3-methylphenyl)-1H-indol-2-yl)ethan-1-ol (C45) (1.6 g, 57%). $^1$H NMR (400 MHz, Chloroform-d) δ 5.08 (hept, J=6.3 Hz, 1H), 3.83 (d, J=6.5 Hz, 2H), 3.18 (d, J=2.9 Hz, 6H), 2.62-2.48 (m, 2H), 2.42 (td, J=6.5, 0.9 Hz, 1H), 2.28-2.15 (m, 2H), 1.29 (d, J=6.3 Hz, 6H).

Step 2: Synthesis of Isopropyl 1-(fluoromethyl)-3,3-dimethoxycyclobutane-1-carboxylate (C46)

A solution of isopropyl 1-(hydroxymethyl)-3,3-dimethoxy-cyclobutanecarboxylate (C45) (2.6 g, 11.19 mmol) in dichloromethane (20 mL) was cooled to −78° C. To the solution was added 2,6-lutidine (2.2 mL, 19 mmol) and $Tf_2O$ (2.6 mL, 15.45 mmol). The mixture was warmed slowly overnight to room temperature then quenched with water. The mixture was extracted with dichloromethane, washed with sat aq. $NaHCO_3$ solution, sat aq. $NH_4Cl$ solution then brine. Drying over $Na_2SO_4$, filtration and concentration gave the triflate intermediate. This was dissolved in THE (20 mL) and cooled to −78° C. To the solution was added tetrabutylammonium fluoride solution (1 M, 22 mL, 22 mmol), stirred and warmed slowly for 1 hours to room temperature. The reaction was quenched at room temperature with water, extracted with EtOAc, washed with brine, dried over $Na_2SO_4$, filtered and concentrated. Purification by column chromatography (40 g column; 0-30% EtOAc in heptane) gave isopropyl-1-(fluoromethyl)-3,3-dimethoxycyclobutane-1-carboxylate (C46) (2.4 g, 92%). $^1$H NMR (400 MHz, Chloroform-d) δ 5.08 (p, J=6.3 Hz, 1H), 4.71 (s, 1H), 4.59 (s, 1H), 3.18 (d, J=0.6 Hz, 7H), 2.67-2.51 (m, 3H), 2.28-2.17 (m, 2H), 1.28 (d, J=6.2 Hz, 6H).

Step 3: Synthesis of 2-(4-(benzyloxy)-1-(4-fluoro-3-methylphenyl)-1H-indol-2-yl)ethan-1-ol (S18)

To a solution of isopropyl 1-(fluoromethyl)-3,3-dimethoxycyclobutane-1-carboxylate (C46) in MeOH (10 mL) was added NaOH (3 M, 4 mL, 12 mmol) and the mixture stirred overnight at 55° C. The reaction was concentrated and neutralized with HCl to pH 3. The mixture was extracted with dichloromethane, dried over $Na_2SO_4$ filtered and concentrated to give product S18 (550 mg, 45%). $^1$H NMR (400 MHz, Chloroform-d) δ 4.87 (s, 1H), 4.75 (d, J=1.0 Hz, 2H), 4.64 (s, 1H), 3.68-3.57 (m, 2H), 3.32-3.23 (m, 2H), 3.19 (d, J=3.0 Hz, 5H), 2.69-2.61 (m, 2H), 2.36-2.25 (m, 2H).

Preparation of S19

Ethyl 1-(difluoromethyl)-4-oxocyclohexane-1-carboxylate (S19)

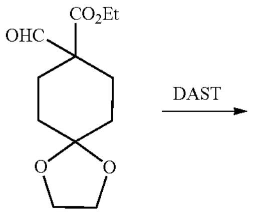

C47

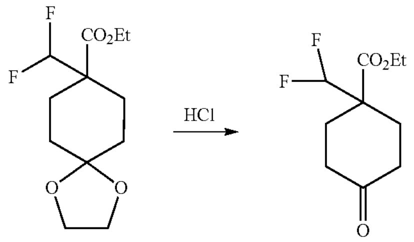

C48 S19

Step 1. Synthesis of ethyl 8-(difluoromethyl)-1,4-dioxaspiro[4.5]decane-8-carboxylate (C48)

To a solution of ethyl 8-formyl-1,4-dioxaspiro[4.5]decane-8-carboxylate C47 (0.9 g, 3.72 mmol) in dichloromethane (15 mL) was added DAST (1.1 mL, 8.33 mmol) and stirred overnight. The reaction was diluted with dichloromethane, washed with sat. aq. $NaHCO_3$ solution, dried ($Na_2SO_4$), filtered and concentrated. Purification by column chromatography (12 g column; 0-30% EtOAc in heptane) gave ethyl 8-(difluoromethyl)-1,4-dioxaspiro[4.5]decane-8-carboxylate C48 (800 mg, 81%). $^1$H NMR (400 MHz, Chloroform-d) δ 5.79 (t, J=56.3 Hz, 1H), 4.26 (q, J=7.1 Hz, 2H), 3.96 (d, J=2.2 Hz, 4H), 2.26-2.14 (m, 2H), 1.91-1.64 (m, 7H), 1.31 (t, J=7.1 Hz, 3H).

Step 2. Synthesis of ethyl 1-(difluoromethyl)-4-oxocyclohexane-1-carboxylate (S19)

To the product ethyl 8-(difluoromethyl)-1,4-dioxaspiro[4.5]decane-8-carboxylate C48 (800 mg, 3.03 mmol) in acetone (15 mL) was added HCl (18 mL of a 2 M solution, 36 mmol) and the mixture stirred overnight at room temperature. After concentration, the residue was extracted with dichloromethane, dried over $Na_2SO_4$, filtered and concentrated to give ethyl 1-(difluoromethyl)-4-oxocyclohexane-1-carboxylate (S19) (640 mg, 78%). $^1$H NMR (400 MHz, Chloroform-d) δ 5.98 (t, J=56.1 Hz, 1H), 4.33 (q, J=7.1 Hz, 2H), 2.61-2.31 (m, 6H), 2.09-1.91 (m, 2H), 1.35 (t, J=7.1 Hz, 3H).

Preparation of S20

1-(Difluoromethyl)-3,3-dimethoxycyclobutane-1-carboxylic acid (S20)

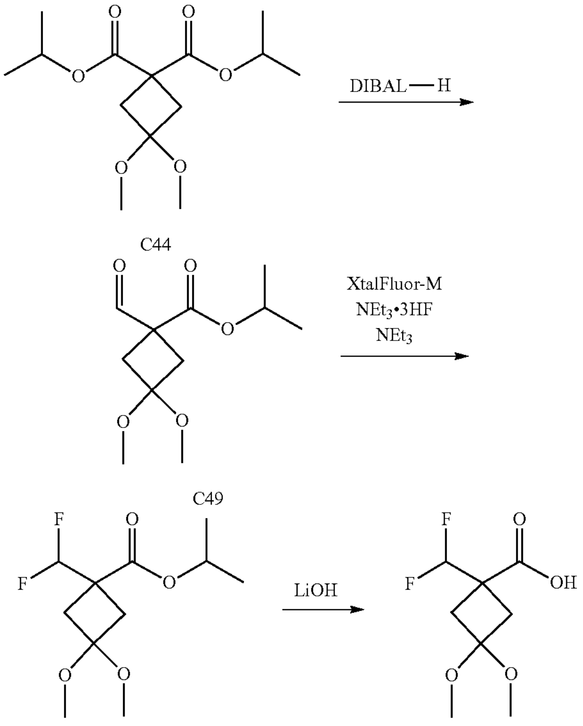

C44

C49

C50

S20

Step 1: Synthesis of Isopropyl 1-formyl-3,3-dimethoxycyclobutane-1-carboxylate (C49)

A solution of diisopropyl 3,3-dimethoxycyclobutane-1,1-dicarboxylate C44 (7.5 g, 26.0 mmol) in THE (50 mL) was cooled down to −78° C. To the solution was added DIBAL (50 mL of a 1M solution, 50 mmol) and stirred for 2 h at −78° C. The reaction was quenched with $NH_4Cl$. 200 ml of saturated Rochelle's salt was added and the mixture stirred for 2 h. The mixture was extracted with EtOAc, dried over $Na_2SO_4$ filtered and concentrated. Purification by column chromatography (40 g column; 0-30% EtOAc in heptane) gave $C_{49}$ (3.2 g, 53%). $^1$H NMR (400 MHz, Chloroform-d) δ 9.69 (d, J=2.1 Hz, 1H), 5.38-4.65 (m, 1H), 3.38-2.81 (m, 6H), 2.84-2.38 (m, 4H), 1.55-0.97 (m, 6H).

Step 2: Synthesis of Isopropyl 1-(difluoromethyl)-3,3-dimethoxycyclobutane-1-carboxylate (C50)

To a solution of triethylamine trihydrofluoride (2.8 mL, 17.2 mmol) and TEA (1.25 mL, 8.97 mmol) in dichloromethane (25 mL) at 0° C. was added XtalFluor-M (3.2 g, 13.17 mmol) and isopropyl 1-formyl-3,3-dimethoxy-cyclobutanecarboxylate C49 (2.0 g, 8.69 mmol). The mixture was warmed to 25° C. and allowed to stir at that temperature for 16 h. The reaction was quenched with sat. $NaHCO_3$ and extracted with dichloromethane. The organic layer was dried ($Na_2SO_4$) and concentrated to afford product C50 (2.18 g, 100%). $^1$H NMR (400 MHz, Chloroform-d) δ 6.05 (t, J=56.6 Hz, 1H), 5.29-4.92 (m, 1H), 3.18 (d, J=3.9 Hz, 6H), 2.73-2.56 (m, 2H), 2.57-2.29 (m, 2H), 1.28 (dd, J=13.0, 6.3 Hz, 6H).

Step 3: Synthesis of 1-(difluoromethyl)-3,3-dimethoxycyclobutane-1-carboxylic acid (S20)

To a solution of isopropyl 1-(difluoromethyl)-3,3-dimethoxy-cyclobutanecarboxylate $C_{50}$ (2.20 g, 8.72 mmol) in MeOH (10 mL), THE (10 mL) and water (5 mL) was added $LiOH{\cdot}H_2O$ (1.46 g, 34.9 mmol) and the mixture was microwaved for 4 h. The reaction mixture was concentrated, neutralized with HCl (17 mL of 2 M, 34 mmol) and back extracted with dichloromethane (3×40 ml). The organic layer was dried ($Na_2SO_4$) and concentrated to afford product S20 (400 mg, 22%). The product was taken to next steps without further purification. 1H NMR (400 MHz, Chloroform-d) δ 6.13 (t, J=56.3 Hz, 1H), 3.20 (d, J=7.8 Hz, 6H), 2.78-2.36 (m, 4H).

Preparation of S21

1-(Difluoromethyl)-4-oxocyclohexane-1-carboxylic acid (S21)

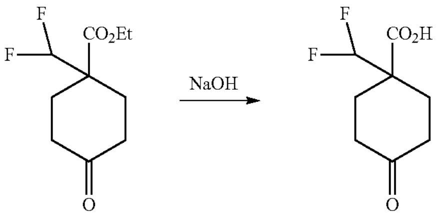

S19 S21

To a solution of S19 (500 mg, 2.27 mmol) in THE (2 mL) and EtOH (2 mL) was added NaOH (3 M, 1.5 mL, 4.5 mmol) and stirred overnight. The reaction as neutralized to pH 3 with aq. HCl and extracted with EtOAc. The organic layer was dried ($Na_2SO_4$), filtered and concentrated. Purification by column chromatography (40 g column; 0-40% EtOAc in heptane) gave S21 (380 mg, 87%). $^1$H NMR (400 MHz, Chloroform-d) δ 6.03 (t, J=55.9 Hz, 1H), 2.66-2.39 (m, 4H), 2.16-1.98 (m, 2H), 1.93-1.83 (m, 2H).

Preparation of S22

Methyl-3-fluoro-4-(2-methyloxiran-2-yl)benzoate (S22)

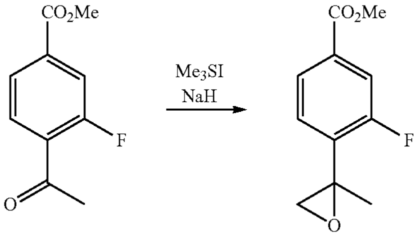

C51 S22

A flame dried flask was charged with trimethylsulfonium iodide (850 mg, 4.17 mmol) and sodium hydride (170 mg, 4.25 mmol). The flask was maintained under nitrogen before introducing DMSO (3 mL) and THE (3 mL). The mixture was allowed to stir at 25° C. for 30 min. The reaction was cooled to 0° C. and methyl 4-acetyl-3-fluoro-benzoate C51 (400 mg, 2.04 mmol) in THE (2 mL) was added and the reaction was gradually warmed to 25° C. and stirred at that temperature for 16 h. The reaction was quenched with sat. aq. $NH_4Cl$ and ethyl acetate, the layers separated and the organics concentrated and purified using column chromatography (12 g gold column) to afford product S22 (240 mg, 56%). LCMS m/z 211.13 $[M+H]^+$.

Compound 1

(1R,3R)-5'-(4-Fluoro-3-methylphenyl)-9'-hydroxy-3-methyl-4',5'-dihydro-3'H-spiro[cyclobutane-1,1'-pyrano[4,3-b]indole]-3-carboxylic acid (1)

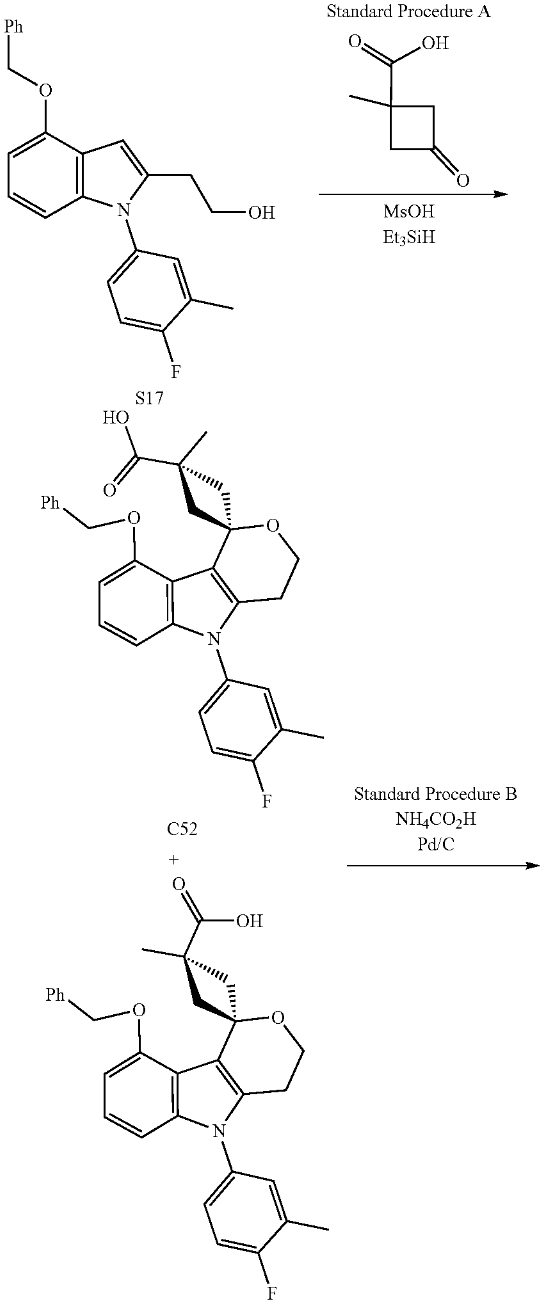

S17

C52

+

C53

-continued

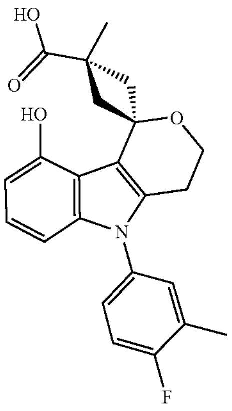

1

Standard Procedure A

Step 1: Synthesis of (R,3R)-9'-(benzyloxy)-5'-(4-fluoro-3-methylphenyl)-3-methyl-4',5'-dihydro-3'H-spiro[cyclobutane-1,1'-pyrano[4,3-b]indole]-3-carboxylic acid (C52) and (1S,3S)-9'-(benzyloxy)-5'-(4-fluoro-3-methylphenyl)-3-methyl-4',5'-dihydro-3'H-spiro[cyclobutane-1,1'-pyrano[4,3-b]indole]-3-carboxylic acid (C53)

To a mixture of 2-[4-benzyloxy-1-(4-fluoro-3-methyl-phenyl)indol-2-yl]ethanol S17 (207 mg, 0.551 mmol) and 1-methyl-3-oxo-cyclobutanecarboxylic acid (230 mg, 1.795 mmol) in DCE (1.75 mL) was added methanesulfonic acid (61 μL, 0.94 mmol) then triethylsilane (89 μL, 0.557 mmol) and the resulting dark solution stirred at room temperature. After 15 min, the reaction was directly purified by column chromatography (24 g gold column; 5-40% EtOAc in heptane).

First to elute was 9-benzyloxy-5-(4-fluoro-3-methyl-phenyl)-1'-methyl-spiro[3,4-dihydropyrano[4,3-b]indole-1,3'-cyclobutane]-1'-carboxylic acid $C_{52}$ (88 mg, 32%). $^1$H NMR (400 MHz, Chloroform-d) δ 7.45-7.41 (m, 2H), 7.37-7.32 (m, 2H), 7.24 (d, J=7.3 Hz, 1H), 7.17-7.10 (m, 3H), 6.87 (t, J=8.1 Hz, 1H), 6.71 (dd, J=8.2, 0.7 Hz, 1H), 6.41 (dd, J=8.0, 0.8 Hz, 1H), 5.35 (s, 2H), 3.94 (t, J=5.4 Hz, 2H), 3.62-3.54 (m, 2H), 2.61 (t, J=5.3 Hz, 2H), 2.40-2.29 (m, 5H), 1.67 (s, 3H). LCMS m/z 486.29 $[M+H]^+$. X-ray crystallography confirmed this stereoisomer as trans. Diagnostic $^1$H NMR chemical shifts associated with this characterized stereoisomer were used to structurally assign other compounds within the series.

Second to elute was (1S,3S)-9'-(benzyloxy)-5'-(4-fluoro-3-methylphenyl)-3-methyl-4',5'-dihydro-3'H-spiro[cyclobutane-1,1'-pyrano[4,3-b]indole]-3-carboxylic acid (C53) (88 mg, 30%). $^1$H NMR (400 MHz, Chloroform-d) δ 7.41-7.36 (m, 2H), 7.31 (ddd, J=7.6, 6.8, 1.4 Hz, 2H), 7.27-7.22 (m, 1H), 7.10-7.00 (m, 3H), 6.88 (t, J=8.1 Hz, 1H), 6.67 (dd, J=8.2, 0.7 Hz, 1H), 6.50-6.47 (m, 1H), 5.39 (s, 2H), 3.92 (t, J=5.4 Hz, 2H), 3.16-3.09 (m, 2H), 2.78-2.69 (m, 2H), 2.57 (t, J=5.4 Hz, 2H), 2.26 (d, J=2.0 Hz, 3H), 1.31 (s, 3H). LCMS m/z 486.29 $[M+H]^+$.

Standard Procedure B

Step 2: Synthesis of (1R,3R)-5'-(4-fluoro-3-methylphenyl)-9'-hydroxy-3-methyl-4',5'-dihydro-3'H-spiro[cyclobutane-1,1'-pyrano[4,3-b]indole]-3-carboxylic acid (1)

A mixture of 9-benzyloxy-5-(4-fluoro-3-methyl-phenyl)-1'-methyl-spiro[3,4-dihydropyrano[4,3-b]indole-1,3'-cyclobutane]-1'-carboxylic acid $C_{52}$ (88 mg, 0.179 mmol), 10% Pd/C (50 mg, Degussa wet), $NH_4CO_2H$ (150 mg) in EtOH (5 mL) and EtOAc (2 mL) was stirred at room temperature. The reaction mixture was filtered through Celite® with the aid of EtOH and then concentrated. Water and dichloromethane were added and the layers were separated through a phase separator again and the organics concentrated. Purification by column chromatography (12 g column; 0-10% MeOH in dichloromethane) gave (1R,3R)-5'-(4-fluoro-3-methylphenyl)-9'-hydroxy-3-methyl-4',5'-dihydro-3'H-spiro[cyclobutane-1,1'-pyrano[4,3-b]indole]-3-carboxylic acid (1) (12.6 mg, 17%). $^1H$ NMR (400 MHz, Methanol-d4) δ 7.26-7.12 (m, 3H), 6.85 (t, J=7.9 Hz, 1H), 6.57 (dd, J=8.2, 0.8 Hz, 1H), 6.43 (dd, J=7.7, 0.8 Hz, 1H), 3.89 (t, J=5.4 Hz, 2H), 3.52-3.42 (m, 2H), 2.55 (t, J=5.3 Hz, 2H), 2.33 (d, J=2.0 Hz, 3H), 2.22-2.13 (m, 2H), 1.66 (s, 3H). LCMS m/z 396.21 $[M+H]^+$.

Compound 2

(1S,3S)-9'-(benzyloxy)-5'-(4-fluoro-3-methylphenyl)-3-methyl-4',5'-dihydro-3'H-spiro[cyclobutane-1,1'-pyrano[4,3-b]indole]-3-carboxylic acid (2)

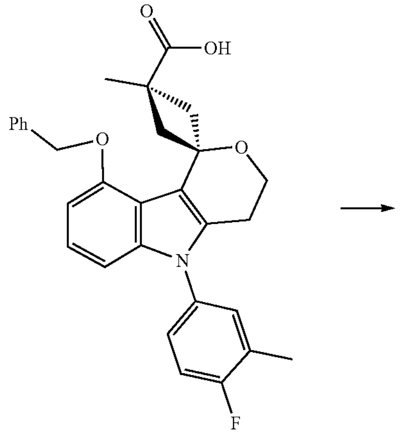

C53

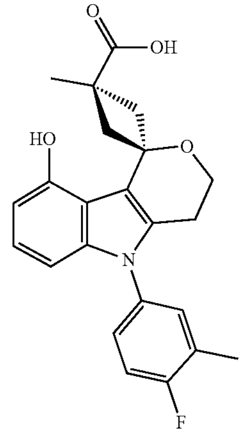

2

(1S,3S)-5'-(4-Fluoro-3-methylphenyl)-9'-hydroxy-3-methyl-4',5'-dihydro-3'H-spiro[cyclobutane-1,1'-pyrano[4,3-b]indole]-3-carboxylic acid (2) was prepared from $C_{53}$ (25.5 mg, 37%) according to Standard Procedure B. $^1H$ NMR (400 MHz, Methanol-$d_4$) δ 7.24-7.12 (m, 3H), 6.91-6.84 (m, 1H), 6.58 (dd, J=8.2, 0.8 Hz, 1H), 6.46 (dd, J=7.7, 0.8 Hz, 1H), 3.85 (t, J=5.4 Hz, 2H), 3.13-3.03 (m, 2H), 2.77-2.69 (m, 2H), 2.54 (t, J=5.4 Hz, 2H), 2.33 (d, J=2.0 Hz, 3H), 1.57 (s, 3H). LCMS m/z 396.17 $[M+H]^+$.

Compound 3 and Compound 4

2-((1S,3S)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)acetic acid (3) and 2-((R,3R)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)acetic acid (4)

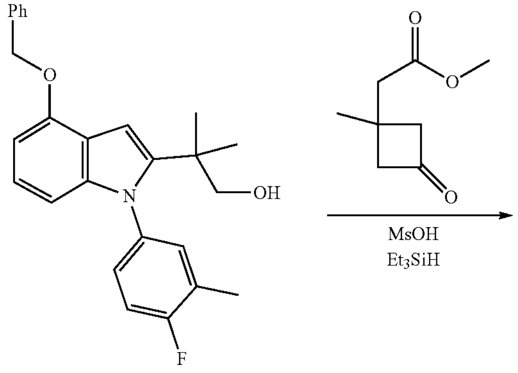

S1

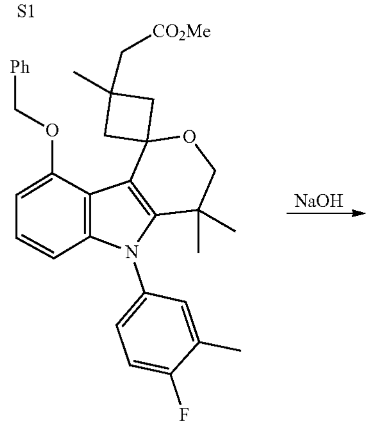

C54

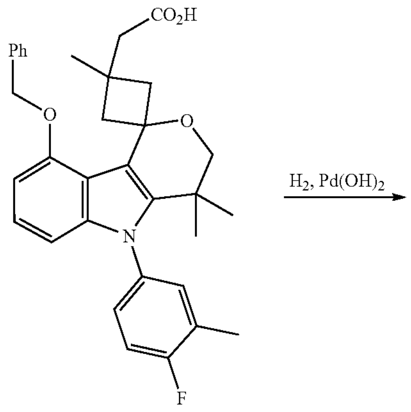

C55

-continued

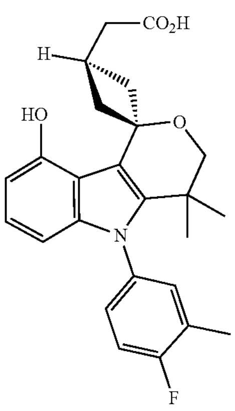

+

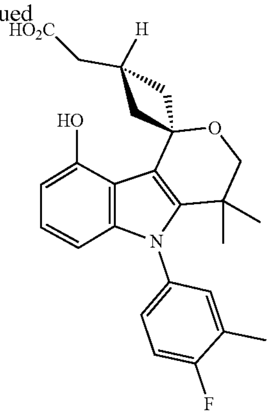

3 4

Step 1: Synthesis of methyl-2-(9'-(benzyloxy)-5'-(4-fluoro-3-methylphenyl)-3,4',4'-trimethyl-4',5'-dihydro-3'H-spiro[cyclobutane-1,1'-pyrano[4,3-b]indol]-3-yl)acetate (C54)

A reaction vial was charged with 2-[4-benzyloxy-1-(4-fluoro-3-methyl-phenyl)indol-2-yl]-2-methyl-propan-1-ol S1 (90 mg, 0.223 mmol), methyl 2-(3-oxocyclobutyl)acetate (45 mg, 0.317 mmol) and dichloromethane (900 μL). To the mixture was added methanesulfonic acid (36 mg, 0.375 mmol) and $Et_3SiH$ (6 μL, 0.0376 mmol). The mixture was stirred for 30 min at room temperature. Direct purification by 12 g silica gel cartridge eluting with 0-50% EtOAc/heptane gave methyl-2-(9'-(benzyloxy)-5'-(4-fluoro-3-methylphenyl)-3,4',4'-trimethyl-4',5'-dihydro-3'H-spiro[cyclobutane-1,1'-pyrano[4,3-b]indol]-3-yl)acetate (C54) (90 mg, 76%) as a mixture of cis and trans isomers. LCMS m/z 528.6 $[M+H]^+$.

Step 2: Synthesis of 2-(9'-(benzyloxy)-5'-(4-fluoro-3-methylphenyl)-3,4',4'-trimethyl-4',5'-dihydro-3'H-spiro[cyclobutane-1,1'-pyrano[4,3-b]indol]-3-yl) acetic acid (C55)

To the methyl-2-(9'-(benzyloxy)-5'-(4-fluoro-3-methylphenyl)-3,4',4'-trimethyl-4',5'-dihydro-3'H-spiro[cyclobutane-1,1'-pyrano[4,3-b]indol]-3-yl)acetate (C54) (90 mg, 0.171 mmol) in MeOH (5 mL) was added NaOH (2M, 1 mL, 2 mmol) and the mixture stirred for 3 hours at 50° C. then neutralized to pH 3 with HCl. The mixture was concentrated and then extracted with EtOAc, dried over ($Na_2SO_4$), filtered and concentrated. Purification by column chromatography (0-30% EtOAc/heptane) gave 2-(9'-(benzyloxy)-5'-(4-fluoro-3-methylphenyl)-3,4',4'-trimethyl-4',5'-dihydro-3'H-spiro[cyclobutane-1,1'-pyrano[4,3-b]indol]-3-yl)acetic acid (C55) (45 mg, 39%). LCMS m/z 514.6 $[M+H]^+$.

Step 3: Synthesis of 2-((1S,3S)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)acetic acid (3) and 2-((1R,3R)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)acetic acid (4)

A mixture of 2-(9'-(benzyloxy)-5'-(4-fluoro-3-methylphenyl)-3,4',4'-trimethyl-4',5'-dihydro-3'H-spiro[cyclobutane-1,1'-pyrano[4,3-b]indol]-3-yl)acetic acid (C55) (45 mg, 0.0876 mmol) and $Pd(OH)_2$ (20 mg, 0.142 mmol) in EtOAc (10 mL) and MeOH (1 mL) was stirred for 1 h under a hydrogen balloon. The reaction was filtered though a layer of Celite® and concentrated. Purification by reverse phase chromatography gave 2-((1S,3S)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)acetic acid (3) (16.1 mg, 41%), $^1H$ NMR (400 MHz, Chloroform-d) δ 7.25-7.12 (m, 3H), 6.91 (t, J=7.9 Hz, 1H), 6.46 (d, J=7.5 Hz, 1H), 6.42-6.31 (m, 1H), 3.50 (s, 2H), 3.05 (q, J=8.1 Hz, 1H), 2.91 (s, 3H), 2.76 (d, J=7.6 Hz, 2H), 2.53 (t, J=10.3 Hz, 3H), 2.35 (d, J=2.0 Hz, 3H), 1.09 (d, J=3.6 Hz, 6H). LCMS m/z 424.6 $[M+H]^+$.

Chromatography also gave 2-((1R,3R)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)acetic acid (4) (7.8 mg, 20%), $^1H$ NMR (400 MHz, Chloroform-d) δ 7.26-7.07 (m, 3H), 6.90 (t, J=7.9 Hz, 1H), 6.46 (d, J=7.6 Hz, 1H), 6.37 (d, J=8.2 Hz, 1H), 3.47 (s, 2H), 3.28 (s, 2H), 2.87 (s, 3H), 2.34 (d, J=1.9 Hz, 3H), 2.14 (d, J=12.7 Hz, 2H), 1.07 (d, J=3.5 Hz, 6H). LCMS m/z 424.6 $[M+H]^+$ Compound 5 and Compound 6

(1S,3S)-5'-(4-fluoro-3-methylphenyl)-9'-hydroxy-3,4',4'-trimethyl-4',5'-dihydro-3'H-spiro[cyclobutane-1,1'-pyrano[4,3-b]indole]-3-carboxylic acid (5) and (1R,3R)-5'-(4-fluoro-3-methylphenyl)-9'-hydroxy-3,4',4'-trimethyl-4',5'-dihydro-3'H-spiro[cyclobutane-],1'-pyrano[4,3-b]indole]-3-carboxylic acid (6)

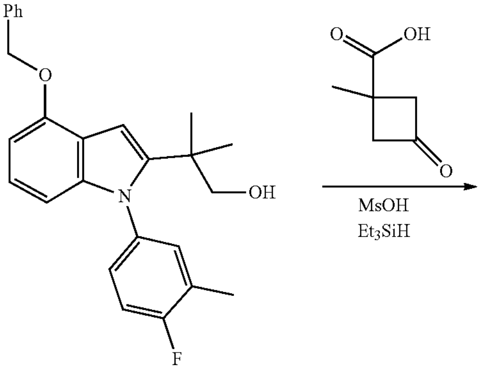

S1

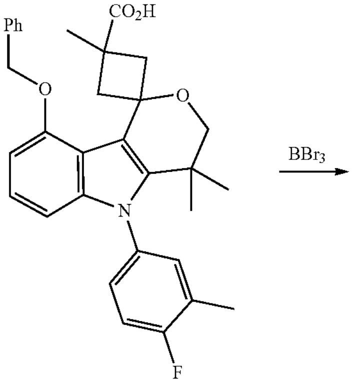

C56

-continued

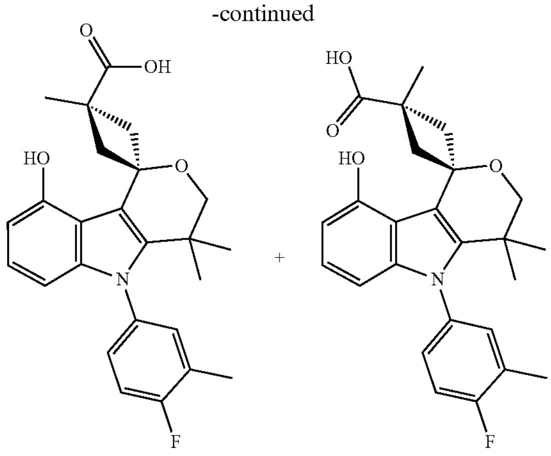

5 6

Step 1. Synthesis of 9'-(benzyloxy)-5'-(4-fluoro-3-methylphenyl)-3,4',4'-trimethyl-4',5'-dihydro-3'H-spiro[cyclobutane-1,1'-pyrano[4,3-b]indole]-3-carboxylic acid (C48)

To a mixture of 2-[4-benzyloxy-1-(4-fluoro-3-methyl-phenyl)indol-2-yl]-2-methyl-propan-1-ol S1 (110 mg, 0.272 mmol) and 1-methyl-3-oxo-cyclobutanecarboxylic acid (87 mg, 0.679 mmol) in DCE (500 μL) was added methanesulfonic acid (30 μL, 0.462 mmol) then triethylsilane (109 μL, 0.682 mmol) and the resulting deep red solution stirred at 45° C. After 2 hours, the reaction was directly purified by column chromatography (24 g gold column, 0-20% MeOH in dichloromethane) to give 9'-(benzyloxy)-5'-(4-fluoro-3-methylphenyl)-3,4',4'-trimethyl-4',5'-dihydro-3'H-spiro[cyclobutane-1,1'-pyrano[4,3-b]indole]-3-carboxylic acid (C56) (140 mg, 100%). LCMS m/z 514.28 $[M+H]^+$.

Step 2. Synthesis of (1S,3S)-5'-(4-fluoro-3-methylphenyl)-9'-hydroxy-3,4',4'-trimethyl-4',5'-dihydro-3'H-spiro[cyclobutane-1,1'-pyrano[4,3-b]indole]-3-carboxylic acid (5) and (1R,3R)-5'-(4-fluoro-3-methylphenyl)-9'-hydroxy-3,4',4'-trimethyl-4',5'-dihydro-3'H-spiro[cyclobutane-1,1'-pyrano[4,3-b]indole]-3-carboxylic acid (6)

To a solution of 9'-(benzyloxy)-5'-(4-fluoro-3-methylphenyl)-3,4',4'-trimethyl-4',5'-dihydro-3'H-spiro[cyclobutane-1,1'-pyrano[4,3-b]indole]-3-carboxylic acid (C56) (140 mg, 0.273 mmol) in dichloromethane (5 mL) at 0-5° C. was added $BBr_3$ (1M in heptane, 730 μL, 0.73 mmol) over 10 min. After 20 min, sat aq. $NH_4Cl$ was added at same temp and the cold bath removed. The layers were separated with the aid of a phase separator. The aqueous layer was re-extracted with dichloromethane and the layers were separated through a phase separator again and the combined organics concentrated. Purification by column chromatography (24 g gold column; 0-10% MeOH in dichloromethane) gave (1S,3S)-5'-(4-fluoro-3-methylphenyl)-9'-hydroxy-3,4',4'-trimethyl-4',5'-dihydro-3'H-spiro[cyclobutane-1,1'-pyrano[4,3-b]indole]-3-carboxylic acid 5 (11.5 mg, 9%). $^1H$ NMR (400 MHz, DMSO-$d_6$) δ 11.89 (s, 1H), 9.89 (s, 1H), 7.38-7.23 (m, 3H), 6.80 (t, J=7.9 Hz, 1H), 6.46 (dd, J=7.7, 0.9 Hz, 1H), 6.10 (dd, J=8.1, 0.8 Hz, 1H), 3.35 (s, 2H), 2.98-2.89 (m, 2H), 2.69-2.59 (m, 2H), 2.29 (d, J=1.9 Hz, 3H), 1.49 (s, 3H), 0.97 (s, 3H), 0.96 (s, 3H). LCMS m/z 424.26 $[M+H]^+$.

Chromatography also gave (1R,3R)-5'-(4-fluoro-3-methylphenyl)-9'-hydroxy-3,4',4'-trimethyl-4',5'-dihydro-3'H-spiro[cyclobutane-1,1'-pyrano[4,3-b]indole]-3-carboxylic acid 6 (18.3 mg, 14%). $^1H$ NMR (400 MHz, DMSO-$d_6$) δ 11.69 (br s, 1H), 9.65 (br s, 1H), 7.41-7.24 (m, 3H), 6.77 (t, J=7.9 Hz, 1H), 6.50-6.45 (m, 1H), 6.08 (dd, J=8.2, 0.8 Hz, 1H), 2.55-2.45 (m, 2H), 2.29 (d, J=1.9 Hz, 3H), 2.12-2.05 (m, 2H), 1.59 (s, 3H), 0.99 (s, 3H), 0.98 (s, 3H). LCMS m/z 424.26 $[M+H]^+$.

Compound 7 and Compound 8

2-(((1S,3S)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)oxy)acetic acid (7) and 2-(((1R,3R)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)oxy)acetic acid (8)

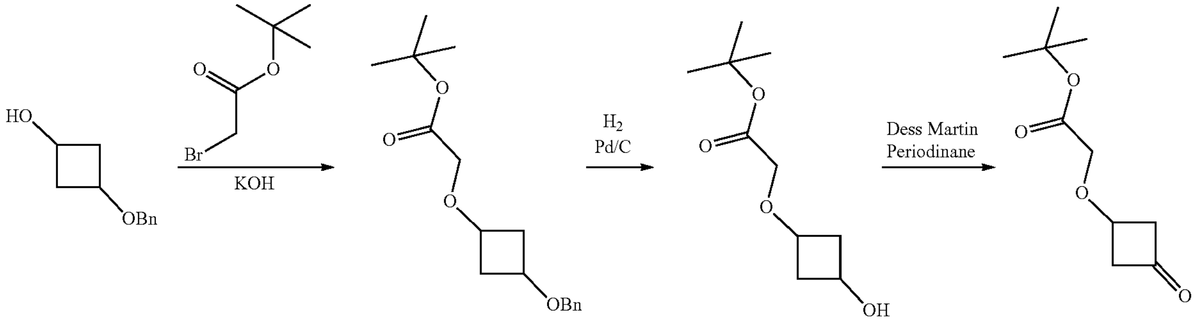

C57 C58 C59 C60

-continued

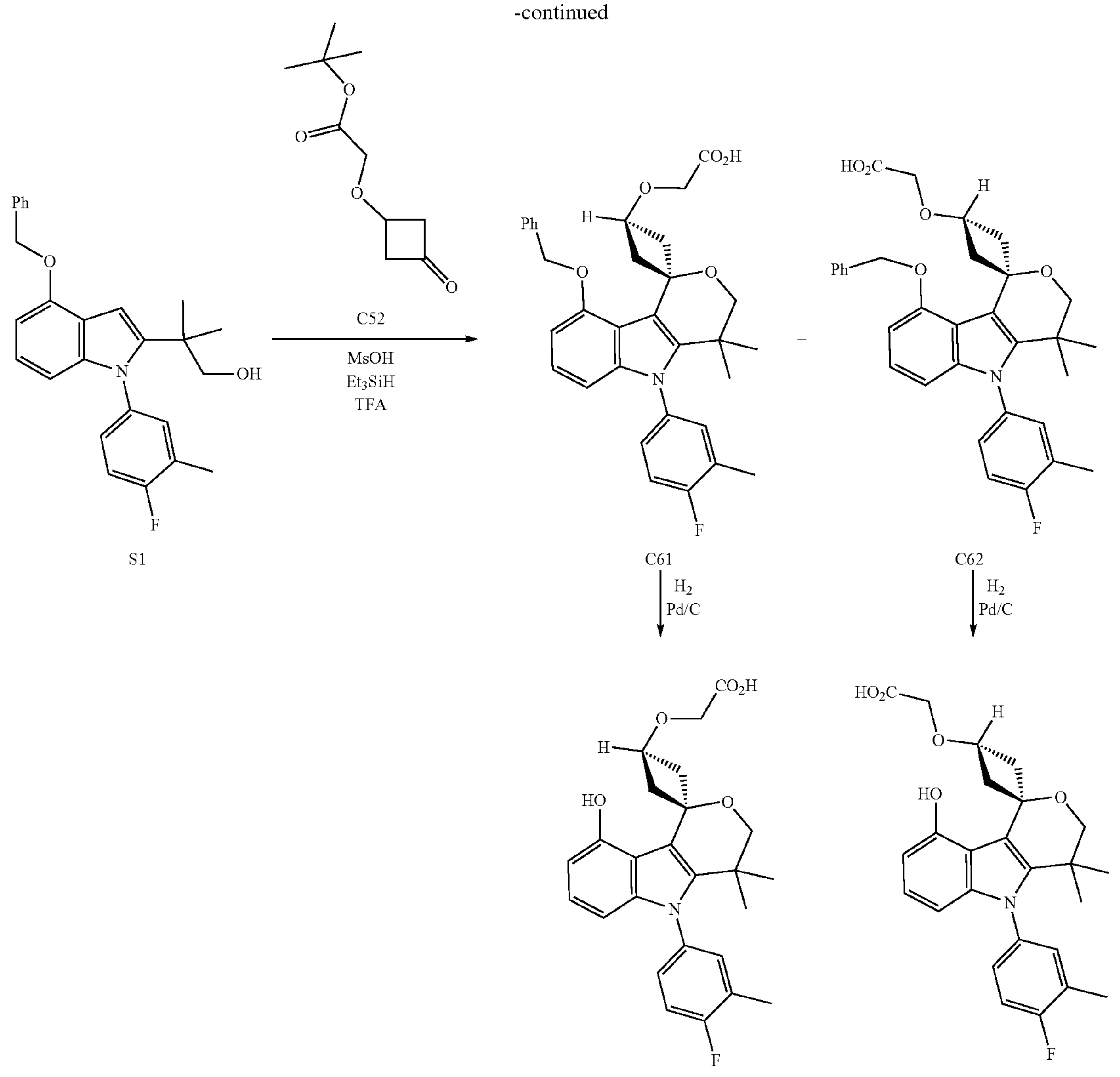

S1 C61 + C62

7 8

Step 1. Synthesis of tert-butyl-2-(3-benzyloxycyclobutoxy)acetate (C58)

To a solution of 3-benzyloxycyclobutanol (C57) (22 g, 123 mmol) in toluene (200 mL) at 0° C. was added potassium hydroxide (180 mL of 35% w/v, 1.123 mol). The mixture was stirred at 0° C. for 30 min followed by the addition of tert-butyl 2-bromoacetate (45 mL, 305 mmol) and tetrabutylammonium hydrogen sulfate (4.5 g, 13.3 mmol). The reaction was allowed to stir at room temperature for 16 hours. The layers were separated and the aqueous layer was extracted with ether, the combined organic layers were dried and concentrated to afford tert-butyl-2-(3-benzyloxycyclobutoxy)acetate (C58) (32.2 g, 89%).

Step 2. Synthesis of tert-butyl-2-(3-hydroxycyclobutoxy)acetate (C59)

Pd/C (5 g) was added to tert-butyl 2-(3-benzyloxycyclobutoxy)acetate (C58) (32.1 g, 110 mmol) in MeOH (500 mL) and the mixture exposed to an atmosphere of hydrogen and stirred overnight. The reaction as filtered through Celite® and the filtrate was evaporated to dryness giving tert-butyl-2-(3-hydroxycyclobutoxy)acetate (C59) (22.2 g, 100%). $^1H$ NMR (400 MHz, Chloroform-d) δ 3.91-3.79 (m, 1H), 3.83 (s, 2H), 3.67-3.56 (m, 1H), 2.67 (dtd, J=9.5, 6.6, 3.0 Hz, 2H), 1.93 (dtd, J=9.4, 7.6, 2.9 Hz, 2H), 1.43 (s, 9H).

Step 3. Synthesis of tert-butyl-2-(3-oxocyclobutoxy)acetate (C60)

To a solution of tert-butyl-2-(3-hydroxycyclobutoxy)acetate (C59) (5 g, 24.7 mmol) in dichloromethane (100 mL) was added Dess Martin Periodinane (15 g, 35.4 mmol) in five portion. Water (500 μL, 27.7 mmol) was added slowly over 10 min. The reaction was stirred at room temperature for 2 h then diluted with ether, washed with 10% $Na_2S203$ and sat. $NaHCO_3$ solution (1:1), then brine. The organic layer was dried ($Na_2SO_4$), filtered and evaporated to dryness. Purification by column chromatography (220 g, eluting with 0-100% ethyl acetate in heptane) gave tert-butyl-2-(3-oxocyclobutoxy)acetate (C60) (3.70 g, 75%). $^1$H NMR (400 MHz, Chloroform-d) δ 4.36 (tt, J=6.5, 4.7 Hz, 1H), 3.91 (s, 2H), 3.23-3.03 (m, 4H), 1.40 (s, 9H).

Step 4. Synthesis of 2-(((1S,3S)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)oxy)acetic acid (C61) and 2-(((1r,3r)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)oxy)acetic acid (C62)

A flask was charged with 2-[4-benzyloxy-1-(4-fluoro-3-methyl-phenyl)indol-2-yl]-2-methyl-propan-1-ol (S1) (600 mg, 1.49 mmol), tert-butyl-2-(3-oxocyclobutoxy)acetate (C60) (500 mg, 2.50 mmol) in dichloromethane (4 mL). Methanesulfonic acid (120 μL, 1.85 mmol) and triethylsilane (50 μL, 0.313 mmol) were added and the mixture stirred for 2 hours. TFA (1 mL, 13.0 mmol) was added to the reaction, stirred for 10 min, then the solvent evaporated. Purification by column chromatography (80 g gold column, eluting with 0-100% ethyl acetate in heptane) gave 2-(((1S,3S)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)oxy)acetic acid (C61) (138 mg, 14%). LCMS m/z 530.44 [M+H]$^+$.

Chromatography also gave 2-(((1R,3R)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)oxy)acetic acid (C62) (185 mg, 20%). LCMS m/z 530.44 [M+H]$^+$.

Step 5. Synthesis of 2-(((1S,3S)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)oxy)acetic acid (7)

The product 7 was prepared from 2-(((1S,3S)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)oxy)acetic acid (C61) according to Standard Procedure B by replacing ammonium formate with hydrogen gas at room temperature and using EtOH and THE as solvents. (64.5 mg, 73%). $^1$H NMR (400 MHz, Methanol-d4) δ 7.25-7.12 (m, 3H), 6.81 (t, J=7.9 Hz, 1H), 6.42 (d, J=7.6 Hz, 1H), 6.18 (d, J=8.1 Hz, 1H), 4.47 (dq, J=7.1, 4.2, 3.4 Hz, 1H), 4.08 (s, 2H), 3.44 (s, 2H), 3.28-3.18 (m, 2H), 2.46-2.37 (m, 2H), 2.33 (d, J=2.1 Hz, 3H), 1.08-1.03 (m, 6H). LCMS m/z 440.37 [M+H]$^+$.

Step 6. Synthesis of 2-(((1R,3R)-5'-(4-fluoro-3-methylphenyl)-9'-hydroxy-4',4'-dimethyl-4',5'-dihydro-3'H-spiro[cyclobutane-1,1'-pyrano[4,3-b]indol]-3-yl)oxy)acetic acid (8)

The product 8 was prepared from 2-(((1s,3s)-9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)oxy)acetic acid (C62) according to Standard Procedure B by replacing ammonium formate with hydrogen gas at room temperature and using EtOH and THE as solvents. (74.6 mg, 59%). $^1$H NMR (400 MHz, Methanol-d4) δ 7.21-7.05 (m, 3H), 6.76 (t, J=7.9 Hz, 1H), 6.42 (dd, J=7.6, 0.9 Hz, 1H), 6.14 (dd, J=8.3, 0.9 Hz, 1H), 4.44 (p, J=7.4 Hz, 1H), 4.09 (s, 2H), 3.37 (s, 2H), 3.29 (s, 1H), 3.27 (dd, J=7.1, 4.1 Hz, 1H), 2.55 (ddd, J=9.4, 6.9, 3.0 Hz, 2H), 2.30 (d, J=2.0 Hz, 3H), 1.01 (d, J=3.1 Hz, 6H). LCMS m/z 440.37 [M+H]$^+$.

Compound 9

(1R,4R)-4-fluoro-5'-(4-fluoro-3-methylphenyl)-9'-hydroxy-4',4'-dimethyl-4',5'-dihydro-3'H-spiro[cyclohexane-1,1'-pyrano[4,3-b]indole]-4-carboxylic acid (9)

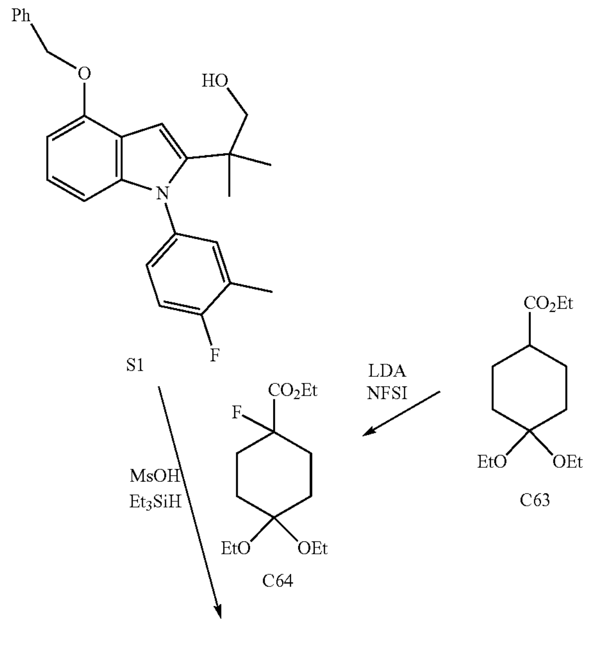

-continued

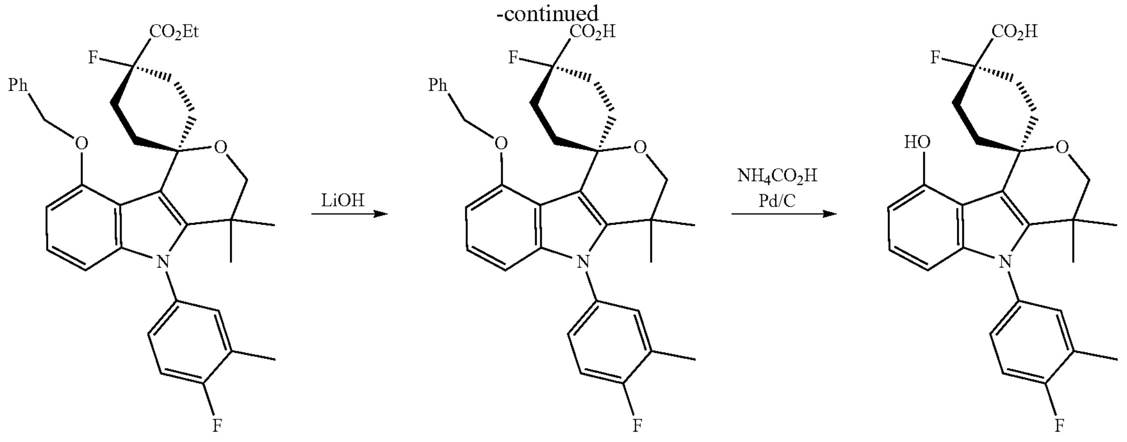

C65 C66 9

Step 1. Synthesis of ethyl-4,4-diethoxy-1-fluorocyclohexane-1-carboxylate (S64)

LDA (2 M, 14 mL, 28 mmol) was added to a stirred solution of ethyl 4,4-diethoxycyclohexanecarboxylate C63 (3.2 g, 13.1 mmol) in THF (50 mL) at −10° C. The resulting brown solution was stirred at −10° C. for 30 min. The reaction was cooled to −78° C. and N-(benzenesulfonyl)-N-fluoro-benzenesulfonamide (6.4 g, 20.3 mmol) in THF (20 mL) was added. The resulting solution was gradually warmed to room temperature over 2 hours, quenched with saturated $NH_4Cl$, extracted with ether and washed with brine. The organic layer was dried over $Na_2SO_4$ and concentrated to give a semi solid. Purification by column chromatography (Combiflash ISCO Lumen with ELSD, 80 g gold column, eluting with 0-100% ethyl acetate in heptane) to afford ethyl-4,4-diethoxy-1-fluoro-cyclohexanecarboxylate (S64) (1.75 g, 51%) as an oil. $^1$H NMR (400 MHz, Chloroform-d) δ 4.23 (q, J=7.1 Hz, 2H), 3.50 (q, J=6.9 Hz, 2H), 3.42 (q, J=7.1 Hz, 2H), 2.15-1.99 (m, 1H), 1.99-1.90 (m, 5H), 1.83-1.65 (m, 2H), 1.29 (t, J=7.1 Hz, 3H), 1.17 (dt, J=7.9, 7.1 Hz, 6H).

Step 2. Synthesis of ethyl (1R,4R)-9'-(benzyloxy)-4-fluoro-5'-(4-fluoro-3-methylphenyl)-4',4'-dimethyl-4',5'-dihydro-3'H-spiro[cyclohexane-1,1'-pyrano[4,3-b]indole]-4-carboxylate (C65)

Prepared according to Standard Procedure A using intermediate S1 and ethyl 4,4-diethoxy-1-fluoro-cyclohexanecarboxylate (C64) in place of a ketone. The reaction was carried out in dichloromethane rather than DCE giving $C_{65}$ (227 mg, 61%). LCMS m/z 574.2 [M+H]$^+$.

Step 3. Synthesis of (1R,4R)-9'-(benzyloxy)-4-fluoro-5'-(4-fluoro-3-methylphenyl)-4',4'-dimethyl-4',5'-dihydro-3'H-spiro[cyclohexane-1,1'-pyrano[4,3-b]indole]-4-carboxylic acid (C66)

To a solution of ethyl-9-benzyloxy-1'-fluoro-5-(4-fluoro-3-methyl-phenyl)-4,4-dimethyl-spiro[3H-pyrano[4,3-b]indole-1,4'-cyclohexane]-1'-carboxylate (C65) (227 mg, 0.242 mmol) in MeOH (1.5 mL) and dichloromethane (2 mL) was added lithium hydroxide (110 mg, 2.62 mmol) and the mixture was stirred at 25° C. for 2 hours. The reaction was neutralized with HCl (2 M, 1.3 mL, 2.6 mmol), the layers separated and the aqueous layer extracted with dichloromethane and the combined organics concentrated. Purification by column chromatography (80 g gold column, eluting with 0-60% ethyl acetate in heptane) gave (1R,4R)-9'-(benzyloxy)-4-fluoro-5'-(4-fluoro-3-methylphenyl)-4',4'-dimethyl-4',5'-dihydro-3'H-spiro[cyclohexane-1,1'-pyrano[4,3-b]indole]-4-carboxylic acid (C66) (120 mg, 91%). $^1$H NMR (400 MHz, Chloroform-d) δ 7.51-7.37 (m, 2H), 7.37-7.29 (m, 2H), 7.28 (t, J=1.4 Hz, 1H), 7.21-7.06 (m, 3H), 6.86 (t, J=8.1 Hz, 1H), 6.44 (dd, J=7.9, 0.8 Hz, 1H), 6.35 (dd, J=8.2, 0.7 Hz, 1H), 5.39 (s, 2H), 3.51 (s, 2H), 3.08 (t, J=14.0 Hz, 2H), 2.45 (dt, J=41.6, 12.2 Hz, 2H), 2.33 (d, J=1.9 Hz, 3H), 1.94 (t, J=12.4 Hz, 4H), 1.07 (d, J=2.3 Hz, 6H).

Step 4. Synthesis of (1R,4R)-4-fluoro-5'-(4-fluoro-3-methylphenyl)-9'-hydroxy-4',4'-dimethyl-4',5'-dihydro-3'H-spiro[cyclohexane-1,1'-pyrano[4,3-b]indole]-4-carboxylic acid (9)

Prepared according to Standard Procedure B starting from $C_{66}$ giving product 9 (68.5 mg, 65%). The reaction was carried out in EtOH and THF at 50° C. $^1$H NMR (400 MHz, DMSO-$d_6$) δ 13.07 (s, 1H), 9.77 (s, 1H), 7.47-7.15 (m, 3H), 6.78 (t, J=7.9 Hz, 1H), 6.49-6.23 (m, 1H), 6.10 (dd, J=8.2, 0.9 Hz, 1H), 4.11 (q, J=5.3 Hz, 1H), 3, 3.17 (d, J=5.1 Hz, 2H), 2.94 (t, J=13.5 Hz, 1H), 2.41-2.12 (m, 5H), 1.76 (dd, J=33.4, 13.4 Hz, 4H), 1.01 (d, J=2.3 Hz, 6H). LCMS m/z 456.23 [M+H]$^+$.

Compound 10

1-(5'-(4-Fluoro-3-methylphenyl)-9'-hydroxy-4',4'-dimethyl-4',5'-dihydro-3'H-spiro[cyclobutane-1,1'-pyrano[4,3-b]indol]-3-yl)-3,5-dimethyl-]H-pyrazole-4-carboxylic acid (21)

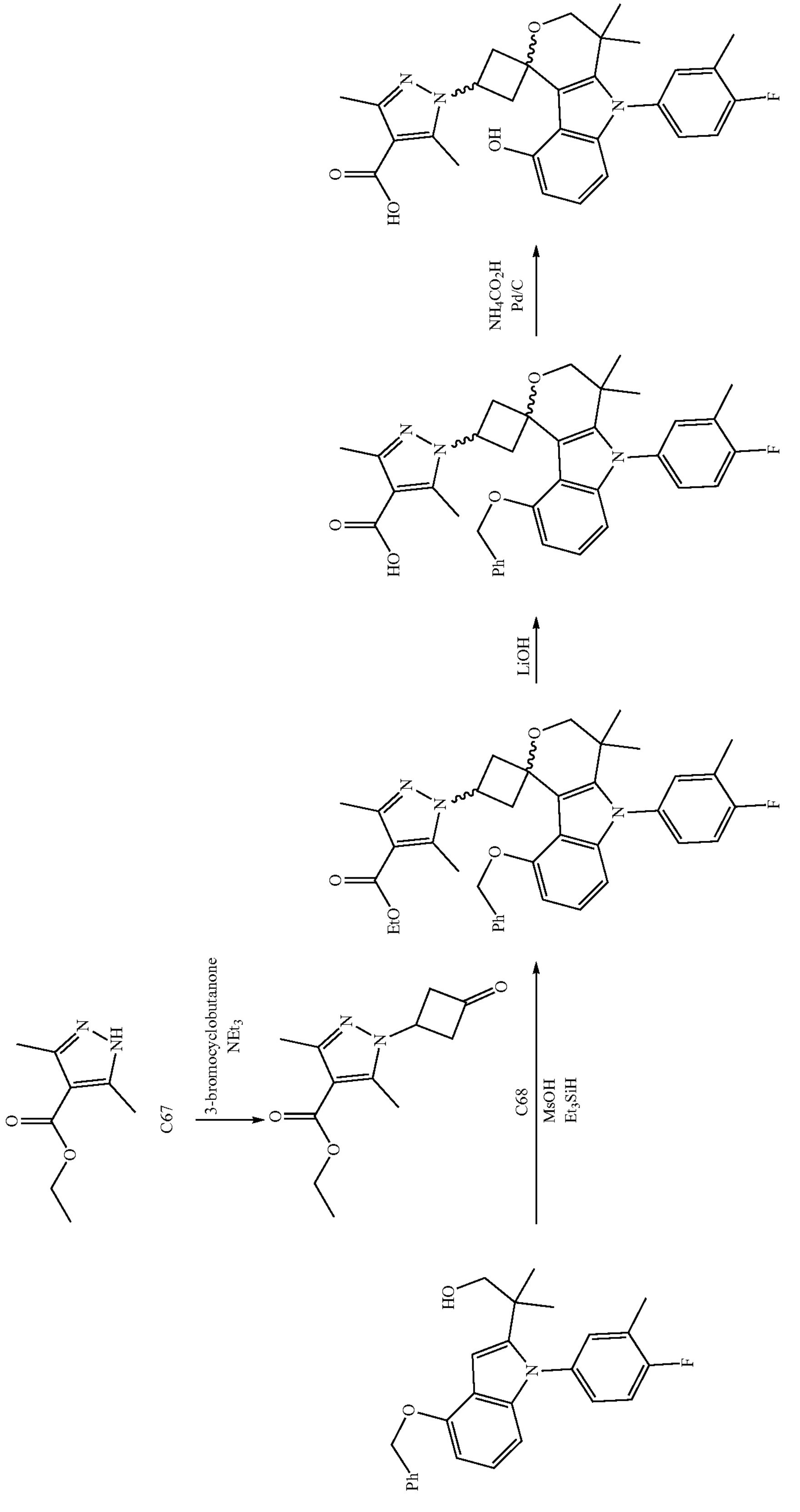
C67
S1
C69
C70
10

Step 1. Synthesis of Ethyl-3,5-dimethyl-1-(3-oxocyclobutyl)-1H-pyrazole-4-carboxylate (C68)

To a solution of 3-bromocyclobutanone (300 mg, 2.014 mmol) in trichloro(deuterio)methane (10 mL) was added triethylamine (310 μL, 2.22 mmol) and the mixture was allowed to stir for 30 min. NMR indicated conversion to cyclobutenone. Ethyl 3,5-dimethyl-1H-pyrazole-4-carboxylate C67 (340 mg, 2.02 mmol) was added and the mixture was stirred for 2 hours. The reaction was quenched with sat. $NH_4Cl$ and extracted with dichloromethane and then concentrated to give the product C68 (416 mg, 87%). $^1H$ NMR (400 MHz, Chloroform-d) δ 4.92 (tt, J=8.0, 6.2 Hz, 1H), 4.46-4.05 (m, 2H), 3.99-3.63 (m, 2H), 3.61-3.28 (m, 2H), 2.54 (d, J=1.3 Hz, 3H), 2.40 (d, J=1.4 Hz, 3H), 1.34 (td, J=7.1, 1.3 Hz, 3H).

Step 2. Synthesis of ethyl-1-(9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)-3,5-dimethyl-]H-pyrazole-4-carboxylate (C69)

Standard Procedure A was employed starting from $C_{68}$ but using dichloromethane in place of DCE. This gave product (C69). LCMS m/z 622.48 $[M+H]^+$.

Step 3. Synthesis of 1-(9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)-3,5-dimethyl-]H-pyrazole-4-carboxylic acid (C70)

To a solution of ethyl-1-(9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)-3,5-dimethyl-1H-pyrazole-4-carboxylate (C69) (109 mg, 0.175 mmol) in MeOH (800 μL), THE (1 mL) and water (500 μL) was added lithium hydroxide hydrate (75 mg, 1.79 mmol) and the mixture was microwaved at 100° C. for 2 h. The mixture was evaporated, neutralized with HCl (2 M, 1 mL, 2 mmol) and extracted with dichloromethane three times. The organic layer was dried and concentrated and purified using reverse phase chromatography (TFA modifier, 15.5 g column) to afford 1-(9'-(benzyloxy)-5'-(4-fluoro-3-methylphenyl)-4',4'-dimethyl-4',5'-dihydro-3'H-spiro[cyclobutane-1,1'-pyrano[4,3-b]indol]-3-yl)-3,5-dimethyl-1H-pyrazole-4-carboxylic acid (C70) (35 mg, 33%) as mixture of isomers and the mixture was taken to next step without further purification. LCMS m/z 594.49 $[M+H]^+$.

Step 4. Synthesis of 1-(5'-(4-Fluoro-3-methylphenyl)-9'-hydroxy-4',4'-dimethyl-4',5'-dihydro-3'H-spiro[cyclobutane-1,1'-pyrano[4,3-b]indol]-3-yl)-3,5-dimethyl-]H-pyrazole-4-carboxylic acid (10)

Standard Procedure B was employed starting from $C_{70}$. It was modified by using MeOH and THE as solvents and also heated at 50° C. This gave product (10). $^1H$ NMR (400 MHz, Chloroform-d) δ 7.19-7.03 (m, 3H), 6.84 (dt, J=16.0, 7.9 Hz, 1H), 6.45 (dd, J=29.1, 7.6 Hz, 1H), 6.23 (t, J=8.8 Hz, 1H), 4.91 (p, J=8.2 Hz, 1H), 3.78 (tt, J=8.7, 3.5 Hz, 2H), 3.47 (d, J=11.2 Hz, 2H), 2.84 (ddd, J=13.1, 6.9, 3.1 Hz, 2H), 2.50 (d, J=12.5 Hz, 3H), 2.41 (d, J=12.6 Hz, 3H), 2.29 (d, J=1.9 Hz, 3H), 1.13-0.93 (m, 6H). LCMS m/z 504.43 $[M+H]^+$. Compounds 11-19

Compounds 11-19 were prepared from S1 and the appropriate carbonyl reagent

TABLE 1

Preparation of Compounds 11-19

| Compound | Method/Product | Ketone | $^1H$ NMR; LCMS m/z |
|---|---|---|---|
| 11 | From S1 according to Standard procedures A and B[a] 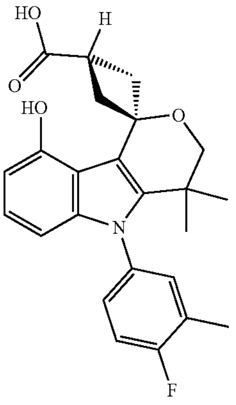 | 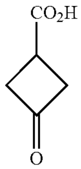 | $^1H$ NMR (400 MHz, DMSO-d6) δ 11.84 (s, 1H), 9.77 (s, 1H), 7.40-7.24 (m, 3H), 6.78 (t, J = 7.9 Hz, 1H), 6.47 (dd, J = 7.8, 0.9 Hz, 1H), 6.09 (dd, J = 8.2, 0.9 Hz, 1H), 3.39 (s, 2H), 3.32-3.18 (m, 3H), 2.37-2.33 (m, 2H), 2.29 (d, J = 1.9 Hz, 3H), 1.00 (s, 3H), 0.99 (s, 3H); LCMS m/z 410.26 [M + H]$^+$. |

TABLE 1-continued

Preparation of Compounds 11-19

| Compound | Method/Product | Ketone | $^1H$ NMR; LCMS m/z |
| --- | --- | --- | --- |
| 12 | From S1 according to Standard procedures A and B[a] 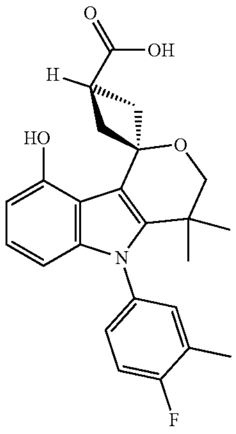 | 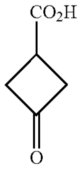 | $^1H$ NMR (400 MHz, DMSO-d6) δ 12.01 (s, 1H), 9.78 (s, 1H), 7.41-7.22 (m, 3H), 6.84-6.78 (m, 1H), 6.47 (dd, J = 7.8, 0.9 Hz, 1H), 6.12 (dd, J = 8.2, 0.8 Hz, 1H), 3.33 (s, 2H), 3.21-3.13 (m, 1H), 3.08 (t, J = 11.1 Hz, 2H), 2.48-2.44 (m, 1H), 2.29 (d, J = 2.0 Hz, 3H), 0.98 (s, 3H), 0.97 (s, 3H); LCMS m/z 410.39 $[M + H]^+$. |
| 13 | From S1 according to Standard procedures A and B[b] 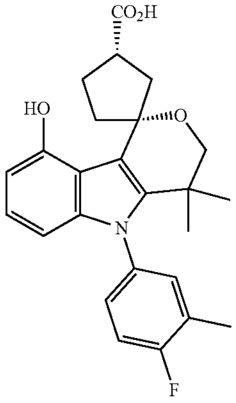 | 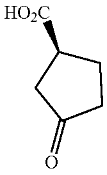 | $^1H$ NMR (400 MHz, Methanol-d4) δ 7.30-7.00 (m, 3H), 6.76 (t, J = 7.9 Hz, 1H), 6.35 (dd, J = 7.7, 0.8 Hz, 1H), 6.14 (dd, J = 8.2, 0.8 Hz, 1H), 3.53-3.28 (m, 3H), 3.21-3.02 (m, 1H), 2.81 (dd, J = 13.8, 10.7 Hz, 1H), 2.64 (td, J = 12.4, 7.6 Hz, 1H), 2.34-2.22 (m, 4H), 2.22-1.84 (m, 3H), 1.01 (d, J = 9.3 Hz, 6H). LCMS m/z 424.3 $[M + H]^+$. |
| 14 | From S1 according to Standard procedures A and B[c] 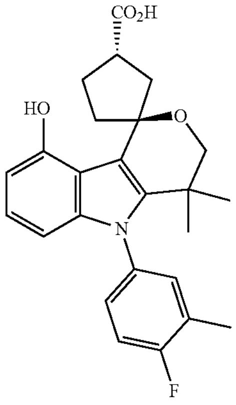 | 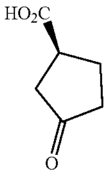 | $^1H$ NMR (400 MHz, Methanol-d4) δ 7.19-6.93 (m, 3H), 6.86-6.64 (m, 1H), 6.34 (dd, J = 7.7, 0.8 Hz, 1H), 6.18 (dd, J = 8.2, 0.8 Hz, 1H), 3.44-3.33 (m, 2H), 3.19-3.07 (m, 1H), 2.99-2.86 (m, 1H), 2.76 (dddd, J = 12.9, 10.5, 6.7, 1.9 Hz, 1H), 2.24 (d, J =1.9 Hz, 3H), 2.23-2.01 (m, 3H), 1.94 (tdd, J = 8.6, 4.9, 2.4 Hz, 1H), 0.97 (dd, J = 21.5, 1.9 Hz, 6H). LCMS m/z 424.4 $[M + H]^+$. |

TABLE 1-continued

| Preparation of Compounds 11-19 | | | |
|---|---|---|---|
| Compound | Method/Product | Ketone | $^{1}$H NMR; LCMS m/z |
| 15 | From S1 according to Standard procedures A and B[c] 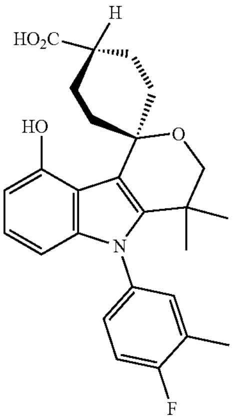 | 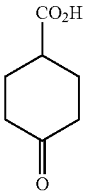 | $^{1}$HNMR (400 MHz, Chloroform-d) δ 7.26-7.07 (m, 4H), 6.84-6.73 (m, 1H), 6.32 (ddd, J = 11.7, 7.9, 0.9 Hz, 2H), 3.53 (s, 2H), 2.83 (dd, J = 26.7, 11.3 Hz, 3H), 2.35 (d, J = 1.9 Hz, 3H), 2.14 (d, J = 18.5 Hz, 4H), 1.92 (d, J = 14.8 Hz, 2H), 1.09 (s, 6H). LCMS m/z 438.5 [M + H]$^+$. |
| 16 | From S1 according to Standard procedures A and B[d,e] 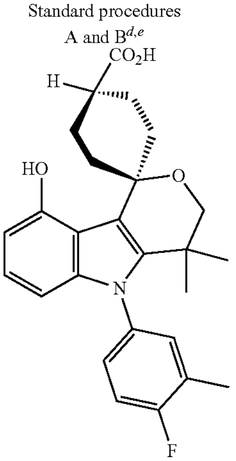 | 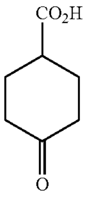 | $^{1}$H NMR (400 MHz, Chloroform-d) δ 7.25-7.11 (m, 3H), 6.91 (dd, J = 8.2, 7.6 Hz, 1H), 6.42 (ddd, J = 14.5, 7.9, 0.8 Hz, 2H), 5.17 (d, J = 14.6 Hz, 1H), 3.52 (s, 2H), 2.79-2.50 (m, 2H), 2.36 (d, J = 2.0 Hz, 3H), 2.05-1.85 (m, 5H), 1.08 (d, J = 3.3 Hz, 6H). LCMS m/z 438.6 [M + H]$^+$. |

TABLE 1-continued

| Preparation of Compounds 11-19 | | | |
|---|---|---|---|
| Compound | Method/Product | Ketone | $^1H$ NMR; LCMS m/z |
| 17 | From S1 according to Standard procedures A and $B^{d,f,g}$ 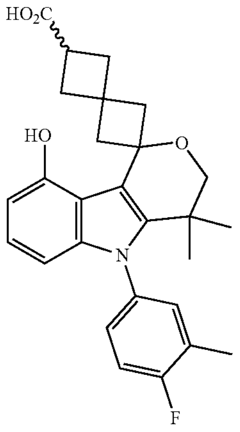 | 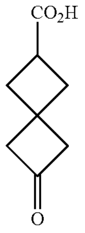 [SMILES: O=C1CC2(C1)CC(C(=O)O)C2] | $^1H$ NMR (400 MHz,Chloroform-d) δ 7.25-7.11 (m, 3H), 6.91 (dd, J = 8.2, 7.6 Hz, 1H), 6.44 (dd, J = 7.6, 0.8 Hz, 1H), 6.38 (dd, J = 8.3, 0.8 Hz, 1H), 3.58-3.38 (m, 2H), 3.25-3.08 (m, 3H), 2.60 (dd, J = 8.5, 2.2 Hz, 2H), 2.53-2.29 (m, 8H), 1.08 (t, J = 4.0 Hz, 6H). LCMS m/z 450.6 $[M + H]^+$. |
| 18 | From S1 according to Standard procedures A and $B^{b,d,f}$ 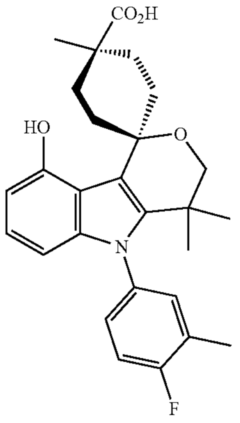 | 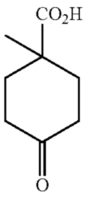 | $^1H$ NMR (400 MHz, Methanol-d4) δ 7.32-7.18 (m, 3H), 6.89-6.78 (m, 1H), 6.42 (dd, J = 7.7, 0.9 Hz, 1H), 6.19 (dd, J = 8.2, 0.9 Hz, 1H), 3.51 (s, 3H), 2.88 (td, J = 14.1, 4.1 Hz, 2H), 2.36 (d, J =1.9 Hz, 3H), 2.22 (d, J = 4.1 Hz, 1H), 1.77 (d, J =14.0 Hz, 2H), 1.57 (d, J = 2.9 Hz, 2H), 1.08 (s, 6H). LCMS m/z 452.1 $[M + H]^+$. |

TABLE 1-continued

| Preparation of Compounds 11-19 | | | |
|---|---|---|---|
| Compound | Method/Product | Ketone | $^1$H NMR; LCMS m/z |
| 19 | From S1 according to Standard procedures A and B[e,h] 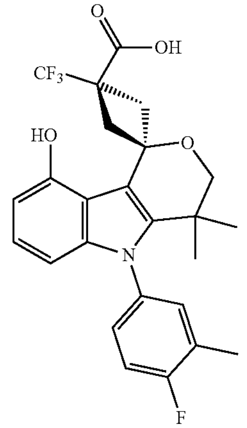 | 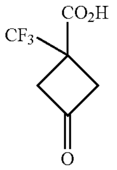 | $^1$H NMR (400 MHz, Methanol-d4) δ 7.30-7.08 (m, 3H), 6.81 (t, J = 7.9 Hz, 1H), 6.42 (d, J = 7.6 Hz, 1H), 6.15 (d, J = 8.1 Hz, 1H), 3.76-3.57 (m, 2H), 3.42 (s, 2H), 2.88-2.69 (m, 2H), 2.33 (d, J = 2.0 Hz, 3H), 2.15 (s, 1H), 1.05 (s, 6H). LCMS m/z 478.6 [M + H]$^+$. |

[a]Standard procedure A carried out at 45° C.
[b]Instead of ammonium formate, the reaction was carried out according to Standard Procedure B but using formic acid at 50° C. in MeOH and THF.
[c]Identical procedure as for compound 13 but replacing EtOH for MeOH in the reduction step.
[d]Standard procedure A modified by replacing DCE with dichloromethane.
[e]Standard Procedure B modified by replacing ammonium formate with hydrogen at room temperature.
[f]Standard procedure A modified by removing $Et_3SiH$.
[g]Standard procedure B modified by using $Pd(OH)_2$ instead of Pd/C and in MeOH and EtOAc as solvents.
[h]Standard procedure A modified by replacing DCE with dichloromethane at 50° C. in a closed vessel.

Compound 20 and Compound 21

5"-(4-Fluoro-3-methylphenyl)-9"-hydroxy-4",4"-dimethyl-4",5"-dihydro-3"H-dispiro[cyclobutane-1,1'-cyclobutane-3',1"-pyrano[4,3-b]indole]-3-carboxylic acid (20) and enantiomer (21)

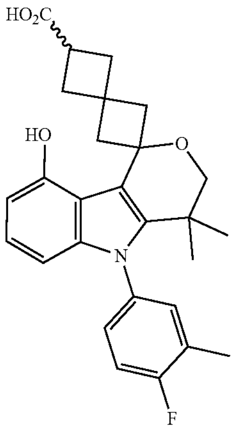

17

SFC separation

-continued

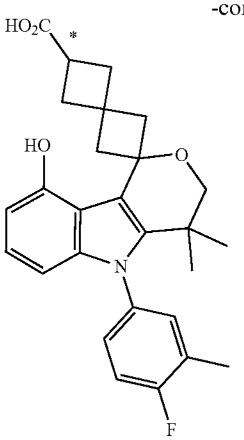

+

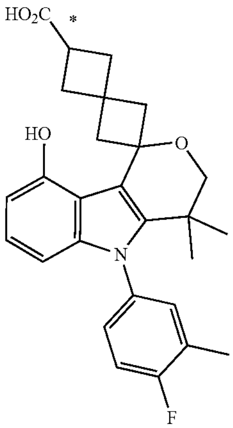

20 21

Separation of 5"-(4-Fluoro-3-methylphenyl)-9"-hydroxy-4",4"-dimethyl-4",5"-dihydro-3"H-dispiro[cyclobutane-1,1'-cyclobutane-3',1"-pyrano[4,3-b]indole]-3-carboxylic acid (17) by chiral SFC gave 5"-(4-fluoro-3-methylphenyl)-9"-hydroxy-4",4"-dimethyl-4",5"-dihydro-3"H-dispiro[cyclobutane-1,1'-cyclobutane-3',1"-pyrano[4,3-b]indole]-3-carboxylic acid (20). $^1$H NMR (400 MHz, Chloroform-d) δ 7.16-6.99 (m, 3H), 6.81 (dd, J=8.2, 7.6 Hz, 1H), 6.34 (dd, J=7.6, 0.8 Hz, 1H), 6.28 (dd, J=8.2, 0.8 Hz, 1H), 3.37 (s, 2H), 3.17-82.96 (s, 2H), 2.59-2.46 (m, 2H), 2.46-2.33 (i, 3H), 2.31-2.20 (m, 4H), 0.98 (t, J=4.3 Hz, 6H). LCMS m/z 450.6 [M+H]$^+$.

SFC separation also gave 5"-(4-fluoro-3-methylphenyl)-9"-hydroxy-4",4"-dimethyl-4",5"-dihydro-3"H-dispiro[cyclobutane-1,1'-cyclobutane-3',1''-pyrano[4,3-b]indole]-3-carboxylic acid (21). $^1$H NMR (400 MHz, Chloroform-d) 67.16 (p, J=7.3 Hz, 4H), 6.91 (t, J=7.8 Hz, 1H), 6.41 (dd, J=21.4, 7.9 Hz, 2H), 5.07 (s, 1H), 3.46 (s, 2H), 3.17 (s, 1H), 2.60 (d, J=8.5 Hz, 2H), 2.49 (d, J=9.4 Hz, 2H), 2.35 (s, 4H), 1.08 (s, 6H). LCMS m/z 450.6 [M+H]$^+$.

Compounds 22-29

Compounds 22-29 Prepared from S2 or S3 and the appropriate ketone or ketone equivalent

TABLE 2

Preparation of Compounds 22-29

| Compound | Method/Product | Ketone | $^1$H NMR; LCMS m/z |
|---|---|---|---|
| 22 | From S2 according to Standard procedures A and B[a,b] 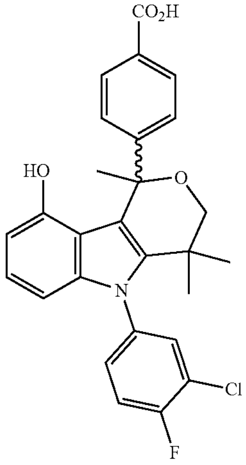 | 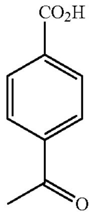 | $^1$H NMR (400 MHz, Methanol-d4) δ 7.95-7.90 (m, 2H), 7.67 (ddd, J = 10.9, 6.7, 2.0 Hz, 1H), 7.59 (dq, J = 8.6, 1.9 Hz, 2H), 7.52-7.46 (m, 2H), 6.94-6.88 (m, 1H), 6.42 (dt, J = 7.7, 0.9 Hz, 1H), 6.27 (dd, J = 8.2, 0.9 Hz, 1H), 2.19 (d, J= 1.0 Hz, 3H), 1.37 (d, J = 2.4 Hz, 3H), 0.87 (d, J = 2.6 Hz, 3H). LCMS m/z 480.52 [M + H]$^+$. |
| 23 | From S2 according to Standard procedures A and B[c,d] 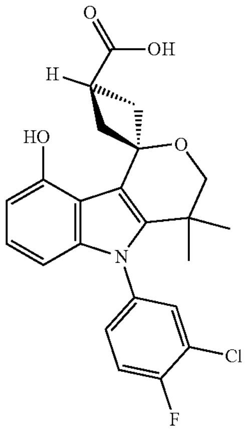 | 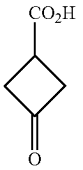 | $^1$H NMR (400 MHz, DMSO-$d_6$) δ 12.01 (s, 1H) 9.84 (s, 1H), 7.82 (dd, J = 6.7, 2.6 Hz, 1H), 7.62 (t, J = 8.9 Hz, 1H), 7.49 (ddd, J = 8.7, 4.4, 2.6 Hz, 1H), 6.84 (t, J = 7.9 Hz, 1H), 6.50 (dd, J = 7.8, 0.9 Hz, 1H), 6.16 (dd, J = 8.2, 0.8 Hz, 1H), 3.22-3.04 (m, 4H), 2.48-2.44 (m, 1H), 0.98 (s, 6H); LCMS m/z 430.2 [M + H]$^+$. |

TABLE 2-continued

Preparation of Compounds 22-29

| Compound | Method/Product | Ketone | $^1H$ NMR; LCMS m/z |
|---|---|---|---|
| 24 | From S2 according to Standard procedures A and B[c,d] 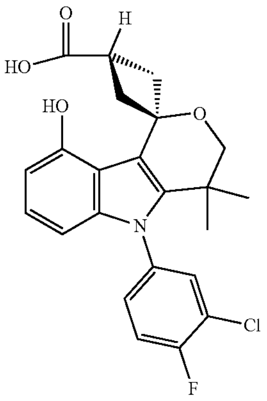 | 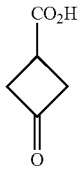 | $^1H$ NMR (400 MHz, DMSO-$d_6$) δ 11.86 (s, 1H), 9.83 (s, 1H), 7.83 (dd, J = 6.7, 2.5 Hz, 1H), 7.62 (t, J = 8.9 Hz, 1H), 7.50 (ddd, J = 8.7, 4.4, 2.6 Hz, 1H), 6.81 (t, J = 7.9 Hz, 1H), 6.50 (dd, J = 7.7, 0.9 Hz, 1H), 6.13 (dd, J = 8.2, 0.8 Hz, 1H), 3.40 (s, 2H), 3.31-3.16 (m, 3H), 2.35 (d, J = 3.1 Hz, 2H), 1.00 (s, 6H). LCMS m/z 429.98 $[M + H]^+$. |
| 25 | From S2 according to synthetic procedure for compound 13[a,f,g] 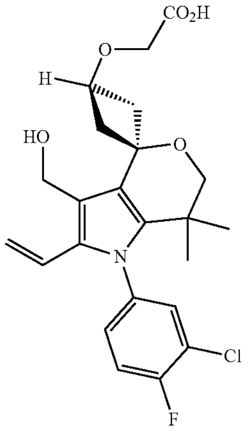 | 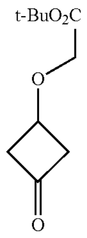 C60 | $^1H$ NMR (400 MHz, Methanol-d4) δ 7.53 (dd, J = 6.7, 2.6 Hz, 1H), 7.44 (t, J = 8.8 Hz, 1H), 7.35(dt, J = 8.6, 3.1Hz, 1H), 6.85 (t, J = 7.9 Hz, 1H), 6.44 (d, J = 7.7 Hz, 1H), 6.19 (d, J = 8.2 Hz, 1H), 4.47 (s, 1H), 4.08 (s, 2H), 3.45 (s, 2H), 3.25-3.16 (m, 2H), 2.41 (d, J = 13.2 Hz, 2H), 1.07 (s, 6H). LCMS m/z 460.31 $[M + H]^+$. |
| 26 | From S2 according to synthetic procedure for compound 13[a,f,g] 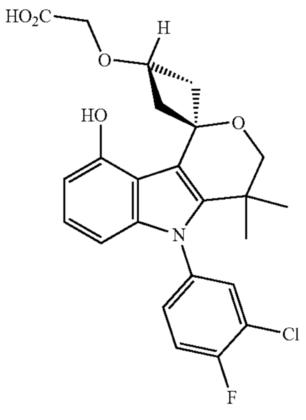 | 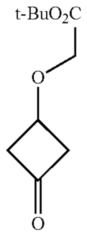 C60 | $^1H$ NMR (400 MHz, Methanol-d4) δ 7.53 (dd, J = 6.6, 2.5 Hz, 1H), 7.44 (t, J = 8.8 Hz, 1H), 7.34 (dt, J = 8.2, 3.4 Hz, 1H), 6.84 (t, J = 7.9 Hz, 1H), 6.44 (d, J = 7.7 Hz, 1H), 6.18 (d, J = 8.2 Hz, 1H), 4.43 (t, J = 7.4 Hz, 1H), 4.09 (s, 2H), 3.43 (s, 2H), 3.29 (d, J = 13.4 Hz, 2H), 2.55 (dd, J = 11.3, 6.7 Hz, 2H), 1.06 (s, 6H). LCMS m/z 460.36 $[M + H]^+$. |

TABLE 2-continued

| Preparation of Compounds 22-29 | | | |
|---|---|---|---|
| Compound | Method/Product | Ketone | $^1$H NMR; LCMS m/z |
| 27 | From S2 according to Standard procedures A and B[a,b,e] 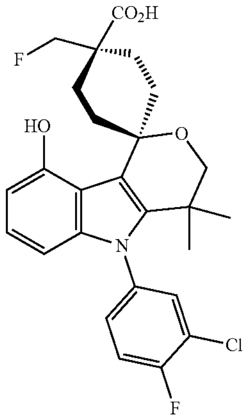 | 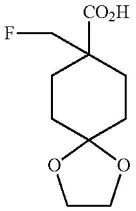 | $^1$H NMR (400 MHz, DMSO-d6) δ 12.47 (s, 1H), 10.06 (s, 1H), 7.81 (dd, J = 6.7, 2.6 Hz, 1H), 7.62 (t, J = 8.9 Hz, 1H), 7.49 (ddd, J = 8.7, 4.4, 2.6 Hz, 1H), 6.83 (t, J = 7.9 Hz, 1H), 6.48 (dd, J = 7.8, 0.9 Hz, 1H), 6.17 (dd, J = 8.2, 0.8 Hz, 1H), 5.00 (d, J = 46.9 Hz, 2H), 3.44 (s, 2H), 2.58 (d, J = 13.9 Hz, 2H), 2.06 (t, J = 14.1 Hz, 2H), 1.77-1.59 (m, 4H), 1.01 (s, 3H), 1.00 (s, 3H). LCMS m/z 490.08 (M + H]$^+$. |
| 28 | From S2 according to Standard procedures A and B[a,b,e] 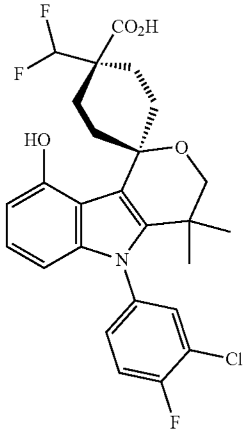 | 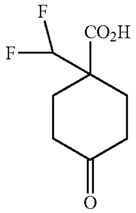 S21 | $^1$H NMR (400 MHz, Methanol-d4) δ 7.54 (dd, J = 6.6, 2.5 Hz, 1H), 7.46 (t, J = 8.8 Hz, 1H), 7.37 (ddd, J = 8.7, 4.3, 2.5 Hz, 1H), 6.85 (t, J = 8.0 Hz, 1H), 6.71 (t, J = 55.7 Hz, 1H), 6.43 (dd, J = 7.7, 0.8 Hz, 1H), 6.21 (dd, J = 8.2, 0.8 Hz, 1H), 3.51 (d, J = 1.2 Hz, 1H), 2.79 (t, J = 14.3 Hz, 2H), 2.16 (t, J = 14.4 Hz, 2H), 2.02 (d, J = 14.1 Hz, 2H), 1.84 (d, J = 14.7 Hz, 2H), 1.08 (s, 6H). LCMS m/z 508.08 [M + H]$^+$. |

TABLE 2-continued

| Preparation of Compounds 22-29 | | | |
|---|---|---|---|
| Compound | Method/Product | Ketone | $^1$H NMR; LCMS m/z |
| 29 | From S3 according to Standard procedures A and B[c,f] 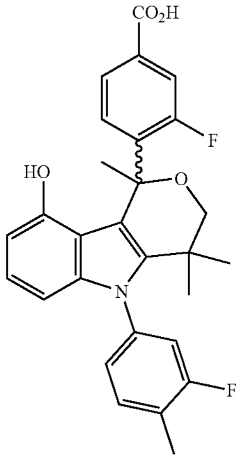 | 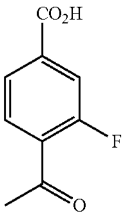 | $^1$H NMR (400 MHz, Methanol-d4) δ 7.66 (dd, J = 12.6, 1.7 Hz, 1H), 7.57 (dt, J = 8.1, 1.4 Hz, 1H), 7.44 (q, J = 8.8 Hz, 1H), 7.29 (t, J = 8.0 Hz, 1H), 7.21-7.12 (m, 2H), 6.86 (td, J = 8.0, 2.4 Hz, 1H), 6.38 (dt, J = 7.7, 1.0 Hz, 1H), 6.25 (ddd, J = 8.3, 3.3, 0.8 Hz, 1H), 3.30-3.22 (m, 2H), 2.40 (d, J = 1.9 Hz, 3H), 2.28 (d, J = 1.7 Hz, 3H), 1.36 (s, 3H), 0.81 (s, 3H). LCMS m/z 478.14 $[M + H]^+$. |

[a]Standard procedure A modified by replacing DCE with dichloromethane at a temperature between room temperature and 50° C. in a closed vessel.
[b]Standard Procedure B modified by replacing ammonium formate with hydrogen at room temperature and using MeOH and EtOAc as solvents.
[c]Standard procedure A modified by replacing DCE with dichloromethane.
[d]Standard procedure B modified by using the $BBr_3$ in dichloromethane conditions as described for the synthesis compounds 5 and 6.
[e]Standard procedure A modified by removing $Et_3SiH$.
[f]Standard Procedure B modified by replacing ammonium formate with hydrogen at room temperature and using EtOH as solvent or EtOH and THF as co-solvents.
[g]1 mL of TFA was added on completion of the reductive alkylation reaction and the mixture stirred for 10 min.

Compound 30

2-(((1R,3R)-5'-(3,4-Difluorophenyl)-9'-hydroxy-4',4'-dimethyl-4',5'-dihydro-3'H-spiro[cyclobutane-1,1'-pyrano[4,3-b]indol]-3-yl)oxy)propanoic acid (30)

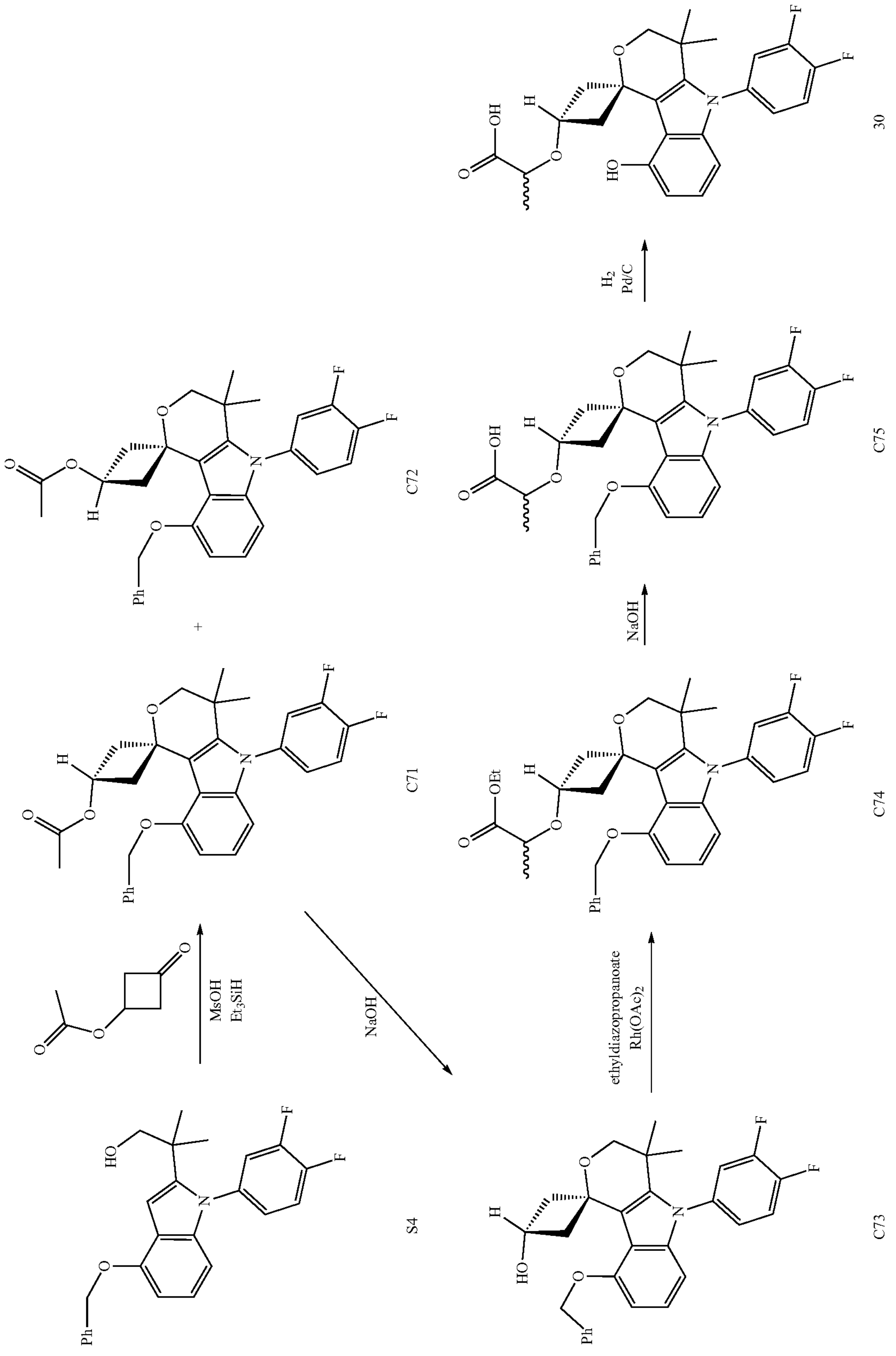
S4
C71
+
C72
C73
C74
C75
30

Step 1. Synthesis of (1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl acetate (C71) and (1s,3s)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl acetate (C72)

A vial was charged with 2-[4-benzyloxy-1-(3,4-difluorophenyl)indol-2-yl]-2-methyl-propan-1-ol (1.2 g, 2.95 mmol), (3-oxocyclobutyl) acetate (750 mg, 5.85 mmol), dichloromethane (5 mL), then added triethylsilane (200 μL, 1.25 mmol) and methanesulfonic acid (300 μL, 4.62 mmol). After 4 hour, the reaction was directly purified by column chromatography (120 g gold column, eluting with 0-100% ethyl acetate in heptane) to give product C71 (805 mg, 48%), LCMS m/z 518.51 $[M+H]^+$ and product C72 (400 mg, 21%), LCMS m/z 518.47 $[M+H]^+$.

Step 2. Synthesis of (1R,3R)-9'-(benzyloxy)-5'-(3,4-difluorophenyl)-4',4'-dimethyl-4',5'-dihydro-3'H-spiro[cyclobutane-],1'-pyrano[4,3-b]indol]-3-ol (C73)

NaOH (3 mL of 2 M, 6.000 mmol) was added to a mixture of (1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl acetate (C71) (800 mg, 1.30 mmol) in MeOH (10 mL) and THE (10 mL) and the reaction stirred at 60° C. for 2 hour. It was then acidified with 0.1 N HCl and extracted with EtOAc (3×150 mL).

The combined organic fractions were washed with brine (1×50 mL), water (2×50 mL), dried over sodium sulfate, filtered and concentrated. Purification by column chromatography (120 g gold column, eluting with 0-100% ethyl acetate in heptane) gave (1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-ol (C73) (700 mg, 98%). LCMS m/z 476.47 $[M+H]^+$.

Step 3. Synthesis of ethyl 2-(((1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl)oxy)propanoate (C74)

Ethyl 2-diazopropanoate (75 mg, 0.585 mmol) was added dropwise over 10 min to a mixture of 9-benzyloxy-5-(3,4-difluorophenyl)-4,4-dimethyl-spiro[3H-pyrano[4,3-b]indole-1,3'-cyclobutane]-1'-ol C73 (100 mg, 0.210 mmol), diacetoxyrhodium (10 mg, 0.0453 mmol) in dichloromethane (2 mL). Another batch of diacetoxyrhodium (10 mg, 0.0453 mmol) was added then ethyl-2-diazopropanoate (75 mg, 0.585 mmol) dropwise over 10 min. After a further 10 min, the reaction was directly purified by column chromatography (40 g gold column, eluting with 0-100% ethyl acetate in heptane) to give ethyl 2-(((1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl)oxy)propanoate (C74) (90 mg, 61%). LCMS m/z 576.53 $[M+H]^+$.

Step 4. Synthesis of 2-(((1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl)oxy)propanoic acid (C75)

NaOH (750 μL of 2M, 1.5 mmol) was added to 2-(((1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl)oxy)propanoate (C74) (90 mg, 0.142 mmol) in MeOH (3 mL) and THE (2 mL). After 1 h at 60° C., the reaction was cooled to room temperature DMSO (2 mL) and TFA (200 μL, 2.60 mmol) were added and most of the solvent was evaporated. Purification by reverse phase chromatography (50 g column, eluting with 10-100% ACN in water with 0.1% TFA) gave 2-(((1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl)oxy)propanoic acid (C75) (85 mg, 105%). LCMS m/z 548.54 $[M+H]^+$.

Step 5. Synthesis of 2-(((1R,3R)-5'-(3,4-difluorophenyl)-9'-hydroxy-4',4'-dimethyl-4',5'-dihydro-3'H-spiro[cyclobutane-],1'-pyrano[4,3-b]indol]-3-yl)oxy) propanoic acid (30)

A reaction vessel was charged with 2-(((1R,3R)-9'-(benzyloxy)-5'-(3,4-difluorophenyl)-4',4'-dimethyl-4',5'-dihydro-3'H-spiro[cyclobutane-1,1'-pyrano[4,3-b]indol]-3-yl) oxy)propanoic acid (C75) (80 mg, 0.14 mmol) and EtOH (5 mL) and Pd/C (50 mg, 0.04698 mmol) was added. The flask was evacuated and then hydrogen was introduced by balloon. After 2 hours, the reaction was filtered through Celite® and concentrated. Purification by reverse phase chromatography (50 g column, eluting with 10-100% ACN in water with 0.1% FA) gave product 30 (50.1 mg, 76%). $^1H$ NMR (400 MHz, Chloroform-d) δ 7.46-7.08 (m, 3H), 6.94 (t, J=7.9 Hz, 1H), 6.59 (d, J=7.7 Hz, 1H), 6.33 (d, J=8.2 Hz, 1H), 4.64 (t, J=7.3 Hz, 1H), 4.20 (q, J=6.9 Hz, 1H), 3.62-3.27 (m, 4H), 2.73 (q, J=9.9, 9.2 Hz, 2H), 1.57 (d, J=6.9 Hz, 3H), 1.09 (t, J=4.3 Hz, 6H). LCMS m/z 458.42 $[M+H]^+$.

Compound 31

2-(((1S,3S)-5'-(3,4-difluorophenyl)-9'-hydroxy-4',4'-dimethyl-4',5'-dihydro-3'H-spiro[cyclobutane-1,1'-pyrano[4,3-b]indol]-3-yl)oxy)propanoic acid (31)

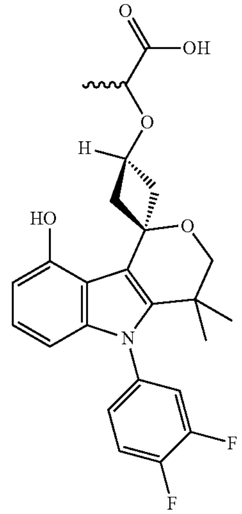 [SMILES: CC(O[C@H]1C[C@]2(C1)OCC(C)(C)c1c2c2c(O)cccc2n1-c1ccc(F)c(F)c1)C(=O)O]

This was prepared in an identical fashion to 30 but using intermediate $C_{72}$ rather than $C_{71}$ in Step 2.

$^1H$ NMR (400 MHz, Methanol-d4) δ 7.44 (dt, J=10.5, 8.8 Hz, 1H), 7.35 (ddd, J=10.3, 7.1, 2.5 Hz, 1H), 7.18 (ddt, J=8.5, 4.0, 2.0 Hz, 1H), 6.83 (t, J=7.9 Hz, 1H), 6.42 (d, J=7.6

Hz, 1H), 6.19 (d, J=8.2 Hz, 1H), 4.46 (ddt, J=10.0, 6.9, 2.9 Hz, 1H), 4.03 (q, J=6.8 Hz, 1H), 3.43 (s, 2H), 3.26-3.11 (m, 2H), 2.43 (dt, J=14.6, 2.8 Hz, 1H), 2.34 (dt, J=12.9, 2.7 Hz, 1H), 1.43 (d, J=6.9 Hz, 3H), 1.06 (dd, J=11.7, 8.3 Hz, 6H). LCMS m/z 458.38 $[M+H]^+$.

Compounds 32-63

Compounds 32-63 were prepared from S4 and the appropriate ketone or ketone equivalent.

TABLE 3

Preparation of Compounds 32-63

| Compound | Method/Product | Ketone | $^1$H NMR; LCMS m/z |
| --- | --- | --- | --- |
| 32 | From S4 according to Standard procedures A and B[a,b] 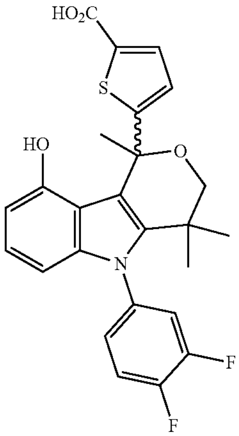 | 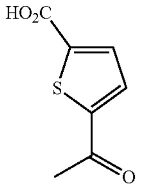 | $^1$H NMR (400 MHz, Chloroform-d) δ 7.74 (d, J = 3.9 Hz, 1H), 7.43-7.30 (m, 2H), 7.27-7.19 (m, 1H), 7.08 (dd, J = 4.9, 3.9 Hz, 1H), 6.98 (ddd, J = 8.3, 7.7, 2.3 Hz, 1H), 6.49-6.39 (m, 2H), 3.58 (d, J = 11.4 Hz, 1H), 3.42 (dd, J = 11.3, 6.2 Hz, 1H), 2.28 (d, J = 0.8 Hz, 3H), 1.35 (s, 3H), 0.95 (d, J = 3.1 Hz, 3H). LCMS m/z 470.65 $[M + H]^+$. |
| 33 | From S4 according to Standard procedures A and B[c,d] 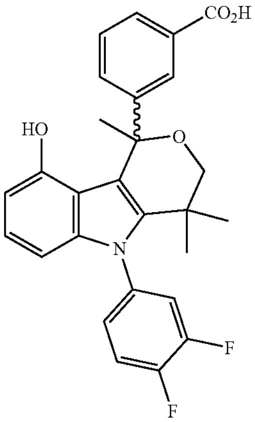 | 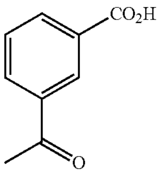 | $^1$H NMR (400 MHz, Methanol-d4) δ 8.24 (dt, J = 3.4, 1.7 Hz, 1H), 7.88 (dt, J = 7.7, 1.3 Hz, 1H), 7.67 (dddd, J = 7.8, 2.9, 1.9, 1.2 Hz, 1H), 7.56-7.36 (m, 2H), 7.36-7.17 (m, 2H), 6.85 (ddd, J = 8.2, 7.7, 2.7 Hz, 1H), 6.39 (ddd, J = 7.7, 2.4, 0.8 Hz, 1H), 6.23 (ddd, J = 8.2, 3.5, 0.8 Hz, 1H), 3.26 (d, J = 8.0 Hz, 2H), 2.18 (s, 3H), 1.31 (d, J = 2.6 Hz, 3H), 0.85 (d, J = 3.6 Hz, 3H). LCMS m/z 464.19 $[M + H]^+$. |

TABLE 3-continued

| Preparation of Compounds 32-63 | | | |
|---|---|---|---|
| Compound | Method/Product | Ketone | $^1$H NMR; LCMS m/z |
| 34 | From S4 according to Standard procedures A and B[c,d] 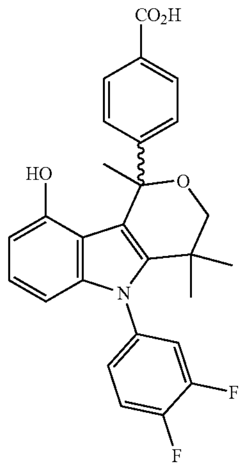 | 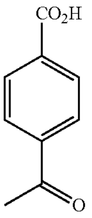 | $^1$H NMR (400 MHz, Chloroform-d) δ 7.90 (d, J = 7.3 Hz, 2H), 7.61-7.51 (m, 2H), 7.41 (t, J = 2.5 Hz, 1H), 7.37-7.25 (m, 2H), 7.21 (s, 1H), 6.89 (d, J = 8.4 Hz, 1H), 6.33-6.22 (m, 1H), 3.24 (s, 2H), 2.17 (d, J = 3.6 Hz, 3H), 1.31 (d, J = 3.4 Hz, 3H), 0.81 (s, 3H). LCMS m/z 464.15 [M + H]$^+$. |
| 35 | From S4 according to Standard procedures A and B[b,e] 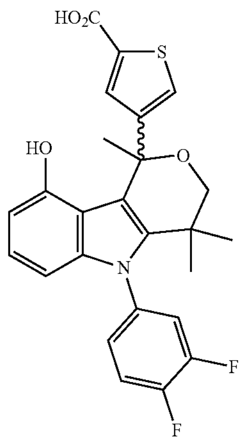 | 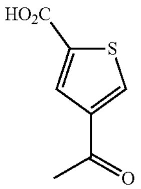 | $^1$H NMR (400 MHz, DMSO-d6) δ 13.00 (s, 1H), 9.44 (d, J = 3.1 Hz, 1H), 7.86-7.74 (m, 1H), 7.70-7.60 (m, 2H), 7.50 (d, J = 1.4 Hz, 1H), 7.45-7.35 (m, 1H), 6.84 (td, J = 7.9, 2.1 Hz, 1H), 6.38 (ddd, J = 7.7, 2.2, 0.8 Hz, 1H), 6.20 (ddd, J = 7.8, 6.8, 0.8 Hz, 1H), 3.31-3.20 (m, 2H), 2.07 (s, 3H), 1.23 (d, J = 7.9 Hz, 3H), 0.82 (d, J = 8.9 Hz, 3H). LCMS m/z 470.31 [M + H]$^+$. |

TABLE 3-continued

| Preparation of Compounds 32-63 | | | |
|---|---|---|---|
| Compound | Method/Product | Ketone | $^1$H NMR; LCMS m/z |
| 36 | From S4 according to Standard procedures A and B[c,e] 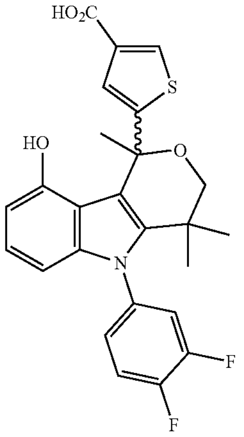 | 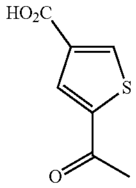 | $^1$H NMR (400 MHz, Chloroform-d) δ 8.11 (dd, J = 1.4, 0.7 Hz, 1H), 7.34-7.10 (m, 4H), 6.89 (td, J = 8.0, 2.2 Hz, 1H), 6.38 (ddd, J = 7.7, 1.5, 0.8 Hz, 1H), 6.32 (ddd, J = 8.3, 5.1,0.8 Hz, 1H), 3.49-3.43 (m, 1H), 3.32 (dd, J = 11.3, 5.3 Hz, 1H), 2.16 (s, 3H), 1.24 (s, 3H), 0.86 (d, J = 1.4 Hz, 3H). LCMS m/z 470.35 $[M + H]^+$. |
| 37 | From S4 according to Standard procedures A and B[c,d] 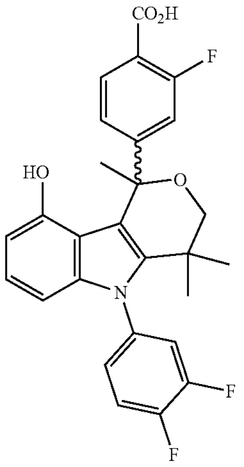 | 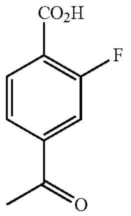 | $^1$H NMR (400 MHz, Methanol-d4) δ 7.82 (t, J = 7.9 Hz, 1H), 7.51 (q, J = 8.6 Hz, 2H), 7.38 (d, J = 8.2 Hz, 1H), 7.31 (s, 1H), 7.23 (d, J = 12.7 Hz, 1H), 6.90 (dd, J = 9.0, 6.9 Hz, 1H), 6.41 (d, J = 7.7 Hz, 1H), 6.26 (dd, J = 8.2, 2.3 Hz, 1H), 3.34 (m, 1H), 3.25 (m, 1H), 2.14 (s, 3H), 1.35 (s, 3H), 0.85 (d, J = 3.3 Hz, 3H). LCMS m/z 482.19 $[M + H]^+$. |

TABLE 3-continued

| Preparation of Compounds 32-63 | | | |
|---|---|---|---|
| Compound | Method/Product | Ketone | $^1$H NMR; LCMS m/z |
| 38 | From S4 according to Standard procedures A and B[c,f] 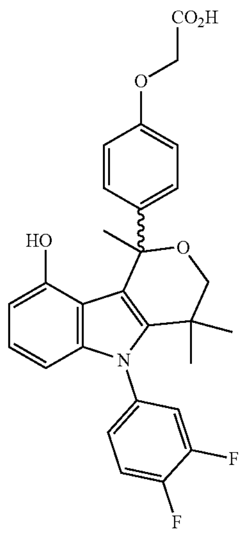 | 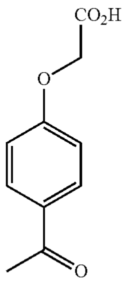 | $^1$H NMR (400 MHz, Methanol-d4) δ 7.50-7.34 (m, 3H), 7.35 (s, 1H), 7.23 (ddd, J = 8.6, 3.9, 2.2 Hz, 1H), 6.83 (td, J = 7.9, 2.7 Hz, 1H), 6.81-6.72 (m, 2H), 6.37 (ddd, J = 7.7, 1.9, 0.8 Hz, 1H), 6.21 (ddd, J = 8.2, 4.2, 0.8 Hz, 1H), 4.59 (s, 2H), 3.27 (d, J = 11.3 Hz, 1H), 3.18 (dd, J = 11.2, 8.2 Hz, 1H), 2.13 (s, 3H), 1.31 (d, J = 1.9 Hz, 3H), 0.81 (d, J = 1.5 Hz, 3H). LCMS m/z 494.16 [M + H]$^+$. |
| 39 | From S4 according to Standard procedures A and B[c,f] 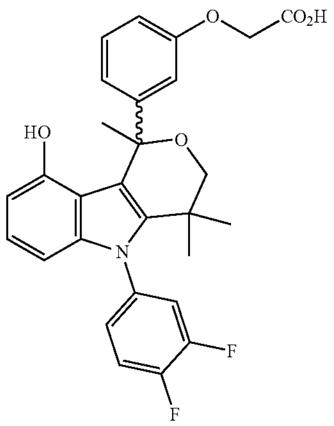 | 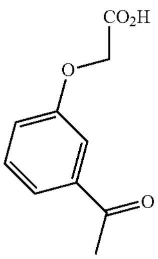 | $^1$H NMR (400 MHz, Methanol-d4) δ 7.52-7.38 (m, 2H), 7.26 (ddd, J = 8.4, 3.9, 2.0 Hz, 1H), 7.15 (td, J = 7.7, 1.5 Hz, 1H), 7.11 (dq, J = 7.8, 1.5 Hz, 1H), 7.03 (td, J = 2.9, 1.5 Hz, 1H), 6.85 (td, J = 8.0, 2.5 Hz, 1H), 6.77 (ddd, J = 7.8, 2.7, 1.4 Hz, 1H), 6.39 (ddd, J = 7.7, 1.9, 0.9 Hz, 1H), 6.22 (ddd, J = 8.2, 3.3, 0.8 Hz, 1H), 4.55 (dd, J = 16.4, 0.8 Hz, 1H), 4.49 (dd, J = 16.3, 2.5 Hz, 1H), 3.35-3.17 (m, 2H), 2.14 (s, 3H), 1.35 - 1.30 (m, 3H), 0.81 (d, J = 1.7 Hz, 3H). LCMS m/z 494.43 [M + H]$^+$. |

TABLE 3-continued

Preparation of Compounds 32-63

| Compound | Method/Product | Ketone | $^1H$ NMR; LCMS m/z |
|---|---|---|---|
| 40 | From S4 according to Standard procedures A and B[b,c] 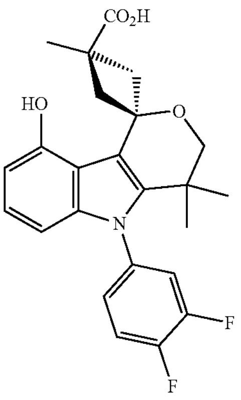 | 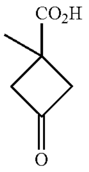 | $^1H$ NMR (400 MHz, DMSO-d6) δ 8 11.92 (s, 1H), 9.94 (s, 1H), 7.72 (ddd, J = 11.2, 7.3, 2.6 Hz, 1H), 7.64 (dt, J = 10.5, 8.9 Hz, 1H), 7.37-7.29 (m, 1H), 6.83 (t, J = 7.9 Hz, 1H), 6.49 (dd, J = 7.7, 0.8 Hz, 1H), 6.15 (dd, J = 8.1, 0.8 Hz, 1H), 2.94 (dd, J = 24.8, 11.2 Hz, 2H), 2.66-2.59 (m, 2H), 1.49 (s, 3H), 1.00 (s, 3H), 0.96 (s, 3H). LCMS m/z 428.27 $[M + H]^+$. |
| 41 | From S4 according to Standard procedures A and B[b,c] 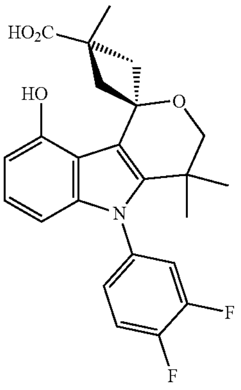 | 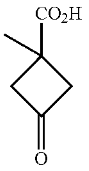 | $^1H$ NMR (400 MHz, DMSO-d6) δ 11.76 (br s, 1H), 9.70 (s, 1H), 7.73 (ddd, J = 11.2, 7.3, 2.5 Hz, 1H), 7.64 (dt, J = 10.6, 8.9 Hz, 1H), 7.37-7.29 (m, 1H), 6.80 (t, J = 7.9 Hz, 1H), 6.51 (dd, J = 7.7, 0.9 Hz, 1H), 6.13 (dd, J = 8.2, 0.8 Hz, 1H), 3.39(s, 2H), 3.45-3.29 (m, 2H), 2.13-2.03 (m, 2H), 1.59 (s, 3H), 1.02 (s, 3H), 0.98 (s, 3H). LCMS m/z 428.22 $[M + H]^+$. |
| 42 | From S4 according to Standard procedures A and B[c,d] 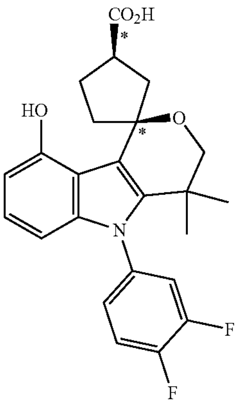 | 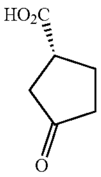 | $^1H$ NMR (400 MHz, Chloroform-d) δ 7.29 (dt, J = 7.9, 5.0 Hz, 1H), 7.20 (dq, J = 7.2, 4.0, 3.6 Hz, 2H), 6.86 (td, J = 7.9, 3.0 Hz, 1H), 6.51-6.34 (m, 1H), 6.26 (td, J = 8.1, 3.9 Hz, 1H), 3.47 (m, 2H), 3.24 (qd, J = 10.3, 6.0, 5.2 Hz, 1H), 2.95 (dq, J = 15.5, 5.6, 5.0 Hz, 1H), 2.77-2.57 (m, 1H), 2.38-2.25 (m, 1H), 2.17 (t, J = 8.6 Hz, 2H), 2.13-2.01 (m, 1H), 1.06-0.94 (m, 6H). LCMS m/z 428.36 $[M + H]^+$. |

TABLE 3-continued

| Preparation of Compounds 32-63 | | | |
|---|---|---|---|
| Compound | Method/Product | Ketone | $^{1}$H NMR; LCMS m/z |
| 43 | From S4 according to Standard procedures A and B[c,g,h] 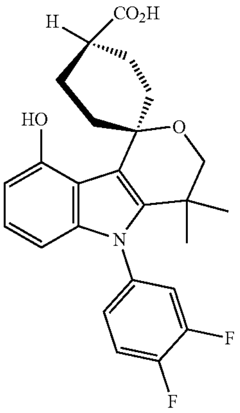 | 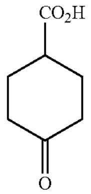 | $^{1}$H NMR (400 MHz, Chloroform-d) δ 7.42-7.32 (m, 1H), 7.28-7.22 (m, 1H), 7.18 (ddd, J = 8.9, 4.1, 1.9 Hz, 1H), 6.94 (dd, J = 8.2, 7.6 Hz, 1H), 6.46 (dd, J = 7.7, 0.8 Hz, 1H), 6.39 (dd, J = 8.3, 0.8 Hz, 1H), 5.33 (d, J = 4.8 Hz, 1H), 3.52 (d, J = 1.2 Hz, 2H), 2.79-2.56 (m, 3H), 2.05-1.90 (m, 3H), 1.10 (d, J = 5.8 Hz, 6H). LCMS m/z 442.5 [M + H]$^+$. |
| 44 | From S4 according to Standard procedures A and B[c,d,h,i] 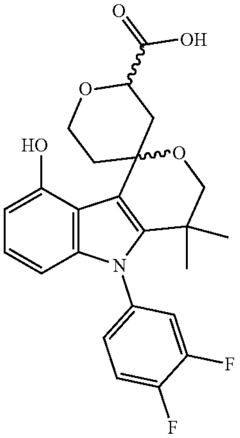 | 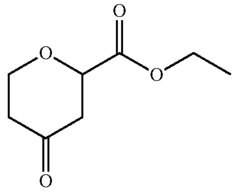 | $^{1}$H NMR (400 MHz, Methanol-d4) δ 7.59-7.33 (m, 2H), 7.31-7.13 (m, 1H), 6.85 (t, J = 8.0 Hz, 1H), 6.44 (dd, J = 7.7, 0.8 Hz, 1H), 6.21 (dd, J = 8.2, 0.8 Hz, 1H), 4.54-4.39 (m, 1H), 4.08-3.86 (m, 2H), 3.56 (t, J = 3.1 Hz, 2H), 3.01 (dd, J = 12.9, 9.8 Hz, 1H), 2.18-2.01 (m, 1H), 1.78-1.57 (m, 1H), 1.11 (t, J = 9.8 Hz, 6H). LCMS m/z 444.6 [M + H]$^+$. |
| 45 | From S4 according to Standard procedures A and B[c,d,h,j] 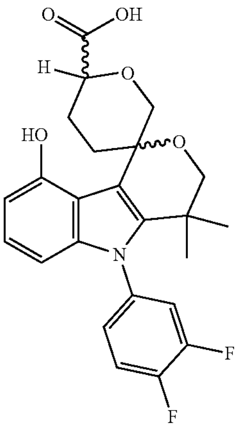 | 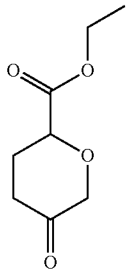 | $^{1}$H NMR (400 MHz, Methanol-d4) δ 7.61-7.35 (m, 2H), 7.317.20 (m, 1H), 6.89 (t, J = 8.0 Hz, 1H), 6.48 (dd, J = 7.8, 0.8 Hz, 1H), 6.25 (dd, J = 8.2, 0.8 Hz, 1H), 4.75 (dd, J = 11.9, 9.8 Hz, 1H), 4.23 (dd, J = 11.7, 2.5 Hz, 1H), 4.00-3.83 (m, 1H), 3.66-3.44 (m, 2H), 3.23-2.97 (m, 1H), 2.22-1.87 (m, 1H), 1.12 (dd, J = 11.1, 6.9 Hz, 6H). LCMS m/z 444.6 [M + H]$^+$. |

TABLE 3-continued

| Preparation of Compounds 32-63 | | | |
|---|---|---|---|
| Compound | Method/Product | Ketone | $^1$H NMR; LCMS m/z |
| 46 | From S4 according to Standard procedures A and B$^{c,d,h,j}$ 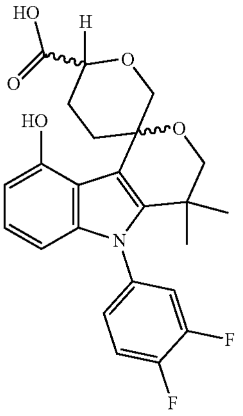 | 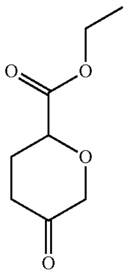 | $^1$H NMR (400 MHz, Methanol-d4) δ 7.60-7.36 (m, 2H), 7.25 (dq, J = 8.6, 1.8 Hz, 1H), 6.86 (t, J = 7.9 Hz, 1H), 6.44 (dd, J = 7.7, 0.8 Hz, 1H), 6.21 (dt, J = 8.3, 0.9 Hz, 1H), 4.53-4.37 (m, 1H), 3.76-3.52 (m, 3H), 2.98 (d, J = 14.2 Hz, 0H), 2.38 (d, J = 6.8 Hz, 1H), 2.19 (s, 1H), 1.87 (d, J = 12.3 Hz, 1H), 1.12 (dd, J = 17.2, 10.7 Hz, 6H). LCMS m/z 444.6 [M + H]$^+$. |
| 47 | From S4 according to Standard procedures A and B$^{c,d,k,n}$ 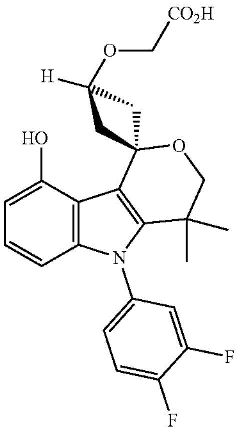 | 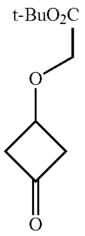 C60 | $^1$H NMR (400 MHz, Methanol-d4) δ 7.51-7.40 (m, 1H), 7.36 (ddd, J = 10.4, 7.1, 2.5 Hz, 1H), 7.20 (ddt, J = 8.5, 4.1, 1.9 Hz, 1H), 6.84 (t, J = 7.9 Hz, 1H), 6.43 (d, J = 7.7 Hz, 1H), 6.20 (d, J = 8.2 Hz, 1H), 4.46 (td, J = 6.8, 3.4 Hz, 1H), 4.07 (s, 2H), 3.44 (s, 2H), 3.24-3.13 (m, 2H), 2.40 (dt, J = 12.1, 2.6 Hz, 2H), 1.07 (d, J = 8.6 Hz, 6H). LCMS m/z 444.38 [M + H]$^+$ |

TABLE 3-continued

| Preparation of Compounds 32-63 | | | |
|---|---|---|---|
| Compound | Method/Product | Ketone | $^1$H NMR; LCMS m/z |
| 48 | From S4 according to Standard procedures A and B[c,d,k,n] 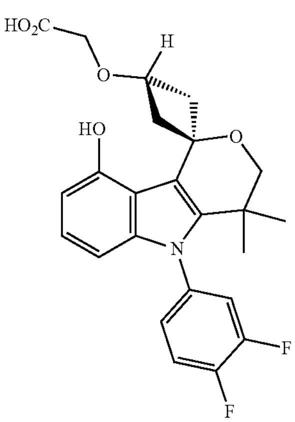 | 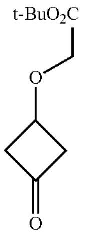 C60 | $^1$H NMR (400 MHz, Methanol-d4) δ 7.46 (q, J = 9.2 Hz, 1H), 7.36 (ddd, J = 10.4, 7.2, 2.5 Hz, 1H), 7.20 (dd, J = 7.8, 3.6 Hz, 1H), 6.84 (t, J = 7.9 Hz, 1H), 6.44 (d, J = 7.7 Hz, 1H), 6.19 (d, J = 8.1 Hz, 1H), 4.44 (q, J = 7.4 Hz, 1H), 4.09 (s, 2H), 3.42 (s, 2H), 3.37-3.21 (m, 2H), 2.55 (dt, J = 11.4, 5.8 Hz, 2H), 1.06 (d, J = 8.6 Hz, 6H). LCMS m/z 444.38 $[M + H]^+$. |
| 49 | From S4 according to Standard procedures A and B[c,h,d,k] 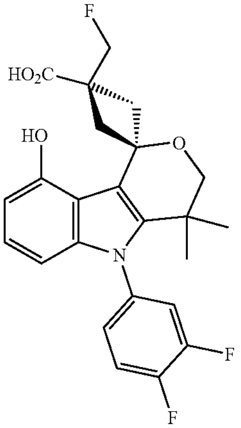 | 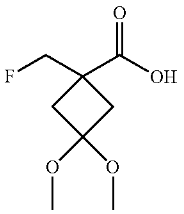 S18 | $^1$H NMR (400 MHz, Methanol-d4) δ 7.57-7.32 (m, 2H), 7.22 (d, J = 9.3 Hz ,1H), 6.84 (t, J = 7.9 Hz, 1H), 6.44 (d, J = 7.7 Hz, 1H), 6.19 (d, J = 8.2 Hz, 1H), 3.44 (d, J = 5.0 Hz, 3H), 2.38-2.18 (m, 2H), 1.08 (d, J = 9.2 Hz, 6H). LCMS m/z 446.5 $[M + H]^+$. |
| 50 | From S4 according to Standard procedures A and B[c,h,d,k] 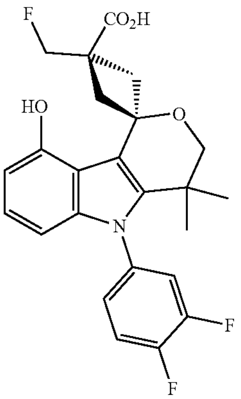 | 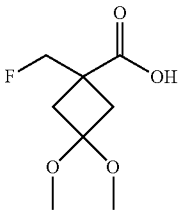 S18 | $^1$H NMR (400 MHz, Methanol-d4) δ 7.56-7.35 (m, 2H), 7.23 (s, 0H), 6.91-6.81 (m, 1H), 6.46 (dd, J = 7.7, 0.8 Hz, 1H), 6.21 (dd, J = 8.2, 0.8 Hz, 1H), 3.44 (d, J = 1.0 Hz, 2H), 2.70 (d, J = 12.6 Hz, 2H), 2.03 (s, 1H), 1.07 (d, J = 9.1 Hz, 7H). LCMS m/z 446.3 $[M + H]^+$. |

TABLE 3-continued

| Preparation of Compounds 32-63 | | | |
|---|---|---|---|
| Compound | Method/Product | Ketone | $^1$H NMR; LCMS m/z |
| 51 | Racemic 36 was separated by chiral SFC 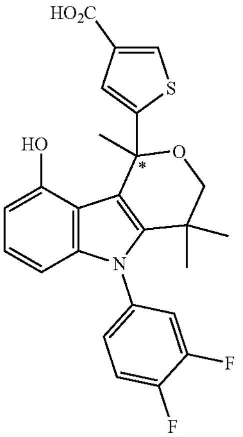 | N/A | $^1$H NMR (400 MHz, DMSO-d6) δ 9.52 (s, 1H), 8.12 (d, J = 4.3 Hz, 1H), 7.67 (q, J = 9.6 Hz, 2H), 7.43 (m, 1H), 7.24-7.15 (m, 1H), 6.88 (td, J = 7.9, 2.5 Hz, 1H), 6.48 (dd, J = 7.7, 2.2 Hz, 1H), 6.24 (t, J = 8.4 Hz, 1H), 3.5-3.4 (m, 2H), 2.25-2.15 (m, 3H), 1.32 (d, J = 7.9 Hz, 3H), 0.88 (d, J = 6.8 Hz, 3H). LCMS m/z 470.08 [M + H]$^+$. |
| 52 | Racemic 36 was separated by chiral SFC 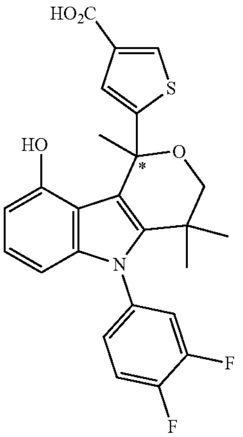 | N/A | $^1$H NMR (400 MHz, DMSO-d6) δ 9.52 (s, 1H), 8.12 (d, J = 4.3 Hz, 1H), 7.67 (q, J = 9.6 Hz, 2H), 7.43 (m, 1H), 7.24-7.15 (m, 1H), 6.88 (td, J = 7.9, 2.5 Hz, 1H), 6.48 (dd, J = 7.7, 2.2 Hz, 1H), 6.24 (t, J = 8.4 Hz, 1H), 3.5-3.4 (m, 2H), 2.25-2.15 (m, 3H), 1.32 (d, J = 7.9 Hz, 3H), 0.88 (d, J = 6.8 Hz, 3H). LCMS m/z 470.35 [M + H]$^+$. |
| 53 | Racemic 35 was separated by chiral SFC 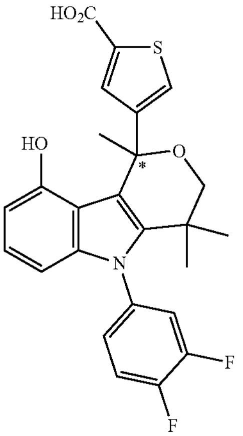 | N/A | $^1$H NMR (400 MHz, DMSO-d6) δ 13.00 (s, 1H), 9.44 (d, J = 3.1 Hz, 1H), 7.86-7.74 (m, 1H), 7.70-7.60 (m, 2H), 7.50 (d, J = 1.4 Hz, 1H), 7.45-7.35 (m, 1H), 6.84 (td, J = 7.9, 2.1 Hz, 1H), 6.38 (ddd, J = 7.7, 2.2, 0.8 Hz, 1H), 6.20 (ddd, J = 7.8, 6.8, 0.8 Hz, 1H), 3.31-3.20 (m, 2H), 2.07 (s, 3H), 1.23 (d, J = 7.9 Hz, 3H), 0.82 (d, J = 8.9 Hz, 3H). LCMS m/z 470.4 [M + H]$^+$. |

TABLE 3-continued

| Preparation of Compounds 32-63 | | | |
|---|---|---|---|
| Compound | Method/Product | Ketone | $^1$H NMR; LCMS m/z |
| 54 | Racemic 35 was separated by chiral SFC 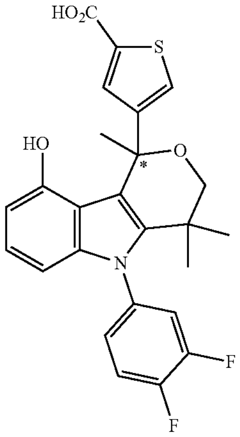 | N/A | $^1$H NMR (400 MHz, DMSO-d6) δ 13.00 (s, 1H), 9.44 (d, J = 3.1 Hz, 1H), 7.86-7.74 (m, 1H), 7.70-7.60 (m, 2H), 7.50 (d, J = 1.4 Hz, 1H), 7.45-7.35 (m, 1H), 6.84 (td, J = 7.9, 2.1 Hz, 1H), 6.38 (ddd, J = 7.7, 2.2, 0.8 Hz, 1H), 6.20 (ddd, J = 7.8, 6.8, 0.8 Hz, 1H), 3.31-3.20 (m, 2H), 2.07 (s, 3H), 1.23 (d, J = 7.9 Hz, 3H), 0.82 (d, J = 8.9 Hz, 3H). LCMS m/z 470.31 [M + H]$^+$. |
| 55 | Racemic 32 was separated by chiral SFC 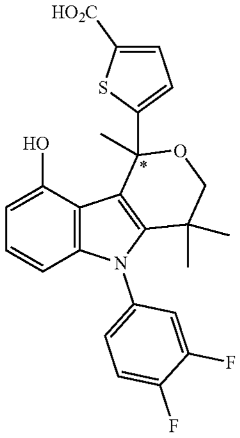 | N/A | $^1$H NMR (400 MHz, Chloroform-d) δ 7.73 (d, J = 3.9 Hz, 1H), 7.42-7.30 (m, 3H), 7.23 (d, J = 9.2 Hz, 1H), 7.08 (dd, J = 4.9, 3.8 Hz, 1H), 6.98 (td, J = 8.1, 2.3 Hz, 1H), 6.48-6.44 (m, 1H), 6.42 (ddd, J = 8.3, 5.2, 0.8 Hz, 1H), 3.58 (d, J = 11.4 Hz, 1H), 3.42 (dd, J = 11.3, 6.1Hz, 1H), 2.29-2.25 (m, 3H), 1.35 (s, 3H), 0.94 (d, J = 3.1 Hz, 3H). LCMS m/z 470.31 [M + H]$^+$. |
| 56 | Racemic 32 was separated by chiral SFC 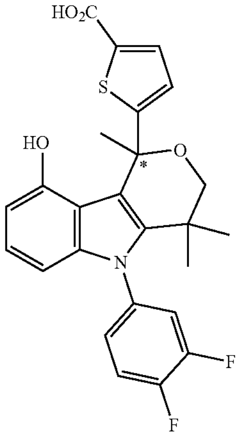 | N/A | $^1$H NMR (400 MHz, Chloroform-d) δ 7.73 (d, J = 3.9 Hz, 1H), 7.42-7.30 (m, 3H), 7.23 (d, J = 9.2 Hz, 1H), 7.08 (dd, J = 4.9, 3.8 Hz, 1H), 6.98 (td, J = 8.1, 2.3 Hz, 1H), 6.48-6.44 (m, 1H), 6.42 (ddd, J = 8.3, 5.2, 0.8 Hz, 1H), 3.58 (d, J = 11.4 Hz, 1H), 3.42 (dd, J = 11.3, 6.1Hz, 1H), 2.29-2.25 (m, 3H), 1.35 (s, 3H), 0.94 (d, J = 3.1 Hz, 3H). LCMS m/z 470.35 [M + H]$^+$. |

TABLE 3-continued

| Preparation of Compounds 32-63 | | | |
|---|---|---|---|
| Compound | Method/Product | Ketone | $^1$H NMR; LCMS m/z |
| 57 | From S4 according to Standard procedures A and B[c,g,h] 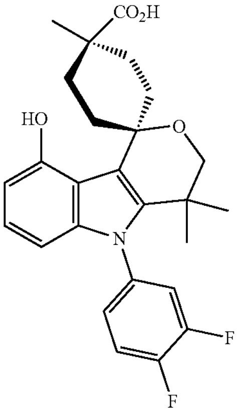 | 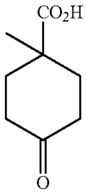 | $^1$H NMR (400 MHz, Chloroform-d) δ 7.42-7.32 (m, 1H), 7.27-7.22 (m, 1H), 7.18 (ddd, J = 8.8, 3.9, 1.8 Hz, 1H), 6.99-6.92 (m, 1H), 6.46 (dd, J = 7.6, 0.8 Hz, 1H), 6.39 (dd, J = 8.2, 0.8 Hz, 1H), 5.41 (s, 1H), 3.58-3.44 (m, 2H), 2.83-2.66 (m, 2H), 2.30 (td, J = 13.7, 4.2 Hz, 2H), 1.87 (dd, J = 19.1, 10.9 Hz, 2H), 1.63 (d, J = 13.0 Hz, 3H), 1.53 (s, 3H), 1.09 (d, J = 5.7 Hz, 6H). LCMS m/z 456.7 [M + H]$^+$. |
| 58 | From S4 according to Standard procedures A and B[c,d,l] 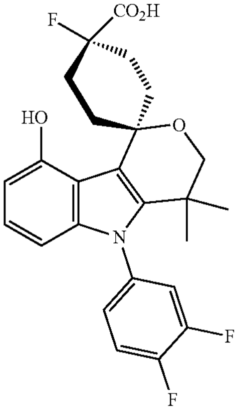 | 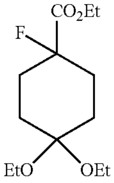 C64 | $^1$H NMR (300 MHz, Methanol-d4) δ 7.43 (dt, J = 10.2, 8.7 Hz, 1H), 7.31 (ddd, J = 10.7, 7.1,2.5 Hz, 1H), 7.21 (ddt, J = 8.4, 4.1, 2.0 Hz, 1H), 6.85 (t, J = 8.0 Hz, 1H), 6.44 (dd, J = 7.7, 0.9 Hz, 1H), 6.22 (dd, J = 8.2, 0.9 Hz, 1H), 3.53 (s, 2H), 3.12 (ddd, J = 13.9, 9.0, 5.2 Hz, 2H), 2.40 (dtd, J = 39.2, 14.1, 4.7 Hz, 2H), 1.86 (q, J = 13.3, 12.9 Hz, 4H), 1.10 (d, J = 6.0 Hz, 6H). LCMS m/z 460.36 [M + H]$^+$. |
| 59 | From S4 according to Standard procedures A and B[c,d,h] 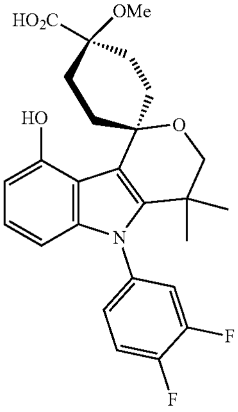 | 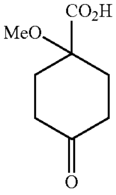 | $^1$H NMR (400 MHz, MeOD-d) δ 7.47 (q, J = 10.4, 10.0 Hz, 1H), 7.37 (dd, J = 10.5, 7.5 Hz, 1H), 7.23 (s, 1H), 6.81 (td, J = 7.9, 2.2 Hz, 1H), 6.39 (dd, J = 7.7, 2.4 Hz, 1H), 6.17 (dd, J = 8.3, 2.4 Hz, 1H), 3.50 (t, J = 2.2 Hz, 2H), 2.86 (q, J = 13.0 Hz, 2H), 2.26 (d, J = 12.0 Hz, 2H), 1.87 (d, J = 13.6 Hz, 4H), 1.29 (d, J = 2.3 Hz, 3H), 1.08 (d, J = 10.3 Hz, 6H). LCMS m/z 472.2 [M + H]$^+$. |

TABLE 3-continued

| Preparation of Compounds 32-63 | | | |
|---|---|---|---|
| Compound | Method/Product | Ketone | $^1$H NMR; LCMS m/z |
| 60 | From S4 according to Standard procedures A and B[c,d,h] 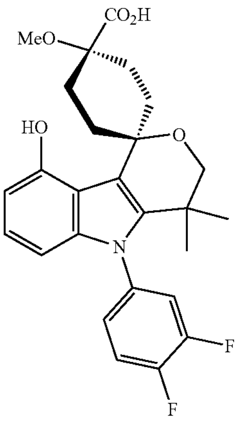 | 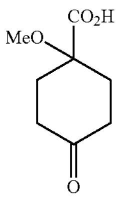 | $^1$H NMR (400 MHz, Acetone-d6) δ 8.71 (s, 1H), 7.65-7.43 (m, 2H), 7.37-7.25 (m, 1H), 6.89-6.76 (m, 1H), 6.54 (dd, J = 7.7, 0.9 Hz, 1H), 6.24 (dd, J = 8.2, 0.8 Hz, 1H), 3.51 (d, J = 2.4 Hz, 2H), 3.33 (s, 3H), 2.90-3.03 (m, 2H), 2.35-2.16 (m, 2H), 1.96- 1.61 (m, 4H), 1.10 (d, J = 12.8 Hz, 6H). LCMS m/z 472.0 $[M + H]^+$. |
| 61 | From S4 according to Standard procedures A and B[c,g,h] 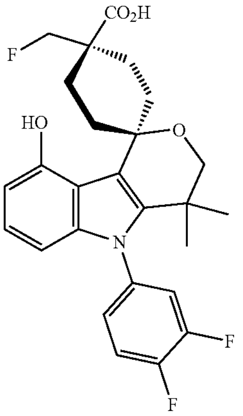 | 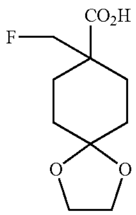 | $^1$H NMR (400 MHz, DMSO-d6) δ 12.48 (s, 1H), 10.05 (s, 1H), 7.79-7.56 (m, 1H), 7.33 (d, J = 8.9 Hz, 1H), 6.82 (t, J = 8.0 Hz, 1H), 6.48 (dd, J = 7.7, 0.9 Hz, 1H), 6.17 (dd, J = 8.2, 0.8 Hz, 1H), 5.00 (d, J = 46.9 Hz, 2H), 4.03 (q, J = 7.1 Hz, 2H), 3.44 (s, 2H), 2.58 (m, 2H), 2.05 (q, J = 8.9, 8.0 Hz, 2H), 1.67 (t, J = 14.8 Hz, 3H), 1.03 (s, 3H), 0.98 (s, 3H). LCMS m/z 474.1 $[M + H]^+$. |

TABLE 3-continued

| Preparation of Compounds 32-63 | | | |
|---|---|---|---|
| Compound | Method/Product | Ketone | $^1$H NMR; LCMS m/z |
| 62 | From S4 according to Standard procedures A and B[c,m] 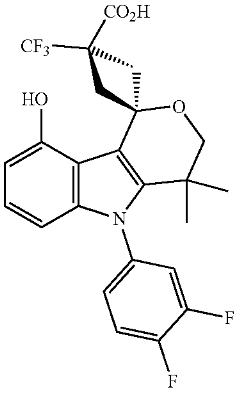 | 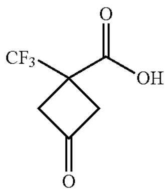 [SMILES: O=C1CC(C(=O)O)(C(F)(F)F)C1] | $^1$H NMR (400 MHz, Methanol-d4) δ 7.58-7.30 (m, 2H), 7.28-7.14 (m, 1H), 6.90-6.82 (m, 1H), 6.44 (dd, J = 7.7, 0.8 Hz, 1H), 6.18 (dd, J = 8.2, 0.8 Hz, 1H), 3.64 (dd, J = 18.2, 10.8 Hz, 2H), 3.43 (d, J = 0.9 Hz, 2H), 2.89-2.60 (m, 2H), 1.07 (d, J = 8.5 Hz, 6H). LCMS m/z 482.3 [M + H]$^+$ |
| 63 | From S4 according to Standard procedures A and B[c,d,h] 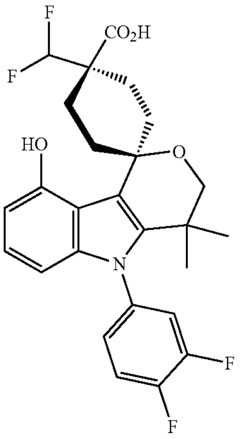 | 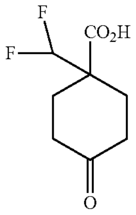 S19 | $^1$H NMR (400 MHz, Methanol-d4) δ 7.56-7.15 (m, 3H), 6.89-6.78 (m, 1H), 6.47-6.40 (m, 1H), 6.22 (dd, J = 8.2, 0.8 Hz, 1H), 3.50 (d, J = 2.7 Hz, 2H), 2.87-2.61 (m, 3H), 2.24-1.73 (m, 6H), 1.14-0.95 (m, 6H). LCMS m/z 492.2 [M + H]$^+$. |

[a]Standard procedure A modified by replacing DCE with dichloromethane at 50° C. in a closed vessel.

[b]Standard Procedure B modified by replacing ammonium formate with hydrogen at room temperature and using MeOH and EtOAc as solvents.

[c]Standard procedure A modified by replacing DCE with dichloromethane.

[d]Standard procedure B modified by using EtOH and THF as solvents.

[e]Standard procedure B modified by using the $BBr_3$ in dichloromethane conditions as described for the synthesis compounds 5 and 6.

[f]Standard procedure B modified by replacing ammonium formate with hydrogen at room temperature and using EtOH as solvent.

[g]Standard Procedure B modified by replacing ammonium formate with hydrogen and replacing Pd/C with $Pd(OH)_2$ and using MeOH and EtOAc as solvents.

[h]Standard procedure A modified by removing $Et_3SiH$.

[i]Before the debenzylation step, the ester was hydrolyzed using the same procedure as described for the synthesis of compound C55, with the following modifications: THF and MeOH as solvents, 1M NaOH for 1 h at 50° C.

[j]Before the debenzylation step, the ester was hydrolyzed using the same procedure as described for the synthesis of compound C55, with the following modifications: THF and MeOH as solvents, 1M NaOH for 1 h at 50° C.

[k]Standard procedure B modified by replacing ammonium formate with hydrogen

[l]Before the debenzylation step, the ester was hydrolyzed using the same procedure as described for the synthesis of compound C55, with the following modifications: dichloromethane and MeOH as solvents, LiOH as base for 2 h at room temperature.

[m]Standard Procedure B modified by replacing ammonium formate with hydrogen and replacing Pd/C with $Pd(OH)_2$ and using MeOH and THF as solvents.

[n]1 mL of TFA was added on completion of the reductive alkylation reaction and the mixture stirred for 10 min.

Compound 64

2-(5'-(3,4-difluorophenyl)-7'fluoro-9'-hydroxy-4',4'-dimethyl-2-oxo-4',5'-dihydro-3'H-spiro[piperidine-4,1'-pyrano[4,3-b]indol]-1-yl)acetic acid (64)

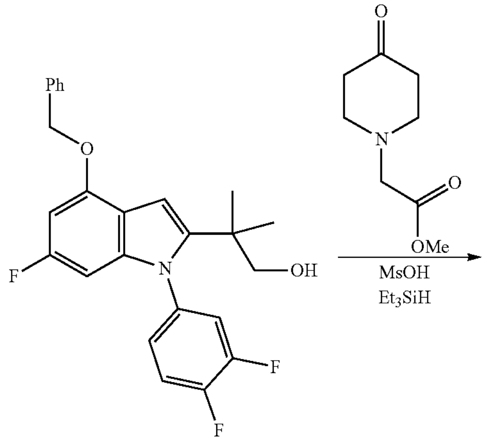

S5

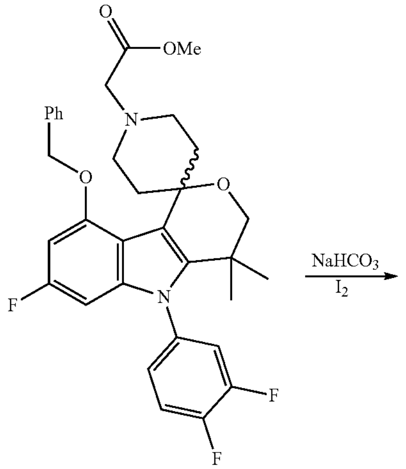

C76

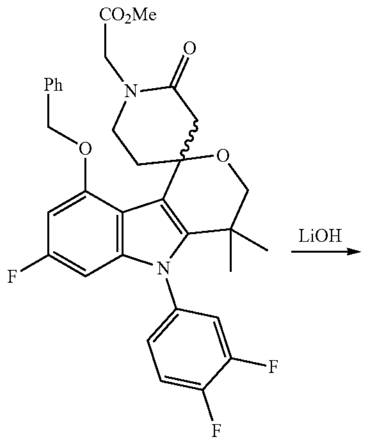

C77

-continued

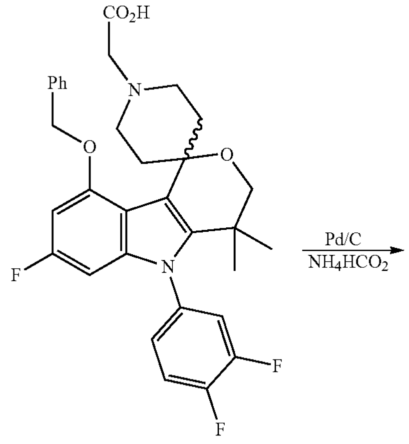

C78

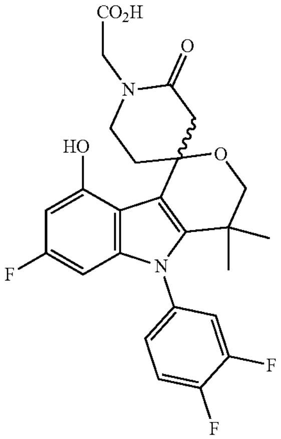

64

Step 1: Synthesis of Methyl-2-(9'-(benzyloxy)-5'-(3,4-difluorophenyl)-4',4'-dimethyl-4',5'-dihydro-3'H-spiro[piperidine-4,1'-pyrano[4,3-b]indol]-1-yl)acetate (C76)

This reaction was carried out according to Standard Procedure A from S5 employing methyl 2-(4-oxo-1-piperidyl)acetate as the ketone component giving C76 (120 mg, 44%). Dichloromethane was used rather than DCE as solvent. $^1H$ NMR (400 MHz, Chloroform-d) δ 7.67-7.58 (m, 2H), 7.47-7.29 (m, 4H), 7.22-7.10 (m, 2H), 6.42 (dd, J=11.7, 2.1 Hz, 1H), 6.07 (dd, J=9.1, 2.1 Hz, 1H), 5.36 (s, 2H), 3.73 (s, 3H), 3.50 (s, 2H), 3.25 (s, 2H), 3.02-2.82 (m, 2H), 2.73 (pd, J=10.1, 9.1, 3.5 Hz, 4H), 1.77 (dq, J=13.7, 2.6 Hz, 2H), 1.08 (s, 6H).

Step 2: Synthesis of Methyl-2-(9'-(benzyloxy)-5'-(3,4-difluorophenyl)-7'-fluoro-4',4'-dimethyl-2-oxo-4',5'-dihydro-3'H-spiro[piperidine-4,1'-pyrano[4,3-b]indol]-1-yl)acetate (C77)

To a mixture of methyl-2-(9'-(benzyloxy)-5'-(3,4-difluorophenyl)-7'-fluoro-4',4'-dimethyl-4',5'-dihydro-3'H-spiro[piperidine-4,1'-pyrano[4,3-b]indol]-1-yl)acetate (C76) (120 mg, 0.207 mmol) and sodium bicarbonate (2 mL of 1 M, 2 mmol) in THE (6 mL) was added molecular iodine (395 mg, 1.56 mmol). The reaction mixture was stirred for 40 min then quenched with sat. $NaHCO_3$, sodium thiosulfate (10 mL). Purification by column chromatography (12 g column; 10-50% EtOAc in heptane) gave $C_{77}$ (75 mg, 58%). $^1H$ NMR (400 MHz, Chloroform-d) δ 7.56-7.34 (m, 6H), 7.28-7.11 (m, 2H), 6.47 (dd, J=11.3, 2.1 Hz, 1H), 6.13 (ddd, J=9.1, 2.1, 1.0 Hz, 1H), 5.25-4.98 (m, 2H), 4.39 (d, J=17.1 Hz, 1H), 3.72-3.83 (m 4H), 3.59-3.36 (m, 4H), 2.97-2.67 (m, 3H), 1.94 (ddt, J=11.2, 5.0, 3.1 Hz, 1H), 1.14-1.01 (m, 6H). LCMS m/z 593.27 $[M+H]^+$.

Step 3: Synthesis of 2-(9'-(benzyloxy)-5'-(3,4-difluorophenyl)-7 fluoro-4',4'-dimethyl-2-oxo-4',5'-dihydro-3'H-spiro[piperidine-4,1'-pyrano[4,3-b]indol]-1-yl)acetic acid (C78)

To a solution of methyl 2-[9-benzyloxy-5-(3,4-difluorophenyl)-7'-fluoro-4,4-dimethyl-2'-oxo-spiro[3H-pyrano[4,3-b]indole-1,4'-piperidine]-1'-yl]acetate $C_{77}$ (65.0 mg, 0.110 mmol) in MeOH (0.5 mL), THE (1 mL) and water (0.5 mL) was added LiOH (50 mg, 1.19 mmol) and the mixture was stirred at 25° C. for 2 h. The reaction was neutralized with aq. HCl (630 µL of a 2 M solution, 1.26 mmol) and extracted with dichloromethane and the organics concentrated. Purification by column chromatography (12 g gold column; 0-60% EtOAc in heptane) gave C78 (63.5 mg, 51%). LCMS m/z 579.23 $[M+H]^+$.

Step 4: Synthesis of 2-(5'-(3,4-difluorophenyl)-9'-hydroxy-4',4'-dimethyl-2-oxo-4',5'-dihydro-3'H-spiro[piperidine-4,1'-pyrano[4,3-b]indol]-1-yl)acetic acid (64)

This reaction was carried out according to Standard Procedure B from C78 using EtOH and THF as solvents to give product 64 (3.8 mg, 14%). $^1H$ NMR (400 MHz, Methanol-d4) δ 7.26-7.21 (m, 1H), 7.16 (dddd, J=9.8, 7.2, 5.1, 2.5 Hz, 1H), 7.12-7.04 (m, 1H), 6.22 (dd, J=11.0, 2.2 Hz, 1H), 5.90 (dd, J=9.4, 2.2 Hz, 1H), 4.36 (d, J=17.4 Hz, 1H), 3.83 (d, J=17.3 Hz, 1H), 3.76-3.61 (m, 2H), 3.42 (t, J=2.2 Hz, 2H), 3.28-3.22 (m, 1H), 3.21-3.02 (m, 1H), 2.73-2.53 (m, 1H), 2.00 (d, J=14.0 Hz, 1H), 0.98 (dd, J=15.8, 2.0 Hz, 6H). LCMS m/z 489.16 $[M+H]^+$.

Compounds 65-82

Compounds 65-82 were prepared from S5 and the appropriate ketone or ketone equivalent.

TABLE 4

| Preparation of Compounds 65-82 | | | |
|---|---|---|---|
| Compound | Method/Product | Ketone | $^1H$ NMR; LCMS m/z |
| 65 | From S5 according to Standard procedures A and $B^{a,b,c}$ 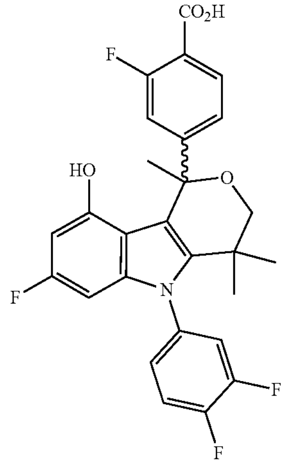 [SMILES: CC1(C)COC(C)(c2ccc(C(=O)O)c(F)c2)c2c1n(-c1ccc(F)c(F)c1)c1cc(F)cc(O)c21] | 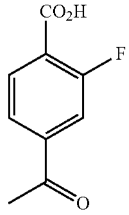 | $^1H$ NMR (400 MHz, Methanol-d4) δ 7.83 (t, J = 7.9 Hz, 1H), 7.60-7.46 (m, 2H), 7.41-7.27 (m, 2H), 7.22 (dt, J = 12.7, 1.7 Hz, 1H), 6.22 (dt, J = 11.1, 2.1 Hz, 1H), 6.03-5.90 (m, 1H), 3.29-3.20 (m, 2H), 2.11 (s, 3H), 2.03 (s, 1H), 1.32 (s, 3H), 0.84 (d, J = 1.0 Hz, 3H). LCMS m/z 500.19 $[M + H]^+$. |

TABLE 4-continued

| Preparation of Compounds 65-82 | | | |
|---|---|---|---|
| Compound | Method/Product | Ketone | $^1$H NMR; LCMS m/z |
| 66 | From S5 according to Standard procedures A and B[a,b,c] 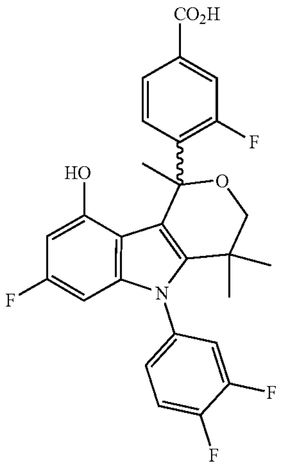 [SMILES: CC1(C)COC(C)(c2ccc(C(=O)O)cc2F)c2c1n(-c1ccc(F)c(F)c1)c1cc(F)cc(O)c21] | 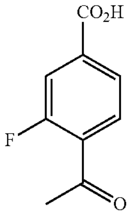 | $^1$H NMR (400 MHz, Methanol-d4) δ 7.73-7.45 (m, 4H), 7.37-7.19 (m, 2H), 6.19 (ddd, J = 11.2, 2.2, 1.6 Hz, 1H), 5.96 (ddd, J = 9.4, 2.8, 2.1 Hz, 1H), 3.26 (d, J = 11.3 Hz, 2H), 2.25 (dd, J = 1.8, 0.9 Hz, 3H), 1.34 (s, 3H), 0.83 (s, 3H). LCMS m/z 500.1 [M + H]$^+$. |
| 67 | From S5 according to Standard procedures A and B[a,d] 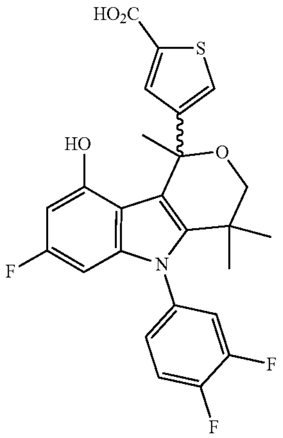 [SMILES: CC1(C)COC(C)(c2csc(C(=O)O)c2)c2c1n(-c1ccc(F)c(F)c1)c1cc(F)cc(O)c21] | 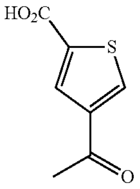 | $^1$H NMR (400 MHz, DMSO-d6) δ 13.09 (s, 1H), 10.00 (d, J = 2.0 Hz, 1H), 7.82 (ddt, J = 18.4, 11.3, 5.0 Hz, 1H), 7.72-7.62 (m, 1H), 7.60 (s, 1H), 7.43 (d, J = 16.7 Hz, 2H), 6.22 (dt, J = 11.4, 2.1 Hz, 1H), 5.98 (td, J = 9.7, 2.2 Hz, 1H), 3.31-3.19 (m, 2H), 2.04 (s, 3H), 1.21 (d, J = 8.1 Hz, 3H), 0.81 (d, J = 9.7 Hz, 3H). LCMS m/z 488.4 [M + H]$^+$. |
| 68 | From S5 according to Standard procedures A and B[a,e] 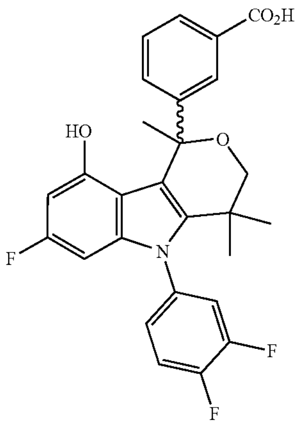 [SMILES: CC1(C)COC(C)(c2cccc(C(=O)O)c2)c2c1n(-c1ccc(F)c(F)c1)c1cc(F)cc(O)c21] | 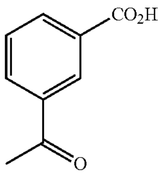 | $^1$H NMR (400 MHz, DMSO-d6) δ 10.06 (s, 1H), 8.08 (s, 1H), 7.84 (dd, J = 18.3, 8.1 Hz, 2H), 7.73-7.62 (m, 1H), 7.57 (d, J = 7.8 Hz, 1H), 7.46-7.33 (m, 2H), 6.23 (dt, J = 11.9, 3.2 Hz, 1H), 6.04-5.95 (m, 1H), 3.30-3.23 (m, 1H), 3.10 (m, 1H), 2.06 (s, 3H), 1.24 (m, 3H), 0.81 (d, J = 8.8 Hz, 3H). LCMS m/z 482.37 [M + H]$^+$. |

TABLE 4-continued

Preparation of Compounds 65-82

| Compound | Method/Product | Ketone | $^1H$ NMR; LCMS m/z |
| --- | --- | --- | --- |
| 69 | From S5 according to Standard procedures A and B[a,d] 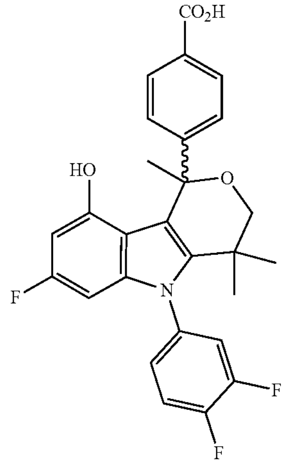 [SMILES: CC1(C)COC(C)(c2ccc(C(=O)O)cc2)c2c1n(-c1ccc(F)c(F)c1)c1cc(F)cc(O)c21] | 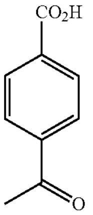 | $^1H$ NMR (400 MHz, DMSO-d6) δ 10.48 (br s, 1H), 8.36 (d, J = 8.1 Hz, 2H), 8.23-8.07 (m, 2H), 8.02 (d, J = 8.1 Hz, 2H), 7.89 (s, 1H), 6.81-6.72 (m, 1H), 6.51-6.41 (m, 1H), 3.78-3.59 (m, 2H), 2.58 (s, 3H), 1.75 (d, J = 4.1 Hz, 3H), 1.29 (d, J = 4.3 Hz, 3H). LCMS m/z 482.33 $[M + H]^+$. |
| 70 | From S5 according to Standard procedures A and B[a,e] 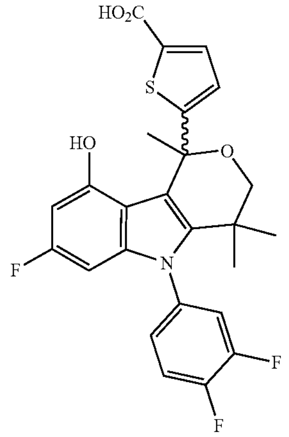 [SMILES: CC1(C)COC(C)(c2ccc(C(=O)O)s2)c2c1n(-c1ccc(F)c(F)c1)c1cc(F)cc(O)c21] | 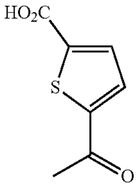 | $^1H$ NMR (400 MHz, Chloroform-d) δ 7.74 (d, J = 3.8 Hz, 1H), 7.39 (q, J = 8.7 Hz, 1H), 7.35-7.31 (m, 1H), 7.26-7.19 (m, 1H), 7.08 (dd, J = 4.7, 3.8 Hz, 1H), 6.27 (dt, J = 10.4, 2.0 Hz, 1H), 6.11 (ddd, J = 9.2, 4.3, 2.1 Hz, 1H), 3.55 (d, J = 11.3 Hz, 1H), 3.41 (dd, J = 11.4, 5.3 Hz, 1H), 2.24 (d, J = 0.9 Hz, 3H), 1.32 (d, J = 1.8 Hz, 3H), 0.94 (d, J = 1.2 Hz, 3H). LCMS m/z 488.4 $[M + H]^+$. |

TABLE 4-continued

| Preparation of Compounds 65-82 | | | |
|---|---|---|---|
| Compound | Method/Product | Ketone | $^1$H NMR; LCMS m/z |
| 71 | From S5 according to Standard procedures A and B[a,b,c] 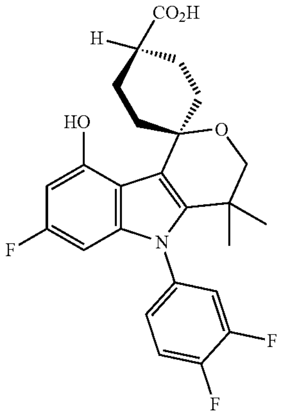 | 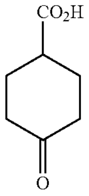 | $^1$H NMR (400 MHz, Methanol-d4) δ 7.56-7.30 (m, 2H), 7.26-7.14 (m, 1H), 6.23 (dd, J = 11.1, 2.2 Hz, 1H), 5.89 (dd, J = 9.5, 2.2 Hz, 1H), 3.48 (d, J = 2.1 Hz, 2H), 2.81-2.64 (m, 2H), 2.44 (s, 1H), 2.03 (s, 1H), 1.99-1.73 (m, 6H), 1.06 (d, J = 6.4 Hz, 6H). LCMS m/z 460.0 [M + H]$^+$. |
| 72 | From S5 according to Standard procedures A and B[a,b,c] 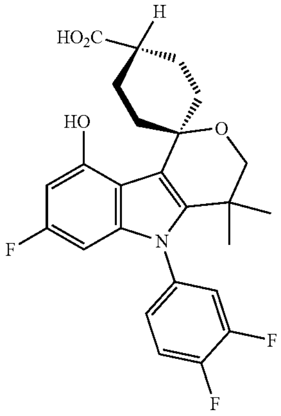 | 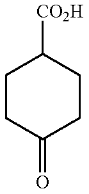 | $^1$H NMR (400 MHz, Methanol-d4) δ 7.56-7.35 (m, 2H), 7.28-7.16 (m, 1H), 6.19 (dd, J = 11.2, 2.2 Hz, 1H), 5.85 (dd, J = 9.5, 2.2 Hz, 1H), 3.47 (d, J = 2.0 Hz, 2H), 2.89-2.58 (m, 4H), 2.04 (d, J = 9.5 Hz, 5H), 1.69 (d, J = 13.7 Hz, 2H), 1.06 (d, J = 6.0 Hz, 6H). LCMS m/z 460.2 [M + H]$^+$. |
| 73 | From S5 according to Standard procedures A and B[a,e,f] 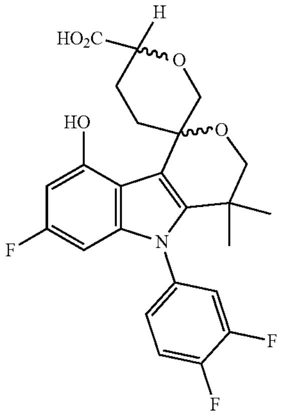 [SMILES: CC1(C)COC2(CCC(C(=O)O)OC2)c2c1n(-c1ccc(F)c(F)c1)c1cc(F)cc(O)c21] | 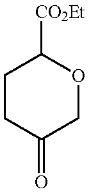 | LCMS m/z 462.05 [M + H]$^+$. |

TABLE 4-continued

Preparation of Compounds 65-82

| Compound | Method/Product | Ketone | $^1$H NMR; LCMS m/z |
|---|---|---|---|
| 74 | From S5 according to Standard procedures A and B[a,e,f] 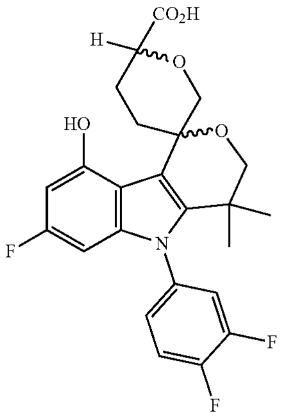 [SMILES: CC1(C)COC2(CCC(C(=O)O)OC2)c2c1n(-c1ccc(F)c(F)c1)c1cc(F)cc(O)c21] | 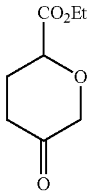 | LCMS m/z 462.14 [M + H]$^+$. |
| 75 | From S5 according to Standard procedures A and B[a,g,j] 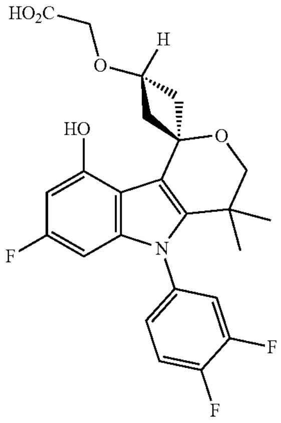 [SMILES: CC1(C)CO[C@]2(C[C@H](OCC(=O)O)C2)c2c1n(-c1ccc(F)c(F)c1)c1cc(F)cc(O)c12] | 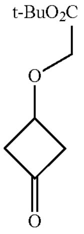 C60 | $^1$H NMR (400 MHz, Methanol-d4) δ 7.39-7.30 (m, 1H), 7.25 (t, J = 9.0 Hz, 1H), 7.05 (d, J = 8.7 Hz, 1H), 6.14 (d, J = 11.0 Hz, 1H), 5.77 (d, J = 9.4 Hz, 1H), 4.29 (p, J = 7.5 Hz, 1H), 3.95 (s, 2H), 3.24 (d, J = 4.4 Hz, 2H), 3.09 (q, J = 10.6, 10.1 Hz, 2H), 2.41 (dd, J = 11.5, 6.7 Hz, 2H), 0.93-0.88 (m, 6H). LCMS m/z 462.39 [M + H]$^+$. |
| 76 | From S5 according to Standard procedures A and B[a,g,j] 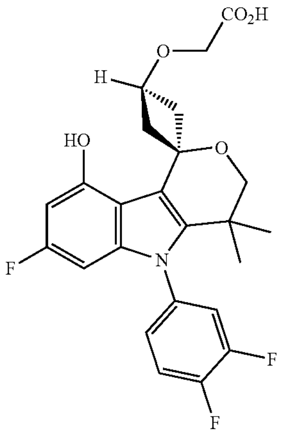 [SMILES: CC1(C)CO[C@]2(C[C@@H](OCC(=O)O)C2)c2c1n(-c1ccc(F)c(F)c1)c1cc(F)cc(O)c12] | 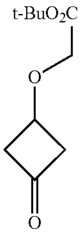 C60 | $^1$H NMR (400 MHz, Methanol-d4) δ 7.48 (q, J = 9.3 Hz, 1H), 7.39 (t, J = 9.3 Hz, 1H), 7.22 (d, J = 8.7 Hz, 1H), 6.24 (d, J = 11.1 Hz, 1H), 5.90 (d, J = 9.4 Hz, 1H), 4.42 (d, J = 7.2 Hz, 1H), 4.07 (s, 2H), 3.43 (s, 2H), 3.17 (dd, J = 13.7, 7.6 Hz, 2H), 2.40 (d, J = 13.3 Hz, 2H), 1.06 (d, J = 4.7 Hz, 6H). LCMS m/z 462.39 [M + H]$^+$. |

TABLE 4-continued
| Preparation of Compounds 65-82 | | | |
|---|---|---|---|
| Compound | Method/Product | Ketone | $^1$H NMR; LCMS m/z |
| 77 | Racemic 68 was separated by chiral SFC 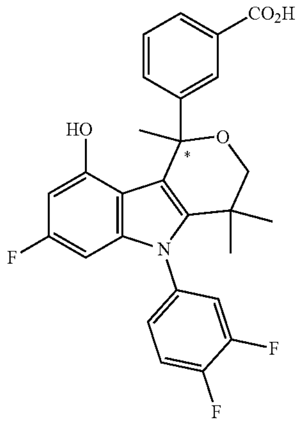 [SMILES: CC1(C)COC(C)(c2cccc(C(=O)O)c2)c2c1n(-c1ccc(F)c(F)c1)c1cc(F)cc(O)c21] | N/A | $^1$H NMR (400 MHz, DMSO-d6) δ 10.06 (s, 1H), 8.08 (s, 1H), 7.84 (dd, J = 18.3, 8.1 Hz, 2H), 7.73-7.62 (m, 1H), 7.57 (d, J = 7.8 Hz, 1H), 7.46-7.33 (m, 2H), 6.23 (dt, J = 11.9, 3.2 Hz, 1H), 6.04-5.95 (m, 1H), 3.30-3.23 (m, 1H), 3.10 (m, 1H), 2.06 (s, 3H), 1.24 (m, 3H), 0.81 (d, J = 8.8 Hz, 3H). LCMS m/z 482.37 (M + H]$^+$. |
| 78 | Racemic 68 was separated by chiral SFC 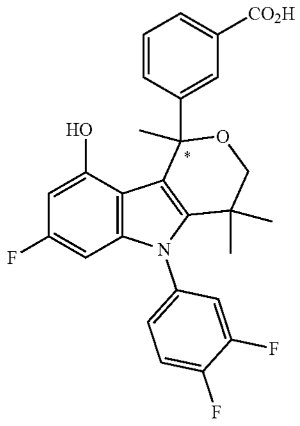 [SMILES: CC1(C)COC(C)(c2cccc(C(=O)O)c2)c2c1n(-c1ccc(F)c(F)c1)c1cc(F)cc(O)c21] | N/A | $^1$H NMR (400 MHz, DMSO-d6) δ 10.06 (s, 1H), 8.08 (s, 1H), 7.84 (dd, J = 18.3, 8.1 Hz, 2H), 7.73-7.62 (m, 1H), 7.57 (d, J = 7.8 Hz, 1H), 7.46-7.33 (m, 2H), 6.23 (dt, J = 11.9, 3.2 Hz, 1H), 6.04-5.95 (m, 1H), 3.30-3.23 (m, 1H), 3.10 (m, 1H), 2.06 (s, 3H), 1.24 (m, 3H), 0.81 (d, J = 8.8 Hz, 3H). LCMS m/z 482.46 [M + H]$^+$. |

TABLE 4-continued

| Preparation of Compounds 65-82 | | | |
|---|---|---|---|
| Compound | Method/Product | Ketone | $^1$H NMR; LCMS m/z |
| 79 | Racemic 67 was separated by chiral SFC 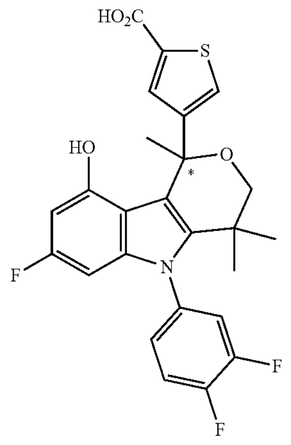 [SMILES: CC1(C)COC(C)(c2csc(C(=O)O)c2)c2c1n(-c1ccc(F)c(F)c1)c1cc(F)cc(O)c21] | N/A | $^1$H NMR (400 MHz, DMSO-d6) δ 13.09 (s, 1H), 10.00 (d, J = 2.0 Hz, 1H), 7.82 (ddt, J = 18.4, 11.3, 5.0 Hz, 1H), 7.72-7.62 (m, 1H), 7.60 (s, 1H), 7.43 (d, J = 16.7 Hz, 2H), 6.22 (dt, J = 11.4, 2.1 Hz, 1H), 5.98 (td, J = 9.7, 2.2 Hz, 1H), 3.31-3.19 (m, 2H), 2.04 (s, 3H), 1.21 (d, J = 8.1 Hz, 3H), 0.81 (d, J = 9.7 Hz, 3H). LCMS m/z 488.4 [M + H]$^+$. |
| 80 | Racemic 67 was separated by chiral SFC 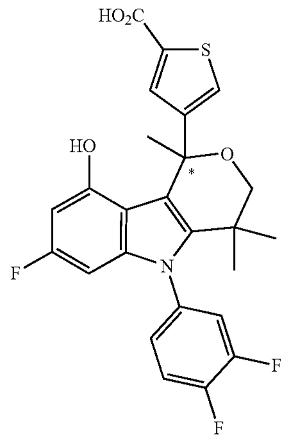 [SMILES: CC1(C)COC(C)(c2csc(C(=O)O)c2)c2c1n(-c1ccc(F)c(F)c1)c1cc(F)cc(O)c21] | N/A | $^1$H NMR (400 MHz, DMSO-d6) δ 13.09 (s, 1H), 10.00 (d, J = 2.0 Hz, 1H), 7.82 (ddt, J = 18.4, 11.3, 5.0 Hz, 1H), 7.72-7.62 (m, 1H), 7.60 (s, 1H), 7.43 (d, J = 16.7 Hz, 2H), 6.22 (dt, J = 11.4, 2.1 Hz, 1H), 5.98 (td, J = 9.7, 2.2 Hz, 1H), 3.31-3.19 (m, 2H), 2.04 (s, 3H), 1.21 (d, J = 8.1 Hz, 3H), 0.81 (d, J = 9.7 Hz, 3H). LCMS m/z 488.4 [M + H]$^+$. |

TABLE 4-continued

| Preparation of Compounds 65-82 | | | |
|---|---|---|---|
| Compound | Method/Product | Ketone | $^1$H NMR; LCMS m/z |
| 81 | From S5 according to Standard procedures A and B[a,c,h] 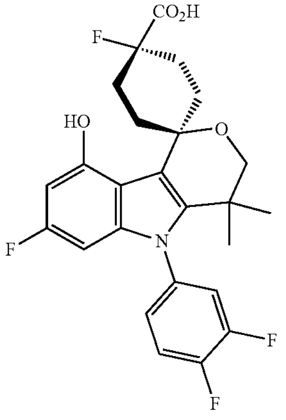 | 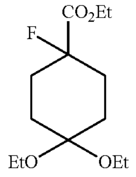 | $^1$H NMR (400 MHz, DMSO-d6) δ 13.11 (s, 1H), 10.41 (s, 1H), 7.89-7.51 (m, 2H), 7.34 (d, J = 8.8 Hz, 0H), 6.27 (dd, J = 11.3, 2.3 Hz, 1H), 5.93 (dd, J = 9.5, 2.2 Hz, 1H), 4.11 (d, J = 5.6 Hz, 1H), 3.45 (s, 2H), 3.17 (d, J = 4.4 Hz, 1H), 2.86 (q, J = 13.6, 13.0 Hz, 2H), 2.39-2.08 (m, 1H), 1.77 (dd, J = 27.2, 13.4 Hz, 4H), 1.00 (d, J = 19.2 Hz, 6H). LCMS m/z 478.19 $[M + H]^+$. |
| 82 | From S5 according to Standard procedures A and B[i,c] 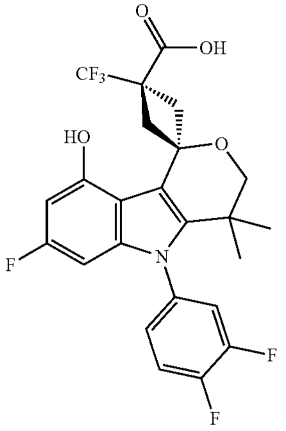 [SMILES: CC1(C)CO[C@]2(C[C@](C(=O)O)(C(F)(F)F)C2)c2c1n(-c1ccc(F)c(F)c1)c1cc(F)cc(O)c12] | 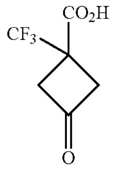 | $^1$H NMR (400 MHz, Methanol-d4) δ 7.56-7.30 (m, 2H), 7.30-7.16 (m, 1H), 6.25 (dd, J = 11.1, 2.2 Hz, 1H), 5.88 (dd, J = 9.5, 2.2 Hz, 1H), 3.57 (dd, J = 16.0, 11.3 Hz, 2H), 3.42 (d, J = 0.8 Hz, 2H), 2.84-2.76 (m, 1H), 2.03 (s, 1H), 1.06 (d, J = 4.9 Hz, 6H). LCMS m/z 500.0 $[M + H]^+$. |

[a]Standard procedure A modified by replacing DCE with dichloromethane.

[b]Standard procedure A modified by removing $Et_3SiH$.

[c]Standard procedure B modified by using EtOH and THF as solvents and heating to somewhere in the range of 40-60° C.

[d]Standard Procedure B modified by replacing ammonium formate with hydrogen at room temperature and using MeOH and EtOAc as solvents.

[e]Standard Procedure B modified by replacing ammonium formate with hydrogen at room temperature and using MeOH as solvent.

[f]Before the debenzylation step, the ester was hydrolyzed using the same procedure as described for the synthesis of compound C47, with the following modifications: THF as solvent, 1M LiOH for 1 hour at room temperature.

[g]Standard Procedure B modified by replacing ammonium formate with hydrogen at room temperature and using EtOH and THF as solvents.

[h]Before the debenzylation step, the ester was hydrolyzed using the same procedure as described for the synthesis of compound C47, with the following modifications: dichloromethane and MeOH as solvents, LiOH as base for 2 hours at room temperature.

[i]Standard procedure A modified by replacing DCE with dichloromethane and heating the reaction in a closed vessel at 55° C.

[j]1 mL of TFA was added on completion of the reductive alkylation reaction and the mixture stirred for 10 minutes.

Compound 83

5-(4-Fluorophenyl)-9-hydroxy-1'-imino-4,4-dimethyl-2',3',4,5,5',6'-hexahydro-1'H,3H-1'λ$^6$-spiro[pyrano[4,3-b]indole-1,4'-thiopyran]1'-oxide (83)

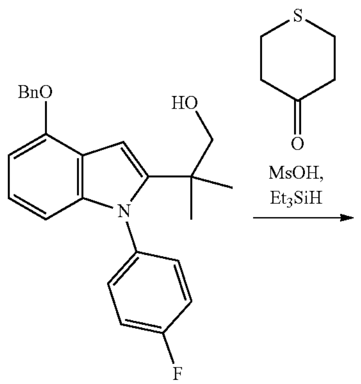

S6

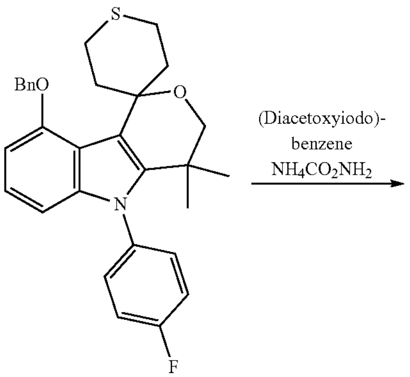

C79

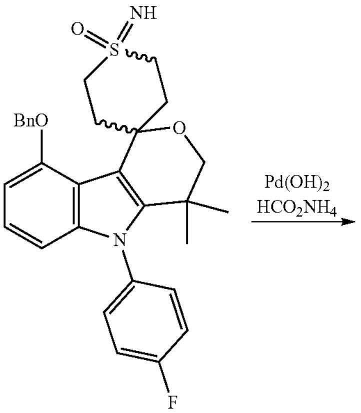

C80

-continued

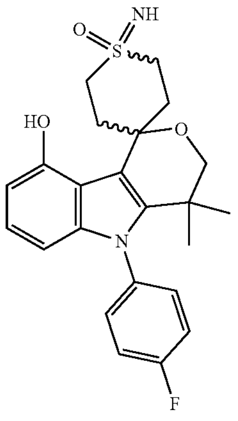

83

Step 1: Synthesis of 9-(benzyloxy)-5-(4-fluorophenyl)-4,4-dimethyl-2',3',4,5,5',6'-hexahydro-3H-spiro[pyrano[4,3-b]indole-1,4'-thiopyran] (C79)

This reaction was carried out from S6 according to Standard Procedure A. dichloromethane was used as solvent giving product C79 (428 mg, 82%). LCMS m/z 444.24 $[M+H]^+$.

Step 2: Synthesis of 9-(benzyloxy)-5-(4-fluorophenyl)-1'-imino-4,4-dimethyl-2',3',4,5,5',6'-hexahydro-1'H,3H-1'λ$^6$-spiro[pyrano[4,3-b]indole-1,4'-thiopyran]1'-oxide (C80)

To a solution of C79 (150 mg, 0.308 mmol) in dichloromethane (3 mL) was added (Diacetoxyiodo)-benzene (218 mg, 0.677 mmol) and ammonium carbamate (84 mg, 1.08 mmol) and the mixture stirred at room temperature overnight. The mixture was diluted with water and extracted twice with dichloromethane and the phases separated with a phase separator. The organics were concentrated. Purification was accomplished by column chromatography (C18 50 g column; aq. TFA/MeCN). The pure fractions were concentrated in vacuo, diluted with dichloromethane, neutralized with aqueous $NaHCO_3$ solution. The organic phase was passed through a phase separator and the resulting filtrate concentrated in vacuo to afford product C80 (220 mg, 47%). $^1$H NMR (400 MHz, DMSO-$d_6$) δ 7.60-7.52 (m, 2H), 7.51-7.44 (m, 2H), 7.42 (d, J=8.7 Hz, 2H), 7.39-7.32 (m, 2H), 7.30-7.22 (m, 1H), 6.88-6.81 (m, 1H), 6.52 (d, J=7.9 Hz, 1H), 6.20 (d, J=8.2 Hz, 1H), 5.42 (s, 2H), 3.54 (d, J=4.2 Hz, 2H), 3.50-3.38 (m, 2H), 3.32-3.22 (m, 2H), 3.07-2.93 (m, 2H), 2.13 (d, J=13.7 Hz, 2H), 1.01 (s, 6H). LCMS m/z 519.37 $[M+H]^+$.

Step 3: Synthesis of 5-(4-fluorophenyl)-9-hydroxy-1'-imino-4,4-dimethyl-2',3',4,5,5',6'-hexahydro-1'H,3H-1'λ$^6$-spiro[pyrano[4,3-b]indole-1,4'-thiopyran]1'-oxide (83)

This reaction was carried out from C80 according to Standard Procedure B with the following modification: $Pd(OH)_2$ was used as catalyst. This gave product 83 (46 mg, 25%). $^1$H NMR (400 MHz, DMSO-d6) δ 10.05 (s, 1H), 7.52-7.35 (m, 4H), 6.80 (dd, J=8.6, 7.3 Hz, 1H), 6.42 (dd, J=7.7, 0.9 Hz, 1H), 6.09 (dt, J=8.3, 1.3 Hz, 1H), 3.52 (d, J=4.2 Hz, 2H), 3.43-3.22 (m, 4H), 2.89 (d, J=12.7 Hz, 2H), 2.05 (d, J=13.1 Hz, 2H), 1.01 (s, 6H). LCMS m/z 429.3 $[M+H]^+$.

Compound 84

2-(((1S,4S)-5'-(4-fluorophenyl)-9'-hydroxy-4',4'-dimethyl-4',5'-dihydro-3'H-spiro[cyclohexane-1,1'-pyrano[4,3-b]indol]-4-yl)oxy)acetic acid (84)

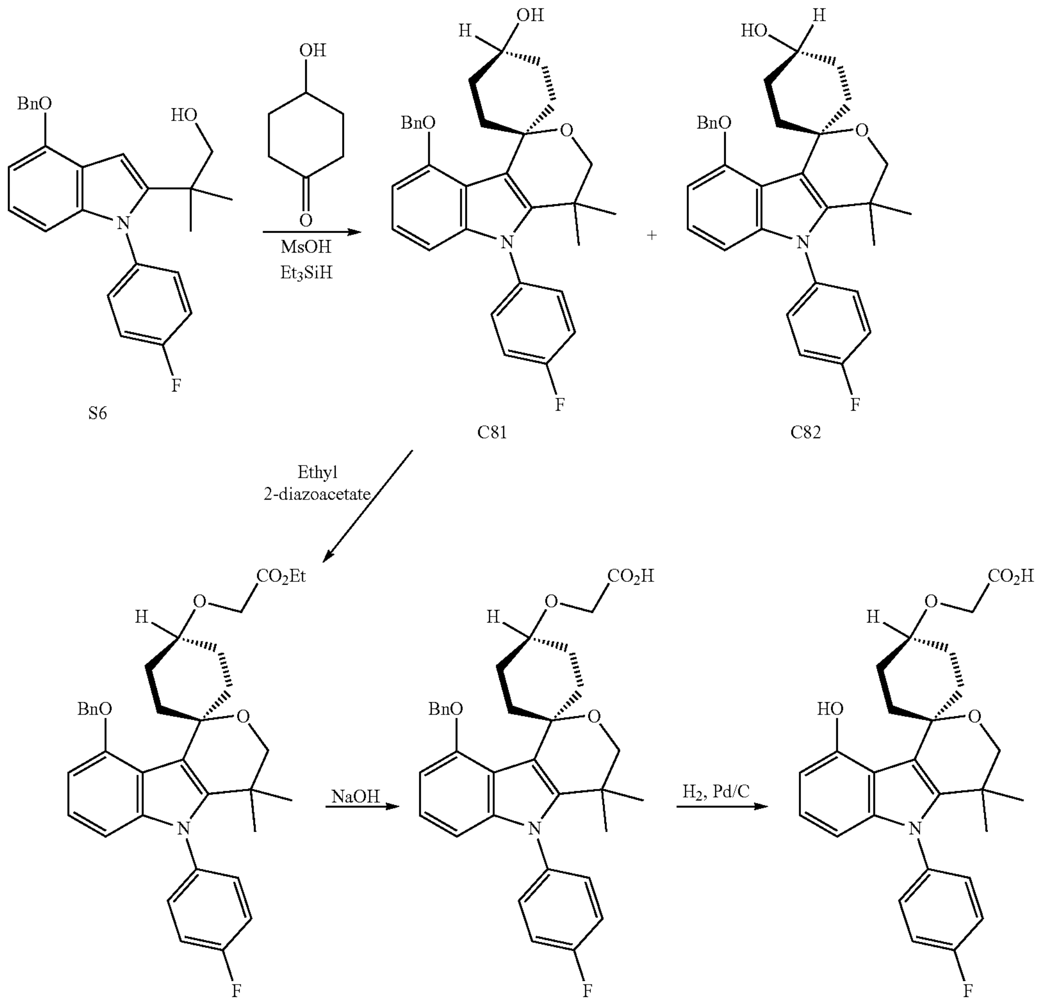

S6 C81 C82

C83 C84 84

Step 1. Synthesis of (1S,4S)-9'-(benzyloxy)-5'-(4-fluorophenyl)-4',4'-dimethyl-4',5'-dihydro-3'H-spiro[cyclohexane-1,1'-pyrano[4,3-b]indol]-4-ol (C81) and (1r,4r)-9'-(benzyloxy)-5'-(4-fluorophenyl)-4',4'-dimethyl-4',5'-dihydro-3'H-spiro[cyclohexane-1,1'-pyrano[4,3-b]indol]-4-ol (C82)

This reaction was carried out according to Standard Procedure A. dichloromethane was used as solvent giving cis product C81 (860 mg, 41%), LCMS m/z 485.43 $[M+H]^+$ and trans product C82 (920 mg, 47%), LCMS m/z 485.48 $[M+H]^+$.

Step 2. Synthesis of ethyl 2-(((1S,4S)-9'-(benzyloxy)-5'-(4-fluorophenyl)-4',4'-dimethyl-4',5'-dihydro-3'H-spiro[cyclohexane-1,1'-pyrano[4,3-b]indol]-4-yl)oxy)acetate (C83)

To a mixture of C81 (200 mg, 0.370 mmol) and diacetoxyrhodium (25 mg, 0.113 mmol) in dichloromethane (5 mL) was added ethyl 2-diazoacetate (13% w/v, 350 µL, 0.399 mmol) dropwise over 10 min and the reaction stirred for 2 hours. Purification by column chromatography (40 g gold column, eluting with 0-100% ethyl acetate in heptane) gave product C83 (140 mg, 59%). LCMS m/z 572.38 $[M+H]^+$.

Step 3. Synthesis of 2-(((1S,4S)-9'-(benzyloxy)-5'-(4-fluorophenyl)-4',4'-dimethyl-4',5'-dihydro-3'H-spiro[cyclohexane-1,1'-pyrano[4,3-b]indol]-4-yl)oxy)acetic acid (C84)

NaOH (2 M, 1 mL, 2 mmol) was added to a solution of C83 (140 mg, 0.217 mmol) in MeOH (3 mL) and THE (2 mL). The reaction was stirred for 1 hour at room temperature. DMSO (2 mL) and TFA (250 µL, 3.25 mmol) were added and the mixture partially concentrated. Purification by reverse phase chromatography (50 g, C18 column, eluting with 10-100% ACN in water with 0.1% TFA) gave product C84 (105 mg, 81%). LCMS m/z 543.36 $[M+H]^+$.

Step 4. Synthesis of 2-(((1S,4S)-5'-(4-fluorophenyl)-9'-hydroxy-4',4'-dimethyl-4',5'-dihydro-3'H-spiro[cyclohexane-1,1'-pyrano[4,3-b]indol]-4-yl)oxy)acetic acid (84)

This reaction was carried out from C84 according to Standard Procedure B with the following modifications: EtOH and THF were used as solvents and hydrogen was used in place of ammonium formate giving product 84 (39 mg, 48%). $^1$H NMR (400 MHz, Methanol-d4) δ 7.39-7.30 (m, 2H), 7.26 (t, J=8.6 Hz, 2H), 6.79 (t, J=7.9 Hz, 1H), 6.39 (d, J=7.6 Hz, 1H), 6.14 (d, J=8.1 Hz, 1H), 4.16 (s, 2H), 3.62 (tt, J=11.4, 4.0 Hz, 1H), 3.48 (s, 2H), 2.80 (td, J=14.2, 13.7, 4.3 Hz, 2H), 1.96-1.84 (m, 4H), 1.79 (dd, J=11.8, 3.8 Hz, 1H), 1.74 (s, 1H), 1.04 (s, 6H). LCMS m/z 454.22 $[M+H]^+$.

Compound 85

4-(5'-(4-fluorophenyl)-9'-hydroxy-4',4'-dimethyl-4',5'-dihydro-3'H-spiro[cyclobutane1,1'pyrano[4,3-b]indol]-3-yl)benzoic acid (85)

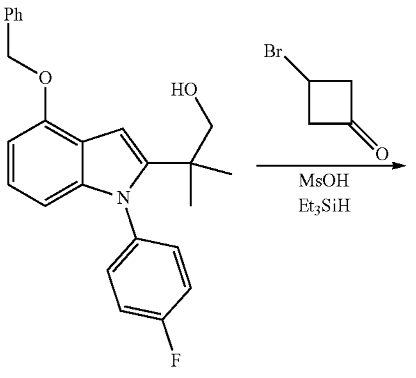

S6

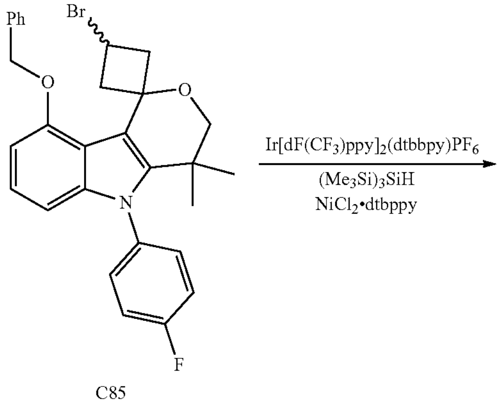

C85

-continued

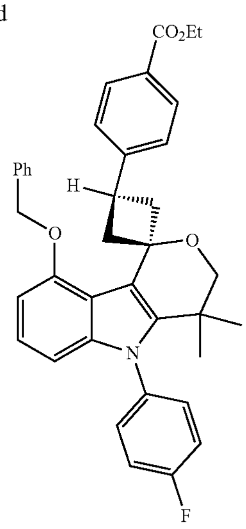

C86

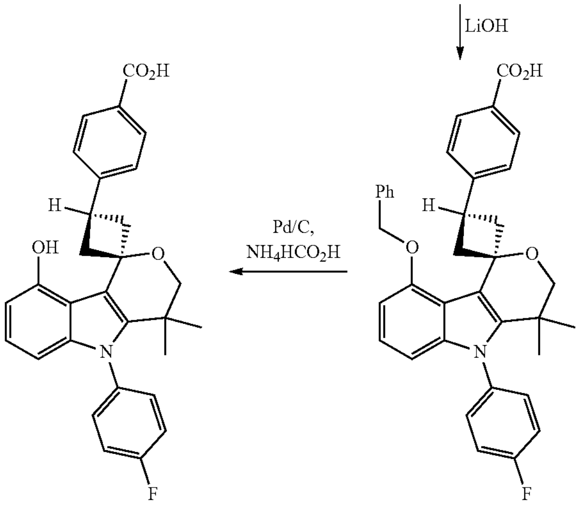

85

C87

Step 1: Synthesis of 9-benzyloxy-3'-bromo-5-(4-fluorophenyl)-4,4-dimethyl-spiro[3H-pyrano[4,3-b]indole-1,1'-cyclobutane] C85

To a mixture of 2-[4-benzyloxy-1-(4-fluorophenyl)indol-2-yl]-2-methyl-propan-1-ol S6 (100.0 mg, 0.257 mmol) and 3-bromocyclobutanone (80.0 mg, 0.537 mmol) in dichloromethane (1.5 mL) was added methanesulfonic acid (35 μL, 0.54 mmol) then triethylsilane (89 μL, 0.557 mmol) and the resulting dark solution stirred at room temperature for 16 h. It was quenched with sat. aq. $NaHCO_3$ and extracted with dichloromethane, filtered through a phase separator and concentrated to afford product C85 as a mixture of isomers (60.0 mg, 41%). LCMS m/z 519.94 $[M+H]^+$.

Step 2: Synthesis of ethyl 4-(9'-(benzyloxy)-5'-(4-fluorophenyl)-4',4'-dimethyl-4',5'-dihydro-3'H-spiro[cyclobutane-1,1'-pyrano[4,3-b]indol]-3-yl)benzoate (C86)

A vial was charged with photocatalyst $Ir[dF(CF_3)ppy]_2(dtbbpy)PF_6$ (4.0 mg, 0.00357 mmol), 9-benzyloxy-3'-bromo-5-(4-fluorophenyl)-4,4-dimethyl-spiro[3H-pyrano[4,3-b]indole-1,1'-cyclobutane] (175 mg, 0.336 mmol) ethyl 4-bromobenzoate (80 mg, 0.349 mmol), bis(trimethylsilyl)

silyl-trimethyl-silane (112 μL, 0.363 mmol) and toluene (960 μL) and 1,4-dioxane (4 mL). To the above mixture was added 2,6-Lutidine (195 mg, 1.82 mmol) and 100 ul of $NiCl_2$·dtbppy (prepared using dichloronickel; 1,2-dimethoxyethane (0.4 mg, 1.820 μmol) and 4-tert-butyl-2-(4-tert-butyl-2-pyridyl)pyridine (0.5 mg, 1.86 mmol). The mixture was sparged with nitrogen for 10 min and irradiated in a photo reactor for 16 h. The reaction was quenched with water and extracted with dichloromethane (3×20 mL). The organic layer was dried, concentrated and purified using column chromatography to give product C86 (63.7 mg, 31%). $^1$H NMR (400 MHz, Chloroform-d) δ 7.77-7.69 (m, 2H), 7.43-7.33 (m, 2H), 7.31-7.20 (m, 3H), 7.20-7.14 (m, 2H), 7.11 (d, J=8.3 Hz, 2H), 7.07-6.97 (m, 2H), 6.83 (t, J=8.0 Hz, 1H), 6.53 (dd, J=7.9, 0.8 Hz, 1H), 6.23 (dd, J=8.3, 0.7 Hz, 1H), 5.11 (s, 2H), 4.17 (q, J=7.1 Hz, 2H), 3.28 (s, 2H), 3.24-3.10 (m, 2H), 2.64 (tt, J=9.7, 4.5 Hz, 1H), 2.31-2.01 (m, 2H), 1.20 (t, J=7.1 Hz, 3H), 0.88 (s, 6H).

Step 3: Synthesis of 4-[9-benzyloxy-5-(4-fluorophenyl)-4,4-dimethyl-spiro[3H-pyrano[4,3-b]indole-1,3'-cyclobutane]-1'-yl]benzoic acid (C87)

To a solution of C86 (70 mg, 0.118 mmol) in MeOH (0.7 mL), THE (0.3 mL) and water (200 μL) was added LiOH·monohydrate (50 mg, 1.19 mmol) and the mixture was stirred at 25° C. for 16 h. The mixture was concentrated in vacuo, neutralized with HCl (0.6 mL of 2 M, 1.19 mmol) and back extracted with dichloromethane (3×10 ml). The organic layer was dried ($Na_2SO_4$) and concentrated to afford 4-[9-benzyloxy-5-(4-fluorophenyl)-4,4-dimethyl-spiro[3H-pyrano[4,3-b]indole-1,3'-cyclobutane]-1'-yl]benzoic acid C87 (50.0 mg, 72%). LCMS m/z 561.82 [M+H]$^+$.

Step 4: Synthesis of 4-[9-benzyloxy-5-(4-fluorophenyl)-4,4-dimethyl-spiro[3H-pyrano[4,3-b]indole-1,3'-cyclobutane]-1'-yl]benzoic acid (85)

To a solution 4-[9-benzyloxy-5-(4-fluorophenyl)-4,4-dimethyl-spiro[3H-pyrano[4,3-b]indole-1,3'-cyclobutane]-1'-yl]benzoic acid C87 in EtOH (1 mL) and THE (0.3 mL) was added 10% Pd/C (20 mg, Degussa wet) and $NH_4CO_2H$ (50.0 mg, 0.79 mmol). The mixture was heated at 50° C. for 1 h. The reaction mixture was filtered, concentrated and purified using 15.5 g HP C18 column (formic acid modifier) to afford ethyl-4-(9'-(benzyloxy)-5'-(4-fluorophenyl)-4',4'-dimethyl-4',5'-dihydro-3'H-spiro[cyclobutane-1,1'-pyrano[4,3-b]indol]-3-yl)benzoate 85 (30 mg, 70%). $^1$H NMR (400 MHz, Methanol-d4) δ 8.01 (d, J=8.0 Hz, 2H), 7.64 (d, J=8.1 Hz, 2H), 7.37 (dd, J=8.7, 5.0 Hz, 2H), 7.22 (t, J=8.4 Hz, 2H), 6.92 (t, J=7.9 Hz, 1H), 6.56 (d, J=7.6 Hz, 1H), 6.29 (d, J=8.2 Hz, 1H), 3.92 (dt, J=10.1, 5.2 Hz, 1H), 3.64-3.50 (m, 4H), 2.72-2.46 (m, 2H), 1.08 (s, 6H). LCMS m/z 472.07 [M+H]$^+$ Compound 86

2-(5'-(4-fluorophenyl)-9'-hydroxy-4',4'-dimethyl-4',5'-dihydro-3'H-spiro[piperidine-4,1'-pyrano[4,3-b]indol]-1-yl)oxazole-4-carboxylic acid (86)

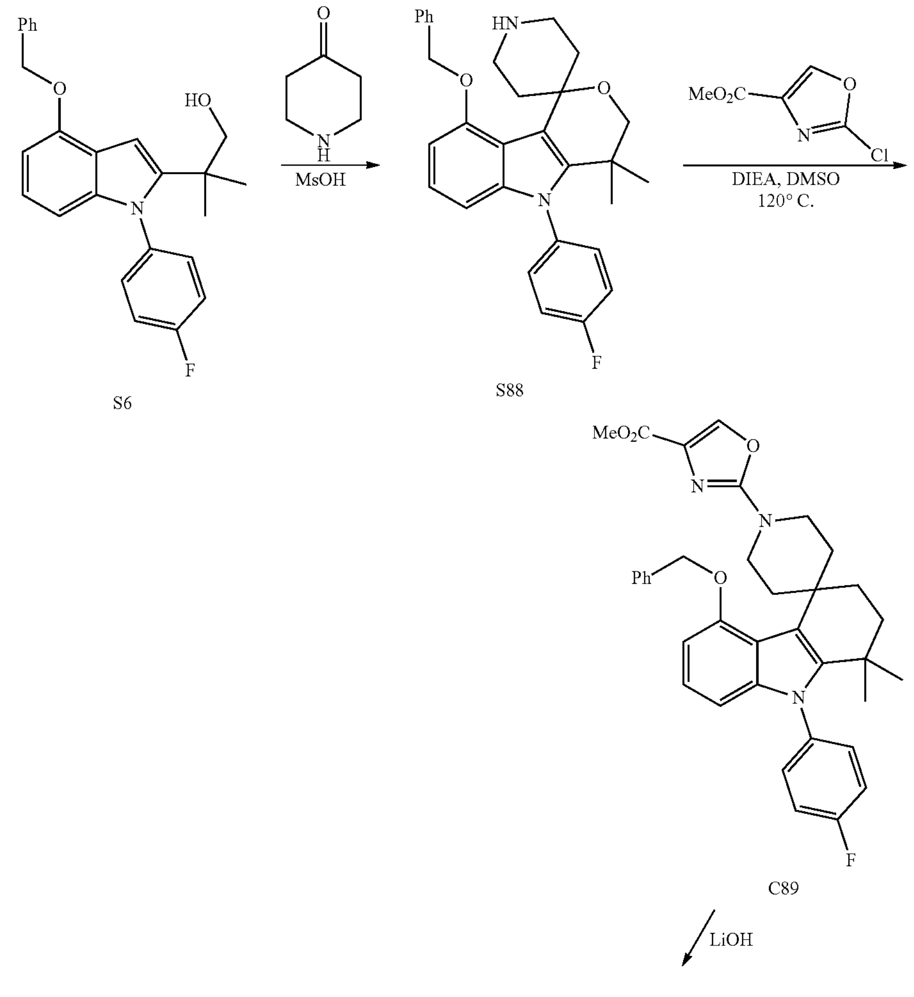

S6

S88

C89

-continued

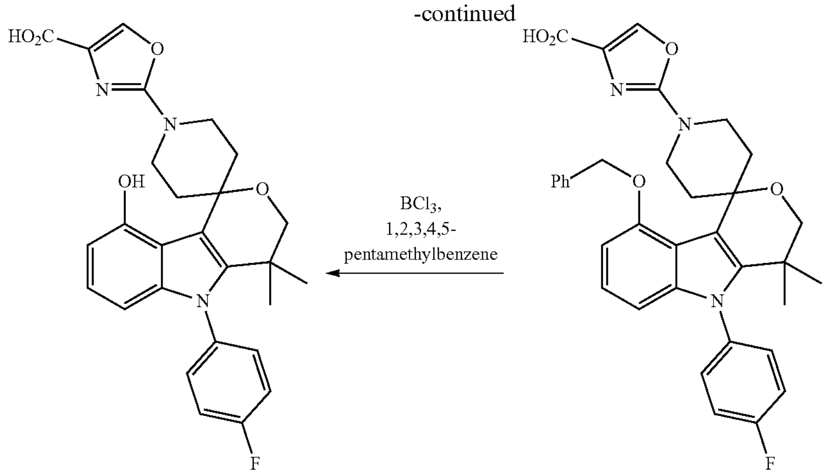

86 C90

Step 1: Synthesis of 9'-(benzyloxy)-5'-(4-fluorophenyl)-4',4'-dimethyl-4',5'-dihydro-3'H-spiro[piperidine-4,1'-pyrano[4,3-b]indole] (C88)

To a mixture of 2-[4-benzyloxy-1-(4-fluorophenyl)indol-2-yl]-2-methyl-propan-1-ol S6 (600.0 mg, 1.541 mmol) and piperidin-4-one hydrochloride (272 mg, 2.02 mmol) in dichloromethane (9 mL) was added methanesulfonic acid (210 μL, 3.24 mmol) and the resulting dark solution stirred at room temperature for 16 hours. The reaction was quenched with sat. aq. $NaHCO_3$ and extracted with dichloromethane (3×30 ml), filtered through a phase separator and concentrated to afford product C88 (740 mg, 91%). LCMS m/z 471.21 $[M+H]^+$.

Step 2: Synthesis 2-[9-benzyloxy-5-(4-fluorophenyl)-4,4-dimethyl-spiro[3H-pyrano[4,3-b]indole-1,4'-piperidine]-1'-yl]oxazole-4-carboxylate (C89)

To a solution of 9-benzyloxy-5-(4-fluorophenyl)-4,4-dimethyl-spiro[3H-pyrano[4,3-b]indole-1,4'-piperidine C88 (240 mg, 0.510 mmol) in DMSO (4 mL) was added methyl 2-chlorooxazole-4-carboxylate (105 mg, 0.650 mmol) and N-ethyl-N-isopropyl-propan-2-amine (140 μL, 0.804 mmol). The mixture was microwaved at 120° C. for 30 min then diluted with dichloromethane (20 mL). It was washed with brine and the layers separated through a phase separator and the organics concentrated to afford crude product C89 (300 mg, 83%) as a dark solid. LCMS m/z 596.11 $[M+H]^+$.

Step 3: Synthesis of 2-[9-benzyloxy-5-(4-fluorophenyl)-4,4-dimethyl-spiro[3H-pyrano[4,3-b]indole-1,4'-piperidine]-1'-yl]oxazole-4-carboxylic acid (C90)

To a solution of methyl 2-[9-benzyloxy-5-(4-fluorophenyl)-4,4-dimethyl-spiro[3H-pyrano[4,3-b]indole-1,4'-piperidine]-1'-yl]oxazole-4-carboxylate C89 (270.0 mg, 0.382 mmol) in MeOH (2 mL), THE (3 mL) and water (600 μL) was added lithium hydroxide hydrate (163 mg, 3.84 mmol) and the mixture was heated at 100° C. for 3 h in a microwave. The mixture was evaporated, neutralized with HCl (1.9 mL of 2 M, 3.8 mmol) and back extracted with dichloromethane (3×20 ml). dichloromethane layer was dried and concentrated to afford 2-[9-benzyloxy-5-(4-fluorophenyl)-4,4-dimethyl-spiro[3H-pyrano[4,3-b]indole-1,4'-piperidine]-1'-yl]oxazole-4-carboxylic acid C90 (30 mg, 13%). LCMS m/z 582.07 $[M+H]^+$ Step 4: Synthesis of 2-(5'-(4-fluorophenyl)-9'-hydroxy-4',4'-dimethyl-4',5'-dihydro-3'H-spiro[piperidine-4,1'-pyrano[4,3-b]indol]-1-yl)oxazole-4-carboxylic acid (86)

To a solution 2-[9-benzyloxy-5-(4-fluorophenyl)-4,4-dimethyl-spiro[3H-pyrano[4,3-b]indole-1,4'-piperidine]-1'-yl] oxazole-4-carboxylic acid C90 (30 mg, 0.0516 mmol) in dichloromethane (6 mL) at 0° C. was added 1,2,3,4,5-pentamethylbenzene (152 mg, 1.03 mmol) and trichloroborane (1.5 mL of 1 M, 1.5 mmol), the mixture was stirred at 0° C. for 10 min. The reaction was quenched with saturated $NaHCO_3$, diluted with dichloromethane and the layers separated through a phase separator. The organic layer was concentrated and purification by reverse phase chromatography (acetonitrile, formic acid modifier) afforded product 86 (6.1 mg, 23%). $^1H$ NMR (400 MHz, Methanol-$d_4$) δ 7.82 (s, 1H), 7.42-7.29 (m, 2H), 7.29-7.14 (m, 2H), 6.86 (t, J=7.9 Hz, 1H), 6.53-6.31 (m, 1H), 6.26 (dd, J=8.2, 0.8 Hz, 1H), 4.00 (dd, J=13.1, 4.7 Hz, 2H), 3.61-3.42 (m, 4H), 3.06 (td, J=13.5, 4.9 Hz, 2H), 1.87 (d, J=13.7 Hz, 2H), 1.08 (s, 6H). LCMS m/z 492.09 [M+H]+

Compound 87

2-(5'-(4-fluorophenyl)-9'-hydroxy-4',4'-dimethyl-4',5'-dihydro-3'H-spiro[piperidine-4,1'-pyrano[4,3-b]indol]-1-yl)oxazole-5-carboxylic acid (87)

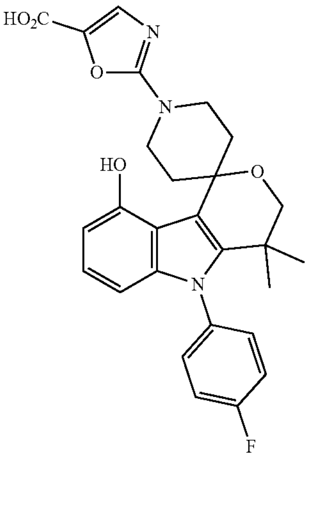 [SMILES: CC1(C)COC2(CCN(c3ncc(C(=O)O)o3)CC2)c2c1n(-c1ccc(F)cc1)c1cccc(O)c21]

Compound 87 was synthesized in an identical manner to 86, using ethyl 2-bromooxazole-5-carboxylate in Step 2. $^1$H NMR (400 MHz, DMSO-$d_6$) δ 9.69 (s, 1H), 7.56 (s, 1H), 7.55-7.36 (m, 4H), 6.88-6.68 (m, 1H), 6.40 (d, J=7.6 Hz, 1H), 6.11 (d, J=8.2 Hz, 1H), 4.10-3.78 (m, 2H), 2.88 (dt, J=13.9, 7.0 Hz, 2H), 2.56-2.47 (m, 4H), 1.81 (d, J=13.6 Hz, 2H), 1.01 (s, 6H). LCMS m/z 492.13 [M+H]$^+$ Compounds 88-177

Compounds 88-177 were prepared from S6 and the appropriate ketone or ketone equivalent.

TABLE 5

Preparation of Compounds 88-177

| Compound | Method/Product | Ketone | $^1$H NMR; LCMS m/z |
|---|---|---|---|
| 88 | From S6 according to Standard procedures A and B[a,b] 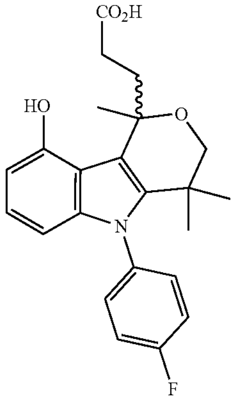 [SMILES: CC1(C)COC(C)(CCC(=O)O)c2c1n(-c1ccc(F)cc1)c1cccc(O)c21] | 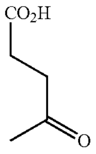 | $^1$H NMR (400 MHz, Chloroform-d) δ 7.47-7.30 (m, 2H), 7.26-7.15 (m, 2H), 6.92 (dd, J = 8.2, 7.6 Hz, 1H), 6.44 (dd, J = 7.6, 0.8 Hz, 1H), 6.37 (dd, J = 8.3, 0.8 Hz, 1H), 3.72 (d, J = 11.3 Hz, 1H), 3.50 (d, J = 11.3 Hz, 1H), 3.04-2.88 (m, 1H), 2.59-2.44 (m, 1H), 2.43-2.27 (m, 2H), 2.04 (s, 1H), 1.81 (s, 3H), 1.30 (s, 3H), 0.89 (s, 3H). LCMS m/z 398.6 [M + H]$^+$. |
| 89 | From S6 according to Standard procedures A and B[a,b,c] 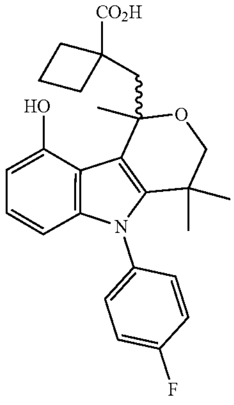 [SMILES: CC1(C)COC(C)(CC2(C(=O)O)CCC2)c2c1n(-c1ccc(F)cc1)c1cccc(O)c21] | 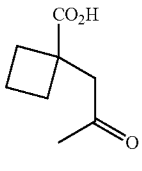 | $^1$H NMR (400 MHz, Methanol-d4) δ 7.44-7.31 (m, 2H), 7.32-7.24 (m, 2H), 6.89-6.80 (m, 1H), 6.46 (dd, J = 7.7, 0.8 Hz, 1H), 6.19 (dd, J = 8.2, 0.8 Hz, 1H), 3.56 (d, J = 11.3 Hz, 1H), 3.00 (d, J = 14.7 Hz, 1H), 2.83 (d, J = 14.7 Hz, 1H), 2.70-2.48 (m, 1H), 2.39-2.18 (m, 1H), 1.98-1.81 (m, 3H), 1.75 (s, 3H), 1.13 (s, 3H), 0.96 (s, 3H). LCMS m/z 438.6 [M + H]$^+$. |

TABLE 5-continued

| Preparation of Compounds 88-177 | | | |
|---|---|---|---|
| Compound | Method/Product | Ketone | $^1$H NMR; LCMS m/z |
| 90 | From S6 according to Standard procedures A and B[a,d,e] 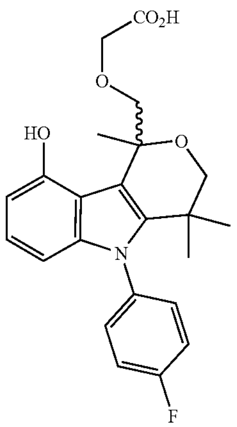 [SMILES: CC1(C)COC(C)(COCC(=O)O)c2c1n(-c1ccc(F)cc1)c1cccc(O)c21] | 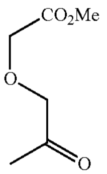 | $^1$H NMR (400 MHz, Chloroform-d) δ 7.34-7.23 (m, 2H), 7.20-7.11 (m, 3H), 6.85 (t, J = 7.9 Hz, 1H), 6.40 (dd, J = 7.7, 0.8 Hz, 1H), 6.29 (dd, J = 8.3, 0.8 Hz, 1H), 4.30 (d, J = 9.9 Hz, 1H), 4.20 (d, J = 17.2 Hz, 1H), 4.05 (d, J = 17.2 Hz, 1H), 3.96 (d, J = 9.9 Hz, 1H), 3.63 (d, J = 11.2 Hz, 1H), 3.50 (d, J = 11.2 Hz, 1H), 1.74 (s, 3H), 1.18 (d, J = 3.9 Hz, 6H). LCMS m/z 414.54 $[M + H]^+$. |
| 91 | From S6 according to Standard procedures A and B[a,f] 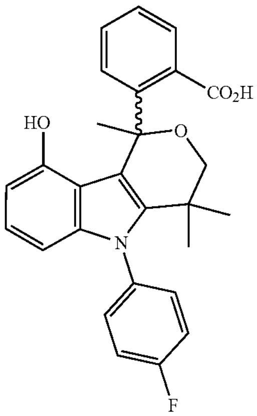 [SMILES: CC1(C)COC(C)(c2ccccc2C(=O)O)c2c1n(-c1ccc(F)cc1)c1cccc(O)c21] | 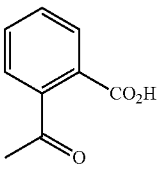 | $^1$H NMR (400 MHz, Methanol-d4) δ 7.58 (dd, J = 7.9, 1.3 Hz, 1H), 7.49-7.18 (m, 7H), 6.99-6.80 (m, 1H), 6.50 (dd, J = 7.7, 0.9 Hz, 1H), 6.18 (dd, J = 8.2, 0.9 Hz, 1H), 3.46-3.23 (m, 2H), 2.31 (s, 3H), 1.36 (s, 3H), 0.70 (s, 3H). LCMS m/z 446.27 $[M + H]^+$. |

TABLE 5-continued

Preparation of Compounds 88-177

| Compound | Method/Product | Ketone | $^1$H NMR; LCMS m/z |
|---|---|---|---|
| 92 | From S6 according to Standard procedures A and B[a,e] 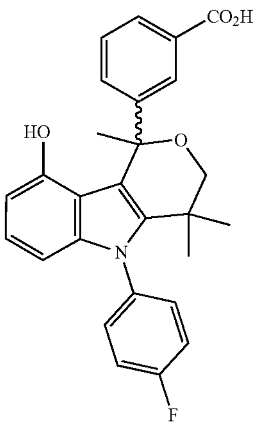 [SMILES: CC1(C)COC(C)(c2cccc(C(=O)O)c2)c2c1n(-c1ccc(F)cc1)c1cccc(O)c21] | 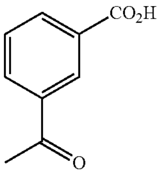 | $^1$H NMR (400 MHz, Methanol-d4) δ 8.23 (t, J = 1.8 Hz, 1H), 7.86 (dt, J = 7.7, 1.4 Hz, 1H), 7.62 (ddd, J = 7.8, 2.0, 1.2 Hz, 1H), 7.48 (tdd, J = 9.2, 4.6, 2.1 Hz, 2H), 7.37-7.23 (m, 3H), 6.84 (dd, J = 8.2, 7.7 Hz, 1H), 6.36 (dd, J = 7.7, 0.8 Hz, 1H), 6.21 (dd, J = 8.2, 0.8 Hz, 1H), 3.27 (s, 2H), 2.18 (s, 3H), 1.33 (s, 3H), 0.84 (s, 3H). LCMS m/z 446.32 [M + H]$^+$. |
| 93 | From S6 according to Standard procedures A and B[a,g] 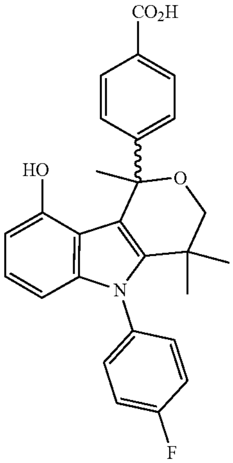 [SMILES: CC1(C)COC(C)(c2ccc(C(=O)O)cc2)c2c1n(-c1ccc(F)cc1)c1cccc(O)c21] | 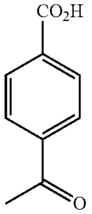 | $^1$H NMR (400 MHz, DMSO-d6) δ 7.89-7.73 (m, 2H), 7.55 (tdd, J = 6.1, 4.5, 2.6 Hz, 2H), 7.48 (d, J = 8.4 Hz, 2H), 7.42 (tdd, J = 8.6, 5.7, 2.5 Hz, 2H), 6.83 (t, J = 7.9 Hz, 1H), 6.37 (dd, J = 7.7, 0.9 Hz, 1H), 6.14 (dd, J = 8.2, 0.8 Hz, 1H), 3.17 (dd, J = 52.3, 11.1 Hz, 2H), 2.09 (s, 3H), 1.23 (s, 3H), 0.76 (s, 3H). LCMS m/z 446.32 [M + H]$^+$. |
| 94 | From S6 according to Standard procedures A and B[a,h] 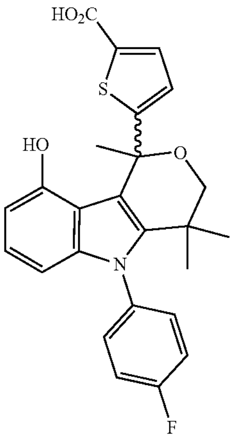 [SMILES: CC1(C)COC(C)(c2ccc(C(=O)O)s2)c2c1n(-c1ccc(F)cc1)c1cccc(O)c21] | 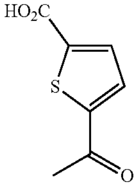 | $^1$H NMR (400 MHz, Chloroform-d) δ 7.64 (d, J = 3.9 Hz, 1H), 7.36-7.27 (m, 2H), 7.19-7.12 (m, 3H), 6.99 (d, J = 3.9 Hz, 1H), 6.90-6.83 (m, 1H), 6.32 (ddd, J = 15.4, 8.0, 0.8 Hz, 2H), 3.40 (dd, J = 68.6, 11.4 Hz, 2H), 2.19 (s, 3H), 1.23 (s, 3H), 0.82 (s, 3H). LCMS m/z 452.3 [M + H]$^+$. |

TABLE 5-continued
| Preparation of Compounds 88-177 | | | |
|---|---|---|---|
| Compound | Method/Product | Ketone | $^1$H NMR; LCMS m/z |
| 95 | From S6 according to Standard procedures A and B[a,f] 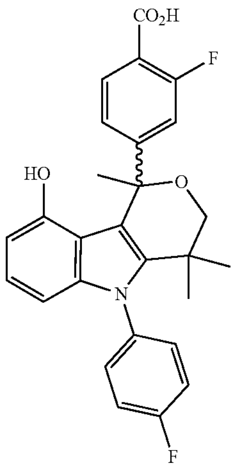 [SMILES: CC1(C)COC(C)(c2ccc(C(=O)O)c(F)c2)c2c1n(-c1ccc(F)cc1)c1cccc(O)c21] | 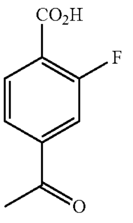 | $^1$H NMR (400 MHz, Chloroform-d) δ 8.44 (s, 1H), 7.67 (t, J = 7.8 Hz, 1H), 7.55-7.44 (m, 2H), 7.36-7.23 (m, 3H), 7.17 (dd, J = 12.4, 1.7 Hz, 1H), 6.87 (t, J = 7.9 Hz, 1H), 6.22 (dd, J = 8.3, 0.8 Hz, 1H), 3.31-3.22 (m, 2H), 2.14 (s, 3H), 1.34 (s, 3H), 0.82 (s, 3H). LCMS m/z 464.62 [M + H]$^+$. |
| 96 | Racemic 93 was separated by chiral SFC 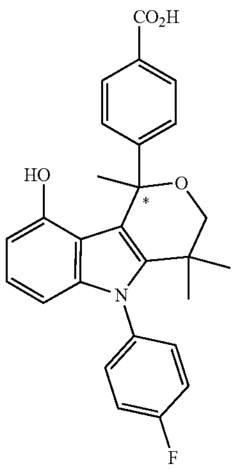 [SMILES: CC1(C)COC(C)(c2ccc(C(=O)O)cc2)c2c1n(-c1ccc(F)cc1)c1cccc(O)c21] | N/A | $^1$H NMR (400 MHz, Chloroform-d) δ 7.52 (s,1H), 7.36-7.30 (m, 3H), 7.24-7.08 (m, 3H), 6.85 (d, J = 28.2 Hz, 2H), 6.51-6.14 (m, 2H), 3.53 (d, J = 11.4 Hz, 1H), 3.31 (d, J = 11.3 Hz, 1H), 2.20 (s, 3H), 1.36-1.13 (m, 3H), 0.82 (s, 3H). LCMS m/z 446.42 [M + H]$^+$. |

TABLE 5-continued

Preparation of Compounds 88-177

| Compound | Method/Product | Ketone | $^{1}H$ NMR; LCMS m/z |
|---|---|---|---|
| 97 | Racemic 93 was separated by chiral SFC 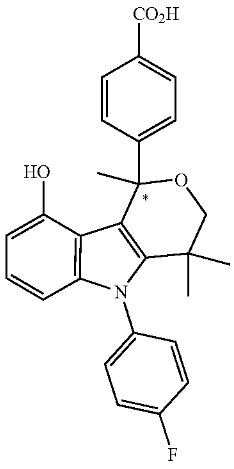 [SMILES: CC1(C)COC(C)(c2ccc(C(=O)O)cc2)c2c1n(-c1ccc(F)cc1)c1cccc(O)c21] | N/A | $^{1}H$ NMR (400 MHz, Chloroform-d) δ 7.52 (s, 1H), 7.35-7.30 (m, 3H), 7.24-7.10 (m, 3H), 6.79 (d, J = 17.4 Hz, 2H), 6.37 (s, 1H), 6.25 (d, J = 8.1 Hz, 1H), 3.52 (d, J = 11.3 Hz, 1H), 3.29 (d, J = 11.3 Hz, 1H), 2.18 (s, 3H), 1.28-1.18 (m, 3H), 0.80 (s, 3H). LCMS m/z 446.15 $[M + H]^{+}$. |
| 98 | From S6 according to Standard procedures A and B[a,i] 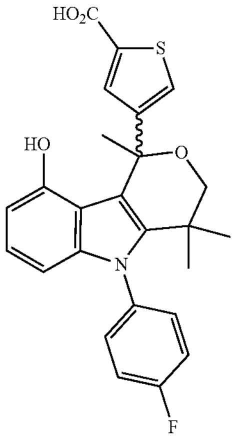 [SMILES: CC1(C)COC(C)(c2csc(C(=O)O)c2)c2c1n(-c1ccc(F)cc1)c1cccc(O)c21] | 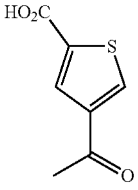 | $^{1}H$ NMR (400 MHz, DMSO-d6) δ 12.99 (s, 1H), 9.41 (s, 1H), 7.65 (d, J = 1.6 Hz, 1H), 7.59-7.38 (m, 5H), 6.82 (t, J = 7.9 Hz, 1H), 6.37 (dd, J = 7.7, 0.9 Hz, 1H), 6.14 (dd, J = 8.2, 0.8 Hz, 1H), 3.31-3.22 (m, 2H), 2.07 (d, J = 2.3 Hz, 3H), 1.22 (s, 3H), 0.79 (s, 3H). LCMS m/z 452.3 $[M + H]^{+}$. |

TABLE 5-continued

Preparation of Compounds 88-177

| Compound | Method/Product | Ketone | $^{1}$H NMR; LCMS m/z |
|---|---|---|---|
| 99 | From S6 according to Standard procedures A and $B^{a,f}$ 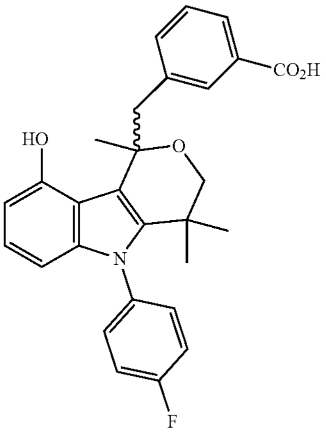 [SMILES: CC1(C)COC(C)(Cc2cccc(C(=O)O)c2)c2c1n(-c1ccc(F)cc1)c1cccc(O)c21] | 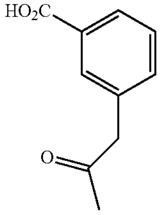 | $^{1}$H NMR (400 MHz, DMSO-d6) δ 12.74 (s, 1H), 9.91 (s, 1H), 7.72 (dt, J = 7.7, 1.5 Hz, 1H), 7.65 (d, J = 1.8 Hz, 1H), 7.50 (ddd, J = 8.6, 5.0, 2.6 Hz, 1H), 7.43-7.33 (m, 2H), 7.27 (t, J = 7.6 Hz, 1H), 7.22-7.15 (m, 2H), 6.85 (t, J = 7.9 Hz, 1H), 6.52 (dd, J = 7.8, 0.9 Hz, 1H), 6.13 (dd, J = 8.2, 0.8 Hz, 1H), 3.67 (d, J = 13.3 Hz, 1H), 3.49-3.36 (m, 3H), 1.63 (s, 3H), 0.84 (s, 3H), 0.62 (s, 3H). LCMS m/z 460.45 $[M + H]^+$. |
| 100 | From S6 according to Standard procedures A and $B^{a,c,f}$ 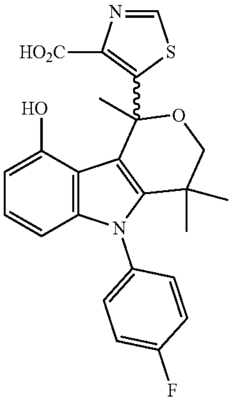 [SMILES: CC1(C)COC(C)(c2scnc2C(=O)O)c2c1n(-c1ccc(F)cc1)c1cccc(O)c21] | 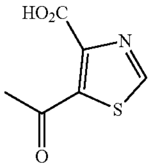 | $^{1}$H NMR (400 MHz, Methanol-d4) δ 8.73 (s, 1H), 7.54-7.39 (m, 2H), 7.38-7.22 (m, 2H), 6.87 (t, J = 8.0 Hz, 1H), 6.42 (dd, J = 7.7, 0.8 Hz, 1H), 6.20 (dd, J = 8.3, 0.8 Hz, 1H), 3.45 (dd, J = 63.3, 11.3 Hz, 2H), 2.41 (s, 3H), 1.35 (s, 3H), 0.80 (s, 3H). LCMS m/z 453.3 $[M + H]^+$. |
| 101 | From S6 according to Standard procedures A and $B^{a,c,j}$ 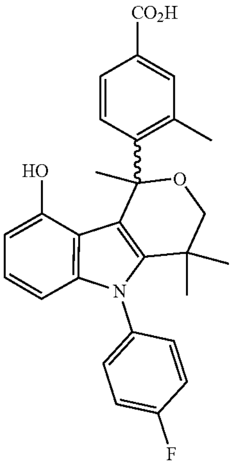 [SMILES: Cc1cc(C(=O)O)ccc1C1(C)OCC(C)(C)c2c1c1c(O)cccc1n2-c1ccc(F)cc1] | 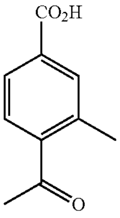 | $^{1}$H NMR (400 MHz, Methanol-d4) δ 8.10 (d, J = 1.8 Hz, 1H), 7.75 (dd, J = 7.9, 1.9 Hz, 1H), 7.56-7.42 (m, 2H), 7.37-7.18 (m, 3H), 6.85 (t, J = 7.9 Hz, 1H), 6.41 (dd, J = 7.7, 0.9 Hz, 1H), 6.18 (dd, J = 8.2, 0.8 Hz, 1H), 3.28 (s, 2H), 2.74 (s, 3H), 2.21 (s, 3H), 1.35 (s, 3H), 0.78 (s, 3H). LCMS m/z 460.0 $[M + H]^+$. |

TABLE 5-continued

| Preparation of Compounds 88-177 | | | |
|---|---|---|---|
| Compound | Method/Product | Ketone | $^1$H NMR; LCMS m/z |
| 102 | From S6 according to Standard procedures A and B[a,c,j] 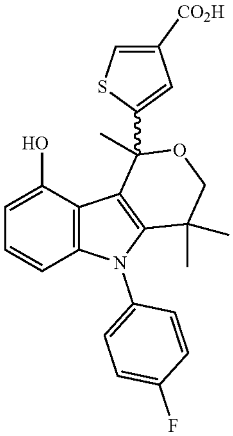 [SMILES: CC1(C)COC(C)(c2cc(C(=O)O)cs2)c2c1n(-c1ccc(F)cc1)c1cccc(O)c21] | 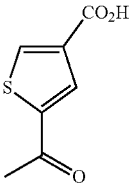 | $^1$H NMR (400 MHz, Methanol-d4) δ 8.07 (d, J = 1.4 Hz, 1H), 7.51-7.39 (m, 2H), 7.37-7.26 (m, 2H), 7.23 (d, J = 1.4 Hz, 1H), 6.84 (dd, J = 8.2, 7.7 Hz, 1H), 6.38 (dd, J = 7.7, 0.8 Hz, 1H), 6.20 (dd, J = 8.2, 0.8 Hz, 1H), 3.52 (d, J = 11.3 Hz, 1H), 3.32 (d, J = 4.6 Hz, 1H), 2.23 (s, 3H), 1.31 (s, 3H), 0.86 (s, 3H). LCMS m/z 452.38 $[M + H]^+$. |
| 103 | Racemic 102 was separated by chiral 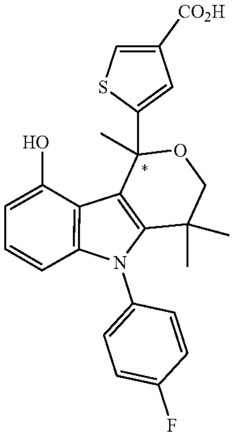 [SMILES: CC1(C)COC(C)(c2cc(C(=O)O)cs2)c2c1n(-c1ccc(F)cc1)c1cccc(O)c21] | N/A | $^1$H NMR (400 MHz, Chloroform-d) δ 7.84 (s, 1H), 7.40-7.23 (m, 3H), 7.20-7.03 (m, 2H), 6.72 (s, 1H), 6.40-6.06 (m, 2H), 3.44 (d, J = 11.3 Hz, 1H), 3.26 (d, J = 11.3 Hz, 1H), 2.11 (s, 3H), 1.19 (s, 3H), 0.85-0.48 (m, 3H). LCMS m/z 452.3 $[M + H]^+$. |
| 104 | Racemic 102 was separated by chiral SFC 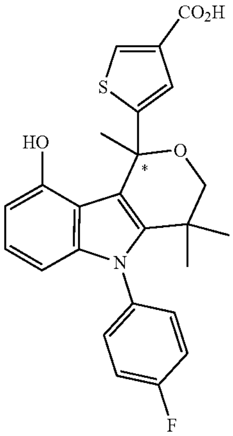 [SMILES: CC1(C)COC(C)(c2cc(C(=O)O)cs2)c2c1n(-c1ccc(F)cc1)c1cccc(O)c21] | N/A | $^1$H NMR (400 MHz, Chloroform-d) δ 7.78 (s, 1H), 7.19 (s, 3H), 7.17-7.06 (m, 2H), 6.69 (s, 1H), 6.39-6.14 (m, 2H), 3.43 (d, J = 11.2 Hz, 1H), 3.25 (d, J = 11.3 Hz, 1H), 2.10 (s, 3H), 1.19 (s, 3H), 0.86-0.66 (m, 3H). LCMS m/z 452.3 $[M + H]^+$. |

TABLE 5-continued

| Preparation of Compounds 88-177 | | | |
|---|---|---|---|
| Compound | Method/Product | Ketone | $^1H$ NMR; LCMS m/z |
| 105 | From S6 according to Standard procedures A and B[a,f] 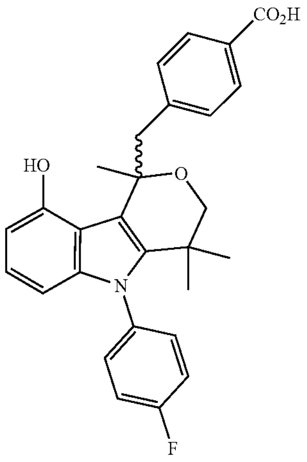 [SMILES: CC1(C)COC(C)(Cc2ccc(C(=O)O)cc2)c2c1n(-c1ccc(F)cc1)c1cccc(O)c21] | 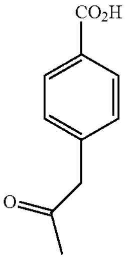 | $^1H$ NMR (400 MHz, DMSO-d6) δ 9.92 (s, 1H), 7.78-7.61 (m, 2H), 7.51-7.43 (m, 1H), 7.39 (tt, J = 8.9, 3.2 Hz, 2H), 7.24-7.16 (m, 1H), 7.11 (d, J = 8.2 Hz, 2H), 6.85 (t, J = 7.9 Hz, 1H), 6.52 (d, J = 7.6 Hz, 1H), 6.14 (d, J = 8.1 Hz, 1H), 3.67 (d, J = 13.1 Hz, 1H), 3.53-3.37 (m, 3H), 1.62 (s, 3H), 0.84 (s, 3H), 0.66 (s, 3H). LCMS m/z 460.36 [M + H]$^+$. |
| 106 | From S6 according to Standard procedures A and B[a,f] 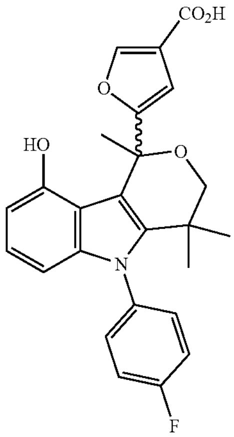 [SMILES: CC1(C)COC(C)(c2cc(C(=O)O)co2)c2c1n(-c1ccc(F)cc1)c1cccc(O)c21] | 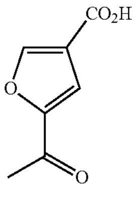 | $^1H$ NMR (400 MHz, Methanol-d4) δ 8.06 (d, J = 0.9 Hz, 1H), 7.52-7.37 (m, 2H), 7.35-7.25 (m, 2H), 6.83 (t, J = 8.0 Hz, 1H), 6.35 (d, J = 7.6 Hz, 1H), 6.27-6.17 (m, 2H), 3.50 (d, J = 11.2 Hz, 1H), 3.31 (d, J = 25.3 Hz, 1H), 2.16 (s, 3H), 1.33 (s, 3H), 0.85 (s, 3H). LCMS m/z 436.28 [M + H]$^+$. |

TABLE 5-continued

| Preparation of Compounds 88-177 | | | |
|---|---|---|---|
| Compound | Method/Product | Ketone | $^1$H NMR; LCMS m/z |
| 107 | From S6 according to Standard procedures A and B[a,d,f] 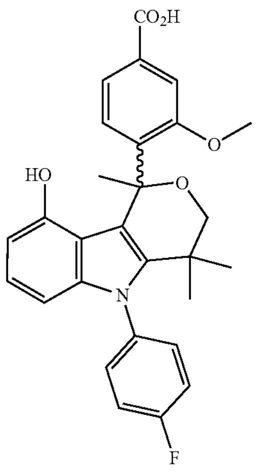 [SMILES: COc1cc(C(=O)O)ccc1C1(C)OCC(C)(C)c2c1c1c(O)cccc1n2-c1ccc(F)cc1] | 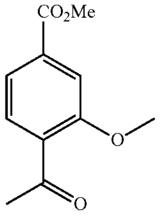 | $^1$H NMR (400 MHz, Chloroform-d) δ 8.03 (s, 1H), 7.70 (d, J = 1.6 Hz, 1H), 7.52 (dd, J = 8.0, 1.7 Hz, 1H), 7.46-7.40 (m, 2H), 7.36 (d, J = 8.0 Hz, 1H), 7.23 (ddt, J = 7.6, 2.9, 1.7 Hz, 1H), 6.96 (dd, J = 8.2, 7.6 Hz, 1H), 6.42 (ddd, J = 18.4, 8.0, 0.8 Hz, 2H), 4.01 (s, 3H), 3.39-3.20 (m, 2H), 2.35 (s, 3H), 1.36 (s, 3H), 0.79 (s, 3H). LCMS m/z 476.34 [M + H]$^+$. |
| 108 | From S6 according to Standard procedures A and B[a,d,f] 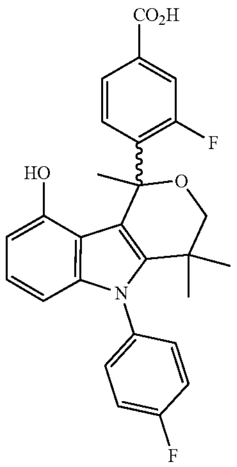 [SMILES: CC1(C)COC(C)(c2ccc(C(=O)O)cc2F)c2c1n(-c1ccc(F)cc1)c1cccc(O)c21] | 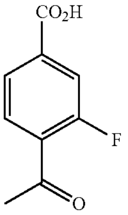 | $^1$H NMR (300 MHz, DMSO-d6) δ 13.13 (s, 1H), 9.34 (s, 1H), 7.67-7.47 (m, 4H), 7.47-7.37 (m, 2H), 7.26 (t, J = 8.2 Hz, 1H), 6.84 (t, J = 7.9 Hz, 1H), 6.37 (dd, J = 7.7, 0.8 Hz, 1H), 6.16 (dd, J = 8.1, 0.8 Hz, 1H), 3.31 (d, J = 10.8 Hz, 1H), 3.13 (d, J = 11.3 Hz, 1H), 2.20 (d, J = 1.7 Hz, 3H), 1.24 (s, 3H), 0.77 (s, 3H). LCMS m/z 464.19 [M + H]$^+$. |

TABLE 5-continued

Preparation of Compounds 88-177

| Compound | Method/Product | Ketone | $^1$H NMR; LCMS m/z |
|---|---|---|---|
| 109 | Racemic 108 was separated by chiral SFC 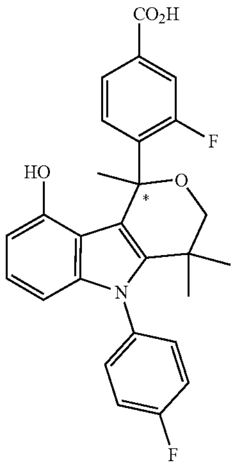 [SMILES: CC1(C)COC(C)(c2ccc(C(=O)O)cc2F)c2c1n(-c1ccc(F)cc1)c1cccc(O)c21] | N/A | $^1$H NMR (400 MHz, Chloroform-d) δ 7.72 (dd, J = 12.1, 1.6 Hz, 1H), 7.61 (dd, J = 8.0, 1.7 Hz, 1H), 7.43-7.27 (m, 3H), 7.23-7.13 (m, 2H), 6.88 (t, J = 7.9 Hz, 1H), 6.34 (dd, J = 7.9, 2.3 Hz, 2H), 3.40-3.14 (m, 2H), 2.24 (d, J = 1.6 Hz, 3H), 1.27 (s, 3H), 0.74 (s, 3H). LCMS m/z 464.37 $[M + H]^+$. |
| 110 | Racemic 108 was separated by chiral SFC 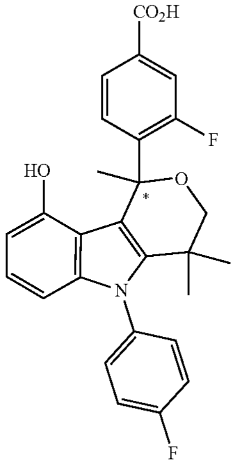 [SMILES: CC1(C)COC(C)(c2ccc(C(=O)O)cc2F)c2c1n(-c1ccc(F)cc1)c1cccc(O)c21] | N/A | $^1$H NMR (400 MHz, Chloroform-d) δ 7.72 (dd, J = 12.0, 1.6 Hz, 1H), 7.60 (dd, J = 8.0, 1.6 Hz, 1H), 7.41-7.26 (m, 3H), 7.19-7.10 (m, 2H), 6.88 (t, J = 7.9 Hz, 1H), 6.47-6.10 (m, 2H), 3.41-3.07 (m, 2H), 2.24 (d, J = 1.5 Hz, 3H), 1.27 (s, 3H), 0.74 (s, 3H). LCMS m/z 464.41 $[M + H]^+$. |
| 111 | From S6 according to Standard procedures A and B[a,J] 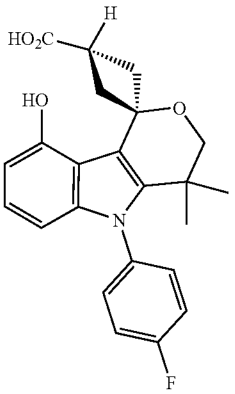 [SMILES: CC1(C)CO[C@]2(C[C@H](C(=O)O)C2)c2c1n(-c1ccc(F)cc1)c1cccc(O)c12] | 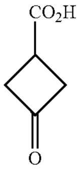 | $^1$H NMR (400 MHz, DMSO-d6) δ 11.85 (s, 1H), 9.80 (s, 1H), 7.47 (ddt, J = 8.2, 5.5, 2.7 Hz, 2H), 7.44-7.36 (m, 2H), 6.79 (t, J = 7.9 Hz, 1H), 6.48 (dd, J = 7.7, 0.9 Hz, 1H), 6.08 (dd, J = 8.1, 0.8 Hz, 1H), 3.40 (s, 2H), 3.27-3.21 (m, 3H), 2.36 (dd, J = 6.8, 3.5 Hz, 2H), 0.98 (s, 6H). LCMS m/z 396.26 $[M + H]^+$. |

TABLE 5-continued

| Preparation of Compounds 88-177 | | | |
|---|---|---|---|
| Compound | Method/Product | Ketone | $^{1}$H NMR; LCMS m/z |
| 112 | From S6 according to Standard procedures A and B[a,l] 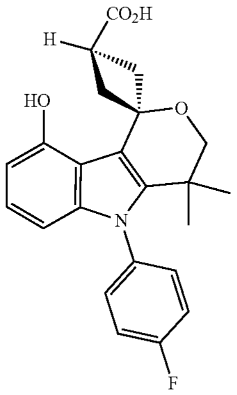 [SMILES: CC1(C)CO[C@]2(C[C@@H](C(=O)O)C2)c2c1n(-c1ccc(F)cc1)c1cccc(O)c12] | 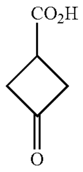 | $^{1}$H NMR (400 MHz, DMSO-d6) δ 11.85 (br s, 1H), 9.80 (s, 1H), 7.47 (ddd, J = 9.0, 5.1, 2.0 Hz, 2H), 7.40 (t, J = 8.7 Hz, 2H), 6.80 (dt, J = 11.1, 7.9 Hz, 1H), 6.48 (dt, J = 7.7, 1.0 Hz, 1H), 6.09 (ddd, J = 10.4, 8.2, 0.8 Hz, 1H), 3.31 (s, 2H), 3.38-3.04 (m, 5H), 0.98 (s, 3H), 0.97 (s, 3H). LCMS m/z 396.26 [M + H]$^{+}$. |
| 113 | From S6 according to Standard procedures A and B[a,c,m] 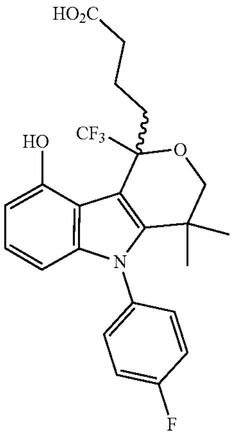 [SMILES: CC1(C)COC(CCCC(=O)O)(C(F)(F)F)c2c1n(-c1ccc(F)cc1)c1cccc(O)c21] | 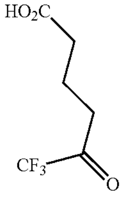 | $^{1}$H NMR (400 MHz, Chloroform-d) δ 7.40 (ddd, J = 10.8, 8.9, 4.9 Hz, 1H), 7.29 (s, 7H), 6.94 (ddd, J = 8.3, 7.6, 0.8 Hz, 1H), 6.58 (dd, J = 1.7, 0.8 Hz, 1H), 6.53 (ddd, J = 7.6, 1.5, 0.7 Hz, 1H), 6.32-6.23 (m, 1H), 4.09 (d, J = 19.6 Hz, 2H), 3.23 (d, J = 7.3 Hz, 1H), 2.74 (t, J = 7.1 Hz, 1H), 2.48-2.30 (m, 2H), 1.95 (t, J = 7.1 Hz, 1H), 1.40 (t, J = 7.3 Hz, 1H), 1.29 (d, J = 2.8 Hz, 6H). LCMS m/z 466.6 [M + H]$^{+}$. |
| 114 | From S6 according to Standard procedures A and B[a,c,n] 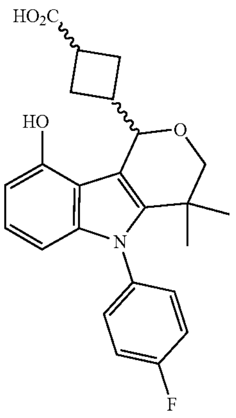 [SMILES: CC1(C)COC(C2CC(C(=O)O)C2)c2c1n(-c1ccc(F)cc1)c1cccc(O)c21] | 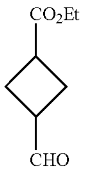 [SMILES: CCOC(=O)C1CC(C=O)C1] | $^{1}$H NMR (400 MHz, Methanol-d4) δ 7.34-7.23 (m, 2H), 7.19 (dddd, J = 10.0, 8.6, 2.6, 1.7 Hz, 2H), 6.76-6.61 (m, 1H), 6.29 (dd, J = 7.7, 0.8 Hz, 1H), 6.11 (dd, J = 8.2, 0.8 Hz, 1H), 4.89 (d, J = 3.2 Hz, 1H), 3.72-3.56 (m, 1H), 3.50 (d, J = 10.7 Hz, 1H), 3.34 (d, J = 10.8 Hz, 1H), 2.78 (tt, J = 9.7, 8.5 Hz, 1H), 2.51 (dt, J = 20.1, 9.8 Hz, 1H), 2.29-2.00 (m, 2H), 1.68 (qd, J = 8.3, 4.1 Hz, 1H), 1.28 (s, 3H), 0.71 (s, 3H). LCMS m/z 410.6 [M + H]$^{+}$. |

TABLE 5-continued

Preparation of Compounds 88-177

| Compound | Method/Product | Ketone | $^1$H NMR; LCMS m/z |
| --- | --- | --- | --- |
| 115 | From S6 according to Standard procedures A and B[a,c,n] 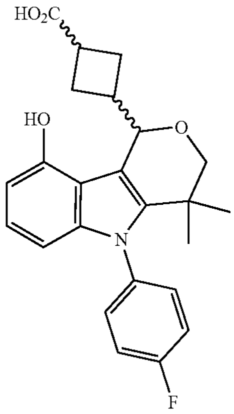 [SMILES: CC1(C)COC(C2CC(C(=O)O)C2)c2c1n(-c1ccc(F)cc1)c1cccc(O)c21] | 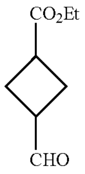 [SMILES: CCOC(=O)C1CC(C=O)C1] | $^1$H NMR (400 MHz, Methanol-d4) δ 7.30 (ddd, J = 9.0, 6.4, 5.0 Hz, 1H), 7.24-7.14 (m, 2H), 6.76-6.64 (m, 1H), 6.28 (dd, J = 7.7, 0.8 Hz, 1H), 6.11 (dd, J = 8.2, 0.8 Hz, 1H), 5.00 (d, J = 3.1 Hz, 1H), 3.76 (dd, J = 3.1, 1.2 Hz, 0H), 3.52 (d, J = 10.7 Hz, 1H), 3.37 (d, J = 10.7 Hz, 1H), 3.07-2.90 (m, 1H), 2.55-2.42 (m, 1H), 2.20 (ddd, J = 33.0, 17.0, 10.1 Hz, 2H), 1.85 (d, J = 7.1 Hz, 1H), 1.33 (s, 3H), 0.71 (s, 3H). LCMS m/z 410.6 $[M + H]^+$. |
| 116 | From S6 according to Standard procedures A and B[a,o] 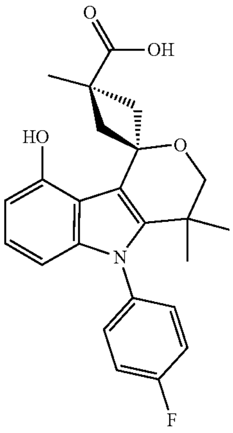 [SMILES: CC1(C)CO[C@]2(C[C@@](C)(C(=O)O)C2)c2c1n(-c1ccc(F)cc1)c1cccc(O)c12] | 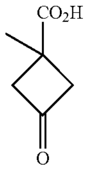 | $^1$H NMR (300 MHz, DMSO-d6) δ 11.89 (s, 1H), 9.90 (s, 1H), 7.56-7.30 (m, 4H), 6.81 (t, J = 7.9 Hz, 1H), 6.47 (d, J = 7.6 Hz, 1H), 6.09 (d, J = 8.1 Hz, 1H), 3.31 (s, 2H), 3.01-2.89 (m, 2H), 2.69-2.58 (m, 2H), 1.49 (s, 3H), 0.96 (s, 5H). LCMS m/z 410.06 $[M + H]^+$. |
| 117 | From S6 according to Standard procedures A and B[a,m,n] 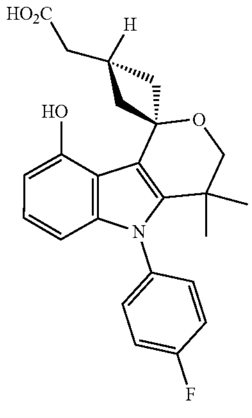 [SMILES: CC1(C)CO[C@]2(C[C@H](CC(=O)O)C2)c2c1n(-c1ccc(F)cc1)c1cccc(O)c12] | 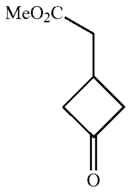 | $^1$H NMR (400 MHz, Chloroform-d) δ 7.44-7.30 (m, 2H), 7.26-7.16 (m, 2H), 6.92 (dd, J = 8.2, 7.6 Hz, 1H), 6.47 (dd, J = 7.6, 0.8 Hz, 1H), 6.37 (dd, J = 8.2, 0.8 Hz, 1H), 3.47 (s, 2H), 3.35-3.24 (m, 2H), 2.89 (s, 3H), 2.19-2.09 (m, 2H), 1.07 (s, 6H). LCMS m/z 410.8 $[M + H]^+$. |

TABLE 5-continued

| Preparation of Compounds 88-177 | | | |
|---|---|---|---|
| Compound | Method/Product | Ketone | $^1$H NMR; LCMS m/z |
| 118 | From S6 according to Standard procedures A and B[a,e] 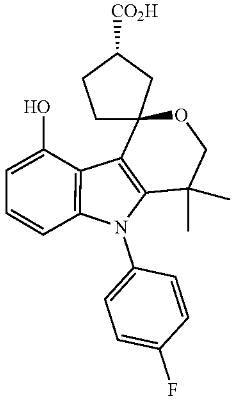 [SMILES: CC1(C)CO[C@]2(CC[C@H](C(=O)O)C2)c2c1n(-c1ccc(F)cc1)c1cccc(O)c21] | 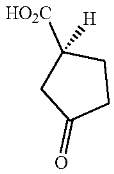 | $^1$H NMR (400 MHz, Methanol-d4) δ 7.32 (ddd, J = 6.8, 4.9, 2.6 Hz, 2H), 7.28-7.11 (m, 2H), 6.74 (t, J = 7.9 Hz, 1H), 6.32 (dd, J = 7.7, 0.8 Hz, 1H), 6.18-5.98 (m, 1H), 3.50-3.35 (m, 2H), 3.11 (dddd, J = 11.6, 8.8, 5.8, 2.2 Hz, 1H), 2.90 (t, J = 12.2 Hz, 1H), 2.81-2.63 (m, 1H), 2.35-1.85 (m, 4H), 1.00 (d, J = 14.2 Hz, 6H). LCMS m/z 410.53 [M + H]$^+$. |
| 119 | From S6 according to Standard procedures A and B[a,e] 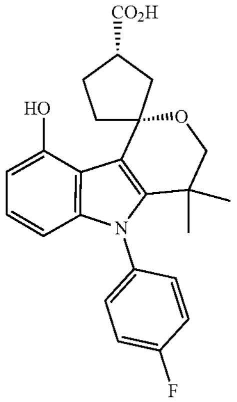 [SMILES: CC1(C)CO[C@@]2(CC[C@H](C(=O)O)C2)c2c1n(-c1ccc(F)cc1)c1cccc(O)c21] | 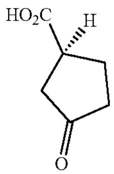 | $^1$H NMR (400 MHz, Chloroform-d) δ 7.46-7.33 (m, 2H), 7.28-7.20 (m, 2H), 6.96 (t, J = 7.9 Hz, 1H), 6.58 (dd, J = 7.6, 0.8 Hz, 1H), 6.36 (dd, J = 8.3, 0.7 Hz, 1H), 3.76-3.53 (m, 2H), 3.37 (ddd, J = 30.1, 14.8, 10.2 Hz, 2H), 2.97-2.74 (m, 1H), 2.47 (dt, J = 13.3, 9.3 Hz, 1H), 2.31 (dd, J = 13.2, 7.8 Hz, 3H), 1.21 (s, 3H), 1.04 (s, 3H). LCMS m/z 410.26 [M + H]$^+$. |
| 120 | From S6 according to Standard procedures A and B[a,e] 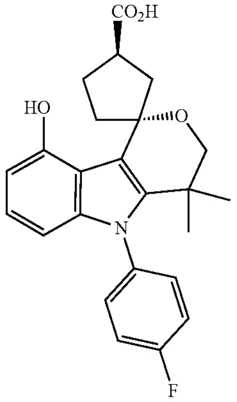 [SMILES: CC1(C)CO[C@@]2(CC[C@@H](C(=O)O)C2)c2c1n(-c1ccc(F)cc1)c1cccc(O)c21] | 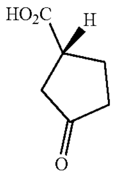 | $^1$H NMR (400 MHz, Methanol-d4) δ 7.29 (ddd, J = 9.1, 5.1, 1.7 Hz, 2H), 7.25-7.08 (m, 2H), 6.86-6.62 (m, 1H), 6.28 (dd, J = 7.7, 0.8 Hz, 1H), 6.06 (dd, J = 8.2, 0.8 Hz, 1H), 3.42-3.30 (m, 2H), 3.07 (dtd, J = 11.6, 8.8, 6.9 Hz, 1H), 2.86 (t, J = 12.2 Hz, 1H), 2.70 (ddd, J = 13.3, 10.9, 6.0 Hz, 1H), 2.22-1.98 (m, 3H), 1.95-1.79 (m, 1H), 0.96 (d, J = 14.1 Hz, 6H). LCMS m/z 410.53 [M + H]$^+$. |

TABLE 5-continued

| Preparation of Compounds 88-177 | | | |
|---|---|---|---|
| Compound | Method/Product | Ketone | $^1H$ NMR; LCMS m/z |
| 121 | From S6 according to Standard procedures A and B[a,e] 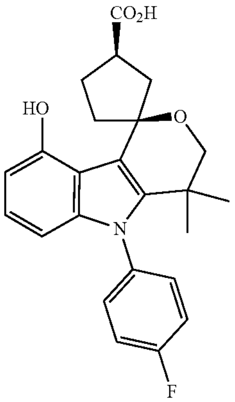 [SMILES: CC1(C)CO[C@]2(CC[C@@H](C(=O)O)C2)c2c1n(-c1ccc(F)cc1)c1cccc(O)c21] | 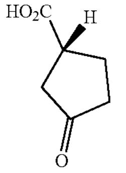 | $^1H$ NMR (400 MHz, Chloroform-d) δ 7.36 (tdt, J = 5.8, 5.0, 2.9, 1.5 Hz, 2H), 7.27-7.16 (m, 3H), 6.93 (t, J = 7.9 Hz, 1H), 6.56 (dd, J = 7.6, 0.8 Hz, 1H), 6.33 (dd, J = 8.2, 0.7 Hz, 1H), 3.69-3.52 (m, 2H), 3.45-3.20 (m, 2H), 2.93-2.76 (m, 1H), 2.44 (dt, J = 13.4, 9.3 Hz, 1H), 2.28 (td, J = 13.2, 5.8 Hz, 3H), 1.18 (s, 3H), 1.01 (s, 3H). LCMS m/z 410.53 $[M + H]^+$. |
| 122 | From S6 according to Standard procedures A and B[a,m,n] 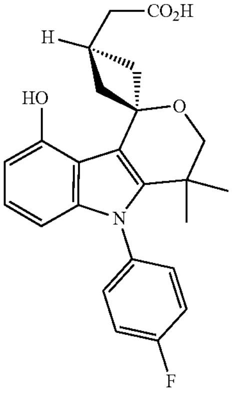 [SMILES: CC1(C)CO[C@]2(C[C@@H](CC(=O)O)C2)c2c1n(-c1ccc(F)cc1)c1cccc(O)c12] | 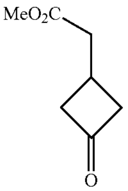 | $^1H$ NMR (400 MHz, Chloroform-d) δ 7.40-7.32 (m, 2H), 7.25-7.19 (m, 2H), 6.91 (t, J = 7.9 Hz, 1H), 6.51-6.43 (m, 1H), 6.36 (dd, J = 8.3, 0.8 Hz, 1H), 3.50 (s, 2H), 3.15-2.98 (m, 1H), 2.93 (t, J = 10.5 Hz, 2H), 2.76 (d, J = 7.6 Hz, 2H), 2.59-2.45 (m, 2H), 1.08 (s, 6H). LCMS m/z 410.6 $[M + H]^+$. |
| 123 | Racemic 106 was separated by chiral SFC 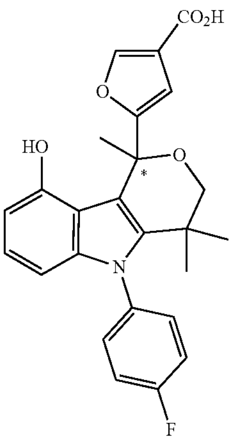 | N/A | LCMS m/z 436.28 $[M + H]^+$. |

TABLE 5-continued

Preparation of Compounds 88-177

| Compound | Method/Product | Ketone | $^1$H NMR; LCMS m/z |
|---|---|---|---|
| 124 | Racemic 106 was separated by chiral SFC<br>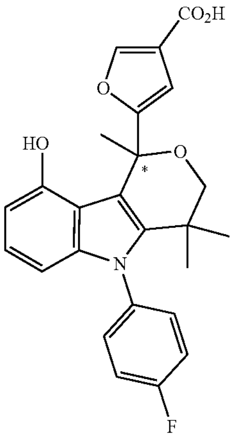 | N/A | LCMS m/z 436.37 [M + H]$^+$. |
| 125 | From S6 according to Standard procedures A and B[a,b,c,n]<br>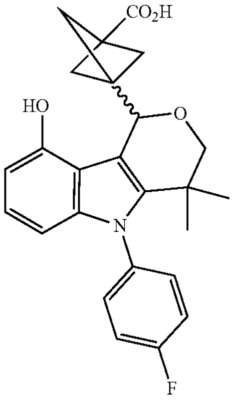 [SMILES: CC1(C)COC(C23CC(C(=O)O)(C2)C3)c2c1n(-c1ccc(F)cc1)c1cccc(O)c21] | 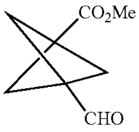 | $^1$H NMR (400 MHz, Methanol-d4) δ 7.51-7.37 (m, 2H), 7.36-7.27 (m, 2H), 6.88-6.79 (m, 1H), 6.40 (dd, J = 7.7, 0.8 Hz, 1H), 6.23 (dd, J = 8.2, 0.8 Hz, 1H), 5.29 (s, 1H), 3.80 (d, J = 11.0 Hz, 1H), 3.38 (d, J = 11.0 Hz, 1H), 2.22-1.99 (m, 7H), 1.07 (d, J = 22.5 Hz, 6H). LCMS m/z 422.6 [M + H]$^+$. |
| 126 | From S6 according to Standard procedures A and B[a,b,c,n]<br>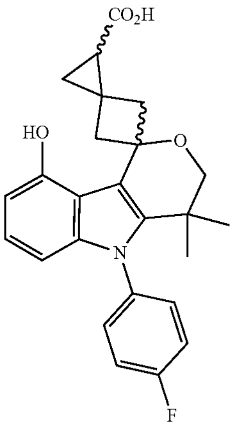 [SMILES: CC1(C)COC2(CC3(CC3C(=O)O)C2)c2c1n(-c1ccc(F)cc1)c1cccc(O)c21] | 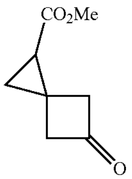 | $^1$H NMR (400 MHz, Methanol-d4) δ 7.37 (ddq, J = 10.0, 5.1, 3.0, 2.3 Hz, 2H), 7.33-7.17 (m, 2H), 6.93-6.76 (m, 1H), 6.44 (dd, J = 7.7, 0.8 Hz, 1H), 6.16 (dd, J = 8.2, 0.8 Hz, 1H), 3.45 (s, 2H), 3.37-3.22 (m, 5H), 2.43 (ddd, J = 12.8, 3.6, 1.4 Hz, 1H), 2.33 (ddd, J = 12.1, 3.5, 1.4 Hz, 1H), 1.71 (dd, J = 8.1, 5.4 Hz, 1H), 1.26-1.14 (m, 2H), 1.05 (d, J = 1.7 Hz, 6H). LCMS m/z 422.5 [M + H]$^+$. |

TABLE 5-continued

| Preparation of Compounds 88-177 | | | |
|---|---|---|---|
| Compound | Method/Product | Ketone | $^1$H NMR; LCMS m/z |
| 127 | From S6 according to Standard procedures A and B[a,b,c,n] 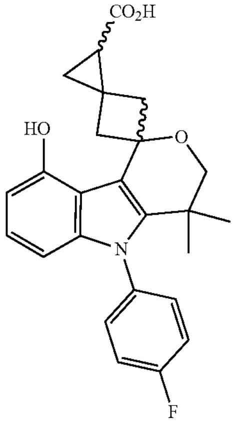 [SMILES: CC1(C)COC2(CC3(CC3C(=O)O)C2)c2c1n(-c1ccc(F)cc1)c1cccc(O)c21] | 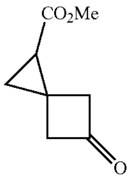 [SMILES: COC(=O)C1CC12CC(=O)C2] | $^1$H NMR (400 MHz, Chloroform-d) δ 7.42-7.31 (m, 2H), 7.22 (td, J = 8.0, 1.5 Hz, 2H), 6.90 (dd, J = 8.3, 7.6 Hz, 1H), 6.44 (dd, J = 7.6, 0.8 Hz, 1H), 6.35 (dd, J = 8.3, 0.7 Hz, 1H), 3.58-3.45 (m, 2H), 3.32 (d, J = 13.0 Hz, 2H), 2.56 (d, J = 12.3 Hz, 1H), 2.45 (d, J = 11.8 Hz, 1H), 1.78 (dd, J = 8.2, 5.5 Hz, 1H), 1.52 (t, J = 5.1 Hz, 1H), 1.36 (dd, J = 8.2, 4.8 Hz, 1H), 1.09 (d, J = 4.3 Hz, 6H). LCMS m/z 422.6 [M + H]$^+$. |
| 128 | Prepared in the same manner as compound 178[p] 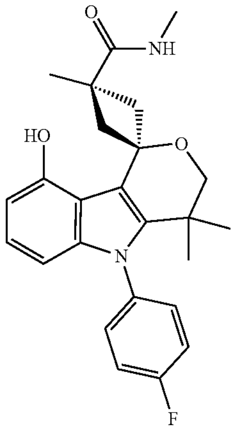 [SMILES: CNC(=O)[C@]1(C)C[C@@]2(C1)OCC(C)(C)c1c2c2c(O)cccc2n1-c1ccc(F)cc1] | N/A | $^1$H NMR (400 MHz, DMSO-d6) δ 9.88 (s, 1H), 7.56-7.35 (m, 5H), 6.84-6.77 (m, 1H), 6.47 (dd, J = 7.7, 0.9 Hz, 1H), 6.08 (dd, J = 8.2, 0.8 Hz, 1H), 3.28 (s, 2H), 2.90 (d, J = 11.8 Hz, 2H), 2.64 (m, 5H), 1.43 (s, 3H), 0.95 (s, 6H). LCMS m/z 423.17 [M + H]$^+$. |
| 129 | From S6 according to Standard procedures A and B[a,b,c] 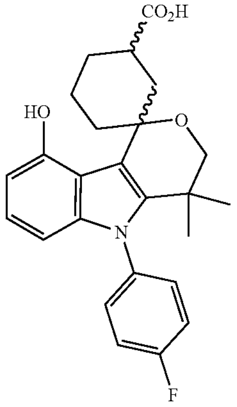 [SMILES: CC1(C)COC2(CCCC(C(=O)O)C2)c2c1n(-c1ccc(F)cc1)c1cccc(O)c21] | 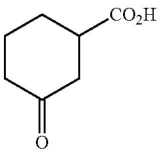 | $^1$H NMR (400 MHz, Methanol-d4) δ 7.48-7.35 (m, 2H), 7.33-7.21 (m, 2H), 6.87-6.73 (m, 1H), 6.39 (dd, J = 7.7, 0.8 Hz, 1H), 6.16 (dd, J = 8.2, 0.8 Hz, 1H), 3.50 (s, 2H), 2.96-2.61 (m, 3H), 2.06 (dd, J = 15.3, 5.1 Hz, 1H), 1.95 (d, J = 12.5 Hz, 1H), 1.81 (d, J = 13.1 Hz, 2H), 1.63 (ddd, J = 28.7, 12.2, 3.3 Hz, 2H), 1.06 (d, J = 9.5 Hz, 6H). LCMS m/z 424.6 [M + H]$^+$. |

TABLE 5-continued

Preparation of Compounds 88-177

| Compound | Method/Product | Ketone | $^1$H NMR; LCMS m/z |
|---|---|---|---|
| 130 | From S6 according to Standard procedures A and B[a,b] 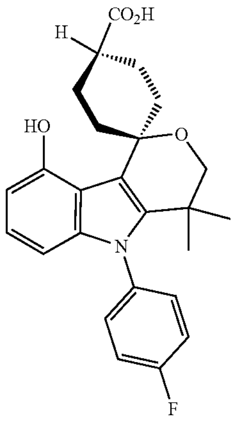 | 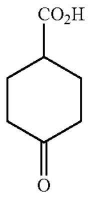 | $^1$H NMR (400 MHz, Methanol-d4) δ 7.45-7.37 (m, 2H), 7.36-7.27 (m, 2H), 6.83 (dd, J = 8.2, 7.7 Hz, 1H), 6.43 (dd, J = 7.6, 0.9 Hz, 1H), 6.18 (dd, J = 8.2, 0.8 Hz, 1H), 3.52 (s, 2H), 2.90-2.76 (m, 2H), 2.57-2.42 (m, 1H), 2.05 (s, 2H), 2.00-1.77 (m, 4H), 1.08 (s, 6H). LCMS m/z 424.6 $[M + H]^+$. |
| 131 | From S6 according to Standard procedures A and B[a,b] 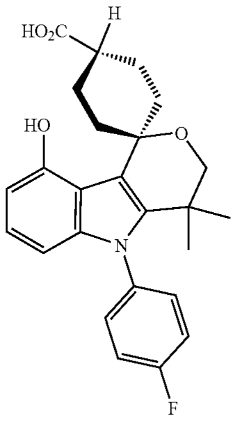 | 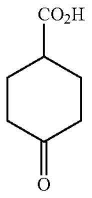 | $^1$H NMR (400 MHz, Chloroform-d) δ 7.43-7.33 (m, 2H), 7.25-7.16 (m, 2H), 6.79 (dd, J = 8.2, 7.6 Hz, 1H), 6.31 (dq, J = 7.6, 0.9 Hz, 2H), 3.53 (s, 2H), 2.91-2.74 (m, 3H), 2.27-2.10 (m, 4H), 1.98-1.83 (m, 2H), 1.08 (s, 6H). LCMS m/z 424.6 $[M + H]^+$. |
| 132 | Racemic 136 was separated by chiral SFC 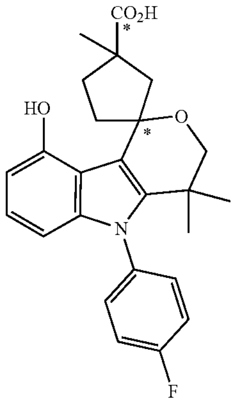 | N/A | $^1$H NMR (400 MHz, Chloroform-d) δ 7.39-7.31 (m, 2H), 7.24-7.12 (m, 2H), 6.92 (t, J = 7.9 Hz, 1H), 6.50 (d, J = 7.6 Hz, 1H), 6.35 (d, J = 8.2 Hz, 1H), 3.67-3.48 (m, 2H), 3.11-2.83 (m, 2H), 2.58-2.32 (m, 2H), 2.21 (dd, J = 13.5, 8.0 Hz, 1H), 2.02-1.84 (m, 1H), 1.48 (s, 3H), 1.14 (s, 3H), 1.02 (s, 3H). LCMS m/z 424.35 $[M + H]^+$. LCMS m/z 424.35 $[M + H]^+$. |

TABLE 5-continued

| Preparation of Compounds 88-177 | | | |
|---|---|---|---|
| Compound | Method/Product | Ketone | $^1H$ NMR; LCMS m/z |
| 133 | Racemic 136 was separated by chiral SFC. This is the enantiomer of compound 127 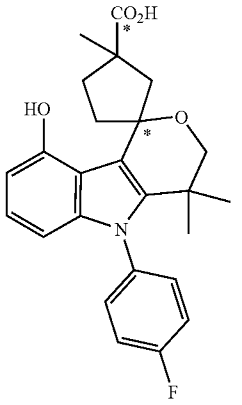 | N/A | $^1H$ NMR (400 MHz, Chloroform-d) δ 7.35 (dd, J = 8.8, 5.0 Hz, 2H), 7.27-7.16 (m, 2H), 6.92 (t, J = 7.9 Hz, 1H), 6.51 (d, J = 7.6 Hz, 1H), 6.35 (d, J = 8.2 Hz, 1H), 3.70-3.37 (m, 2H), 3.20-2.80 (m, 2H), 2.67-2.35 (m, 2H), 2.21 (dd, J = 13.6, 8.0 Hz, 1H), 2.09-1.85 (m, 1H), 1.48 (s, 3H), 1.14 (s, 3H), 1.02 (s, 3H). LCMS m/z 424.39 $[M + H]^+$. |
| 134 | From S6 according to Standard procedures A and B[a,b,c] 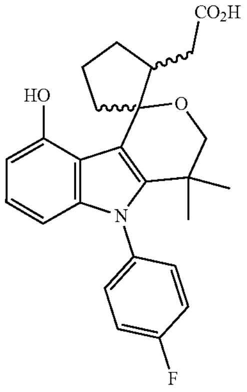 [SMILES: CC1(C)COC2(CCCC2CC(=O)O)c2c1n(-c1ccc(F)cc1)c1cccc(O)c21] | 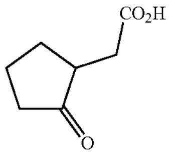 | $^1H$ NMR (400 MHz, Methanol-d4) δ 7.42 (ddtd, J = 7.7, 3.5, 2.4, 1.4 Hz, 2H), 7.32 (dddd, J = 9.2, 5.8, 2.8, 1.2 Hz, 2H), 6.89-6.75 (m, 1H), 6.42 (dd, J = 7.7, 0.8 Hz, 1H), 6.20 (dd, J = 8.2, 0.8 Hz, 1H), 3.69-3.44 (m, 2H), 2.70-2.53 (m, 1H), 2.44-2.22 (m, 2H), 2.20-2.02 (m, 3H), 1.98-1.79 (m, 2H), 1.79-1.59 (m, 1H), 1.40 (s, 3H), 0.77 (s, 3H). LCMS m/z 424.6 $[M + H]^+$. |
| 135 | From S6 according to Standard procedures A and B[a,b,c] 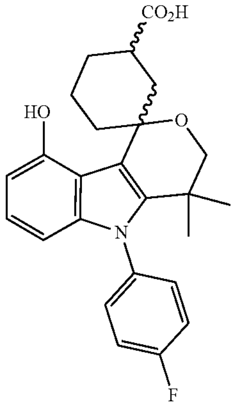 [SMILES: CC1(C)COC2(CCCC(C(=O)O)C2)c2c1n(-c1ccc(F)cc1)c1cccc(O)c21] | 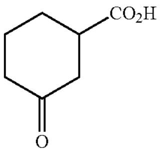 | $^1H$ NMR (400 MHz, Methanol-d4) δ 7.47-7.32 (m, 2H), 7.28 (ddt, J = 10.1, 8.6, 1.7 Hz, 2H), 6.80 (t, J = 7.9 Hz, 1H), 6.40 (dd, J = 7.7, 0.8 Hz, 1H), 6.16 (dd, J = 8.2, 0.8 Hz, 1H), 3.60 (d, J = 11.3 Hz, 1H), 3.21 (d, J = 11.3 Hz, 1H), 2.99-2.79 (m, 2H), 2.59 (d, J = 13.1 Hz, 2H), 2.15 (s, 5H), 1.74-1.39 (m, 3H), 1.22 (s, 3H), 0.83 (s, 3H). LCMS m/z 424.5 $[M + H]^+$. |

TABLE 5-continued

| Preparation of Compounds 88-177 | | | |
|---|---|---|---|
| Compound | Method/Product | Ketone | $^{1}$H NMR; LCMS m/z |
| 136 | From S6 according to Standard procedures A and $B^{a-g}$ 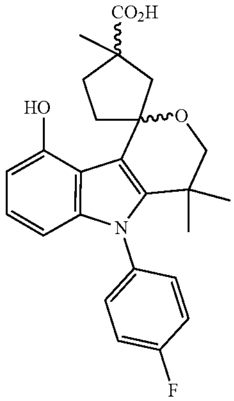 [SMILES: CC1(C(=O)O)CCC2(C1)OCC(C)(C)c1c2c2c(O)cccc2n1-c1ccc(F)cc1] | 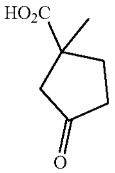 | $^{1}$H NMR (400 MHz, Chloroform-d) δ 7.43-7.31 (m, 2H), 7.28-7.16 (m, 4H), 6.93 (dd, J = 8.3, 7.6 Hz, 1H), 6.46 (dd, J = 7.6, 0.8 Hz, 1H), 6.37 (dd, J = 8.2, 0.8 Hz, 1H), 3.71-3.41 (m, 2H), 3.05-2.84 (m, 2H), 2.57-2.35 (m, 2H), 2.21 (dd, J = 13.6, 8.1 Hz, 1H), 1.92 (ddd, J = 13.5, 9.4, 1.5 Hz, 1H), 1.47 (s, 3H), 1.43 (s, 1H), 1.15 (s, 3H), 1.02 (s, 3H). LCMS m/z 424.62 $[M + H]^+$. |
| 137 | From S6 according to Standard procedures A and $B^{a-g}$ 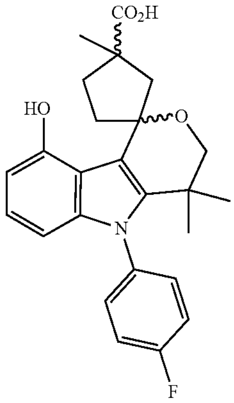 [SMILES: CC1(C(=O)O)CCC2(C1)OCC(C)(C)c1c2c2c(O)cccc2n1-c1ccc(F)cc1] | 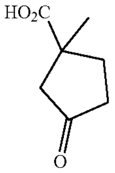 | $^{1}$H NMR (400 MHz, Chloroform-d) δ 7.40-7.23 (m, 3H), 7.20 (ddd, J = 9.2, 7.0, 1.5 Hz, 2H), 6.85 (d, J = 7.9 Hz, 1H), 6.38 (d, J = 7.6 Hz, 1H), 6.32 (d, J = 8.1 Hz, 1H), 3.58-3.38 (m, 3H), 3.25 (d, J = 14.5 Hz, 1H), 2.89-2.71 (m, 1H), 2.59 (dd, J = 12.7, 8.0 Hz, 1H), 2.20-2.11 (m, 2H), 2.11-1.89 (m, 1H), 1.56 (s, 3H), 1.10 (s, 3H), 1.02 (s, 3H). LCMS m/z 424.57 $[M + H]^+$. |
| 138 | From S6 according to Standard procedures A and $B^{a,c,g,n}$ 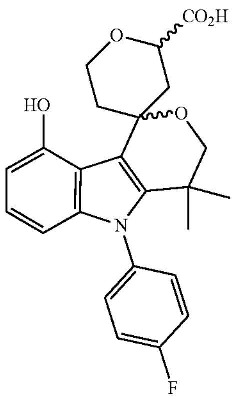 [SMILES: CC1(C)COC2(CCOC(C(=O)O)C2)c2c1n(-c1ccc(F)cc1)c1cccc(O)c21] | 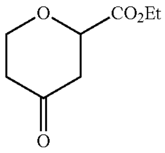 [SMILES: CCOC(=O)C1CC(=O)CCO1] | $^{1}$H NMR (400 MHz, Methanol-d4) δ 7.52-7.37 (m, 1H), 7.38-7.24 (m, 2H), 6.84 (t, J = 7.9 Hz, 1H), 6.45 (dd, J = 7.7, 0.9 Hz, 1H), 6.20 (dd, J = 8.2, 0.9 Hz, 1H), 4.49 (dd, J = 12.2, 2.5 Hz, 1H), 4.11-3.92 (m, 2H), 3.58 (s, 2H), 3.18-2.97 (m, 2H), 2.12 (d, J = 13.5 Hz, 1H), 2.06 (s, 1H), 1.73 (d, J = 14.0 Hz, 1H), 1.11 (d, J = 12.4 Hz, 6H). LCMS m/z 426.3 $[M + H]^+$. |

TABLE 5-continued

| Preparation of Compounds 88-177 | | | |
|---|---|---|---|
| Compound | Method/Product | Ketone | $^1$H NMR; LCMS m/z |
| 139 | From S6 according to Standard procedures A and B[a,c,g,n] 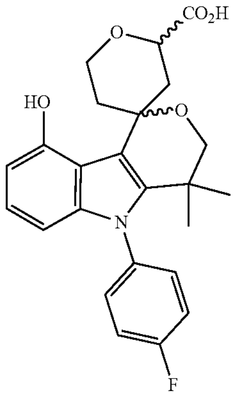 [SMILES: CC1(C)COC2(CCOC(C(=O)O)C2)c2c1n(-c1ccc(F)cc1)c1cccc(O)c21] | 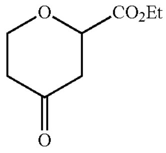 [SMILES: CCOC(=O)C1CC(=O)CCO1] | $^1$H NMR (400 MHz, Methanol-d4) δ 7.53-7.36 (m, 2H), 7.36-7.26 (m, 2H), 6.92-6.77 (m, 1H), 6.46 (dd, J = 7.7, 0.8 Hz, 1H), 6.19 (dd, J = 8.2, 0.8 Hz, 1H), 4.54 (ddd, J = 13.5, 11.3, 2.5 Hz, 1H), 4.38 (d, J = 6.8 Hz, 1H), 3.74 (dd, J = 11.2, 5.3 Hz, 1H), 3.60 (d, J = 11.2 Hz, 1H), 3.28-3.15 (m, 2H), 2.62-2.54 (m, 1H), 1.56 (d, J = 13.4 Hz, 1H), 1.25 (s, 3H), 0.88 (s, 3H). LCMS m/z 426.3 [M + H]$^+$. |
| 140 | From S6 according to Standard procedures A and B[a,c,f,n] 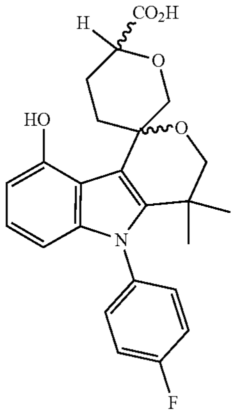 [SMILES: CC1(C)COC2(CCC(C(=O)O)OC2)c2c1n(-c1ccc(F)cc1)c1cccc(O)c21] | 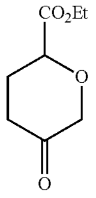 | $^1$H NMR (400 MHz, Methanol-d4) δ 7.38 (dq, J = 5.6, 3.2 Hz, 2H), 7.30 (t, J = 8.7 Hz, 2H), 6.83 (t, J = 8.0 Hz, 1H), 6.44 (dd, J = 7.7, 0.8 Hz, 1H), 6.18 (dd, J = 8.3, 0.8 Hz, 1H), 4.26-4.15 (m, 1H), 3.91 (d, J = 11.6 Hz, 1H), 3.53 (d, J = 7.3 Hz, 2H), 3.17-2.98 (m, 1H), 2.05 (s, 1H), 1.07 (d, J = 10.1 Hz, 6H). LCMS m/z 426.3 [M + H]$^+$. |
| 141 | From S6 according to Standard procedures A and B[a,c,f,n] 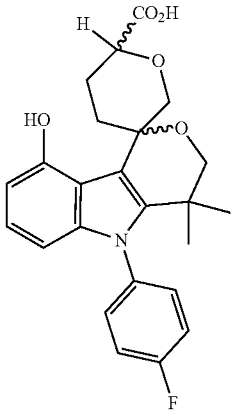 [SMILES: CC1(C)COC2(CCC(C(=O)O)OC2)c2c1n(-c1ccc(F)cc1)c1cccc(O)c21] | 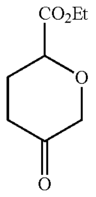 | $^1$H NMR (400 MHz, Methanol-d4) δ 7.38 (ddd, J = 8.9, 5.0, 1.7 Hz, 2H), 7.29 (td, J = 8.2, 1.5 Hz, 2H), 6.81 (t, J = 7.9 Hz, 1H), 6.40 (dd, J = 7.7, 0.8 Hz, 1H), 6.15 (dd, J = 8.2, 0.9 Hz, 1H), 4.49-4.38 (m, 1H), 3.54 (s, 2H), 3.07-2.91 (m, 1H), 2.36 (d, J = 1.8 Hz, 0H), 1.86 (d, J = 13.9 Hz, 1H), 1.07 (d, J = 18.3 Hz, 6H). LCMS m/z 426.3 [M + H]$^+$. |

TABLE 5-continued

Preparation of Compounds 88-177

| Compound | Method/Product | Ketone | $^1$H NMR; LCMS m/z |
|---|---|---|---|
| 142 | From S6 according to Standard procedures A and B[a,c,q,k] 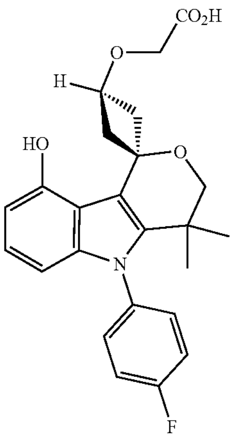 [SMILES: CC1(C)CO[C@]2(C[C@@H](OCC(=O)O)C2)c2c1n(-c1ccc(F)cc1)c1cccc(O)c12] | 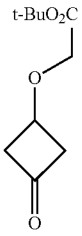 C60 | $^1$H NMR (400 MHz, Methanol-d4) δ 7.49-7.21 (m, 4H), 6.88-6.76 (m, 1H), 6.42 (dd, J = 7.6, 0.8 Hz, 1H), 6.16 (dd, J = 8.2, 0.8 Hz, 1H), 4.46 (tt, J = 6.9, 2.7 Hz, 1H), 4.08 (s, 2H), 3.44 (s, 2H), 3.27-3.14 (m, 2H), 2.48-2.35 (m, 2H), 1.05 (s, 6H). LCMS m/z 426.27 [M + H]$^+$. |
| 143 | From S6 according to Standard procedures A and B[a,c,q,k] 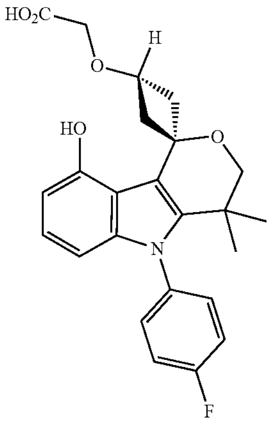 [SMILES: CC1(C)CO[C@]2(C[C@H](OCC(=O)O)C2)c2c1n(-c1ccc(F)cc1)c1cccc(O)c12] | 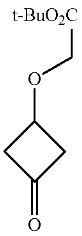 C60 | $^1$H NMR (400 MHz, Methanol-d4) δ 7.43-7.20 (m, 4H), 6.85-6.75 (m, 1H), 6.42 (dd, J = 7.7, 0.8 Hz, 1H), 6.14 (dd, J = 8.2, 0.8 Hz, 1H), 5.47 (s, 1H), 4.49-4.38 (m, 1H), 4.09 (s, 2H), 3.41 (s, 2H), 3.30-3.24 (m, 2H), 2.62-2.49 (m, 2H), 1.03 (s, 6H). LCMS m/z 426.27 [M + H]$^+$. |
| 144 | From S6 according to Standard procedures A and B[a,c,f,n] 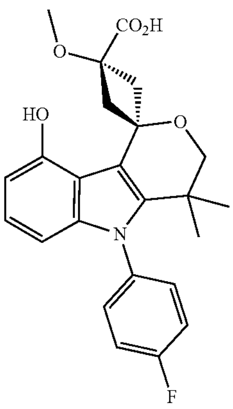 [SMILES: CO[C@]1(C(=O)O)C[C@]2(C1)OCC(C)(C)c1c2c2c(O)cccc2n1-c1ccc(F)cc1] | 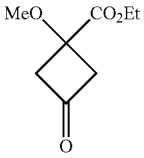 | $^1$H NMR (400 MHz, Methanol-d4) δ 7.38 (ddt, J = 8.3, 5.5, 2.8 Hz, 2H), 7.34-7.25 (m, 2H), 6.88-6.75 (m, 1H), 6.42 (dd, J = 7.7, 0.8 Hz, 1H), 6.16 (dd, J = 8.2, 0.8 Hz, 1H), 3.47-3.37 (m, 3H), 3.33 (s, 3H), 2.86-2.74 (m, 2H), 1.05 (s, 6H). LCMS m/z 426.5 [M + H]$^+$. |

TABLE 5-continued

| Preparation of Compounds 88-177 | | | |
|---|---|---|---|
| Compound | Method/Product | Ketone | $^1H$ NMR; LCMS m/z |
| 145 | From S6 according to Standard procedures A and B[a,f] 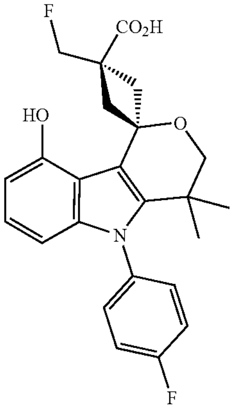 [SMILES: CC1(C)CO[C@]2(C[C@@](CF)(C(=O)O)C2)c2c1n(-c1ccc(F)cc1)c1cccc(O)c12] | 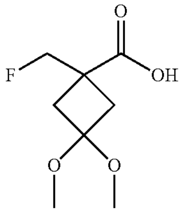 S18 | $^1H$ NMR (400 MHz, Chloroform-d) δ 7.42-7.33 (m, 2H), 7.29 (m, 1H), 7.04-6.92 (m, 1H), 6.52 (dd, J = 7.6, 0.8 Hz, 1H), 6.39 (dd, J = 8.3, 0.8 Hz, 1H), 5.58 (s, 1H), 5.06 (s, 1H), 4.94 (s, 1H), 3.66 (s, 2H), 3.49-3.36 (m, 2H), 2.84-2.73 (m, 2H), 2.04 (s, 2H), 1.13 (s, 6H). LCMS m/z 428.53 $[M + H]^+$. |
| 146 | From S6 according to Standard procedures A and B[a,o] 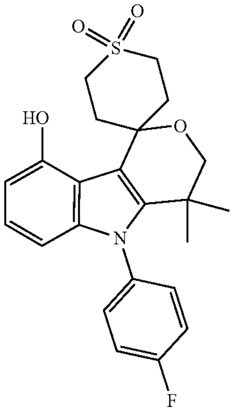 [SMILES: CC1(C)COC2(CCS(=O)(=O)CC2)c2c1n(-c1ccc(F)cc1)c1cccc(O)c21] | 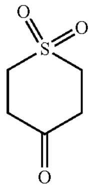 | $^1H$ NMR (400 MHz, DMSO-d6) δ 10.08 (s, 1H), 7.47 (ddt, J = 8.3, 5.5, 2.7 Hz, 2H), 7.41 (dd, J = 9.9, 7.6 Hz, 2H), 6.81 (t, J = 7.9 Hz, 1H), 6.44 (dd, J = 7.7, 0.9 Hz, 1H), 6.11 (dd, J = 8.2, 0.9 Hz, 1H), 3.53 (s, 2H), 3.49-3.33 (m, 4H), 3.00 (d, J = 12.1 Hz, 2H), 2.14 (d, J = 12.7 Hz, 2H), 1.01 (s, 6H). LCMS m/z 430.29 $[M + H]^+$. |
| 147 | From S6 according to Standard procedures A and B[a,o] 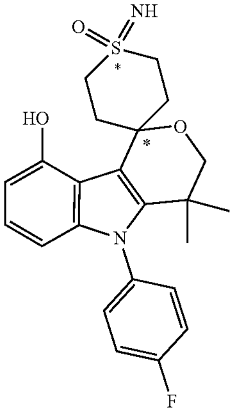 | N/A | $^1H$ NMR (400 MHz, DMSO-d6) δ 10.02 (s, 1H), 7.53-7.34 (m, 4H), 6.80 (t, J = 7.9 Hz, 1H), 6.44 (dd, J = 7.7, 0.9 Hz, 1H), 6.09 (dd, J = 8.2, 0.8 Hz, 1H), 3.52 (s, 2H), 3.47-3.34 (m, 4H), 2.96 (d, J = 11.0 Hz, 2H), 2.05 (d, J = 12.0 Hz, 2H), 1.00 (s, 6H). |

TABLE 5-continued

| Preparation of Compounds 88-177 | | | |
|---|---|---|---|
| Compound | Method/Product | Ketone | $^1$H NMR; LCMS m/z |
| 148 | Racemic 83 was separated by chiral SFC. This is the enantiomer of 147 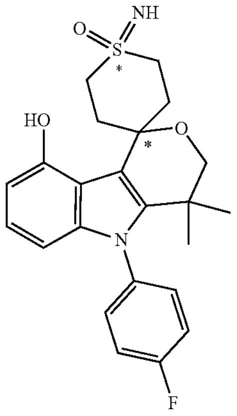 | N/A | $^1$H NMR (400 MHz, DMSO-d6) δ 10.05 (s, 1H), 7.54-7.31 (m, 4H), 6.80 (t, J = 7.9 Hz, 1H), 6.42 (d, J = 7.7 Hz, 1H), 6.10 (d, J = 8.1 Hz, 1H), 3.65 (s, 1H), 3.51 (s, 2H), 3.37 (d, J = 16.8 Hz, 4H), 2.89 (d, J = 12.8 Hz, 2H), 2.05 (d, J = 13.5 Hz, 2H), 1.01 (s, 5H). |
| 149 | Racemic 92 was separated by chiral SFC 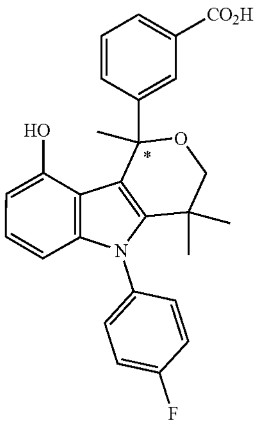 | N/A | $^1$H NMR (300 MHz, Chloroform-d) δ 8.41 (t, J = 1.7 Hz, 1H), 8.03 (d, J = 7.6 Hz, 1H), 7.79 (dt, J = 8.0, 1.3 Hz, 1H), 7.56-7.35 (m, 3H), 7.37-7.21 (m, 2H), 6.95 (t, J = 7.9 Hz, 1H), 6.42 (dd, J = 7.9, 2.5 Hz, 2H), 3.44-3.19 (m, 2H), 2.22 (s, 3H), 1.31 (s, 3H), 0.92 (s, 3H). LCMS m/z 446.32 [M + H]$^+$. |
| 150 | Racemic 92 was separated by chiral SFC. This is the enantiomer of 149 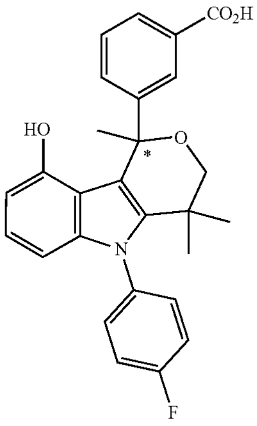 | N/A | $^1$H NMR (300 MHz, Chloroform-d) δ 8.41 (t, J = 1.7 Hz, 1H), 8.03 (d, J = 7.6 Hz, 1H), 7.79 (dt, J = 8.0, 1.3 Hz, 1H), 7.56-7.35 (m, 3H), 7.37-7.21 (m, 2H), 6.95 (t, J = 7.9 Hz, 1H), 6.42 (dd, J = 7.9, 2.5 Hz, 2H), 3.44-3.19 (m, 2H), 2.22 (s, 3H), 1.31 (s, 3H), 0.92 (s, 3H). LCMS m/z 446.62 [M + H]$^+$. |

TABLE 5-continued

| Preparation of Compounds 88-177 | | | |
| --- | --- | --- | --- |
| Compound | Method/Product | Ketone | $^1$H NMR; LCMS m/z |
| 151 | From S6 according to Standard procedures A and B[a,m,r] 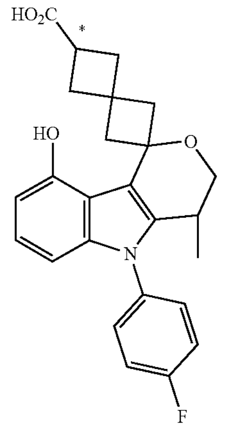 | 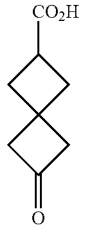 [SMILES: O=C1CC2(C1)CC(C(=O)O)C2] | $^1$H NMR (400 MHz, Chloroform-d) δ 7.45-7.31 (m, 2H), 7.27-7.14 (m, 2H), 6.91 (dd, J = 8.3, 7.6 Hz, 1H), 6.45 (dd, J = 7.6, 0.8 Hz, 1H), 6.36 (dd, J = 8.2, 0.7 Hz, 1H), 3.47 (s, 2H), 3.27-3.07 (m, 3H), 2.60 (dd, J = 8.4, 2.0 Hz, 2H), 2.55-2.30 (m, 4H), 1.08 (d, J = 4.9 Hz, 6H). LCMS m/z 436.5 $[M + H]^+$. |
| 152 | From S6 according to Standard procedures A and B[a,m,r] 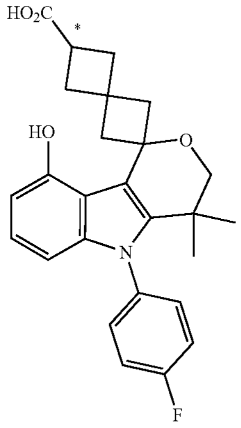 | 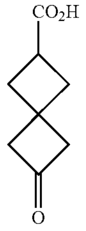 [SMILES: O=C1CC2(C1)CC(C(=O)O)C2] | $^1$H NMR (400 MHz, Methanol-d4) δ 7.43-7.20 (m, 4H), 6.80 (dd, J = 8.2, 7.7 Hz, 1H), 6.40 (dd, J = 7.7, 0.8 Hz, 1H), 6.15 (dd, J = 8.2, 0.8 Hz, 1H), 3.42 (d, J = 2.2 Hz, 2H), 3.28-2.96 (m, 3H), 2.57-2.29 (m, 6H), 2.27-2.18 (m, 1H), 1.09-0.96 (m, 6H). LCMS m/z 436.3 $[M + H]^+$. |
| 153 | Racemic 94 was separated by chiral SFC 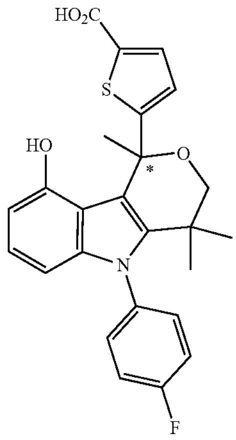 | N/A | $^1$H NMR (400 MHz, Chloroform-d) δ 7.42 (d, J = 35.8 Hz, 3H), 7.25-7.11 (m, 2H), 6.82 (d, J = 17.4 Hz, 2H), 6.40 (s, 1H), 6.28 (d, J = 8.1 Hz, 1H), 3.55 (d, J = 11.3 Hz, 1H), 3.31 (d, J = 11.3 Hz, 1H), 2.21 (s, 3H), 1.37-1.25 (s 3H), 0.82 (s, 3H). LCMS m/z 452.18 $[M + H]^+$. |

TABLE 5-continued

| Preparation of Compounds 88-177 | | | |
|---|---|---|---|
| Compound | Method/Product | Ketone | $^1H$ NMR; LCMS m/z |
| 154 | Racemic 94 was separated by chiral SFC. This is the enantiomer of 153 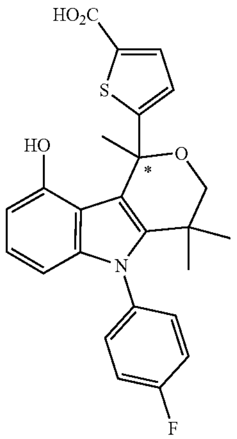 | N/A | $^1H$ NMR (400 MHz, Chloroform-d) δ 7.42 (d, J = 35.8 Hz, 3H), 7.25-7.11 (m, 2H), 6.82 (d, J = 17.4 Hz, 2H), 6.40 (s, 1H), 6.28 (d, J = 8.1 Hz, 1H), 3.55 (d, J = 11.3 Hz, 1H), 3.31 (d, J = 11.3 Hz, 1H), 2.21 (s, 3H), 1.37-1.25 (s 3H), 0.82 (s, 3H). LCMS m/z 452.14 $[M + H]^+$. |
| 155 | From S6 according to Standard procedures A and B[a,c,f,n] 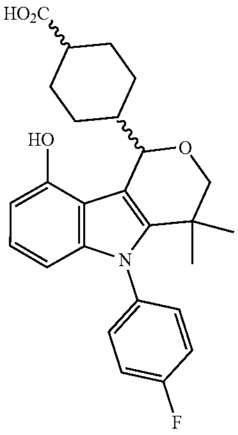 [SMILES: CC1(C)COC(C2CCC(C(=O)O)CC2)c2c1n(-c1ccc(F)cc1)c1cccc(O)c21] | 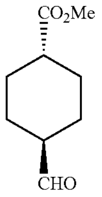 | LCMS m/z 438.2 $[M + H]^+$. |
| 156 | Prepared in the same manner as compound 178[s] 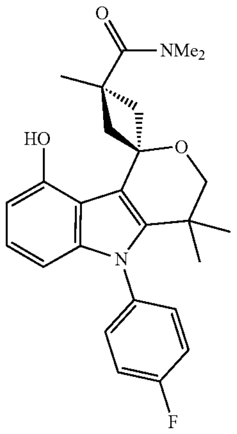 [SMILES: CN(C)C(=O)[C@]1(C)C[C@@]2(C1)OCC(C)(C)c1c2c2c(O)cccc2n1-c1ccc(F)cc1] | N/A | LCMS m/z 437.18 $[M + H]^+$. |

TABLE 5-continued

| Preparation of Compounds 88-177 | | | |
|---|---|---|---|
| Compound | Method/Product | Ketone | $^1H$ NMR; LCMS m/z |
| 157 | From S6 according to Standard procedures A and B[a,c,m] 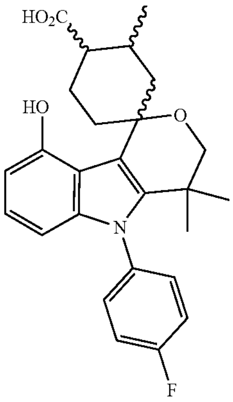 [SMILES: CC1CC2(CCC1C(=O)O)OCC(C)(C)c1c2c2c(O)cccc2n1-c1ccc(F)cc1] | 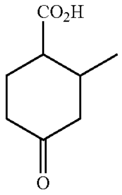 | $^1H$ NMR (400 MHz, Chloroform-d) δ 7.39 (ddtd, J = 7.5, 5.1, 2.4, 1.3 Hz, 2H), 7.27-7.18 (m, 2H), 6.85 (t, J = 7.9 Hz, 1H), 6.51 (dd, J = 7.7, 0.9 Hz, 1H), 6.33 (dd, J = 8.2, 0.9 Hz, 1H), 3.53 (s, 2H), 2.87-2.62 (m, 3H), 2.54-2.34 (m, 1H), 2.28 (t, J = 4.8 Hz, 1H), 2.06-1.87 (m, 1H), 1.22-0.99 (m, 9H). LCMS m/z 438.6 [M + H]$^+$. |
| 158 | From S6 according to Standard procedures A and B[a,b,c] 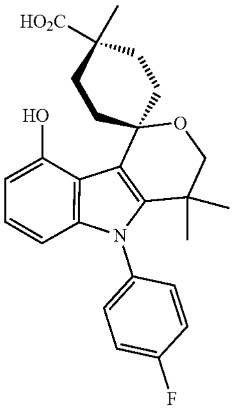 | 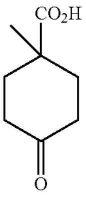 | $^1H$ NMR (400 MHz, Chloroform-d) δ 7.41-7.31 (m, 2H), 7.23-7.15 (m, 2H), 6.78 (dd, J = 8.3, 7.6 Hz, 1H), 6.28 (ddd, J = 15.5, 7.9, 0.8 Hz, 2H), 3.53 (s, 2H), 2.84 (td, J = 13.9, 3.8 Hz, 2H), 2.17 (d, J = 13.0 Hz, 2H), 1.93 (d, J = 14.4 Hz, 2H), 1.81 (td, J = 13.6, 3.9 Hz, 2H), 1.37 (s, 3H), 1.08 (s, 6H). LCMS m/z 438.6 [M + H]$^+$. |
| 159 | From S6 according to Standard procedures A and B[a,c,m] 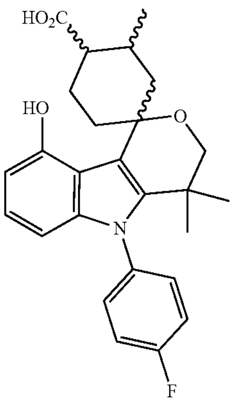 [SMILES: CC1CC2(CCC1C(=O)O)OCC(C)(C)c1c2c2c(O)cccc2n1-c1ccc(F)cc1] | 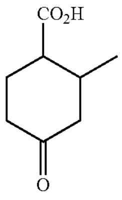 | $^1H$ NMR (400 MHz, Chloroform-d) δ 7.43-7.33 (m, 1H), 7.23 (t, J = 8.3 Hz, 2H), 6.95-6.87 (m, 1H), 6.49-6.41 (m, 1H), 6.41-6.34 (m, 1H), 5.15 (s, 1H), 3.48 (d, J = 35.6 Hz, 1H), 2.98-2.63 (m, 2H), 2.33-2.15 (m, 0H), 2.07 (s, 2H), 1.23 (dd, J = 20.4, 13.2 Hz, 5H), 1.13-0.83 (m, 6H). LCMS m/z 438.7 [M + H]$^+$. |

TABLE 5-continued

| Preparation of Compounds 88-177 | | | |
|---|---|---|---|
| Compound | Method/Product | Ketone | $^{1}H$ NMR; LCMS m/z |
| 160 | From S6 according to Standard procedures A and B[a,b,c] 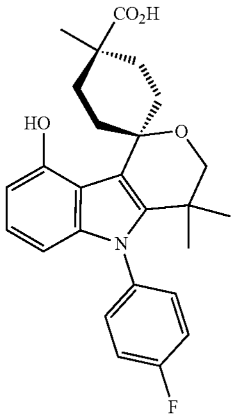 | 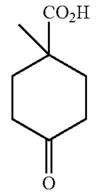 | $^{1}H$ NMR (400 MHz, Chloroform-d) δ 7.44-7.32 (m, 2H), 7.26-7.19 (m, 2H), 6.92 (dd, J = 8.2, 7.6 Hz, 1H), 6.45 (dd, J = 7.6, 0.9 Hz, 1H), 6.38 (dd, J = 8.2, 0.8 Hz, 1H), 3.51 (s, 2H), 2.75 (td, J = 14.0, 4.1 Hz, 2H), 2.30 (td, J = 13.6, 4.2 Hz, 2H), 1.87 (d, J = 13.9 Hz, 2H), 1.68-1.58 (m, 2H), 1.53 (s, 3H), 1.07 (s, 6H). LCMS m/z 438.57 $[M + H]^{+}$. |
| 161 | From S6 according to Standard procedures A and B[a,f,t] 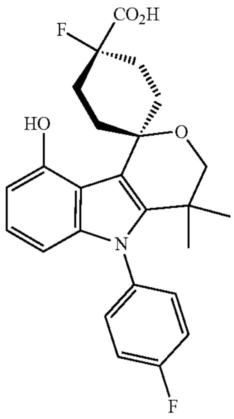 | 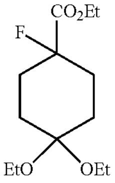 C64 | $^{1}H$ NMR (400 MHz, Chloroform-d) δ 7.31-7.16 (m, 3H), 7.11 (td, J = 8.6, 1.9 Hz, 2H), 6.83-6.65 (m, 1H), 6.36 (dt, J = 7.7, 1.2 Hz, 1H), 6.17 (dt, J = 8.2, 1.3 Hz, 1H), 3.41 (d, J = 1.7 Hz, 2H), 3.12-2.83 (m, 2H), 2.31 (dtd, J = 42.3, 13.9, 4.4 Hz, 2H), 1.88-1.68 (m, 4H), 0.96 (s, 6H). LCMS m/z 442.31 $[M + H]^{+}$. |

TABLE 5-continued

| Preparation of Compounds 88-177 | | | |
|---|---|---|---|
| Compound | Method/Product | Ketone | $^1H$ NMR; LCMS m/z |
| 162 | From S6 according to Standard procedures A and B[a,f] 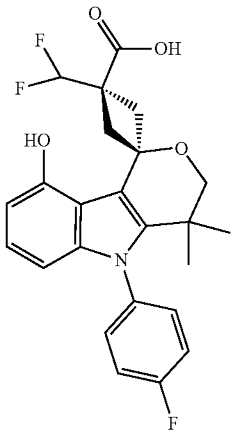 [SMILES: CC1(C)CO[C@]2(C[C@](C(=O)O)(C(F)F)C2)c2c1n(-c1ccc(F)cc1)c1cccc(O)c12] | 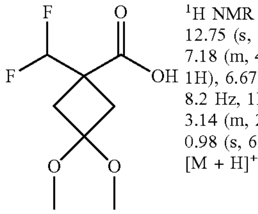 S20 | $^1H$ NMR (400 MHz, DMSO-d6) δ 12.75 (s, 1H), 10.10 (s, 1H), 7.53-7.18 (m, 4H), 6.84 (t, J = 7.9 Hz, 1H), 6.67-6.22 (m, 2H), 6.13 (d, J = 8.2 Hz, 1H), 3.37 (s, 2H), 3.28-3.14 (m, 2H), 2.77-2.57 (m, 2H), 0.98 (s, 6H). LCMS m/z 446.02 $[M + H]^+$. |
| 163 | From S6 according to Standard procedures A and B[a,f] 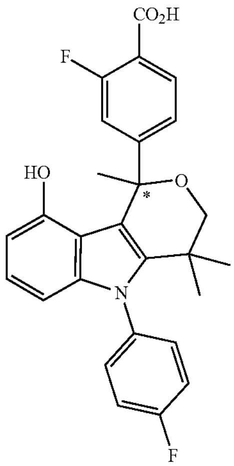 [SMILES: CC1(C)COC(C)(c2ccc(C(=O)O)c(F)c2)c2c1n(-c1ccc(F)cc1)c1cccc(O)c21] | N/A | $^1H$ NMR (400 MHz, Methanol-d4) δ 7.60 (s, 1H), 7.46 (dtt, J = 11.3, 4.9, 2.4 Hz, 2H), 7.31 (tdd, J = 8.7, 3.8, 2.5 Hz, 3H), 7.18 (d, J = 11.2 Hz, 1H), 6.86 (t, J = 7.9 Hz, 1H), 6.39 (dd, J = 7.7, 0.8 Hz, 1H), 6.28-6.10 (m, 1H), 3.26 (s, 2H), 2.14 (s, 3H), 1.33 (s, 3H), 0.81 (s, 3H). LCMS m/z 464.15 $[M + H]^+$. |

TABLE 5-continued

| Compound | Method/Product | Ketone | $^1H$ NMR; LCMS m/z |
|---|---|---|---|
| Preparation of Compounds 88-177 | | | |
| 164 | Racemic 95 was separated by chiral SFC. This is the enantiomer of 163 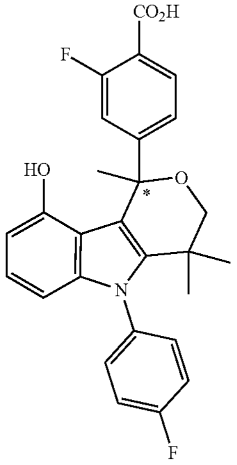 [SMILES: CC1(C)COC(C)(c2ccc(C(=O)O)c(F)c2)c2c1n(-c1ccc(F)cc1)c1cccc(O)c21] | N/A | $^1H$ NMR (400 MHz, Methanol-d4) δ 7.64 (t, J = 7.8 Hz, 1H), 7.46 (tdd, J = 10.1, 5.1, 2.4 Hz, 2H), 7.31 (tdd, J = 7.7, 3.7, 2.0 Hz, 3H), 7.16 (dd, J = 12.3, 1.6 Hz, 1H), 6.86 (t, J = 8.0 Hz, 1H), 6.47-6.29 (m, 1H), 6.21 (d, J = 8.1 Hz, 1H), 3.31-3.20 (m, 2H), 2.14 (s, 3H), 1.33 (s, 3H), 0.81 (s, 3H). LCMS m/z 464.19 $[M + H]^+$. |
| 165 | From S6 according to Standard procedures A and B[a,b,c,n] 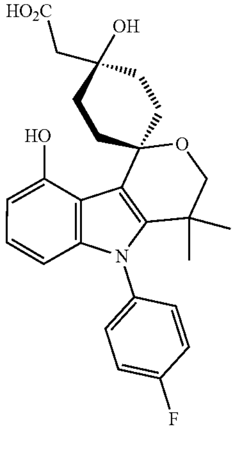 | 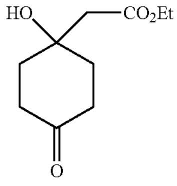 [SMILES: CCOC(=O)CC1(O)CCC(=O)CC1] | $^1H$ NMR (400 MHz, Methanol-d4) δ 7.37-7.27 (m, 2H), 7.25-7.12 (m, 2H), 6.71 (dd, J = 8.2, 7.7 Hz, 1H), 6.32 (dd, J = 7.7, 0.8 Hz, 1H), 6.08 (dd, J = 8.2, 0.9 Hz, 1H), 3.39 (s, 2H), 2.89 (d, J = 4.2 Hz, 1H), 2.39 (s, 2H), 1.90 (td, J = 13.7, 4.4 Hz, 2H), 1.64 (dd, J = 37.5, 13.7 Hz, 4H), 0.96 (s, 6H). LCMS m/z 454.6 $[M + H]^+$. |

TABLE 5-continued

| Preparation of Compounds 88-177 | | | |
|---|---|---|---|
| Compound | Method/Product | Ketone | $^1H$ NMR; LCMS m/z |
| 166 | From S6 according to Standard procedures A and B[a,b,c,n] 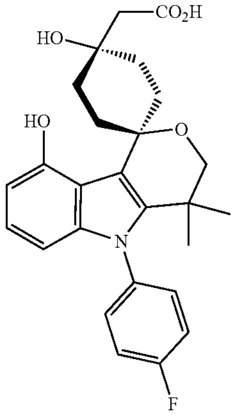 | 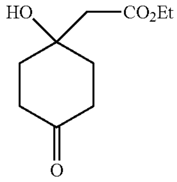 [SMILES: CCOC(=O)CC1(O)CCC(=O)CC1] | $^1H$ NMR (400 MHz, Methanol-d4) δ 7.28 (ddt, J = 8.2, 5.5, 2.7 Hz, 2H), 7.24-7.12 (m, 2H), 6.76-6.63 (m, 1H), 6.31 (dd, J = 7.7, 0.8 Hz, 1H), 6.06 (dd, J = 8.2, 0.8 Hz, 1H), 3.40 (s, 2H), 2.88 (s, 2H), 2.79-2.58 (m, 2H), 2.03-1.85 (m, 2H), 1.71 (t, J = 14.3 Hz, 4H), 0.96 (s, 6H). LCMS m/z 452.32 $[M + H]^+$. |
| 167 | From S6 according to Standard procedures A and B[a,c,f] 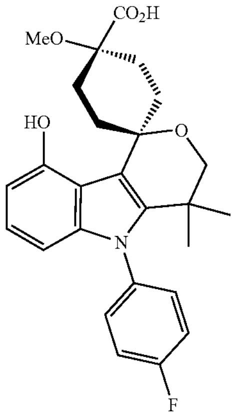 | 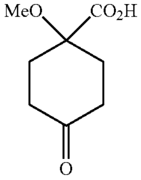 [SMILES: COC1(C(=O)O)CCC(=O)CC1] | $^1H$ NMR (400 MHz, Chloroform-d) δ 7.42-7.29 (m, 3H), 7.20 (t, J = 8.5 Hz, 2H), 6.91-6.81 (m, 1H), 6.49 (dd, J = 7.7, 0.9 Hz, 1H), 6.27 (dd, J = 8.2, 0.9 Hz, 1H), 3.52 (d, J = 14.6 Hz, 6H), 2.92 (td, J = 13.9, 3.9 Hz, 2H), 2.28 (td, J = 14.0, 4.1 Hz, 2H), 1.96-1.75 (m, 4H), 1.05 (s, 6H). LCMS m/z 454.2 $[M + H]^+$. |

TABLE 5-continued

| Preparation of Compounds 88-177 | | | |
|---|---|---|---|
| Compound | Method/Product | Ketone | $^1$H NMR; LCMS m/z |
| 168 | From S6 according to Standard procedures A and B[a,c,j] 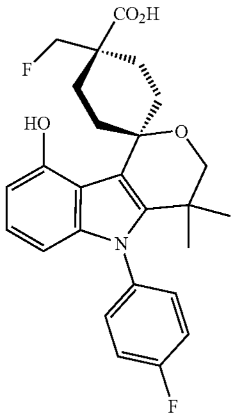 | 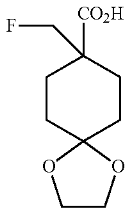 | $^1$H NMR (400 MHz, DMSO-d6) δ 12.50 (s, 1H), 10.03 (s, 1H), 7.55-7.31 (m, 4H), 6.89-6.75 (m, 1H), 6.46 (dd, J = 7.7, 0.9 Hz, 1H), 6.11 (dd, J = 8.1, 0.9 Hz, 1H), 5.00 (d, J = 46.9 Hz, 2H), 3.44 (s, 2H), 2.59 (dd, J = 15.4, 11.4 Hz, 2H), 2.11-2.01 (m, 2H), 1.68 (dd, J = 26.1, 13.4 Hz, 4H), 0.98 (s, 6H). LCMS m/z 456.15 [M + H]$^+$. |
| 169 | From S6 according to Standard procedures A and B[a,k] 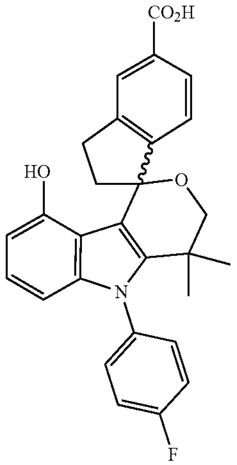 [SMILES: CC1(C)COC2(CCc3cc(C(=O)O)ccc32)c2c1n(-c1ccc(F)cc1)c1cccc(O)c21] | 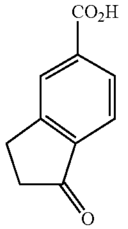 | $^1$H NMR (400 MHz, DMSO-d6) δ 12.76 (s, 1H), 8.96 (s, 1H), 7.87 (d, J = 1.5 Hz, 1H), 7.70 (dd, J = 7.9, 1.5 Hz, 1H), 7.65-7.52 (m, 2H), 7.51-7.39 (m, 2H), 7.01 (d, J = 7.8 Hz, 1H), 6.73 (t, J = 7.9 Hz, 1H), 6.14 (dd, J = 16.1, 7.9 Hz, 2H), 3.44 (s, 2H), 3.23-2.96 (m, 3H), 2.48-2.41 (m, 1H), 1.12 (s, 3H), 1.04 (s, 3H). LCMS m/z 458.38 [M + H]$^+$. |

TABLE 5-continued
| Preparation of Compounds 88-177 | | | |
|---|---|---|---|
| Compound | Method/Product | Ketone | $^1H$ NMR; LCMS m/z |
| 170 | From S6 according to Standard procedures A and B[a,k] 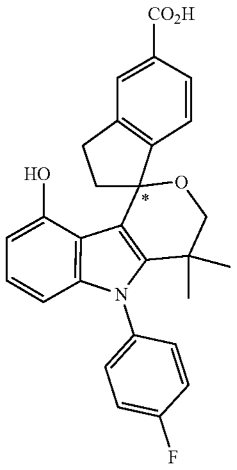 [SMILES: CC1(C)COC2(CCc3cc(C(=O)O)ccc32)c2c1n(-c1ccc(F)cc1)c1cccc(O)c21] | N/A | LCMS m/z 458.38 $[M + H]^+$. |
| 171 | Racemic 169 was separated by chiral SFC. This is the enantiomer of 170 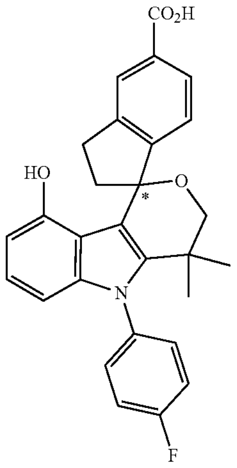 [SMILES: CC1(C)COC2(CCc3cc(C(=O)O)ccc32)c2c1n(-c1ccc(F)cc1)c1cccc(O)c21] | N/A | LCMS m/z 458.38 $[M + H]^+$. |

TABLE 5-continued

| Preparation of Compounds 88-177 | | | |
|---|---|---|---|
| Compound | Method/Product | Ketone | $^1$H NMR; LCMS m/z |
| 172 | From S6 according to Standard procedures A and B[a,c,f] 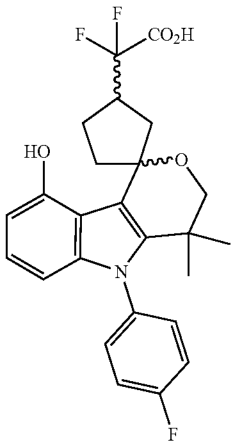 [SMILES: CC1(C)COC2(CCC(C(F)(F)C(=O)O)C2)c2c1n(-c1ccc(F)cc1)c1cccc(O)c21] | 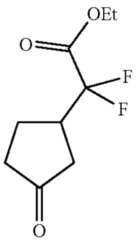 [SMILES: CCOC(=O)C(F)(F)C1CCC(=O)C1] | $^1$H NMR (400 MHz, Methanol-d4) δ 7.39 (ddt, J = 6.3, 4.8, 2.5 Hz, 2H), 7.29 (tt, J = 8.3, 7.6, 1.8 Hz, 2H), 6.80 (td, J = 7.9, 1.8 Hz, 1H), 6.38 (ddd, J = 7.7, 2.8, 0.8 Hz, 1H), 6.16 (ddd, J = 8.2, 6.0, 0.8 Hz, 1H), 3.45 (d, J = 8.5 Hz, 2H), 2.99-2.58 (m, 2H), 2.22-1.82 (m, 2H), 1.18-0.90 (m, 6H). |
| 173 | From S6 according to Standard procedures A and B[a,c] 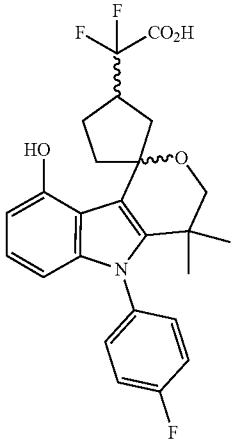 [SMILES: CC1(C)COC2(CCC(C(F)(F)C(=O)O)C2)c2c1n(-c1ccc(F)cc1)c1cccc(O)c21] | 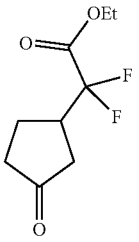 [SMILES: CCOC(=O)C(F)(F)C1CCC(=O)C1] | $^1$H NMR (400 MHz, Methanol-d4) δ 7.49-7.35 (m, 2H), 7.34-7.17 (m, 2H), 6.80 (td, J = 7.9, 1.8 Hz, 1H), 6.38 (ddd, J = 7.7, 2.7, 0.8 Hz, 1H), 6.16 (ddd, J = 8.2, 5.9, 0.8 Hz, 1H), 3.45 (d, J = 8.6 Hz, 2H), 3.05-2.59 (m, 1H), 2.21-1.83 (m, 3H), 1.14-0.91 (m, 6H). LCMS m/z 460.5 [M + H]$^+$. |

TABLE 5-continued
| Preparation of Compounds 88-177 | | | |
|---|---|---|---|
| Compound | Method/Product | Ketone | $^1$H NMR; LCMS m/z |
| 174 | From S6 according to Standard procedures A and B[a,b] 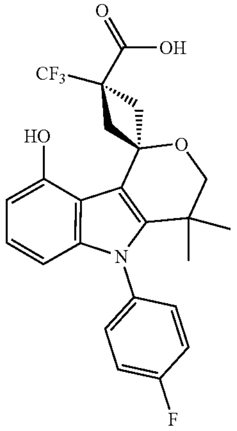 [SMILES: CC1(C)CO[C@]2(C[C@](C(=O)O)(C(F)(F)F)C2)c2c1n(-c1ccc(F)cc1)c1cccc(O)c12] 174 | 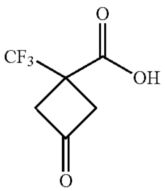 [SMILES: O=C1CC(C(=O)O)(C(F)(F)F)C1] | $^1$H NMR (400 MHz, Methanol-d4) δ 7.48-7.25 (m, 4H), 6.85 (dd, J = 8.2, 7.7 Hz, 1H), 6.45 (dd, J = 7.7, 0.8 Hz, 1H), 6.16 (dd, J = 8.2, 0.8 Hz, 1H), 3.77-3.61 (m, 2H), 3.45 (s, 2H), 2.87-2.73 (m, 2H), 1.07 (s, 6H). LCMS m/z 464.5 [M + H]$^+$. |
| 175 | From S6 according to Standard procedures A and B[a,k,u] 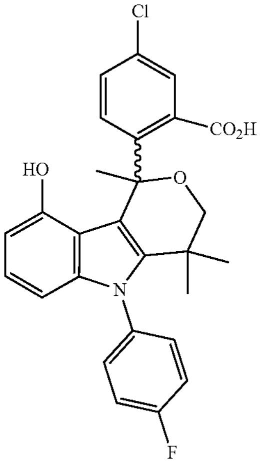 [SMILES: CC1(C)COC(C)(c2ccc(Cl)cc2C(=O)O)c2c1n(-c1ccc(F)cc1)c1cccc(O)c21] | 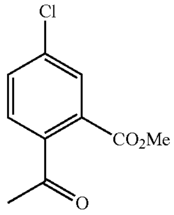 | $^1$H NMR (400 MHz,) δ 7.55 (d, J = 8.6 Hz, 1H), 7.46-7.13 (m, 6H), 6.85 (t, J = 8.0 Hz, 1H), 6.46 (d, J = 7.7 Hz, 1H), 6.15 (d, J = 8.1 Hz, 1H), 3.24 (s, 2H), 2.25 (s, 3H), 1.31 (s, 3H), 0.67 (s, 3H). LCMS m/z 480.34 [M + H]$^+$. |

TABLE 5-continued

Preparation of Compounds 88-177

| Compound | Method/Product | Ketone | $^1$H NMR; LCMS m/z |
| --- | --- | --- | --- |
| 176 | From S6 according to Standard procedures A and B[a,c,j] 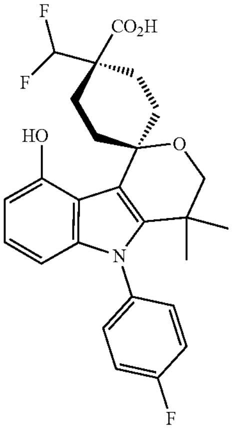 | 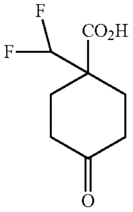 S21 | $^1$H NMR (400 MHz, Methanol-d4) δ 7.38 (ddt, J = 8.3, 5.5, 2.7 Hz, 2H), 7.33-7.26 (m, 2H), 6.84-6.79 (m, 1H), 6.72 (t, J = 55.7 Hz, 1H), 6.41 (dd, J = 7.7, 0.8 Hz, 1H), 6.18 (dd, J = 8.2, 0.9 Hz, 1H), 3.50 (s, 2H), 2.80 (td, J = 14.3, 4.2 Hz, 2H), 2.16 (t, J = 14.1 Hz, 2H), 2.02 (d, J = 13.2 Hz, 2H), 1.85 (d, J = 14.6 Hz, 2H), 1.06 (s, 6H). LCMS m/z 474.19 $[M + H]^+$. |
| 177 | From S6 according to Standard procedures A and B[a,c,j] 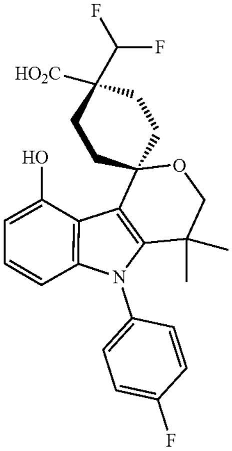 | 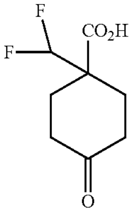 S21 | $^1$H NMR (400 MHz, Methanol-d4) δ 7.42-7.38 (m, 2H), 7.34-7.29 (m, 2H), 6.83-6.79 (m, 1H), 6.40 (dd, J = 7.7, 0.8 Hz, 1H), 6.16 (dd, J = 8.2, 0.9 Hz, 1H), 5.80 (t, J = 56.6 Hz, 1H), 5.51 (s, 1H), 3.51 (s, 2H), 2.95-2.89 (m, 2H), 2.09 (d, J = 12.7 Hz, 2H), 1.98 (td, J = 13.1, 4.0 Hz, 2H), 1.83 (d, J = 14.1 Hz, 2H), 1.08 (s, 6H). LCMS m/z 474.15 $[M + H]^+$. |

aStandard procedure A modified by replacing DCE with dichloromethane.

[b]Standard Procedure B modified by replacing ammonium formate with hydrogen and replacing Pd/C with $Pd(OH)_2$ and using MeOH or EtOAc as solvent or MeOH and EtOAc as co-solvents.

[c]Standard procedure A modified by removing $Et_3SiH$.

[d]Before the debenzylation step, the ester was hydrolyzed using the same procedure as described for the synthesis of compound C55, with the following modifications: THF, MeOH and water as solvents, LiOH as base for 2 h at temperatures between room temperature and 70° C. on a hotplate or in the microwave.

[e]Standard Procedure B modified by using MeOH as the only solvent and heating to somewhere in the range of 40-60° C.

[f]Standard procedure B modified by using EtOH and THF as solvents and heating to somewhere in the range of 40-60° C.

[g]Standard procedure B modified by using MeOH and THF as solvents and heating to somewhere in the range of 40-60° C.

[h]Standard Procedure B modified by using EtOH as the only solvent.

[i]Standard procedure B modified by using the $BBr_3$ in dichloromethane conditions as described for the synthesis compounds 5 and 6.

[j]Standard Procedure B modified by replacing ammonium formate with hydrogen and using MeOH as solvent or MeOH and EtOAc as co-solvents.

[k]Standard Procedure B modified by replacing ammonium formate with hydrogen and using EtOH or THF as solvent or EtOH and THF as co-solvents.

[l]Standard Procedure B modified by replacing ammonium formate with hydrogen and using THF as solvent.

[m]Standard Procedure B modified by replacing ammonium formate with hydrogen and replacing Pd/C with $Pd(OH)_2$ and using MeOH and THF as solvents.

[n]Before the debenzylation step, the ester was hydrolyzed using the same procedure as described for the synthesis of compound C55, with the following modifications: THF as solvent or THF and MeOH as co-solvents, 3M NaOH, at a temperature between room temperature and 50° C.

[o]Standard Procedure B modified by replacing ammonium formate with hydrogen gas

[p]Using methanamine (2M in THF) instead of ammonium hydroxide.

[q]1 mL of TFA was added on completion of the reductive alkylation reaction and the mixture stirred for 10 min.

[r]The enantiomers of the reductive alkylation step racemic product were separated by chiral SFC and each taken on in the benzyl deprotection step separately.

TABLE 5-continued

| Preparation of Compounds 88-177 | | | |
|---|---|---|---|
| Compound | Method/Product | Ketone | $^1$H NMR; LCMS m/z |

[s]Using dimethylamine (40 wt % in water) instead of ammonium hydroxide.

[t]Before the debenzylation step, the ester was hydrolyzed using the same procedure as described for the synthesis of compound C55, with the following modifications: dichloromethane and MeOH as solvents, LiOH as base at room temperature.

[u]Before the debenzylation step, the ester was hydrolyzed using the same procedure as described for the synthesis of compound C55, with the following modifications: MeOH as solvent, 6M NaOH at 120° C. in the microwave.

Compound 178

(1S,3S)-5'-(4-fluorophenyl)-9'-hydroxy-3,4',4'-trimethyl-4',5'-dihydro-3'H-spiro[cyclobutane-1,1'-pyrano[4,3-b]indole]-3-carboxamide (178)

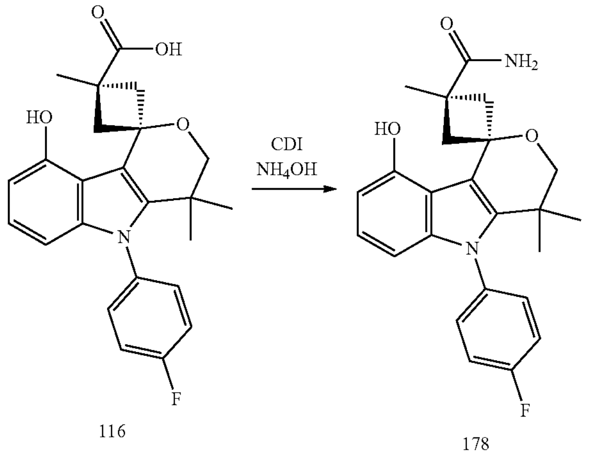 [SMILES: CC1(C)CO[C@]2(C[C@@](C)(C(=O)O)C2)c2c1n(-c1ccc(F)cc1)c1cccc(O)c12 ; CC1(C)CO[C@]2(C[C@@](C)(C(N)=O)C2)c2c1n(-c1ccc(F)cc1)c1cccc(O)c12]

116 178

A flask was charged with (1S,3S)-5'-(4-fluorophenyl)-9'-hydroxy-3,4',4'-trimethyl-4',5'-dihydro-3'H-spiro[cyclobutane-1,1'-pyrano[4,3-b]indole]-3-carboxylic acid 111 (96 mg, 0.235 mmol) and CDI (130 mg, 0.802 mmol) then THE (2 mL) and the mixture stirred at room temperature. After 4 h, ammonium hydroxide (500 μL of 28% w/v, 4.0 mmol) was added at room temperature. After 40 min, brine and EtOAc was added and the layers separated. The combined organics were dried ($Na_2SO_4$), filtered and concentrated. Ether was added, the mixture sonicated and then filtered off a white solid. Further purification by column chromatography (C18 AQ 40 g column; aq. TFA/MeCN). The pure fractions were partially concentrated, water added and the mixture extracted with EtOAc. The layers were separated. The aqueous layer was re-extracted with EtOAc and the combined organics concentrated. EtOAc was added and the product 178 was filtered off (27.9 mg, 28%). $^1$H NMR (400 MHz, DMSO-$d_6$) δ 9.87 (s, 1H), 7.50-7.36 (m, 4H), 7.13 (s, 1H), 6.84-6.77 (m, 1H), 6.64 (s, 1H), 6.47 (dd, J=7.7, 0.9 Hz, 1H), 6.08 (dd, J=8.2, 0.8 Hz, 1H), 3.29 (s, 2H), 2.93-2.83 (m, 2H), 2.69-2.60 (m, 2H), 1.46 (s, 3H), 0.96 (s, 6H). LCMS m/z 409.13 [M+H]$^+$.

Compound 179

(1S,3S)-8'-Chloro-5'-(4-fluorophenyl)-9'-hydroxy-3,4',4'-trimethyl-4',5'-dihydro-3'H-spiro[cyclobutane-1,1'-pyrano[4,3-b]indole]-3-carboxylic acid (179)

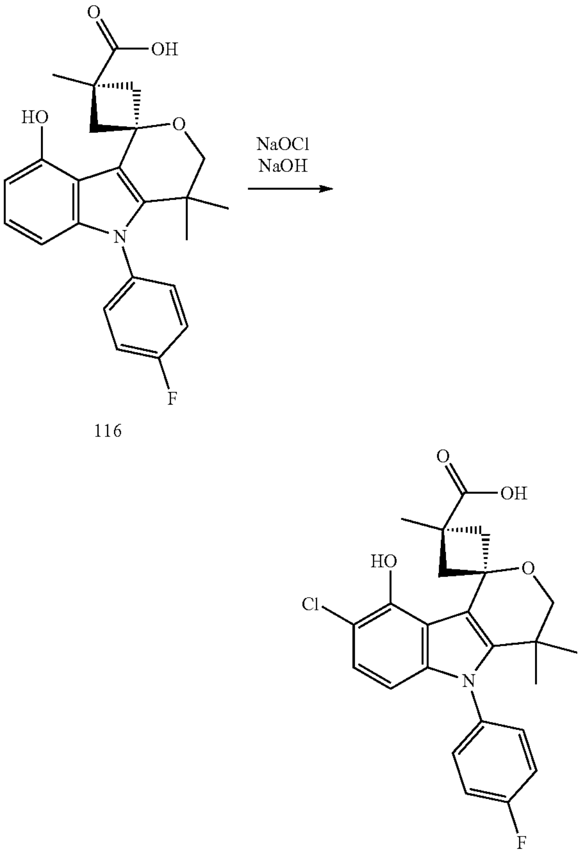

116

179

To (1S,3S)-5'-(4-fluorophenyl)-9'-hydroxy-3,4',4'-trimethyl-4',5'-dihydro-3'H-spiro[cyclobutane-1,1'-pyrano[4,3-b]indole]-3-carboxylic acid 116 (48 mg, 0.117 mmol) in a 2-dram vial was added NaOH (1.5 mL of 1 M, 1.5 mmol) which dissolved the solid. Within 1 min, sodium hypochlorite (300 μL of 5% w/v, 0.202 mmol) was added and the reaction immediately went a tan color. After 10 min, water (3 mL) was added followed by HCl (3 mL of a 1 M solution, 3 mmol) and the mixture was extracted with dichloromethane ×3. The layers were separated with the aid of a phase separator and the combined organics concentrated. Purification was achieved by column chromatography (C18 50 g column; aq. TFA/MeCN). Pure fractions were partially concentrated and the mixture extracted with dichloromethane. The layers were separated with the aid of a phase separator cartridge. The aqueous layer was re-extracted with dichloromethane and the combined organics concentrated. Trituration with EtOAc gave a white solid which was dried on a frit. 8-chloro-5-(4-fluorophenyl)-9-hydroxy-1',4,4-trimethyl-spiro[3H-pyrano[4,3-b]indole-1,3'-cyclobutane]-1'-carboxylic acid (179) (2.2 mg, 4%). $^{1}$H NMR (400 MHz, DMSO-$d_6$) δ 11.90 (s, 1H), 9.62 (s, 1H), 7.53-7.46 (m, 2H), 7.45-7.37 (m, 2H), 6.98 (d, J=8.7 Hz, 1H), 6.16 (d, J=8.7 Hz, 1H), 3.32 (s, 2H), 2.92 (d, J=11.4 Hz, 2H), 2.69-2.60 (m, 2H), 1.51 (s, 3H), 0.96 (s, 6H). LCMS m/z 444.24 $[M+H]^{+}$. X-ray crystallography confirmed ortho-chlorination.

Compounds 180-185

Compounds 180-185 were prepared from S7 and the appropriate ketone.

TABLE 6

Preparation of Compounds 180-185

| Compound | Method/Product | Ketone | $^{1}$H NMR; LCMS m/z |
|---|---|---|---|
| 180 | From S7 according to Standard procedures A and B[a, b, c] 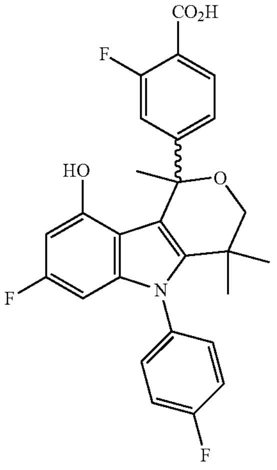 | 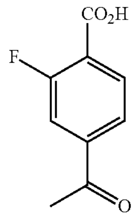 | $^{1}$H NMR (400 MHz, Methanol-d4) δ 8.37 (s, 1H), 7.71 (t, J = 7.9 Hz, 1H), 7.57-7.42 (m, 1H), 7.42-7.25 (m, 3H), 7.17 (dd, J = 12.4, 1.7 Hz, 1H), 6.19 (dd, J = 11.2, 2.2 Hz, 1H), 5.89 (dd, J = 9.5, 2.2 Hz, 1H), 3.26 (d, J = 5.9 Hz, 2H), 2.11 (s, 3H), 1.31 (s, 3H), 0.81 (s, 3H). LCMS m/z 482.2 $[M + H]^{+}$. |
| 181 | From S7 according to Standard procedures A and B[a, b, c] 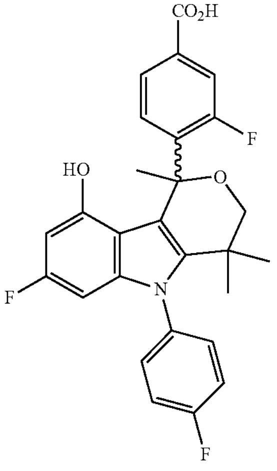 | 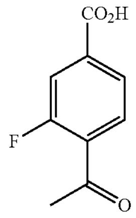 | $^{1}$H NMR (400 MHz, Methanol-d4) δ 7.76-7.56 (m, 2H), 7.54-7.44 (m, 2H), 7.42-7.19 (m, 3H), 6.18 (dd, J = 11.1, 2.2 Hz, 1H), 5.90 (dd, J = 9.6, 2.2 Hz, 1H), 3.25 (d, J = 11.3 Hz, 2H), 2.25 (d, J = 1.7 Hz, 2H), 2.03 (s, 1H), 1.33 (s, 3H), 0.80 (s, 3H). LCMS m/z 482.1 $[M + H]^{+}$. |

TABLE 6-continued

| Compound | Method/Product | Ketone | $^1$H NMR; LCMS m/z |
|---|---|---|---|
| Preparation of Compounds 180-185 | | | |
| 182 | Racemic 181 was separated by chiral SFC 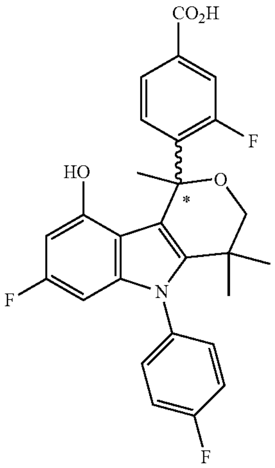 | N/A | $^1$H NMR (400 MHz, Chloroform-d) δ 7.68 (d, J = 12.4 Hz, 1H), 7.57 (d, J = 8.1 Hz, 1H), 7.48-7.38 (m, 2H), 7.24 (ddt, J = 11.5, 5.9, 2.6 Hz, 3H), 6.24 (dd, J = 10.9, 2.2 Hz, 1H), 6.00 (dd, J = 9.4, 2.2 Hz, 1H), 3.49-3.18 (m, 2H), 2.28 (d, J = 1.5 Hz, 3H), 1.32 (s, 3H), 0.79 (s, 3H). LCMS m/z 482.2 $[M + H]^+$. |
| 183 | Racemic 181 was separated by chiral SFC. This is the enantiomer of 182 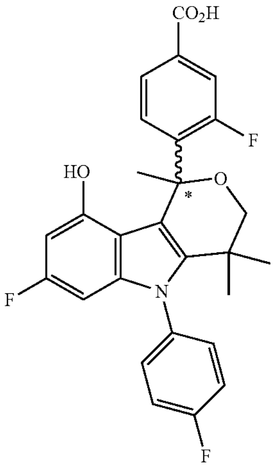 | N/A | $^1$H NMR (400 MHz, Ethanol-d6) δ 7.68-7.39 (m, 4H), 7.34 (ddt, J = 11.0, 6.4, 2.2 Hz, 2H), 7.19 (t, J = 8.0 Hz, 1H), 6.17 (dd, J = 11.2, 2.2 Hz, 1H), 5.89 (dd, J = 9.6, 2.2 Hz, 1H), 3.28 (d, J = 2.1 Hz, 2H), 2.25 (d, J = 1.6 Hz, 3H), 1.33 (s, 3H), 0.79 (s, 3H). LCMS m/z 482.0 $[M + H]^+$. |

TABLE 6-continued

| Preparation of Compounds 180-185 | | | |
|---|---|---|---|
| Compound | Method/Product | Ketone | $^1$H NMR; LCMS m/z |
| 184 | From S7 according to Standard procedures A and B[a, b, c] 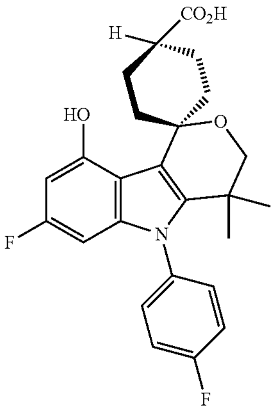 | 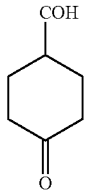 | $^1$H NMR (400 MHz, Methanol-d4) δ 7.48-7.21 (m, 4H), 6.21 (dd, J = 11.1, 2.2 Hz, 1H), 5.83 (dd, J = 9.6, 2.2 Hz, 1H), 3.48 (s, 2H), 2.85-2.59 (m, 2H), 2.44 (m, 1H), 2.03 (m, 1H), 1.98-1.67 (m, 6H), 1.04 (s, 6H). LCMS m/z 442.0 [M + H]$^+$. |
| 185 | From S7 according to Standard procedures A and B[a, b, c] 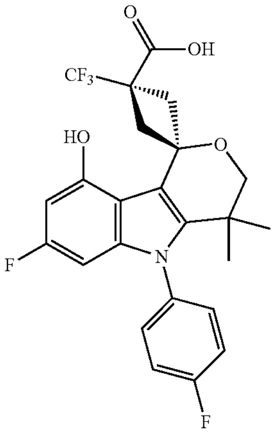 | 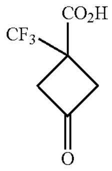 | $^1$H NMR (400 MHz, Methanol-d4) δ 7.49-7.17 (m, 4H), 6.24 (dd, J = 11.1, 2.2 Hz, 1H), 5.82 (dd, J = 9.5, 2.2 Hz, 1H), 3.68-3.51 (m, 2H), 3.41 (s, 2H), 2.84-2.73 (m, 2H), 2.03 (s, 1H), 1.03 (s, 6H). LCMS m/z 482.0 [M + H]$^+$. |

[a]Standard procedure A modified by replacing DCE with dichloromethane.

[b]Standard procedure A modified by removing $Et_3SiH$.

[c]Standard procedure B modified by using EtOH and THF as solvents and heating at a temperature in the range of 50-55° C.

Compounds 186-189

Compounds 186-189 were prepared from S8 and the appropriate ketone.

TABLE 7

Preparation of Compounds 186-189

| Compound | Method/Product | Ketone | $^1$H NMR; LCMS m/z |
|---|---|---|---|
| 186 | From S8 according to Standard procedures A and B[a, b] 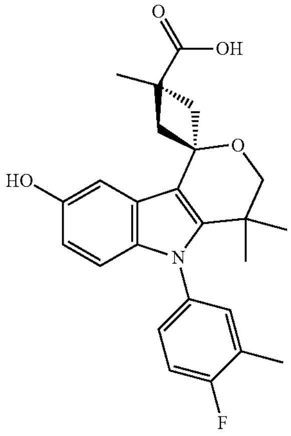 | 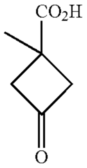 | $^1$H NMR (300 MHz, DMSO-d6) δ 12.16 (br s, 1H), 8.91 (br s, 1H), 7.40-7.22 (m, 3H), 7.04 (d, J = 1.9 Hz, 1H), 6.59-6.50 (m, 2H), 3.30 (s, 2H), 2.78-2.53 (m, 4H), 2.29 (d, J = 1.9 Hz, 3H), 1.61 (s, 3H), 0.97 (d, J = 1.9 Hz, 6H). LCMS m/z 424.21 [M + H]$^+$. |
| 187 | From S8 according to Standard procedures A and B[a, b] 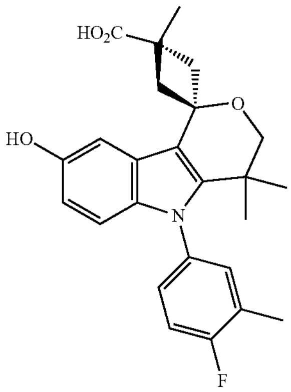 | 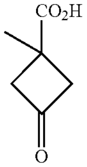 | $^1$H NMR (300 MHz, DMSO-d6) δ 12.42 (s, 1H), 8.78 (s, 1H), 7.40-7.26 (m, 3H), 7.10 (d, J = 2.2 Hz, 1H), 6.59 (dd, J = 8.7, 2.2 Hz, 1H), 6.50 (d, J = 8.7 Hz, 1H), 3.41 (s, 2H), 3.08 (d, J = 12.6 Hz, 2H), 2.29 (d, J = 1.9 Hz, 3H), 2.17-2.10 (m, 2H), 1.61 (s, 3H), 1.00 (d, J = 2.1 Hz, 6H). LCMS m/z 424.26 [M + H]$^+$. |

TABLE 7-continued

Preparation of Compounds 186-189

| Compound | Method/Product | Ketone | $^1$H NMR; LCMS m/z |
|---|---|---|---|
| 188 | From S8 according to Standard procedures A and B[a, b] 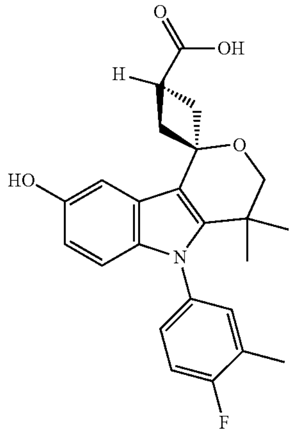 | 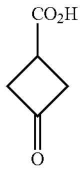 | $^1$H NMR (400 MHz, DMSO-d6) δ 12.27 (br s, 1H), 8.84 (s, 1H), 7.41-7.24 (m, 3H), 7.03 (d, J = 2.0 Hz, 1H), 6.60-6.49 (m, 2H), 3.37 (s, 2H), 3.36-3.26 (m, 1H), 2.91-2.83 (m, 2H), 2.61-2.54 (m, 2H), 2.29 (d, J = 1.8 Hz, 3H), 0.98 (d, J = 1.9 Hz, 6H). LCMS m/z 410.21 $[M + H]^+$. |
| 189 | From S8 according to Standard procedures A and B[a, b] 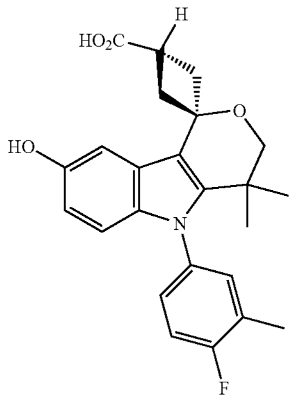 | 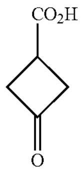 | $^1$H NMR (400 MHz, DMSO-d6) δ 12.33 (br s, 1H), 8.87 (s, 1H), 7.41-7.25 (m, 3H), 7.14 (d, J = 2.1 Hz, 1H), 6.59 (dd, J = 8.7, 2.2 Hz, 1H), 6.52 (d, J = 8.7 Hz, 1H), 3.41 (s, 2H), 3.30-3.22 (m, 1H), 2.86 (t, J = 10.4 Hz, 2H), 2.40 (dd, J = 12.6, 9.1 Hz, 2H), 2.29 (d, J = 1.8 Hz, 3H), 1.00 (d, J = 2.4 Hz, 6H). LCMS m/z 410.17 $[M + H]^+$. |

[a]Standard procedure A modified by removing $Et_3SiH$ and heating at 45° C.

[b]Standard procedure B modified by using the $BBr_3$ in dichloromethane conditions as described for the synthesis compounds 7 and 8.

Compound 190 and Compound 191

Compounds 190-191 Prepared from S9 and the appropriate ketone.

TABLE 8

Preparation of Compounds 190-191

| Compound | Method/Product | Ketone | $^1$H NMR; LCMS m/z |
|---|---|---|---|
| 190 | From S9 according to Standard procedure A[a, b] 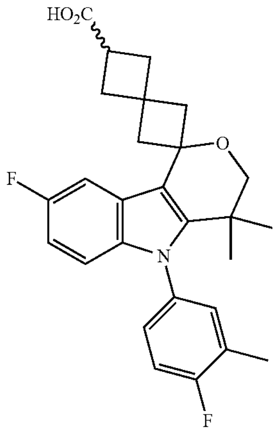 | 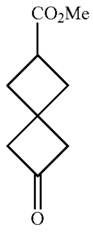 [SMILES: COC(=O)C1CC2(CC(=O)C2)C1] | $^1$H NMR (400 MHz, DMSO-d6) δ 12.06 (s, 2H), 7.47-7.28 (m, 3H), 7.19 (dd, J = 9.9, 2.5 Hz, 1H), 6.91 (td, J = 9.1, 2.6 Hz, 1H), 6.71 (dd, J = 8.9, 4.6 Hz, 1H), 3.57 (s, 1H), 3.39 (s, 1H), 3.07 (d, J = 2.2 Hz, 3H), 3.02 (t, J = 8.4 Hz, 1H), 2.79-2.64 (m, 2H), 2.46-2.23 (m, 5H), 2.20-2.07 (m, 2H), 1.85-1.71 (m, 1H), 1.11 (s, 6H). LCMS m/z 452.26 $[M + H]^+$. |
| 191 | From S9 according to Standard procedure A 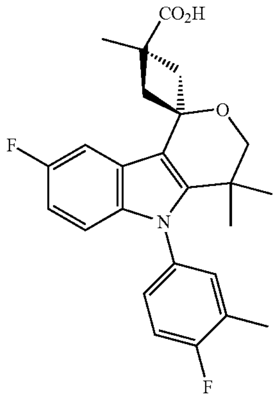 | 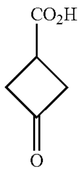 | $^1$H NMR (400 MHz, DMSO-d6) δ 12.22 (s, 1H), 7.49-7.29 (m, 4H), 6.92 (td, J = 9.2, 2.5 Hz, 1H), 6.71 (dd, J = 8.9, 4.6 Hz, 1H), 3.45 (td, J = 10.0, 5.2 Hz, 1H), 3.39 (s, 2H), 2.89 (dd, J = 13.4, 10.0 Hz, 2H), 2.58-2.45 (m, 2H), 2.30 (d, J = 1.9 Hz, 3H), 1.00 (d, J = 1.1 Hz, 6H). LCMS m/z 412.15 $[M + H]^+$. |

[a]Standard procedure A carried out at 50° C.

[b]The product from Standard procedure A was hydrolyzed using the same procedure as described for the synthesis of compound C47, with the following modifications: dioxane as solvent, aq. 1M LiOH as base at 160° C. in the microwave.

Compound 192

4-(9-(4-Fluorophenyl)-5-hydroxy-1,1,4-trimethyl-1,3,4,9-tetrahydropyrano[3,4-b]indol-4-yl)benzoic acid 192

Standard Synthetic Sequence A

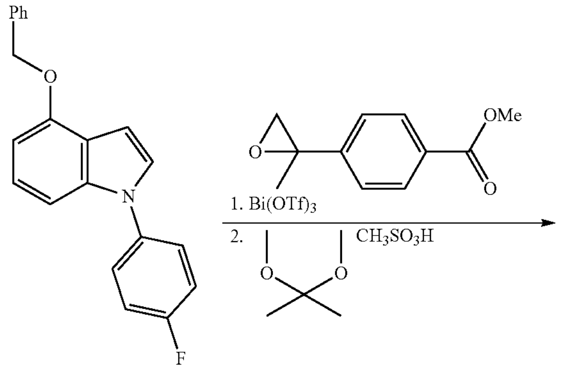

S10

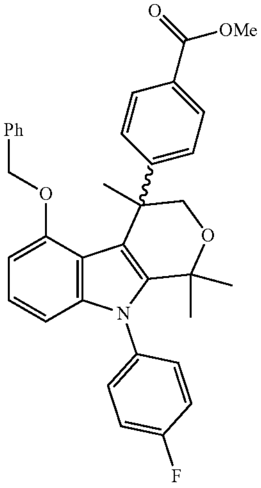

C91

LiOH

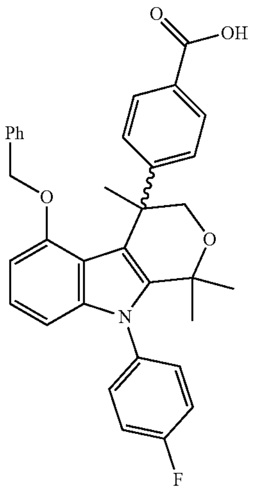

C92

$NH_4HCO_2H$
Pd/C

-continued

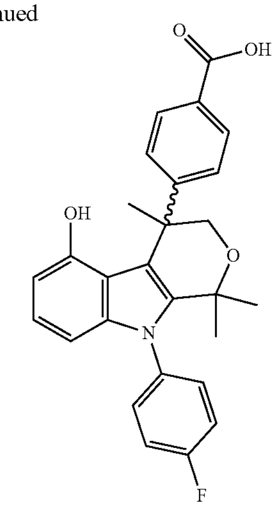

192

Standard Synthetic Sequence A

Step 1: Synthesis of methyl-4-(5-(benzyloxy)-9-(4-fluorophenyl)-1,1,4-trimethyl-1,3,4,9-tetrahydropyrano[3,4-b]indol-4-yl)benzoate (C91)

To a solution of 4-benzyloxy-1-(4-fluorophenyl)indole S10 (700 mg, 2.21 mmol) and bismuth(III) trifluromethanesulfonate (81 mg, 0.131 mmol) in dichloromethane (14 mL) at −10° C. was added a solution methyl 4-(2-methyloxiran-2-yl)benzoate (661 mg, 3.44 mmol) dropwise. The reaction was allowed to stir at −10° C. for 30 minutes. LC/MS indicated presence of desired epoxide opened product, quenched with sat. aq. $NaHCO_3$ and extracted with dichloromethane, concentrated and flushed through ISCO (40 g gold column) to afford crude methyl-4-[1-[4-benzyloxy-1-(4-fluorophenyl)indol-3-yl]-2-hydroxy-1-methyl-ethyl]benzoate (305 mg, 17%). LCMS m/z 510.08 $(M+H)^+$. To a solution of methyl 4-[1-[4-benzyloxy-1-(4-fluorophenyl)indol-3-yl]-2-hydroxy-1-methyl-ethyl]benzoate (300 mg, 0.3648 mmol) in dichloromethane (3 mL) was added 2,2-dimethoxypropane (300.0 μL, 2.440 mmol) and methanesulfonic acid (30.0 μL, 0.4623 mmol). The mixture was allowed to stir at 25° C. for 16 h. The mixture was quenched with saturated aqueous $NaHCO_3$, extracted with dichloromethane, concentrated and purified using ISCO (24 g gold column; 0-60% ethyl acetate in heptane to afford methyl-4-[5-benzyloxy-9-(4-fluorophenyl)-1,1,4-trimethyl-3H-pyrano[3,4-b]indol-4-yl]benzoate (C91) (174 mg, 73%). $^1H$ NMR (400 MHz, Chloroform-d) δ 7.79-7.54 (m, 2H), 7.36-7.25 (m, 2H), 7.20-7.02 (m, 8H), 6.87 (t, J=8.0 Hz, 1H), 6.84-6.69 (m, 2H), 6.48-6.13 (m, 2H), 4.72 (d, J=11.8 Hz, 1H), 4.46 (d, J=11.7 Hz, 1H), 3.82 (s, 3H), 3.75-3.60 (m, 1H), 1.79 (s, 3H), 1.33 (s, 3H), 1.26 (s, 3H). LCMS m/z 550.03 $(M+H)^+$ Step 2: Synthesis of 4-[5-benzyloxy-9-(4-fluorophenyl)-1,1,4-trimethyl-3H-pyrano[3,4-b]indol-4-yl]benzoic acid (C92)

To a solution of methyl 4-[5-benzyloxy-9-(4-fluorophenyl)-1,1,4-trimethyl-3H-pyrano[3,4-b]indol-4-yl]benzoate C91 (170 mg, 0.309 mmol) in MeOH (1.5 mL), THE (2 mL) and water (750 μL) was added lithium hydroxide hydrate (132 mg, 3.15 mmol) and the mixture was heated at 80° C. for 2 hours. The mixture was evaporated, neutralized with HCl (2 M, 1.6 mL, 3.2 mmol) and back extracted with dichloromethane (3×40 ml). The dichloromethane layer was dried ($Na_2SO_4$) and concentrated to afford product C92 (165 mg, 81%). LCMS m/z 536.43 $[M+H]^+$.

Step 3: Synthesis of 4-[9-(4-fluorophenyl)-5-hydroxy-1,1,4-trimethyl-3H-pyrano[3,4-b]indol-4-yl] benzoic acid (192)

To a solution of 4-[5-benzyloxy-9-(4-fluorophenyl)-1,1,4-trimethyl-3H-pyrano[3,4-b]indol-4-yl]benzoic acid C92 (165 mg, 0.308 mmol) in EtOH (3 mL) and THE (1 mL) was added 10% Pd/C (70 mg, Degussa type, wet) and $NH_4CO_2H$ (180 mg, 2.86 mmol). The mixture was heated at 50° C. for 1 hr. The reaction mixture was filtered, concentrated and purified using 15.5 g reverse phase chromatography (15.5 g C18 column, formic acid modifier) to afford 4-[9-(4-fluorophenyl)-5-hydroxy-1,1,4-trimethyl-3H-pyrano[3,4-b]indol-4-yl]benzoic acid 192 (75 mg, 51%). $^1$H NMR (400 MHz, Methanol-d4) δ 7.95-7.77 (m, 2H), 7.48-7.34 (m, 4H), 7.20 (dddd, J=9.2, 7.8, 3.7, 2.1 Hz, 2H), 6.83 (t, J=7.9 Hz, 1H), 6.25 (ddd, J=20.4, 7.9, 0.8 Hz, 2H), 3.89-3.65 (m, 2H), 1.93 (s, 3H), 1.38 (s, 3H), 1.31 (s, 3H). LCMS m/z 446.24 $[M+H]^+$ Compounds 193-199

Compounds 193-199 were prepared from S10 or S11 and the appropriate epoxide and ketone/ketone equivalent.

TABLE 9

| Preparation of Compounds 193-199 | | | | |
|---|---|---|---|---|
| Compound | Method/Product | Epoxide | Ketone | $^1$H NMR; LCMS m/z |
| 193 | Racemic 192 was separated by chiral SFC 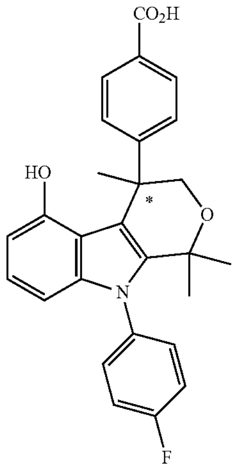 | N/A | N/A | $^1$H NMR (400 MHz, Chloroform-d) δ 7.87 (s, 2H), 7.28 (m, 4H), 7.12 (t, J = 8.5 Hz, 2H), 6.72 (s, 1H), 6.19 (s, 2H), 3.76 (d, J = 40.2 Hz, 1H), 3.45 (d, J = 90.4 Hz, 1H), 1.77 (d, J = 6.6 Hz, 3H), 1.33 (s, 3H), 1.21 (s, 3H). LCMS m/z 446.36 $[M + H]^+$. |
| 194 | From S10 according to Standard Synthetic Sequence A 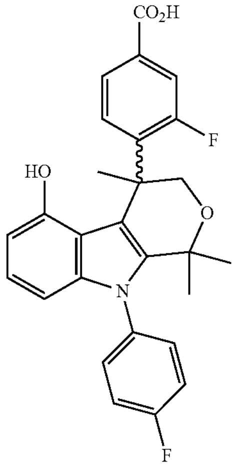 | 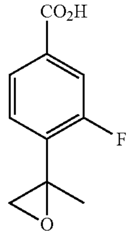 S22 | 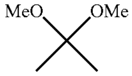 | $^1$H NMR (400 MHz, Methanol-d4) δ 7.70-7.52 (m, 2H), 7.48-7.34 (m, 2H), 7.36-7.20 (m, 3H), 6.82 (dd, J = 8.2, 7.7 Hz, 1H), 6.31 (dd, J = 7.7, 0.8 Hz, 1H), 6.17 (dd, J = 8.2, 0.8 Hz, 1H), 4.23 (d, J = 11.7 Hz, 1H), 3.87 (d, J = 11.6 Hz, 1H), 1.99 (d, J = 2.3 Hz, 3H), 1.37 (s, 3H), 1.30 (s, 3H). LCMS m/z 464.19 $[M + H]^+$. |

TABLE 9-continued

| Preparation of Compounds 193-199 | | | | |
|---|---|---|---|---|
| Compound | Method/Product | Epoxide | Ketone | $^1$H NMR; LCMS m/z |
| 195 | From S10 according to Standard Synthetic Sequence A 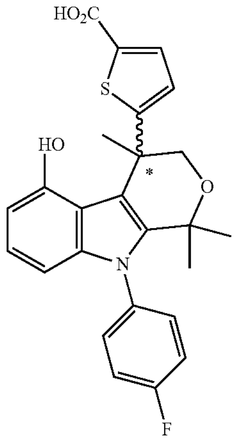 | 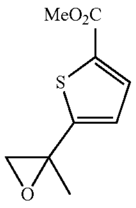 | 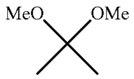 | $^1$H NMR (300 MHz, Chloroform-d) δ 7.44-7.24 (m, 2H), 7.10-6.97 (m, 3H), 6.81-6.58 (m, 2H), 6.20 (d, J = 7.5 Hz, 1H), 6.03 (dd, J = 8.6, 3.6 Hz, 1H), 3.97-3.77 (m, 1H), 3.71 (d, J = 4.3 Hz, 1H), 1.82 (d, J = 3.8 Hz, 3H), 1.20 (t, J = 5.6 Hz, 6H). LCMS m/z 452.14 [M + H]$^+$. |
| 196 | Racemic 195 was separated by chiral SFC 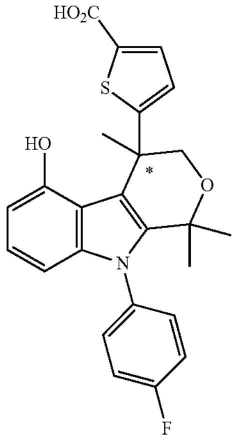 | N/A | N/A | $^1$H NMR (400 MHz, Chloroform-d) δ 7.59 (d, J = 33.9 Hz, 1H), 7.36 (s, 2H), 7.23 (t, J = 8.1 Hz, 2H), 6.87 (s, 2H), 6.41 (s, 1H), 6.28 (s, 1H), 3.85 (d, J = 44.3 Hz, 2H), 1.94 (s, 3H), 1.44 (s, 3H), 1.40- 1.28 (m, 3H). LCMS m/z 452.09 [M + H]$^+$. |

TABLE 9-continued
| Preparation of Compounds 193-199 | | | | |
|---|---|---|---|---|
| Compound | Method/Product | Epoxide | Ketone | $^1$H NMR; LCMS m/z |
| 197 | Racemic 195 was separated by chiral SFC 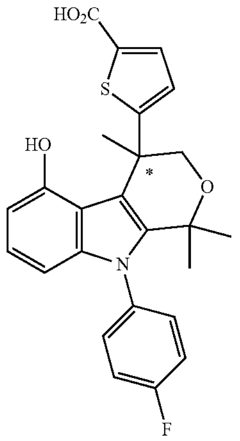 | N/A | N/A | $^1$H NMR (400 MHz, Chloroform-d) δ 7.59 (d, J = 33.9 Hz, 1H), 7.36 (s, 2H), 7.23 (t, J = 8.1 Hz, 2H), 6.87 (s, 2H), 6.41 (s, 1H), 6.28 (s, 1H), 3.85 (d, J = 44.3 Hz, 2H), 1.94 (s, 3H), 1.44 (s, 3H), 1.40-1.28 (m, 3H). LCMS m/z 452.09 $[M + H]^+$. |
| 198 | From S11 according to Standard Synthetic 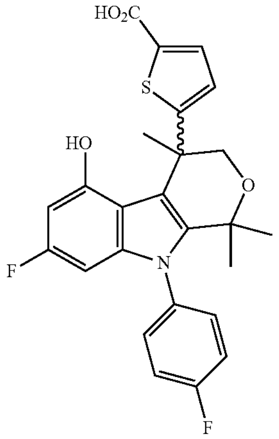 | 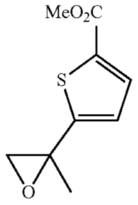 | 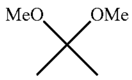 | $^1$H NMR (400 MHz, DMSO-d6) δ 10.02 (s, 1H), 7.57-7.31 (m, 5H), 6.91 (d, J = 3.8 Hz, 1H), 6.18 (dd, J = 11.4, 2.3 Hz, 1H), 5.89-5.76 (m, 2H), 3.99-3.65 (m, 2H), 1.90 (s, 3H), 1.29 (d, J = 18.8 Hz, 6H). LCMS m/z 470.13 $[M + H]^+$. |

TABLE 9-continued

| Preparation of Compounds 193-199 | | | | |
|---|---|---|---|---|
| Compound | Method/Product | Epoxide | Ketone | $^1$H NMR; LCMS m/z |
| 199 | From S10 according to Standard Synthetic Sequence A 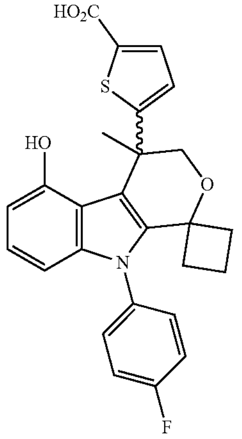 | 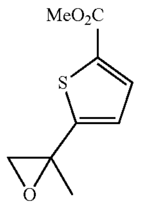 | 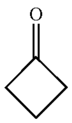 | $^1$H NMR (400 MHz, Chloroform-d) δ 7.76 (d, J = 3.9 Hz, 1H), 7.52 (dd, J = 8.4, 5.0 Hz, 2H), 7.35-7.29 (m, 2H), 7.04 (d, J = 3.9 Hz, 1H), 6.96 (dd, J = 8.3, 7.7 Hz, 1H), 6.42 (ddd, J = 17.3, 8.0, 0.8 Hz, 2H), 3.90-3.77 (m, 2H), 2.47-2.34 (m, 4H), 2.01 (s, 3H), 1.91-1.80 (m, 1H), 1.11-0.99 (m, 1H). LCMS m/z 464.10 $[M + H]^+$. |

Compound 200

Compound 200 was prepared from S12 and the appropriate ketone

TABLE 10

| Preparation of Compound 200 | | | |
|---|---|---|---|
| Compound | Method/Product | Ketone | $^1$H NMR; LCMS m/z |
| 200 | From S12 according to Standard procedures A and B[a, b] 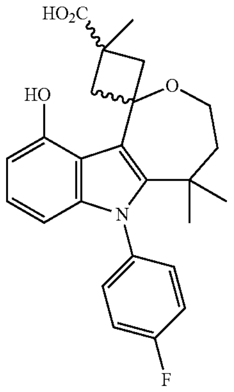 | 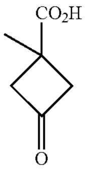 | $^1$H NMR (400 MHz, Chloroform-d) δ 7.44-7.35 (m, 2H), 7.27-7.20 (m, 2H), 6.92 (dd, J = 8.2, 7.7 Hz, 1H), 6.58-6.51 (m, 2H), 6.25 (dt, J = 8.3, 0.8 Hz, 1H), 4.14 (t, J = 7.1 Hz, 2H), 3.48-3.37 (m, 2H), 2.85-2.73 (m, 2H), 1.87 (t, J = 7.2 Hz, 2H), 1.47 (s, 3H), 1.33 (s, 6H). LCMS m/z 424.3 $[M + H]^+$. |

[a]Standard procedure A carried out at 60° C. in dichloromethane in a closed vial.

[b]Standard Procedure B modified by replacing ammonium formate with hydrogen and using EtOH as solvent.

Compound 201

9-(4-fluorophenyl)-5-hydroxy-1,1-dimethyl-2-oxo-1,2,3,9-tetrahydrospiro[carbazole-4,1'-cyclobutane]-3'-carboxylic acid (201)

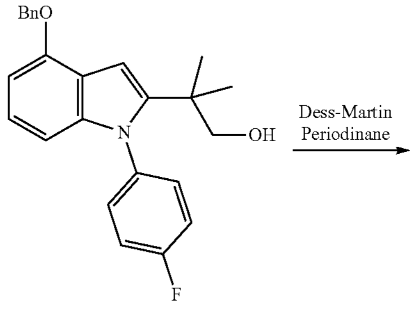

S6

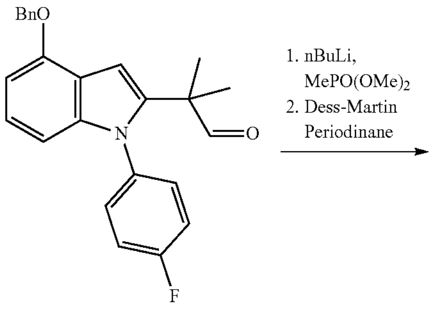

C93

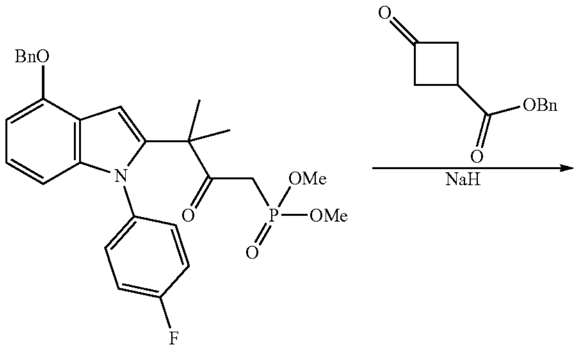

C94

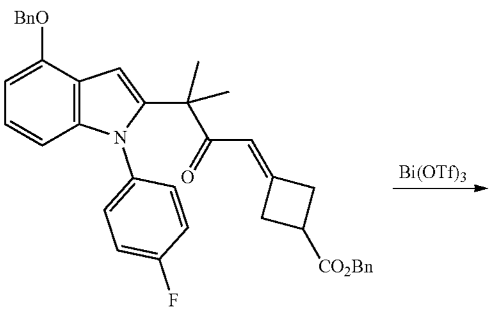

C95

-continued

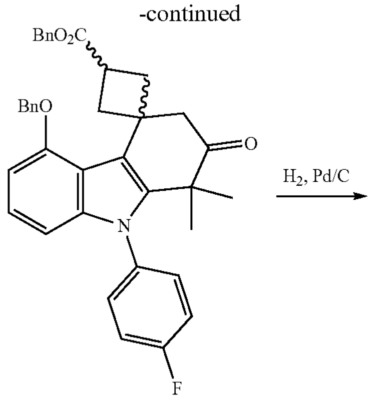

C96

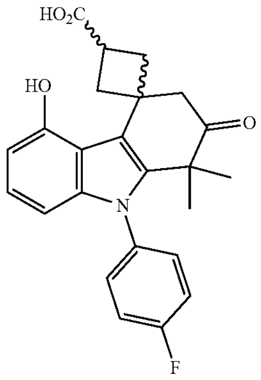

201

Step 1: Synthesis of 2-(4-(benzyloxy)-1-(4-fluorophenyl)-1H-indol-2-yl)-2-methylpropanal (C93)

To a mixture of S6 (7.24 g, 18.6 mmol) in dichloromethane (100 mL) was added Dess-Martin periodinane (10 g, 23.6 mmol) with ice-bath cooling. After a few minutes, the reaction mixture was removed from the cooling bath. After 3 h, the reaction was concentrated and then purified through a silica plug (200 g) with dichloromethane to give product C93 (6.3 g, 87%). $^1$H NMR (400 MHz, Chloroform-d) δ 9.55 (s, 1H), 7.59-7.53 (m, 2H), 7.49-7.43 (m, 2H), 7.41-7.36 (m, 1H), 7.27-7.17 (m, 4H), 7.05 (t, J=8.0 Hz, 1H), 6.83 (d, J=0.8 Hz, 1H), 6.65 (dd, J=7.8, 0.6 Hz, 1H), 6.43 (dt, J=8.3, 0.7 Hz, 1H), 5.28 (s, 2H), 1.39 (s, 6H).

Step 2: Synthesis of dimethyl (3-(4-(benzyloxy)-1-(4-fluorophenyl)-1H-indol-2-yl)-3-methyl-2-oxobutyl)phosphonate (C94)

A solution of [methoxy(methyl)phosphoryl]oxymethane (2.5 mL, 23.1 mmol) in THF (25 mL) was cooled to −78° C. and nBuLi (2.5M, 7.7 mL, 19.3 mmol) was added over 17 min. After 45 min, C93 (3 g, 7.74 mmol) in THF (11 mL) was added at −78° C. over 15 min. After stirring for a further 5 min at −78° C., the reaction mixture was placed in an ice bath. After 45 min, the reaction was quenched with sat aq. $NH_4Cl$. Ethyl acetate was added and the reaction mixture stood overnight. The next day water and EtOAc were added and a white insoluble material was filtered off. The filtrate layers were separated and the aq. layer extracted with EtOAc. The combined organics were dried ($Na_2SO_4$), filtered and concentrated.

To a solution of this residue in dichloromethane (80 mL) with ice bath cooling was added $NaHCO_3$ (780 mg, 9.29 mmol) then Dess-Martin periodinane (4.3 g, 10.1 mmol). After 75 min, sat. aq. sodium bicarbonate (100 mL) and 1M sodium thiosulfate (50 mL) were added and the mixture vigorously stirred for 15 min. The layers were separated with the aid of a phase separator. The aqueous layer was re-extracted with dichloromethane and the layers were separated through a phase separator again and the combined organics concentrated. Purification by column chromatography (120 g gold column; 20-75% EtOAc in heptane) gave product C94 (2.14 g, 54%). $^1H$ NMR (400 MHz, Chloroform-d) δ 7.58-7.53 (m, 2H), 7.47-7.42 (m, 2H), 7.41-7.35 (m, 1H), 7.26-7.14 (m, 4H), 7.04 (t, J=8.0 Hz, 1H), 6.85 (d, J=0.8 Hz, 1H), 6.64 (d, J=7.7 Hz, 1H), 6.42-6.37 (m, 1H), 5.26 (s, 2H), 3.74 (d, J=11.2 Hz, 6H), 3.11 (d, J=20.5 Hz, 2H), 1.42 (s, 6H). LCMS m/z 510.57 $[M+H]^+$.

Step 3: Synthesis of benzyl-3-(3-(4-(benzyloxy)-1-(4-fluorophenyl)-1H-indol-2-yl)-3-methyl-2-oxobutylidene)cyclobutane-1-carboxylate (C95)

To a suspension of NaH (60% w/w, 97 mg, 2.43 mmol) in THE (5 mL) was added C94 (1.13 g, 2.21 mmol) in THE (6 mL) over 5 min. A solution of benzyl 3-oxocyclobutanecarboxylate (454 mg, 2.22 mmol) in THE (2 mL) was added and the mixture heated at 50° C. overnight. Sat. aq. $NH_4Cl$ was added and the mixture extracted with EtOAc twice. The combined organics were concentrated and then purification by column chromatography (C18 AQ 100 g column; aq. TFA/MeCN) gave product C95 as a pale yellow sticky solid (524 mg, 40%). $^1H$ NMR (400 MHz, Chloroform-d) δ 7.58-7.53 (m, 2H), 7.47-7.40 (m, 2H), 7.39-7.31 (m, 5H), 7.19-7.13 (m, 2H), 7.13-7.04 (m, 2H), 7.01 (t, J=8.0 Hz, 1H), 6.82 (d, J=0.8 Hz, 1H), 6.63 (dd, J=7.9, 0.6 Hz, 1H), 6.41-6.38 (m, 1H), 6.19 (q, J=2.2 Hz, 1H), 5.26 (s, 2H), 5.19-5.11 (m, 2H), 3.41-3.26 (m, 3H), 3.10-2.94 (m, 2H), 1.42 (s, 3H), 1.33 (s, 3H). LCMS m/z 588.41 $[M+H]^+$.

Step 4: Synthesis of benzyl-5-(benzyloxy)-9-(4-fluorophenyl)-1,1-dimethyl-2-oxo-1,2,3,9-tetrahydrospiro[carbazole-4,1'-cyclobutane]-3'-carboxylate (C96)

To a solution of C95 (479 mg, 0.815 mmol) in deuterated MeCN (10 mL) was added bismuth triflate (130 mg, 0.210 mmol) at room temperature. After 2 hours, the reaction was concentrated. The residue was purified by column chromatography (C18 150 g column; aq. TFA/MeCN) and the relevant fractions concentrated. MeOH was added and product C96 as a pale yellow solid was filtered off (397 mg, 83%). LCMS m/z 588.41 $[M+H]^+$.

Step 5: Synthesis of 9-(4-fluorophenyl)-5-hydroxy-1,1-dimethyl-2-oxo-1,2,3,9-tetrahydrospiro[carbazole-4,1'-cyclobutane]-3'-carboxylic acid (201)

Carried out in accordance with Standard Procedure B from C96 but replacing ammonium formate with hydrogen gas and using MeOH, EtOAc and THE and solvents. 201 was obtained as a mixture of isomers. One isomer was annotated: $^1H$ NMR (400 MHz, DMSO-d6) δ 7.51 (dd, J=8.8, 5.1 Hz, 2H), 7.42 (t, J=8.7 Hz, 2H), 6.83 (t, J=7.9 Hz, 1H), 6.53 (d, J=7.7 Hz, 1H), 6.02 (d, J=8.1 Hz, 1H), 3.40-3.20 (m, 3H), 3.06 (s, 2H), 2.11 (m, 2H), 1.16 (s, 6H). LCMS m/z 408.27 $[M+H]^+$.

Compound 202

9-(4-fluorophenyl)-2,5-dihydroxy-1,1-dimethyl-1,2,3,9-tetrahydrospiro[carbazole-4,1'-cyclobutane]-3'-carboxylic acid (202)

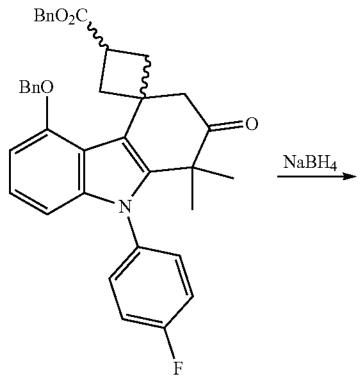

C96

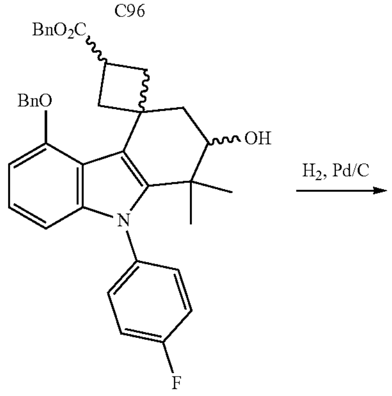

C97

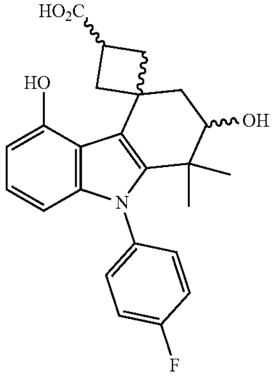

202

Step 1: Synthesis of benzyl5-(benzyloxy)-9-(4-fluorophenyl)-2-hydroxy-1,1-dimethyl-1,2,3,9-tetrahydrospiro[carbazole-4,1'-cyclobutane]-3'-carboxylate (C97)

To a solution of C96 (307 mg, 0.522 mmol) in 2-MeTHF (9 mL) was added sodium borohydride (80 mg, 2.12 mmol) at room temperature. After 5 h, 250 mg more reductant was added and stirring continued overnight. Water and EtOAc were added and the layers separated. The aqueous layer was re-extracted with EtOAc and the combined organics were dried ($Na_2SO_4$), filtered and concentrated to give product C97 as a straw-colored oil (308 mg, 100%). LCMS m/z 590.93 [M+H]$^+$.

Step 2: Synthesis of 9-(4-fluorophenyl)-2,5-dihydroxy-1,1-dimethyl-1,2,3,9-tetrahydrospiro[carbazole-4,1'-cyclobutane]-3'-carboxylic acid (202)

Carried out in accordance with Standard Procedure B from C97 but replacing ammonium formate with hydrogen gas and using THE as solvent giving two isomers of which 202 was biologically active (31 mg, 14%). $^1$H NMR (400 MHz, Methanol-d4) δ 7.42-7.24 (m, 4H), 6.80 (dd, J=8.2, 7.7 Hz, 1H), 6.45 (dd, J=7.6, 0.9 Hz, 1H), 6.07 (dd, J=8.2, 0.9 Hz, 1H), 3.57-3.44 (m, 2H), 3.42-3.33 (m, 1H), 2.96 (t, J=11.0 Hz, 1H), 2.44-2.35 (m, 2H), 2.26 (d, J=11.5 Hz, 1H), 2.08 (t, J=12.4 Hz, 1H), 1.15 (s, 3H), 0.97 (s, 3H). LCMS m/z 410.3 [M+H]$^+$.

Compound 203

(1S,3S)-5'-(4-fluoro-3-methylphenyl)-9'-hydroxy-3',3'-dimethyl-4',5'-dihydro-3'H-spiro[cyclobutane-1,1'-pyrano[4,3-b]indole]-3-carboxylic acid (203)

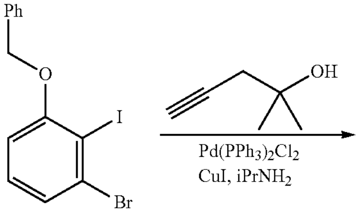

C2

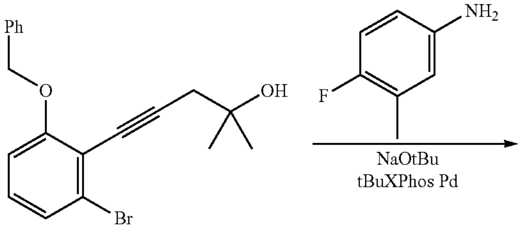

C98

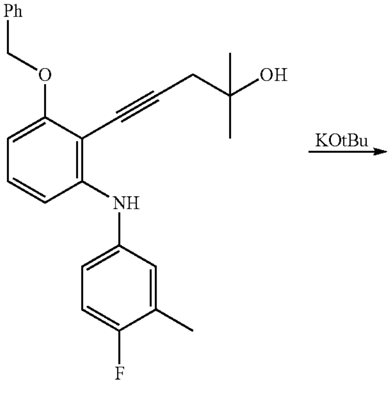

C99

-continued

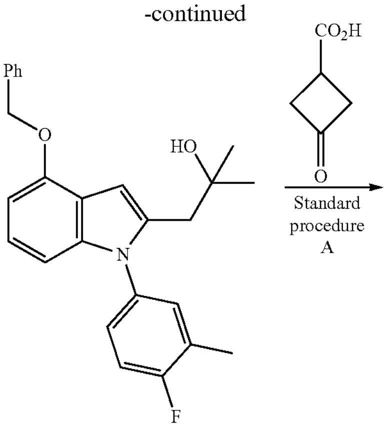

C100

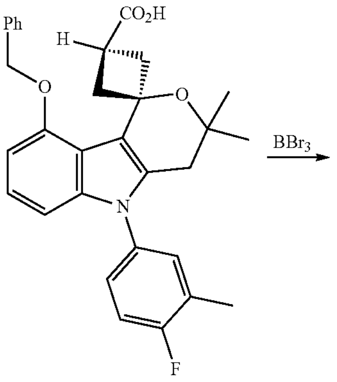

C101

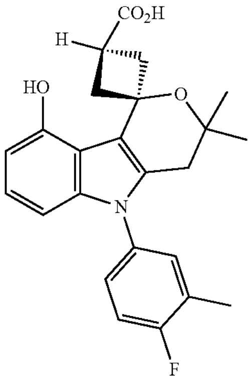

203

Step 1: Synthesis of 5-(2-(benzyloxy)-6-bromophenyl)-2-methylpent-4-yn-2-ol (C98)

A 20 mL dram vial with a red pressure relief cap was successively charged with 1-benzyloxy-3-bromo-2-iodobenzene C2 (3.51 g, 9.02 mmol), 2-methylpent-4-yn-2-ol (930 mg, 9.48 mmol) and then DMF (14 mL). Nitrogen gas was bubbled through the mixture for 15-20 min. To this solution, was added $Pd(PPh_3)_2Cl_2$ (410 mg, 0.584 mmol). CuI (172 mg, 0.903 mmol) was added then diethylamine (1.4 mL, 13.5 mmol) and the mixture was heated to 40° C. for 60 h. The reaction mixture was then directly loaded onto a reverse phase column for purification (C18 275 g column; 5-95% MeCN in aq. TFA). The pure fractions were combined and partially concentrated under reduced pressure. The mixture was extracted with ethyl acetate. The organic layers were combined and dried over sodium sulfate and then concentrated under reduced pressure to afford product C98 (2.01 g, 62%). $^1$H NMR (400 MHz, Chloroform-d) δ

7.40-7.20 (m, 5H), 7.11 (dd, J=8.1, 1.0 Hz, 1H), 6.98 (t, J=8.2 Hz, 1H), 6.77 (dd, J=8.4, 1.0 Hz, 1H), 5.06 (s, 2H), 2.61 (s, 2H), 2.20 (s, 1H), 1.27 (s, 6H).

Step 2: Synthesis of 5-(2-(benzyloxy)-6-((4-fluoro-3-methylphenyl)amino)phenyl)-2-methylpent-4-yn-2-ol (C99)

Nitrogen was bubbled through a solution of 5-(2-benzyloxy-6-bromo-phenyl)-2-methyl-pent-4-yn-2-ol C98 (2.01 g, 5.60 mmol) and 4-fluoro-2-methyl-aniline (840 mg, 6.71 mmol) in dioxane (4.5 mL) and t-BuOH (7.5 mL) for 10 min. Sodium t-butoxide (915 mg, 9.52 mmol) and tBuXphosPalladacycle (195 mg, 0.284 mmol) were added and bubbling was continued for another 5 min before the vial was placed on a heating block set at 45° C. overnight. Water and ethyl acetate were added. The aqueous layer was re-extracted with ethyl acetate and the organic layers were separated and dried over sodium sulfate. The combined organic layers were concentrated under reduced pressure. Purification by column chromatography (80 g column; 0-25% EtOAc in heptane) gave product C99 (2.26 g, 100%). $^1$H NMR (400 MHz, Chloroform-d) δ 7.58-7.54 (m, 1H), 7.51-7.33 (m, 4H), 7.19-6.93 (m, 4H), 6.84-6.63 (m, 2H), 6.55-6.38 (m, 1H), 5.28 (s, 1H), 5.14 (d, J=11.6 Hz, 1H), 2.86 (d, J=1.2 Hz, 1H), 2.71 (s, 1H), 2.37 (d, J=2.1 Hz, 1H), 2.29-2.25 (m, 1H), 2.22 (d, J=2.0 Hz, 1H), 1.31 (d, J=18.2 Hz, 5H), 1.17-1.12 (m, 3H), 1.08 (s, 1H).

Step 3: Synthesis of 1-(4-(benzyloxy)-1-(4-fluoro-3-methylphenyl)-1H-indol-2-yl)-2-methylpropan-2-ol (C100)

To a solution of C99 (2.26 g, 5.60 mmol) in 2-MeTHF (20 mL) was added potassium t-butoxide (5.6 mL of 1 M, 5.60 mmol) at room temperature and the reaction mixture stirred overnight. Ethyl acetate and water, brine and saturated ammonium chloride were added, the layers separated the organic layer dried over sodium sulfate and concentrated under reduced pressure. The crude product was purified via column chromatography (80 g gold Silica column, (0-100% ethyl acetate in heptane). Fractions 10-13 were combined to afford 980 mg of the indole product C100 (980 mg, 43%). $^1$H NMR (400 MHz, Chloroform-d) δ 7.56-7.51 (m, 2H), 7.44-7.31 (m, 3H), 7.13 (td, J=5.6, 3.0 Hz, 2H), 7.02 (t, J=8.0 Hz, 1H), 6.75-6.71 (m, 1H), 6.67 (d, J=8.3 Hz, 1H), 6.63 (d, J=7.8 Hz, 1H), 5.25 (s, 2H), 2.84 (s, 2H), 2.34 (d, J=2.0 Hz, 3H), 2.19 (d, J=2.0 Hz, 1H), 1.71 (s, 1H), 1.12 (d, J=1.6 Hz, 6H). LCMS m/z 404.27 [M+H]$^+$.

Step 4: Synthesis of (1S,3S)-9'-(benzyloxy)-5'-(4-fluoro-3-methylphenyl)-3',3'-dimethyl-4',5'-dihydro-3'H-spiro[cyclobutane-1,1'-pyrano[4,3-b]indole]-3-carboxylic acid (C101)

Carried out in accordance with Standard Procedure A from $C_{100}$ using 3-oxocyclobutanecarboxylic acid as ketone giving product C101 (58 mg, 49%). LCMS m/z 500.58 [M+H]$^+$.

Step 5: Synthesis of (1S,3S)-5'-(4-fluoro-3-methylphenyl)-9'-hydroxy-3',3'-dimethyl-4',5'-dihydro-3'H-spiro[cyclobutane-1,1'-pyrano[4,3-b]indole]-3-carboxylic acid (203)

To a solution of C101 (58 mg, 0.116 mmol) in dichloromethane (3.5 mL) at 0-5° C. was added $BBr_3$ (290 μL of 1 M, 0.290 mmol) dropwise over 3 min. After 15 min, the reaction was quenched with water. dichloromethane was added and the layers separated with a phase separator. The organics were concentrated. Purification by column chromatography (4 g GOLD column; 0-10% MeOH in dichloromethane) gave product 203 (10.7 mg, 21%). $^1$H NMR (400 MHz, Methanol-d4) δ 7.23-7.17 (m, 2H), 7.16-7.11 (m, 1H), 6.88 (dd, J=8.2, 7.6 Hz, 1H), 6.60 (dd, J=8.2, 0.9 Hz, 1H), 6.49 (dd, J=7.7, 0.8 Hz, 1H), 3.42-3.36 (m, 1H), 3.27-3.20 (m, 2H), 2.79-22.72 (i, 2H), 2.44 (s, 2H), 2.33 (d, J=2.0 Hz, 3H), 1.29 (s, 6H). LCMS m/z 410.16 [M+H]$^+$.

Compound 204

Compound 204 Prepared from $C_2$ and the appropriate alkyne using the same procedure as for compound 203.

TABLE 11

| Preparation of Compound 204 | | | |
|---|---|---|---|
| Compound | Method/Product | Alkyne | $^1$H NMR; LCMS m/z |
| 204 | Same procedure as for compound 203[a] 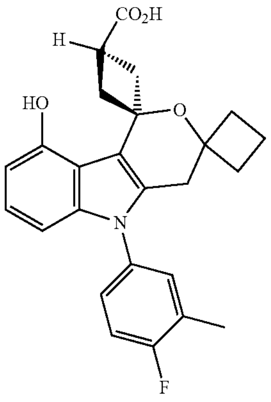 | 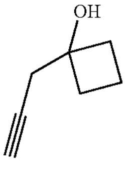 | $^1$H NMR (400 MHz, Methanol-d4) δ 7.26-7.13 (m, 3H), 6.92-6.85 (m, 1H), 6.60 (dd, J = 8.2, 0.8 Hz, 1H), 6.48 (dd, J = 7.7, 0.8 Hz, 1H), 3.36 (ddd, J = 10.3, 6.6, 4.5 Hz, 1H), 3.27-3.18 (m, 2H), 2.84-2.76 (m, 2H), 2.65 (s, 2H), 2.45-2.36 (m, 2H), 2.35 (d, J = 2.0 Hz, 3H), 1.89-1.77 (m, 3H), 1.62-1.51 (m, 1H). LCMS m/z 422.19 [M + H]$^+$. |

[a]For Step 5, standard procedure B was employed rather than the $BBr_3$ based method.

Compound 205 and Compound 206

Compounds 205-206 were prepared from S14 and the appropriate ketone

TABLE 12

Preparation of Compounds 205-206

| Compound | Method/Product | Ketone | $^1H$ NMR; LCMS m/z |
|---|---|---|---|
| 205 | From S14 according to Standard procedures A and B[a, b] 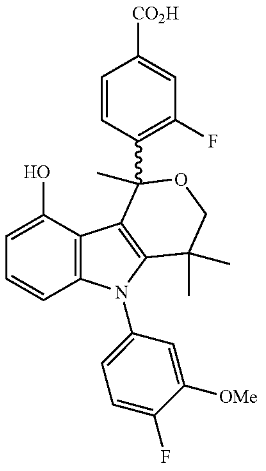 | 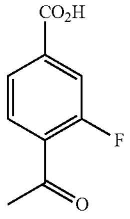 | $^1H$ NMR (400 MHz, Chloroform-d) δ 7.75 (dd, J = 12.1, 1.7 Hz, 1H), 7.63 (dt, J = 8.1, 1.7 Hz, 1H), 7.34 (dt, J = 10.4, 7.9 Hz, 1H), 7.20-7.16 (m, 1H), 7.01-6.95 (m, 2H), 6.95-6.89 (m, 1H), 6.42 (ddd, J = 8.2, 4.5, 0.8 Hz, 1H), 6.37 (dt, J = 7.6, 0.8 Hz, 1H), 3.84 (d, J = 4.6 Hz, 3H), 3.37-3.20 (m, 2H), 2.26 (dd, J = 3.8, 1.6 Hz, 3H), 1.33 (d, J = 4.7 Hz, 3H), 0.80 (d, J = 4.9 Hz, 3H). LCMSm/z 494.39 $[M + H]^+$. |
| 206 | From S14 according to Standard procedures A and B[a, b] 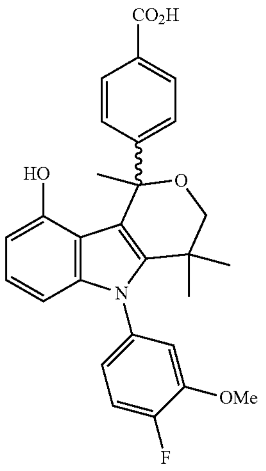 | 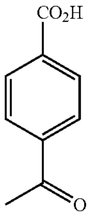 | $^1H$ NMR (400 MHz, Chloroform-d) δ 8.07 (d, J = 8.4 Hz, 2H), 7.73-7.66 (m, 2H), 7.29-7.23 (m, 1H), 7.08-7.02 (m, 2H), 6.99 (ddd, J = 8.3, 7.6, 1.7 Hz, 1H), 6.51-6.43 (m, 2H), 3.92 (d, J = 4.3 Hz, 3H), 3.33 (q, J = 11.3 Hz, 2H), 2.22 (d, J = 3.2 Hz, 3H), 1.38 (d, J = 1.9 Hz, 3H), 0.91 (d, J = 7.0 Hz, 3H). LCMS m/z 476.47 $[M + H]^+$. |

[a]Standard procedure A carried out in dichloromethane not DCE.

[b]Standard Procedure B modified by replacing ammonium formate with hydrogen and using MeOH as solvent.

Compound 207 and Compound 208

Compounds 207-208 were prepared from S16 and the appropriate ketone

TABLE 13

Preparation of Compounds 207-208

| Compound | Method/Product | Ketone | $^1H$ NMR; LCMS m/z |
|---|---|---|---|
| 207 | From S146 according to Standard procedures A and B[a, b, c] 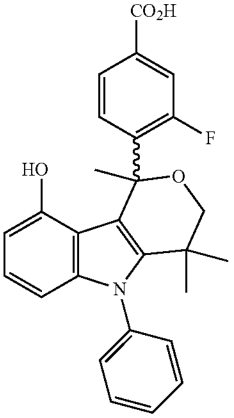 | 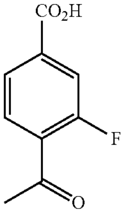 | $^1H$ NMR (400 MHz, Methanol-d4) δ 7.66 (dd, J = 12.6, 1.7 Hz, 1H), 7.57 (tdt, J = 5.6, 4.0, 2.3 Hz, 4H), 7.43 (dq, J = 7.0, 1.9 Hz, 2H), 7.31 (t, J = 8.0 Hz, 1H), 6.84 (t, J = 7.9 Hz, 1H), 6.37 (d, J = 7.6 Hz, 1H), 6.21 (d, J = 8.1 Hz, 1H), 3.34-3.22 (m, 2H), 2.30 (d, J = 1.7 Hz, 3H), 1.35 (s, 3H), 0.78 (s, 3H). LCMS m/z 446.36 $[M + H]^+$. |
| 208 | From S16 according to Standard procedures A and B[a, b] 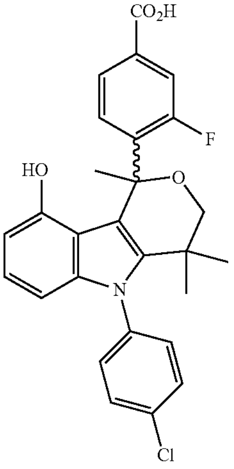 | 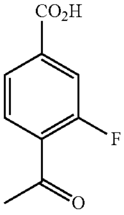 | $^1H$ NMR (400 MHz, Methanol-d4) δ 7.66 (dd, J = 12.5, 1.7 Hz, 1H), 7.65-7.54 (m, 3H), 7.45 (d, J = 8.5 Hz, 2H), 7.29 (t, J = 8.0 Hz, 1H), 6.87 (t, J = 8.0 Hz, 1H), 6.39 (d, J = 7.6 Hz, 1H), 6.23 (d, J = 8.2 Hz, 1H), 3.27 (d, J = 11.2 Hz, 2H), 2.29 (d, J = 1.6 Hz, 3H), 1.36 (s, 3H), 0.81 (s, 3H). LCMS m/z 480.48 $[M + H]^+$. |

[a]Standard procedure A carried out in dichloromethane not DCE.

[b]Standard Procedure B modified by replacing ammonium formate with hydrogen and using EtOH as solvent.

[b]This was a side product observed from over-reduction during the synthesis of compound 208.

Compound 209 and Compound 210

Compounds 209-210 were prepared from S15 and the appropriate ketone.

TABLE 14

Preparation of Compounds 209-210

| Compound | Method/Product | Ketone | $^1$H NMR; LCMS m/z |
|---|---|---|---|
| 209 | From S15 according to Standard procedures A and B[a, b] 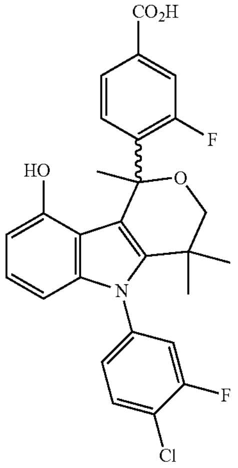 | 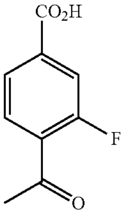 | $^1$H NMR (400 MHz, Methanol-d4) δ 7.75-7.61 (m, 2H), 7.57 (dd, J = 8.1, 1.7 Hz, 1H), 7.44 (dt, J = 9.5, 2.6 Hz, 1H), 7.33-7.24 (m, 2H), 6.88 (td, J = 8.0, 2.5 Hz, 1H), 6.40 (dt, J = 7.8, 1.1 Hz, 1H), 6.26 (ddd, J = 8.3, 4.0, 0.8 Hz, 1H), 3.36-3.23 (m, 2H), 2.28 (dd, J = 1.6, 0.9 Hz, 3H), 1.36 (s, 3H), 0.83 (s, 3H). LCMS m/z 498.17 $[M + H]^+$. |
| 210 | From S15 according to Standard procedures A and B[a, b, c] 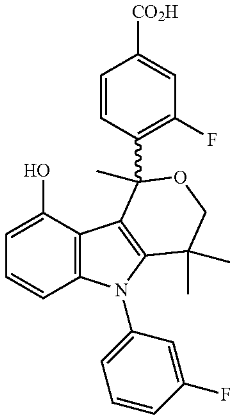 | 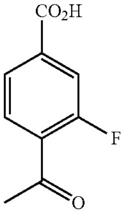 | $^1$H NMR (400 MHz, Methanol-d4) δ 7.66 (dd, J = 12.6, 1.7 Hz, 1H), 7.64-7.53 (m, 2H), 7.38-7.21 (m, 4H), 6.87 (td, J = 8.0, 2.1 Hz, 1H), 6.39 (dt, J = 7.7, 1.0 Hz, 1H), 6.25 (ddd, J = 8.2, 3.4, 0.8 Hz, 1H), 3.37-3.23 (m, 2H), 2.29 (d, J = 1.8 Hz, 3H), 1.36 (s, 3H), 0.81 (d, J = 1.2 Hz, 3H). LCMS m/z 464.37 $[M + H]^+$. |

[a]Standard procedure A carried out in dichloromethane not DCE.

[b]Standard Procedure B modified by replacing ammonium formate with hydrogen and using EtOH as solvent.

[b]This was a side product observed from over-reduction during the synthesis of compound 209.

Assays for Detecting and Measuring AAT Modulator Properties of Compounds

A. AAT Function Assay (MSD Assay NL20-SI Cell Line)

Alpha-1 antitrypsin (AAT) is a SERPIN (serine protease inhibitor) that inactivates enzymes by binding to them covalently. This assay measured the amount of functionally active AAT in a sample in the presence of the disclosed compounds 1-210 by determining the ability of AAT to form an irreversible complex with human neutrophil Elastase (hNE). In practice, the sample (cell supernatant, blood sample, or other) was incubated with excess hNE to allow AAT-Elastase complex to be formed with all functional AAT in the sample. This complex was then captured to a microplate coated with an anti-AAT antibody. The complex captured to the plate was detected with a labeled anti-Elastase antibody and quantitated using a set of AAT standards spanning the concentration range present in the sample. Meso Scale Discovery (MSD) plate reader, Sulfo-tag labeling, and microplates were used to provide high sensitivity and wide dynamic range.

Materials:

| Reagents/Plates | Concentration |
|---|---|
| Goat anti-human Alpha-1-Antitrypsin Polyclonal Antibody Use at 5 μg/mL in phosphate buffered saline (PBS) | 1 mL @ 1 mg/mL |
| Human Neutrophil Elastase Stock at 3.4 μM (0.1 mg + 1 mL PBS) Working at 1 μg/mL (34 nm) in MSD Assay buffer (1% bovine serum albumin (BSA)) | 100 μg lyophilized |
| Mouse anti-human Neutrophil Elastase Monoclonal Antibody Sulfo-tagged @ 12:1 using MSD Gold Sulfo-tag N-hydroxysuccinimide (NHS) ester; use at 0.45 μg/mL in MSD Assay buffer (1% BSA) | 900 μg/mL |
| M-AAT (Alpha-1-Antitrypsin) | 5 mg lyophilized |
| MSD Blocker A (BSA) 5% solution in PBS for blocking 1% solution in PBS for assay buffer | 250 mL |
| MSD Read Buffer T (4X) with Surfactant | 1 L or 250 mL |
| MSD 384 high bind plates | |
| Polypropylene for dilution 384 well plate | |
| Tissue culture treated black well 384 well plate | |
| INSTRUMENT(S): | |
| Meso Sector S600 | |
| Bravo | |
| Washer dispenser | |
| Multidrop Combi | |

Assay Protocol

Day 1 Cell Culture

1. Harvest NL20 human bronchial epithelial cells expressing human Z-AAT in OptiMEM™ containing Pen/Strep (P/S)
2. Seed at 16,000 cells/well in 30 μL (384 well plate)
3. Centrifuge plates briefly up to speed (1200 rpm) and place into 37° C. incubator overnight Day 2: Compound Addition and Coating Plates with Capture Antibody Compound Addition:

1. Dispense 40 μL of OptiMEM™ (P/S) with doxycycline (1:1000 stock=0.1 μM final) to each well of the compound plate using a multidrop Combi in hood
2. Remove cell plate from incubator, flip/blot and take immediately to Bravo to transfer compounds
3. Return plates to incubator overnight Coat MSD Plates 1. Dilute capture antibody (Polyclonal Goat anti-AAT) to 5 μg/mL (1:200) in PBS (no BSA).
2. Dispense 25 μL of diluted capture antibody into all wells of MSD 384-well High Bind plate using the Multidrop equipped with a standard cassette.
3. Incubate overnight at 4° C.

Prepare Blocker A (BSA) Solutions

1. Prepare solution of 5% MSD Blocker A (BSA) following the manufacturer's instructions.
2. Further dilute the 5% MSD Blocker A in PBS to 1% (Blocker A) as needed.

Day 3: Run MSD Assay

Block Plates

1. Wash plate 1× with 50 μL Wash buffer (PBS+0.5% Tween 20), and adds 35 μL 5% Block A buffer to block non-specific binding on washer dispenser
2. Rotate plates on shaker for 1 hour at 600 rpm Prepare M-AAT Standards 1. Dilute M-AAT stock to 1.6 μg/mL in 1% BSA Blocker A (Stock in −70° C.); then prepare 12×1:2 serial dilutions in 1% Blocker A
2. The top starting final concentration on MSD plate is 320 ng/mL. These dilutions correspond to a final concentration of 320, 160, 80, 40, 20, 10, 5, 2.5, 1.25, 0.625, 0.312, 0.156 ng/mL.

Dilution Plate

1. Add 80 μL of 1% Assay buffer to all wells except columns 1/24 (standards) with Multidrop Combi
2. Add diluted standards to columns 1 and 24
3. Centrifuge dilution plates 1200 rpm briefly Cell Plate 1. Aspirate columns which will have the standards from the cell plates in the hood using 16-pin aspirator Prepare Human Neutrophil Elastase (hNE)

1. Prepare 1 μg/mL Human Neutrophil Elastase by diluting in 1% Blocker A.
   a. Small 100 μg vial—add 1 mL PBS (100 μg/mL)
      i. This can then be diluted 1:100 in 1% Assay Buffer for a final 1 μg/mL concentration MSD—add hNE (20 μL/well)

1. After the MSD plate has blocked for at least 1 hour, wash plate 1× with 50 μL Wash buffer (PBS+0.5% Tween 20) and then add 20 μL hNE to each well Bravo-Cell Plate-Dilution Plate-MSD Plate Using the Bravo aspirate 10 μL from the cell plate, transfer to the dilution plate (9-fold dilution)

1. Mix 25 μL 3×, then aspirate 5 μL, transfer to MSD plate (5-fold dilution)
2. Mix 10 μL 3×. Total dilution is 45 fold.
3. Shake plates at 600 rpm for 1.5 hours Add Functional Detection hNE Antibody 1. Wash plate 1× with wash buffer
2. Add 25 μL Sulfo-tagged anti-Elastase Monoclonal Mouse anti-Elastase) diluted to 0.45 μg/mL (1:2000) in 1% Blocker A into all wells of the functional activity MSD plates using the washer/dispenser
   Note: The dilution required for sufficient signal must be determined for each new lot of labeled antibody.
3. Incubate at room temperature shaking at 600 rpm for 1 hour.

Final Wash and MSD Imager Read

1. Wash the plate 1×, and add 25 μL of Wash Buffer to the plate.
2. Make 2× Read buffer
3. Remove wash buffer from MSD plate
4. Transfer 35 μL 2× Read Buffer to MSD plate using Bravo and take to MSD to read immediately Data analysis in MSD Discovery Workbench 4.0 software and $EC_{50}$ values were determined using Genedata.

B. Biochemical Assay (Z-AAT Elastase Activity Assay)

This assay measured the modulation of compounds 1-210 on Z-AAT SERPIN activity using purified Z-AAT protein and purified human neutrophil elastase (hNE). Normally, when active monomeric Z-AAT encounters a protease such as trypsin or elastase, it forms a 1:1 covalent "suicide" complex in which both the AAT and protease are irreversibly inactivated. However, compounds binding to Z-AAT can lead to a decrease in SERPIN activity. In such cases, when a protease encounters compound-bound Z-AAT, the protease cleaves and inactivates Z-AAT without itself being inactivated.

Materials

Reagents

PBS buffer (media prep)+0.01% BRIJ35 detergent (Calbiochem catalog #203728)

Opti-MEM media (Fisher 11058-021)

Human neutrophil elastase (hNE, Athens Research #16-14-051200)

3.4 μM stock (0.1 mg/mL) prepared in 50 mM Na Acetate, pH 5.5, 150 mM NaCl, stored at −80° C.

Elastase substrate V (ES V, fluorescent peptide substrate MeOSuc-Ala-Ala-Pro-Val-AMC, Calbiochem catalog #324740)

20 mM stock in DMSO, stored at −20° C.

Purified Z-AAT protein from human plasma;

12.9 μM (0.67 mg/mL) Z-AAT Vertex Cambridge Sample 4942, from patient #061-SSN, stored at −80 C Plates Corning 4511 (384 well black low volume)

Instruments

PerkinElmer® EnVision™

Assay Protocol

Pre-Incubation of Z-AAT with Compounds 1. 7.5 μL of Z-AAT (20 nM) was incubated with Compounds 1-210 in a GCA plate for 1 hour at room temperature Addition of hNE 1. 7.5 ul of HNE solution (3 nM in PBS+0.01% BRIJ35) added into GCA plate
2. Incubate plate for 30 minutes to allow Z-AAT/HNE suicide complex formation.

Addition of Substrate and Read Plate on PE Envision 1. 7.5 μL of substrate (300 μM solution of elastase substrate (ES V) in PBS+0.01% BRIJ35) dispensed per well into GCA plate
2. Immediately read on Envision.

C. EC50 and Z-AAT Elastase Activity Data for Compounds 1-210

The compounds of Formula (I) are useful as modulators of AAT activity. Table 15 below illustrates the $EC_{50}$ of the compounds 1-210 using procedures described in Section A above). Table 15 below also provides the Z-AAT elastase activity using procedures described in Section B above. In Table 15 below, the following meanings apply for both $EC_{50}$ and $IC_{50}$:

TABLE 15

$EC_{50}$ data for Compounds 1-210

| Compound No. | NL20 Functional EC50 (μM) | Z-AAT Elastase Activity IC50 (μM) |
|---|---|---|
| 1 | + | N.D. |
| 2 | + | N.D. |
| 3 | + | N.D. |
| 4 | ++ | N.D. |
| 5 | +++ | + |
| 6 | + | N.D. |
| 7 | +++ | + |
| 8 | + | N.D. |
| 9 | ++ | + |
| 10 | + | + |
| 11 | + | N.D. |
| 12 | ++ | + |
| 13 | +++ | + |
| 14 | + | N.D. |
| 15 | + | N.D. |
| 16 | +++ | + |
| 17 | ++ | N.D. |
| 18 | +++ | ++ |
| 19 | +++ | + |
| 20 | + | N.D. |
| 21 | + | N.D. |
| 22 | +++ | +++ |
| 23 | ++ | + |
| 24 | + | N.D. |
| 25 | ++ | ++ |
| 26 | + | N.D. |
| 27 | +++ | +++ |
| 28 | +++ | +++ |
| 29 | + | + |
| 30 | + | N.D. |
| 31 | ++ | + |
| 32 | +++ | ++ |
| 33 | +++ | +++ |
| 34 | +++ | +++ |
| 35 | +++ | +++ |
| 36 | +++ | +++ |
| 37 | +++ | +++ |
| 38 | +++ | +++ |
| 39 | +++ | +++ |
| 40 | ++ | + |
| 41 | + | N.D. |
| 42 | ++ | + |
| 43 | +++ | + |
| 44 | + | N.D. |
| 45 | + | N.D. |
| 46 | + | N.D. |
| 47 | ++ | + |
| 48 | + | N.D. |
| 49 | + | N.D. |
| 50 | +++ | + |
| 51 | +++ | +++ |
| 52 | ++ | ++ |
| 53 | +++ | +++ |
| 54 | ++ | ++ |

TABLE 15-continued

EC$_{50}$ data for Compounds 1-210

| Compound No. | NL20 Functional EC50 (μM) | Z-AAT Elastase Activity IC50 (μM) |
|---|---|---|
| 55 | +++ | +++ |
| 56 | + | ++ |
| 57 | +++ | +++ |
| 58 | ++ | + |
| 59 | + | N.D. |
| 60 | + | + |
| 61 | +++ | +++ |
| 62 | +++ | + |
| 63 | +++ | +++ |
| 64 | + | +++ |
| 65 | +++ | + |
| 66 | +++ | + |
| 67 | +++ | + |
| 68 | +++ | N.D. |
| 69 | +++ | N.D. |
| 70 | +++ | +++ |
| 71 | +++ | + |
| 72 | + | N.D. |
| 73 | + | ++ |
| 74 | + | N.D. |
| 75 | + | ++ |
| 76 | +++ | +++ |
| 77 | +++ | +++ |
| 78 | +++ | ++ |
| 79 | +++ | +++ |
| 80 | +++ | ++ |
| 81 | ++ | +++ |
| 82 | +++ | +++ |
| 83 | + | N.D. |
| 84 | ++ | ++ |
| 85 | +++ | N.D. |
| 86 | + | + |
| 87 | + | N.D. |
| 88 | + | N.D. |
| 89 | ++ | N.D. |
| 90 | ++ | + |
| 91 | ++ | + |
| 92 | +++ | +++ |
| 93 | +++ | +++ |
| 94 | +++ | ++ |
| 95 | +++ | ++ |
| 96 | + | + |
| 97 | +++ | +++ |
| 98 | +++ | +++ |
| 99 | +++ | +++ |
| 100 | + | + |
| 101 | ++ | + |
| 102 | +++ | ++ |
| 103 | +++ | +++ |
| 104 | ++ | ++ |
| 105 | +++ | ++ |
| 106 | +++ | ++ |
| 107 | +++ | +++ |
| 108 | +++ | +++ |
| 109 | +++ | +++ |
| 110 | ++ | ++ |
| 111 | + | N.D. |
| 112 | + | N.D. |
| 113 | + | N.D. |
| 114 | ++ | + |
| 115 | + | N.D. |
| 116 | ++ | + |
| 117 | + | N.D. |
| 118 | + | N.D. |
| 119 | ++ | + |
| 120 | + | N.D. |
| 121 | ++ | + |
| 122 | + | N.D. |
| 123 | +++ | +++ |
| 124 | + | + |
| 125 | + | N.D. |
| 126 | + | N.D. |
| 127 | + | N.D. |
| 128 | ++ | N.D. |
| 129 | + | N.D. |

TABLE 15-continued

EC$_{50}$ data for Compounds 1-210

| Compound No. | NL20 Functional EC50 (μM) | Z-AAT Elastase Activity IC50 (μM) |
|---|---|---|
| 130 | ++ | + |
| 131 | + | N.D. |
| 132 | ++ | N.D. |
| 133 | +++ | + |
| 134 | + | N.D. |
| 135 | ++ | + |
| 136 | +++ | + |
| 137 | + | N.D. |
| 138 | + | N.D. |
| 139 | ++ | N.D. |
| 140 | + | N.D. |
| 141 | + | N.D. |
| 142 | ++ | + |
| 143 | + | N.D. |
| 144 | + | N.D. |
| 145 | +++ | + |
| 146 | + | N.D. |
| 147 | + | N.D. |
| 148 | + | N.D. |
| 149 | +++ | +++ |
| 150 | +++ | + |
| 151 | + | N.D. |
| 152 | + | N.D. |
| 153 | +++ | +++ |
| 154 | ++ | ++ |
| 155 | + | N.D. |
| 156 | ++ | N.A. |
| 157 | + | N.D. |
| 158 | + | N.D. |
| 159 | ++ | N.D. |
| 160 | +++ | +++ |
| 161 | ++ | + |
| 162 | +++ | ++ |
| 163 | + | + |
| 164 | ++ | +++ |
| 165 | + | N.D. |
| 166 | + | N.D. |
| 167 | + | N.D. |
| 168 | +++ | +++ |
| 169 | ++ | + |
| 170 | + | N.D. |
| 171 | ++ | + |
| 172 | + | + |
| 173 | + | + |
| 174 | +++ | + |
| 175 | +++ | ++ |
| 176 | +++ | ++ |
| 177 | + | + |
| 178 | ++ | + |
| 179 | ++ | N.D. |
| 180 | +++ | +++ |
| 181 | +++ | ++ |
| 182 | +++ | +++ |
| 183 | ++ | ++ |
| 184 | +++ | +++ |
| 185 | +++ | +++ |
| 186 | ++ | + |
| 187 | + | N.D. |
| 188 | + | N.D. |
| 189 | + | N.D. |
| 190 | ++ | N.D. |
| 191 | + | N.D. |
| 192 | ++ | ++ |
| 193 | +++ | + |
| 194 | ++ | ++ |
| 195 | ++ | + |
| 196 | + | N.D. |
| 197 | ++ | ++ |
| 198 | +++ | ++ |
| 199 | ++ | +++ |
| 200 | + | + |
| 201 | + | N.D. |
| 202 | + | N.D. |
| 203 | + | N.D. |
| 204 | + | N.D. |

TABLE 15-continued

| EC$_{50}$ data for Compounds 1-210 | | |
|---|---|---|
| Compound No. | NL20 Functional EC50 (μM) | Z-AAT Elastase Activity IC50 (μM) |
| 205 | +++ | ++ |
| 206 | +++ | ++ |
| 207 | +++ | +++ |
| 208 | +++ | ++ |
| 209 | +++ | ++ |
| 210 | +++ | +++ |

"+++" means <1.2 μM;
"++" means between 1.2 μM and 3.0 μM;
"+" means greater than 3.0 μM; and
"N/A" means activity not assessed.
For IC$_{50}$, "N.D." means activity not detected up to 30 □M.

OTHER EMBODIMENTS

This description provides merely exemplary embodiments of the disclosed subject matter. One skilled in the art will readily recognize from the disclosure and accompanying claims, that various changes, modifications and variations can be made therein without departing from the spirit and scope of the disclosure as defined in the following claims.

What is claimed is:

1. A compound represented by one of the following structural formulae:

(Ia)

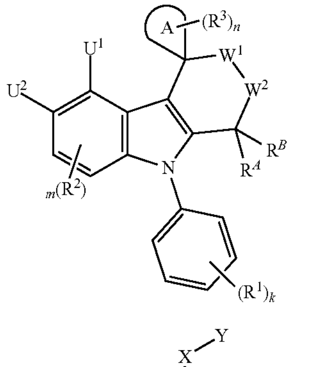

(Ib)

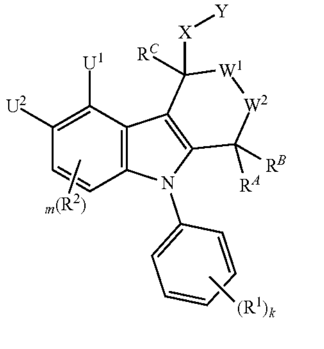

a tautomer thereof, a deuterated derivative of the compound or tautomer, or a pharmaceutically acceptable salt of any of the foregoing, wherein:

$W^1$ is absent or a bond, —O—, or —$CR^DR^D$—;

$W^2$ is —O—, —$(CR^DR^D)_p$—, or —C═O;

provided that $W^1$ and $W^2$ are not both —O—;

$R^A$ and $R^B$ are each independently hydrogen, halogen, —OH, $C_1$-$C_3$ alkyl, $C_1$-$C_3$ haloalkyl, or $C_1$-$C_3$ alkoxy;

or alternatively $R^A$ and $R^B$ are each independently $C_1$-$C_3$ alkyl or $C_1$-$C_3$ alkoxy, and/or $R^A$ and $R^B$ together with their intervening C atom form a $C_3$-$C_6$ cycloalkyl or a 3 to 6-membered heterocyclyl containing at least one oxygen atom;

$R^C$ is independently hydrogen, —OH, $C_1$-$C_3$ alkyl, or $C_1$-$C_3$ haloalkyl;

$R^D$, for each occurrence, is independently hydrogen, halogen, —OH, $C_1$-$C_3$ alkyl, $C_1$-$C_3$ haloalkyl, or $C_1$-$C_3$ alkoxy;

or alternatively $R^D$, for each occurrence, is independently $C_1$-$C_3$ alkyl or $C_1$-$C_3$ alkoxy, and two $R^D$ groups together with their intervening C atom form a $C_3$-$C_6$ cycloalkyl or a 3 to 6-membered heterocyclyl containing at least one oxygen atom;

$U^1$ and $U^2$ are each independently hydrogen, halogen, —$NH_2$, —$CH_3$, or —OH;

provided that one of $U^1$ and $U^2$ is —OH or —$NH_2$ but $U^1$ and $U^2$ are not both —OH or —$NH_2$ and $U^1$ and $U^2$ are not both hydrogen;

Ring A is $C_3$-$C_{12}$ carbocyclyl or 3 to 12-membered heterocyclyl;

X is absent, —$(CR^ER^E)_q$—, or —$CH_2OCH_2$—; wherein:

$R^E$, for each occurrence, is independently hydrogen, halogen, —OH, $C_1$-$C_3$ alkyl, $C_1$-$C_3$ haloalkyl, or $C_1$-$C_3$ alkoxy;

Y is —COOH or

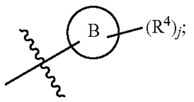

Ring B is $C_3$-$C_{12}$ cycloalkyl, a 3 to 12-membered heterocyclyl, a phenyl, or a 5 or 6-membered heteroaryl;

$R^1$ and $R^2$, for each occurrence, are each independently halogen, cyano, $C_1$-$C_3$ alkyl, $C_1$-$C_3$ haloalkyl, $C_1$-$C_3$ alkoxy, $C_1$-$C_3$ haloalkoxy, or O—($C_3$-$C_6$ cycloalkyl); and $R^3$, for each occurrence, is independently halogen, cyano, $C_1$-$C_3$ alkyl, $C_1$-$C_3$ haloalkyl, $C_1$-$C_3$ alkoxy, —OH, —$O(CR^fR^f)_rCOOH$, ═O, —COOH, —C(═O)$NR^fR^f$, —$(CR^fR^f)_rCOOH$, phenyl, or 5 or 6-membered heteroaryl; wherein:

$R^f$ for each occurrence, is independently hydrogen, halogen, or —$CH_3$; and the phenyl, or the 5 or 6-membered heteroaryl of $R^3$ is optionally substituted with 1 to 3 groups independently selected from halogen, cyano, $C_1$-$C_2$ alkyl, $C_1$-$C_2$haloalkyl, $C_1$-$C_2$ alkoxy, —OH, and —COOH;

$R^4$, for each occurrence, is independently halogen, cyano, $C_1$-$C_2$ alkyl, $C_1$-$C_2$haloalkyl, $C_1$-$C_2$ alkoxy, —COOH, —$CH_2COOH$, or —$OCH_2COOH$;

k and n are each independently an integer selected from 0, 1, 2, and 3;

j and m are each independently an integer selected from 0, 1, and 2;

p and r are each independently an integer selected from 1 and 2; and q is an integer selected from 1, 2, and 3.

2. The compound, tautomer, deuterated derivative, or pharmaceutically acceptable salt according to claim 1, wherein:

$R^A$ and $R^B$ are each independently hydrogen, halogen, —OH, $C_1$-$C_2$ alkyl, $C_1$-$C_2$haloalkyl, or $C_1$-$C_2$ alkoxy;

or alternatively $R^A$ and $R^B$ are each independently $C_1$-$C_3$ alkyl, and or $R^A$ and $R^B$ together with their intervening C atom form a cyclopropyl or a cyclobutyl; and $R^D$, for each occurrence, is independently hydrogen, halogen, —OH, $C_1$-$C_2$ alkyl, $C_1$-$C_2$ haloalkyl, or $C_1$-$C_2$ alkoxy;

or alternatively $R^D$, for each occurrence, is independently $C_1$-$C_3$ alkyl, and or two $R^D$ groups together with their intervening C atom form a cyclopropyl or a cyclobutyl.

3. The compound, tautomer, deuterated derivative, or pharmaceutically acceptable salt according to claim 1, wherein the compound is represented by one of the following structural formulae:

(IIa-1)

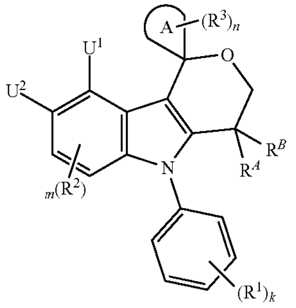

(IIa-2)

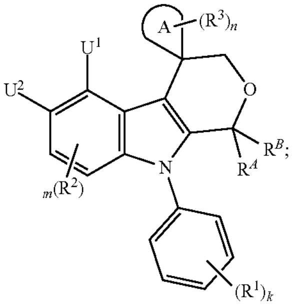

and wherein $R^A$ and $R^B$ are each independently hydrogen or $C_1$-$C_2$ alkyl.

4. The compound, tautomer, deuterated derivative, or pharmaceutically acceptable salt according to claim 1, wherein:

$U^1$ is —$NH_2$ or —OH; and $U^2$ is hydrogen, halogen, or —$CH_3$—.

5. The compound, tautomer, deuterated derivative, or pharmaceutically acceptable salt according to claim 1, wherein the compound is represented by the following structural formula:

(IIIa)

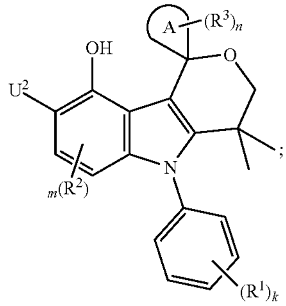

;

and wherein $U^2$ is hydrogen, F, or Cl.

6. The compound, tautomer, deuterated derivative, or pharmaceutically acceptable salt according to claim 1, wherein Ring A is optionally substituted with $R^3$ and Ring A is 4 to 9-membered carbocyclyl or 5 or 6-membered heterocyclyl.

7. The compound, tautomer, deuterated derivative, or pharmaceutically acceptable salt according to claim 1, wherein Ring A is optionally substituted with $R^3$ and Ring A is cyclobutyl, cyclopentyl, cyclohexyl, spiro[3.3]heptanyl, tetrahydro-2H-pyranyl, piperidinyl, spiro[2.3]hexanyl, 1-iminohexahydro-1λ$^6$-thiopyranyl 1-oxide, tetrahydro-2H-thiopyranyl 1,1-dioxide, or 2,3-dihydro-1H-indenyl.

8. The compound, tautomer, deuterated derivative, or pharmaceutically acceptable salt according to claim 1, wherein Ring A is optionally substituted with $R^3$ and Ring A is

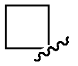 , 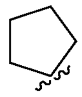 , 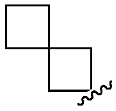 , 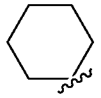 , 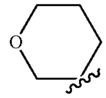 , 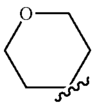 , 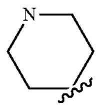 , 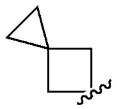 , 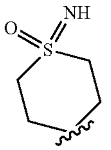 , 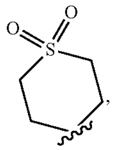 , or 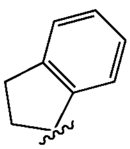 .

9. The compound, tautomer, deuterated derivative, or pharmaceutically acceptable salt according to claim 1, wherein $R^3$, for each occurrence, is independently halogen, $C_1$-$C_2$ alkyl, $C_1$-$C_2$haloalkyl, $C_1$-$C_2$ alkoxy, —OH, —O$(CR^fR^f)_r$COOH, =O, —COOH, —C(=O)$NR^fR^f$, —$(CR^fR^f)_r$COOH, phenyl, or a 5-membered heteroaryl; wherein:

$R^f$ for each occurrence, is independently hydrogen or —$CH_3$; and the phenyl or the 5-membered heteroaryl of $R^3$ is optionally substituted with 1 to 3 groups independently selected from halogen, $C_1$-$C_2$ alkyl, $C_1$-$C_2$ alkoxy, —OH, and —COOH.

10. The compound, tautomer, deuterated derivative, or pharmaceutically acceptable salt according to claim 1, wherein:

$R^3$, for each occurrence, is independently F, —$CH_3$, —$CF_3$, —$CHF_2$, —$CH_2F$, —OH, —$OCH_3$, —COOH, —$CH_2COOH$, —$CF_2COOH$, —C(=O)$NH_2$, —C(=O)$NHCH_3$, —C(=O)$N(CH_3)_2$, =O, —$OCH_2COOH$, —$OCHCH_3COOH$, phenyl, pyrazolyl, or oxazolyl; wherein:

the phenyl of $R^3$ is substituted with —COOH;

the pyrazolyl of $R^3$ is substituted with —COOH and —$CH_3$; and the oxazolyl of $R^3$ is substituted with —COOH.

11. The compound, tautomer, deuterated derivative, or pharmaceutically acceptable salt according to claim 1, wherein the compound is represented by one of the following structural formulae:

(IVa-1)

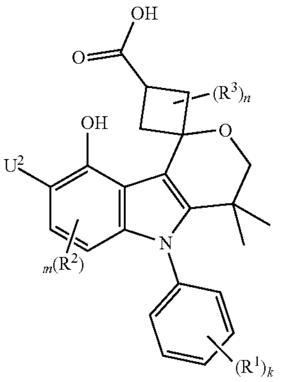

(IVa-2)

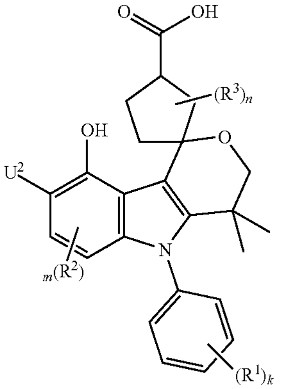

(IVa-3)

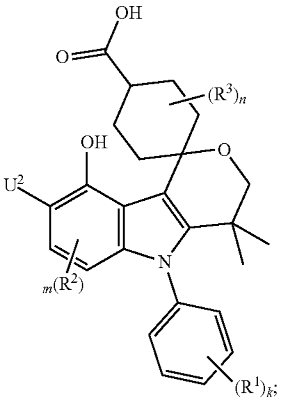

and wherein n is an integer selected from 0, 1, and 2.

12. The compound, tautomer, deuterated derivative, or pharmaceutically acceptable salt according to claim 1, wherein the compound is represented by one of the following structural formulae:

(Va-1)

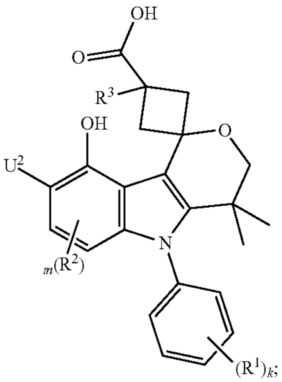

(Va-2)

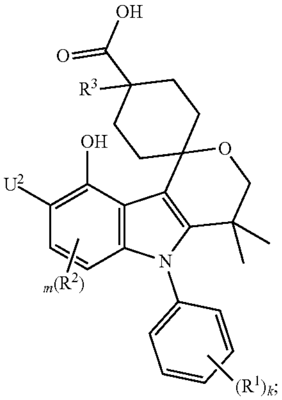

and wherein $R^3$ is F, —$CH_3$, —$CF_3$, —$CHF_2$, —$CH_2F$, —OH, or —$OCH_3$.

13. The compound, tautomer, deuterated derivative, or pharmaceutically acceptable salt according to claim 1, wherein the compound is represented by one of the following structural formulae:

(IIb-1)

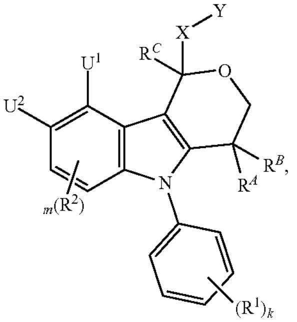

-continued (IIb-2)

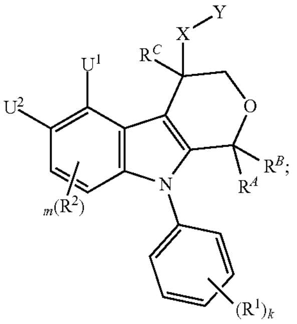

wherein:

$R^A$ and $R^B$ are each independently hydrogen, halogen, —OH, $C_1$-$C_2$ alkyl, $C_1$-$C_2$haloalkyl, or $C_1$-$C_2$ alkoxy;

$R^C$ is independently hydrogen, $C_1$-$C_2$ alkyl, or $C_1$-$C_2$haloalkyl; and X is absent, $—(CR^ER^E)_q—$, or $—CH_2OCH_2—$; wherein:

$R^E$, for each occurrence, is independently hydrogen, $C_1$-$C_2$ alkyl, or $C_1$-$C_2$ alkoxy.

14. The compound, tautomer, deuterated derivative, or pharmaceutically acceptable salt according to claim 1, wherein:

$R^A$ and $R^B$ are each independently hydrogen or $C_1$-$C_2$ alkyl;

$U^1$ is $—NH_2$ or —OH;

$U^2$ is hydrogen, halogen, or $—CH_3$; and

X is absent, $—CH_2—$, $—(CH_2)_2—$, $—(CH_2)_3—$, or $—CH_2OCH_2—$.

15. The compound, tautomer, deuterated derivative, or pharmaceutically acceptable salt according 1, wherein the compound is represented by one of the following structural formulae:

(IIIb-1)

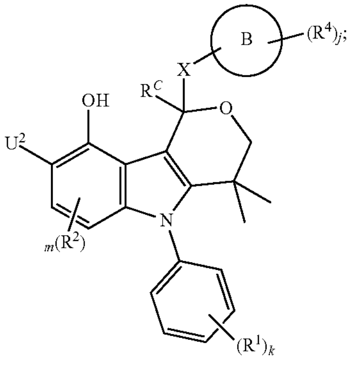

-continued (IIIb-2)

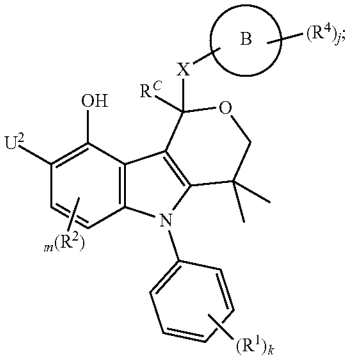

wherein:

$U^2$ is hydrogen, F, or Cl;

$R^C$ is hydrogen, $—CH_3$, or $—CF_3$; and

X is absent or $—CH_2—$.

16. The compound, tautomer, deuterated derivative, or pharmaceutically acceptable salt according to claim 1, wherein the compound is represented by one of the following structural formulae:

(IVb-1)

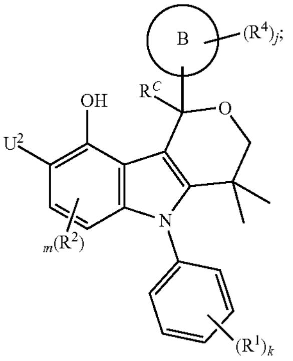

(IVb-2)

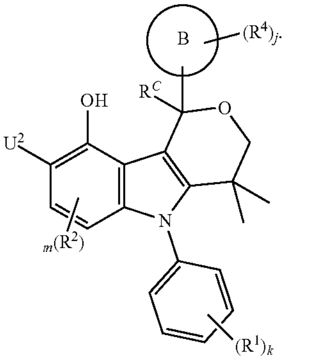

17. The compound, tautomer, deuterated derivative, or pharmaceutically acceptable salt according to claim 1, wherein Ring B is optionally substituted with $R^4$ and Ring B is $C_3$-$C_6$ cycloalkyl, phenyl, or 5-membered heteroaryl.

18. The compound, tautomer, deuterated derivative, or pharmaceutically acceptable salt according to claim 1, wherein Ring B is optionally substituted with $R^4$ and Ring B is

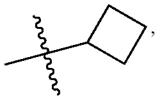,
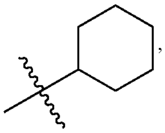,
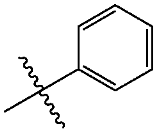,
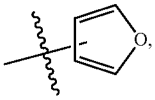,
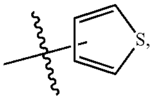,
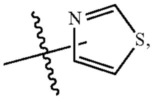,
or
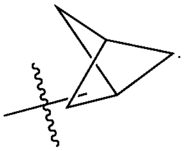.

19. The compound, tautomer, deuterated derivative, or pharmaceutically acceptable salt according to claim 1, wherein Ring B is optionally substituted with $R^4$ and Ring B is

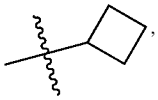,
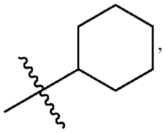,
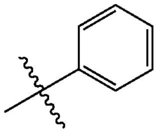,
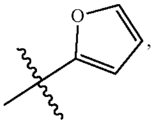,
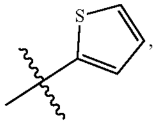,
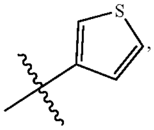,
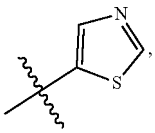,
or
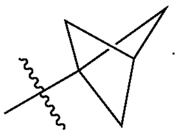.

20. The compound, tautomer, deuterated derivative, or pharmaceutically acceptable salt according claim 1, wherein $R^4$, for each occurrence, is independently F, Cl, —$CH_3$, —$OCH_3$, —COOH, or —$OCH_2COOH$.

21. The compound, tautomer, deuterated derivative, or pharmaceutically acceptable salt according to claim 1, wherein the compound is represented by one of the following structural formulae:

(Vb-1)

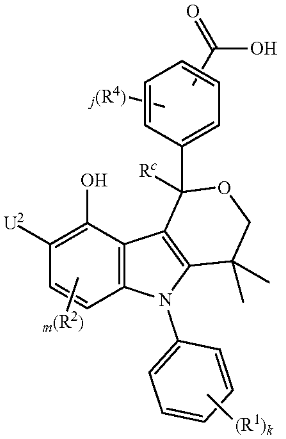

-continued (Vb-2)

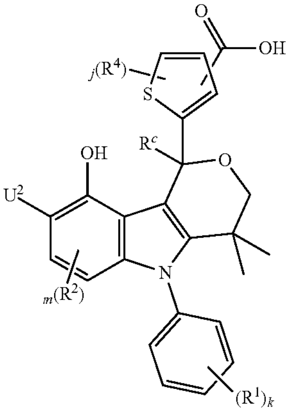

(Vb-3)

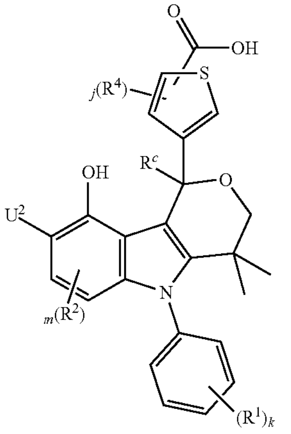

(Vb-4)

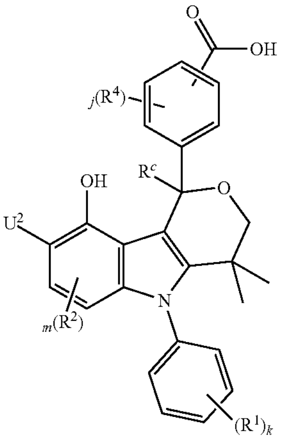

-continued (Vb-5)

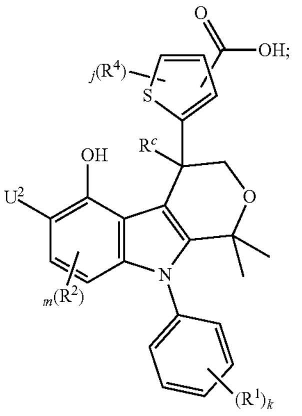

and wherein j is an integer selected from 0, 1, and 2.

22. The compound, tautomer, deuterated derivative, or pharmaceutically acceptable salt according to claim 1, wherein the compound is represented by one of the following structural formulae:

(VIb-1)

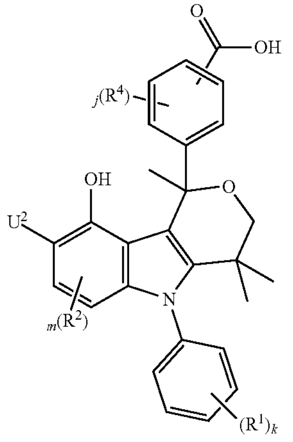

(VIb-2)

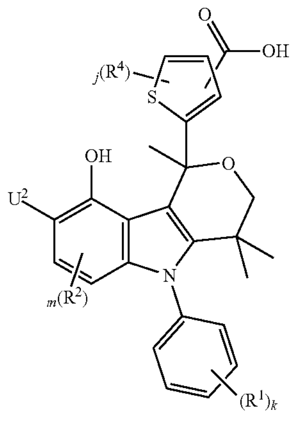

-continued (VIb-3)

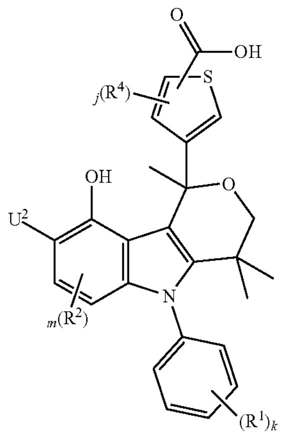

(VIb-4)

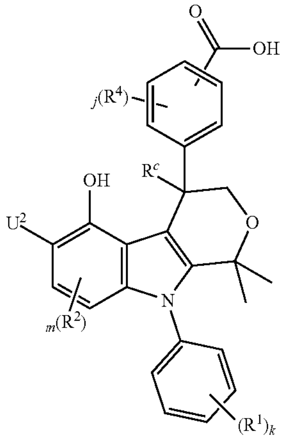

(VIb-5)

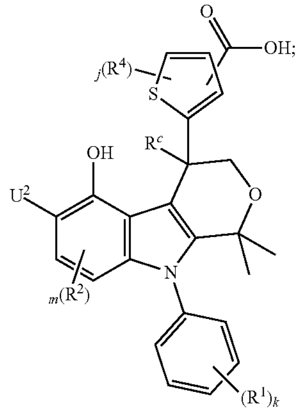

and wherein j is an integer selected from 0, 1, and 2.

23. The compound, tautomer, deuterated derivative, or pharmaceutically acceptable salt according to claim 1, wherein:

X is $—(CH_2)_2—$, $—(CH_2)_3—$, or $—CH_2OCH_2—$; and

Y is —COOH.

24. The compound, tautomer, deuterated derivative, or pharmaceutically acceptable salt according to claim 1, wherein $R^1$ and $R^2$, for each occurrence, are each independently halogen, $C_1$-$C_2$ alkyl, or $C_1$-$C_2$ alkoxy.

25. The compound, tautomer, deuterated derivative, or pharmaceutically acceptable salt according to claim 1, wherein $R^1$, for each occurrence, is independently F, Cl, $—CH_3$, or $—OCH_3$.

26. The compound, tautomer, deuterated derivative, or pharmaceutically acceptable salt according to claim 1, wherein $R^2$, for each occurrence, is F; and wherein m is an integer selected from 0 and 1.

27. The compound, tautomer, deuterated derivative, or pharmaceutically acceptable salt according to claim 1, wherein k is an integer selected from 1 and 2.

28. The compound, tautomer, deuterated derivative, or pharmaceutically acceptable salt according to claim 1, wherein m is 0.

29. A compound selected from:

1

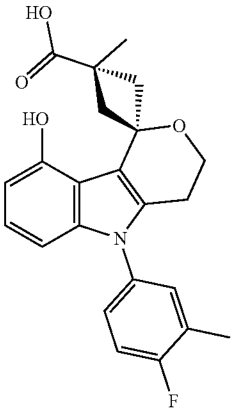

2

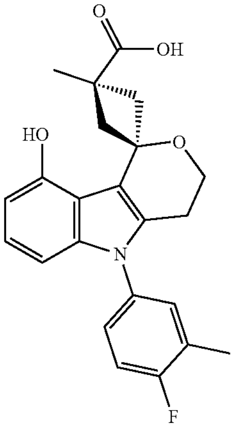

3

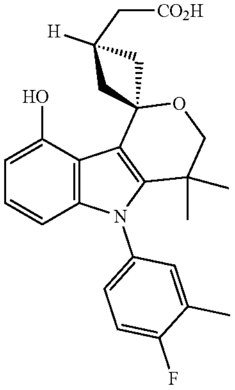

-continued

4

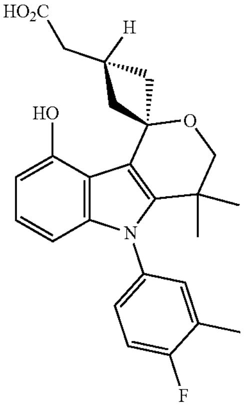

5

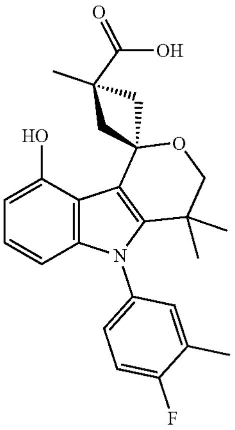

6

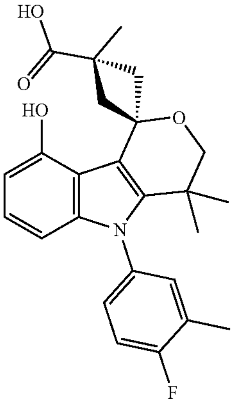

7
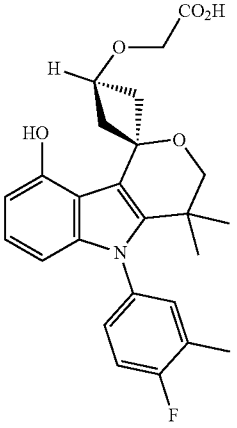
8
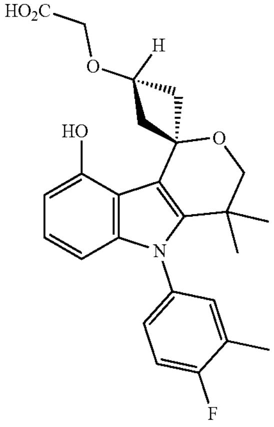
9
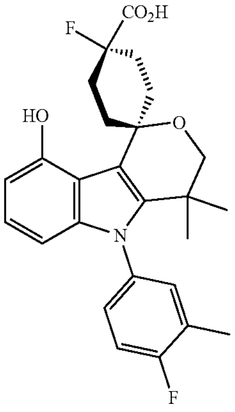
10
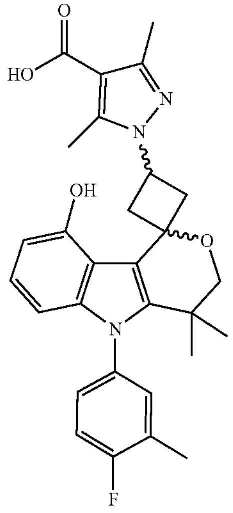
11
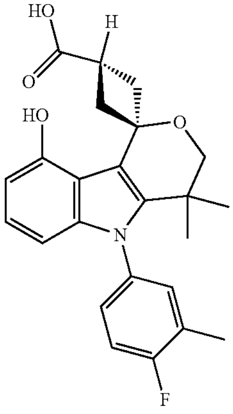
12
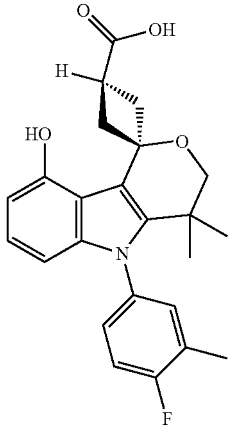

13
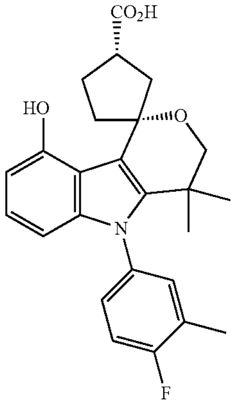
14
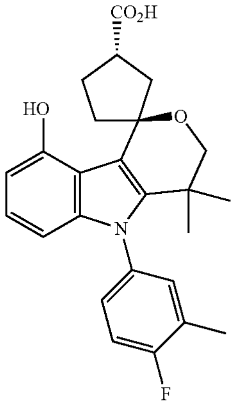
15
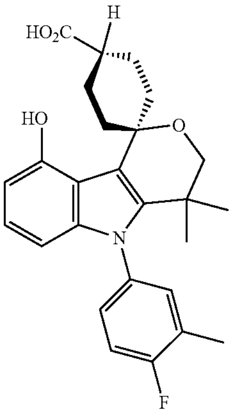
16
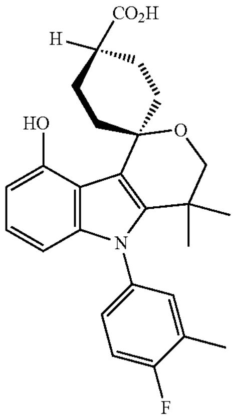
17
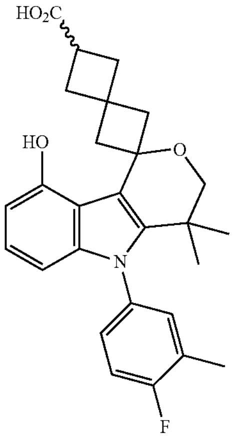
18
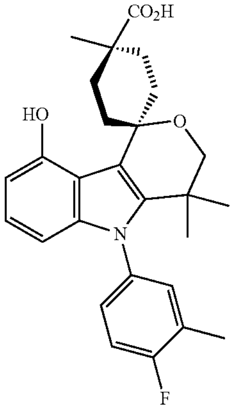
19
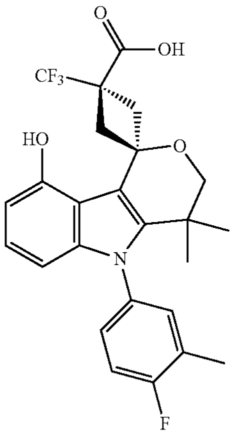

-continued
20
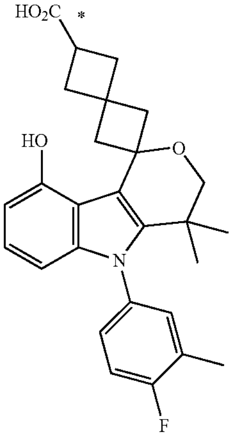
21
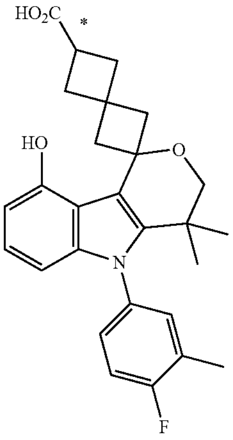
22
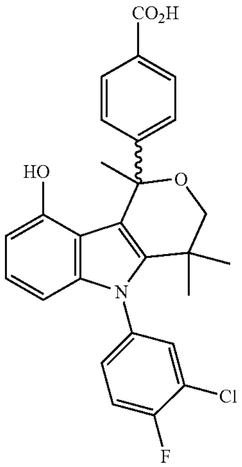
-continued
23
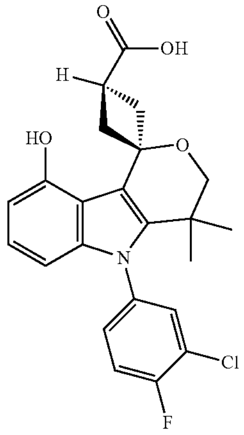
24
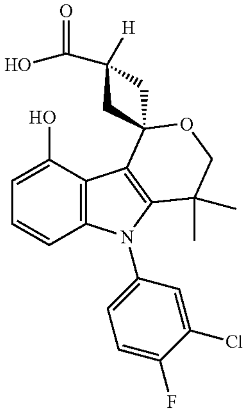
25
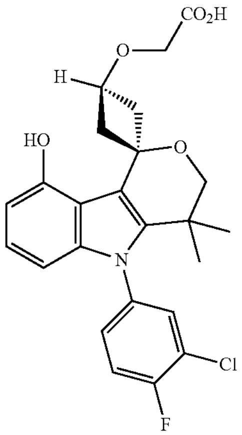

26
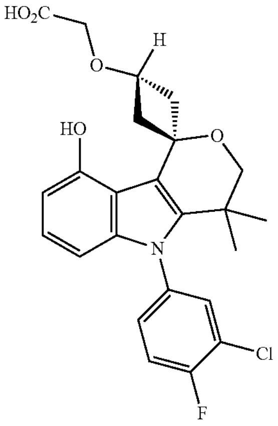
27
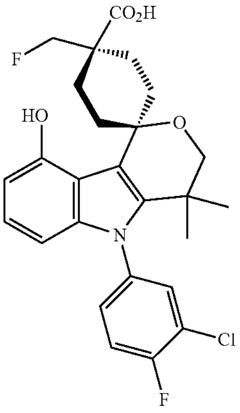
28
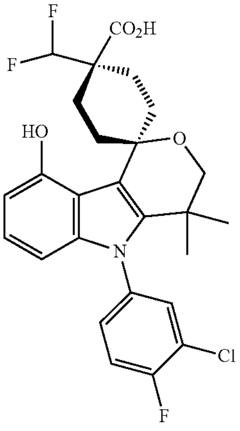
29
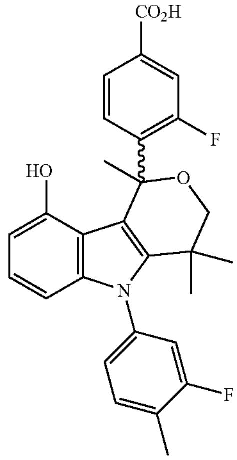
30
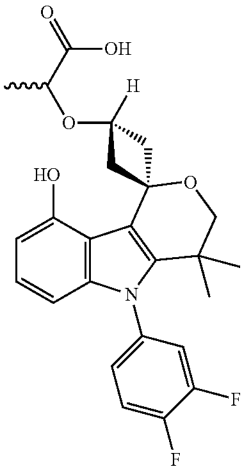
31
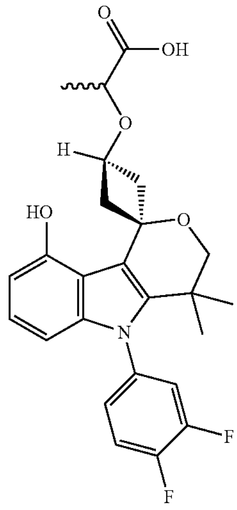

-continued
32
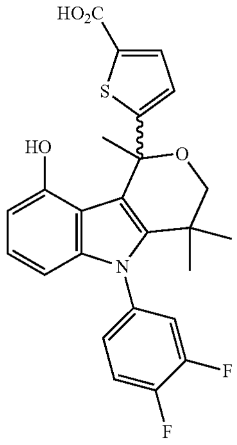
33
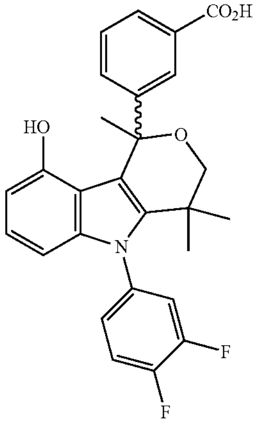
34
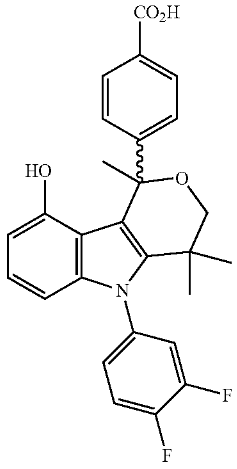
-continued
35
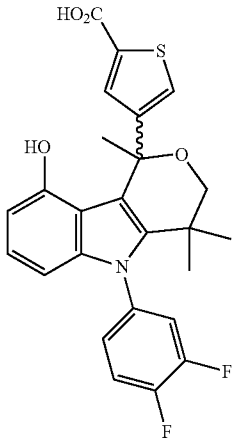
36
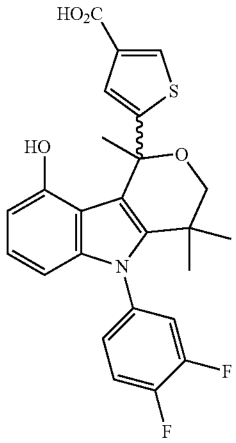
37
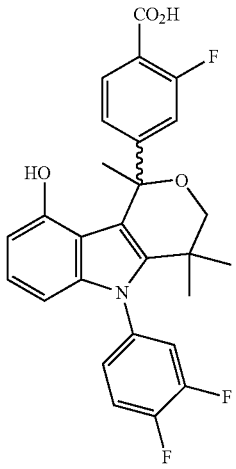

-continued
38
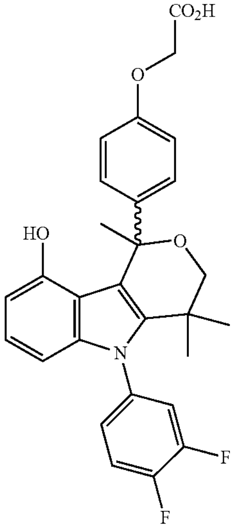
39
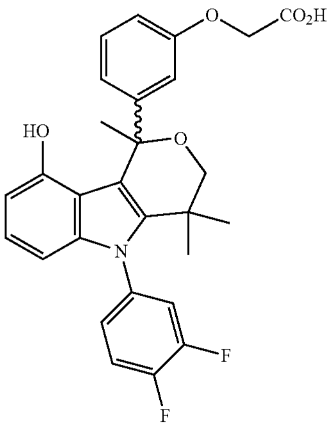
40
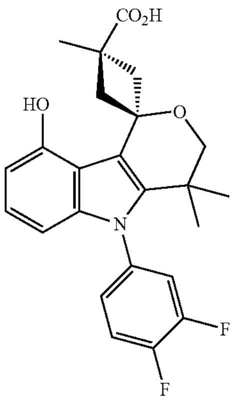
-continued
41
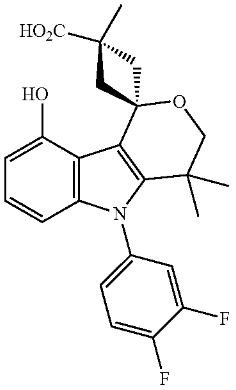
42
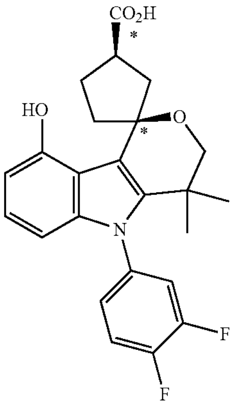
43
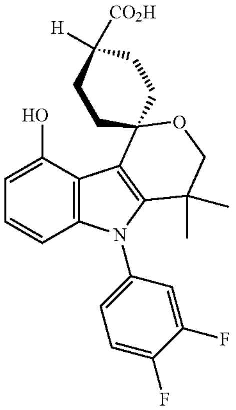
44
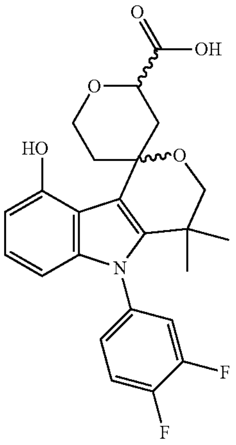

-continued
45
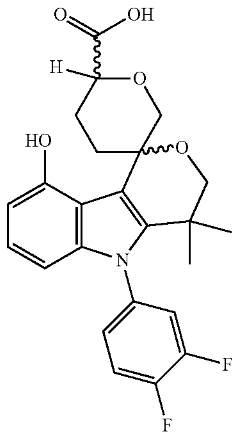
46
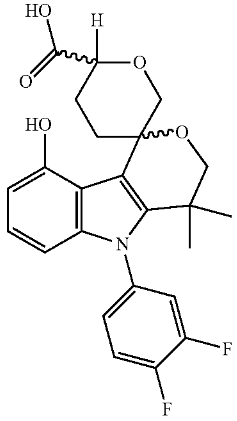
47
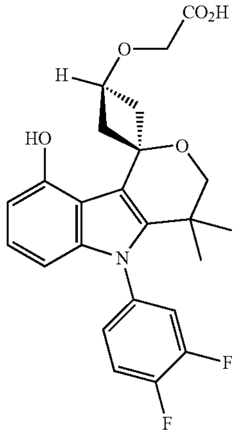
-continued
48
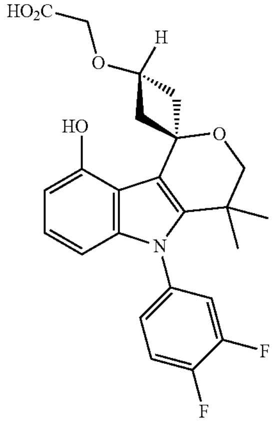
49
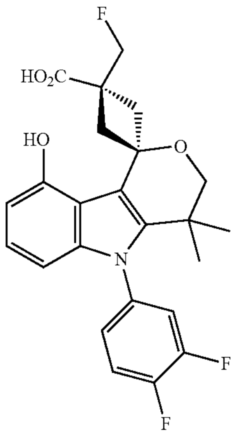
50
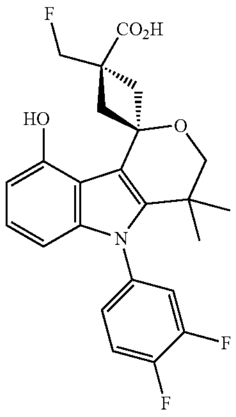

-continued
51
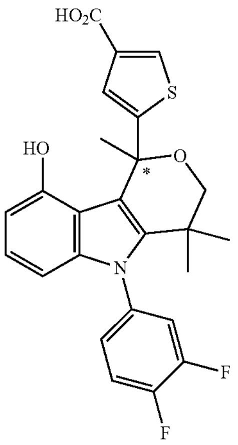
52
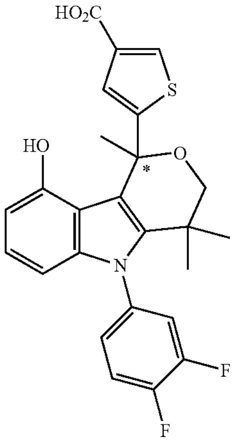
53
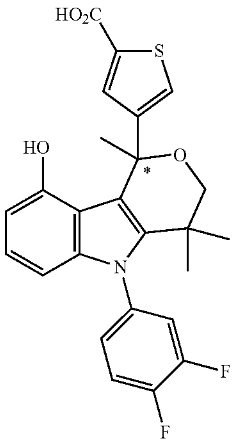
-continued
54
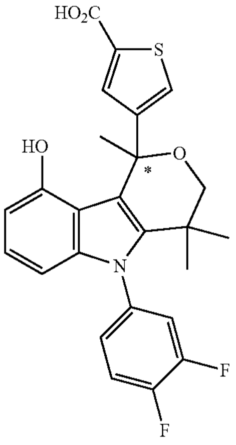
55
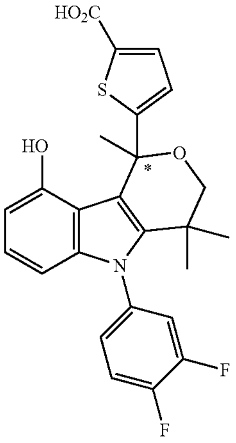
56
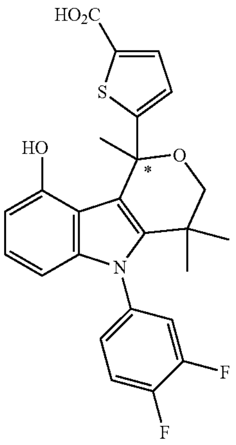

-continued
57
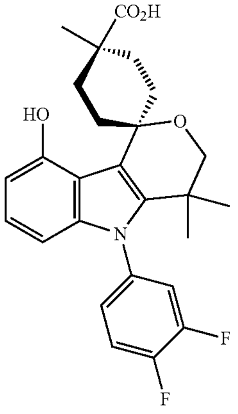
58
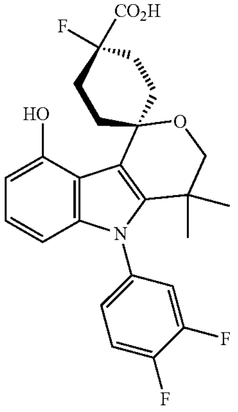
59
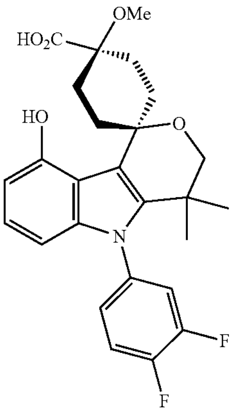
60
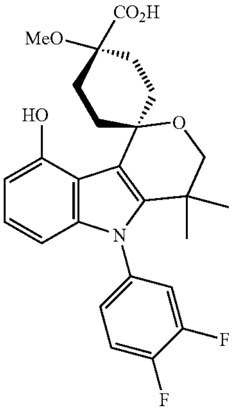
-continued
61
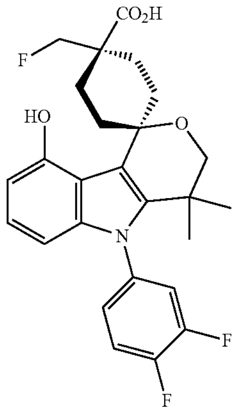
62
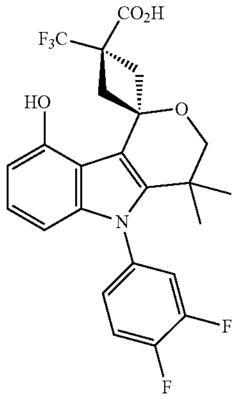
63
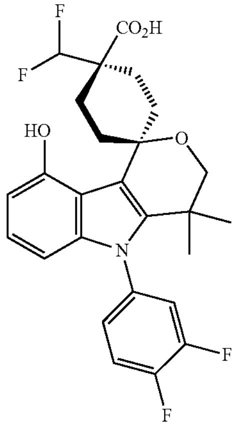

-continued
64
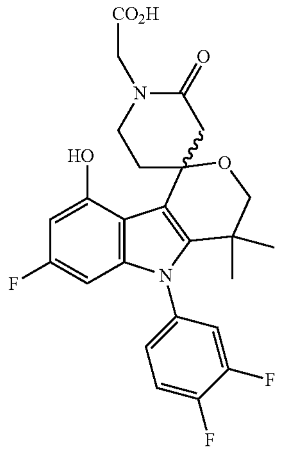
67
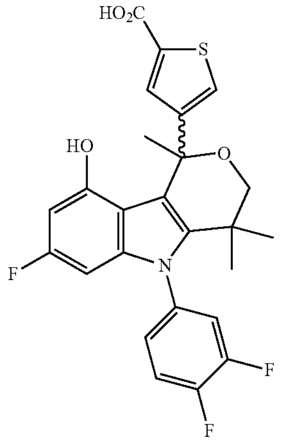
65
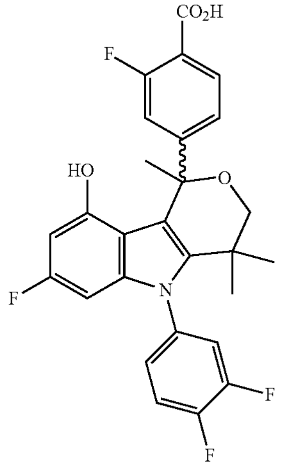
68
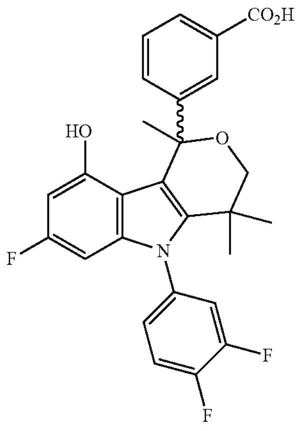
66
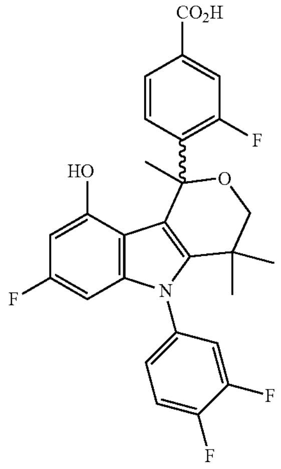
69
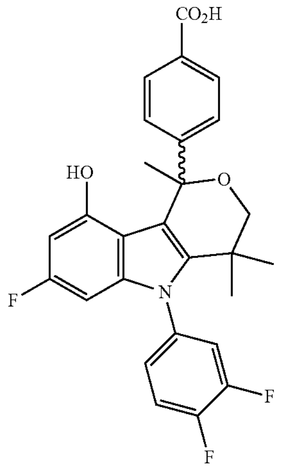

-continued
70
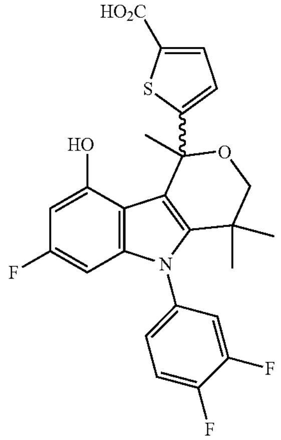
71
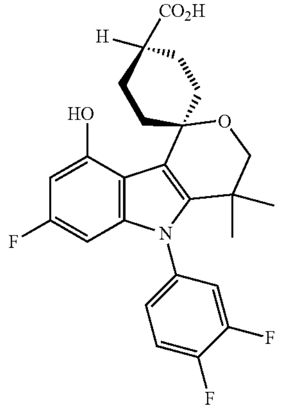
72
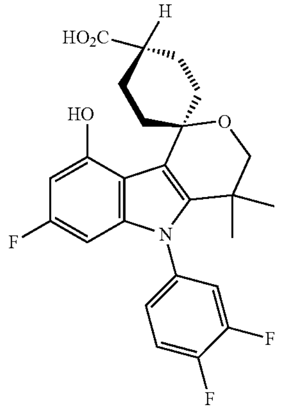
-continued
73
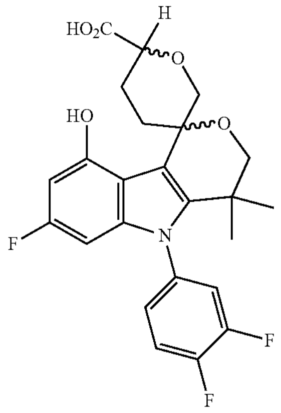
74
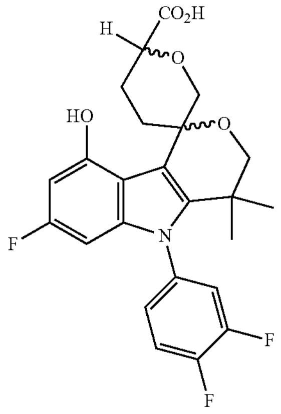
75
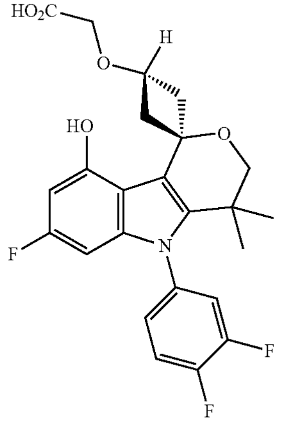

-continued
76
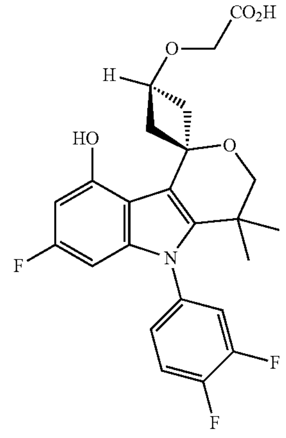
77
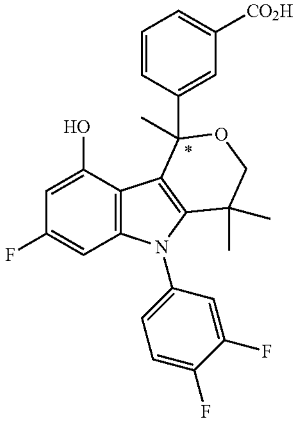
78
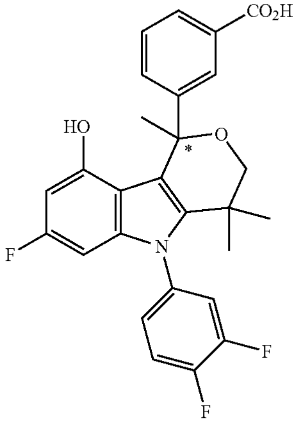
-continued
79
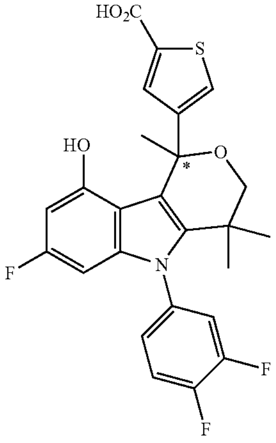
80
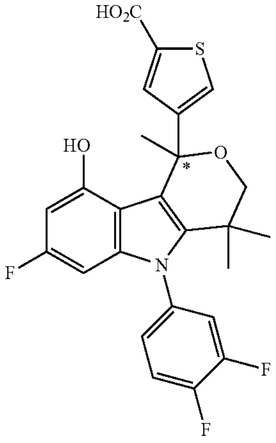
81
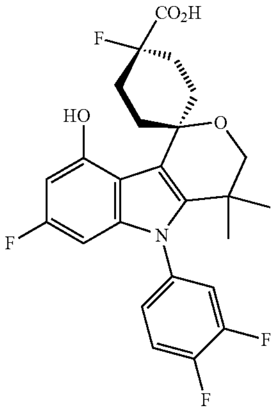

-continued
82
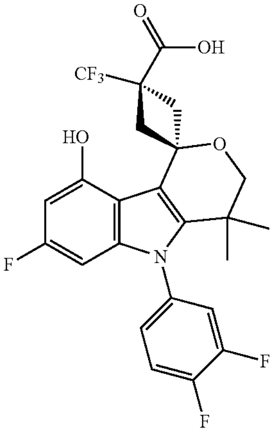
83
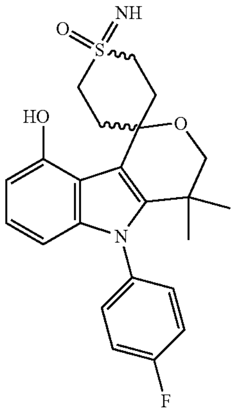
84
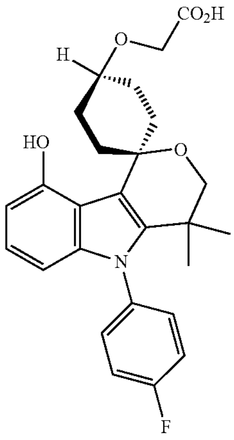
-continued
85
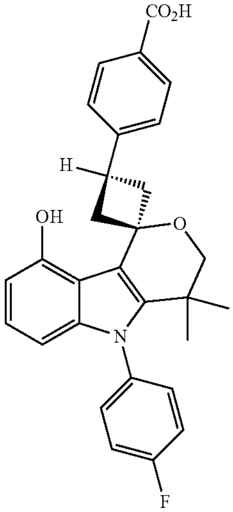
86
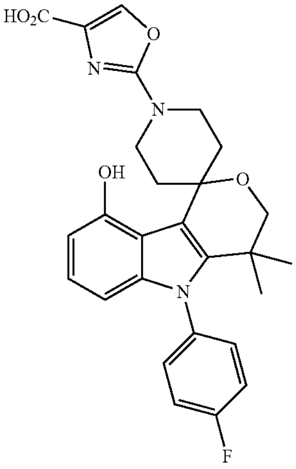
87
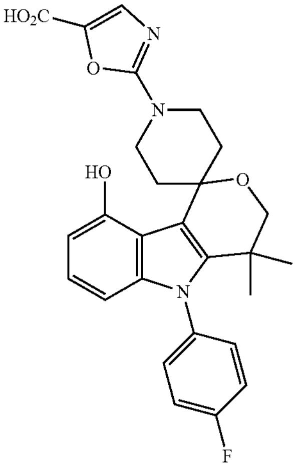

-continued
88
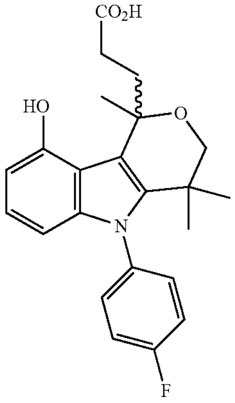
89
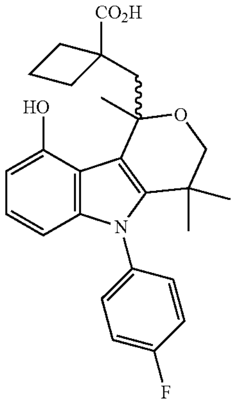
90
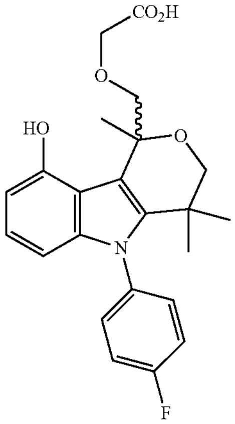
91
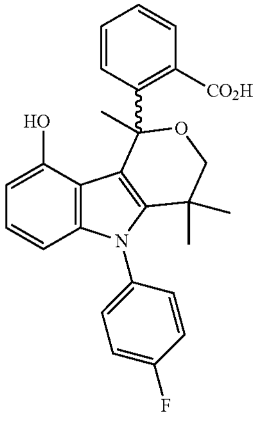
-continued
92
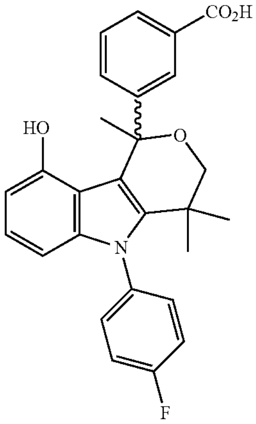
93
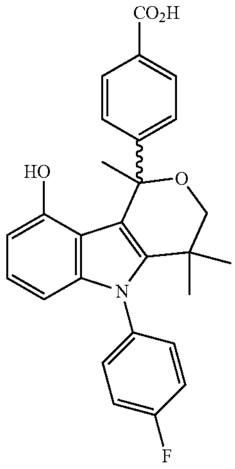
94
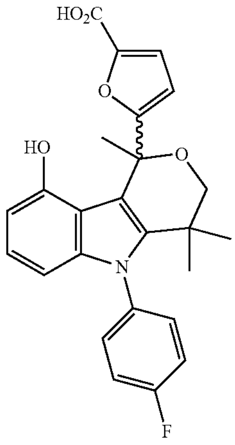

-continued
95
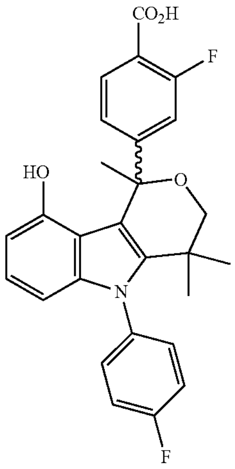
96
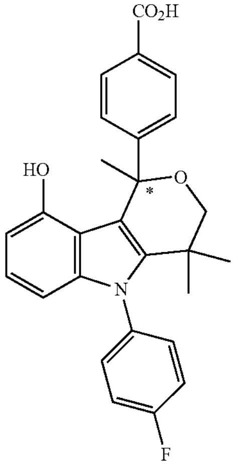
97
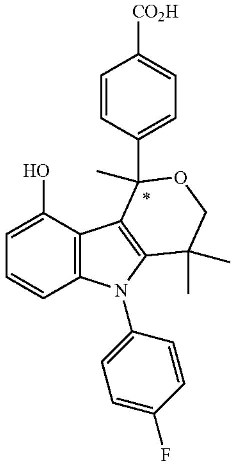
-continued
98
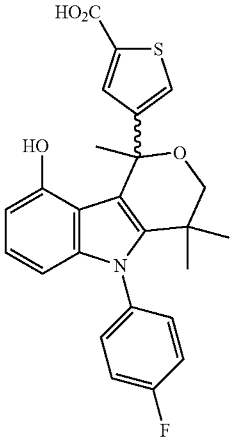
99
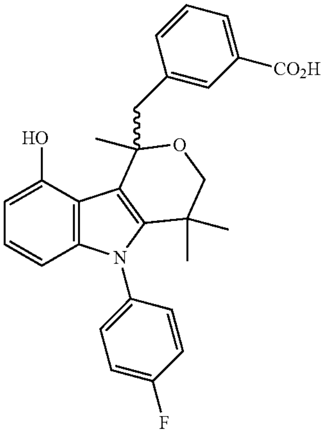
100
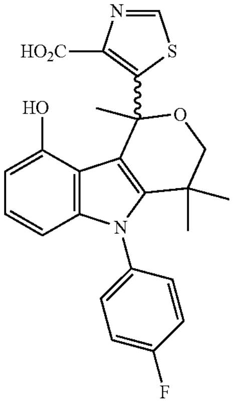

-continued
101
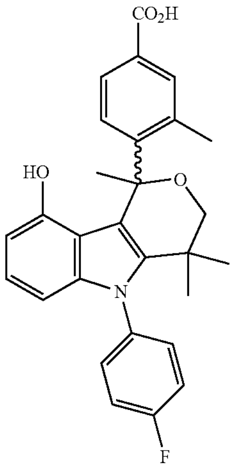
102
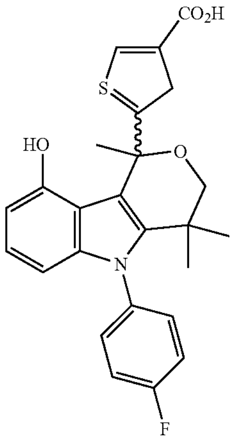
103
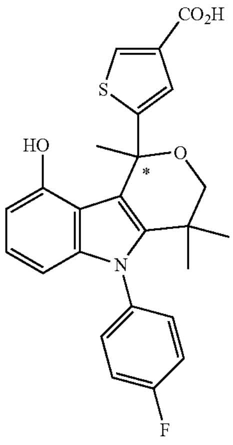
-continued
104
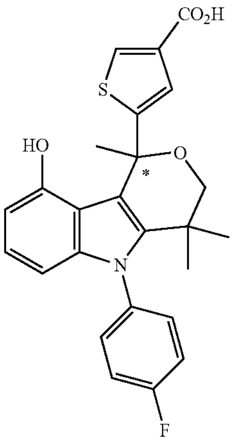
105
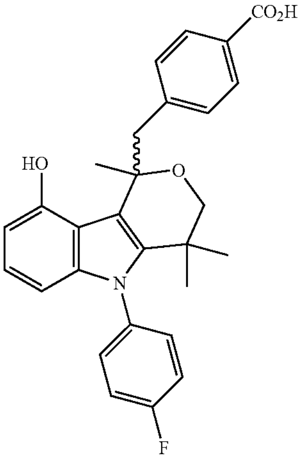
106
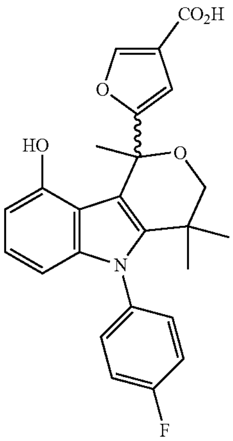

-continued
107
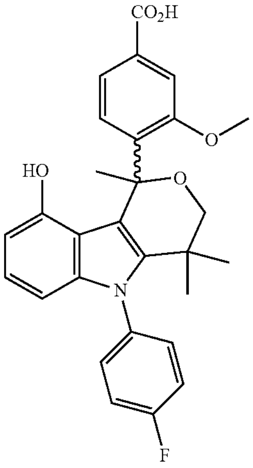
108
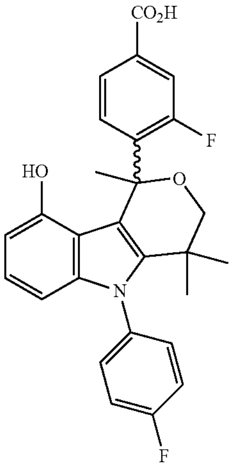
109
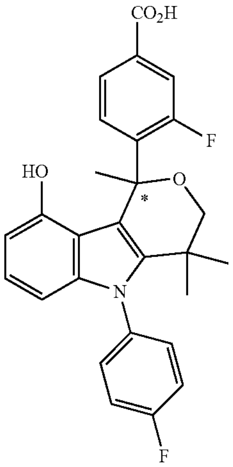
-continued
110
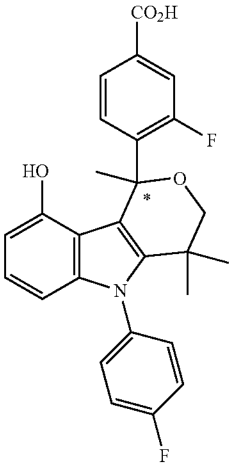
111
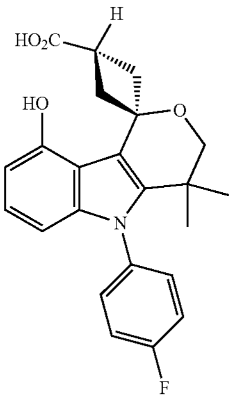
112
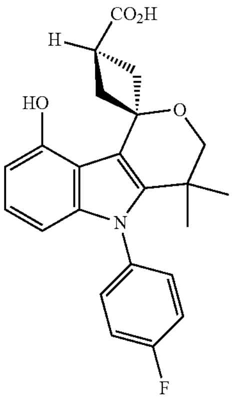

-continued
113
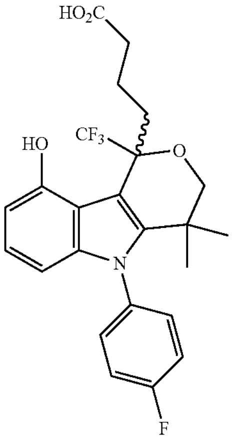
114
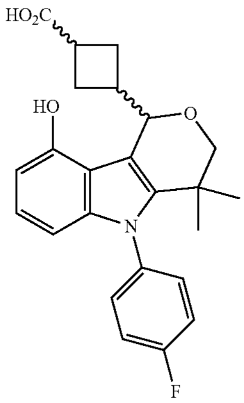
115
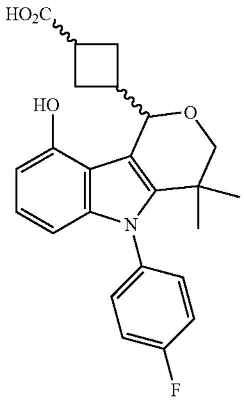
-continued
116
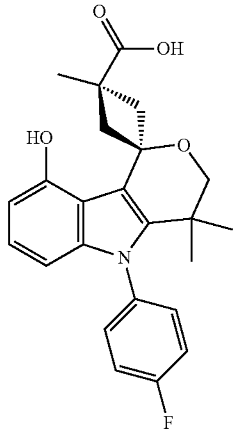
117
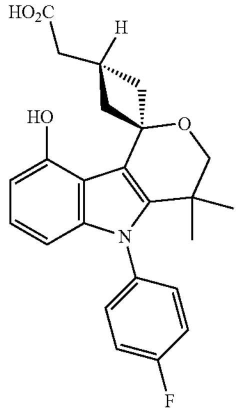
118
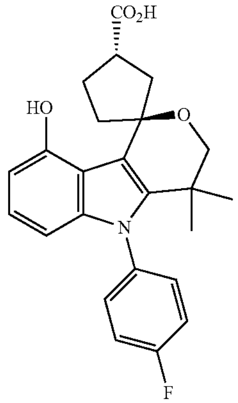
119
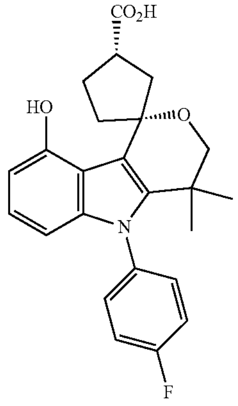

-continued
120
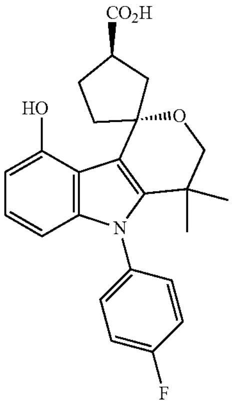
121
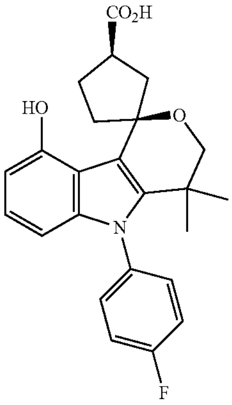
122
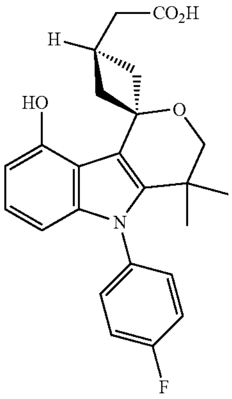
123
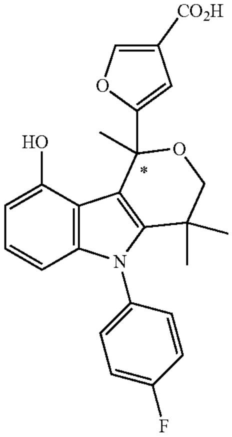
-continued
124
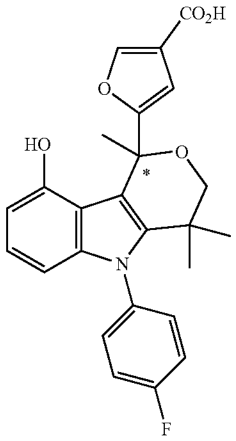
125
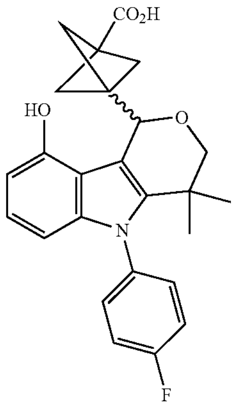
126
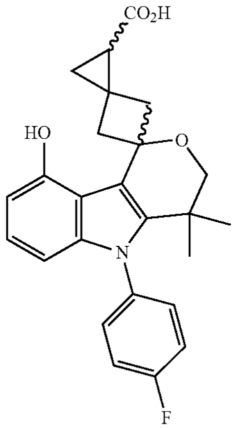

-continued
127
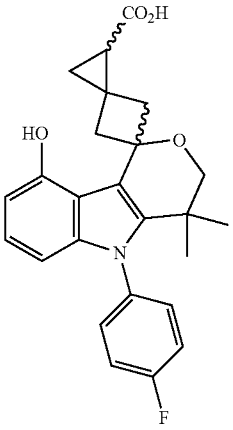
128
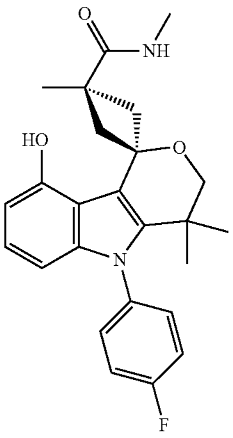
129
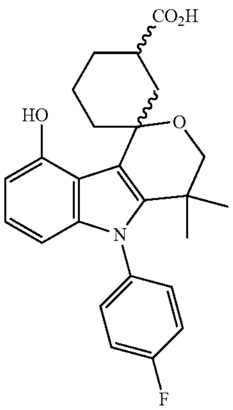
-continued
130
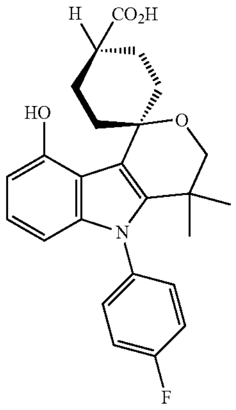
131
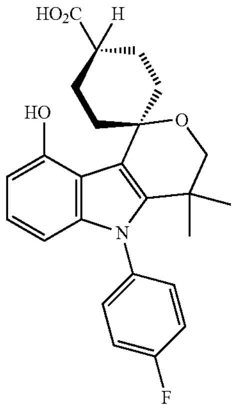
132
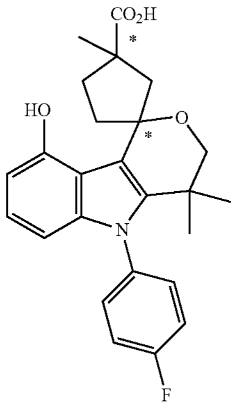
133
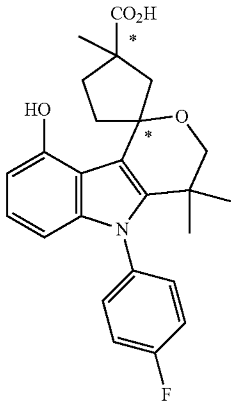

-continued
134
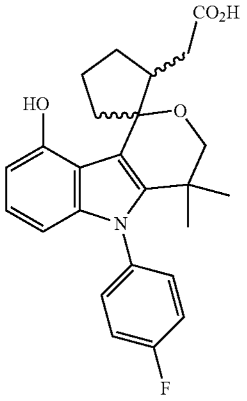
135
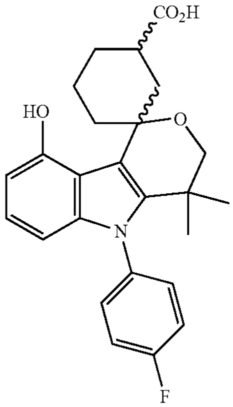
136
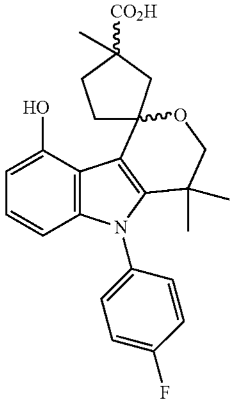
137
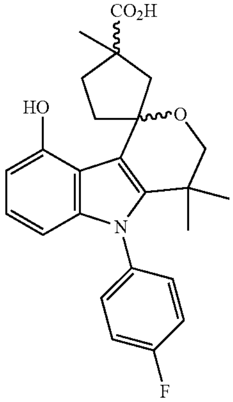
-continued
138
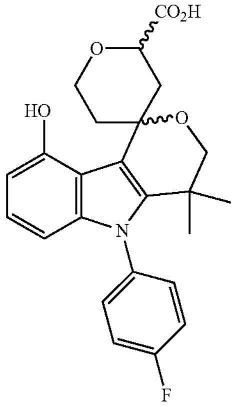
139
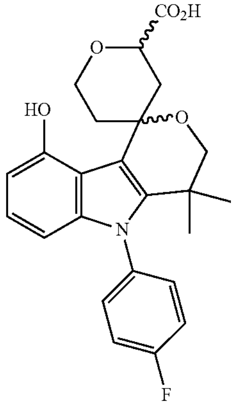
140
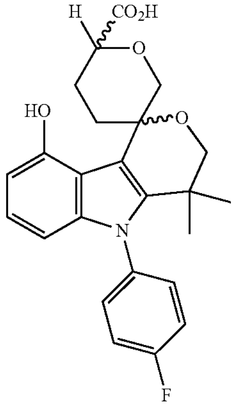
141
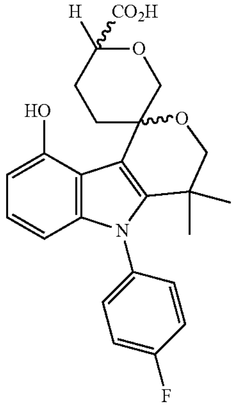

-continued
142
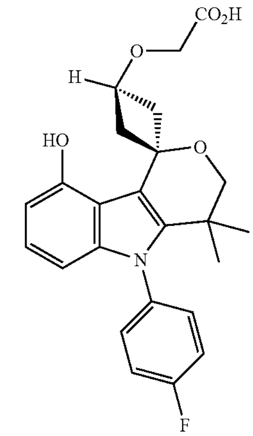
143
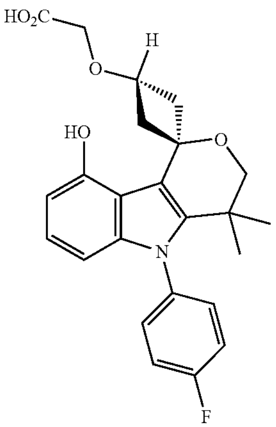
144
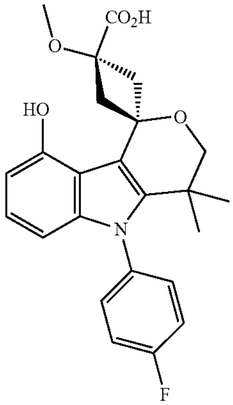
-continued
145
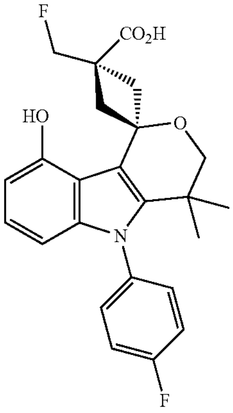
146
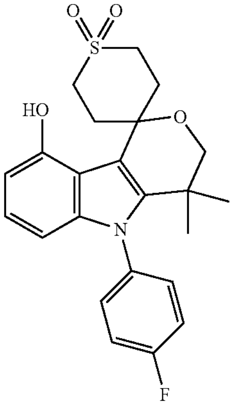
147
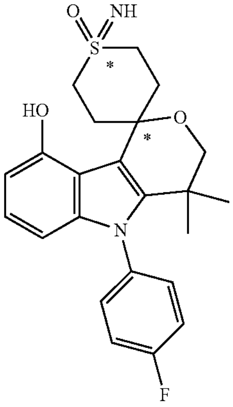
148
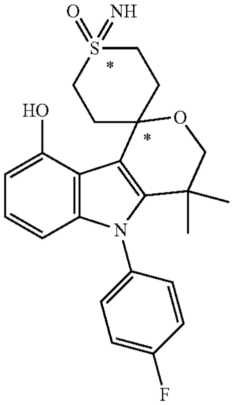

-continued
149
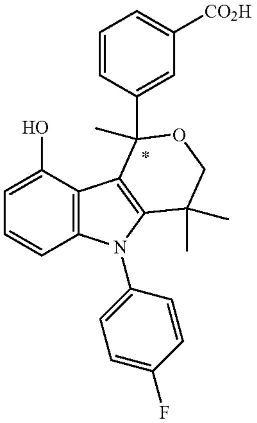
150
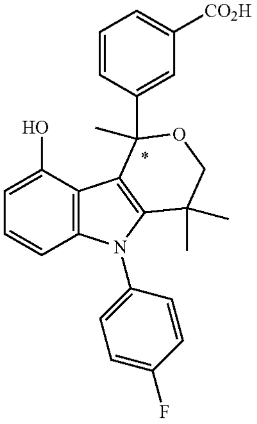
151
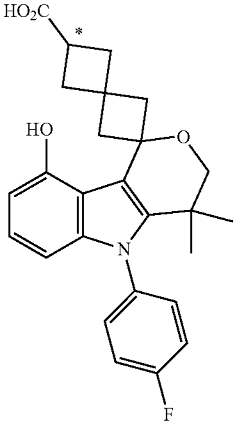
-continued
152
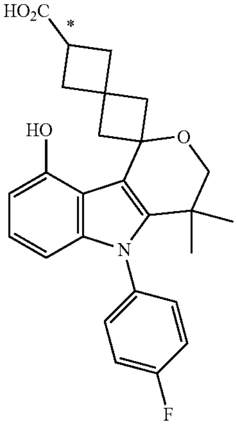
153
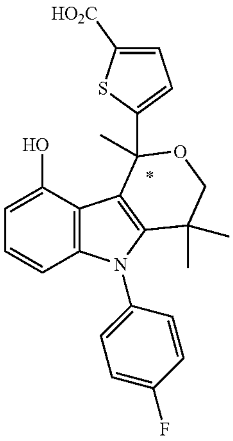
154
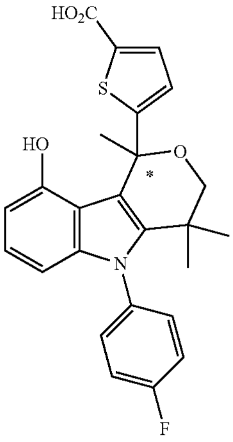

-continued
155
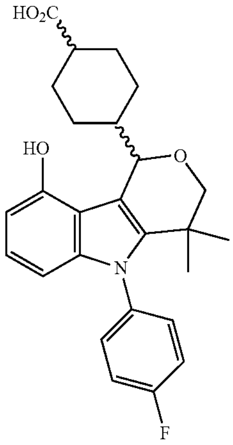
156
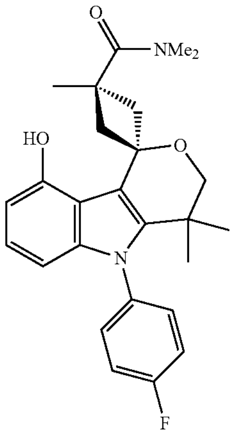
157
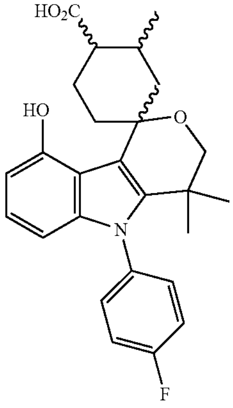
-continued
158
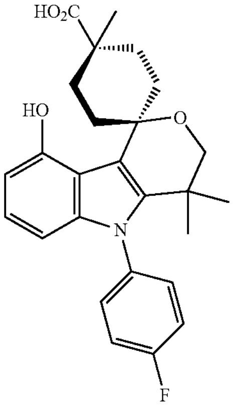
159
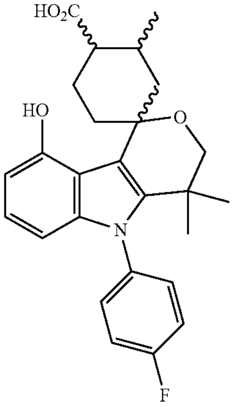
160
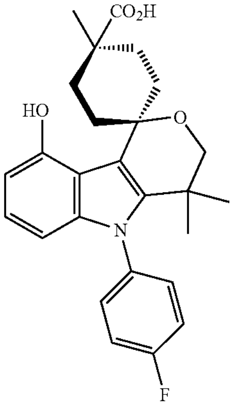
161
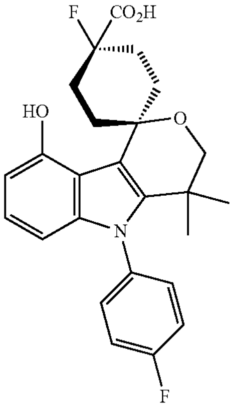

-continued
162
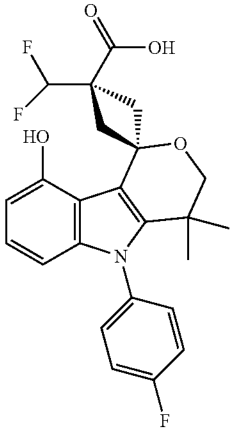
163
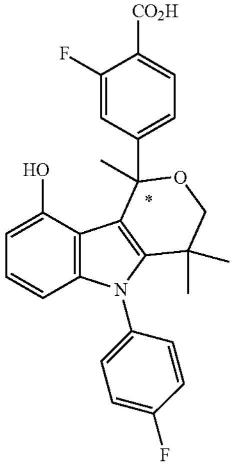
164
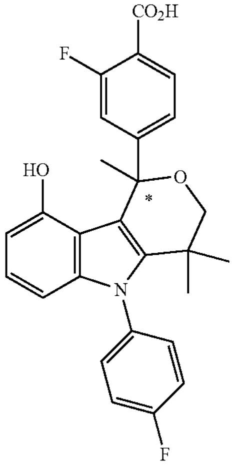
-continued
165
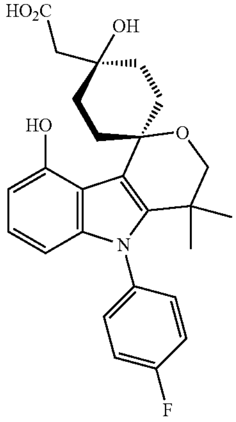
166
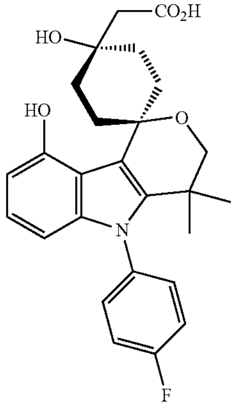
167
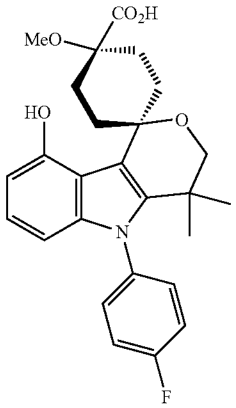
168
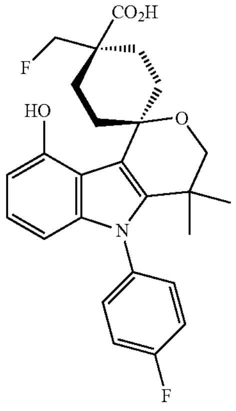

-continued
169
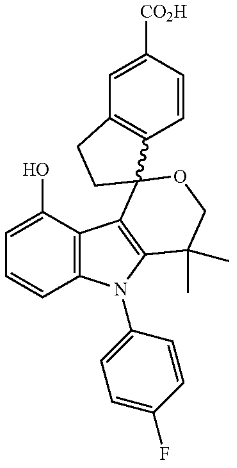
170
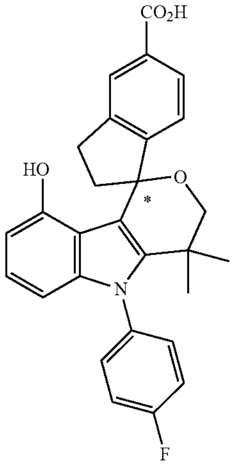
171
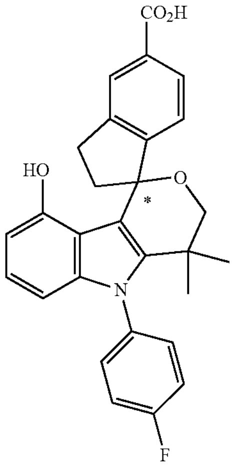
-continued
172
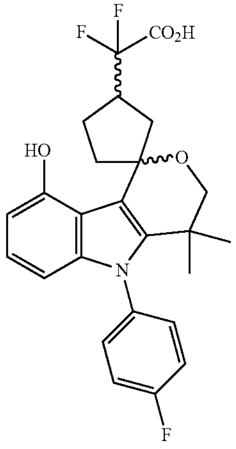
173
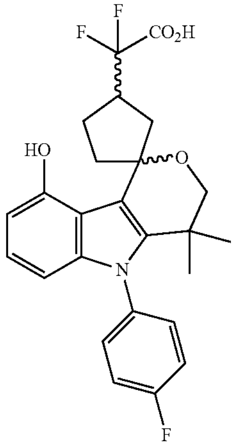
174
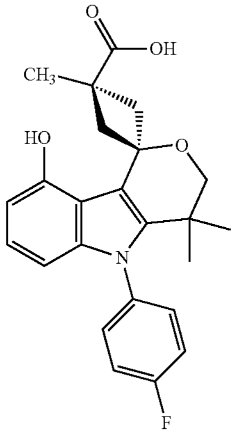

175
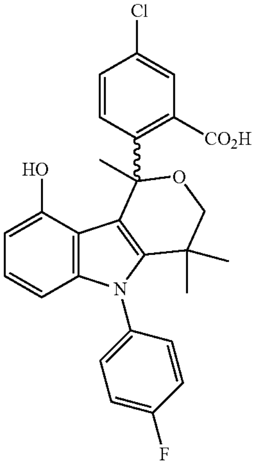
176
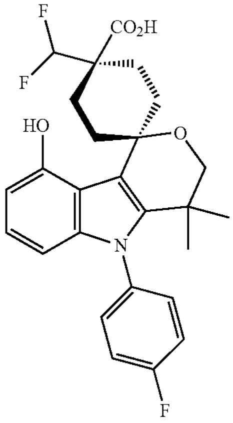
177
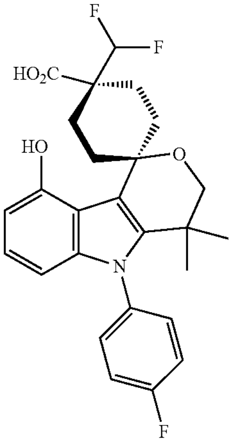
178
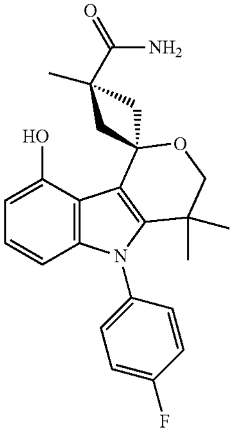
179
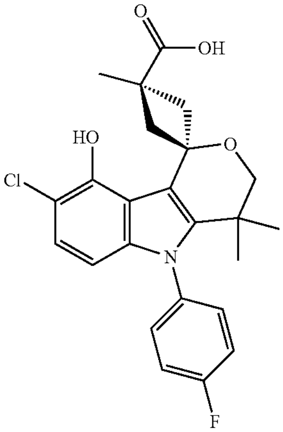
180
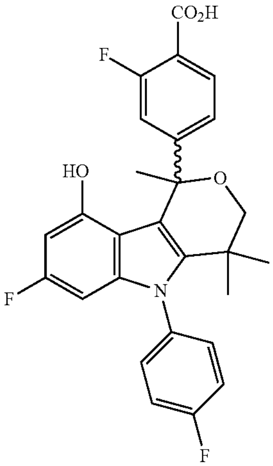

-continued
181
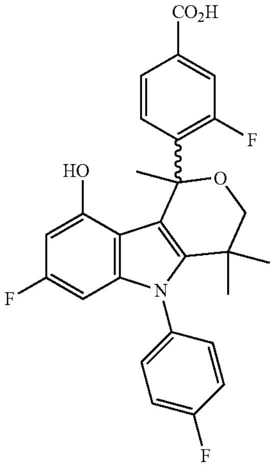
182
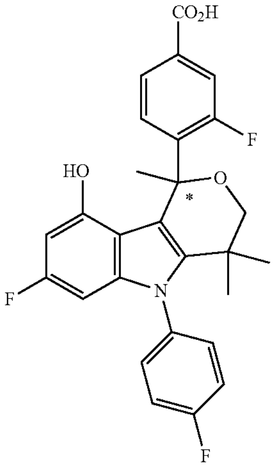
183
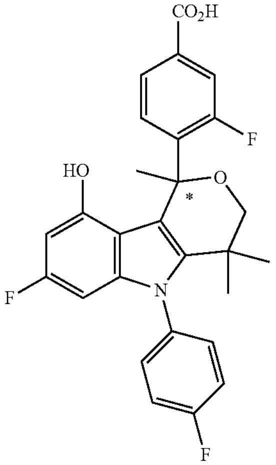
-continued
184
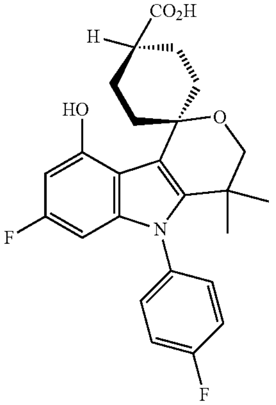
185
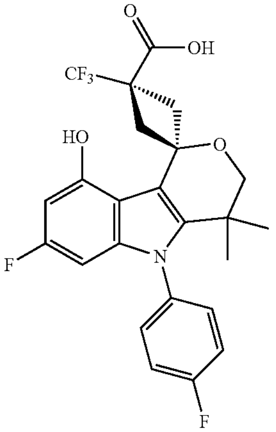
186
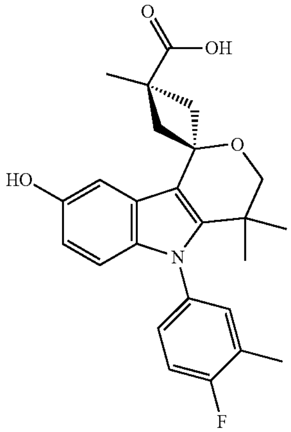

-continued
187
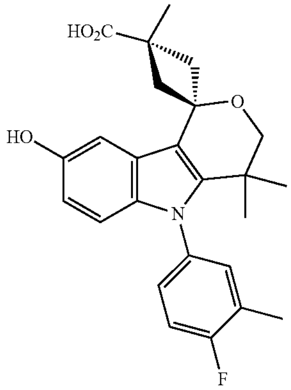
188
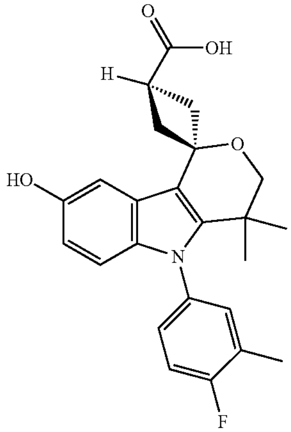
189
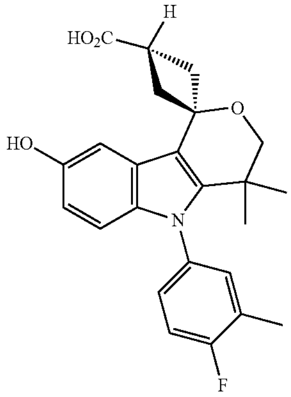
190
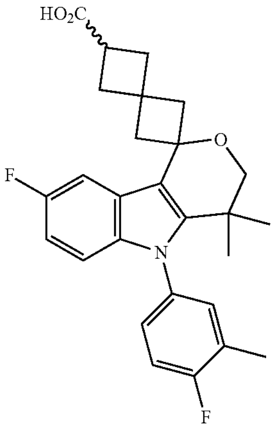
-continued
191
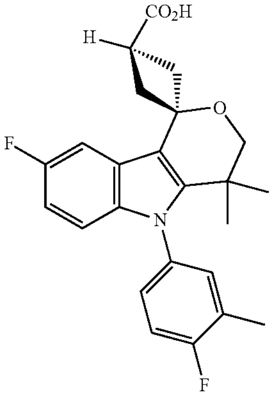
192
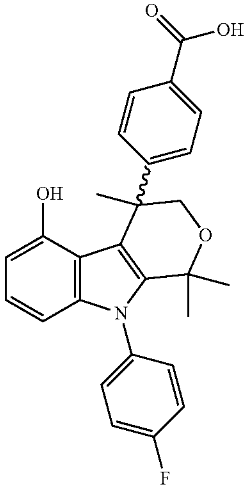
193
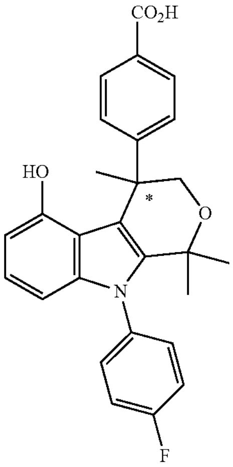

-continued
194
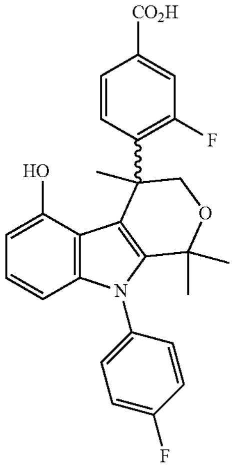
195
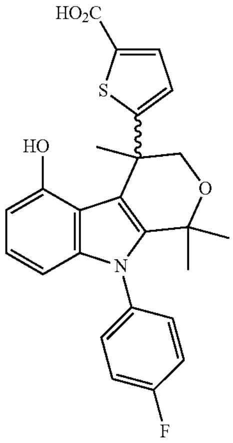
196
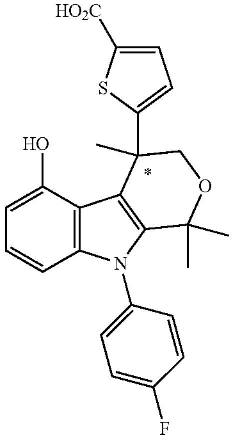
-continued
197
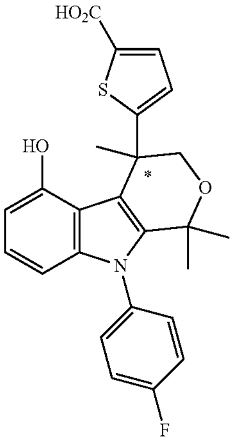
198
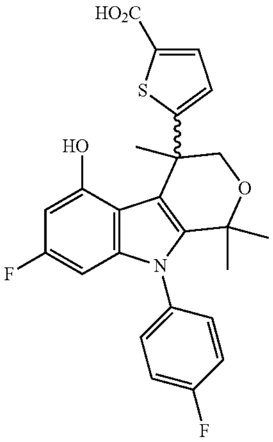
199
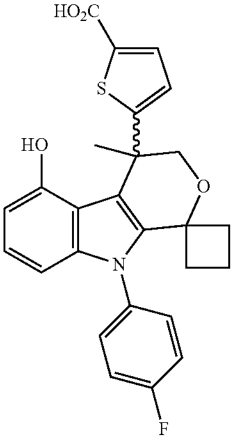

-continued
200
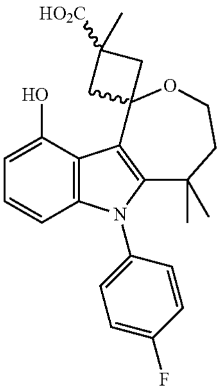
201
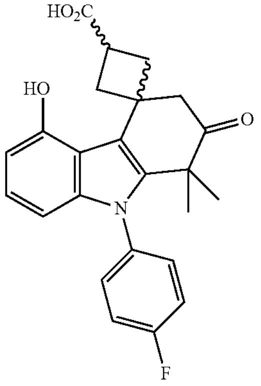
202
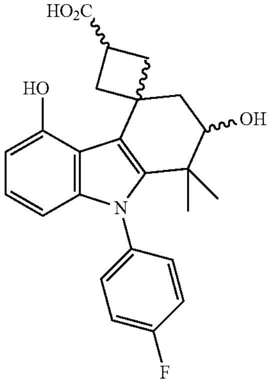
203
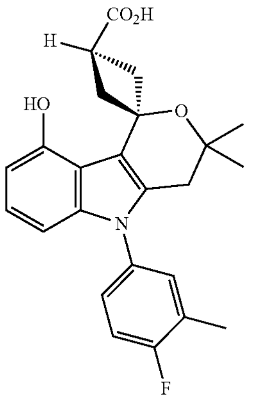
-continued
204
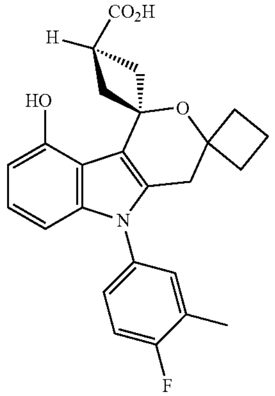
205
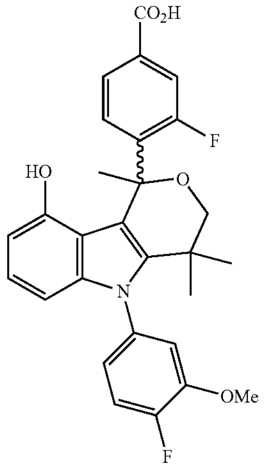
206
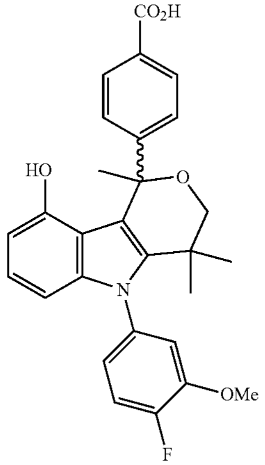

-continued

207

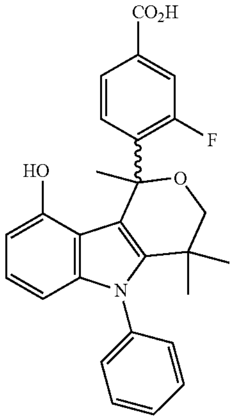

208

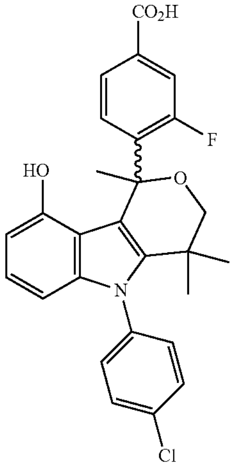

209

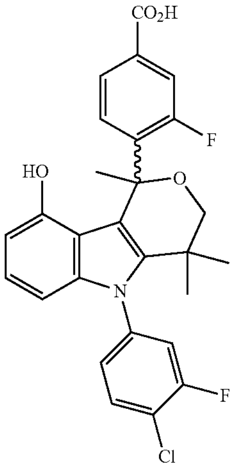

-continued

210

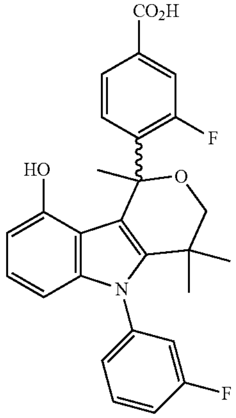

tautomers thereof, deuterated derivatives of the compounds and tautomers, and pharmaceutically acceptable salts of the compounds, tautomers, and deuterated derivatives.

30. A pharmaceutical composition comprising at least one compound according to claim 1, a tautomer thereof, a deuterated derivative of that compound or tautomer, or a pharmaceutically acceptable salt of any of the foregoing.

31. A method of treating alpha-1 antitrypsin (AAT) deficiency comprising administering to a patient in need thereof a therapeutically effective amount of at least one compound, tautomer, deuterated derivative, or pharmaceutically acceptable salt according to claim 1.

32. A method of modulating alpha-1 antitrypsin (AAT) activity comprising the step of contacting said AAT with a therapeutically effective amount of at least one compound, tautomer, deuterated derivative, or pharmaceutically acceptable salt according to claim 1.

33. The method of claim 31, wherein said therapeutically effective amount of the at least one compound, tautomer, deuterated derivative, or pharmaceutically acceptable salt is administered in combination with AAT augmentation therapy and/or AAT replacement therapy.

* * * * *